US011713459B2

(12) United States Patent
Rawlings et al.

(10) Patent No.: US 11,713,459 B2
(45) Date of Patent: Aug. 1, 2023

(54) EXPRESSION OF FOXP3 IN EDITED CD34+ CELLS

(71) Applicant: Seattle Children's Hospital, Seattle, WA (US)

(72) Inventors: David J. Rawlings, Seattle, WA (US); Iram F. Khan, Seattle, WA (US); Yuchi Chiang Honaker, Seattle, WA (US); Swati Singh, Seattle, WA (US); Karen Sommer, Seattle, WA (US); Andrew M. Scharenberg, Seattle, WA (US)

(73) Assignee: SEATTLE CHILDREN'S HOSPITAL, Seattle, WA (US)

( * ) Notice: Subject to any disclaimer, the term of this patent is extended or adjusted under 35 U.S.C. 154(b) by 0 days.

(21) Appl. No.: 16/981,223

(22) PCT Filed: Apr. 25, 2019

(86) PCT No.: PCT/US2019/029082

§ 371 (c)(1),
(2) Date: Sep. 15, 2020

(87) PCT Pub. No.: WO2019/210042

PCT Pub. Date: Oct. 31, 2019

(65) Prior Publication Data

US 2021/0054376 A1 Feb. 25, 2021

Related U.S. Application Data

(60) Provisional application No. 62/663,545, filed on Apr. 27, 2018.

(51) Int. Cl.

| | |
|---|---|
| ***C12N 15/87*** | (2006.01) |
| ***C12N 15/00*** | (2006.01) |
| ***C07H 21/04*** | (2006.01) |
| ***A61K 48/00*** | (2006.01) |
| ***C12N 15/113*** | (2010.01) |
| ***C12N 9/22*** | (2006.01) |
| ***A61K 35/15*** | (2015.01) |
| ***C12N 5/0783*** | (2010.01) |
| *A01K 67/00* | (2006.01) |

(52) U.S. Cl.

CPC ............ *C12N 15/113* (2013.01); *A61K 35/15* (2013.01); *C12N 5/0637* (2013.01); *C12N 9/22* (2013.01); *C12N 2310/20* (2017.05); *C12N 2501/60* (2013.01); *C12N 2800/80* (2013.01)

(58) Field of Classification Search

CPC ...... C12N 15/113; C12N 9/22; C12N 5/0637; C12N 2310/20; C12N 2800/80; C12N 2501/60; A61K 35/15

See application file for complete search history.

(56) References Cited

U.S. PATENT DOCUMENTS

| | | | | |
|---|---|---|---|---|
| 10,968,426 | B2 * | 4/2021 | Meissner | C12N 5/0696 |
| 2015/0368611 | A1 | 12/2015 | Seong | |
| 2016/0184362 | A1 | 6/2016 | Duchateau et al. | |
| 2016/0230188 | A1 | 8/2016 | Rabinovich | |
| 2019/0247443 | A1 | 8/2019 | Scharenberg et al. | |
| 2020/0123224 | A1 | 4/2020 | Scharenberg | |
| 2020/0347404 | A1 * | 11/2020 | Kohn | A61K 38/1709 |
| 2021/0253652 | A1 | 8/2021 | Scharenberg | |

FOREIGN PATENT DOCUMENTS

| | | |
|---|---|---|
| EP | 1 430 124 | 11/2013 |
| WO | WO 02/090600 | 11/2002 |
| WO | WO 08/009977 | 1/2008 |
| WO | WO 08/095141 | 8/2008 |
| WO | WO 08/141282 | 11/2008 |
| WO | WO 08/154399 | 12/2008 |
| WO | WO 09/067349 | 5/2009 |
| WO | WO 09/114097 | 9/2009 |
| WO | WO 12/018930 | 2/2012 |
| WO | WO 14/180943 | 11/2014 |
| WO | WO 14/191128 | 12/2014 |
| WO | WO 15/121454 | 8/2015 |
| WO | WO 15/140347 | 9/2015 |
| WO | WO 14/184744 | 3/2016 |
| WO | WO 16/115179 | 7/2016 |
| WO | WO 2016/123578 A1 | 8/2016 |
| WO | WO 16/183041 | 11/2016 |

(Continued)

OTHER PUBLICATIONS

Allan et al., Jan. 2008, Generation of potent and stable human CD4+ T regulatory cells by activation-independent expression of FOXP3, Mol Ther. 16(1):194-202.

Baron et al., 2007, DNA demethylation in the human FPXP3 locus discriminates regulatory T cells from activate FPXP3+ conventional T ceils, Eur J Immunol. 37(9):2378-89.

Bettini et al., May 25, 2012, Loss of epigenetic modification driven by the Foxp3 transcription factor leads to regulator T cell insufficiency, Immunity, 36(5):717-730.

Challita et al., Feb. 1995, Multiple modifications in cis elements of the long terminal repeat of retroviral vectors lead to increased expression and decreased DNA methylation in embryonic carcinoma cells, J. Virol. 69(2):748-755.

Darce et al., May 25, 2012, An N-terminal mutation of the Foxp3 transcription factor alleviates arthritis but exacerbates diabetes, Immunity. 36(5):731-741.

(Continued)

*Primary Examiner* — Quang Nguyen

(74) *Attorney, Agent, or Firm* — Knobbe, Martens, Olson & Bear LLP

(57) ABSTRACT

Aspects of the invention described herein concern the incorporation of a FOXP3 cDNA (e.g., full-length human codon-optimized cDNA) into a FOXP3 gene or a non-FOXP3 locus so as to provide constitutive or regulated FOXP3 expression in a primary human $CD34^+$ cells or cells derived from edited $CD34^+$ cells. In some embodiments, guide RNA sequences that are directed to FOXP3, AAVS1, or other candidate loci are used for CRISPR/Cas9-mediated gene regulation, and gene delivery cassettes for HDR based gene-modification are provided.

10 Claims, 6 Drawing Sheets

Specification includes a Sequence Listing.

(56) References Cited

FOREIGN PATENT DOCUMENTS

| | | | |
|---|---|---|---|
| WO | WO 17/186718 | | 11/2017 |
| WO | WO 18/031762 | | 2/2018 |
| WO | WO 2018/073391 | A1 | 4/2018 |
| WO | WO 2018/081470 | A1 | 5/2018 |
| WO | WO 2018/205926 | A1 | 11/2018 |
| WO | WO 19/040655 | | 2/2019 |
| WO | WO 19/241549 | | 12/2019 |

OTHER PUBLICATIONS

Engels et al., Aug. 10, 2003, Retroviral Vectors for High-Level Transgene Expression in T Lymphocytes, Human Gene Therapy, 14:1155-1168.

Fantini et al., 2004, Cutting edge: TGF-β induces a regulatory phenotype in CD4+CD25-T cells through Foxp3 induction and down-regulation of Smad7, J Immunol. 172(9):5149-5153.

Fontenot et al., Apr. 2003, Foxp3 programs the development and function of CD4+CD25+ regulatory T cells, Nat Immunol. 4(4):330-336.

Fransson et al. 2012, CAR/FoxP3-engineered T regulatory cells target the CNS and suppress EAE upon intranasal delivery, Journal of Neuroinflammation, 9:112.

Ghali et al., 2017, Induced regulatory T cells are phenotypically unstable and do not protect mice from rapidly progressive glomerulopephritis, Immunology. 150(1):100-114.

Honaker et al., 2020, Gene editing to induce FOXP3 expression in human CD4+ T cells leads to a stable regulatory phenotype and function, Sci Transl Med. 12(546):eaay6422, 18 pp.

Hori et al., Feb. 14, 2003, Control of regulatory T cell development by the transcription factor Foxp3, Science. 299(5609):1057-1061.

Hubbard et al., May 1, 2016, Nuclease-targeted gene-editing of FOXP3 in primary T cells creates a stable and functional T phenotype, Mol Ther. 24(Suppl. 1):S18 (ASGCT Abstract).

Hubbard, May 2016, Nuclease-targeted gene-editing of FOXP3 in primary T cells creates a stable and functional $T_{reg}$ phenotype, PowerPoint presentation, 22 pp.

Konya et al., 2013, T Cells as Treatment Targets in Systemic Lupus Erythematosus, Rheumatology: Current Research, 3(2), pp. 3 pages.

Loser et al., 2005, In vitro-generated regulatory T cells induced by Foxp3-retrovirus infection control murine contact allergy and systemic autoimmunity, Gene Ther. 12(17):1294-1304.

Okada et al., 2017, Stabilization of Foxp3 expression by CRISPR-dCas9-based epigenome editing in mouse primary T cells, Epigenetics Chromatin. 10:24.

Passerini et al., Dec. 11, 2013, CD4+ T cells from IPEX patients convert into functional and stable regulatory T cells by FOXP3 gene transfer, Sci Transl Med. 5(215):215ra174.

Qin et al., May 2010, Systematic Comparison of Constitutive Promoters and the Doxycycline-Inducible Promoter, PLOS One, 5(5):el 0611-1-el 0611-4.

Riley J.L., et al., "Human T Regulatory Cells as Therapeutic Agents: Take a Billion or So of These and Call Me in the Morning," Immunity, vol. 30, Issue No. 5, pp. 656-665 (May 2009).

Schubert et al., 2001, Scurfin (FOXP3) acts as a repressor of transcription and regulates T cell activation, J Biol Chem. 276(40):37672-37679.

Schumann et al., Jul. 27, 2015, Generation of knock-in primary human T cells using Cas9 ribonucleoproteins, Proceedings of the National Academy of Sciences, 112(33):10437-10442.

Wright et al. Nov. 10, 2009, Adoptive therapy with redirected primary regulatory T cells results in antigen-specific suppression of arthritis, PNAS 106(45):19078-19083.

Goodwin et al., May 2016, 123. Gene editing as a therapeutic approach to treat IPEX syndrome, Molecular Therapy, 24:S51-S52.

Honaker et al., Nov. 28, 2018, Conversion of T-effector cells to immunosuppressive T-regulatory-like cells by CRISPR/Cas9-mediated integration of a FOXP3 transgene, Blood, 132:3490.

Kornete et al., Feb. 14, 2018, Highly efficient and versatile plasmid-based gene editing in primary T cells, The Journal of Immunology, 200(7):2489-2501.

International Search Report for PCT/US2019/029082 dated Aug. 16, 2019.

Eyquem et al., Mar. 2, 2017, Targeting a CAR to the TRAC locus with CRISPR/Cas9 enhances tumor rejection, Nature, 543:113-117.

Lombardo et al., Aug. 21, 2011, Site-specific integration and tailoring of cassette design for sustainable gene transfer, Nature Methos, 8(10):861-869.

* cited by examiner

EXPRESSION OF FOXP3 IN EDITED CD34+ CELLS

CROSS REFERENCE TO RELATED APPLICATIONS

This application is a U.S. National Phase Application of PCT International Application Number PCT/US2019/029082, filed on Apr. 25, 2019, designating the United States of America and published in the English language, which is an International Application of and claims the benefit of priority to U.S. Provisional Application No. 62/663,545, filed on Apr. 27, 2018. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided as a file entitled SeqList-SCRI-188NP, created Sep. 15, 2020, which is approximately 428 Kb in size. The information in the electronic format of the Sequence Listing is incorporated herein by reference in its entirety.

FIELD

Aspects of the invention described herein concern the incorporation of a FOXP3 coding sequence into a FOXP3 gene or a non-FOXP3 locus in $CD34^+$ cells to provide constitutive or regulated FOXP3 expression in the edited $CD34^+$ cells or cells derived therefrom, such as T cells.

BACKGROUND

Lentiviral gene transfer of FOXP3 (also known as forkhead box protein P3, forkhead box P3, AAID, DIETER, IPEX, JM2, PIDX, XPID, or scurfin) has been previously described by Chen, C. et al. (2011). *Transplant. Proc.* 43(5):2031-2048, Passerini, L. et al. (2013). *Sci. Transl. Med.,* 5(215):215ra174, and Passerini, L. et al. (2017). *Front. Immunol.* 8:1282; all are hereby expressly incorporated by reference in their entireties. Passerini et al. (2017) had previously reported the development of methods to restore Treg function in T lymphocytes from patients carrying mutations in FOXP3. As described by Passerini et al. (2017), lentiviral mediated gene transfer was used in $CD4^+$ T cells and effector T cells which were converted into effector T cells, which exhibited characteristics of Treg-like cells and endowed the cells with potent in vitro and in vivo suppressive activity. Passerini also demonstrated conversion of $CD4^+$ T cells into Treg cells after lentiviral mediated FOXP3 gene transfer, in which the cells were shown to be stable in inflammatory conditions Passerini et al. (2013). Chen et al. (2011) also describes the adoptive transfer of engineered T cells, in which the T cells were infected with a lentiviral vector encoding a FOXP3-IRES-GFP fragment. These cells were shown to protect recipients from GvHD in a murine model. The need for new approaches to express and regulate FOXP3 in a primary human lymphocytes is manifest.

Many investigators are interested in treating auto-immune diseases with regulatory T cells, due to the possibility for these cells to induce antigen specific tolerance. There are many forms of regulatory T cells ("$T_{regs}$"), with current nomenclature dividing $T_{regs}$ into those which are generated in the thymus in the course of T cell development, denoted as thymic regulatory T cells or "$tT_{regs}$", and peripherally induced regulatory T cells, denoted as peripheral regulatory T cells or "$pT_{regs}$."

A key aspect of regulatory T cell biology is the expression of the transcription factor FOXP3. FOXP3 is thought to be required to specify the regulatory T cell lineage. This concept is based on the observation that humans who lack FOXP3 develop severe autoimmune disease starting in the neonatal period. The use of either $tT_{regs}$ or $pT_{regs}$ for therapy of autoimmune disease may not be optimal because FOXP3 expression is believed to be subject to epigenetic regulation. In $tT_{regs}$, an upstream region in the FOXP3 gene known as the "thymus specific demethylated region" is demethylated, a state which is thought to result in stable FOXP3 expression. Generally, full demethylation is not observed in $pT_{regs}$. Under inflammatory conditions, FOXP3 may be silenced epigenetically in $pT_{regs}$, and possibly $tT_{regs}$ (although some investigators believe that $tT_{regs}$ are completely stable), potentially resulting in conversion of $pT_{regs}$ to pro-inflammatory CD4 T cells. The potential lack of stability of $pT_{regs}$ is a significant concern, as infusion of $pT_{regs}$ that revert to an inflammatory phenotype may result in a worsening of autoimmune symptoms.

SUMMARY

Described herein is a system comprising: a deoxyribonucleic acid (DNA) endonuclease or nucleic acid encoding the DNA endonuclease; a guide RNA (gRNA) comprising a spacer sequence that is complementary to a sequence within a FOXP3 gene, AAVS1 locus, or a TRA gene in a $CD34^+$ cell, or nucleic acid encoding the gRNA; and a donor template comprising a nucleic acid sequence encoding a FOXP3 or a functional derivative thereof. In some embodiments, the gRNA comprises: i) a spacer sequence from any one of SEQ ID NOs: 1-7, 15-20, and 27-29 or a variant thereof having no more than 3 mismatches compared to any one of SEQ ID NOs: 1-7, 15-20, and 27-29; ii) a spacer sequence from any one of SEQ ID NOs: 1-7 or a variant thereof having no more than 3 mismatches compared to any one of SEQ ID NOs: 1-7; or iii) a spacer sequence from any one of SEQ ID NOs: 2, 3, and 5 or a variant thereof having no more than 3 mismatches compared to any one of SEQ ID NOs: 2, 3, and 5. In some embodiments, the FOXP3 or functional derivative thereof is wild-type human FOXP3. In some embodiments, the DNA endonuclease is a Cas9. In some embodiments, the nucleic acid encoding the DNA endonuclease is an mRNA. In some embodiments, the donor template is encoded in an adeno-associated virus (AAV) vector. In some embodiments, the DNA endonuclease or nucleic acid encoding the DNA endonuclease is formulated in a liposome or lipid nanoparticle.

Also described herein is a method of editing a genome in a $CD34^+$ cell, the method comprising providing any one of the systems described herein to the cell. In some embodiments, the $CD34^+$ cell is not a germ cell.

The present disclosure also describes a genetically modified $CD34^+$ cell, and a composition comprising a genetically modified $CD34^+$ cell, in which the genome of the cell is edited by any one of the methods described herein. In some embodiments, the genetically modified $CD34^+$ cell is not a germ cell.

Further described is a method of treating a disease or condition associated with FOXP3 in a subject, comprising providing any one of the systems described herein to a $CD34^+$ cell in the subject. The disease or condition can be an inflammatory disease or an autoimmune disease, such as IPEX syndrome or Graft-versus-Host disease (GVHD). In some embodiments, the genetically modified $CD34^+$ cell is not a germ cell.

DETAILED DESCRIPTION

Figure 1:
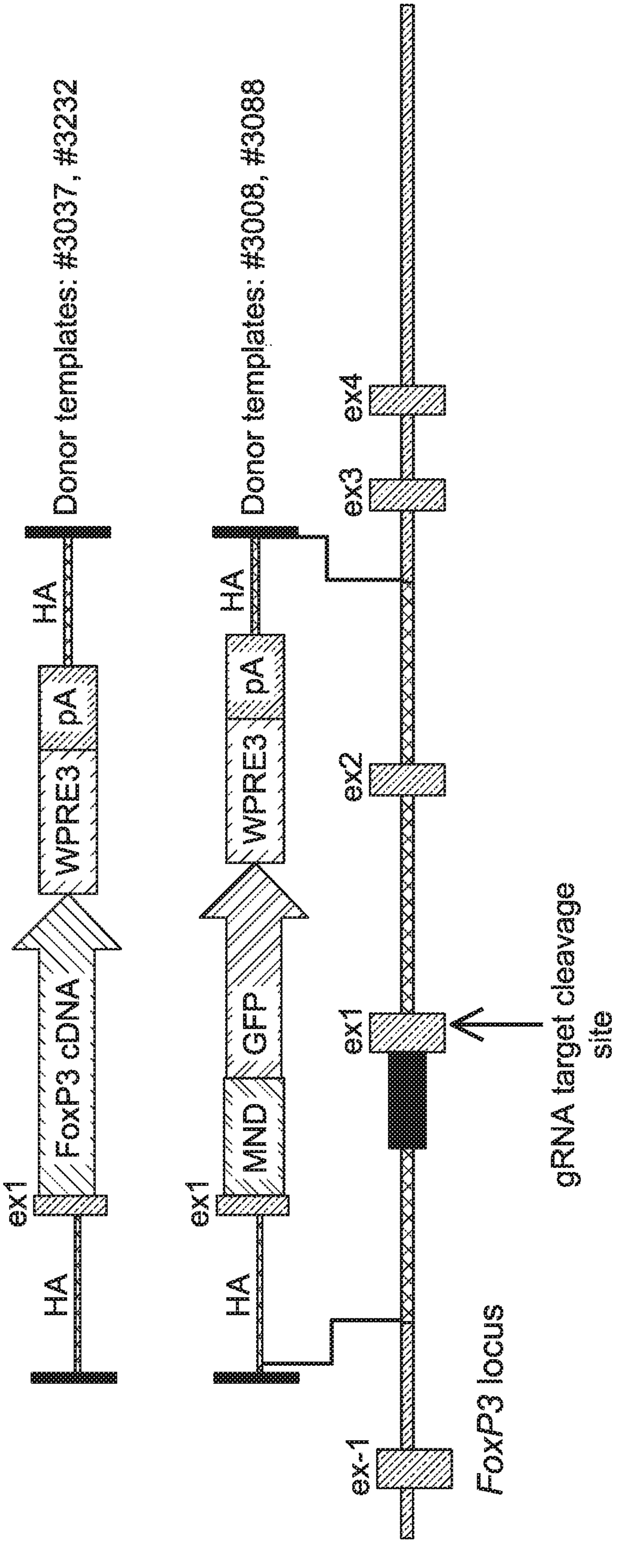
FIG. 1 shows schematics for two different AAV donor template designs configured for integration of a donor cassette into a FOXP3 gene, one for expression of FOXP3 from a heterologous FOXP3 cDNA under the control of an endogenous FOXP3 promoter (top schematic), and the other for expression of GFP under a heterologous MND promoter (bottom schematic). HA: homology arms; MND: MND promoter; pA: SV40 polyadenylation signal.

Expression of FOXP3 from a DNA sequence (e.g., codon-optimized DNA sequence, such as for expression in human cells) that is integrated in a FOXP3 gene or a non-FOXP3 locus is described herein. Guide RNAs are used to target a FOXP3 gene (e.g., murine, human and nonhuman primate) or a non-FOXP3 locus for CRISPR/Cas-mediated genome editing. Accordingly, aspects of the invention concern the utilization of novel guide RNAs in combination with Cas proteins to create DNA breaks at a FOXP3 gene or non-FOXP3 loci to facilitate integration of a FOXP3 coding sequence. In some embodiments, the integration is by non-homologous end joining (NHEJ) or homology directed repair (HDR) in association with a donor template containing the FOXP3 coding sequence. Several embodiments described herein can be used in combination with a broad range of selection markers such as LNG FR, RQR8, CISC/DISC/uDISC or others and can be multiplexed with editing of other loci or co-expression of other gene products including cytokines.

As described in greater detail below, Applicant has identified guide RNAs, which in combination with Cas9 protein and novel AAV donor templates containing gene delivery cassettes, generate a high frequency of on-target cleavage and integration of the gene delivery cassette into a FOXP3 gene in primary human $CD34^+$ cells. In addition, sustained engraftment of the edited $CD34^+$ cells in NSG recipient mice was achieved, along with long-term expression of a GFP reporter construct integrated into a FOXP3 gene. These findings demonstrate that the genome editing systems such as the CRISPR/Cas systems described herein are capable of resulting in efficient editing to effect expression of a human wild-type FOXP3 in human hematopoietic stem cells and sustained engraftment at levels that are predicted to provide a clinical benefit in diseases or disorders having aberrant FOXP3 function, e.g., following autologous adoptive cell therapy in IPEX subjects. Previous studies suggested that IPEX subjects with as little as a 5% donor chimerism exhibit clinical benefit following allogeneic stem cell transplantation. See, Seidel, M. G. et al. (2009). *Blood,* 113(22):5689-5691.

The use of CRISPR/Cas systems including gRNAs and donor templates configured to insert the cDNA for a FOXP3 gene at an endogenous FOXP3 gene offers a promising therapy for inflammatory diseases, such as the autoimmune disease IPEX syndrome. In the context of treating IPEX syndrome, this disease can be caused by a diversity of mutations spread over the entire gene, and thus inserting the entire FOXP3 cDNA (e.g., human codon optimized) at the start codon may be desired. Utilizing the endogenous FOXP3 promoter upon cell differentiation from the $CD34^+$ cell is expected to provide the necessary transcriptional signals required for optimal levels of FOXP3 expression.

Definitions

As used herein, the terms "nucleic acid" and "nucleic acid molecule" include but are not limited to, for example, polynucleotides or oligonucleotides such as deoxyribonucleic acid (DNA) or ribonucleic acid (RNA), oligonucleotides, fragments generated by the polymerase chain reaction (PCR), and fragments generated by any of ligation, scission, endonuclease action, exonuclease action, and by synthetic generation. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, or azido groups, or sugars can be functionalized as ethers or esters. Moreover, the entire sugar moiety can be replaced with sterically and electronically similar structures, such as aza-sugars or carbocyclic sugar analogs. Examples of modifications in a base moiety include alkylated purines or pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, or phosphoramidate. The term "nucleic acid molecule" also includes so-called "peptide nucleic acids," which comprise naturally-occurring or modified nucleic acid bases attached to a polyamide backbone. Nucleic acids can be either single stranded or double stranded.

"Coding strand" as used herein includes but is not limited to, for example, the DNA strand which has the same base sequence as the RNA transcript produced (although with thymine replaced by uracil). It is this strand, which contains codons, while the non-coding strand contains anti-codons.

"Regulatory element" as used herein includes but is not limited to, for example, a segment of a nucleic acid molecule, which is capable of increasing or decreasing the expression of specific genes within an organism, e.g., one that has the ability to affect the transcription and/or translation of an operably linked transcribable DNA molecule. Regulatory elements such as promoters (e.g. an MND promoter), leaders, introns, or transcription termination regions are DNA molecules that have gene regulatory activity and play an integral part in the overall expression of genes in living cells. Isolated regulatory elements, such as promoters, that function in plants are therefore useful for modifying plant phenotypes through the methods of genetic engineering. Regulation of gene expression is an essential feature of all living organisms and viruses. Without being limiting, examples of regulatory elements can include, CAAT box, CCAAT box, Pribnow box, TATA box, SECIS element, mRNA polyadenylation signals, A-box, Z-box, C-box, E-box, G-box, hormone responsive elements, such as insulin gene regulatory sequences, DNA binding domains, activation domains, and/or enhancer domains.

In some embodiments, a guide RNA includes an additional segment at either the 5' or 3' end that provides for any of the features described above. For example, a suitable third segment can include a 5' cap (e.g. a 7-methylguanylate cap (m7G)); a 3' polyadenylated tail (e.g., a 3' poly(A) tail); a riboswitch sequence (e.g. to allow for regulated stability and/or regulated accessibility by proteins and protein complexes); a stability control sequence; a sequence that forms a dsRNA duplex (e.g., a hairpin)); a sequence that targets the RNA to a subcellular location (e.g. nucleus, mitochondria, or chloroplasts, and the like); a modification or sequence that provides for tracking (e.g. direct conjugation to a fluorescent molecule, conjugation to a moiety that facilitates fluorescent detection, a sequence that allows for fluorescent detection, etc.); a modification or sequence that provides a binding site for proteins (e.g. proteins that act on DNA. including transcriptional activators, transcriptional repressors, DNA methyltransferases, DNA demethylases, histone acetyltransferases, or histone deacetylases, and the like); and combinations thereof.

A guide RNA and a Cas endonuclease (e.g., a Cas9 endonuclease) may form a ribonucleoprotein complex (e.g., bind via non-covalent interactions). The guide RNA provides target specificity to the complex by comprising a nucleotide sequence that is complementary to a sequence of a target DNA. The site-specific modifying enzyme of the complex provides the endonuclease activity. In other words, the site-specific modifying enzyme is guided to a target DNA sequence (e.g. a target sequence in a chromosomal nucleic acid; a target sequence in an extrachromosomal nucleic acid, e.g. an episomal nucleic acid, a minicircle, etc.; a target sequence in a mitochondrial nucleic acid; a target sequence in a chloroplast nucleic acid; or a target sequence in a plasmid; etc.) by virtue of its association with the protein-binding segment of the guide RNA.

"FOXP3" as used herein includes but is not limited to, for example, a protein that is involved in immune system responses. The FOXP3 gene (also known as forkhead box protein P3, forkhead box P3, AAID, DIETER, IPEX, JM2, PIDX, XPID, or scurfin) contains 11 coding exons. FOXP3 is a specific marker of natural T regulatory cells ($nT_{regs}$, a lineage of T cells) and adaptive/induced T regulatory cells ($a/iT_{regs}$). Induction or administration of FOXP3 positive T cells has, in animal studies, lead to marked reductions in (autoimmune) disease severity in models of diabetes, multiple sclerosis, asthma, inflammatory bowel disease, thyroiditis or renal disease. However, T cells have been able to show plasticity in studies. Thus, the use of regulatory T cells in therapy can be risky, as the T regulatory cell transferred to the subject may change into T helper 17 (Th17) cells, which are pro-inflammatory rather than regulatory cells. As such, methods are provided herein to avoid the risks that may arise from regulatory cells changing into pro-inflammatory cells. For example, FOXP3 expressed from an iTreg is used as a master regulator of the immune system and is used for tolerance and immune suppression. Treg are believed to play a critical role in multiple autoimmune diseases, such as IPEX syndrome, Type 1 diabetes, systemic lupus erythematosus, and rheumatoid arthritis. Approaches to augment human Treg number or function are in current trials including low-dose IL-2 and adoptive transfer of autologous expanded Treg. The efficacy of IL-2 therapy is limited due to its pleotropic activity and potential "off target" effects that may increase inflammation. Adoptive Treg therapy is likely limited by in vivo stability and viability of expanded $T_{regs}$ and their lack of relevant antigen specificity.

"Nuclease" as used herein includes but is not limited to, for example, a protein or an enzyme capable of cleaving the phosphodiester bonds between the nucleotide subunits of nucleic acids. The nuclease described herein, is used for "gene editing" which is a type of genetic engineering in which DNA is inserted, deleted or replaced in the genome of a living organism using a nuclease or an engineered nuclease or nucleases. Without being limiting, the nuclease can be of a CRISPR/Cas system (e.g., a CRISPR/Cas9 system), a zinc finger nuclease, or TALEN nuclease. The nuclease can be used to target a locus, e.g., a locus on a nucleic acid sequence.

"Coding exon" as used herein includes but is not limited to, for example, any part of a gene that will encode a part of the final mature RNA produced by that gene after introns have been removed by RNA splicing. The term exon refers to both the DNA sequence within a gene and to the corresponding sequence in RNA transcripts. In RNA splicing, introns are removed and exons are covalently joined to one another as part of generating the mature messenger RNA.

"Cas endonuclease" or "Cas nuclease" as used herein includes but is not limited to, for example, an RNA-guided DNA endonuclease enzyme associated with the CRISPR (Clustered Regularly Interspaced Short Palindromic Repeats) adaptive immunity system. Herein, "Cas endonuclease" refers to both naturally-occurring and recombinant Cas endonucleases.

"Cas9" or "CAS9" (also known as Csn1 and Csx12) as used herein includes but is not limited to, for example, an RNA-guided DNA endonuclease enzyme associated with the CRISPR (Clustered Regularly Interspaced Short Palindromic Repeats) adaptive immunity system. Herein, the "Cas9" refers to both naturally-occurring and recombinant Cas9s.

"Zinc finger nuclease" as used herein includes but is not limited to, for example, an artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes.

"TALEN" or "Transcription activator-like effector nuclease" as used herein includes but is not limited to, for example, restriction enzymes that can be engineered to cut specific sequences of DNA. They are made by fusing a TAL effector DNA-binding domain to a DNA cleavage domain (a nuclease which cuts DNA strands). Transcription activator-like effectors (TALEs) can be engineered to bind practically any desired DNA sequence, so when combined with a nuclease, DNA can be cut at specific locations. The restriction enzymes can be introduced into cells, for use in gene editing or for genome editing in situ, a technique known as genome editing with engineered nucleases. Alongside zinc finger nucleases and CRISPR/Cas, TALEN is a tool in the field of genome editing.

The term "knock-in" includes but is not limited to, for example, a genetic engineering method that involves the one-for-one substitution of DNA sequence information with a wild-type copy in a genetic locus or the insertion of sequence information not found within the locus.

A "promoter" as used herein includes but is not limited to, for example, nucleotide sequence that directs the transcription of a structural gene. In some embodiments, a promoter is located in the 5' non-coding region of a gene, proximal to the transcriptional start site of a structural gene. Sequence elements within promoters that function in the initiation of transcription are often characterized by consensus nucleotide sequences. It is a region of DNA that initiates transcription of a particular gene. Promoters are located near the transcription start sites of genes, on the same strand and upstream on the DNA (towards the 5' region of the sense strand). Promoters can be at or about 100, 200, 300, 400, 500, 600, 700, 800, or 1000 base pairs long or within a range defined by any two of the aforementioned lengths. As used herein, a promoter can be constitutively active, repressible or inducible. If a promoter is an inducible promoter, then the rate of transcription increases in response to an inducing agent. In contrast, the rate of transcription is not regulated by an inducing agent if the promoter is a constitutive promoter. Repressible promoters are also known. Without being limiting, examples of promoters can include a constitutive promoter, a heterologous weak promoter (e.g., a promoter that generates less expression than the endogenous promoter and/or a constitutive promoter) or inducible promoters. Examples can include EF1 alpha promoter, a PGK promoter, an MND promoter, KI promoter, Ki-67 gene promoter, or a promoter inducible by a drug such as tamoxifen and/or its metabolites. Commonly used constitutive promoters can include but are not limited to SV40, CMV, UBC, EF1A, PGK, or CAGG for mammalian systems.

"Transcriptional enhancer domain" as used herein includes but is not limited to, for example, a short (50-1500 bp) region of DNA that can be bound by proteins (activators) to increase or promote or enhance the likelihood that transcription of a particular gene will occur or the level of transcription that takes place. These activator proteins are usually referred to as transcription factors. Enhancers are generally cis-acting, located up to 1 Mbp (1,000,000 bp) away from the gene and can be upstream or downstream from the start site, and either in the forward or backward direction. An enhancer may be located upstream or downstream of the gene it regulates. A plurality of enhancer domains may be used In some embodiments, to generate greater transcription e.g., multimerized activation binding domains can be used to further enhance or increase the level of transcription. Furthermore, an enhancer doesn't need to be located near the transcription initiation site to affect transcription, as some have been found located in several hundred thousand base pairs upstream or downstream of the start site. Enhancers do not act on the promoter region itself, but are bound by activator proteins. These activator proteins interact with the mediator complex, which recruits polymerase II and the general transcription factors, which then begin transcribing the genes. Enhancers can also be found within introns. An enhancer's orientation may even be reversed without affecting its function. Additionally, an enhancer may be excised and inserted elsewhere in the chromosome, and still affect gene transcription. In some embodiments, the enhancers are used to silence the inhibition mechanisms that prevent transcription of the FOXP3 gene. An example of an enhancer binding domain is the TCR alpha enhancer. In some embodiments, the enhancer domain is a TCR alpha enhancer. In some embodiments, the enhancer binding domain is placed upstream from a promoter such that it activates the promoter to increase transcription of the protein. In some embodiments, the enhancer binding domain is placed upstream of a promoter to activate the promoter to increase transcription of the FOXP3 gene.

"Transcriptional activator domains" or "Transcriptional activation domain" as used herein include but are not limited to, for example, specific DNA sequences that can be bound by a transcription factor, in which the transcription factor can thereby control the rate of transcription of genetic information from DNA to messenger RNA. Specific transcription factors can include but is not limited to SP1, AP1, C/EBP, heat shock factor, ATF/CREB, c-Myc, Oct-1 or NF-1. In some embodiments, the activator domains are used to silence the inhibition mechanisms that prevent transcription of the FOXP3 gene.

"Ubiquitous chromatin opening element," (UCOE) as used herein includes but is not limited to, for example, elements that are characterized by unmethylated CpG islands spanning dual, divergently transcribed promoters of housekeeping genes. The UCOE represent promising tools to avoid silencing and sustain transgene expression in a wide variety of cellular models including cell lines, multipotent hematopoietic stem cells, as well as PSCs and their differentiated progeny.

"Operably linked" as used herein includes but is not limited to, for example, functional linkage between a regulatory sequence and a heterologous nucleic acid sequence resulting in expression of the latter. In some embodiments, the first molecule is joined to a second molecule, wherein the molecules are so arranged that the first molecule affects the function of the second molecule. The two molecules may be part of a single contiguous molecule and may be adjacent. For example, a promoter is operably linked to a transcribable DNA molecule if the promoter modulates transcription of the transcribable DNA molecule of interest in a cell.

The term "concentration" used in the context of a molecule such as peptide fragment refers to an amount of molecule, e.g., the number of moles of the molecule, present in a given volume of solution.

The terms "individual," "subject" and "host" are used interchangeably herein and refer to any subject for whom diagnosis, treatment, or therapy is desired. In some aspects, the subject is a mammal. In some aspects, the subject is a human being. In some aspects, the subject is a human patient. In some aspects, the subject can have or is suspected of having a disorder or health condition associated with FOXP3. In some aspects, the subject is a human who is diagnosed with a risk of disorder or health condition associated with FOXP3 at the time of diagnosis or later. In some cases, the diagnosis with a risk of disorder or health condition associated with FOXP3 can be determined based on the presence of one or more mutations in an endogenous gene encoding the FOXP3 or nearby genomic sequence that may affect the expression of a FOXP3. For example, in some aspects, the subject can have or is suspected of having an autoimmune disorder and/or has one or more symptoms of an autoimmune disorder. In some aspects, the subject is a human who is diagnosed with a risk of an autoimmune disorder at the time of diagnosis or later. In some cases, the diagnosis with a risk of an autoimmune disorder can be determined based on the presence of one or more mutations in an endogenous FOXP3 gene or genomic sequence near the FOXP3 gene in the genome that may affect the expression of the FOXP3 gene.

The term "treatment," when used in referring to a disease or condition, means that at least an amelioration of the symptoms associated with the condition afflicting an individual is achieved, where amelioration is used in a broad sense to refer to at least a reduction in the magnitude of a parameter, e.g., a symptom, associated with the condition (e.g., an autoimmune disorder) being treated. As such, treatment also includes situations where the pathological condition, or at least symptoms associated therewith, are completely inhibited, e.g., prevented from happening, or eliminated entirely such that the host no longer suffers from the condition, or at least the symptoms that characterize the condition. Thus, treatment includes: (i) prevention, that is, reducing the risk of development of clinical symptoms, including causing the clinical symptoms not to develop, e.g., preventing disease progression; (ii) inhibition, that is, arresting the development or further development of clinical symptoms, e.g., mitigating or completely inhibiting an active disease.

The terms "effective amount," "pharmaceutically effective amount," or "therapeutically effective amount" as used herein mean a sufficient amount of the composition to provide the desired utility when administered to a subject having a particular condition. In the context of ex vivo treatment of an autoimmune disorder, the term "effective amount" refers to the amount of a population of therapeutic cells or their progeny needed to prevent or alleviate at least one or more signs or symptoms of an autoimmune disorder, and relates to a sufficient amount of a composition having the therapeutic cells or their progeny to provide the desired effect, e.g., to treat symptoms of an autoimmune disorder of a subject. The term "therapeutically effective amount" therefore refers to a number of therapeutic cells or a composition having therapeutic cells that is sufficient to promote a particular effect when administered to a subject in need of treatment, such as one who has or is at risk for an autoimmune disorder. An effective amount would also include an amount sufficient to prevent or delay the development of a symptom of the disease, alter the course of a symptom of the disease (for example but not limited to, slow the progression of a symptom of the disease), or reverse a symptom of the disease. In the context of in vivo treatment of an autoimmune disorder in a subject (e.g., a patient) or genome edition in a cell cultured in vitro, an effective amount refers to an amount of components used for genome edition such as gRNA, donor template and/or a site-directed polypeptide (e.g. DNA endonuclease) needed to edit the genome of the cell in the subject or the cell cultured in vitro. It is understood that for any given case, an appropriate "effective amount" can be determined by one of ordinary skill in the art using routine experimentation.

"Autoimmune disorder" as used herein includes but is not limited to, for example, abnormally low activity or over activity of the immune system. In cases of immune system over activity, the body attacks and damages its own tissues (autoimmune diseases). Immune deficiency diseases decrease the body's ability to fight invaders, causing vulnerability to infections. Without being limiting, examples of autoimmune disorders or autoimmune diseases, which can be inhibited, ameliorated or treated by using the compositions and methods described herein can include, for example, systemic lupus, scleroderma, hemolytic anemia, vasculitis, type I diabetes, Graves disease, rheumatoid arthritis, multiple sclerosis, Goodpasture's syndrome, myopathy, severe combined immunodeficiency, DiGeorge syndrome, Hyperimmunoglobulin E syndrome, Common variable immunodeficiency, Chronic granulomatous disease, Wiskott-Aldrich syndrome, Autoimmune lymphoproliferative syndrome, Hyper IgM syndrome, Leukocyte adhesion deficiency, NF-κB Essential Modifier (NEMO) Mutations, Selective immunoglobulin A deficiency, X-linked agammaglobulinemia, X-linked lymphoproliferative disease, IPEX, Immune dysregulation, polyendocrinopathy, enteropathy, immunodysregulation polyendocrinopathy enteropathy X-linked (IPEX) syndrome or Ataxia-telangiectasia. Immune disorders can be analyzed, for example, by examination of the profile of neural-specific autoantibodies or other biomarkers when detected in serum or cerebrospinal fluid in subjects. In some exemplary methods provided herein, the methods are for treatment, amelioration, or inhibition of autoimmune disorders. In some embodiments, the autoimmune disorder is systemic lupus, scleroderma, hemolytic anemia, vasculitis, type I diabetes, Graves disease, rheumatoid arthritis, multiple sclerosis, Goodpasture's syndrome, myopathy, severe combined immunodeficiency, DiGeorge syndrome, Hyperimmunoglobulin E syndrome, Common variable immunodeficiency, Chronic granulomatous disease, Wiskott-Aldrich syndrome, Autoimmune lymphoproliferative syndrome, Hyper IgM syndrome, Leukocyte adhesion deficiency, NF-κB Essential Modifier (NEMO) Mutations, Selective immunoglobulin A deficiency, X-linked agammaglobulinemia, X-linked lymphoproliferative disease, IPEX, Immune dysregulation, polyendocrinopathy, enteropathy, immunodysregulation polyendocrinopathy enteropathy X-linked (IPEX) syndrome or Ataxia-telangiectasia or any combination thereof.

"IPEX syndrome" refers to immunodysregulation polyendocrinopathy enteropathy X-linked syndrome and is a rare disease linked to the dysfunction of the transcription factor FOXP3, widely considered to be the master regulator of the regulatory T cell lineage. Subjects suffering from IPEX syndrome may have symptoms such as autoimmune enteropathy, psoriasiform or eczematous dermatitis, nail dystrophy, autoimmune endocrinopathies, or autoimmune skin conditions such as alopecia universalis or bullous pemphigoid. IPEX syndrome is an autoimmune disease in which the immune system attacks the body's own tissues and organs. The syndrome leads to loss of $CD4^+CD25^+$ T regulatory cells, and loss of the expression of the transcription factor FOXP3. FOXP3 decrease is believed to be a consequence of unchecked T cell activation, which is secondary to loss of regulatory T cells.

"Organ transplantation" as used herein includes but is not limited to, for example, the moving of an organ from one body to another or from a donor site to another location on the person's own body, to replace the recipient's damaged or absent organ. Organs and/or tissues that are transplanted within the same person's body are called autografts. Transplants that are recently performed between two subjects of the same species are called allografts. Allografts can either be from a living or cadaveric source. In some embodiments described herein, a method of treating, inhibiting, or ameliorating side effects of organ transplantation in a subject, such as organ rejection is provided.

Organs that can be transplanted, for example, are the heart, kidneys, liver, lungs, pancreas, intestine, or thymus. Tissues for transplant can include, for example, bones, tendons (both referred to as musculoskeletal grafts), cornea, skin, heart valves, nerves or veins. Kidneys, liver or the heart are the most commonly transplanted organs. Cornea or musculoskeletal grafts are the most commonly transplanted tissues.

In some embodiments described herein, a method of treating, inhibiting, or ameliorating side effects of organ transplantation in a subject, such as organ rejection is provided. In some embodiments, the subject is also selected to receive anti-rejection medications. In some embodiments, the anti-rejection medications comprise Prednisone, Imuran (azathioprine), Collect (mycophenolate mofetil, or MMF), Myfortic (mycophenolic acid), Rapamune (sirolimus), Neoral (cyclosporine), or Prograf (tacrolimus).

In some embodiments, the subject is selected for inhibition, amelioration, or treatment with the engineered cells set forth in the embodiments herein. In some embodiments, the subject has side effects to anti-inflammatory drugs or anti-rejection drugs. As such, the selected subjects are provided with the exemplary cells or compositions provided herein. Side effects from anti-rejection drugs can include interactions with other medications that can raise or lower tacrolimus levels in the blood, kidney toxicity, high blood pressure, neurotoxicity (tremor, headache, tingling, and/or insomnia), Diabetes mellitis (high blood sugar), diarrhea, nausea, hair loss or high potassium or any combination thereof. As such, the subjects are selected for the methods of treatment, inhibition, or amelioration described herein. Such selection or identification can be made by clinical or diagnostic evaluation.

"Organ rejection" or "transplant rejection" as used herein includes but is not limited to, for example, transplanted tissue rejected by the recipient's immune system, which destroys the transplanted tissue.

"Graft-versus-Host disease" (GVHD or GvHD) as used herein includes but is not limited to, for example, a medical complication following the receipt of transplanted tissue from a genetically different person. GVHD is commonly associated with stem cell or bone marrow transplant but the term also applies to other forms of tissue graft. Immune cells in the donated tissue recognize the recipient as foreign and not "self." In some embodiments herein, the methods provided can be used for preventing or ameliorating the complications that can arise from GVHD.

"Pharmaceutical excipient" as used herein includes but is not limited to, for example, the inert substance that the cells in the composition are provided in.

A "chimeric antigen receptor" (CAR) described herein, also known as chimeric T cell receptor, includes but is not limited to, for example, an artificial T cell receptor or a genetically engineered receptor, which grafts a desired specificity onto an immune effector cell. A CAR may be a synthetically designed receptor comprising a ligand binding domain of an antibody or other protein sequence that binds to a molecule associated with the disease or disorder and is linked via a spacer domain to one or more intracellular signaling domains of a T cell or other receptors, such as a costimulatory domain. In some embodiments, a cell, such as a mammalian cell, is manufactured wherein the cell comprises a nucleic acid encoding a fusion protein and wherein the cell comprises a chimeric antigen receptor. These receptors can be used to graft the specificity of a monoclonal antibody or a binding portion thereof onto a T cell, for example. In some embodiments herein, the genetically engineered cell further comprises a sequence that encodes a chimeric antigen receptor. In some embodiments, the chimeric antigen receptor is specific for a molecule on a tumor cell. A chimeric antigen receptor or an engineered cell expressing a T cell receptor can be used to target a specific tissue in need for FOXP3. Some embodiments herein comprise methods for targeting specific tissues for providing and delivering a FOXP3. In some embodiments, the tissue is a transplanted tissue. In some embodiments, the chimeric antigen receptor is specific for a target molecule on the transplanted tissue.

As described herein, the genetically-engineered cells are engineered to express FOXP3, and as such, they are also described in the embodiments herein as "Treg-phenotype" cells. The cells can be $CD34^+$ cells, e.g., $CD34^+$ hematopoietic stem cells.

As used herein, "protein sequence" includes but is not limited to, for example, a polypeptide sequence of amino acids that is the primary structure of a protein. As used herein "upstream" refers to positions 5' of a location on a polynucleotide, and positions toward the N-terminus of a location on a polypeptide. As used herein "downstream" refers to positions 3' of a location on nucleotide, and positions toward the C-terminus of a location on a polypeptide. Thus, the term "N-terminal" refers to the position of an element or location on a polynucleotide toward the N-terminus of a location on a polypeptide.

As used herein, the term "expression," or "protein expression" refers to the translation of a transcribed RNA molecule into a protein molecule. Protein expression may be characterized by its temporal, spatial, developmental, or morphological qualities, as well as, by quantitative or qualitative indications. In some embodiments, the protein or proteins are expressed such that the proteins are positioned for dimerization in the presence of a ligand.

The functional equivalent or fragment of the functional equivalent, in the context of a protein, may have one or more conservative amino acid substitutions. The term "conservative amino acid substitution" refers to substitution of an amino acid for another amino acid that has similar properties as the original amino acid. The groups of conservative amino acids are as follows:

| Group | Name of the amino acids |
| --- | --- |
| Aliphatic | Gly, Ala, Val, Leu, Ile |
| Hydroxyl or Sulfhydryl/ Selenium-containing | Ser, Cys, Thr, Met |
| Cyclic | Pro |
| Aromatic | Phe, Tyr, Trp |
| Basic | His, Lys, Arg |
| Acidic and their Amide | Asp, Glu, Asn, Gln |

Conservative substitutions may be introduced in any position of a predetermined peptide or fragment thereof. It may however also be desirable to introduce non-conservative substitutions, particularly, but not limited to, a non-conservative substitution in any one or more positions. A non-conservative substitution leading to the formation of a functionally equivalent fragment of the peptide would for example differ substantially in polarity, in electric charge, and/or in steric bulk while maintaining the functionality of the derivative or variant fragment.

"Percentage of sequence identity" is determined by comparing two optimally aligned sequences over a comparison window, wherein the portion of the polynucleotide or polypeptide sequence in the comparison window may have additions or deletions (i.e., gaps) as compared to the reference sequence (which does not have additions or deletions) for optimal alignment of the two sequences. In some cases, the percentage can be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity" in the context of two or more nucleic acid or polypeptide sequences, refer to two or more sequences or subsequences that are the same or have a specified percentage of amino acid residues or nucleotides that are the same (e.g., 60%, 65%, 70%, 75%, 80%, 85%, 90%, 95%, 98%, or 99% identity over a specified region, e.g., the entire polypeptide sequences or individual domains of the polypeptides), when compared and aligned for maximum correspondence over a comparison window or designated region as measured using one of the following sequence comparison algorithms or by manual alignment and visual inspection. Such sequences are then said to be "substantially identical." This definition also refers to the complement of a test sequence.

The term "complementary" or "substantially complementary," interchangeably used herein, means that a nucleic acid (e.g., DNA or RNA) has a sequence of nucleotides that enables it to non-covalently bind, i.e., form Watson-Crick base pairs or G/U base pairs, to another nucleic acid in a sequence-specific, antiparallel, manner (i.e., a nucleic acid specifically binds to a complementary nucleic acid). As is known in the art, standard Watson-Crick base-pairing includes: adenine (A) pairing with thymidine (T), adenine (A) pairing with uracil (U), and guanine (G) pairing with cytosine (C).

A DNA sequence that "encodes" a particular RNA is a DNA nucleic acid sequence that can be transcribed into RNA. A DNA polynucleotide may encode an RNA (mRNA) that is translated into protein, or a DNA polynucleotide may encode an RNA that is not translated into protein (e.g., tRNA, rRNA, or a guide RNA; also referred to herein as "non-coding" RNA or "ncRNA"). A "protein coding sequence or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences.

As used herein, "codon" refers to a sequence of three nucleotides that together form a unit of genetic code in a DNA or RNA molecule. As used herein the term "codon degeneracy" refers to the nature in the genetic code permitting variation of the nucleotide sequence without affecting the amino acid sequence of an encoded polypeptide.

The term "codon-optimized" or "codon optimization" refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism. Codon usage tables are readily available, for example, at the "Codon Usage Database". By utilizing the knowledge on codon usage or codon preference in each organism, one of ordinary skill in the art can apply the frequencies to any given polypeptide sequence and produce a nucleic acid fragment of a codon-optimized coding region which encodes the polypeptide, but which uses codons optimal for a given species. Codon-optimized coding regions can be designed by various methods known to those skilled in the art.

The term "recombinant" or "engineered" when used with reference, for example, to a cell, a nucleic acid, a protein, or a vector, indicates that the cell, nucleic acid, protein, or vector has been modified by or is the result of laboratory methods. Thus, for example, recombinant or engineered proteins include proteins produced by laboratory methods. Recombinant or engineered proteins can include amino acid residues not found within the native (non-recombinant or wild-type) form of the protein or can be include amino acid residues that have been modified, e.g., labeled. The term can include any modifications to the peptide, protein, or nucleic acid sequence. Such modifications may include the following: any chemical modifications of the peptide, protein, or nucleic acid sequence, including of one or more amino acids, deoxyribonucleotides, or ribonucleotides; addition, deletion, or substitution of one or more of amino acids in the peptide or protein; or addition, deletion, or substitution of one or more of nucleic acids in the nucleic acid sequence.

The term "genomic DNA" or "genomic sequence" refers to the DNA of a genome of an organism including, but not limited to, the DNA of the genome of a bacterium, fungus, archaeon, plant, or animal.

As used herein, "transgene," "exogenous gene" or "exogenous sequence," in the context of nucleic acid, refers to a nucleic acid sequence or gene that was not present in the genome of a cell but artificially introduced into the genome, e.g., via genome-edition.

As used herein, "endogenous gene" or "endogenous sequence," in the context of nucleic acid, refers to a nucleic acid sequence or gene that is naturally present in the genome of a cell, without being introduced via any artificial means.

"Vector," "expression vector," or "construct" is a nucleic acid used to introduce heterologous nucleic acids into a cell that has regulatory elements to provide expression of the heterologous nucleic acids in the cell. Vectors include but are not limited to plasmid, minicircles, yeast, and viral genomes. In some embodiments, the vectors are plasmid, minicircles, yeast, or viral genomes. In some embodiments, the vector is a viral vector. In some embodiments, the viral vector is a lentivirus. In some embodiments, the vector is an adeno-associated viral (AAV) vector. In some embodiments, the vector is for protein expression in a bacterial system such as *E. coli*. As used herein, the term "expression," or "protein expression" refers to refers to the translation of a transcribed RNA molecule into a protein molecule. Protein expression may be characterized by its temporal, spatial, developmental, or morphological qualities as well as by quantitative or qualitative indications. In some embodiments, the protein or proteins are expressed such that the proteins are positioned for dimerization in the presence of a ligand. In some embodiments, the vector is a viral vector. In some embodiments, the viral vector is a lentivirus. In some embodiments, the vector is an adeno-associated viral (AAV) vector (such as, without limitation, AAV1, AAV2, AAV3, AAV4, AAV5, AAV6, AAV7, AAV8, AAV9, AAV10, or AAV11).

As used herein, “fusion proteins” or “chimeric proteins” include but are not limited to, for example, proteins created through the joining of two or more genes that originally coded for separate proteins or portions of proteins. The fusion proteins can also be made up of specific protein domains from two or more separate proteins. Translation of this fusion gene can result in a single or multiple polypeptides with functional properties derived from each of the original proteins. Recombinant fusion proteins can be created artificially by recombinant DNA technology for use in biological research or therapeutics. Such methods for creating fusion proteins are known to those skilled in the art. Some fusion proteins combine whole peptides and therefore can contain all domains, especially functional domains, of the original proteins. However, other fusion proteins, especially those that are non-naturally occurring, combine only portions of coding sequences and therefore do not maintain the original functions of the parental genes that formed them. In some embodiments, a fusion protein is provided, wherein the fusion protein comprises an interferon or a PD-1 protein or both.

A “conditional” or “inducible” promoter as used herein includes but is not limited to, for example, a nucleic acid construct that comprises a promoter that provides for gene expression in the presence of an inducer and does not substantially provide for gene expression in the absence of the inducer.

“Constitutive” as used herein refer to the nucleic acid construct that comprises a promoter that is constitutive, and thus provides for expression of a polypeptide that is continuously produced.

In some embodiments, the inducible promoter has a low level of basal activity. In some embodiments, wherein a lentiviral vector is used, the level of basal activity in uninduced cells is 20%, 15%, 10%, 5%, 4%, 3%, 2%, 1% or less (but not zero) or within a range defined by any two of the aforementioned values, as compared to when cells are induced to express the gene. The level of basal activity can be determined by measuring the amount of the expression of the transgene (e.g. marker gene) in the absence of the inducer (e.g. drug) using flow cytometry. In some embodiments described herein a marker protein such as Akt is used for determination of expression.

In some embodiments, the inducible promoter provides for a high level of induced activity, as compared to uninduced or basal activity. In some embodiments, the level of activity in the induced state is 2, 4, 6, 8, 9 or 10 fold or greater than the activity level in the uninduced state or within a range defined by any two of the aforementioned values. In some embodiments, transgene expression under control of the inducible promoter is turned off in the absence of a transactivator in less than 10, 8, 6, 4, 2, or 1 days excluding 0 days or within a range defined by any two of the aforementioned time periods.

In some embodiments, an inducible promoter is designed or modified to provide for a low level of basal activity, a high level of inducibility, and/or a short time for reversibility.

“Woodchuck Hepatitis Virus (WHP) Posttranscriptional Regulatory Element (WPRE) is a DNA sequence that, when transcribed creates a tertiary structure enhancing expression. These elements may be used to increase expression of genes delivered by viral vectors. In the embodiments described herein, the WPRE3 element is used to enhance the expression of the delivered nucleic acid, such as delivered cDNA.

In some embodiments, the immunomodulatory imide drug used in the approaches described herein may comprise: thalidomide (including analogues, derivatives, or pharmaceutically acceptable salts thereof. Thalidomide may include Immunoprin, Thalomid, Talidex, Talizer, Neurosedyn, α-(N-Phthalimido)glutarimide, 2-(2,6-dioxopiperidin-3-yl)-2,3-dihydro-1H-isoindole-1,3-dione); or pomalidomide (including analogues, derivatives, or pharmaceutically acceptable salts thereof. Pomalidomide may include Pomalyst, Imnovid, (RS)-4-Amino-2-(2,6-dioxopiperidin-3-yl)isoindole-1,3-dione); or lenalidomide (including analogues, derivatives, or pharmaceutically acceptable salts thereof. Lenalidomide may include Revlimid, (RS)-3-(4-Amino-1-oxo-1,3-dihydro-2H-isoindol-2-yl)piperidine-2,6-dione); or apremilast (including analogues, derivatives, or pharmaceutically acceptable salts thereof. Apremilast may include Otezla, CC-10004, N-{2-[(1 S)-1-(3-Ethoxy-4-methoxyphenyl)-2-(methylsulfonyl) ethyl]-1,3-dioxo-2,3-dihydro-1H-isoindol-4-yl}acetamide); or any combinations thereof.

As used herein, the term “extracellular binding domain” refers to a domain of a complex that is outside of the cell, and which is configured to bind to a specific atom or molecule. In some embodiments, the extracellular binding domain of a CISC is a FKBP domain or a portion thereof. In some embodiments, the extracellular binding domain is an FRB domain or a portion thereof. In some embodiments, the extracellular binding domain is configured to bind a ligand or agent, thereby stimulating dimerization of two CISC components. In some embodiments, the extracellular binding domain is configured to bind to a cytokine receptor modulator.

The CISC (chemically induced signaling complex) is a multicomponent synthetic protein complex configured for co-expression in a host cell as two chimeric proteins as described in International Patent Application No. PCT/US2017/065746, the disclosure of which is expressly incorporated by reference herein in its entirety. Each chimeric protein component of the CISC has one half of a rapamycin binding complex as an extracellular domain, fused to one half of an intracellular signaling complex. Delivery of nucleic acids encoding the CISC to host cells permits intracellular signaling in the cells that can be controlled by the presence of rapamycin or a rapamycin-related chemical compound.

Rapamycin-driven CISC dimerization can trigger intracellular signaling, the presence of rapamycin can also inhibit the growth and the viability of host cells, thereby limiting their utility for use in therapeutic, as well as, research endeavors. Consequently, new compositions and methods are needed, which permit the use of rapamycin-mediated CISC intracellular signaling but which remediate the negative effects that rapamycin or rapamycin-related compounds have on the growth and viability of host cells.

“Dimeric chemical-induced signaling complex,” “dimeric CISC,” or “dimer” as used herein refers to two components of a CISC, which may or may not be fusion protein complexes that join together. “Dimerization” refers to the process of the joining together of two separate entities into a single entity, for example in response to binding of the entities to a ligand (for example, rapamycin). In some embodiments, a ligand or agent stimulates dimerization. In some embodiments, dimerization refers to homodimerization, or the joining of two identical entities, such as two identical CISC components. In some embodiments, dimerization refers to heterodimerization, of the joining of two different entities, such as two different and distinct CISC components. In some embodiments, the dimerization of the CISC components results in a cellular signaling pathway. In some embodiments, the dimerization of the CISC components allows for the selective expansion of a cell or a population of cells. Additional CISC systems can include a CISC gibberellin CISC dimerization system, or a SLF-TMP CISC dimerization system. Other chemically inducible dimerization (CID) systems and component parts may be used.

As used herein, "chemical-induced signaling complex" or "CISC" refers to an engineered complex that initiates a signal into the interior of a cell as a direct outcome of ligand-induced dimerization. A CISC may be a homodimer (dimerization of two identical components) or a heterodimer (dimerization of two distinct components). Thus, as used herein the term "homodimer" refers to a dimer of two protein components described herein with identical amino acid sequences. The term "heterodimer" refers to a dimer of two protein components described herein with non-identical amino acid sequences.

The CISC may be a synthetic complex as described herein in greater detail. "Synthetic" as used herein refers to a complex, protein, dimer, or composition, as described herein, which is not natural, or that is not found in nature. In some embodiments, an IL2R-CISC refers to a signaling complex that involves interleukin-2 receptor components. In some embodiments, an IL2/15-CISC refers to a signaling complex that involves receptor signaling subunits that are shared by interleukin-2 and interleukin-15. In some embodiments, an IL7-CISC refers to a signaling complex that involves an interleukin-7 receptor components. A CISC may thus be termed according to the component parts that make up the components of a given CISC. One of skill in the art will recognize that the component parts of the chemical-induced signaling complex may be composed of a natural or a synthetic component useful for incorporation into a CISC. Thus, the examples provided herein are not intended to be limiting.

"FKBP" as used herein, is a FK506 binding protein domain. FKBP refers to a family of proteins that have prolyl isomerase activity and are related to the cyclophilins in function, though not in amino acid sequence. FKBPs have been identified in many eukaryotes from yeast to humans and function as protein folding chaperones for proteins containing proline residues. Along with cyclophilin, FKBPs belong to the immunophilin family. The term FKBP comprises, for example, FKBP12 as well as, proteins encoded by the genes AIP; AIPL1; FKBP1A; FKBP1B; FKBP2; FKBP3; FKBPS; FKBP6; FKBP7; FKBP8; FKBP9; FKBP9L; FKBP10; FKBP11; FKBP14; FKBP15; FKBP52; or LOC541473; comprising homologs thereof and functional protein fragments thereof.

"FRB" as used herein, as a FKBP rapamycin binding domain. FRB domains are polypeptide regions (protein "domains") that are configured to form a tripartite complex with an FKBP protein and rapamycin or a rapalog thereof. FRB domains are present in a number of naturally occurring proteins, comprising mTOR proteins (also referred to in the literature as FRAP, RAPT 1, or RAFT) from human and other species; yeast proteins comprising Tor1 or Tor2; or a Candida FRAP homolog. Both FKBP and FRB are major constituents in the mammalian target of rapamycin (mTOR) signaling.

A "naked FKBP rapamycin binding domain polypeptide" or a "naked FRB domain polypeptide" (which can also be referred to as an "FKBP rapamycin binding domain polypeptide" or an "FRB domain polypeptide") refers to a polypeptide comprising only the amino acids of an FRB domain or a protein wherein at or about 90%, 91%, 92%, 93%, 94%, 95%, 96%, 97%, 98%, 99%, or 100% of the amino acids of the protein are amino acids of an FRB domain. The FRB domain can be expressed as a 12 kDa soluble protein (Chen, J. et al. (1995). *Proc. Natl. Acad. Sci. U.S.A.,* 92(11):4947-4951). The FRB domain forms a four helix bundle, a common structural motif in globular proteins. Its overall dimensions are 30 Å by 45 Å by 30 Å, and all four helices) have short underhand connections similar to the cytochrome b562 fold (Choi, J. et al. (1996). *Science,* 273(5272):239-242). In some embodiments, the naked FRB domain comprises the amino acids of SEQ ID NO: 37: (MEMWHEGLEEASRLYFGERNVKGMFEVLEPLHAMMERGPQTLKETSFNQAYGRD LMEAQEWCRKYMKSGNVKDLTQAWDLYYHVFRRISK; SEQ ID NO: 37), or SEQ ID NO:38: (MEMWHEGLEEASRLYFGERNVKGMFEVLEPLHAMMERGPQTLKETSFNQAYGRD LMEAQEWCRKYMKSGNVKDLLQAWDLYYHVFRRISK; SEQ ID NO: 38).

As used herein, the term "activate" refers to an increase in at least one biological activity of a protein of interest. Similarly, the term "activation" refers to a state of a protein of interest being in a state of increased activity. The term "activatable" refers to the ability of a protein of interest to become activated in the presence of a signal, an agent, a ligand, a compound, or a stimulus. In some embodiments, a dimer, as described herein, is activated in the presence of a signal, an agent, a ligand, a compound, or a stimulus, and becomes a signaling competent dimer. As used herein, the term "signaling competent" refers to the ability or configuration of the dimer so as to be capable of initiating or sustaining a downstream signaling pathway.

As used herein, the term "signaling domain" refers to a domain of the fusion protein or CISC component that is involved in a signaling cascade inside the cell, such as a mammalian cell. A signaling domain refers to a signaling moiety that provides to cells, such as T cells, a signal which, in addition to the primary signal provided by for instance the CD3 zeta chain of the TCR/CD3 complex, mediates a cellular response, such as a T cell response, comprising, but not limited to, activation, proliferation, differentiation, or cytokine secretion or any combination thereof. In some embodiments, the signaling domain is N-terminal to the transmembrane domain, the hinge domain, and the extracellular domain. In some embodiments, the signaling domain is a synthetic or a natural domain. In some embodiments, the signaling domain is a concatenated cytoplasmic signaling domain. In some embodiments, the signaling domain is a cytokine signaling domain. In some embodiments, the signaling domain is an antigen signaling domain. In some embodiments, the signaling domain is an interleukin-2 receptor subunit gamma (IL2Rγ or IL2Rg) domain. In some embodiments, the signaling domain is an interleukin-2 receptor subunit beta (IL2Rβ or IL2Rb) domain or a truncated IL2Rβ domain (such as the truncated IL2Rβ domain comprising the amino acid sequence of SEQ ID NO:5). In some embodiments, binding of an agent or ligand to the extracellular binding domain causes a signal transduction through the signaling domain by the activation of a signaling pathway, as a result of dimerization of the CISC components. As used herein, the term "signal transduction" refers to the activation of a signaling pathway by a ligand or an agent binding to the extracellular domain. Activation of a signal is a result of the binding of the extracellular domain to the ligand or agent, resulting in CISC dimerization.

As used herein, the term "IL2Rb" or "IL2Rβ" refers to an interleukin-2 receptor subunit beta. Similarly, the term "IL2Rg" or IL2Rγ" refers to an interleukin-2 receptor subunit gamma, and the term "IL2Ra" or "IL2Rα" refers to an interleukin-2 receptor subunit alpha. The IL-2 receptor has three forms, or chains, alpha, beta, and gamma, which are also subunits for receptors for other cytokines. IL2Rβ and IL2Rγ are members of the type I cytokine receptor family. "IL2R" as used herein refers to interleukin-2 receptor, which is involved in T cell-mediated immune responses. IL2R is involved in receptor-mediated endocytosis and transduction of mitogenic signals from interleukin 2. Similarly, the term "IL-2/15R" refers to a receptor signaling subunit that is shared by IL-2 and IL-15, and may include a subunit alpha (IL2/15Ra or IL2/15Rα), beta (IL2/15Rb or IL2/15Rβ, or gamma (IL2/15Rg or IL2/15Rγ).

In some embodiments, a chemical-induced signaling complex is a heterodimerization activated signaling complex comprising two components. In some embodiments, the first component comprises an extracellular binding domain that is one part of a heterodimerization pair, an optional hinge domain, a transmembrane domain, and one or more concatenated cytoplasmic signaling domains. In some embodiments, the second component comprises an extracellular binding domain that is the other part of a heterodimerization pair, an optional hinge domain, a transmembrane domain, and one or more concatenated cytoplasmic signaling domains. Thus, in some embodiments, there are two distinct modification events. In some embodiments, the two CISC components are expressed in a cell, such as a mammalian cell. In some embodiments, the cell, such as a mammalian cell, or a population of cells, such as a population of mammalian cells, is contacted with a ligand or agent that causes heterodimerization, thereby initiating a signal. In some embodiments, a homodimerization pair dimerize, whereby a single CISC component is expressed in a cell, such as a mammalian cell, and the CISC components homodimerize to initiate a signal.

As used herein, the term "selective expansion" refers to an ability of a desired cell, such as a mammalian cell, or a desired population of cells, such as a population of mammalian cells, to expand. In some embodiments, selective expansion refers to the generation or expansion of a pure population of cells, such as mammalian cells, that have undergone two genetic modification events. One component of a dimerization CISC is part of one modification and the other component is the other modification. Thus, one component of the heterodimerizing CISC is associated with each genetic modification. Exposure of the cells to a ligand allows for selective expansion of only the cells, such as mammalian cells, having both desired modifications. Thus, in some embodiments, the only cells, such as mammalian cells, that will be able to respond to contact with a ligand are those that express both components of the heterodimerization CISC.

As used herein, the term "cytokine receptor modulator" refers to an agent, which modulates the phosphorylation of a downstream target of a cytokine receptor, the activation of a signal transduction pathway associated with a cytokine receptor, and/or the expression of a particular protein such as a cytokine. Such an agent may directly or indirectly modulate the phosphorylation of a downstream target of a cytokine receptor, the activation of a signal transduction pathway associated with a cytokine receptor, and/or the expression of a particular protein such as a cytokine. Thus, examples of cytokine receptor modulators include, but are not limited to, cytokines, fragments of cytokines, fusion proteins or antibodies or binding portions thereof that immunospecifically bind to a cytokine receptor or a fragment thereof. Further, examples of cytokine receptor modulators include, but are not limited to, peptides, polypeptides (e.g., soluble cytokine receptors), fusion proteins or antibodies or binding portions thereof that immunospecifically bind to a cytokine or a fragment thereof.

As used herein, the term "hinge domain" refers to a domain that links the extracellular binding domain to the transmembrane domain, and may confer flexibility to the extracellular binding domain. In some embodiments, the hinge domain positions the extracellular domain close to the plasma membrane to minimize the potential for recognition by antibodies or binding fragments thereof. In some embodiments, the extracellular binding domain is located N-terminal to the hinge domain. In some embodiments, the hinge domain may be natural or synthetic.

As used herein, the term "transmembrane domain" or "TM domain" refers to a domain that is stable in a membrane, such as in a cell membrane. The terms "transmembrane span," "integral protein," and "integral domain" are also used herein. In some embodiments, the hinge domain and the extracellular domain is located N-terminal to the transmembrane domain. In some embodiments, the transmembrane domain is a natural or a synthetic domain. In some embodiments, the transmembrane domain is an IL-2 transmembrane domain.

As used herein, "host cell" comprises any cell type, such as a mammalian cell, that is susceptible to transformation, transfection, or transduction, with a nucleic acid construct or vector. In some embodiments, the host cell, such as a mammalian cell, is a T cell or a T regulatory cell (abbreviated herein as "Treg" or "$T_{reg}$"). In some embodiments, the host cell, such as a mammalian cell, is a hematopoietic stem cell. In some embodiments, the host cell is a $CD34^+$ cell, e.g., a $CD34^+$ hematopoietic stem cell. As used herein, the term "population of cells" refers to a group of cells, such as mammalian cells, comprising more than one cell. In some embodiments, a cell, such as a mammalian cell, is manufactured, wherein the cell comprises the protein sequence as described herein or an expression vector that encodes the protein sequence as described herein.

As used herein, the term "transformed" or "transfected" refers to a cell, such as a mammalian cell, tissue, organ, or organism into which a foreign polynucleotide molecule, such as a construct, has been introduced. The introduced polynucleotide molecule may be integrated into the genomic DNA of the recipient cell, such as a mammalian cell, tissue, organ, or organism such that the introduced polynucleotide molecule is inherited by subsequent progeny. A "transgenic" or "transfected" cell, such as a mammalian cell, or organism also comprises progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules. "Transduction" refers to virus-mediated gene transfer into cells, such as mammalian cells.

As used herein, a "mammal" comprises, without limitation, mice, rats, rabbits, guinea pigs, dogs, cats, sheep, goats, cows, horses, primates, such as monkeys, chimpanzees, or apes, and, in particular, humans. In some embodiments, the subject is human.

A "marker sequence," as described herein, encodes a protein that is used for selecting or tracking a protein or cell, such as a mammalian cell, that has a protein of interest. In the embodiments described herein, the fusion protein provided can comprise a marker sequence that can be selected in experiments, such as flow cytometry.

"Epitope" as used herein, refers to a part of an antigen or molecule that is recognized by the immune system comprising antibodies, T cells, or B-cells. Epitopes usually have at least 7 amino acids and can be a linear or a conformational epitope. In some embodiments, a cell, such as a mammalian cell, expressing a fusion protein is provided, wherein the cell further comprises a chimeric antigen receptor. In some embodiments, the chimeric antigen receptor comprises a scFv that can recognize an epitope on a cancer cell. "Isolating," or "purifying" when used to describe the various polypeptides or nucleic acids disclosed herein, refers to a polypeptide or nucleic acid that has been identified and separated and/or recovered from a component of its natural environment. In some embodiments, the isolated polypeptide or nucleic acid is free of association with all components with which it is naturally associated. Contaminant components of its natural environment are materials that would generally interfere with diagnostic or therapeutic uses for the polypeptide or nucleic acid, and can include enzymes, hormones, or other proteinaceous or non-proteinaceous solutes. In some embodiments, a method is provided wherein the method comprises delivering the nucleic acid of any one of the embodiments described herein or the expression vector of any one of the embodiments described herein to a bacterial cell, mammalian cell or insect cell, growing the cell up in a culture, inducing expression of the fusion protein and purifying the fusion protein for treatment.

"Percent (%) amino acid sequence identity" with respect to the CISC sequences identified herein is defined as the percentage of amino acid residues in a candidate sequence that are identical with the amino acid residues in the reference sequence for each of the extracellular binding domain, hinge domain, transmembrane domain, and/or the signaling domain, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, comprising any algorithms needed to achieve maximal alignment over the full-length of the sequences being compared. For example, % amino acid sequence identity values generated using the WU-BLAST-2 computer program (Altschul, S. F. et al. (1996). *Methods Enzymol.,* 266:460-480) uses several search parameters, most of which are set to the default values. Those that are not set to default values (e.g., the adjustable parameters) are set with the following values: overlap span=1, overlap fraction=0.125, word threshold (T)=11 and scoring matrix=BLOSUM62. In some embodiments of the CISC, the CISC comprises an extracellular binding domain, a hinge domain, a transmembrane domain, and a signaling domain, wherein each domain comprises a natural, synthetic, or a mutated or truncated form of the native domain (such as a truncated interleukin 2 receptor beta signaling domain). In some embodiments, a mutated or truncated form of any given domain comprises an amino acid sequence with 100%, 95%, 90%, 85% sequence identity, or a percent sequence identity that is within a range defined by any two of the aforementioned percentages to a sequence set forth in a sequence provided herein.

"T cells" or "T lymphocytes" as used herein can be from any mammalian, e.g., primate, species, comprising monkeys, dogs, and humans. In some embodiments, the T cells are allogeneic (from the same species but different donor) as the recipient subject; In some embodiments the T cells are autologous (the donor and the recipient are the same); In some embodiments, the T cells are syngeneic (the donor and the recipients are different but are identical twins).

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "comprising at least." When used in the context of a process, the term "comprising" means that the process comprises at least the recited steps, but may include additional steps. When used in the context of a compound, composition or device, the term "comprising" means that the compound, composition or device comprises at least the recited features or components, but may also include additional features or components.

Genome Editing Systems

Provided herein are systems for genome editing in a cell, e.g., a $CD34^+$ cell, to modulate the expression, function, or activity of a FOXP3, such as by targeted integration of a nucleic acid encoding a FOXP3 or a functional derivative thereof into the genome of the cell. The disclosures also provide, inter alia, systems for providing a therapy to a subject having or suspected of having a disorder or health condition associated with FOXP3, employing ex vivo and/or in vivo genome editing. In some embodiments, the subject has or is suspected of having an autoimmune disease (e.g., IPEX syndrome) or a disorder that results from organ transplant (e.g., Graft-versus-Host Disease (GVHD)).

Some embodiments relate to a system comprising (a) a DNA endonuclease or nucleic acid encoding the DNA endonuclease; (b) a gRNA (e.g., an sgRNA) or nucleic acid encoding the gRNA, wherein the gRNA is capable of targeting the DNA endonuclease to a FOXP3 gene or a non-FOXP3 locus (e.g., AAVS1 (i.e., adeno-associated virus integration site in the genome of a cell)), and (c) a donor template comprising a FOXP3 coding sequence. In some embodiments, the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1 endonuclease, or a functional derivative thereof. In some embodiments, the DNA endonuclease is a Cas endonuclease, such as a Cas9 endonuclease (e.g., a Cas9 endonuclease from *Streptococcus pyogenes*). In some embodiments, the gRNA comprises a spacer sequence complementary to a target sequence in a FOXP3 gene. In some embodiments, the gRNA comprises a spacer sequence complementary to a target sequence in exon 1 of a FOXP3 gene. In some embodiments, the gRNA comprises a spacer sequence from any one of SEQ ID NOs: 1-7 and 27-29 or a variant thereof having no more than 3 mismatches compared to any one of SEQ ID NOs: 1-7 and 27-29. In some embodiments, the gRNA comprises a spacer sequence from any one of SEQ ID NOs: 1-7 or a variant thereof having no more than 3 mismatches compared to any one of SEQ ID NOs: 1-7. In some embodiments, the gRNA comprises a spacer sequence from any one of SEQ ID NOs: 2, 3, and 5, or a variant thereof having no more than 3 mismatches compared to any one of SEQ ID NOs: 2, 3, and 5. In some embodiments, the gRNA comprises a spacer sequence complementary to a target sequence in a non-FOXP3 locus (e.g., AAVS1). In some embodiments, the gRNA comprises a spacer sequence from any one of SEQ ID NOs: 15-20 or a variant thereof having no more than 3 mismatches compared to any one of SEQ ID NOs: 15-20. In some embodiments, the FOXP3 coding sequence encodes FOXP3 or a functional derivative thereof. In some embodiments, the FOXP3 coding sequence is a FOXP3 cDNA. An exemplary FOXP3 cDNA sequence can be found in the AAV donor template having the nucleotide sequence of SEQ ID NO: 34. In some embodiments, the nucleic acid sequence encoding a FOXP3 or a functional derivative thereof has at least or at least about 70% sequence identity, e.g., at least or at least about 75%, 80%, 85%, 90%, 92%, 93%, 94%, 95%, 96%, 97%, 98%, 99% or greater sequence identity, to a sequence according to SEQ ID NO: 110 or 111. In some embodiments, the system comprises the DNA endonuclease. In some embodiments, the system comprises nucleic acid encoding the DNA endonuclease. In some embodiments, the system comprises the gRNA. In some embodiments, the gRNA is an sgRNA. In some embodiments, the system comprises nucleic acid encoding the gRNA. In some embodiments, the system further comprises one or more additional gRNAs or nucleic acid encoding the one or more additional gRNAs.

In some embodiments, according to any of the systems described herein, the gRNA comprises a spacer sequence from any one of SEQ ID NOs: 1-7, 15-20, and 27-29, or a variant thereof having no more than 3 mismatches compared to any one of SEQ ID NOs: 1-7, 15-20, and 27-29. In some embodiments, the gRNA comprises a spacer sequence from any one of SEQ ID NOs: 1-7 or a variant thereof having no more than 3 mismatches compared to any one of SEQ ID NOs: 1-7. In some embodiments, the gRNA comprises a spacer sequence from any one of SEQ ID NOs: 2, 3, and 5 or a variant thereof having no more than 3 mismatches compared to any one of SEQ ID NOs: 2, 3, and 5. In some embodiments, the gRNA comprises a spacer sequence from SEQ ID NO: 2 or a variant thereof having no more than 3 mismatches compared to SEQ ID NO: 2. In some embodiments, the gRNA comprises a spacer sequence from SEQ ID NO: 3 or a variant thereof having no more than 3 mismatches compared to SEQ ID NO: 3. In some embodiments, the gRNA comprises a spacer sequence from SEQ ID NO: 5 or a variant thereof having no more than 3 mismatches compared to SEQ ID NO: 5.

In some embodiments, according to any of the systems described herein, the Cas DNA endonuclease is a Cas9 endonuclease. In some embodiments, the Cas9 endonuclease is from *Streptococcus pyogenes* (spCas9). In some embodiments, the Cas9 is from *Staphylococcus lugdunensis* (SluCas9).

In some embodiments, according to any of the systems described herein, the system comprises a nucleic acid encoding the DNA endonuclease. In some embodiments, the nucleic acid encoding the DNA endonuclease is codon-optimized for expression in a host cell. In some embodiments, the nucleic acid encoding the DNA endonuclease is codon-optimized for expression in a human cell. In some embodiments, the nucleic acid encoding the DNA endonuclease is DNA, such as a DNA plasmid. In some embodiments, the nucleic acid encoding the DNA endonuclease is RNA, such as mRNA.

In some embodiments, according to any of the systems described herein, the nucleic acid sequence encoding a FOXP3 or a functional derivative thereof is codon-optimized for expression in a host cell. In some embodiments, the nucleic acid sequence encoding the FOXP3 or a functional derivative thereof is codon-optimized for expression in a human cell.

In some embodiments, according to any of the systems described herein, the donor template comprises a donor cassette comprising the nucleic acid sequence encoding a FOXP3 or a functional derivative thereof, and a promoter configured to express the FOXP3 or functional derivative thereof. Exemplary promoters include the MND promoter, PGK promoter, and EF1 promoter. In some embodiments, the promoter has a sequence of any one of SEQ ID NOS: 147-149, or a variant having at least 85%, 90%, 91%, 92%, 93%, 94%, 95%, 96%, 97%, 98%, or 99% identity to any one of SEQ ID NOS: 147-149. In some embodiments, the donor template is encoded in an Adeno Associated Virus (AAV) vector. In some embodiments, the AAV vector is an AAV6 vector.

In some embodiments, according to any of the systems described herein, the donor template comprises a donor cassette comprising the nucleic acid sequence encoding a FOXP3 or a functional derivative thereof, and lacks an exogenous promoter configured to express the FOXP3 or functional derivative thereof. In some embodiments, the cell is a $CD34^+$ cell, and expression of the FOXP3 or functional derivative thereof relies on an endogenous promoter in the cell. In some embodiments, the donor template is encoded in an Adeno Associated Virus (AAV) vector. In some embodiments, the AAV vector is an AAV6 vector.

In some embodiments, according to any of the systems described herein, the donor template comprises a donor cassette comprising the nucleic acid sequence encoding a FOXP3 or a functional derivative thereof, and the donor template is configured such that the donor cassette is capable of being integrated into a genomic locus targeted by a gRNA in the system by homology directed repair (HDR). In some embodiments, the donor cassette is flanked on both sides by homology arms corresponding to sequences in the targeted genomic locus. In some embodiments, the homology arms are at least or at least about 0.2 kb (such as at least or at least about any of 0.3 kb, 0.4 kb, 0.5 kb, 0.6 kb, 0.7 kb, 0.8 kb, 0.9 kb, 1 kb, or greater) in length. In some embodiments, the homology arms are at least or at least about 0.6 kb in length. Exemplary homology arms include homology arms from donor templates having the sequence of SEQ ID NO: 34 or 161. In some embodiments, the donor template is encoded in an Adeno Associated Virus (AAV) vector. In some embodiments, the AAV vector is an AAV6 vector.

In some embodiments, according to any of the systems described herein, the donor template comprises a donor cassette comprising the nucleic acid sequence encoding a FOXP3 or a functional derivative thereof, and the donor template is configured such that the donor cassette is capable of being integrated into a genomic locus targeted by a gRNA in the system by non-homologous end joining (NHEJ). In some embodiments, the donor cassette is flanked on one or both sides by a gRNA target site. In some embodiments, the donor cassette is flanked on both sides by a gRNA target site. In some embodiments, the gRNA target site is a target site for a gRNA in the system. In some embodiments, the gRNA target site of the donor template is the reverse complement of a cell genome gRNA target site for a gRNA in the system. In some embodiments, the donor template is encoded in an Adeno Associated Virus (AAV) vector. In some embodiments, the AAV vector is an AAV6 vector.

In some embodiments, according to any of the systems described herein, the donor template comprises a donor cassette comprising the nucleic acid sequence encoding a FOXP3 or a functional derivative thereof, and the donor template further comprises a regulatory element enhancing stable expression. Exemplary regulatory elements enhancing stable expression include WPRE and UCOE. In some embodiments, the WPRE is a full-length WPRE. In some embodiments, the WPRE is a truncated WPRE. Exemplary WPREs include WPREs from a donor template having the sequence of any one of SEQ ID NOs: 33, 34, and 161. In some embodiments, the donor template is encoded in an Adeno Associated Virus (AAV) vector. In some embodiments, the AAV vector is an AAV6 vector.

In some embodiments, according to any of the systems described herein, the donor template comprises a donor cassette comprising the nucleic acid sequence encoding a FOXP3 or a functional derivative thereof, and the donor template further comprises a nucleic acid encoding a selectable marker. In some embodiments, the selectable marker is a surface marker that allows for selection of cells expressing the selectable marker. In some embodiments, the selectable marker is a low-affinity nerve growth factor receptor (LNGFR) polypeptide, a green fluorescent protein (GFP), or a functional derivative thereof. In some embodiments, the LNGFR polypeptide or a functional derivative thereof comprises an amino acid sequence of SEQ ID NO: 144 or a variant thereof having at least 85%, 90%, 91%, 92%, 93%, 94%, 95%, 96%, 97%, 98%, or 99% identity to the amino acid sequence of SEQ ID NO: 144. In some embodiments, the nucleic acid encoding the GFP or functional derivative thereof has a nucleic acid sequence of the GFP encoding region of any one of SEQ ID NOS: 33, 35, and 36. In some embodiments, the donor template is encoded in an Adeno Associated Virus (AAV) vector. In some embodiments, the AAV vector is an AAV6 vector.

In some embodiments, according to any of the systems described herein, the donor template comprises a donor cassette comprising the nucleic acid sequence encoding a FOXP3 or a functional derivative thereof, and the donor template further comprises a nucleic acid encoding a 2A self-cleaving peptide between adjacent system component-encoding nucleic acids. In some embodiments, the donor template comprise nucleic acid encoding a 2A self-cleaving peptide between each of the adjacent system component-encoding nucleic acids. In some embodiments, each of the 2A self-cleaving peptides is, independently, a T2A self-cleaving peptide or a P2A self-cleaving peptide. For example, in some embodiments, the donor template comprises, in order from 5' to 3', a nucleic acid encoding expression of a FOXP3 or functional variant thereof, nucleic acid encoding a 2A self-cleaving peptide, and a nucleic acid encoding a selectable marker. In some embodiments, the donor template comprises a nucleic acid of any one of SEQ ID NOS: 72 and 73, or a variant of a nucleic acid having at least 85%, 90%, 91%, 92%, 93%, 94%, 95%, 96%, 97%, 98%, or 99% identity to any one of SEQ ID NOS: 72 and 73. In some embodiments, the donor template is encoded in an Adeno Associated Virus (AAV) vector. In some embodiments, the AAV vector is an AAV6 vector.

Exemplary donor templates include donor templates having any one of the sequences of SEQ ID NOS:33-36 and 161. In some embodiments, the donor template comprises the sequence of SEQ ID NO: 34 or 161. In some embodiments, the donor template is encoded in an Adeno Associated Virus (AAV) vector. In some embodiments, the AAV vector is an AAV6 vector.

In some embodiments, according to any of the systems described herein, the DNA endonuclease or nucleic acid encoding the DNA endonuclease is formulated in a liposome or lipid nanoparticle. In some embodiments, the liposome or lipid nanoparticle also comprises the gRNA. In some embodiments, the liposome or lipid nanoparticle is a lipid nanoparticle. In some embodiments, the system comprises a lipid nanoparticle comprising nucleic acid encoding the DNA endonuclease and the gRNA. In some embodiments, the nucleic acid encoding the DNA endonuclease is an mRNA encoding the DNA endonuclease.

In some embodiments, according to any of the systems described herein, the DNA endonuclease is complexed with the gRNA, forming a ribonucleoprotein (RNP) complex.

Nucleic Acids

Genome-Targeting Nucleic Acid or Guide RNA

The present disclosure provides a genome-targeting nucleic acid that can direct the activities of an associated polypeptide (e.g., a site-directed polypeptide or DNA endonuclease) to a specific target sequence within a target nucleic acid. In some embodiments, the genome-targeting nucleic acid is an RNA. A genome-targeting RNA is referred to as a "guide RNA" or "gRNA" herein. A guide RNA has at least a spacer sequence that can hybridize to a target nucleic acid sequence of interest and a CRISPR repeat sequence. In Type II systems, the gRNA also has a second RNA referred to as a tracrRNA sequence. In the Type II guide RNA (gRNA), the CRISPR repeat sequence and tracrRNA sequence hybridize to each other to form a duplex. In the Type V guide RNA (gRNA), the crRNA forms a duplex. In both systems, the duplex binds a site-directed polypeptide such that the guide RNA and site-direct polypeptide form a complex. The genome-targeting nucleic acid provides target specificity to the complex by virtue of its association with the site-directed polypeptide. The genome-targeting nucleic acid thus directs the activity of the site-directed polypeptide.

In some embodiments, the genome-targeting nucleic acid is a double-molecule guide RNA. In some embodiments, the genome-targeting nucleic acid is a single-molecule guide RNA. A double-molecule guide RNA has two strands of RNA. The first strand has in the 5' to 3' direction, an optional spacer extension sequence, a spacer sequence and a minimum CRISPR repeat sequence. The second strand has a minimum tracrRNA sequence (complementary to the minimum CRISPR repeat sequence), a 3' tracrRNA sequence and an optional tracrRNA extension sequence. A single-molecule guide RNA (sgRNA) in a Type II system has, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may have elements that contribute additional functionality (e.g., stability) to the guide RNA. The single-molecule guide linker links the minimum CRISPR repeat and the minimum tracrRNA sequence to form a hairpin structure. The optional tracrRNA extension has one or more hairpins. A single-molecule guide RNA (sgRNA) in a Type V system has, in the 5' to 3' direction, a minimum CRISPR repeat sequence and a spacer sequence.

By way of illustration, guide RNAs used in the CRISPR/Cas/Cpf1 system, or other smaller RNAs can be readily synthesized by chemical means as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides.

One approach used for generating RNAs of greater length is to produce two or more molecules that are ligated together. Much longer RNAs, such as those encoding a Cas endonuclease (e.g., a Cas9 or Cpf1 endonuclease), are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

In some embodiments, provided herein is a guide RNA (gRNA) comprising a spacer sequence that is complementary to a genomic sequence within or near a FOXP3 gene in a cell. In some embodiments, the gRNA comprises a spacer sequence from any one of SEQ ID NOs: 1-7 and 27-29 or a variant thereof having no more than 3 mismatches compared to any one of SEQ ID NOs: 1-7 and 27-29. In some embodiments, the gRNA comprises a spacer sequence from any one of SEQ ID NOs: 1-7 or a variant thereof having no more than 3 mismatches compared to any one of SEQ ID NOs: 1-7. In some embodiments, the gRNA comprises a spacer sequence from any one of SEQ ID NOs: 2, 3, and 5 or a variant thereof having no more than 3 mismatches compared to any one of SEQ ID NOs: 2, 3, and 5.

In some embodiments, provided herein is a guide RNA (gRNA) comprising a spacer sequence that is complementary to a genomic sequence within or near an AAVS1 locus in a cell. In some embodiments, the gRNA comprises a spacer sequence from any one of SEQ ID NOs: 15-20 or a variant thereof having no more than 3 mismatches compared to any one of SEQ ID NOs: 15-20.

Guide RNA made by in vitro transcription may contain mixtures of full length and partial guide RNA molecules. Chemically synthesized guide RNA molecules are generally composed of >75% full length guide molecules and in addition may contain chemically modified bases, such as those that make the guide RNA more resistant to cleavage by nucleases in the cell.

Spacer Extension Sequence

In some embodiments of genome-targeting nucleic acids, a spacer extension sequence can modify activity, provide stability or provide a location for modifications of a genome-targeting nucleic acid. A spacer extension sequence can modify on- or off-target activity or specificity. In some embodiments, a spacer extension sequence is provided. A spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. A spacer extension sequence can have a length of or about 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. A spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000, or more nucleotides. In some embodiments, a spacer extension sequence is less than 10 nucleotides in length. In some embodiments, a spacer extension sequence is between 10-30 nucleotides in length. In some embodiments, a spacer extension sequence is between 30-70 nucleotides in length.

In some embodiments, the spacer extension sequence has another moiety (e.g., a stability control sequence, an endoribonuclease binding sequence, or a ribozyme). In some embodiments, the moiety decreases or increases the stability of a nucleic acid targeting nucleic acid. In some embodiments, the moiety is a transcriptional terminator segment (i.e., a transcription termination sequence). In some embodiments, the moiety functions in a eukaryotic cell. In some embodiments, the moiety functions in a prokaryotic cell. In some embodiments, the moiety functions in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, or chloroplasts, and the like), a modification or sequence that provides for tracking (e.g., direct conjugation to a fluorescent molecule, conjugation to a moiety that facilitates fluorescent detection, or a sequence that allows for fluorescent detection, etc.), or a modification or sequence that provides a binding site for proteins (e.g., proteins that act on DNA, including transcriptional activators, transcriptional repressors, DNA methyltransferases, DNA demethylases, histone acetyltransferases, or histone deacetylases, and the like).

Spacer Sequence

The spacer sequence hybridizes to a sequence in a target nucleic acid of interest. The spacer of a genome-targeting nucleic acid interacts with a target nucleic acid in a sequence-specific manner via hybridization (i.e., base pairing). The nucleotide sequence of the spacer thus varies depending on the sequence of the target nucleic acid of interest.

In a CRISPR/Cas system herein, the spacer sequence is designed to hybridize to a target nucleic acid that is located 5' of a PAM of a Cas endonuclease used in the system. The spacer can perfectly match the target sequence or can have mismatches. Each Cas endonuclease has a particular PAM sequence that it recognizes in a target DNA. For example, Cas9 from *S. pyogenes* recognizes in a target nucleic acid a PAM that has the sequence 5'-NRG-3', where R has either A or G, where N is any nucleotide and N is immediately 3' of the target nucleic acid sequence targeted by the spacer sequence.

In some embodiments, the target nucleic acid sequence has 20 nucleotides. In some embodiments, the target nucleic acid has less than 20 nucleotides but not zero. In some embodiments, the target nucleic acid has more than 20 nucleotides. In some embodiments, the target nucleic acid has at least: 5, 10, 15, 16, 17, 18, 19, 20, 21, 22, 23, 24, 25, 30, or more nucleotides. In some embodiments, the target nucleic acid has at most: 5, 10, 15, 16, 17, 18, 19, 20, 21, 22, 23, 24, 25, 30, or more nucleotides. In some embodiments, the target nucleic acid sequence has 20 bases immediately 5' of the first nucleotide of the PAM. In some embodiments, the PAM sequence used in the compositions and methods of the present disclosure as a sequence recognized by *S. pyogenes* Cas9 is NGG.

In some embodiments, the spacer sequence that hybridizes to the target nucleic acid has a length of at least or at least about 6 nucleotides (nt). The spacer sequence can be at least or at least about 6 nt, at or about 10 nt, at or about 15 nt, at or about 18 nt, at or about 19 nt, at or about 20 nt, at or about 25 nt, at or about 30 nt, at or about 35 nt or at or about 40 nt, from or from about 6 nt to or to about 80 nt, from or from about 6 nt to or to about 50 nt, from or from about 6 nt to or to about 45 nt, from or from about 6 nt to or to about 40 nt, from or from about 6 nt to or to about 35 nt, from or from about 6 nt to or to about 30 nt, from or from about 6 nt to or to about 25 nt, from or from about 6 nt to or to about 20 nt, from or from about 6 nt to or to about 19 nt, from or from about 10 nt to or to about 50 nt, from or from about 10 nt to or to about 45 nt, from or from about 10 nt to or to about 40 nt, from or from about 10 nt to or to about 35 nt, from or from about 10 nt to or to about 30 nt, from or from about 10 nt to or to about 25 nt, from or from about 10 nt to or to about 20 nt, from or from about 10 nt to or to about 19 nt, from or from about 19 nt to or to about 25 nt, from or from about 19 nt to or to about 30 nt, from or from about 19 nt to or to about 35 nt, from or from about 19 nt to or to about 40 nt, from or from about 19 nt to or to about 45 nt, from or from about 19 nt to or to about 50 nt, from or from about 19 nt to or to about 60 nt, from or from about 20 nt to or to about 25 nt, from or from about 20 nt to or to about 30 nt, from or from about 20 nt to or to about 35 nt, from or from about 20 nt to or to about 40 nt, from or from about 20 nt to or to about 45 nt, from or from about 20 nt to or to about 50 nt, or from or from about 20 nt to or to about 60 nt. In some embodiments, the spacer sequence has 20 nucleotides. In some embodiments, the spacer has 19 nucleotides. In some embodiments, the spacer has 18 nucleotides. In some embodiments, the spacer has 17 nucleotides. In some embodiments, the spacer has 16 nucleotides. In some embodiments, the spacer has 15 nucleotides.

In some embodiments, the percent complementarity between the spacer sequence and the target nucleic acid is at least or at least about 30%, at least or at least about 40%, at least or at least about 50%, at least or at least about 60%, at least or at least about 65%, at least or at least about 70%, at least or at least about 75%, at least or at least about 80%, at least or at least about 85%, at least or at least about 90%, at least or at least about 95%, at least or at least about 97%, at least or at least about 98%, at least or at least about 99%, or 100%. In some embodiments, the percent complementarity between the spacer sequence and the target nucleic acid is at most or at most about 30%, at most or at most about 40%, at most or at most about 50%, at most or at most about 60%, at most or at most about 65%, at most or at most about 70%, at most or at most about 75%, at most or at most about 80%, at most or at most about 85%, at most or at most about 90%, at most or at most about 95%, at most or at most about 97%, at most or at most about 98%, at most or at most about 99%, or 100%. In some embodiments, the percent complementarity between the spacer sequence and the target nucleic acid is 100% over the six contiguous 5'-most nucleotides of the target sequence of the complementary strand of the target nucleic acid. In some embodiments, the percent complementarity between the spacer sequence and the target nucleic acid is at least 60% over or over about 20 contiguous nucleotides. In some embodiments, the length of the spacer sequence and the target nucleic acid can differ by 1 to 6 nucleotides, which can be thought of as a bulge or bulges.

In some embodiments, the spacer sequence is designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion, or deletion), methylation status, presence of SNPs, and the like.

Minimum CRISPR Repeat Sequence

In some embodiments, a minimum CRISPR repeat sequence is a sequence with at least or at least about 30%, at or about 40%, at or about 50%, at or about 60%, at or about 65%, at or about 70%, at or about 75%, at or about 80%, at or about 85%, at or about 90%, at or about 95%, or 100% sequence identity to a reference CRISPR repeat sequence (e.g., crRNA from *S. pyogenes*).

In some embodiments, a minimum CRISPR repeat sequence has nucleotides that can hybridize to a minimum tracrRNA sequence in a cell. The minimum CRISPR repeat sequence and a minimum tracrRNA sequence form a duplex, i.e., a base-paired double-stranded structure. Together, the minimum CRISPR repeat sequence and the minimum tracrRNA sequence bind to the site-directed polypeptide. At least a part of the minimum CRISPR repeat sequence hybridizes to the minimum tracrRNA sequence. In some embodiments, at least a part of the minimum CRISPR repeat sequence has at least or at least about 30%, at or about 40%, at or about 50%, at or about 60%, at or about 65%, at or about 70%, at or about 75%, at or about 80%, at or about 85%, at or about 90%, at or about 95%, or 100% complementarity to the minimum tracrRNA sequence. In some embodiments, at least a part of the minimum CRISPR repeat sequence has at most or at most about 30%, at or about 40%, at or about 50%, at or about 60%, at or about 65%, at or about 70%, at or about 75%, at or about 80%, at or about 85%, at or about 90%, at or about 95%, or 100% complementarity to the minimum tracrRNA sequence.

The minimum CRISPR repeat sequence can have a length from or from about 7 nucleotides to or to about 100 nucleotides. For example, the length of the minimum CRISPR repeat sequence is from or from about 7 nucleotides (nt) to or to about 50 nt, from or from about 7 nt to or to about 40 nt, from or from about 7 nt to or to about 30 nt, from or from about 7 nt to or to about 25 nt, from or from about 7 nt to or to about 20 nt, from or from about 7 nt to or to about 15 nt, from or from about 8 nt to or to about 40 nt, from or from about 8 nt to or to about 30 nt, from or from about 8 nt to or to about 25 nt, from or from about 8 nt to or to about 20 nt, from or from about 8 nt to or to about 15 nt, from or from about 15 nt to or to about 100 nt, from or from about 15 nt to or to about 80 nt, from or from about 15 nt to or to about 50 nt, from or from about 15 nt to or to about 40 nt, from or from about 15 nt to or to about 30 nt, or from or from about 15 nt to or to about 25 nt. In some embodiments, the minimum CRISPR repeat sequence is approximately 9 nucleotides in length. In some embodiments, the minimum CRISPR repeat sequence is approximately 12 nucleotides in length.

In some embodiments, the minimum CRISPR repeat sequence is at least or at least about 60% identical to a reference minimum CRISPR repeat sequence (e.g., wild-type crRNA from *S. pyogenes*) over a stretch of at least 6, 7, or 8 contiguous nucleotides. For example, the minimum CRISPR repeat sequence is at least or at least about 65% identical, at least or at least about 70% identical, at least or at least about 75% identical, at least or at least about 80% identical, at least or at least about 85% identical, at least or at least about 90% identical, at least or at least about 95% identical, at least or at least about 98% identical, at least or at least about 99% identical or 100% identical to a reference minimum CRISPR repeat sequence over a stretch of at least 6, 7, or 8 contiguous nucleotides.

Minimum tracrRNA Sequence

In some embodiments, a minimum tracrRNA sequence is a sequence with at least or at least about 30%, at or about 40%, at or about 50%, at or about 60%, at or about 65%, at or about 70%, at or about 75%, at or about 80%, at or about 85%, at or about 90%, at or about 95%, or 100% sequence identity to a reference tracrRNA sequence (e.g., wild type tracrRNA from *S. pyogenes*).

In some embodiments, a minimum tracrRNA sequence has nucleotides that hybridize to a minimum CRISPR repeat sequence in a cell. A minimum tracrRNA sequence and a minimum CRISPR repeat sequence form a duplex, i.e., a base-paired double-stranded structure. Together, the minimum tracrRNA sequence and the minimum CRISPR repeat bind to a site-directed polypeptide. At least a part of the minimum tracrRNA sequence can hybridize to the minimum CRISPR repeat sequence. In some embodiments, the minimum tracrRNA sequence is at least or at least about 30%, at or about 40%, at or about 50%, at or about 60%, at or about 65%, at or about 70%, at or about 75%, at or about 80%, at or about 85%, at or about 90%, at or about 95%, or 100% complementarity to the minimum CRISPR repeat sequence.

The minimum tracrRNA sequence can have a length from or from about 7 nucleotides to or to about 100 nucleotides. For example, the minimum tracrRNA sequence can be from or from about 7 nucleotides (nt) to or to about 50 nt, from or from about 7 nt to or to about 40 nt, from or from about 7 nt to or to about 30 nt, from or from about 7 nt to or to about 25 nt, from or from about 7 nt to or to about 20 nt, from or from about 7 nt to or to about 15 nt, from or from about 8 nt to or to about 40 nt, from or from about 8 nt to or to about 30 nt, from or from about 8 nt to or to about 25 nt, from or from about 8 nt to or to about 20 nt, from or from about 8 nt to or to about 15 nt, from or from about 15 nt to or to about 100 nt, from or from about 15 nt to or to about 80 nt, from or from about 15 nt to or to about 50 nt, from or from about 15 nt to or to about 40 nt, from or from about 15 nt to or to about 30 nt or from or from about 15 nt to or to about 25 nt long. In some embodiments, the minimum tracrRNA sequence is approximately 9 nucleotides in length. In some embodiments, the minimum tracrRNA sequence is approximately 12 nucleotides. In some embodiments, the minimum tracrRNA consists of tracrRNA nt 23-48 described in Jinek, M. et al. (2012). *Science,* 337(6096):816-821.

In some embodiments, the minimum tracrRNA sequence is at least or at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence is at least or at least about 65% identical, at or about 70% identical, at or about 75% identical, at or about 80% identical, at or about 85% identical, at or about 90% identical, at or about 95% identical, at or about 98% identical, at or about 99% identical or 100% identical to a reference minimum tracrRNA sequence over a stretch of at least 6, 7, or 8 contiguous nucleotides.

In some embodiments, the duplex between the minimum CRISPR RNA and the minimum tracrRNA has a double helix. In some embodiments, the duplex between the minimum CRISPR RNA and the minimum tracrRNA has at least or at least about 1, 2, 3, 4, 5, 6, 7, 8, 9, or 10 or more nucleotides. In some embodiments, the duplex between the minimum CRISPR RNA and the minimum tracrRNA has at most or at most about 1, 2, 3, 4, 5, 6, 7, 8, 9, or 10 or more nucleotides.

In some embodiments, the duplex has a mismatch (i.e., the two strands of the duplex are not 100% complementary). In some embodiments, the duplex has at least or at least about 1, 2, 3, 4, or 5 or mismatches. In some embodiments, the duplex has at most or at most about 1, 2, 3, 4, or 5 or mismatches. In some embodiments, the duplex has no more than 2 mismatches.

Bulges

In some embodiments, there is a "bulge" in the duplex between the minimum CRISPR RNA and the minimum tracrRNA. The bulge is an unpaired region of nucleotides within the duplex. In some embodiments, the bulge contributes to the binding of the duplex to the site-directed polypeptide. A bulge has, on one side of the duplex, an unpaired 5'-XXXY-3' where X is any purine and Y has a nucleotide that can form a wobble pair with a nucleotide on the opposite strand, and an unpaired nucleotide region on the other side of the duplex. The number of unpaired nucleotides on the two sides of the duplex can be different.

In one example, the bulge has an unpaired purine (e.g., adenine) on the minimum CRISPR repeat strand of the bulge. In some embodiments, a bulge has an unpaired 5'-AAGY-3' of the minimum tracrRNA sequence strand of the bulge, where Y has a nucleotide that can form a wobble pairing with a nucleotide on the minimum CRISPR repeat strand.

In some embodiments, a bulge on the minimum CRISPR repeat side of the duplex has at least 1, 2, 3, 4, or 5 or more unpaired nucleotides. In some embodiments, a bulge on the minimum CRISPR repeat side of the duplex has at most 1, 2, 3, 4, or 5 or more unpaired nucleotides. In some embodiments, a bulge on the minimum CRISPR repeat side of the duplex has 1 unpaired nucleotide.

In some embodiments, a bulge on the minimum tracrRNA sequence side of the duplex has at least 1, 2, 3, 4, 5, 6, 7, 8, 9, or 10 or more unpaired nucleotides. In some embodiments, a bulge on the minimum tracrRNA sequence side of the duplex has at most 1, 2, 3, 4, 5, 6, 7, 8, 9, or 10 or more unpaired nucleotides. In some embodiments, a bulge on a second side of the duplex (e.g., the minimum tracrRNA sequence side of the duplex) has 4 unpaired nucleotides.

In some embodiments, a bulge has at least one wobble pairing. In some embodiments, a bulge has at most one wobble pairing. In some embodiments, a bulge has at least one purine nucleotide. In some embodiments, a bulge has at least 3 purine nucleotides. In some embodiments, a bulge sequence has at least 5 purine nucleotides. In some embodiments, a bulge sequence has at least one guanine nucleotide. In some embodiments, a bulge sequence has at least one adenine nucleotide.

Hairpins

In various embodiments, one or more hairpins are located 3' to the minimum tracrRNA in the 3' tracrRNA sequence.

In some embodiments, the hairpin starts at least or at least about 1, 2, 3, 4, 5, 6, 7, 8, 9, 10, 15, or 20 or more nucleotides 3' from the last paired nucleotide in the minimum CRISPR repeat and minimum tracrRNA sequence duplex. In some embodiments, the hairpin can start at most or at most about 1, 2, 3, 4, 5, 6, 7, 8, 9, or 10 or more nucleotides 3' of the last paired nucleotide in the minimum CRISPR repeat and minimum tracrRNA sequence duplex.

In some embodiments, a hairpin has at least or at least about 1, 2, 3, 4, 5, 6, 7, 8, 9, 10, 15, or 20 or more consecutive nucleotides. In some embodiments, a hairpin has at most or at most about 1, 2, 3, 4, 5, 6, 7, 8, 9, 10, 15, or more consecutive nucleotides.

In some embodiments, a hairpin has a CC di-nucleotide (i.e., two consecutive cytosine nucleotides).

In some embodiments, a hairpin has duplexed nucleotides (e.g., nucleotides in a hairpin, hybridized together). For example, a hairpin has a CC di-nucleotide that is hybridized to a GG di-nucleotide in a hairpin duplex of the 3' tracrRNA sequence.

One or more of the hairpins can interact with guide RNA-interacting regions of a site-directed polypeptide.

In some embodiments there are two or more hairpins, and in some embodiments there are three or more hairpins.

3' tracrRNA Sequence

In some embodiments, a 3' tracrRNA sequence has a sequence with at least or at least about 30%, at or about 40%, at or about 50%, at or about 60%, at or about 65%, at or about 70%, at or about 75%, at or about 80%, at or about 85%, at or about 90%, at or about 95%, or 100% sequence identity to a reference tracrRNA sequence (e.g., a tracrRNA from *S. pyogenes*).

In some embodiments, the 3' tracrRNA sequence has a length from or from about 6 nucleotides to or to about 100 nucleotides. For example, the 3' tracrRNA sequence can have a length from or from about 6 nucleotides (nt) to or to about 50 nt, from or from about 6 nt to or to about 40 nt, from or from about 6 nt to or to about 30 nt, from or from about 6 nt to or to about 25 nt, from or from about 6 nt to or to about 20 nt, from or from about 6 nt to or to about 15 nt, from or from about 8 nt to or to about 40 nt, from or from about 8 nt to or to about 30 nt, from or from about 8 nt to or to about 25 nt, from or from about 8 nt to or to about 20 nt, from or from about 8 nt to or to about 15 nt, from or from about 15 nt to or to about 100 nt, from or from about 15 nt to or to about 80 nt, from or from about 15 nt to or to about 50 nt, from or from about 15 nt to or to about 40 nt, from or from about 15 nt to or to about 30 nt, or from or from about 15 nt to or to about 25 nt. In some embodiments, the 3' tracrRNA sequence has a length of approximately 14 nucleotides.

In some embodiments, the 3' tracrRNA sequence is at least or at least about 60% identical to a reference 3' tracrRNA sequence (e.g., wild type 3' tracrRNA sequence from *S. pyogenes*) over a stretch of at least 6, 7, or 8 contiguous nucleotides. For example, the 3' tracrRNA sequence is at least or at least about 60% identical, at or about 65% identical, at or about 70% identical, at or about 75% identical, at or about 80% identical, at or about 85% identical, at or about 90% identical, at or about 95% identical, at or about 98% identical, at or about 99% identical, or 100% identical, to a reference 3' tracrRNA sequence (e.g., wild type 3' tracrRNA sequence from *S. pyogenes*) over a stretch of at least 6, 7, or 8 contiguous nucleotides.

In some embodiments, a 3' tracrRNA sequence has more than one duplexed region (e.g., hairpin, hybridized region). In some embodiments, a 3' tracrRNA sequence has two duplexed regions.

In some embodiments, the 3' tracrRNA sequence has a stem loop structure. In some embodiments, a stem loop structure in the 3' tracrRNA has at least 1, 2, 3, 4, 5, 6, 7, 8, 9, 10, 15, or 20 or more nucleotides. In some embodiments, the stem loop structure in the 3' tracrRNA has at most 1, 2, 3, 4, 5, 6, 7, 8, 9, or 10 or more nucleotides. In some embodiments, the stem loop structure has a functional moiety. For example, the stem loop structure can have an aptamer, a ribozyme, a protein-interacting hairpin, a CRISPR array, an intron, or an exon. In some embodiments, the stem loop structure has at least or at least about 1, 2, 3, 4, or 5 or more functional moieties. In some embodiments, the stem loop structure has at most or at most about 1, 2, 3, 4, or 5 or more functional moieties.

In some embodiments, the hairpin in the 3' tracrRNA sequence has a P-domain. In some embodiments, the P-domain has a double-stranded region in the hairpin.

tracrRNA Extension Sequence

In some embodiments, a tracrRNA extension sequence can be provided whether the tracrRNA is in the context of single-molecule guides or double-molecule guides. In some embodiments, a tracrRNA extension sequence has a length from or from about 1 nucleotide to or to about 400 nucleotides. In some embodiments, a tracrRNA extension sequence has a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. In some embodiments, a tracrRNA extension sequence has a length from or from about 20 to or to about 5000 or more nucleotides. In some embodiments, a tracrRNA extension sequence has a length of more than 1000 nucleotides. In some embodiments, a tracrRNA extension sequence has a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, or more nucleotides but not zero. In some embodiments, a tracrRNA extension sequence can have a length of less than 1000 nucleotides but not zero. In some embodiments, a tracrRNA extension sequence has less than 10 nucleotides in length but not zero. In some embodiments, a tracrRNA extension sequence is 10-30 nucleotides in length. In some embodiments, tracrRNA extension sequence is 30-70 nucleotides in length.

In some embodiments, the tracrRNA extension sequence has a functional moiety (e.g., a stability control sequence, ribozyme, or endoribonuclease binding sequence). In some embodiments, the functional moiety has a transcriptional terminator segment (e.g., a transcription termination sequence). In some embodiments, the functional moiety has a total length from or from about 10 nucleotides (nt) to or to about 100 nucleotides, from or from about 10 nt to or to about 20 nt, from or from about 20 nt to or to about 30 nt, from or from about 30 nt to or to about 40 nt, from or from about 40 nt to or to about 50 nt, from or from about 50 nt to or to about 60 nt, from or from about 60 nt to or to about 70 nt, from or from about 70 nt to or to about 80 nt, from or from about 80 nt to or to about 90 nt, or from or from about 90 nt to or to about 100 nt, from or from about 15 nt to or to about 80 nt, from or from about 15 nt to or to about 50 nt, from or from about 15 nt to or to about 40 nt, from or from about 15 nt to or to about 30 nt, or from or from about 15 nt to or to about 25 nt. In some embodiments, the functional moiety functions in a eukaryotic cell. In some embodiments, the functional moiety functions in a prokaryotic cell. In some embodiments, the functional moiety functions in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), or a modification or sequence that provides a binding site for proteins (e.g., proteins that act on DNA, including transcriptional activators, transcriptional repressors, DNA methyltransferases, DNA demethylases, histone acetyltransferases, or histone deacetylases, and the like). In some embodiments, a tracrRNA extension sequence has a primer binding site or a molecular index (e.g., barcode sequence). In some embodiments, the tracrRNA extension sequence has one or more affinity tags.

Single-Molecule Guide Linker Sequence

In some embodiments, the linker sequence of a single-molecule guide nucleic acid has a length from or from about 3 nucleotides to or to about 100 nucleotides. In Jinek, M. et al. (2012). *Science,* 337(6096):816-821, for example, a simple 4 nucleotide "tetraloop" (-GAAA-) was used. An illustrative linker has a length from or from about 3 nucleotides (nt) to or to about 90 nt, from or from about 3 nt to or to about 80 nt, from or from about 3 nt to or to about 70 nt, from or from about 3 nt to or to about 60 nt, from or from about 3 nt to or to about 50 nt, from or from about 3 nt to or to about 40 nt, from or from about 3 nt to or to about 30 nt, from or from about 3 nt to or to about 20 nt, from or from about 3 nt to or to about 10 nt. For example, the linker can have a length from or from about 3 nt to or to about 5 nt, from or from about 5 nt to or to about 10 nt, from or from about 10 nt to or to about 15 nt, from or from about 15 nt to or to about 20 nt, from or from about 20 nt to or to about 25 nt, from or from about 25 nt to or to about 30 nt, from or from about 30 nt to or to about 35 nt, from or from about 35 nt to or to about 40 nt, from or from about 40 nt to or to about 50 nt, from or from about 50 nt to or to about 60 nt, from or from about 60 nt to or to about 70 nt, from or from about 70 nt to or to about 80 nt, from or from about 80 nt to or to about 90 nt, or from or from about 90 nt to or to about 100 nt. In some embodiments, the linker of a single-molecule guide nucleic acid is between 4 and 40 nucleotides. In some embodiments, a linker is at least or at least about 100, 500, 1000, 1500, 2000, 2500, 3000, 3500, 4000, 4500, 5000, 5500, 6000, 6500, or 7000 or more nucleotides. In some embodiments, a linker is at most or at most about 100, 500, 1000, 1500, 2000, 2500, 3000, 3500, 4000, 4500, 5000, 5500, 6000, 6500, or 7000 or more nucleotides.

Linkers can have any of a variety of sequences, although in some embodiments, the linker will not have sequences that have extensive regions of homology with other portions of the guide RNA, which might cause intramolecular binding that could interfere with other functional regions of the guide. In Jinek, M. et al. (2012). *Science,* 337(6096):816-821, a simple 4 nucleotide sequence -GAAA- was used, but numerous other sequences, including longer sequences can likewise be used.

In some embodiments, the linker sequence has a functional moiety. For example, the linker sequence can have one or more features, including an aptamer, a ribozyme, a protein-interacting hairpin, a protein binding site, a CRISPR array, an intron, or an exon. In some embodiments, the linker sequence has at least or at least about 1, 2, 3, 4, or 5 or more functional moieties. In some embodiments, the linker sequence has at most or at most about 1, 2, 3, 4, or 5 or more functional moieties.

In some embodiments, a genomic location targeted by gRNAs in accordance with the preset disclosure can be at, within, or near the FOXP3 gene in a genome, e.g., a human genome. Exemplary guide RNAs targeting such locations include the spacer sequences of SEQ ID NOs: 1-7, 15-20, and 27-29. For example, a gRNA including a spacer sequence from SEQ ID NO: 1 can have a spacer sequence including i) the sequence of SEQ ID NO: 1, ii) the sequence from position 2 to position 20 of SEQ ID NO: 1, iii) the sequence from position 3 to position 20 of SEQ ID NO: 1, iv) the sequence from position 4 to position 20 of SEQ ID NO: 1, and so forth. As is understood by the person of ordinary skill in the art, each guide RNA is designed to include a spacer sequence complementary to its genomic target sequence. For example, each of the spacer sequences of SEQ ID NOs: 1-7, 15-20, and 27-29 can be put into a single RNA chimera or a crRNA (along with a corresponding tracrRNA). See Jinek, M. et al. (2012). *Science,* 337 (6096):816-821, and Deltcheva, E. et al. (2011). *Nature,* 471:602-607.

Donor DNA or Donor Template

Site-directed polypeptides, such as a DNA endonuclease, can introduce double-strand breaks or single-strand breaks in nucleic acids, e.g., genomic DNA. The double-strand break can stimulate a cell's endogenous DNA-repair pathways (e.g., homology-dependent repair (HDR) or non-homologous end joining or alternative non-homologous end joining (A-NHEJ) or microhomology-mediated end joining (MMEJ). NHEJ can repair cleaved target nucleic acid without the need for a homologous template. This can sometimes result in small deletions or insertions (indels) in the target nucleic acid at the site of cleavage and can lead to disruption or alteration of gene expression. HDR, which is also known as homologous recombination (HR) can occur when a homologous repair template, or donor, is available.

The homologous donor template has sequences that are homologous to sequences flanking the target nucleic acid cleavage site. The sister chromatid is generally used by the cell as the repair template. However, for the purposes of genome editing, the repair template is often supplied as an exogenous nucleic acid, such as a plasmid, duplex oligonucleotide, single-strand oligonucleotide, double-stranded oligonucleotide, or viral nucleic acid. With exogenous donor templates, it is common to introduce an additional nucleic acid sequence (such as a transgene) or modification (such as a single or multiple base change or a deletion) between the flanking regions of homology so that the additional or altered nucleic acid sequence also becomes incorporated into the target locus. MMEJ results in a genetic outcome that is similar to NHEJ in that small deletions and insertions can occur at the cleavage site. MMEJ makes use of homologous sequences of a few base pairs flanking the cleavage site to drive a favored end-joining DNA repair outcome. In some instances, it can be possible to predict likely repair outcomes based on analysis of potential microhomologies in the nuclease target regions.

Thus, in some cases, homologous recombination is used to insert an exogenous polynucleotide sequence into the target nucleic acid cleavage site. An exogenous polynucleotide sequence is termed a donor polynucleotide (or donor or donor sequence or polynucleotide donor template) herein. In some embodiments, the donor polynucleotide, a portion of the donor polynucleotide, a copy of the donor polynucleotide, or a portion of a copy of the donor polynucleotide is inserted into the target nucleic acid cleavage site. In some embodiments, the donor polynucleotide is an exogenous polynucleotide sequence, i.e., a sequence that does not naturally occur at the target nucleic acid cleavage site.

When an exogenous DNA molecule is supplied in sufficient concentration inside the nucleus of a cell in which the double-strand break occurs, the exogenous DNA can be inserted at the double-strand break during the NHEJ repair process and thus become a permanent addition to the genome. These exogenous DNA molecules are referred to as donor templates in some embodiments. If the donor template contains a coding sequence for a gene of interest such as a FOXP3 gene optionally together with relevant regulatory sequences such as promoters, enhancers, polyA sequences and/or splice acceptor sequences (also referred to herein as a "donor cassette"), the gene of interest can be expressed from the integrated copy in the genome resulting in permanent expression for the life of the cell. Moreover, the integrated copy of the donor DNA template can be transmitted to the daughter cells when the cell divides.

In the presence of sufficient concentrations of a donor DNA template that contains flanking DNA sequences with homology to the DNA sequence either side of the double-strand break (referred to as homology arms), the donor DNA template can be integrated via the HDR pathway. The homology arms act as substrates for homologous recombination between the donor template and the sequences either side of the double-strand break. This can result in an error-free insertion of the donor template in which the sequences either side of the double-strand break are not altered from that in the unmodified genome.

Supplied donors for editing by HDR vary markedly but generally contain the intended sequence with small or large flanking homology arms to allow annealing to the genomic DNA. The homology regions flanking the introduced genetic changes can be 30 bp or smaller, or as large as a multi-kilobase cassette that can contain promoters, cDNAs, etc. Both single-stranded and double-stranded oligonucleotide donors can be used. These oligonucleotides range in size from less than 100 nt to over many kb, though longer ssDNA can also be generated and used. Double-stranded donors are often used, including PCR amplicons, plasmids, and mini-circles. In general, it has been found that an AAV vector is a very effective means of delivery of a donor template, though the packaging limits for individual donors is <5 kb. Active transcription of the donor increased HDR three-fold, indicating the inclusion of promoter can increase conversion. Conversely, CpG methylation of the donor can decrease gene expression and In some embodiments, the donor DNA can be supplied with the nuclease or independently by a variety of different methods, for example by transfection, nanoparticle, micro-injection, or viral transduction. A range of tethering options can be used to increase the availability of the donors for HDR in some embodiments. Examples include attaching the donor to the nuclease, attaching to DNA binding proteins that bind nearby, or attaching to proteins that are involved in DNA end binding or repair.

In addition to genome editing by NHEJ or HDR, site-specific gene insertions can be conducted that use both the NHEJ pathway and HR. A combination approach can be applicable in certain settings, possibly including intron/exon borders. NHEJ can prove effective for ligation in the intron, while the error-free HDR can be better suited in the coding region.

In some embodiments, an exogenous sequence that is intended to be inserted into a genome is a nucleotide sequence encoding a FOXP3 or a functional derivative thereof. The functional derivative of a FOXP3 can include a derivative of the FOXP3 that has a substantial activity of a wild-type FOXP3, such as the wild-type human FOXP3, e.g., at least or at least about 30%, at or about 40%, at or about 50%, at or about 60%, at or about 70%, at or about 80%, at or about 90%, at or about 95% or at or about 100% of the activity that the wild-type FOXP3 exhibits. In some embodiments, the functional derivative of a FOXP3 can have at least or at least about 30%, at or about 40%, at or about 50%, at or about 60%, at or about 70%, at or about 80%, at or about 85%, at or about 90%, at or about 95%, at or about 96%, at or about 97%, at or about 98% or at or about 99% amino acid sequence identity to the FOXP3, e.g., the wild-type FOXP3. In some embodiments, one having ordinary skill in the art can use a number of methods known in the field to test the functionality or activity of a compound, e.g., a peptide or protein. The functional derivative of the FOXP3 can also include any fragment of the wild-type FOXP3 or fragment of a modified FOXP3 that has conservative modification on one or more of amino acid residues in the full length, wild-type FOXP3. Thus, in some embodiments, a nucleic acid sequence encoding a functional derivative of a FOXP3 can have at least or at least about 30%, at or about 40%, at or about 50%, at or about 60%, at or about 70%, at or about 80%, at or about 85%, at or about 90%, at or about 95%, at or about 96%, at or about 97%, at or about 98% or at or about 99% nucleic acid sequence identity to a nucleic acid sequence encoding the FOXP3, e.g., the wild-type FOXP3. In some embodiments, the FOXP3 is human wild-type FOXP3.

In some embodiments where the insertion of a nucleic acid encoding a FOXP3 or a functional derivative thereof is concerned, a cDNA of the FOXP3 gene or a functional derivative thereof can be inserted into a genome of a subject having a defective FOXP3 gene or its regulatory sequences. In such a case, a donor DNA or donor template can be an expression cassette or vector construct having a sequence encoding the FOXP3 or a functional derivative thereof, e.g., a cDNA sequence.

In some embodiments, according to any of the donor templates described herein comprising a donor cassette, the donor cassette is flanked on one or both sides by a gRNA target site. For example, such a donor template may comprise a donor cassette with a gRNA target site 5' of the donor cassette and/or a gRNA target site 3' of the donor cassette. In some embodiments, the donor template comprises a donor cassette with a gRNA target site 5' of the donor cassette. In some embodiments, the donor template comprises a donor cassette with a gRNA target site 3' of the donor cassette. In some embodiments, the donor template comprises a donor cassette with a gRNA target site 5' of the donor cassette and a gRNA target site 3' of the donor cassette. In some embodiments, the donor template comprises a donor cassette with a gRNA target site 5' of the donor cassette and a gRNA target site 3' of the donor cassette, and the two gRNA target sites comprise the same sequence. In some embodiments, the donor template comprises at least one gRNA target site, and the at least one gRNA target site in the donor template comprises the same sequence as a gRNA target site in a target locus into which the donor cassette of the donor template is to be integrated. In some embodiments, the donor template comprises at least one gRNA target site, and the at least one gRNA target site in the donor template comprises the reverse complement of a gRNA target site in a target locus into which the donor cassette of the donor template is to be integrated. In some embodiments, the donor template comprises a donor cassette with a gRNA target site 5' of the donor cassette and a gRNA target site 3' of the donor cassette, and the two gRNA target sites in the donor template comprises the same sequence as a gRNA target site in a target locus into which the donor cassette of the donor template is to be integrated. In some embodiments, the donor template comprises a donor cassette with a gRNA target site 5' of the donor cassette and a gRNA target site 3' of the donor cassette, and the two gRNA target sites in the donor template comprises the reverse complement of a gRNA target site in a target locus into which the donor cassette of the donor template is to be integrated.

In some embodiments, provided herein is a donor template comprising a nucleotide sequence encoding a FOXP3 or a functional derivative thereof for targeted integration into a FOXP3 gene, wherein the donor template comprises, from 5' to 3', i) a first gRNA target site; ii) a splice acceptor; iii) the nucleotide sequence encoding a FOXP3 or a functional derivative thereof; and iv) a polyadenylation signal. In some embodiments, the donor template further comprises a second gRNA target site downstream of the iv) polyadenylation signal. In some embodiments, the first gRNA target site and the second gRNA target site are the same. In some embodiments, the donor template further comprises a polynucleotide spacer between the i) first gRNA target site and the ii) splice acceptor. In some embodiments, the polynucleotide spacer is 18 nucleotides in length. In some embodiments, the donor template is flanked on one side by a first AAV ITR and/or flanked on the other side by a second AAV ITR. In some embodiments, the first AAV ITR is an AAV2 ITR and/or the second AAV ITR is an AAV2 ITR. In some embodiments, the FOXP3 is human wild-type FOXP3.

Nucleic Acid Encoding a Site-Directed Polypeptide or DNA Endonuclease

In some embodiments, the methods of genome edition and compositions therefore can use a nucleic acid sequence (or oligonucleotide) encoding a site-directed polypeptide or DNA endonuclease. The nucleic acid sequence encoding the site-directed polypeptide can be DNA or RNA. If the nucleic acid sequence encoding the site-directed polypeptide is RNA, it can be covalently linked to a gRNA sequence or exist as a separate sequence. In some embodiments, a peptide sequence of the site-directed polypeptide or DNA endonuclease can be used instead of the nucleic acid sequence thereof.

Vectors

In another aspect, the present disclosure provides a nucleic acid having a nucleotide sequence encoding a genome-targeting nucleic acid of the disclosure, a site-directed polypeptide of the disclosure, and/or any nucleic acid or proteinaceous molecule necessary to carry out the embodiments of the methods of the disclosure. In some embodiments, such a nucleic acid is a vector (e.g., a recombinant expression vector).

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, or vectors derived from retroviruses such as Rous Sarcoma Virus, Harvey Sarcoma Virus, avian leukosis virus, a lentivirus, human immunodeficiency virus, myeloproliferative sarcoma virus, or mammary tumor virus) or other recombinant vectors. Other vectors contemplated for eukaryotic target cells include, but are not limited to, the vectors pXT1, pSG5, pSVK3, pBPV, pMSG, or pSVLSV40 (Pharmacia). Additional vectors contemplated for eukaryotic target cells include, but are not limited to, the vectors pCTx-1, pCTx-2, or pCTx-3. Other vectors can be used so long as they are compatible with the host cell.

In some embodiments, a vector has one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. In some embodiments, the vector is a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early or late SV40, long terminal repeats (LTRs) from retrovirus, human elongation factor-1 promoter (EF1), a hybrid construct having the cytomegalovirus (CMV) enhancer fused to the chicken beta-actin promoter (CAG), murine stem cell virus promoter (MSCV), phosphoglycerate kinase-1 locus promoter (PGK), or mouse metallothionein-I.

For expressing small RNAs, including guide RNAs used in connection with Cas endonuclease, various promoters such as RNA polymerase III promoters, including for example U6 or H1, can be useful. Descriptions of and parameters for enhancing the use of such promoters are known in art, and additional information and approaches are regularly being described; see, e.g., Ma, H. et al. (2014). *Molecular Therapy—Nucleic Acids* 3, e161, doi:10.1038/mtna.2014.12.

The expression vector can also contain a ribosome binding site for translation initiation and a transcription terminator. The expression vector can also include appropriate sequences for amplifying expression. The expression vector can also include nucleotide sequences encoding non-native tags (e.g., histidine tag, hemagglutinin tag, or green fluorescent protein, etc.) that are fused to the site-directed polypeptide, thus resulting in a fusion protein. In some embodiments, a promoter is an inducible promoter (e.g., a heat shock promoter, tetracycline-regulated promoter, steroid-regulated promoter, metal-regulated promoter, or estrogen receptor-regulated promoter, etc.). In some embodiments, a promoter is a constitutive promoter (e.g., CMV promoter, or UBC promoter). In some embodiments, the promoter is a spatially restricted or temporally restricted promoter (e.g., a tissue specific promoter, or a cell type specific promoter, etc.). In some embodiments, a vector does not have a promoter for at least one gene to be expressed in a host cell if the gene is going to be expressed, after it is inserted into a genome, under an endogenous promoter present in the genome.

Site-Directed Polypeptide or DNA Endonuclease

Modifications of a target DNA due to NHEJ and/or HDR can lead to, for example, mutations, deletions, alterations, integrations, gene correction, gene replacement, gene tagging, transgene insertion, nucleotide deletion, gene disruption, translocations, and/or gene mutation. The process of integrating non-native nucleic acid into genomic DNA is an example of genome editing.

A site-directed polypeptide is a nuclease used in genome editing to cleave DNA. The site-directed polypeptide can be administered to a cell or a subject as either: one or more polypeptides, or one or more mRNAs encoding the polypeptide.

In the context of a CRISPR/Cas or CRISPR/Cpf1 system, the site-directed polypeptide can bind to a guide RNA that, in turn, specifies the site in the target DNA to which the polypeptide is directed. In embodiments of CRISPR/Cas or CRISPR/Cpf1 systems herein, the site-directed polypeptide is an endonuclease, such as a DNA endonuclease.

In some embodiments, a site-directed polypeptide has a plurality of nucleic acid-cleaving (e.g., nuclease) domains. Two or more nucleic acid-cleaving domains can be linked together via a linker. In some embodiments, the linker has a flexible linker. Linkers can have 1, 2, 3, 4, 5, 6, 7, 8, 9, 10, 11, 12, 13, 14, 15, 16, 17, 18, 19, 20, 21, 22, 23, 24, 25, 30, 35, 40, or more amino acids in length.

Naturally-occurring wild-type Cas9 enzymes have two nuclease domains, an HNH nuclease domain and a RuvC domain. Cas9 enzymes contemplated herein have an HNH or HNH-like nuclease domain, and/or a RuvC or RuvC-like nuclease domain.

HNH or HNH-like domains have a McrA-like fold. HNH or HNH-like domains has two antiparallel β-strands and an α-helix. HNH or HNH-like domains has a metal binding site (e.g., a divalent cation binding site). HNH or HNH-like domains can cleave one strand of a target nucleic acid (e.g., the complementary strand of the crRNA targeted strand).

RuvC or RuvC-like domains have an RNaseH or RNaseH-like fold. RuvC/RNaseH domains are involved in a diverse set of nucleic acid-based functions including acting on both RNA and DNA. The RNaseH domain has 5 β-strands surrounded by a plurality of a-helices. RuvC/RNaseH or RuvC/RNaseH-like domains have a metal binding site (e.g., a divalent cation binding site). RuvC/RNaseH or RuvC/RNaseH-like domains can cleave one strand of a target nucleic acid (e.g., the non-complementary strand of a double-stranded target DNA).

In some embodiments, the site-directed polypeptide has an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary site-directed polypeptide [e.g., Cas9 from *S. pyogenes*, US2014/0068797 Sequence ID No. 8 or Sapranauskas, R. et al. (2011). *Nucleic Acids Res,* 39(21): 9275-9282], and various other site-directed polypeptides).

In some embodiments, the site-directed polypeptide has an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to the nuclease domain of a wild-type exemplary site-directed polypeptide (e.g., Cas9 from *S. pyogenes*, supra).

In some embodiments, a site-directed polypeptide has at least 70, 75, 80, 85, 90, 95, 97, 99, or 100% identity to a wild-type site-directed polypeptide (e.g., Cas9 from *S. pyogenes*, supra) over 10 contiguous amino acids. In some embodiments, a site-directed polypeptide has at most: 70, 75, 80, 85, 90, 95, 97, 99, or 100% identity to a wild-type site-directed polypeptide (e.g., Cas9 from *S. pyogenes*, supra) over 10 contiguous amino acids. In some embodiments, a site-directed polypeptide has at least: 70, 75, 80, 85, 90, 95, 97, 99, or 100% identity to a wild-type site-directed polypeptide (e.g., Cas9 from *S. pyogenes*, supra) over 10 contiguous amino acids in an HNH nuclease domain of the site-directed polypeptide. In some embodiments, a site-directed polypeptide has at most: 70, 75, 80, 85, 90, 95, 97, 99, or 100% identity to a wild-type site-directed polypeptide (e.g., Cas9 from *S. pyogenes*, supra) over 10 contiguous amino acids in an HNH nuclease domain of the site-directed polypeptide. In some embodiments, a site-directed polypeptide has at least: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide. In some embodiments, a site-directed polypeptide has at most: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide.

In some embodiments, the site-directed polypeptide has a modified form of a wild-type exemplary site-directed polypeptide. The modified form of the wild-type exemplary site-directed polypeptide has a mutation that reduces the nucleic acid-cleaving activity of the site-directed polypeptide. In some embodiments, the modified form of the wild-type exemplary site-directed polypeptide has less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from *S. pyogenes*, supra) but not zero. The modified form of the site-directed polypeptide can also have no substantial nucleic acid-cleaving activity. When a site-directed polypeptide is a modified form that has no substantial nucleic acid-cleaving activity, it is referred to herein as "enzymatically inactive."

In some embodiments, the modified form of the site-directed polypeptide has a mutation such that it can induce a single-strand break (SSB) on a target nucleic acid (e.g., by cutting only one of the sugar-phosphate backbones of a double-strand target nucleic acid). In some embodiments, the mutation results in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from *S. pyogenes*, supra) but not zero. In some embodiments, the mutation results in one or more of the plurality of nucleic acid-cleaving domains retaining the ability to cleave the complementary strand of the target nucleic acid, but reducing its ability to cleave the non-complementary strand of the target nucleic acid. In some embodiments, the mutation results in one or more of the plurality of nucleic acid-cleaving domains retaining the ability to cleave the non-complementary strand of the target nucleic acid, but reducing its ability to cleave the complementary strand of the target nucleic acid. For example, residues in the wild-type exemplary *S. pyogenes* Cas9 polypeptide, such as Asp10, His840, Asn854, and Asn856, are mutated to inactivate one or more of the plurality of nucleic acid-cleaving domains (e.g., nuclease domains). In some embodiments, the residues to be mutated correspond to residues Asp10, His840, Asn854, and Asn856 in the wild-type exemplary *S. pyogenes* Cas9 polypeptide (e.g., as determined by sequence and/or structural alignment). Non-limiting examples of mutations include D10A, H840A, N854A, or N856A. One skilled in the art will recognize that mutations other than alanine substitutions are suitable.

In some embodiments, a D10A mutation is combined with one or more of H840A, N854A, or N856A mutations to produce a site-directed polypeptide substantially lacking DNA cleavage activity. In some embodiments, a H840A mutation is combined with one or more of D10A, N854A, or N856A mutations to produce a site-directed polypeptide substantially lacking DNA cleavage activity. In some embodiments, a N854A mutation is combined with one or more of H840A, D10A, or N856A mutations to produce a site-directed polypeptide substantially lacking DNA cleavage activity. In some embodiments, a N856A mutation is combined with one or more of H840A, N854A, or D10A mutations to produce a site-directed polypeptide substantially lacking DNA cleavage activity. Site-directed polypeptides that have one substantially inactive nuclease domain are referred to as "nickases".

In some embodiments, variants of RNA-guided endonucleases, for example Cas9, can be used to increase the specificity of CRISPR-mediated genome editing. Wild type Cas endonucleases are generally guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13 nt of homology, and thereby resulting in elevated potential for binding and double-strand nucleic acid cleavage by a CRISPR/Cas complex elsewhere in the target genome—also known as off-target cleavage. Because nickase variants of Cas endonucelases each only cut one strand, to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable the double-strand break to form. As described in the art, nickases can also be used to promote HDR versus NHEJ. HDR can be used to introduce selected changes into target sites in the genome through the use of specific donor sequences that effectively mediate the desired changes. Descriptions of various CRISPR/Cas systems for use in gene editing can be found, e.g., in International Patent Application no. WO2013/176772, and in Sander, J. D. et al. (2014). *Nature Biotechnology,* 32(4):347-355, and references cited therein.

In some embodiments, the site-directed polypeptide (e.g., variant, mutated, enzymatically inactive or conditionally enzymatically inactive site-directed polypeptide) targets nucleic acid. In some embodiments, the site-directed polypeptide (e.g., variant, mutated, enzymatically inactive or conditionally enzymatically inactive endoribonuclease) targets DNA. In some embodiments, the site-directed polypeptide (e.g., variant, mutated, enzymatically inactive or conditionally enzymatically inactive endoribonuclease) targets RNA.

In some embodiments, the site-directed polypeptide has one or more non-native sequences (e.g., the site-directed polypeptide is a fusion protein).

In some embodiments, the site-directed polypeptide has an amino acid sequence having at least 15% amino acid identity to a Cas endonuclease from a bacterium (e.g., *S. pyogenes*), a nucleic acid binding domain, and two nucleic acid cleaving domains (e.g., an HNH domain and a RuvC domain).

In some embodiments, the site-directed polypeptide has an amino acid sequence having at least 15% amino acid identity to a Cas endonuclease from a bacterium (e.g., *S. pyogenes*), and two nucleic acid cleaving domains (e.g., an HNH domain and a RuvC domain).

In some embodiments, the site-directed polypeptide has an amino acid sequence having at least 15% amino acid identity to a Cas endonuclease from a bacterium (e.g., *S. pyogenes*), and two nucleic acid cleaving domains, wherein one or both of the nucleic acid cleaving domains have at least 50% amino acid identity to a nuclease domain from a Cas endonuclease from a bacterium (e.g., *S. pyogenes*).

In some embodiments, the site-directed polypeptide has an amino acid sequence having at least 15% amino acid identity to a Cas endonuclease from a bacterium (e.g., *S. pyogenes*), two nucleic acid cleaving domains (e.g., an HNH domain and a RuvC domain), and non-native sequence (for example, a nuclear localization signal) or a linker linking the site-directed polypeptide to a non-native sequence.

In some embodiments, the site-directed polypeptide has an amino acid sequence having at least 15% amino acid identity to a Cas endonuclease from a bacterium (e.g., *S. pyogenes*), two nucleic acid cleaving domains (e.g., an HNH domain and a RuvC domain), wherein the site-directed polypeptide has a mutation in one or both of the nucleic acid cleaving domains that reduces the cleaving activity of the nuclease domains by at least 50%.

In some embodiments, the site-directed polypeptide has an amino acid sequence having at least 15% amino acid identity to a Cas endonuclease from a bacterium (e.g., *S. pyogenes*), and two nucleic acid cleaving domains (e.g., an HNH domain and a RuvC domain), wherein one of the nuclease domains has mutation of aspartic acid 10, and/or wherein one of the nuclease domains has mutation of histidine 840, and wherein the mutation reduces the cleaving activity of the nuclease domain(s) by at least 50%.

In some embodiments, the one or more site-directed polypeptides, e.g., DNA endonucleases, include two nickases that together effect one double-strand break at a specific locus in the genome, or four nickases that together effect two double-strand breaks at specific loci in the genome. Alternatively, one site-directed polypeptide, e.g., DNA endonuclease, affects one double-strand break at a specific locus in the genome.

In some embodiments, a polynucleotide encoding a site-directed polypeptide can be used to edit genome. In some of such embodiments, the polynucleotide encoding a site-directed polypeptide is codon-optimized according to methods known in the art for expression in the cell containing the target DNA of interest. For example, if the intended target nucleic acid is in a human cell, a human codon-optimized polynucleotide encoding a Cas endonuclease (e.g., a Cas9) is contemplated for use for producing the Cas endonuclease polypeptide.

The following provides some examples of site-directed polypeptides that can be used in various embodiments of the disclosures.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." When expressed, the repeats can form secondary hairpin structures (e.g., hairpins) and/or unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA has a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also has polynucleotide sequences encoding CRISPR Associated (Cas) genes. Cas genes encode endonucleases involved in the biogenesis and the interference stages of crRNA function in prokaryotes. Some Cas genes have homologous secondary and/or tertiary structures.

Type II CRISPR Systems crRNA biogenesis in a Type II CRISPR system in nature requires a trans-activating CRISPR RNA (tracrRNA). The tracrRNA is modified by endogenous RNaseIII, and then hybridizes to a crRNA repeat in the pre-crRNA array. Endogenous RNaseIII is recruited to cleave the pre-crRNA. Cleaved crRNAs are subjected to exoribonuclease trimming to produce the mature crRNA form (e.g., 5' trimming). The tracrRNA remains hybridized to the crRNA, and the tracrRNA and the crRNA associate with a site-directed polypeptide (e.g., a Cas endonuclease, such as a Cas9). The crRNA of the crRNA-tracrRNA-Cas complex guides the complex to a target nucleic acid to which the crRNA can hybridize. Hybridization of the crRNA to the target nucleic acid activates the Cas endonuclease for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek, M. et al. (2012). Science, 337(6096): 816-821 showed that the CRISPR/Cas9 system is useful for RNA-programmable genome editing, and International Patent Application no. WO 2013/176772 provides numerous examples and applications of the CRISPR/Cas endonuclease system for site-specific gene editing.

Type V CRISPR Systems

Type V CRISPR systems have several important differences from Type II systems. For example, Cpf1 is a single RNA-guided endonuclease that, in contrast to Type II systems, lacks tracrRNA. In fact, Cpf1-associated CRISPR arrays are processed into mature crRNAs without the requirement of an additional trans-activating tracrRNA. The Type V CRISPR array is processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems start with 20-24 nucleotides of spacer sequence followed by about 22 nucleotides of direct repeat. Also, Cpf1 utilizes a T-rich protospacer-adjacent motif such that Cpf1-crRNA complexes efficiently cleave target DNA preceded by a short T-rich PAM, which is in contrast to the G-rich PAM following the target DNA for Type II systems. Thus, Type V systems cleave at a point that is distant from the PAM, while Type II systems cleave at a point that is adjacent to the PAM. In addition, in contrast to Type II systems, Cpf1 cleaves DNA via a staggered DNA double-stranded break with a 4 or 5 nucleotide 5' overhang. Type II systems cleave via a blunt double-stranded break. Similar to Type II systems, Cpf1 contains a predicted RuvC-like endonuclease domain, but lacks a second HNH endonuclease domain, which is in contrast to Type II systems.

Cas Genes/Polypeptides and Protospacer Adjacent Motifs

Figure 5:
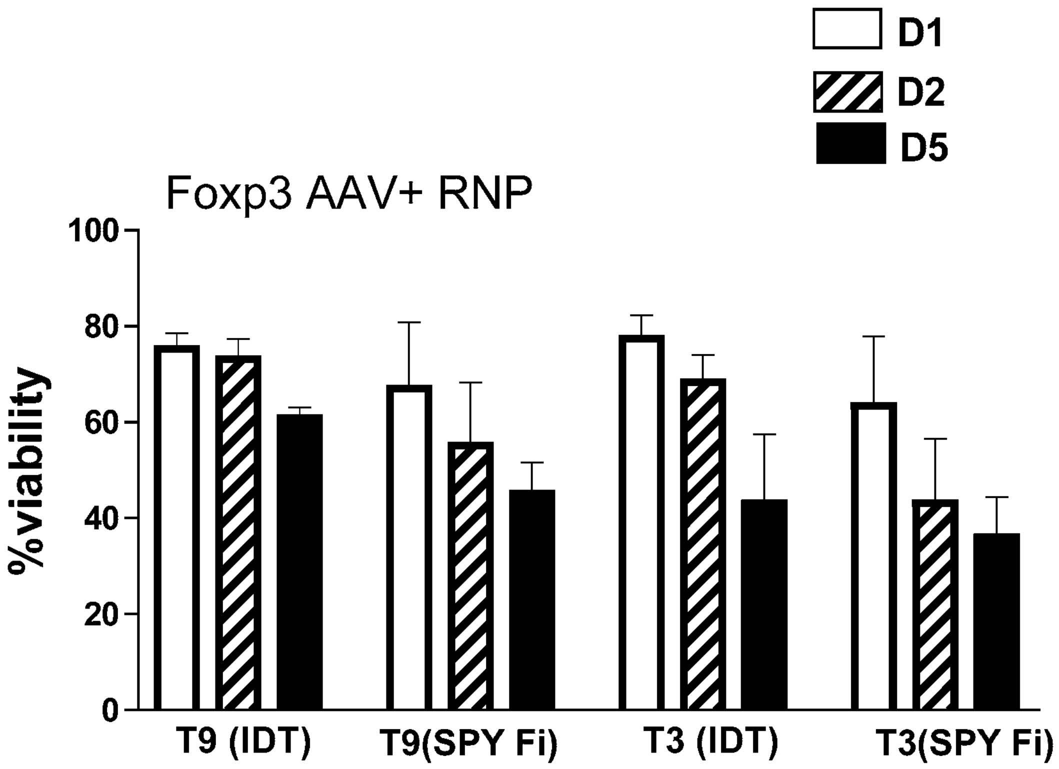
FIG. 5 is a bar graph showing the comparison of cell viabilities of $CD34^+$ cells edited with RNPs containing Cas9 from two different sources (Alt-R S.p. Cas9 Nuclease V3 from IDT or SpyFi Cas9 from Aldevron) along with AAV donor templates and two different gRNAs targeting FOXP3 (T3 or T9).

Exemplary CRISPR/Cas polypeptides include the Cas9 polypeptides in FIG. 1 of Fonfara, I. et al. (2014). *Nucleic Acids Res.,* 42(4):2577-2590. The CRISPR/Cas gene naming system has undergone extensive rewriting since the Cas genes were discovered. FIG. 5 of Fonfara, supra, provides PAM sequences for the Cas9 polypeptides from various species.

Complexes of a Genome-Targeting Nucleic acid and a Site-Directed Polypeptide

A genome-targeting nucleic acid interacts with a site-directed polypeptide (e.g., a nucleic acid-guided nuclease such as Cas9), thereby forming a complex. The genome-targeting nucleic acid (e.g., gRNA) guides the site-directed polypeptide to a target nucleic acid.

As stated previously, in some embodiments the site-directed polypeptide and genome-targeting nucleic acid can each be administered separately to a cell or a subject. On the other hand, in some other embodiments the site-directed polypeptide can be pre-complexed with one or more guide RNAs, or one or more crRNA together with a tracrRNA. The pre-complexed material can then be administered to a cell or a subject. Such pre-complexed material is known as a ribonucleoprotein particle (RNP).

Methods of Editing Genome

One approach to express a FOXP3 protein or functional derivative thereof in an organism in need thereof is to use genome editing to target the integration of a nucleic acid comprising a coding sequence encoding the FOXP3 protein into an endogenous FOXP3 gene or a non-FOXP3 gene that is sufficiently expressed in a relevant cell type (e.g., T cell) in such a way that expression of the integrated coding sequence is driven by the endogenous promoter of the endogenous FOXP3 gene or non-FOXP3 gene. In some embodiments, where a non-FOXP3 gene is targeted, it is desirable that the expression of the non-FOXP3 gene be specific to the targeted cell type, e.g., $CD34^+$ cells such as $CD34^+$ hematopoietic stem cells, or cells derived therefrom (e.g., T cells) to avoid expression in non-relevant cell types.

In some embodiments, a knock-in strategy involves knocking-in a sequence encoding a FOXP3 or a functional derivative thereof, such as a wild-type FOXP3 gene (e.g., a wild-type human FOXP3 gene), a FOXP3 cDNA, or a FOXP3 minigene (having natural or synthetic enhancer and promoter, one or more exons, and natural or synthetic introns, and natural or synthetic 3'UTR and polyadenylation signal) into a genomic sequence. In some embodiments, the genomic sequence where the FOXP3-encoding sequence is inserted is at, within, or near the FOXP3 gene. In some embodiments, the genomic sequence where the FOXP3-encoding sequence is inserted is at, within, or near exon 1 of the FOXP3 gene.

In some embodiments, provided herein are methods to knock-in a sequence encoding a FOXP3 or a functional derivative thereof into a genome. In one aspect, the present disclosure provides insertion of a nucleic acid comprising a sequence encoding a FOXP3 or a functional derivative thereof into a genome of a cell. In some embodiments, the FOXP3-encoding sequence encodes a wild-type FOXP3. The functional derivative of FOXP3 can include a derivative of FOXP3 that has a substantial activity of a wild-type FOXP3, such as the wild-type human FOXP3, e.g., at least or at least about 30%, at or about 40%, at or about 50%, at or about 60%, at or about 70%, at or about 80%, at or about 90%, at or about 95% or at or about 100% of the activity that the wild-type FOXP3 exhibits. In some embodiments, the functional derivative of FOXP3 has at least or at least about 30%, at or about 40%, at or about 50%, at or about 60%, at or about 70%, at or about 80%, at or about 85%, at or about 90%, at or about 95%, at or about 96%, at or about 97%, at or about 98% or at or about 99% amino acid sequence identity to a FOXP3, e.g., a wild-type FOXP3. In some embodiments, the FOXP3 is encoded by a nucleotide sequence that lacks introns (e.g., FOXP3 cDNA). One having ordinary skill in the art can use methods known in the art to test the functionality or activity of a FOXP3 derivative. The functional derivative of a FOXP3 can also include any fragment of a wild-type FOXP3 that has conservative modifications on one or more amino acid residues in a full length, wild-type FOXP3. Thus, in some embodiments, a nucleic acid sequence encoding a functional derivative of a FOXP3 can have at least or at least about 30%, at or about 40%, at or about 50%, at or about 60%, at or about 70%, at or about 80%, at or about 85%, at or about 90%, at or about 95%, at or about 96%, at or about 97%, at or about 98% or at or about 99% nucleic acid sequence identity to a nucleic acid sequence encoding the FOXP3, e.g., a wild-type FOXP3. In some embodiments, the FOXP3 or a functional variant thereof is a human wild-type FOXP3.

In some embodiments, the genome editing methods utilize a DNA endonuclease such as a CRISPR/Cas endonuclease to genetically introduce (knock-in) a sequence encoding a FOXP3 or a functional derivative thereof. In some embodiments, the DNA endonuclease is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, a homolog thereof, a recombinant of the naturally occurring molecule, a codon-optimized, or modified version thereof, or a combination of any of the foregoing. In some embodiments, the DNA endonuclease is a Cas9. In some embodiments, the Cas9 is from *Streptococcus pyogenes* (spCas9). In some embodiments, the Cas9 is from *Staphylococcus lugdunensis* (SluCas9).

In some embodiments, the cell subject to the genome-edition has one or more mutation(s) in the genome which results in a decrease of the expression of an endogenous FOXP3 gene as compared to the expression in a normal cell that does not have such mutation(s). The normal cell can be a healthy or control cell that is originated (or isolated) from a different subject who does not have FOXP3 gene defects. In some embodiments, the cell subject to the genome-edition can be originated (or isolated) from a subject who is in need of treatment of a FOXP3 gene related condition or disorder, e.g. a subject suffering from an autoimmune disorder (e.g., IPEX syndrome). Therefore, in some embodiments the expression of an endogenous FOXP3 gene in such cell is at or about 10%, at or about 20%, at or about 30%, at or about 40%, at or about 50%, at or about 60%, at or about 70%, at or about 80%, at or about 90% or at or about 100% decreased as compared to the expression of an endogenous FOXP3 gene in the normal cell.

In some embodiments, provided herein is a method of editing a genome in a $CD34^+$ cell, the method comprising providing the following to the $CD34^+$ cell: (a) a Cas DNA endonuclease (e.g., a Cas9 endonuclease) or nucleic acid encoding the Cas DNA endonuclease; (b) a gRNA (e.g., an sgRNA) or nucleic acid encoding the gRNA, wherein the gRNA is capable of targeting the Cas DNA endonuclease to a FOXP3 gene or a non-FOXP3 locus (e.g., AAVS1) in the genome of a cell, and (c) a donor template comprising a FOXP3 coding sequence. In some embodiments, the Cas DNA endonuclease is a Cas9 endonuclease (e.g., a Cas9 endonuclease from *Streptococcus pyogenes*). In some embodiments, the gRNA comprises a spacer sequence complementary to a target sequence in a FOXP3 gene. In some embodiments, the gRNA comprises a spacer sequence complementary to a target sequence in exon 1 of a FOXP3 gene. In some embodiments, the gRNA comprises a spacer sequence from any one of SEQ ID NOs: 1-7 and 27-29 or a variant thereof having no more than 3 mismatches compared to any one of SEQ ID NOs: 1-7 and 27-29. In some embodiments, the gRNA comprises a spacer sequence from any one of SEQ ID NOs: 1-7 or a variant thereof having no more than 3 mismatches compared to any one of SEQ ID NOs: 1-7. In some embodiments, the gRNA comprises a spacer sequence from any one of SEQ ID NOs: 2, 3, and 5, or a variant thereof having no more than 3 mismatches compared to any one of SEQ ID NOs: 2, 3, and 5. In some embodiments, the gRNA comprises a spacer sequence complementary to a target sequence in a non-FOXP3 locus (e.g., AAVS1). In some embodiments, the gRNA comprises a spacer sequence from any one of SEQ ID NOs: 15-20 or a variant thereof having no more than 3 mismatches compared to any one of SEQ ID NOs: 15-20. In some embodiments, the FOXP3 coding sequence encodes FOXP3 or a functional derivative thereof. In some embodiments, the FOXP3 coding sequence is a FOXP3 cDNA. An exemplary FOXP3 cDNA sequence can be found in the AAV donor template having the nucleotide sequence of SEQ ID NO: 34. In some embodiments, the method comprises providing to the $CD34^+$ cell the Cas DNA endonuclease. In some embodiments, the method comprises providing to the $CD34^+$ cell nucleic acid encoding the Cas DNA endonuclease. In some embodiments, the method comprises providing to the $CD34^+$ cell the gRNA. In some embodiments, the gRNA is an sgRNA. In some embodiments, the method comprises providing to the $CD34^+$ cell nucleic acid encoding the gRNA. In some embodiments, the method further comprises providing to the $CD34^+$ cell one or more additional gRNAs or nucleic acid encoding the one or more additional gRNAs.

In some embodiments, according to any of the methods of editing a genome in a cell described herein, the DNA endonuclease is a Cas9. In some embodiments, the Cas9 is from *Streptococcus pyogenes* (spCas9). In some embodiments, the Cas9 is from *Staphylococcus lugdunensis* (SluCas9).

In some embodiments, according to any of the methods of editing a genome in a cell described herein, the nucleic acid sequence encoding a FOXP3 or a functional derivative thereof is codon-optimized for expression in the cell. In some embodiments, the cell is a human cell.

In some embodiments, according to any of the methods of editing a genome in a cell described herein, the method employs a nucleic acid encoding the DNA endonuclease. In some embodiments, the nucleic acid encoding the DNA endonuclease is codon-optimized for expression in the cell. In some embodiments, the cell is a human cell, e.g., a human $CD34^+$ cell. In some embodiments, the nucleic acid encoding the DNA endonuclease is DNA, such as a DNA plasmid. In some embodiments, the nucleic acid encoding the DNA endonuclease is RNA, such as mRNA.

In some embodiments, according to any of the methods of editing a genome in a cell described herein, the donor template comprises a donor cassette comprising the nucleic acid sequence encoding a FOXP3 or a functional derivative thereof, and the donor template is configured such that the donor cassette is capable of being integrated into the genomic locus targeted by the gRNA of (b) by homology directed repair (HDR). In some embodiments, the donor cassette is flanked on both sides by homology arms corresponding to sequences in the targeted genomic locus. In some embodiments, the homology arms are at least or at least about 0.2 kb (such as at least or at least about any of 0.3 kb, 0.4 kb, 0.5 kb, 0.6 kb, 0.7 kb, 0.8 kb, 0.9 kb, or 1 kb, or greater) in length. In some embodiments, the homology arms are at least or at least about 0.8 kb in length. Exemplary homology arms include homology arms from donor templates having the sequence of SEQ ID NO: 34 or 161. Exemplary donor templates include donor templates having the sequence of SEQ ID NO: 34 or 161. In some embodiments, the donor template is encoded in an Adeno Associated Virus (AAV) vector. In some embodiments, the AAV vector is an AAV6 vector.

In some embodiments, according to any of the methods of editing a genome in a cell described herein, the donor template comprises a donor cassette comprising the nucleic acid sequence encoding a FOXP3 or a functional derivative thereof, and the donor template is configured such that the donor cassette is capable of being integrated into the genomic locus targeted by the gRNA of (b) by non-homologous end joining (NHEJ). In some embodiments, the donor cassette is flanked on one or both sides by a gRNA target site. In some embodiments, the donor cassette is flanked on both sides by a gRNA target site. In some embodiments, the gRNA target site is a target site for a gRNA in the system. In some embodiments, the gRNA target site of the donor template is the reverse complement of a cell genome gRNA target site for a gRNA in the system. In some embodiments, the donor template is encoded in an Adeno Associated Virus (AAV) vector. In some embodiments, the AAV vector is an AAV6 vector.

In some embodiments, according to any of the methods of editing a genome in a cell described herein, the DNA endonuclease or nucleic acid encoding the DNA endonuclease is formulated in a liposome or lipid nanoparticle. In some embodiments, the liposome or lipid nanoparticle also comprises the gRNA. In some embodiments, the liposome or lipid nanoparticle is a lipid nanoparticle. In some embodiments, the method employs a lipid nanoparticle comprising nucleic acid encoding the DNA endonuclease and the gRNA. In some embodiments, the nucleic acid encoding the DNA endonuclease is an mRNA encoding the DNA endonuclease.

In some embodiments, according to any of the methods of editing a genome in a cell described herein, the DNA endonuclease is pre-complexed with the gRNA, forming a ribonucleoprotein (RNP) complex. In some embodiments, the RNP complex is provided to the cell by electroporation. In some embodiments, the donor template is an AAV donor template encoded in an AAV vector (e.g., an AAV6 vector). In some embodiments, the AAV donor template is provided to the cell at or around the same time that the RNP complex is provided to the cell. For example, in some embodiments, the cell is electroporated with the RNP complex and transduced with the AAV donor template on the same day. In some embodiments, the cell is electroporated with the RNP complex and transduced with the AAV donor template, wherein the electroporation and transduction are carried out no greater than or no greater than about 12 hours (such as no greater than or no greater than about any of 11 hours, 10 hours, 9 hours, 8 hours, 7 hours, 6 hours, 5 hours, 4 hours, 3 hours, 2 hours, or 1 hour, or less) apart. In some embodiments, the cell is electroporated with the RNP complex, plated, and transduced with the AAV donor template. In some embodiments, the cell is pre-stimulated in the presence of cytokines (e.g., TPO, SCF, FLT3L, or IL6 or any combination thereof) and/or small molecules (e.g., UM171 or StemRegenin (SR1)) capable of promoting HSC proliferation or self-renewal prior to providing the RNP and AAV donor template to the cell. In some embodiments, the pre-stimulation is carried out for at least or at least about 12 hours (such as at least or at least about any of 16 hours, 20 hours, 24 hours, 36 hours, or 48 hours, or more). In some embodiments, the pre-stimulation is carried out for at least or at least about 48 hours. In some embodiments, the pre-stimulation is carried out in a cell composition comprising the cell, and the concentration of cells in the cell composition and/or the culture media are such that at least or at least about 10% (e.g., at least or at least about 20%, 30%, 40%, or 50%) of the cells in the cell composition remain quiescent at the end of the pre-stimulation. In some embodiments, from or from about 10% to or to about 60% (e.g., from or from about 10% to or to about 50%, from or from about 10% to or to about 40%, or from or from about 10% to or to about 30%) of the cells in the cell composition remain quiescent at the end of the pre-stimulation. In some embodiments, the concentration of cells in the cell composition is no greater than or no greater than about $5\times10^5$ (such as no greater than or no greater than about any of $4\times10^5$, $3\times10^5$, $2.5\times10^5$, $2\times10^5$, $1\times10^5$, $0.5\times10^5$, or fewer) cells/ml. In some embodiments, the concentration of cells in the cell composition is no greater than or no greater than about $2.5\times10^5$ cells/ml.

In some embodiments, according to any of the methods of editing a genome in a cell described herein, the frequency of targeted integration of the donor template into a FOXP3 gene in the cell genome is from or from about 0.1% to or to about 99%. In some embodiments, the frequency of targeted integration is from or from about 2% to or to about 70% (such as from or from about 2% to or to about 65%, from or from about 2% to or to about 55%, from or from about 3% to or to about 70%, from or from about 5% to or to about 70%, from or from about 5% to or to about 60%, from or from about 5% to or to about 50%, from or from about 10% to or to about 60%, or from or from about 10% to or to about 50%). In some embodiments, the cell is a cell in a subject, such as a human subject.

Target Sequence Selection

In some embodiments, shifts in the location of the 5' boundary or the 3' boundary or both relative to particular reference loci are used to facilitate or enhance particular applications of gene editing, which depend in part on the endonuclease system selected for the editing, as further described and illustrated herein.

In a first, non-limiting aspect of such target sequence selection, many endonuclease systems have rules or criteria that guide the initial selection of potential target sites for cleavage, such as the requirement of a PAM sequence motif in a particular position adjacent to the DNA cleavage sites in the case of CRISPR Type II or Type V endonucleases.

In another, non-limiting aspect of target sequence selection or optimization, the frequency of "off-target" activity for a particular combination of target sequence and gene editing endonuclease (e.g., the frequency of DSBs occurring at sites other than the selected target sequence) is assessed relative to the frequency of on-target activity. In some cases, cells that have been correctly edited at the desired locus can have a selective advantage relative to other cells. Illustrative, but non-limiting, examples of a selective advantage include the acquisition of attributes such as enhanced rates of replication, persistence, resistance to certain conditions, enhanced rates of successful engraftment or persistence in vivo following introduction into a subject, and other attributes associated with the maintenance or increased numbers or viability of such cells. In other cases, cells that have been correctly edited at the desired locus can be positively selected for by one or more screening methods used to identify, sort, or otherwise select for cells that have been correctly edited. Both selective advantage and directed selection methods can take advantage of the phenotype associated with the correction. In some embodiments, cells can be edited two or more times to create a second modification that creates a new phenotype that is used to select or purify the intended population of cells. Such a second modification could be created by adding a second gRNA for a selectable or screenable marker. In some cases, cells can be correctly edited at the desired locus using a DNA fragment that contains the cDNA and also a selectable marker.

In embodiments, whether any selective advantage is applicable or any directed selection is to be applied in a particular case, target sequence selection is also guided by consideration of off-target frequencies to enhance the effectiveness of the application and/or reduce the potential for undesired alterations at sites other than the desired target. As described further and illustrated herein and in the art, the occurrence of off-target activity is influenced by a number of factors including similarities and dissimilarities between the target site and various off-target sites, as well as the particular endonuclease used. Bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein, and others are known in the art.

Another aspect of target sequence selection relates to homologous recombination events. Sequences sharing regions of homology can serve as focal points for homologous recombination events that result in deletion of intervening sequences. Such recombination events occur during the normal course of replication of chromosomes and other DNA sequences, and also at other times when DNA sequences are being synthesized, such as in the case of repairs of double-strand breaks (DSBs), which occur on a regular basis during the normal cell replication cycle but can also be enhanced by the occurrence of various events (such as UV light and other inducers of DNA breakage) or the presence of certain agents (such as various chemical inducers). Many such inducers cause DSBs to occur indiscriminately in the genome, and DSBs are regularly being induced and repaired in normal cells. During repair, the original sequence can be reconstructed with complete fidelity, however, in some cases, small insertions or deletions (referred to as "indels") are introduced at the DSB site.

DSBs can also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems, such as CRISPR, in which homology directed repair is used to insert a sequence of interest, provided through use of a "donor" polynucleotide, into a desired chromosomal location.

Regions of homology between particular sequences, which can be small regions of "microhomology" that can have as few as ten base pairs or less, can also be used to bring about desired deletions. For example, a single DSB is introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process.

In some circumstances, however, selecting target sequences within regions of homology can also give rise to much larger deletions, including gene fusions (when the deletions are in coding regions), which can or cannot be desired given the particular circumstances.

The examples provided herein further illustrate the selection of various target regions for the creation of DSBs designed to insert a FOXP3-encoding gene, as well as the selection of specific target sequences within such regions that are designed to minimize off-target events relative to on-target events. In some embodiments, the target locus is selected from a FOXP3 gene, an AAVS1 locus, and a TRA gene.

Nucleic Acid Modifications

In some embodiments, polynucleotides introduced into cells have one or more modifications that can be used individually or in combination, for example, to enhance activity, stability, or specificity, alter delivery, reduce innate immune responses in host cells, or for other enhancements, as further described herein and known in the art.

In certain embodiments, modified polynucleotides are used in a CRISPR/Cas system (e.g., a CRISPR/Cas9 system), in which case the guide RNAs (either single-molecule guides or double-molecule guides) and/or a DNA or an RNA encoding a Cas endonuclease introduced into a cell can be modified, as described and illustrated below. Such modified polynucleotides can be used in the CRISPR/Cas system to edit any one or more genomic loci.

Using a CRISPR/Cas system for purposes of non-limiting illustrations of such uses, modifications of guide RNAs can be used to enhance the formation or stability of a CRISPR/Cas genome editing complex having guide RNAs, which can be single-molecule guides or double-molecule, and a Cas endonuclease. Modifications of guide RNAs can also or alternatively be used to enhance the initiation, stability, or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in embodiments in which a Cas endonuclease is introduced into the cell to be edited via an RNA that needs to be translated to generate endonuclease, because increasing the half-life of guide RNAs introduced at the same time as the RNA encoding the endonuclease can be used to increase the time that the guide RNAs and the encoded Cas or Cpf1 endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNAses present in the cell), modifications that enhance translation of the resulting product (e.g., the endonuclease), and/or modifications that decrease the likelihood or degree to which the RNAs introduced into cells elicit innate immune responses.

Combinations of modifications, such as the foregoing and others, can likewise be used. In the case of CRISPR/Cas, for example, one or more types of modifications can be made to guide RNAs (including those exemplified above), and/or one or more types of modifications can be made to RNAs encoding Cas endonuclease (including those exemplified above).

Delivery

In some embodiments, any nucleic acid molecules used in the methods provided herein, e.g., a nucleic acid encoding a genome-targeting nucleic acid of the disclosure or a site-directed polypeptide, are packaged into or on the surface of delivery vehicles for delivery to cells. Delivery vehicles contemplated include, but are not limited to, nanospheres, liposomes, quantum dots, nanoparticles, polyethylene glycol particles, hydrogels, or micelles. As described in the art, a variety of targeting moieties can be used to enhance the preferential interaction of such vehicles with desired cell types or locations.

Introduction of the complexes, polypeptides, or nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, or nanoparticle-mediated nucleic acid delivery, and the like.

In embodiments, guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by viral or non-viral delivery vehicles known in the art, such as electroporation or lipid nanoparticles. In some embodiments, the DNA endonuclease can be delivered as one or more polypeptides, either alone or pre-complexed with one or more guide RNAs, or one or more crRNA together with a tracrRNA.

In embodiments, polynucleotides can be delivered by non-viral delivery vehicles including, but not limited to, nanoparticles, liposomes, ribonucleoproteins, positively charged peptides, small molecule RNA-conjugates, aptamer-RNA chimeras, or RNA-fusion protein complexes. Some exemplary non-viral delivery vehicles are described in Peer, D. et al. (2011). *Gene Therapy,* 18: 1127-1133 (which focuses on non-viral delivery vehicles for siRNA that are also useful for delivery of other polynucleotides).

In embodiments, polynucleotides, such as guide RNA, sgRNA, or mRNA encoding an endonuclease, can be delivered to a cell or a subject by a lipid nanoparticle (LNP).

While several non-viral delivery methods for nucleic acids have been tested both in animal models and in humans the most well developed system is lipid nanoparticles. Lipid nanoparticles (LNP) are generally composed of an ionizable cationic lipid and 3 or more additional components, generally cholesterol, DOPE, and a polyethylene glycol (PEG) containing lipid, see, e.g. Example 2. The cationic lipid can bind to the positively charged nucleic acid forming a dense complex that protects the nucleic from degradation. During passage through a micro fluidics system the components self-assemble to form particles in the size range of 50 to 150 nM in which the nucleic acid is encapsulated in the core complexed with the cationic lipid and surrounded by a lipid bilayer like structure. After injection into the circulation of a subject these particles can bind to apolipoprotein E (apoE). ApoE is a ligand for the LDL receptor and mediates uptake into the hepatocytes of the liver via receptor mediated endocytosis. LNP of this type have been shown to efficiently deliver mRNA and siRNA to the hepatocytes of the liver of rodents, primates, or humans. After endocytosis, the LNP are present in endosomes. The encapsulated nucleic acid undergoes a process of endosomal escape mediate by the ionizable nature of the cationic lipid. This delivers the nucleic acid into the cytoplasm where mRNA can be translated into the encoded protein. After endosomal escape a Cas mRNA (e.g., a Cas9 mRNA) is translated into Cas protein and can form a complex with the gRNA. In some embodiments, inclusion of a nuclear localization signal into the Cas protein sequence promotes translocation of the Cas protein/gRNA complex to the nucleus. Alternatively, the small gRNA crosses the nuclear pore complex and form complexes with Cas protein in the nucleus. Once in the nucleus the gRNA/Cas complex scan the genome for homologous target sites and generate double-strand breaks preferentially at the desired target site in the genome. The half-life of RNA molecules in vivo is generally short, on the order of hours to days. Similarly, the half-life of proteins tends to be short, on the order of hours to days. Thus, in some embodiments, delivery of the gRNA and Cas mRNA using an LNP can result in only transient expression and activity of the gRNA/Cas complex. This can provide the benefit of reducing the frequency of off-target cleavage and, thus minimize the risk of genotoxicity in some embodiments. LNP are generally less immunogenic than viral particles. While many humans have preexisting immunity to AAV there is no pre-existing immunity to LNP. In additional and adaptive immune response against LNP is unlikely to occur which enables repeat dosing of LNP.

Several different ionizable cationic lipids have been developed for use in LNP. These include C12-200 (Love, K. T. et al. (2010). *Proc. Natl. Acad. Sci. U.S.A.,* 107(5):1864-1869), MC3, LN16, MD1 among others. In one type of LNP a GalNac moiety is attached to the outside of the LNP and acts as a ligand for uptake into the liver via the asialyloglycoprotein receptor. Any of these cationic lipids are used to formulate LNP for delivery of gRNA and Cas mRNA to the liver.

In some embodiments, an LNP refers to any particle having a diameter of less than 1000 nm, 500 nm, 250 nm, 200 nm, 150 nm, 100 nm, 75 nm, 50 nm, or 25 nm. Alternatively, a nanoparticle can range in size from 1-1000 nm, 1-500 nm, 1-250 nm, 25-200 nm, 25-100 nm, 35-75 nm, or 25-60 nm.

LNPs can be made from cationic, anionic, or neutral lipids. Neutral lipids, such as the fusogenic phospholipid DOPE or the membrane component cholesterol, can be included in LNPs as 'helper lipids' to enhance transfection activity and nanoparticle stability. Limitations of cationic lipids include low efficacy owing to poor stability and rapid clearance, as well as, the generation of inflammatory or anti-inflammatory responses. LNPs can also have hydrophobic lipids, hydrophilic lipids, or both hydrophobic and hydrophilic lipids.

Any lipid or combination of lipids that are known in the art can be used to produce an LNP. Examples of lipids used to produce LNPs are: DOTMA, DOSPA, DOTAP, DMRIE, DC-cholesterol, DOTAP-cholesterol, GAP-DMORIE-DPyPE, or GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, or 7C1. Examples of neutral lipids are: DPSC, DPPC, POPC, DOPE, or SM. Examples of PEG-modified lipids are: PEG-DMG, PEG-CerC14, or PEG-CerC20.

In embodiments, the lipids can be combined in any number of molar ratios to produce an LNP. In addition, the polynucleotide(s) can be combined with lipid(s) in a wide range of molar ratios to produce an LNP.

In embodiments, the site-directed polypeptide and genome-targeting nucleic acid can each be administered separately to a cell or a subject. On the other hand, the site-directed polypeptide can be pre-complexed with one or more guide RNAs, or one or more crRNA together with a tracrRNA. The pre-complexed material can then be administered to a cell or a subject. Such pre-complexed material is known as a ribonucleoprotein particle (RNP).

RNA can form specific interactions with RNA or DNA. While this property is exploited in many biological processes, it also comes with the risk of promiscuous interactions in a nucleic acid-rich cellular environment. One solution to this problem is the formation of ribonucleoprotein particles (RNPs), in which the RNA is pre-complexed with an endonuclease. Another benefit of the RNP is protection of the RNA from degradation.

In some embodiments, the endonuclease in the RNP can be modified or unmodified. Likewise, the gRNA, crRNA, tracrRNA, or sgRNA can be modified or unmodified. Numerous modifications are known in the art and can be used.

The endonuclease and sgRNA can be generally combined in a 1:1 molar ratio. Alternatively, the endonuclease, crRNA, and tracrRNA can be generally combined in a 1:1:1 molar ratio. However, a wide range of molar ratios can be used to produce an RNP.

In some embodiments, a recombinant adeno-associated virus (AAV) vector can be used for delivery. Techniques to produce rAAV particles, in which an AAV genome to be packaged that includes the polynucleotide to be delivered, rep, and cap genes, and helper virus functions are provided to a cell are known in the art. Production of rAAV requires that the following components are present within a single cell (denoted herein as a packaging cell): a rAAV genome, AAV rep and cap genes separate from (e.g., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13, or AAV rh.74. Production of pseudotyped rAAV is disclosed in, for example, International Patent Application no. WO 01/83692. Table 1 lists AAV serotype and Genbank Accession No. of some selected AAVs.

TABLE 1

| AAV Serotype | Genbank Accession No. |
|---|---|
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

In some embodiments, a method of generating a packaging cell involves creating a cell line that stably expresses all of the necessary components for AAV particle production. For example, a plasmid (or multiple plasmids) having a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski, R. J. et al. (1982). *Proc. Natl. Acad. Sci. U.S.A.,* 79(6):2077-2081), addition of synthetic linkers containing restriction endonuclease cleavage sites (Laughlin, C. A. et al. (1983). *Gene,* 23(1):65-73) or by direct, blunt-end ligation (Senapathy, P. et al. (1984). *J. Biol. Chem.,* 259: 4661-4666). The packaging cell line is then infected with a helper virus, such as adenovirus. The benefits of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, B. J. (1992). *Curr. Opin. Biotechnol.,* 3(5):533-539; and Muzyczka, M. (1992). *Curr. Top. Microbiol. Immunol.,* 158:97-129). Various approaches are described in Tratschin, J. D. et al. (1984). *Mol. Cell. Biol.,* 4(10):2072-2081; Hermonat, P. L. et al. (1984). *Proc. Natl. Acad. Sci. U.S.A.,* 81(20):6466-6470; Tratschin, J. D. et al. (1985). *Mol. Cell. Biol.,* 5(11):3251-3260; McLaughlin, S. K. et al. (1988). J. Virol., 62(6):1963-1973; and Lebkowski, J. S. et al. (1988). *Mol. Cell. Biol.,* 8(10):3988-3996. Samulski, R. J. et al. (1989), *J. Virol.,* 63(9):3822-3828; U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin, P. et al. (1995). *Vaccine,* 13(13):1244-1250; Paul, R. W. et al. (1993). *Hum. Gene Ther.,* 4(5):609-615; Clark, K. R. et al. (1996). *Gene Ther.* 3(12):1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others. For instance, the serotypes of AAV vectors suitable to hematopoietic stem cell include, but not limited to, AAV2 and AAV6. In some embodiments, the AAV vector serotype is AAV6.

In some embodiments, the AAV vector comprises a nucleic acid sequence having at least or at least about 90% sequence identity (e.g., at least 92%, 93%, 94%, 95%, 96%, 97%, 98%, 99%, 99.2%, 99.5%, 99.6%, 99.7%, 99.8%, 99.9%, or greater) to any one of SEQ ID NOs: 33-36 and 161. In some embodiments, the AAV vector comprises a nucleic acid sequence having at least or at least about 90% sequence identity (e.g., at least 92%, 93%, 94%, 95%, 96%, 97%, 98%, 99%, 99.2%, 99.5%, 99.6%, 99.7%, 99.8%, 99.9%, or greater) to SEQ ID NO: 33. In some embodiments, the AAV vector comprises a nucleic acid sequence having at least or at least about 90% sequence identity (e.g., at least 92%, 93%, 94%, 95%, 96%, 97%, 98%, 99%, 99.2%, 99.5%, 99.6%, 99.7%, 99.8%, 99.9%, or greater) to SEQ ID NO: 34. In some embodiments, the AAV vector comprises a nucleic acid sequence having at least or at least about 90% sequence identity (e.g., at least 92%, 93%, 94%, 95%, 96%, 97%, 98%, 99%, 99.2%, 99.5%, 99.6%, 99.7%, 99.8%, 99.9%, or greater) to SEQ ID NO: 35. In some embodiments, the AAV vector comprises a nucleic acid sequence having at least or at least about 90% sequence identity (e.g., at least 92%, 93%, 94%, 95%, 96%, 97%, 98%, 99%, 99.2%, 99.5%, 99.6%, 99.7%, 99.8%, 99.9%, or greater) to SEQ ID NO: 36. In some embodiments, the AAV vector comprises a nucleic acid sequence having at least or at least about 90% sequence identity (e.g., at least 92%, 93%, 94%, 95%, 96%, 97%, 98%, 99%, 99.2%, 99.5%, 99.6%, 99.7%, 99.8%, 99.9%, or greater) to SEQ ID NO: 161.

In addition to adeno-associated viral vectors, other viral vectors can be used. Such viral vectors include, but are not limited to, lentivirus, alphavirus, enterovirus, pestivirus, baculovirus, herpesvirus, Epstein Barr virus, papovavirus, poxvirus, vaccinia virus, or herpes simplex virus.

In some embodiments, Cas mRNA (e.g., Cas9 mRNA), sgRNA targeting one or two loci in FOXP3 genes, and donor DNA are each separately formulated into lipid nanoparticles, or are all co-formulated into one lipid nanoparticle, or co-formulated into two or more lipid nanoparticles.

In some embodiments, Cas mRNA (e.g., Cas9 mRNA) is formulated in a lipid nanoparticle, while sgRNA and donor DNA are delivered in an AAV vector. In some embodiments, Cas mRNA and sgRNA are co-formulated in a lipid nanoparticle, while donor DNA is delivered in an AAV vector.

Options are available to deliver a Cas endonuclease (e.g., a Cas9 endonuclease) as a DNA plasmid, as mRNA or as a protein. The guide RNA can be expressed from the same DNA, or can be delivered as an RNA. The RNA can be chemically modified to alter or improve its half-life and/or decrease the likelihood or degree of immune response. The endonuclease protein can be complexed with the gRNA prior to delivery. Viral vectors allow efficient delivery; split versions of Cas endonucleases and smaller orthologs of Cas endonucleases can be packaged in AAV, as can donors for HDR. A range of non-viral delivery methods also exist that can deliver each of these components, or non-viral and viral methods can be employed in tandem. For example, nanoparticles can be used to deliver the protein and guide RNA, while AAV can be used to deliver a donor DNA.

In some embodiments that are related to deliver genome-editing components for therapeutic treatments, at least two components are delivered into the nucleus of a cell to be transformed, e.g., $CD34^+$ cells; a sequence-specific nuclease and a DNA donor template. In some embodiments, the AAV is selected from the serotypes AAV2 or AAV6. In some embodiments, the AAV packaged DNA donor template is administered to a subject, e.g., a patient, first by peripheral IV injection followed by the sequence-specific nuclease. The advantage of delivering an AAV packaged donor DNA template first is that the delivered donor DNA template will be stably maintained in the nucleus of the transduced $CD34^+$ cells which allows for the subsequent administration of the sequence-specific nuclease, which will create a double-strand break in the genome with subsequent integration of the DNA donor by HDR or NHEJ. It is desirable in some embodiments that the sequence-specific nuclease remain active in the target cell only for the time required to promote targeted integration of the transgene at sufficient levels for the desired therapeutic effect. If the sequence-specific nuclease remains active in the cell for an extended duration this will result in an increased frequency of double-strand breaks at off-target sites. Specifically, the frequency of off-target cleavage is a function of the off-target cutting efficiency multiplied by the time over which the nuclease is active. Delivery of a sequence-specific nuclease in the form of a mRNA results in a short duration of nuclease activity in the range of hours to a few days because the mRNA and the translated protein are short lived in the cell. Thus, delivery of the sequence-specific nuclease into cells that already contain the donor template is expected to result in the highest possible ratio of targeted integration relative to off-target integration.

In some embodiments, the sequence-specific nuclease is a Cas endonuclease (e.g., a Cas9 endonuclease) used in a CRISPR/Cas system which is composed of a sgRNA directed to a FOXP3 gene together with the Cas endonuclease. In some embodiments, the Cas endonuclease is delivered as a mRNA encoding the Cas protein operably fused to one or more nuclear localization signals (NLS). In some embodiments, the sgRNA and the Cas mRNA are delivered to a $CD34^+$ cell, e.g., a $CD34^+$ hematopoietic stem cell, by packaging into a lipid nanoparticle.

In some embodiments, to promote nuclear localization of a donor template, DNA sequence that can promote nuclear localization of plasmids, e.g., a 366 bp region of the simian virus 40 (SV40) origin of replication and early promoter, can be added to the donor template. Other DNA sequences that bind to cellular proteins can also be used to improve nuclear entry of DNA.

Genetically Modified Cells and Cell Populations

In one aspect, the disclosures herewith provide a method of editing a genome in a cell, thereby creating a genetically modified cell. In some aspects, a population of genetically modified cells are provided. The genetically modified cell therefore refers to a cell that has at least one genetic modification introduced by genome editing (e.g., using a CRISPR/Cas system). In some embodiments, the genetically modified cell is a genetically modified hematopoietic stem cell, e.g. a $CD34^+$ cell such as a $CD34^+$ hematopoietic stem cell. A genetically modified cell having an integrated FOXP3 coding sequence is contemplated herein. In some embodiments, the genetically cell is not a germ cell.

In the embodiments described herein, the cells for therapeutic application are engineered to have stable FOXP3 expression through the use of a gene editing nuclease to modify the regulatory elements of the FOXP3 gene to provide for stable FOXP3 expression. In the exemplary data provided, a promoter is placed upstream of the FOXP3 coding exons (examples of constitutive promoters include EF1 alpha promoter, the PGK promoter, or the MND promoter, among many others) to drive FOXP3 expression, but a variety of approaches are envisioned to modify the regulatory elements so as to allow for stable FOXP3 expression. By several approaches used to modify the endogenous regulatory elements, the claimed therapeutic cell exhibits constitutive expression of the native FOXP3 gene, such that it is no longer susceptible to regulation that could result in FOXP3 gene silencing and reversion to a non-suppressive cell phenotype. Accordingly, in the exemplary methods described herein, the problem of loss of FOXP3 expression due to epigenetic influences on the native regulatory sequences and promoter has been solved.

The proposed method of enforcing FOXP3 expression in a bulk population of $CD34^+$ cells is contemplated. In subjects with auto-immune disease or who are rejecting an organ graft, the endogenous TCR repertoire in the inflammatory T cell population includes TCR's that have the correct binding specificity to recognize the inflamed tissue or the foreign tissue in the organ. These T cells are thought to mediate the auto-inflammatory reaction or organ rejection. By converting a portion of the bulk T cell population to a regulatory phenotype, the TCR specificities present in the pro-inflammatory population will be represented in the therapeutic cell population. This is an improvement over therapies based on thymic regulatory T cells, which is thought to have a distinct and non-overlapping TCR repertoire from inflammatory T cells. In addition, presumably in subjects with auto-immune disease or organ rejection, the existing $tT_{reg}$ population has failed to produce the tolerance necessary to avoid inflammation. The methods described herein can be used for therapy of auto-immune disease and for induction of tolerance to transplanted organs.

A significant disadvantage is the need to use gene editing tools that can efficiently carry out the recombination at the FOXP3 gene. As such, the methods provided show that the use of TALEN nuclease can carry this reaction out efficiently, but in principle, any nuclease platform would serve equally well.

The regulatory T cell therapies can be used for tolerance applications in transplantation and in auto-immunity. Currently, Treg infusions are expanded ex vivo. Phase I studies have shown marginal if any efficacy in T1D, and in some cases there have been benefits in post-transplant GVHD. For next generation engineered regulatory T cells, in some embodiments, these can be chimeric antigen receptor (CAR) directed natural $T_{reg}$s. Effector T cells can also be converted to $T_{regs}$ by FOXP3 expression.

However, there may also be differences between engineered versus natural $T_{regs}$ for methods of treatment. Natural Treg therapy has been considered safe, however too few natural $T_{regs}$ causes autoimmunity. Treg play a critical role in multiple autoimmune diseases (IPEX, T1D, SLE, RA, and EAE, etc). Approaches to augment human Treg number or function are in current trials including low-dose IL-2 and adoptive transfer of autologous expanded Treg. The efficacy of IL-2 therapy is limited due to its pleotropic activity and potential "off target" effects that may increase inflammation. Adoptive Treg therapy is likely limited by in vivo stability and viability of expanded $T_{regs}$ and their lack of relevant antigen specificity.

There are also potential flaws with the use of natural $T_{reg}$s. For example, autoimmune subjects can be genetically predisposed to Treg instability. For example, it is plausible for a CAR bearing nTreg to convert to a CAR T effector cell. nTreg also retain the potential for epigenetic regulation of FOXP3, which may lead to the down regulation of the desired FOXP3 induction. Also, natural $T_{regs}$ might not include the correct TCR (T cell receptor) specificities. The Treg function may also be linked to a selectable marker in which the expanded native Treg cell population may always have contaminating inflammatory cells. Thus, the methods provided herein are an improvement over using the transfer of natural $T_{regs}$ by using engineered cells as there is potential for linking CAR expression to regulatory T cell function to avoid potential engraftment of CAR $T_{regs}$ that have the potential to convert to pro inflammatory CAR T cells.

In some embodiments, the genome of a cell can be edited by inserting a nucleic acid sequence encoding a FOXP3 or a functional derivative thereof into a genomic sequence of the cell. In some embodiments, the cell subject to the genome-edition has one or more mutation(s) in the genome which results in reduction of the expression of endogenous FOXP3 gene as compared to the expression in a normal that does not have such mutation(s). The normal cell can be a healthy or control cell that is originated (or isolated) from a different subject who does not have FOXP3 gene defects. In some embodiments, the cell subject to the genome-edition can be originated (or isolated) from a subject who is in need of treatment of FOXP3 gene related condition or disorder. Therefore, in some embodiments the expression of endogenous FOXP3 gene in such cell is at or about 10%, at or about 20%, at or about 30%, at or about 40%, at or about 50%, at or about 60%, at or about 70%, at or about 80%, at or about 90% or at or about 100% increased as compared to the expression of endogenous FOXP3 gene expression in the normal cell.

Upon successful insertion of the transgene, e.g., a nucleic acid encoding a FOXP3 or a functional derivative thereof, the expression of the introduced nucleic acid encoding a FOXP3 or a functional derivative thereof in the cell can be at least or at least about 10%, at or about 20%, at or about 30%, at or about 40%, at or about 50%, at or about 60%, at or about 70%, at or about 80%, at or about 90%, at or about 100%, at or about 200%, at or about 300%, at or about 400%, at or about 500%, at or about 600%, at or about 700%, at or about 800%, at or about 900%, at or about 1,000%, at or about 2,000%, at or about 3,000%, at or about 5,000%, at or about 10,000% or more as compared to the expression of an endogenous FOXP3 gene of the cell. In some embodiments, the activity of introduced FOXP3-encoding sequence products, including functional derivatives of the FOXP3, in the genome-edited cell can be at least or at least about 10%, at or about 20%, at or about 30%, at or about 40%, at or about 50%, at or about 60%, at or about 70%, at or about 80%, at or about 90%, at or about 100%, at or about 200%, at or about 300%, at or about 400%, at or about 500%, at or about 600%, at or about 700%, at or about 800%, at or about 900%, at or about 1,000%, at or about 2,000%, at or about 3,000%, at or about 5,000%, at or about 10,000% or more as compared to the activity of an endogenous FOXP3 gene of the cell. In some embodiments, the expression of the introduced FOXP3-encoding sequence in the cell is at least or at least about 2 fold, at or about 3 fold, at or about 4 fold, at or about 5 fold, at or about 6 fold, at or about 7 fold, at or about 8 fold, at or about 9 fold, at or about 10 fold, at or about 15 fold, at or about 20 fold, at or about 30 fold, at or about 50 fold, at or about 100 fold, at or about 1000 fold or more of the expression of endogenous FOXP3 gene of the cell. Also, in some embodiments, the activity of introduced FOXP3-encoding sequence products, including functional derivatives of the FOXP3, in the genome-edited cell can be comparable to or more than the activity of endogenous FOXP3 gene products in a normal, healthy cell.

In one embodiment $CD34^+$ cells are genetically modified ex vivo and then re-introduced into the subject where they will give rise to genetically modified T cells that express the inserted FOXP3 gene.

Methods of Making

In some embodiments, a method of making a genetically engineered cell is provided, the method comprising providing a $CD34^+$ cell, wherein the $CD34^+$ cell comprises a first nucleic acid comprising at least one locus, providing a Cas endonuclease (e.g., a Cas9 endonuclease) or a second nucleic acid encoding a Cas endonuclease, introducing the Cas endonuclease or the second nucleic acid into the $CD34^+$ cell, introducing a third nucleic acid encoding at least one gRNA or a set of nucleic acids encoding at least one gRNA, wherein the at least one gRNA is configured to hybridize to the at least one locus; and introducing a fourth nucleic acid into the CD34$^+$ cell, wherein the fourth nucleic acid comprises a gene delivery cassette.

In some embodiments, according to a method of making a genetically engineered cell provided herein, the method further comprises activating the CD34$^+$ cell, wherein the activating is performed before the introducing of the second nucleic acid into the CD34$^+$ cell. In some embodiments, the activating is performed by contacting the CD34$^+$ cell with a cytokine selected from the group consisting of thrombopoietin (TPO), stem cell factor (SCF), FLT3L, and IL-6. The cytokine may be on a bead.

In some embodiments, according to a method of making a genetically engineered cell provided herein, the at least one locus is a FOXP3 gene, AAVS1 locus, or a TRA gene.

In some embodiments, the second nucleic acid, the third nucleic acid, the set of nucleic acids and/or the fourth nucleic acid is provided in one or more vectors. In some embodiments, the one or more vectors is a viral vector. In some embodiments, the viral vector is an Adeno-associated virus (AAV) vector. In some embodiments, the AAV vector is a self-complementary vector. In some embodiments, the AAV vector is a single stranded vector. In some embodiments, the AAV vector is a combination of a self-complementary vector and a single stranded vector.

In some embodiments, the second nucleic acid encoding the Cas endonuclease is an mRNA. In some embodiments, the at least one gRNA comprises a spacer sequence comprising a sequence as set forth in SEQ ID NO: 2, 3 or 5. In some embodiments, the second nucleic acid, the third nucleic acid, the set of nucleic acids and/or the fourth nucleic acid are codon optimized for expression in a eukaryotic cell, such as a human cell. In some embodiments, the fourth nucleic acid comprises a sequence encoding a human codon optimized FOXP3 cDNA sequence. In some embodiments, the fourth nucleic acid further comprises a promoter. In some embodiments, the promoter is an MND promoter, a PGK promoter, or an E2F promoter. In some embodiments, the fourth nucleic acid further comprises a sequence encoding a low affinity nerve growth factor receptor coding sequence (LNGFR), μCISC, CISCγ, FRB or LNGFRe (LNGFR epitope coding sequence). In some embodiments, the fourth nucleic acid further comprises a sequence encoding a low affinity nerve growth factor receptor coding sequence (LNGFR) or LNGFRe (LNGFR epitope coding sequence).

In some embodiments, the method further comprises introducing a fifth nucleic acid into the CD34$^+$ cell, wherein the fifth nucleic acid comprises a second gene delivery cassette. In some embodiments, the fifth nucleic acid is comprised in a vector. In some embodiments, the vector is an AAV vector. In some embodiments, the fifth nucleic acid comprises a sequence encoding CISC, FRB, a marker protein, μCISC, and/or βCISC. In some embodiments, the fifth nucleic acid comprises a sequence encoding a marker protein. In some embodiments, the fourth and or the fifth sequence further comprises a sequence encoding a P2A self-cleaving peptide. In some embodiments, the fourth and or the fifth sequence further comprises a sequence encoding a polyA sequence. In some embodiments, the polyA sequence comprises a SV40polyA or 3'UTR of FOXP3. In some embodiments, the fourth sequence comprises a sequence set forth in any one of SEQ ID NO: 37-42.

In some embodiments, a fourth sequence and a fifth sequence are introduced into the CD34$^+$ cell, wherein the fourth and fifth sequence comprise a sequence that encodes an expression cassette configured to express: FOXP3cDNA-LNGFR and DISC, FOXP3cDNA-LNGFR and μDISC, LNGFR-FOXP3cDNA and DISC, LNGFR-FOXP3cDNA and μDISC, CISCβ-DN and CISCγ-FOXP3cDNA-LNGFR, or CISCβ-DN and CISCγ-LNGFR-FOXP3cDNA, respectively.

In some embodiments, the fourth nucleic acid comprises at least one homology arm with a locus specific sequence, wherein the homology arm length is configured for efficient packaging into an AAV vector.

In some embodiments, the at least one homology arm comprises a length of 0.25, 0.3, 0.45, 0.6 or 0.8 kb or any length in between a range defined by any two aforementioned values.

In some embodiments, the marker is LNGF, RQR8 or EGFRt.

In some embodiments, the method further comprises introducing into the CD34$^+$ cell a sixth nucleic acid encoding a protein or cytokine for co-expression with FOXP3.

In some embodiments, the method further comprises selecting the CD34$^+$ cells by enrichment of the marker.

In some embodiments, the CD34$^+$ cell is contacted with a medium comprising hTPO, hFlt3, hSCF or hIL6.

In some embodiments, a CD34$^+$ cell for expression of FOXP3 is provided, wherein the cell is manufactured by the method of any one of the embodiments herein. In some embodiments, FOXP3 is expressed constitutively or the expression is regulated.

In some embodiments, a CD34$^+$ cell for expression of FOXP3 is provided, the CD34$^+$ cell comprising a nucleic acid encoding a gene encoding FOXP3. In some embodiments, the gene encoding FOXP3 is introduced in a FOXP3 gene or a non-FOXP3 locus. In some embodiments, the non-FOXP3 locus is an AAVS1 locus or a TRA gene.

In some embodiments, the CD34$^+$ cell expresses CISCβ: FRB-IL2Rβ, DISC, CISC-FRB, μDISC, μCISC-FRB, FRB, LNGFR or LNGFRe. In some embodiments, the CD34$^+$ cell comprises a Treg phenotype.

In some embodiments, a composition comprising the CD34$^+$ cell of any one of the embodiments is provided.

In some embodiments, a method for treating, ameliorating, and/or inhibiting a disease and/or a condition in a subject is provided, the method comprising: providing to a subject having a disease and/or a condition the CD34$^+$ cell or the composition of any one of the embodiments herein. In some embodiments, the disease is an autoimmune disease. In some embodiments, the disease is immunodysregulation polyendocrinopathy enteropathy X-linked (IPEX) syndrome. In some embodiments, the condition is Graft-versus-Host Disease (GVHD).

In the embodiments herein, a method of making a genetically engineered cell is provided, the method comprising: providing a CD34$^+$ cell, wherein the CD34$^+$ cell comprises a first nucleic acid comprising at least one locus; providing a Cas endonuclease (e.g., a Cas9 endonuclease) or a second nucleic acid encoding a Cas endonuclease; introducing the Cas endonuclease or the second nucleic acid into the CD34$^+$ cell; introducing a third nucleic acid encoding at least one CRISPR spacer sequence or a set of nucleic acids encoding at least one CRISPR spacer sequence, wherein the at least one CRISPR spacer sequence is configured to hybridize to the at least one locus; and introducing a fourth nucleic acid into the CD34$^+$ cell, wherein the fourth nucleic acid comprises a gene delivery cassette. In some embodiments, the fourth nucleic acid further comprises a promoter. In some embodiments, the promoter is a MND promoter, a PGK promoter or an E2F promoter. In some embodiments, the promoter is a MND promoter. As described in the embodiments herein, the MND promoter is provided in the vector #3008 (pAAV_FoxP3.0.6 kb.MND.GFP.WPRE3.pA) (SEQ ID NO: 33).

In some embodiments, the cells differentiate into T cells, and the T cells express FOXP3. In some embodiments, the endogenous FOXP3 promoter drives expression of the introduced FOXP3 cDNA.

A weak promoter produces less mRNA expression than a stronger promoter, if both are driving expression of the same coding sequences. This can be compared by analyzing, for example, an agarose gel. An example of promoters subject to regulation by proximal chromatin is the EF1alpha short promoter, which is highly active in some loci, but nearly inactive in other loci (Eyquem, J. et al. (2013). *Biotechnol. Bioeng.,* 110(8):2225-2235).

Therapeutic Approach

One aspect provided herein is a gene therapy approach for providing therapy to a subject having or suspected of having a disorder or health condition associated with a FOXP3 protein by editing the genome of the subject. For example, in some embodiments, the disorder or health condition is an autoimmune disease (e.g., IPEX syndrome) or a disorder that results from organ transplant (e.g., GVHD). In some embodiments, the gene therapy approach integrates a nucleic acid comprising a sequence encoding a functional FOXP3 gene into the genome of a relevant cell type in subjects and this can provide a permanent cure for the disorder or health condition. In some embodiments, a cell type subject to the gene therapy approach in which to integrate the FOXP3-encoding sequence is the $CD34^+$ cell, e.g., $CD34^+$ hematopoietic stem cell, because these cells can efficiently differentiate into T cells in the subject.

In another aspect, provided herein are cellular, ex vivo and in vivo methods for using genome engineering tools to create permanent changes to a cell genome by knocking-in a coding sequence encoding a FOXP3 or a functional derivative thereof into a gene locus in the cell genome and restoring FOXP3 activity. Such methods use endonucleases, such as CRISPR-associated (CRISPR/Cas9, Cpf1, and the like) nucleases, to permanently delete, insert, edit, correct, or replace any sequences from the cell genome or insert an exogenous sequence, e.g., a FOXP3-encoding sequence, in a genomic locus in the cell. In this way, the examples set forth in the present disclosure restore the activity of FOXP3 with a single therapeutic step (rather than requiring the delivery of alternative therapies for the lifetime of the subject).

In some embodiments, an ex vivo cell-based therapy is performed using a $CD34^+$ cell that is isolated from a subject, e.g., a $CD34^+$ cell derived from cord blood. Next, the chromosomal DNA of these cells is edited using the systems, compositions, and methods described herein. Finally, the edited cells are implanted into the subject.

One benefit of an ex vivo cell therapy approach is the ability to conduct a comprehensive analysis of the therapeutic prior to administration. All nuclease-based therapeutics have some level of off-target effects. Performing gene correction ex vivo allows one to fully characterize the corrected cell population prior to implantation. Aspects of the disclosure include sequencing the entire genome of the corrected cells to ensure that the off-target cuts, if any, are in genomic locations associated with minimal risk to the subject. Furthermore, populations of specific cells, including clonal populations, can be isolated prior to implantation.

Another embodiment of such methods is an in vivo based therapy. In this method, the chromosomal DNA of the cells in the subject is corrected using the systems, compositions, and methods described herein. In some embodiments, the cells are $CD34^+$ cells.

A benefit of in vivo gene therapy is the ease of therapeutic production and administration. The same therapeutic approach and therapy can be used to treat more than one subject, for example a number of subjects who share the same or similar genotype or allele. In contrast, ex vivo cell therapy generally uses a subject's own cells, which are isolated, manipulated, and returned to the same subject.

In some embodiments, the subject who is in need of the therapy in accordance with the disclosure herein is a subject having symptoms of a disease or condition associated with a FOXP3. For example, in some embodiments, the subject has symptoms of an autoimmune disease (e.g., IPEX syndrome) or a disorder that results from organ transplant (e.g., GVHD). In some embodiments, the subject can be a human suspected of having the disease or condition. Alternatively, the subject can be a human diagnosed with a risk of the disease or condition. In some embodiments, the subject who is in need of the therapy can have one or more genetic defects (e.g., deletion, insertion, and/or mutation) in the endogenous FOXP3 gene or its regulatory sequences such that the activity including the expression level or functionality of the FOXP3 is substantially reduced compared to a normal, healthy subject.

In some embodiments, provided herein is a method of treating or inhibiting a disease or condition associated with a FOXP3 (e.g., an autoimmune disease) in a subject, the method comprising providing the following to a cell in the subject: (a) a guide RNA (gRNA) targeting the FOXP3 gene in the cell genome; (b) a DNA endonuclease or nucleic acid encoding said DNA endonuclease; and (c) a donor template comprising a nucleic acid sequence encoding a FOXP3 or a functional derivative thereof. In some embodiments, the gRNA targets a FOXP3 gene, AAVS1 locus or a TRA gene. In some embodiments, the gRNA comprises a spacer sequence from any one of SEQ ID NOs: 1-7, 15-20, and 27-29.

In some embodiments, provided herein is a method of treating or inhibiting a disease or condition associated with FOXP3 (e.g., an autoimmune disease) in a subject, the method comprising providing the following to a cell in the subject: (a) a gRNA comprising a spacer sequence that is complementary to a genomic sequence within or near an endogenous FOXP3 gene in the cell; (b) a DNA endonuclease or nucleic acid encoding said DNA endonuclease; and (c) a donor template comprising a nucleic acid sequence encoding the FOXP3 or a functional derivative thereof. In some embodiments, the gRNA comprises a spacer sequence from any one of SEQ ID NOs: 1-7 and 27-29 or a variant thereof having no more than 3 mismatches compared to any one of SEQ ID NOs: 1-7 and 27-29. In some embodiments, the gRNA comprises a spacer sequence from any one of SEQ ID NOs: 1-7 or a variant thereof having no more than 3 mismatches compared to any one of SEQ ID NOs: 1-7. In some embodiments, the gRNA comprises a spacer sequence from any one of SEQ ID NOs: 2, 3, and 5 or a variant thereof having no more than 3 mismatches compared to any one of SEQ ID NOs: 2, 3, and 5. In some embodiments, the gRNA comprises a spacer sequence from SEQ ID NO: 2 or a variant thereof having no more than 3 mismatches compared to SEQ ID NO: 2. In some embodiments, the gRNA comprises a spacer sequence from SEQ ID NO: 5 or a variant thereof having no more than 3 mismatches compared to SEQ ID NO: 5. In some embodiments, the cell is a human cell, e.g., a human stem cell, for example a human $CD34^+$ hematopoietic stem cell. In some embodiments, the subject is a patient having or suspected of having an autoimmune disease, e.g., IPEX syndrome or Graft-versus-Host disease. In some embodiments, the subject is diagnosed with a risk of an autoimmune disease, e.g., IPEX syndrome or Graft-versus-Host disease.

In some embodiments, provided herein is a method of treating or inhibiting a disease or condition associated with FOXP3 (e.g., an autoimmune disease) in a subject, the method comprising providing to the subject a genetically modified cell prepared by any of the methods of editing a genome in a cell described herein. In some embodiments, the nucleic acid sequence encoding a FOXP3 or a functional derivative thereof is expressed under the control of the endogenous FOXP3 promoter. In some embodiments, the nucleic acid sequence encoding a FOXP3 or a functional derivative thereof is codon-optimized for expression in the cell. In some embodiments, the cell is a $CD34^+$ cell. In some embodiments, the genetically modified cell is autologous to the subject. In some embodiments, the method further comprises obtaining a biological sample from the subject, wherein the biological sample comprises an input cell, and wherein the genetically modified cell is prepared from the input cell. In some embodiments, the input cell is a $CD34^+$ cell.

Some embodiments include a medicament for use in treating or inhibiting a disease or condition associated with FOXP3 (e.g., an autoimmune disease) in a subject. More embodiments concern a genetically modified $CD34^+$ cell in which the genome of the cell is edited by one of the methods described herein for use in inhibiting or treating a disease or condition associated with FOXP3, such as an inflammatory disease or an autoimmune disease. Additional embodiments concern use of a genetically modified $CD34^+$ cell in which the genome of the cell is edited by any one of the methods herein as a medicament.

Implanting Cells into a Subject

In some embodiments, the ex vivo methods of the disclosure involve implanting the genome-edited cells into a subject who is in need of such method. This implanting step can be accomplished using any method of implantation known in the art. For example, the genetically modified cells can be injected directly in the subject's blood or otherwise administered to the subject.

In some embodiments, the methods disclosed herein include administering, which can be interchangeably used with "introducing" and "transplanting," genetically modified, therapeutic cells into a subject, by a method or route that results in at least partial localization of the introduced cells at a desired site such that a desired effect(s) is produced. The therapeutic cells or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, e.g., long-term engraftment.

When provided prophylactically, the therapeutic cells described herein can be administered to a subject in advance of any symptom of a disease or condition associated with a FOXP3 (e.g., an autoimmune disease, such as IPEX syndrome). Accordingly, in some embodiments the prophylactic administration of a genetically modified stem cell population serves to prevent the occurrence of symptoms of the disease or condition.

When provided therapeutically in some embodiments, genetically modified stem cells are provided at (or after) the onset of a symptom or indication of a disease or condition associated with a FOXP3 (e.g., an autoimmune disease, such as IPEX syndrome), e.g., upon the onset of disease or condition.

For use in the various embodiments described herein, an effective amount of therapeutic cells, e.g., genome-edited stem cells, can be at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof. The therapeutic cells can be derived from one or more donors or can be obtained from an autologous source. In some embodiments described herein, the therapeutic cells are expanded in culture prior to administration to a subject in need thereof.

In some embodiments, modest and incremental increases in the levels of functional FOXP3 expressed in cells of subjects having a disease or condition associated with the FOXP3 (e.g., IPEX syndrome) can be beneficial for ameliorating one or more symptoms of the disease or condition, for increasing long-term survival, and/or for reducing side effects associated with other treatments. Upon administration of such cells to human subjects, the presence of therapeutic cells that are producing increased levels of functional FOXP3 is beneficial. In some embodiments, effective treatment of a subject gives rise to at least or at least about 1%, 3%, 5%, or 7% functional FOXP3 relative to total FOXP3 in the treated subject. In some embodiments, functional FOXP3 is at least or at least about 10% of total FOXP3. In some embodiments, functional FOXP3 is at least, about, or at most 20%, 30%, 40%, 50%, 60%, 70%, 80%, 90%, or 100% of total FOXP3. Similarly, the introduction of even relatively limited subpopulations of cells having significantly elevated levels of functional FOXP3 can be beneficial in various subjects because in some situations normalized cells will have a selective advantage relative to diseased cells. However, even modest levels of therapeutic cells with elevated levels of functional FOXP3 can be beneficial for ameliorating one or more aspects of the disease or condition in subjects. In some embodiments, at or about 10%, at or about 20%, at or about 30%, at or about 40%, at or about 50%, at or about 60%, at or about 70%, at or about 80%, at or about 90% or more of the therapeutic in subjects to whom such cells are administered are producing increased levels of functional FOXP3.

In embodiments, the delivery of a therapeutic cell composition (e.g., a composition comprising a plurality of cells according to any of the cells described herein) into a subject by a method or route results in at least partial localization of the cell composition at a desired site. A cell composition can be administered by any appropriate route that results in effective treatment in the subject, e.g., administration results in delivery to a desired location in the subject where at least a portion of the composition delivered, e.g., at least $1\times10^4$ cells, is delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerobrospinal, or intrasternal injection or infusion. In some embodiments, the route is intravenous. For the delivery of cells, administration by injection or infusion can be made.

In one embodiment, the cells are administered systemically, in other words a population of therapeutic cells are administered other than directly into a target site, tissue, or organ, such that it enters, instead, the subject's circulatory system and, thus, is subject to metabolism and other like processes.

The efficacy of a therapy having a composition for the treatment or inhibition of a disease or condition associated with a FOXP3 (e.g., IPEX syndrome) can be determined by the skilled clinician. However, a therapy is considered effective if any one or all of the signs or symptoms of, as but one example, levels of functional FOXP3 are altered in a beneficial manner (e.g., increased by at least 10%), or other clinically accepted symptoms or markers of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Therapy includes any treatment or inhibition of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

Compositions

In one aspect, the present disclosure provides compositions for carrying out the methods disclosed herein. A composition can include one or more of the following: a genome-targeting nucleic acid (e.g., a gRNA); a site-directed polypeptide (e.g., a DNA endonuclease) or a nucleotide sequence encoding the site-directed polypeptide; and a polynucleotide to be inserted (e.g., a donor template) to effect the desired genetic modification of the methods disclosed herein.

In some embodiments, a composition has a nucleotide sequence encoding a genome-targeting nucleic acid (e.g., a gRNA).

In some embodiments, a composition has a site-directed polypeptide (e.g. DNA endonuclease). In some embodiments, a composition has a nucleotide sequence encoding the site-directed polypeptide.

In some embodiments, a composition has a polynucleotide (e.g., a donor template) to be inserted into a genome.

In some embodiments, a composition has (i) a nucleotide sequence encoding a genome-targeting nucleic acid (e.g., a gRNA) and (ii) a site-directed polypeptide (e.g., a DNA endonuclease) or a nucleotide sequence encoding the site-directed polypeptide.

In some embodiments, a composition has (i) a nucleotide sequence encoding a genome-targeting nucleic acid (e.g., a gRNA) and (ii) a polynucleotide (e.g., a donor template) to be inserted into a genome.

In some embodiments, a composition has (i) a site-directed polypeptide (e.g., a DNA endonuclease) or a nucleotide sequence encoding the site-directed polypeptide and (ii) a polynucleotide (e.g., a donor template) to be inserted into a genome.

In some embodiments, a composition has (i) a nucleotide sequence encoding a genome-targeting nucleic acid (e.g., a gRNA), (ii) a site-directed polypeptide (e.g., a DNA endonuclease) or a nucleotide sequence encoding the site-directed polypeptide and (iii) a polynucleotide (e.g., a donor template) to be inserted into a genome.

In some embodiments of any of the above compositions, the composition has a single-molecule guide genome-targeting nucleic acid. In some embodiments of any of the above compositions, the composition has a double-molecule genome-targeting nucleic acid. In some embodiments of any of the above compositions, the composition has two or more double-molecule guides or single-molecule guides. In some embodiments, the composition has a vector that encodes the nucleic acid targeting nucleic acid. In some embodiments, the genome-targeting nucleic acid is configured to be used with a DNA endonuclease, in particular, a Cas endonuclease (e.g., a Cas9 endonuclease).

In some embodiments, a composition can include one or more gRNAs that can be used for genome-edition, in particular, insertion of a sequence encoding a FOXP3 or a derivative thereof into a genome of a cell. The one or more gRNAs can target a genomic site at, within, or near the endogenous FOXP3 gene. Therefore, in some embodiments, the one or more gRNAs can have a spacer sequence complementary to a genomic sequence at, within, or near a FOXP3 gene.

In some embodiments, a gRNA for a composition comprises a spacer sequence selected from any one of SEQ ID NOs: 1-7, 15-20, or 27-29, and variants thereof having at least or at least about 50%, at or about 55%, at or about 60%, at or about 65%, at or about 70%, at or about 75%, at or about 80%, at or about 85%, at or about 90% or at or about 95% identity or homology to any one of SEQ ID NOs: 1-7, 15-20, or 27-29. In some embodiments, the variants of gRNA for the kit comprise a spacer sequence having at least or at least about 85%, 90%, 91%, 92%, 93%, 94%, 95%, 96%, 97%, 98%, or 99% sequence identity to any one of SEQ ID NOs: 1-7, 15-20, or 27-29.

In some embodiments, a gRNA for a composition has a spacer sequence that is complementary to a target site in the genome. In some embodiments, the spacer sequence is 15 bases to 20 bases in length. In some embodiments, a complementarity between the spacer sequence to the genomic sequence is at least 80%, at least 85%, at least 90%, at least 95%, at least 96%, at least 97%, at least 98%, at least 99% or at least 100%.

In some embodiments, a composition can have a DNA endonuclease or a nucleic acid encoding the DNA endonuclease and/or a donor template having a nucleic acid sequence encoding a FOXP3 or a functional derivative thereof. In some embodiments, the DNA endonuclease is a Cas endonuclease (e.g., a Cas9 endonuclease). In some embodiments, the nucleic acid encoding the DNA endonuclease is DNA or RNA.

In some embodiments, one or more of any nucleic acids for the kit can be encoded in an Adeno Associated Virus (AAV) vector. Therefore, in some embodiments, a gRNA can be encoded in an AAV vector. In some embodiments, a nucleic acid encoding a DNA endonuclease can be encoded in an AAV vector. In some embodiments, a donor template can be encoded in an AAV vector. In some embodiments, two or more nucleic acids can be encoded in a single AAV vector. Thus, in some embodiments, a gRNA sequence and a DNA endonuclease-encoding nucleic acid can be encoded in a single AAV vector.

In some embodiments, a composition can have a liposome or a lipid nanoparticle. Therefore, in some embodiments, any compounds (e.g., a DNA endonuclease or a nucleic acid encoding thereof, gRNA, and donor template) of the composition can be formulated in a liposome or lipid nanoparticle. In some embodiments, one or more such compounds are associated with a liposome or lipid nanoparticle via a covalent bond or non-covalent bond. In some embodiments, any of the compounds can be separately or together contained in a liposome or lipid nanoparticle. Therefore, in some embodiments, each of a DNA endonuclease or a nucleic acid encoding thereof, gRNA, and donor template is separately formulated in a liposome or lipid nanoparticle. In some embodiments, a DNA endonuclease is formulated in a liposome or lipid nanoparticle with gRNA. In some embodiments, a DNA endonuclease or a nucleic acid encoding thereof, gRNA, and donor template are formulated in a liposome or lipid nanoparticle together.

In some embodiments, a composition described above further has one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. In some embodiments, a composition can also include one or more components that can be used to facilitate or enhance the on-target binding or the cleavage of DNA by the endonuclease, or improve the specificity of targeting.

In some embodiments, any components of a composition are formulated with pharmaceutically acceptable excipients such as carriers, solvents, stabilizers, adjuvants, diluents, etc., depending upon the particular mode of administration and dosage form. In embodiments, guide RNA compositions are generally formulated to achieve a physiologically compatible pH, and range from a pH of or about 3 to a pH of or about 11, of or about pH 3 to or to about pH 7, depending on the formulation and route of administration. In some embodiments, the pH is adjusted to a range from or from about pH 5.0 to or to about pH 8. In some embodiments, the composition has a therapeutically effective amount of at least one compound as described herein, together with one or more pharmaceutically acceptable excipients. Optionally, the composition can have a combination of the compounds described herein, or can include a second active ingredient useful in the treatment or prevention of bacterial growth (for example and without limitation, anti-bacterial or anti-microbial agents), or can include a combination of reagents of the disclosure. In some embodiments, gRNAs are formulated with other one or more nucleic acids, e.g., nucleic acid encoding a DNA endonuclease and/or a donor template. Alternatively, a nucleic acid encoding a DNA endonuclease and a donor template, separately or in combination with other nucleic acids, are formulated with the method described above for gRNA formulation.

Suitable excipients can include, for example, carrier molecules that include large, slowly metabolized macromolecules such as proteins, polysaccharides, polylactic acids, polyglycolic acids, polymeric amino acids, amino acid copolymers, or inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, or hydroxyalkylmethylcellulose), stearic acid, liquids (for example and without limitation, oils, water, saline, glycerol, or ethanol), wetting or emulsifying agents, or pH buffering substances, and the like.

In some embodiments, any compounds (e.g., a DNA endonuclease or a nucleic acid encoding thereof, gRNA, and donor template) of a composition can be delivered into a cell via transfection, such as chemical transfection (e.g., lipofection) or electroporation. In some embodiments, a DNA endonuclease can be pre-complexed with a gRNA, forming a ribonucleoprotein (RNP) complex, prior to the provision to the cell. In some embodiments, the RNP complex is delivered into the cell via transfection. In such embodiments, the donor template is delivered into the cell via transfection.

In some embodiments, a composition refers to a therapeutic composition having therapeutic cells that are used in an ex vivo treatment method.

In embodiments, therapeutic compositions contain a physiologically tolerable carrier together with the cell composition, and optionally at least one additional bioactive agent as described herein, dissolved or dispersed therein as an active ingredient. In some embodiments, the therapeutic composition is not substantially immunogenic when administered to a mammal or human subject for therapeutic purposes, unless so desired.

In general, the genetically modified, therapeutic cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation having cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

In some embodiments, a cell composition can also be emulsified or presented as a liposome composition, provided that the emulsification procedure does not adversely affect cell viability. The cells and any other active ingredient can be mixed with one or more excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, or mandelic, and the like. Salts formed with the free carboxyl groups can also be derived from inorganic bases, such as, for example, sodium, potassium, ammonium, calcium, or ferric hydroxides, or such organic bases as isopropylamine, trimethylamine, 2-ethylamino ethanol, histidine, or procaine, and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium or potassium chlorides, dextrose, or polyethylene glycol and other solutes. Liquid compositions can also contain liquid phases in addition to and to the exclusion of water. Exemplary of such additional liquid phases are glycerin, vegetable oils such as cottonseed oil, or water-oil emulsions. The amount of an active compound used in the cell compositions that is effective in the treatment of a particular disorder or condition will depend on the nature of the disorder or condition, and can be determined by known clinical techniques.

Kits

Some embodiments provide a kit that contains any of the above-described compositions, e.g., a composition for genome edition or a cell composition (e.g., a therapeutic cell composition), and one or more additional components.

In some embodiments, a kit can have one or more additional therapeutic agents that can be administered simultaneously or in sequence with the composition for a desired purpose, e.g., genome edition or cell therapy.

In some embodiments, a kit can further include instructions for using the components of the kit to practice the methods. The instructions for practicing the methods are generally recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), can be provided. An example of this embodiment is a kit that includes a web address where the instructions can be viewed and/or from which the instructions can be downloaded. As with the instructions, this means for obtaining the instructions can be recorded on a suitable substrate.

Further Embodiments

In some embodiments, a method of making a genetically engineered cell is provided, the method comprising: providing a $CD34^+$ cell, wherein the $CD34^+$ cell comprises a first nucleic acid comprising at least one locus; providing a CAS9 protein or a second nucleic acid encoding a CAS9 protein; introducing the CAS9 protein or the second nucleic acid into the $CD34^+$ cell; introducing a third nucleic acid encoding at least one CRISPR spacer sequence or a set of nucleic acids encoding at least one CRISPR spacer sequence, wherein the at least one CRISPR spacer sequence is configured to hybridize to the at least one locus; and introducing a fourth nucleic acid into the $CD34^+$ cell, wherein the fourth nucleic acid comprises a gene delivery cassette.

In some embodiments, the method further comprises activating the $CD34^+$ cell, wherein the activating is performed before the introducing of the second nucleic acid into the $CD34^+$ cell. In some embodiments, activating is performed by contacting the $CD34^+$ cell with a cytokine selected from the group consisting of thrombopoietin (TPO), stem cell factor (SCF), FLT3L, and IL-6. In some embodiments, the at least one locus is a FOXP3 gene, AAVS1 locus or a TRA gene. In some embodiments, the second nucleic acid, the third nucleic acid, the set of nucleic acids and/or the fourth nucleic acid is provided in one or more vectors. In some embodiments, the one or more vectors is a viral vector. In some embodiments, the viral vector is an Adeno-associated virus (AAV) vector.

In some embodiments, the AAV vector is a self-complementary vector. In some embodiments, the AAV vector is a single stranded vector. In some embodiments, the AAV vector is a combination of a self-complementary vector and a single stranded vector. In some embodiments, the second nucleic acid encoding the CAS9 protein is an mRNA. In some embodiments, the at least one spacer sequence comprises a sequence as set forth in SEQ ID NO: 2, 3 or 5. In some embodiments, the second nucleic acid, the third nucleic acid, the set of nucleic acids and/or the fourth nucleic acid are codon optimized for expression in a eukaryotic cell, such as a human. In some embodiments, the fourth nucleic acid comprises a sequence encoding a human codon optimized FOXP3 cDNA sequence. In some embodiments, the fourth nucleic acid further comprises a promoter. In some embodiments, the promoter is a MND promoter, a PGK promoter or an E2F promoter. In some embodiments, the fourth nucleic acid further comprises a sequence encoding a low affinity nerve growth factor receptor coding sequence (LNGFR), μCISC, CISCγ, FRB and/or LNGFRe (LNGFR epitope coding sequence). In some embodiments, the fourth nucleic acid further comprises a sequence encoding a low affinity nerve growth factor receptor coding sequence (LNGFR) and/or LNGFRe (LNGFR epitope coding sequence).

In some embodiments, the method further comprises introducing a fifth nucleic acid into the $CD34^+$ cell, wherein the fifth nucleic acid comprises a second gene delivery cassette. In some embodiments, the fifth nucleic acid is comprised in a vector. In some embodiments, the vector is an AAV vector. In some embodiments, the fifth nucleic acid comprises a sequence encoding CISC, FRB, a marker protein, μCISC, and/or βCISC. In some embodiments, the fifth nucleic acid comprises a sequence encoding a marker protein. In some embodiments, the fourth and or the fifth nucleic acid further comprises a sequence encoding a P2A self-cleaving peptide. In some embodiments, the fourth and or the fifth nucleic acid further comprises a sequence encoding a polyA sequence. In some embodiments, the polyA sequence comprises a SV40polyA or 3'UTR of FOXP3. In some embodiments, the fourth nucleic acid comprises a WPRE3 element. In some embodiments, the fourth and/or fifth nucleic acid are introduced into the $CD34^+$ cell, wherein the fourth and/or fifth nucleic acid comprises a sequence that encodes an expression cassette for expression of FOXP3cDNA-LNGFR and DISC, FOXP3cDNA-LNGFR and μDISC, LNGFR-FOXP3cDNA and DISC, LNGFR-FOXP3cDNA and μDISC, CISCβ-DN and CISCγ-FOXP3cDNA-LNGFR, or CISCβ-DN and CISCγ-LNGFR-FOXP3cDNA, respectively. In some embodiments, the fourth and/or fifth nucleic acid are introduced into the $CD34^+$ cell, wherein the fourth and/or fifth nucleic acid comprises a sequence that encodes an expression cassette. In some embodiments, the fourth nucleic acid comprises at least one homology arm with a locus specific sequence, wherein the homology arm length is configured for efficient packaging into an AAV vector. In some embodiments, the at least one homology arm comprises a length of 0.25, 0.3, 0.45, 0.6, 0.8 kb or 1 kb or any length in between a range defined by any two aforementioned values. In some embodiments, the marker is LNGF, RQR8 or EGFRt. In some embodiments, the method further comprises introducing into the $CD34^+$ cell a sixth nucleic acid encoding a protein or cytokine for co-expression with FOXP3. In some embodiments, the protein or cytokine is a T cell receptor, chimeric antigen receptor, or IL10. In some embodiments, the fourth nucleic acid comprises a sequence set forth in SEQ ID NO: 34 or 36. In some embodiments, the method further comprises selecting the $CD34^+$ cells by enrichment of the marker. In some embodiments, the CD34$^+$ cell is contacted with a medium comprising hTPO, hFlt3, hSCF and/or hIL6.

In some embodiments, a CD34$^+$ cell for expression of FOXP3 is provided, wherein the cell is manufactured by the method of any one of the embodiments described herein. In some embodiments, FOXP3 is expressed constitutively or the expression is regulated. The method comprises: providing a CD34$^+$ cell, wherein the CD34$^+$ cell comprises a first nucleic acid comprising at least one locus; providing a CAS9 protein or a second nucleic acid encoding a CAS9 protein; introducing the CAS9 protein or the second nucleic acid into the CD34$^+$ cell; introducing a third nucleic acid encoding at least one CRISPR spacer sequence or a set of nucleic acids encoding at least one CRISPR spacer sequence, wherein the at least one CRISPR spacer sequence is configured to hybridize to the at least one locus; and introducing a fourth nucleic acid into the CD34$^+$ cell, wherein the fourth nucleic acid comprises a gene delivery cassette. In some embodiments, the method further comprises activating the CD34$^+$ cell, wherein the activating is performed before the introducing of the second nucleic acid into the CD34$^+$ cell. In some embodiments, the activating is performed by contacting the CD34$^+$ cell with a cytokine selected from the group consisting of thrombopoietin (TPO), stem cell factor (SCF), FLT3L, and IL-6. In some embodiments, the at least one locus is a FOXP3 gene, AAVS1 locus or a TRA gene. In some embodiments, the second nucleic acid, the third nucleic acid, the set of nucleic acids and/or the fourth nucleic acid is provided in one or more vectors. In some embodiments, the one or more vectors is a viral vector. In some embodiments, the viral vector is an Adeno-associated virus (AAV) vector. In some embodiments, the AAV vector is a self-complementary vector. In some embodiments, the AAV vector is a single stranded vector. In some embodiments, the AAV vector is a combination of a self-complementary vector and a single stranded vector. In some embodiments, the second nucleic acid encoding the CAS9 protein is an mRNA. In some embodiments, the at least one spacer sequence comprises a sequence as set forth in SEQ ID NO: 2, 3 or 5. In some embodiments, the second nucleic acid, the third nucleic acid, the set of nucleic acids and/or the fourth nucleic acid are codon optimized for expression in a eukaryotic cell, such as a human. In some embodiments, the fourth nucleic acid comprises a sequence encoding a human codon optimized FOXP3 cDNA sequence. In some embodiments, the fourth nucleic acid further comprises a promoter. In some embodiments, the promoter is a MND promoter, a PGK promoter or an E2F promoter. In some embodiments, the fourth nucleic acid further comprises a sequence encoding a low affinity nerve growth factor receptor coding sequence (LNGFR), μCISC, CISCγ, FRB and/or LNGFRe (LNGFR epitope coding sequence). In some embodiments, the fourth nucleic acid further comprises a sequence encoding a low affinity nerve growth factor receptor coding sequence (LNGFR) and/or LNGFRe (LNGFR epitope coding sequence). In some embodiments, the method further comprises introducing a fifth nucleic acid into the CD34$^+$ cell, wherein the fifth nucleic acid comprises a second gene delivery cassette. In some embodiments, the fifth nucleic acid is comprised in a vector. In some embodiments, the vector is an AAV vector. In some embodiments, the fifth nucleic acid comprises a sequence encoding CISC, FRB, a marker protein, μCISC, and/or βCISC. In some embodiments, the fifth nucleic acid comprises a sequence encoding a marker protein. In some embodiments, the fourth and or the fifth nucleic acid further comprises a sequence encoding a P2A self-cleaving peptide. In some embodiments, the fourth and/or the fifth nucleic acid further comprises a sequence encoding a polyA sequence. In some embodiments, the polyA sequence comprises a SV40polyA or 3'UTR of FOXP3. In some embodiments, the fourth nucleic acid comprises a WPRE3 element. In some embodiments, the fourth and/or fifth nucleic acid are introduced into the CD34$^+$ cell, wherein the fourth and/or fifth nucleic acid comprises a sequence that encodes an expression cassette for expression of FOXP3cDNA-LNGFR and DISC, FOXP3cDNA-LNGFR and μDISC, LNGFR-FOXP3cDNA and DISC, LNGFR-FOXP3cDNA and μDISC, CISCβ-DN and CISCγ-FOXP3cDNA-LNGFR, or CISCβ-DN and CISCγ-LNGFR-FOXP3cDNA, respectively. In some embodiments, the fourth and/or fifth nucleic acid are introduced into the CD34$^+$ cell, wherein the fourth and/or fifth nucleic acid comprises a sequence that encodes an expression cassette. In some embodiments, the fourth nucleic acid comprises at least one homology arm with a locus specific sequence, wherein the homology arm length is configured for efficient packaging into an AAV vector. In some embodiments, the at least one homology arm comprises a length of 0.25, 0.3, 0.45, 0.6, 0.8 kb or 1 kb or any length in between a range defined by any two aforementioned values. In some embodiments, the marker is LNGF, RQR8 or EGFRt. In some embodiments, the method further comprises introducing into the CD34$^+$ cell a sixth nucleic acid encoding a protein or cytokine for co-expression with FOXP3. In some embodiments, the protein or cytokine is a T cell receptor, chimeric antigen receptor, or IL10. In some embodiments, the fourth nucleic acid comprises a sequence set forth in SEQ ID NO: 34 or 36. In some embodiments, the method further comprises selecting the CD34$^+$ cells by enrichment of the marker. In some embodiments, the CD34$^+$ cell is contacted with a medium comprising hTPO, hFlt3, hSCF and/or hIL6.

In some embodiments, a CD34$^+$ cell for expression of FOXP3 is provided, the CD34$^+$ cell comprising: a nucleic acid encoding a gene encoding FOXP3. In some embodiments, the gene encoding FOXP3 is introduced in a FOXP3 gene or a non-FOXP3 locus. In some embodiments, the non-FOXP3 locus is an AAVS1 locus or a TRA gene. In some embodiments, the CD34$^+$ cell expresses CISCβ: FRB-IL2Rβ, DISC, CISC-FRB, μDISC, μCISC-FRB, FRB, LNGFR and/or LNGFRe. In some embodiments, the CD34$^+$ cell leads to generation progenitors that differentiate within a thymus to generate T cells with a Treg phenotype.

In some embodiments, a composition comprising the CD34$^+$ cell of any one of the embodiments herein is provided.

In some embodiments, a method for treating, ameliorating, and/or inhibiting a disease and/or a condition in a subject is provided, the method comprising: providing to a subject having a disease and/or a condition the CD34$^+$ cell or the composition of any one of the embodiments described herein. In some embodiments, the disease is an autoimmune disease. In some embodiments, the disease is IPEX syndrome. In some embodiments, the condition is Graft-versus-Host Disease (GVHD).

Exemplary Embodiments

Embodiment 1. A method of making a genetically engineered cell, the method comprising: providing a CD34$^+$ cell, wherein the CD34$^+$ cell comprises a first nucleic acid comprising at least one targeted locus; providing a CAS9 protein or a second nucleic acid encoding a CAS9 protein; introducing the CAS9 protein or the second nucleic acid into the $CD34^+$ cell; introducing a third nucleic acid encoding at least one CRISPR spacer sequence or a set of nucleic acids encoding at least one CRISPR spacer sequence, wherein the at least one CRISPR spacer sequence is configured to hybridize to the at least one targeted locus; and introducing a fourth nucleic acid into the $CD34^+$ cell, wherein the fourth nucleic acid comprises a gene delivery cassette.

Embodiment 2. The method of Embodiment 1, wherein the method further comprises activating the $CD34^+$ cell, wherein the activating is performed before the introducing of the second nucleic acid into the $CD34^+$ cell.

Embodiment 3. The method of Embodiment 2, wherein the activating is performed by contacting the $CD34^+$ cell with CD3 and/or CD28.

Embodiment 4. The method of any one of Embodiments 1-3, wherein the at least one targeted locus is a FOXP3 gene, AAVS1 locus or a TRA gene.

Embodiment 5. The method of any one of Embodiments 1-4, wherein the second nucleic acid, the third nucleic acid, the set of nucleic acids and/or the fourth nucleic acid is provided in one or more vectors.

Embodiment 6. The method of Embodiment 5, wherein the one or more vectors is a viral vector.

Embodiment 7. The method of Embodiment 6, wherein the viral vector is an Adeno-associated virus (AAV) vector.

Embodiment 8. The method of Embodiment 7 wherein the AAV vector is a self-complementary vector.

Embodiment 9. The method of Embodiment 7 or 8 wherein the AAV vector is a single stranded vector.

Embodiment 10. The method of any one of Embodiments 7-9, wherein the AAV vector is a combination of a self-complementary vector and a single stranded vector.

Embodiment 11. The method of any one of Embodiments 1-4, wherein the second nucleic acid encoding the CAS9 protein is an mRNA.

Embodiment 12. The method of any one of Embodiments 1-11, wherein the at least one spacer sequence comprises a sequence as set forth in SEQ ID NO: 2, 3 or 5.

Embodiment 13. The method of any one of Embodiments 1-12, wherein the second nucleic acid, the third nucleic acid, the set of nucleic acids and/or the fourth nucleic acid are codon optimized for expression in a eukaryotic cell, such as a human.

Embodiment 14. The method of any one of Embodiments 1-13, wherein the fourth nucleic acid comprises a sequence encoding a human codon optimized FOXP3 cDNA sequence.

Embodiment 15. The method of Embodiment 13, wherein the fourth nucleic acid further comprises a promoter.

Embodiment 16. The method of Embodiment 15, wherein the promoter is a MND promoter, a PGK promoter or an E2F promoter.

Embodiment 17. The method of any one of Embodiments 14-16, wherein the fourth nucleic acid further comprises a sequence encoding a low affinity nerve growth factor receptor coding sequence (LNGFR) and/or LNGFRe (LNGFR epitope coding sequence).

Embodiment 18. The method of any one of Embodiments 1-17, wherein the method further comprises introducing a fifth nucleic into the $CD34^+$ cell, wherein the fifth nucleic acid comprises a second gene delivery cassette.

Embodiment 19. The method of Embodiment 18, wherein the fifth nucleic acid is comprised in a vector.

Embodiment 20. The method of Embodiment 18, wherein the vector is an AAV vector.

Embodiment 21. The method of any one of Embodiments 18-20, wherein the fifth nucleic acid comprises a sequence encoding a marker protein.

Embodiment 22. The method of any one of Embodiments 1-21, wherein the fourth and or the fifth nucleic acid further comprises a sequence encoding a P2A self-cleaving peptide.

Embodiment 23. The method of any one of Embodiments 1-22, wherein the fourth and or the fifth nucleic acid further comprises a sequence encoding a polyA sequence.

Embodiment 24. The method of Embodiment 23, wherein the polyA sequence comprises a SV40polyA or 3'UTR of FOXP3.

Embodiment 25. The method of any one of Embodiments 1-24, wherein the fourth nucleic acid comprises a WPRE3 element.

Embodiment 26. The method of any one of Embodiments 1-25, wherein the fourth and/or fifth nucleic acid are introduced into the $CD34^+$ cell, wherein the fourth and/or fifth nucleic acid comprises a sequence that encodes an expression cassette.

Embodiment 27. The method of any one of Embodiments 1-26, wherein the fourth nucleic acid comprises at least one homology arm with a locus specific sequence, wherein the homology arm length is configured for efficient packaging into an AAV vector.

Embodiment 28. The method of Embodiment 27, wherein the at least one homology arm comprises a length of 0.25, 0.3, 0.45, 0.6, 0.8 kb or 1 kb or any length in between a range defined by any two aforementioned values.

Embodiment 29. The method of any one of Embodiments 21-28, wherein the marker is LNGF, RQR8 or EGFRt.

Embodiment 30. The method of any one of Embodiments 1-29, wherein the method further comprises introducing into the $CD34^+$ cell a sixth nucleic acid encoding a protein or cytokine for co-expression with FOXP3.

Embodiment 31. The method of Embodiment 30, wherein the protein or cytokine is a T cell receptor, chimeric antigen receptor, or IL10.

Embodiment 32. The method of any one of Embodiments 1-31, wherein the fourth nucleic acid comprises a sequence set forth in SEQ ID NO: 34 or 36.

Embodiment 33. The method of any one of Embodiments 1-32, wherein the method further comprises selecting the $CD34^+$ cells by enrichment of the marker.

Embodiment 34. The method of any one of Embodiments 1-33, wherein the $CD34^+$ cell is contacted with a medium comprising hTPO, hFlt3, hSCF and/or hIL6.

Embodiment 35. A $CD34^+$ cell for expression of FOXP3, manufactured by the method of any one of claims 1-34.

Embodiment 36. The $CD34^+$ cell of Embodiment 35, wherein FOXP3 is expressed constitutively or the expression is regulated.

Embodiment 37. A $CD34^+$ cell for expression of FOXP3, the $CD34^+$ cell comprising a nucleic acid encoding a gene encoding FOXP3.

Embodiment 38. The $CD34^+$ cell of Embodiment 37, wherein the gene encoding FOXP3 is introduced in a FOXP3 gene or a non-FOXP3 locus.

Embodiment 39. The $CD34^+$ cell of Embodiment 38, wherein the non-FOXP3 locus is a AAVS1 locus or a TRA gene.

Embodiment 40. The $CD34^+$ cell of any one of Embodiments 35-39, wherein the $CD34^+$ cell leads to generation progenitors that differentiate within a thymus to generate T cells with a Treg phenotype.

Embodiment 41. A composition comprising the $CD34^+$ cell of any one of claims 34-40.

Embodiment 42. A method for treating, ameliorating, and/or inhibiting a disease and/or a condition in a subject, the method comprising: providing to a subject having a disease and/or a condition the $CD34^+$ cell of any one of Embodiments 33-39 or the composition of Embodiment 41.

Embodiment 43. The method of Embodiment 42, wherein the disease is an autoimmune disease.

Embodiment 44. The method of Embodiment 42, wherein the disease is X-linked (IPEX) syndrome.

Embodiment 45. The method of Embodiment 42, wherein the condition is Graft-versus-Host Disease (GVHD) or results from organ transplant.

Some embodiments include a medicament for use in treating or inhibiting a disorder related to a FOXP3 mutation.

In some of the foregoing embodiments, the cell is not a germ cell.

EXAMPLES

Example 1: Editing of $CD34^+$ Cells for FOXP3 Expression

Figure 2:
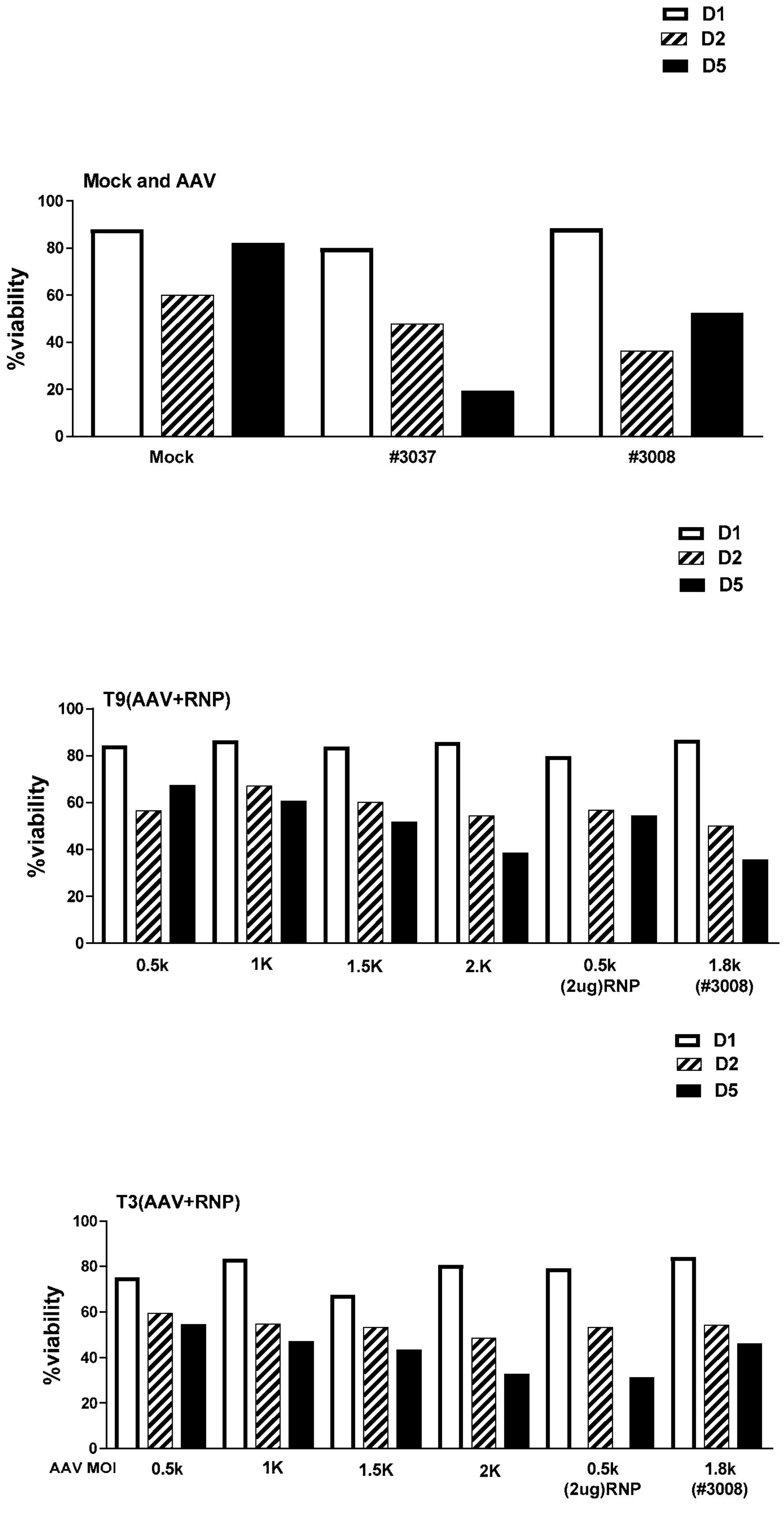
FIG. 2 shows results for the viability of $CD34^+$ cells treated with AAV donor template alone (#3037 or #3008), Cas9/gRNA RNPs (T3 gRNA or T9 gRNA)+AAV donor template (#3037 or #3008), or mock treated at day 1 (D1), day 2 (D2), or day 5 (D5) following treatment.

This example demonstrates the successful editing of $CD34^+$ cells by targeted integrations of an AAV donor into a FOXP3 gene mediated by Cas9 and gRNAs targeting the FOXP3 gene. $CD34^+$ cells were edited at the FOXP3 gene according to the protocol outlined as follows. Cryopreserved $CD34^+$ cells enriched from PBMC mobilized adult donors were thawed and plated at $1\times10^6$ cells/ml in serum-free stem cell growth media [CellGenix GMP SCGM medium (CellGenix Inc.) with thrombopoietin, stem cell factor, FLT3 ligand, and IL-6 (PeproTech) all at 100 ng/ml]. The $CD34^+$ cells were prestimulated in the serum-free stem cell growth media for 48 hours at 37° C., then electroporated with RNPs containing gRNA complexed with Alt-R S.p. Cas9 Nuclease V3 from IDT ("IDT Cas9") (Integrated DNA Technologies, Inc., Coralville, Iowa USA) protein (gRNA/Cas9) at a 1.2:1 molar ratio of gRNA to Cas9 using the Neon® Transfection System (ThermoFisher Scientific). gRNAs with spacer sequence T3 (SEQ ID NO: 2) or T9 (SEQ ID NO: 5) were used in this Example. Following electroporation, the cells were dispensed into a 48-well plate containing 400 μL of media per well and AAV donor templates #3008 (SEQ ID NO: 33) or #3037 (SEQ ID NO: 34) were added at MOIs ranging from 0.5 k to 1.8 k. AAV donor template #3037 contained a FOXP3 cDNA sequence for expression of FOXP3, and AAV donor template #3008 contained a GFP coding sequence under the control of an MND promoter, allowing for estimation of editing rates based on GFP expression (FIG. 1). Twenty-four hours after RNP electroporation and AAV transduction, the media was removed and replaced with fresh stem cell growth media. Analyses of cell viability (FIG. 2) and percent $GFP^+$ cells were performed at days 1, 2 and 5 post-editing. Comparable cell viability was observed across the groups.

To assess editing rates with AAV donor template #3037, "in-out" droplet digital PCR (ddPCR) was performed with the forward primer binding within the codon-optimized FOXP3 cDNA and the reverse primer binding the FOXP3 gene outside the region of homology. A control amplicon of similar size was generated for the ActB gene to serve as a control. All reactions were performed in duplicate. The PCR reactions were partitioned into droplets using a QX200 Droplet Generator (Bio-Rad). Amplification was performed using ddPCR Supermix for probes without UTP (Bio-Rad), 900 nM of primers, 250 nM of probe, 50 ng of genomic DNA, and 1% DMSO. Droplets were analyzed on the QX200 Droplet Digital PCR System (Bio-Rad) using QuantaSoft software (Bio-Rad).

Figure 3:
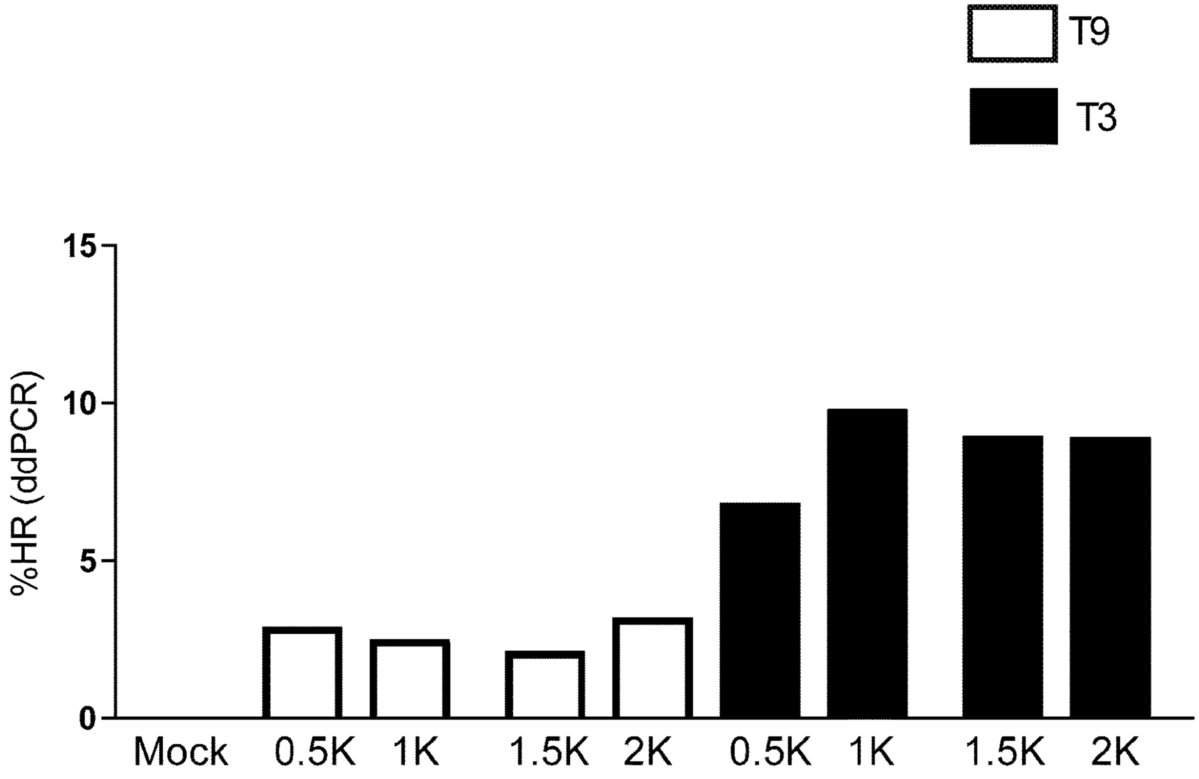
FIG. 3 shows the percent homologous recombination in $CD34^+$ cells that have been edited using Cas9/gRNA RNPs (T3 gRNA or T9 gRNA) and the AAV donor templates shown in FIG. 1.

As shown in FIG. 3, the cells edited using the Cas9/gRNA-T3 RNP (containing a spacer having the sequence of SEQ ID NO: 2) had improved HDR as compared to cells edited using the Cas9/gRNA-T9 RNP (containing a spacer having the sequence of SEQ ID NO: 5) upon transduction with AAV donor template #3037 (SEQ ID NO: 34). Additionally, editing using the Cas9/gRNA-T3 gRNA RNP with AAV donor template #3008 led to higher expression of GFP.

| Treatment Conditions | % live cells | % $GFP^+$ cells |
|---|---|---|
| Mock | 82.1 | 0 |
| AAV | 19.2 | 1.9 |
| Cas9/gRNA-T9 RNP + AAV donor template #3037 | 35.6 | 2.8 |
| Cas9/gRNA-T3 RNP + AAV donor template #3008 | 46.1 | 10.8 |

An alternative AAV donor template configuration with longer homology arms was tested. AAV donor template #3088 (SEQ ID NO: 35), containing a GFP coding sequence, had 0.8 kb arms, with the 3' homology arm modified to position the T3 gRNA cleavage site at the 5' end of the 3' homology arm. Both AAV donor templates #3008 and #3088 were non-cleavable by the gRNA. The table below shows the percent viability of untreated $CD34^+$ cells and $CD34^+$ cells treated with Cas9/gRNA RNP containing the T3 gRNA plus either AAV donor template #3008 or #3088. Cells treated with AAV donor template #3088 had a slightly higher percent viability.

| Treatment Conditions | % cell viability at Day 1 |
|---|---|
| Mock | 84.3 |
| AAV #3088 only | 68.7 |
| T3 RNP + AAV donor template #3008 | 71.6 |
| T3 RNP + AAV donor template #3088 | 72.7 |

The editing rate in $CD34^+$ cells treated with AAV donor template #3088 alone, Cas9/T3 gRNA RNPs+AAV donor template (#3008 or #3088), or mock treated was determined by FACS analysis for $GFP^+$ cells. As shown below, the amount of HR was about 3 fold higher in cells edited using AAV donor template #3088 as compared to AAV donor template #3008. These results suggest that AAV donor templates with 0.8 kb homology arm lengths result in higher editing efficiencies as compared to AAV donor templates with 0.6 kb homology arms. The below tables summarize the results.

| Treatment conditions | % HR at Day 4 |
|---|---|
| Mock | 0 |
| AAV donor template #3088 only | 5.6 |
| T3 RNP + AAV donor template #3008 | 11.9 |
| T3 RNP + AAV donor template #3088 | 48.1 |

| Conditions | % live cells | % GFP+ cells |
|---|---|---|
| Mock | 73.3 | 0 |
| AAV donor template #3088 | 15.7 | 5.6 |
| Cas9/gRNA-T3 RNP + AAV donor template #3088 | 42.1 | 48.1 |
| Cas9/gRNA-T3 RNP + AAV donor template #3008 | 36.0 | 11.9 |

Example 2: Embodiments with Other Spacer Sequences

Additional spacer sequences for targeting the FOXP3 gene are also contemplated for use and are shown in Table 1. gRNAs containing the spacer sequences of SEQ ID NOs: 1, 4, 6 or 7 are made and tested for editing efficiency in $CD34^+$ cells, for example, according to the studies described in Example 1.

gRNAs containing spacer sequences targeting the AAVS1 locus as shown in Table 2 (SEQ ID NOS: 15-20) are also made. These gRNAs may be used with the editing protocols as described in Example 1. gRNAs containing spacer sequences targeting the murine FOXP3 gene (SEQ ID NO: 27-29) and the human TRA gene are also made and tested using the editing protocols as described in Example 1.

Donor templates are also contemplated, which have the following expression cassettes: FOXP3cDNA-LNGFR, LNGFR-FOXP3cDNA, FOXP3cDNA-μDISC, FOXP3cDNA-LNGFRe-μDISC, μDISC-FOXP3cDNA, LNGFRe-μDISC-FOXP3cDNA, DISC, μDISC, CISCβ-DN, CISCγ-FOXP3cDNA-LNGFR and/or CISCγ-LNGFR-FOXP3 cDNA.

Example 3: Delivery of Cas9 RNPs with Different Guide-RNAs

Results gRNAs with T3 and T9 spacer sequences delivered in RNPs upon complexing with two different Cas9 nucleases were evaluated for cell viabilities, allelic disruption rates and homology directed repair rates, when co-delivered with AAV donor template #3008 as described below.

The Cas9/gRNA RNP comprising the T3 spacer sequence outperformed the Cas9/gRNA RNP comprising the T9 spacer sequence in inducing higher allelic disruption and higher HDR. However, the Cas9/gRNA RNP having the T3 spacer sequence was also found to cut at off-target site SLC2A6, as summarized below.

A modified Cas9 protein, SpyFi Cas9 from Aldevron (Fargo, N. Dak., USA), has been reported to exhibit reduced off-target cleavage. No off-target cutting was observed at the SLC2A6 site by the RNP comprising SpyFi Cas9/gRNA targeting FOXP3 with T3 spacer sequence, as measured by ICE. No cleavage at the off-target site was observed with the SpyFi Cas9/gRNA RNP containing either the T3 or T9 spacer sequence.

Methods

Figure 4:
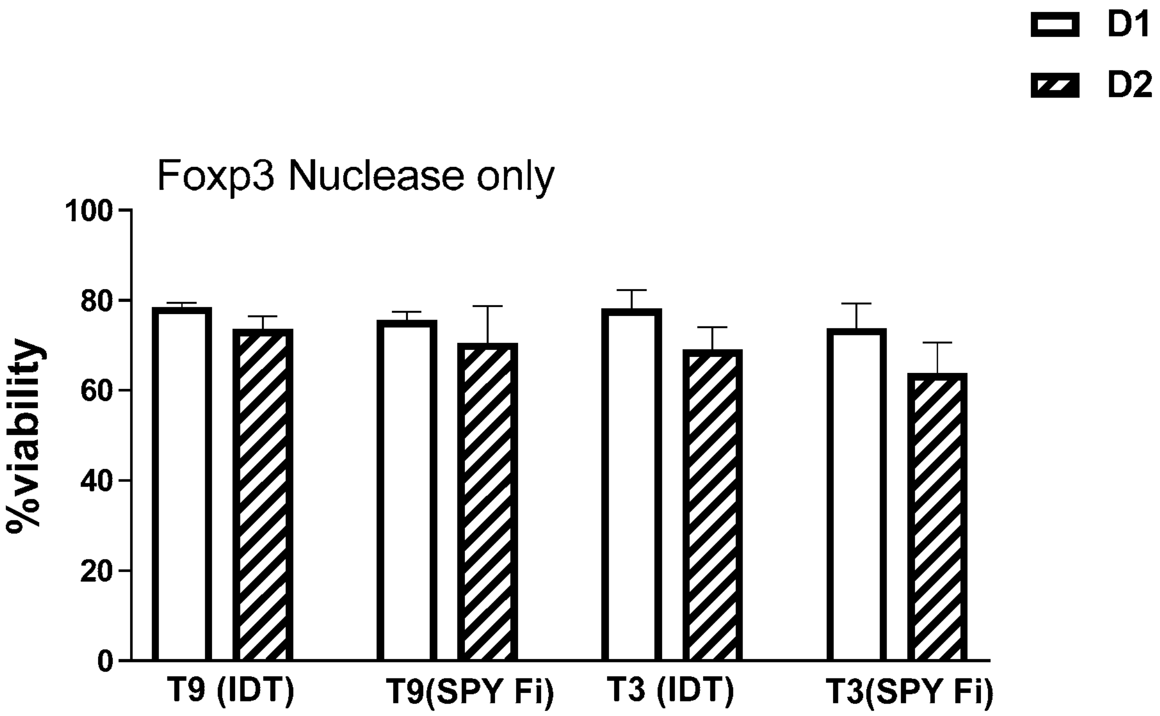
FIG. 4 is a bar graph showing the comparison of cell viabilities of $CD34^+$ cells treated with RNPs containing Cas9 from two different sources (Alt-R S.p. Cas9 Nuclease V3 from IDT or SpyFi Cas9 from Aldevron) and two different gRNAs targeting FOXP3 (T3 or T9).

First, to compare the cell viabilities when $CD34^+$ cells were treated with Cas9 from two different sources (Alt-R S.p. Cas9 Nuclease V3 from IDT or SpyFi Cas9 from Aldevron), adult human Mobilized $CD34^+$ cells were cultured in SCGM media supplemented with TPO, SCF, FLT3L and IL6 (100 ng/ml) for 48 hours, followed by electroporation using Neon® transfection system (Model MPK5000, ThermoFisher Scientific) with 1 μg of Cas9/gRNA RNP comprising T3 or T9 spacer sequence (1:1.2 Cas9:spacer ratio). As shown in FIG. 4, cell viability was assessed by forward and side scatter on days 1 and 2 post editing.

Then, cell viabilities were compared when $CD34^+$ cells were edited with RNPs containing Cas9 from two different sources (Alt-R S.p. Cas9 Nuclease V3 from IDT or SpyFi Cas9 from Aldevron) along with AAV donor templates, as shown in FIG. 5. Adult human mobilized $CD34^+$ cells were cultured in SCGM media supplemented with TPO, SCF, FLT3L and IL6 (100 ng/ml) for 48 hours, followed by electroporation using Neon with 1 ng of RNP comprising T3 or T9 spacer sequence (1:1.2 Cas9: spacer ratio) and AAV transduction. Cell viability was assessed by forward and side scatter on days 1, 2 and 5.

For the comparison of editing rates at the FOXP3 gene, $CD34^+$ cells were edited using RNPs comprising Cas9 from two different sources (Alt-R S.p. Cas9 Nuclease V3 from IDT or SpyFi Cas9 from Aldevron) along with AAV donor templates.

The general in vitro study protocol started from thawed $CD34^+$ cells, which were cultured for 2 days before treatment on Day 0 with RNP and AAV donor template immediately thereafter. AAV washout was performed on Day 1, with FACS assays performed on Days 2 and 5.

Specifically, adult human mobilized $CD34^+$ cells were cultured in SCGM media supplemented with TPO, SCF, FLT3L and IL6 (100 ng/ml) for 48 hours, followed by electroporation using Neon with 1 μg of Cas9/gRNA RNP comprising T3 or T9 spacer sequence (1:1.2 Cas9:gRNA ratio) and transduction with AAV donor template #3008. GFP expression was assessed at day 5 by flow cytometry and shown in the table below.

| Treatment conditions | % $GFP^{high}$ (HR) after transduction with AAV donor template #3008 |
|---|---|
| IDT Cas9/gRNA-T9 RNP | 9.6 ± 5.6 |
| SpyFi Cas9/gRNA-T9 RNP | 13.2 ± 6.05 |
| IDT Cas9/gRNA-T3 RNP | 14.8 ± 4.6 |
| SpyFi Cas9/gRNA-T3 RNP | 22 ± 4.8 |

Moreover, the comparison of NHEJ rates (Inference of CRISPR edits (ICE) scores) at the FOXP3 gene in $CD34^+$ cells edited using Cas9 from two different sources is shown in the table below. Adult human Mobilized $CD34^+$ cells were cultured in SCGM media supplemented with TPO, SCF, FLT3L and IL6 (100 ng/ml) for 48 hours, followed by electroporation using Neon with 1 μg of Cas9/gRNA RNP comprising T3 or T9 spacer sequence (1:1.2 Cas9:gRNA ratio). The cells were cultured for 5 days post editing, followed by genomic DNA extraction. The region around the cut site was amplified, sequenced and analyzed by ICE (Inference of CRISPR Edits) analysis (Hsiau, T. et al. Inference of CRISPR Edits from Sanger Trace Data. bioRxiv 251082). Locus A was a locus on the X chromosome other than FOXP3.

| RNP Spacer | ICE Scores after treatment with RNP comprising indicated Cas9 | |
|---|---|---|
| Sequence | IDT Cas9 | SpyFi Cas9 |
| T9 | 17 ± 9 | 28 ± 11 |
| T3 | 10 ± 2 | 20.5 ± 2.5 |
| Locus A | 18 ± 2 | 29.5 ± 3.5 |

Then, to compare the cleavage efficiency of RNPs comprising T3 or T9 spacer sequences across three different donors, as shown in the table below, adult human mobilized CD34$^+$ cells were cultured in SCGM and transfected using Neon electroporation system. The cells were cultured for 5 days post editing, followed by genomic DNA extraction. The region around the nuclease cut site was amplified, sequenced and analyzed by ICE (Inference of CRISPR Edits) analysis.

| | % cleavage (ICE) by indicated targeting RNP | |
|---|---|---|
| Donor | T3 | T9 |
| A | 21 ± 1 | 12.5 ± 0.5 |
| B | 37 ± 1 | 22.5 ± 0.5 |
| C | 30.5 ± 0.5 | 17 ± 1 |

The cleavage efficiency of RNPs comprising T3 or T9 spacer sequences was also compared across three different donors using IDT Cas9, as shown in the table below. Adult human Mobilized CD34$^+$ cells were cultured in SCGM media supplemented with TPO, SCF, FLT3L and IL6 (100 ng/ml) for 48 hours, followed by electroporation using Neon with 1 ug of Cas9/gRNA RNP comprising T3 or T9 spacer sequence (1:1.2 Cas9: spacer ratio). The cells were cultured for 5 days post editing, followed by genomic DNA extraction. The region around the cut site was amplified, sequenced and analyzed by ICE (Inference of CRISPR Edits) analysis. The region around an off-target cleavage site (SLC2A6) for RNP having T3 spacer sequence was also amplified and subjected to ICE analysis. The off-target site was identified using CCTop-CRISPR/Cas9 target online predictor tool (Stemmer, M. et al. (2017) *Plos One,* 12(4): e0176619).

| | % cleavage (ICE) by indicated targeting RNP T3 | |
|---|---|---|
| Donor | On-target | Off-target |
| A | 21 ± 1 | 2 ± 0 |
| B | 37 ± 1 | 3.5 ± 0.5 |
| C | 30.5 ± 0.5 | 2.5 ± 0.5 |

Further, cleavage efficiency at the FOXP3 gene and at an off-target locus was compared for RNPs comprising T3 or T9 spacer sequences when using IDT Cas9 vs SpyFi Cas9, as shown in the table below. Adult human Mobilized CD34$^+$ cells were cultured as described and electroporated using Neon with 1 μg of Cas9/gRNA RNP comprising T3 or T9 spacer sequence (1:1.2 Cas9: spacer ratio). Either Alt-R S.p. Cas9 Nuclease V3 from IDT or SpyFi Cas9 from Aldevron were used. The cells were cultured for 5 days post editing, followed by genomic DNA extraction. The region around the cut site was amplified, sequenced and analyzed by ICE (Inference of CRISPR Edits) analysis. The region around the top off-target cleavage site (SLC2A6) for the IDT Cas9/gRNA-T3 RNP was also amplified and subjected to ICE analysis. The other RNPs did not show off-target cleavage at SLC2A6. The off-target site was identified using CCTop-CRISPR/Cas9 target online predictor tool.

| RNP at indicated site | % cleavage (ICE) |
|---|---|
| IDT Cas9/gRNA-T3 on-target | 32 |
| IDT Cas9/gRNA-T3 off-target | 2 |
| SpyFi Cas9/gRNA-T3 on-target | 63 |
| IDT Cas9/gRNA-T9 on-target | 35 |
| SpyFi Cas9/gRNA-T9 on-target | 50 |

Example 4: Modification of CD34$^+$ Cell Transfection Protocol

Results

This example describes modified cell transfection protocols for increasing the transfection efficiency of CD34$^+$ cells, using the Lonza nucleofector or the Neon electroporation.

Various programs were tested in parallel with the improved protocol using the Neon electroporation device described in Example 3. Comparable cell viability, transfection and HDR rates to Neon using program CM149 on Lonza were achieved, and this program was used subsequently for our in vivo studies. AAV donor template #3088 was used with the SpyFi Cas9/gRNA RNP containing the T3 spacer sequence. AAV donor template #3088 (SEQ ID NO: 33) as DNA donor yielded higher HDR rates under these conditions as compared to AAV donor template #3008.

Next, the previous CD34$^+$ culturing protocol (Protocol A) was compared to an alternative protocol (Protocol B). Protocol B required cells to be cultured at a lower density during cytokine stimulation than protocol A and used a different culture media. A higher proportion of quiescent cells was achieved in cells cultured using Protocol B compared to Protocol A, suggesting that Protocol B cultures might maintain a higher fraction of quiescent long-term repopulating HSCs. However, a higher dose of AAV had to be delivered to the cells cultured using Protocol B to achieve comparable HDR rates.

Methods

First, cell viabilities were compared when nucleofecting human CD34$^+$ cells with Lonza 4D-Nucleofector™ system (4 different programs) or electroporating with Neon transfection system (Model MPK5000), as shown in table below.

| Electroporation/ | % cell viability after treatment | | |
|---|---|---|---|
| nucleofection | mock | GFP mRNA | T3 RNP |
| Neon | 91.6 | 88.7 | 72.2 |
| Lonza E0100 | 79 | 78.7 | 77.8 |
| Lonza CM149 | 92.8 | 91.3 | 86.6 |
| Lonza DZ-100 | 79.3 | 76.2 | 74.6 |
| Lonza CA137 | 92 | 89.8 | 85.6 |

Adult human mobilized CD34$^+$ cells were cultured in SCGM media supplemented with TPO, SCF, FLT3L and IL6 (100 ng/ml) for 48 hours, followed by electroporation using Neon or nucleofection with Lonza. The cells were either mock transfected or transfected with either 1 μg of each GFP mRNA or 1 μg of RNP comprising SpyFi Cas9 and gRNA containing T3 spacer sequence (1:1.2 Cas9:gRNA ratio). Cell viability was assessed by forward and side scatter. Data from a single CD34+ donor is shown in the above table.

The comparison of GFP mRNA expression when nucleofecting human CD34$^+$ cells with Lonza or electroporating with Neon is shown in table below.

| Electroporation/ nucleofection | % $GFP^+$ cells after treatment | |
|---|---|---|
| | Day 1 | Day 4 |
| Neon | 97.3 | 91.1 |
| Lonza E0100 | 46 | 11.6 |
| Lonza CM149 | 90.1 | 58.6 |
| Lonza DZ-100 | 79.3 | 43 |
| Lonza CA137 | 85.7 | 61 |

Adult human mobilized $CD34^+$ cells were cultured in SCGM media supplemented with TPO, SCF, FLT3L and IL6 (100 ng/ml) for 48 hours, followed by electroporation using Neon or nucleofection with Lonza. The cells were transfected with 1 μg of GFP mRNA and GFP expression was assessed on days 1 and 4. Data from a single CD34+ donor is shown in the above table.

Then, we compared NHEJ rates nucleofecting with Lonza or electroporating human $CD34^+$ cells with Neon, as shown in table below.

| Electroporation/ nucleofection | % NHEJ by ddPCR after treatment with Cas9/gRNA-T3 RNP |
|---|---|
| Neon | 86 |
| Lonza E0100 | 21 |
| Lonza CM149 | 74 |
| Lonza DZ-100 | 56 |
| Lonza CA137 | 73 |

The general in vitro protocol described in Example 3 was used. Adult human mobilized $CD34^+$ cells were cultured in SCGM media supplemented with TPO, SCF, FLT3L and IL6 (100 ng/ml) for 48 hours, followed by electroporation using Neon or nucleofection with Lonza. The cells were transfected with 1 μg of RNP comprising SpyFi Cas9 and gRNA containing T3 spacer sequence (1:1.2 Cas9: spacer ratio). The cells were harvested on day 5 and NHEJ rates were determined using droplet digital PCR. Primers were designed spanning the cut site with the NHEJ probe binding to the T3 spacer sequence cleavage site. A control amplicon of similar size was generated from another region of the FOXP3 gene. Each sample was analyzed in duplicate. The PCR reactions were partitioned into droplets using a QX200 Droplet Generator (Bio-Rad). Amplification was performed using ddPCR Supermix for Probes without UTP (Bio-Rad), 900 nM of primers, 250 nM of Probe, 50 ng of genomic DNA, and 1% DMSO. Droplets were analyzed using the QX200 Droplet Digital PCR System (Bio-Rad) and analyzed using QuantaSoft software (Bio-Rad). Data from a single $CD34^+$ donor is shown on the bar graph. The NHEJ rates were calculated using the formula:

$$NHEJ\text{ rate} = \left(\left(\frac{\text{Signal from } NHEJ \text{ probe}}{\text{Signal from control probe}}\right)_{mock\ sample} - \left(\frac{\text{Signal from } NHEJ \text{ probe}}{\text{Signal from control probe}}\right)_{T3\ RNP\ treated\ sample}\right) \times 100$$

For the comparison of cell viability when using various nucleofection programs on Lonza versus electroporation by Neon, adult mobilized human $CD34^+$ cells were cultured in SCGM media followed by mock electroporation using Neon or nucleofection by Lonza. Cell viability was assessed using forward and side scatter on days 1, 2 and 5. Data from a single $CD34^+$ donor is shown in the table below.

| Electroporation/ nucleofection | % cell viability after mock treatment | | |
|---|---|---|---|
| | Day 1 | Day 2 | Day 5 |
| Neon | 84.8 | 86.4 | 82.2 |
| Lonza E0100 | 68 | 68.2 | 77.7 |
| Lonza CM149 | 67.7 | 79.2 | 78.4 |
| Lonza DZ-100 | 64.5 | 67.3 | 80 |
| Lonza CA137 | 76 | 76.7 | 81.8 |

Then, a comparison of cell viability was performed using various nucleofection programs on Lonza versus electroporation by Neon when introducing RNP and AAV. The general in vitro protocol from Example 3 was used. Adult mobilized human $CD34^+$ cells were cultured in SCGM media followed by RNP comprising SpyFi Cas9 and gRNA containing T3 spacer sequence (1:1.2 Cas9: spacer ratio) (1 μg) electroporation using Neon or nucleofection by Lonza, followed by transduction with AAV donor template #3088, shown schematically in FIG. 1. Cell viability was assessed using forward and side scatter on days 1, 2 and 5. Data from a single $CD34^+$ donor is shown on the bar graph in the table below.

| Electroporation/ nucleofection | % cell viability after treatment with Cas9/gRNA-T3 RNP + AAV donor template #3088 | | |
|---|---|---|---|
| | Day 1 | Day 2 | Day 5 |
| Neon | 69.8 | 54.4 | 55.7 |
| Lonza E0100 | 66.9 | 48 | 49.4 |
| Lonza CM149 | 59.2 | 61.5 | 51.8 |
| Lonza DZ-100 | 57.6 | 43.2 | 37.9 |
| Lonza CA137 | 68.8 | 62.1 | 64.1 |

We then compared the percent GFP expression (HDR) when using various nucleofection programs on Lonza versus electroporation by Neon. AAV donor template #3088 was used for this experiment, which was designed for T3 spacer sequence by placing the T3 spacer sequence cleavage site at the beginning of the 3' homology arm. The general in vitro protocol in Example 3 was followed. Adult mobilized human $CD34^+$ cells were cultured in SCGM media followed by RNP (1 μg) electroporation using Neon or nucleofection by Lonza. This was followed by transduction with AAV donor template (panel A). HDR rates were determined by GFP expression on day 5. Data from a single $CD34^+$ donor is shown in the table below. Program CM149 (Lonza) was chosen for future experiments since it yielded the highest editing rates ($GFP^{high}$) in cells without a significant drop in cell viability.

| Electroporation/ nucleofection | % $GFP^{high}$ after treatment with control or Cas9/gRNA-T3 RNP + AAV donor template #3088 |
|---|---|
| Mock | 0 |
| AAV #3088 only | 0.63 |
| Neon | 36.8 |
| Lonza E0100 | 14.4 |
| Lonza CM149 | 43.4 |
| Lonza DZ-100 | 40.4 |
| Lonza CA137 | 26.1 |

The details of the two different in vitro cell genome editing protocols—Protocol A and B—are shown in the table below.

| Conditions | Protocol A | Protocol B |
|---|---|---|
| Media | SCGM | SFEMII |
| Human cytokines | TPO,FLT3L,SCF,IL6 (100 ng/ml) | |
| Small molecule | UM171 and SR1 | |
| Pre-stimulation: cell concentration/ml | 1.00E+06 | 2.50E+05 |
| Pre-stimulation time | 48 hours | |
| RNP | 1 ug (1.2:1 molar ratio) | |
| cell concentration during EP | 1 million/20 μl rxn with Neon or Lonza | 1 million/20 μl rxn with Lonza |
| AAV MOI | 50 | 50, 100, 200 |
| Cell concentration for transduction | 1 million/0.8 ml | 1 million/1 ml |
| 16 hours after transduction | Add media (virus diluted) | cells move to 0.25 million cell/ml concentration |

For protocol A, mobilized human $CD34^+$ cells were cultured in SCGM media supplemented with TPO, SCF, FLT3L and IL6 (100 ng/ml) plus 35 nm UM171 and 1 uM SR1 for 48 hours at a concentration of $1\times10^6$ cells/ml, followed by nucleofection of 1 μg of RNP comprising SpyFi Cas9 and gRNA containing T3 spacer sequence (1:1.2 Cas9: spacer ratio) using Lonza. The cells were subsequently transduced with AAV donor template at the MOI of 50. After 16 hours post transduction, the AAV was diluted out by adding more media. For protocol B, $CD34^+$ cells were cultured in SFEMII media containing the same supplements as above. The cell density during pre-stimulation was $2.50\times10^5$/ml. Following the 48-hour pre-stimulation, the cells were nucleofected with Lonza and plated at a density of $1\times10^6$ cells/ml prior to transduction with AAV at MOIs of 50, 100 and 200. After 16 hours post transduction, the cells were re-plated at the density of $2.5\times10^5$ cells/ml. Cell viabilities at days 1, 2 and 5 were assessed by forward and side scatter. The data for the comparison of cell viability when using either protocol A or B, from a single $CD34^+$ donor, is shown in the table below.

| | % cell viability after transduction with indicated conditions | | | | |
|---|---|---|---|---|---|
| Protocol | mock | AAV #3088 only | AAV #3088 MOI 50 + RNP | AAV #3088 MOI 100 + RNP | AAV #3088 MOI 200 + RNP |
| A Day 1 | 59.3 | 54.3 | 54.7 | N/A | N/A |
| A Day 2 | 86.1 | 79.2 | 76 | N/A | N/A |
| A Day 5 | 76.6 | 72 | 53.8 | N/A | N/A |
| B Day 1 | 84.3 | 82.6 | 79.7 | 80.4 | 78.6 |
| B Day 2 | 85.5 | 82.1 | 68.1 | 48.9 | 72.3 |
| B Day 5 | 79.1 | 77.2 | 61.9 | 62 | 61.2 |

Then, transduction by AAV donor templates was assessed in $CD34^+$ cells cultured by either protocol A or B using flow cytometry. Percent GFP expression at days 1 and 2 are shown in the table below. Data from a single $CD34^+$ donor is shown.

| | % $GFP^+$ after transduction with indicated AAV donor vector | | | | |
|---|---|---|---|---|---|
| Protocol | mock | AAV #3088 only | AAV MOI 50 + RNP | AAV MOI 100 + RNP | AAV MOI 200 + RNP |
| A Day 1 | 3.07 | 16.1 | 47.7 | N/A | N/A |
| A Day 2 | 0.56 | 10.3 | 34.7 | N/A | N/A |
| B Day 1 | 0.31 | 5.02 | 24 | 26.9 | 28.6 |
| B Day 2 | 0.028 | 7.22 | 25.4 | 36.6 | 37.4 |

HDR rates were then determined by stable GFP expression at day 5 in $CD34^+$ cells cultured using protocol A or B. GFP expression levels were assessed using flow cytometry. Data from a single $CD34^+$ donor is shown in the table below.

| | % $GFP^+$ after transduction with indicated AAV donor vector | | | | |
|---|---|---|---|---|---|
| Protocol | mock | AAV #3088 only | AAV MOI 50 + RNP | AAV MOI 100 + RNP | AAV MOI 200 + RNP |
| A Day 5 | 0 | 0.7 | 47.7 | N/A | N/A |
| B Day 5 | 0 | 0 | 31.9 | 38.1 | 48.9 |

For the comparison of cell cycle status in cells cultured for 48 hours using protocol A or B, as shown in the table below, adult mobilized $CD34^+$ were cultured using protocol A or B as previously described and their cell cycle status determined using the Muse™ cell cycle assay kit (Merck KGaA, Darmstadt, Germany), 48 hours post culturing. The bar graph depicts the percent cells in G0/G1, S or G2/M phases with either culturing protocol. DNA content index plots are shown below the respective bar graphs. This suggested that there was a higher proportion of quiescent cells in $CD34^+$ cultures with SFEMII media using protocol B than SCGM (protocol A).

| Cell | Day 0 before electroporation % cells with indicated media | |
|---|---|---|
| phase | SFEM II (protocol B) | SCGM (protocol A) |
| G0/G1 | 32 | 15 |
| S | 13 | 7 |
| G2/M | 27 | 38 |

Example 5: Modification of Editing of $CD34^+$ Cells from Healthy Subject

The FOXP3 gene was edited with AAV6 donors designed to introduce a FOXP3 cDNA to enable expression using a WPRE element upon targeted integration. $CD34^+$ cells from a single healthy human subject were edited.

FIG. 1 shows a schematic representation of AAV donor template #3232 comprising FOXP3 cDNA vector expressing codon optimized cDNA, WPRE3 element and SV40 polyadenylation site. The table below shows HDR rates when $CD34^+$ cells from a healthy human subject were edited using SpyFi Cas9/T3-gRNA (1:1.2) RNPs and the FOXP3 cDNA vector at different MOI using protocol B as previously described. No RNP or no AAV as control did not exhibit measured % HDR.

| Treatment with RNP and AAV donor template #3232 at indicated MOI (K) | % HDR (by ddPCR) |
|---|---|
| 0.1 | 11.41 |
| 0.2 | 21.3 |
| 0.5 | 34.17 |
| 1.1 | 40.13 |
| 2.2 | 47.35 |

The cell viability of the cells treated as described above at different MOI is shown in the table below. These data suggested that this genome editing approach may provide an effective and sustained long-term cure as it may allow locus specific expression of FOXP3 regardless of the downstream mutation.

| Treatment | AAV MOI (K) | % cell viability at Day 1 |
|---|---|---|
| Mock | None | 80 |
| AAV donor template #3232 | 1.1 | 77.7 |
| RNP + AAV donor template #3232 | 0.1 | 75.3 |
| | 0.2 | 73.4 |
| | 0.5 | 75.8 |
| | 1.1 | 74.5 |
| | 2.2 | 73.8 |

Example 6: HDR-Edited CD34$^+$ Cells Engraftment in Mice

Results

The long-term engraftment of genome-edited (GFP$^+$) CD34$^+$ cells cultured according to Example 4 using either protocol A or B and transfected with AAV donor template #3088 and RNP comprising SpyFi Cas9/T3 gRNA (1:1.2 Cas9:gRNA), using either the Neon or Lonza transfection in NS GW41 recipient mice, was assessed. As illustrated in the table below, acceptable HDR was achieved by treatment with the RNP and AAV donor template combination.

| Treatment conditions | % live cells | % GFP$^{high}$ |
|---|---|---|
| mock | 78.6 | 0 |
| AAV #3088 only | 75.0 | 0.7 |
| AAV #3088 MOI 50 + SpyFi Cas9/T3 RNP (1:1.2 Cas9:gRNA) | 61.2 | 25.2 |

Experimental mice were analyzed 12-16 weeks post-transfer of edited PBSC for engraftment of hCD45$^+$ cells in the bone marrow. As summarized in the tables below, average engraftment of human cells was ~60% in the bone marrow across multiple experiments and ~5% of those cells maintained long-term GFP.

| Treatment | | % hCD45$^+$ (bone marrow) | % hCD45$^+$CD19$^+$ (bone marrow) |
|---|---|---|---|
| Protocol A | Mock | 65.37 ± 12.46 | 51.73 ± 4.997 |
| | Edited | 61.8 ± 11.67 | 47.38 ± 4.515 |
| Protocol B | Mock | 69.08 ± 10.01 | 47.74 ± 3.949 |
| | edited | 65.94 ± 5.685 | 57.97 ± 3.54 |

| Treatment | | % hCD45$^+$CD33$^+$ (bone marrow) | % hCD45$^+$GFP$^+$ (bone marrow) |
|---|---|---|---|
| Protocol A | Mock | 36.47 ± 4.055 | 0.29 ± 0.08 |
| | Edited | 35.76 ± 3.97 | 4.88 ± 2.26 |
| Protocol B | Mock | 39.27 ± 3.155 | 0.16 ± 0.035 |
| | Edited | 30.52 ± 2.93 | 8.2 ± 2.6 |

These data formally demonstrated that FOXP3 gene HDR-edited HSC retained the ability to engraft long-term and retain expression of a donor gene expression cassette. All recipients harbored edited cells in both the myeloid and B cell populations and these lineages were present at ratios equivalent to recipients of mock-edited human CD34$^+$ cells. These data were consistent with editing of a multipotent HSC and indicate that the differentiation capacity of HDR-edited stem cells was not compromised by editing the FOXP3 gene. We did not observe any significant difference in terms of total engraftment with either protocol. Overall, the recipient mice harbored edited cells in the B cell populations and this lineage was present at ratios comparable to recipients of mock-edited human CD34$^+$ cells, suggesting that the differentiation capacity was not compromised by editing the FOXP3 gene.

| Treatment | | % hCD33$^+$GFP$^+$ (bone marrow) | % hCD19$^+$GFP$^+$ (bone marrow) |
|---|---|---|---|
| Protocol A | Mock | 0.024 ± 0.095 | 0.09 ± 0.04 |
| | Edited | 3.76 ± 1.033 | 2.71 ± 1.498 |
| Protocol B | Mock | 0.31 ± 0.09916 | 0.12 ± 0.008 |
| | Edited | 10.55 ± 2.826** | 7.1 ± 2.363* |

Figure 6:
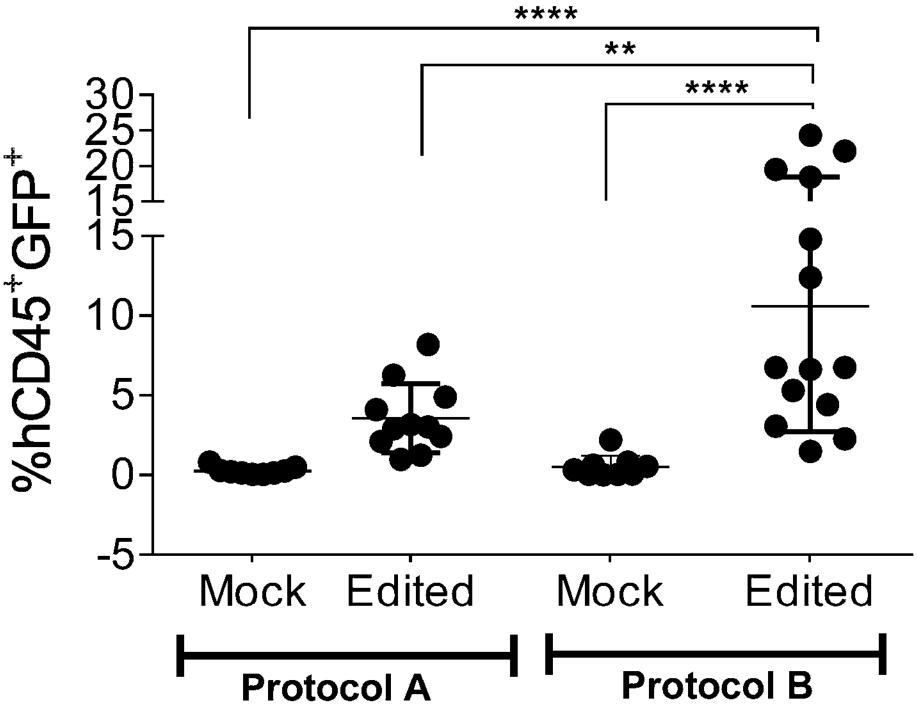
FIG. 6 shows exemplary results for the percent $GFP^+$ among total $hCD45^+$ cells recovered from the spleens of NSGW41 mice engrafted with mock cells or cells edited by SpyFi Cas9/gRNA RNPs targeting FOXP3 (T3). Mean±SEM labeled on graph.
Figure 7:
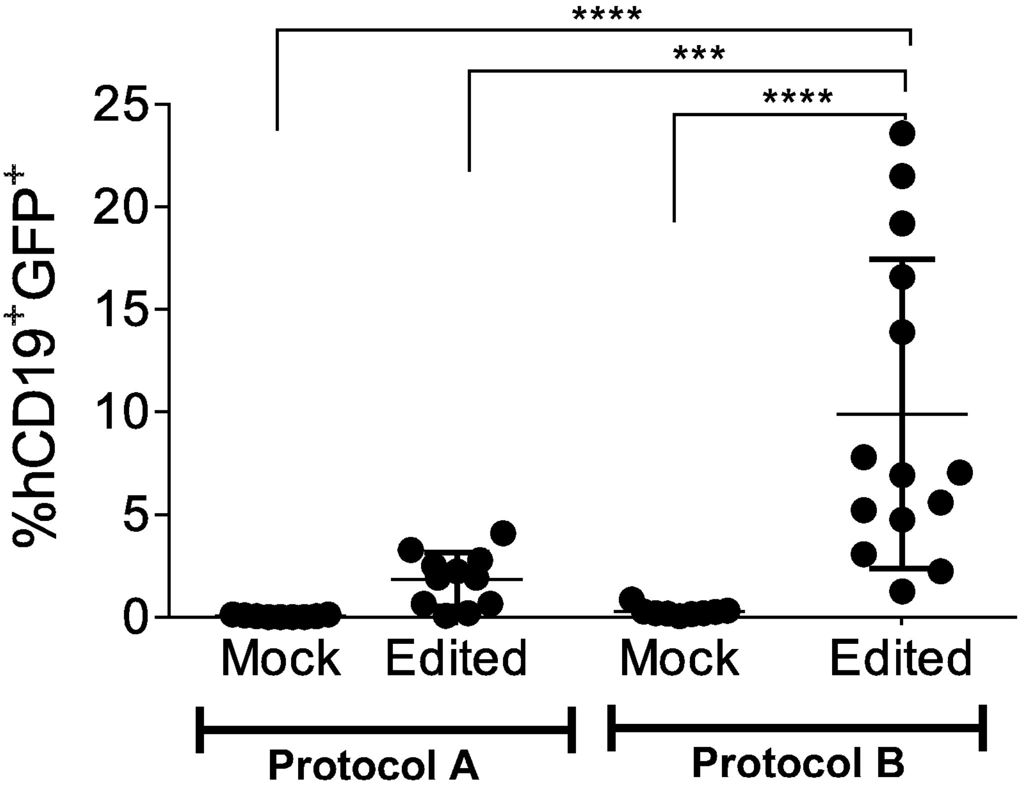
FIG. 7 shows exemplary results for the percent $GFP^+$ cells among human $CD19^+$ cells recovered from the spleens of NSGW41 mice engrafted with mock cells or cells edited by SpyFi Cas9/gRNA RNPs targeting FOXP3 (T3). Mean±SEM labeled on graph.
Figure 8:
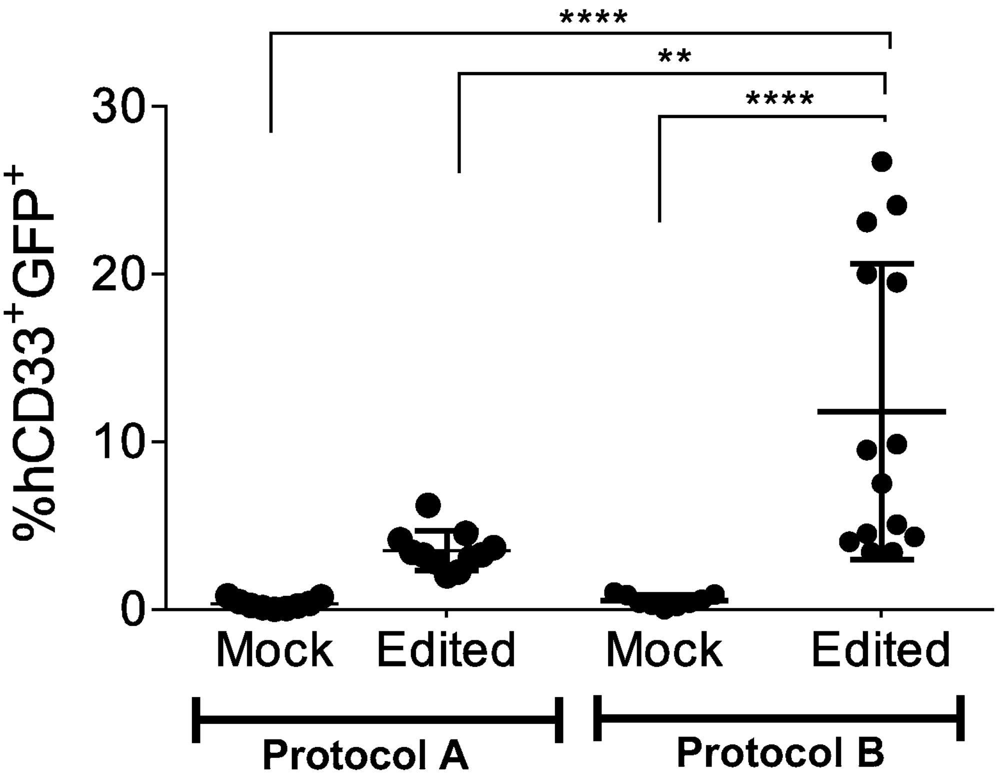
FIG. 8 shows exemplary results for the percent $GFP^+$ cells among human $CD33^+$ cells recovered from the spleens of NSGW41 mice engrafted with mock cells or cells edited by SpyFi Cas9/gRNA RNPs targeting FOXP3 (T3). Mean±SEM labeled on graph.

*P value = 0.0332 compared to mock in protocol A
P value = 0.0021 compared to mock in protocol B or mock in protocol A Average engraftment of human hematopoietic cells within the spleen was slightly lower than bone marrow but comparable between recipient animals treated with mock and HDR-edited cells. HDR-edited GFP$^+$ cells were present in all cell lineages (B, T, myeloid) and were present in ratios comparable to ratios found in the mock treatment. The successful engraftment of GFP$^+$ cells are reflected in the tables below and in FIGS. 6-8**.

| Treatment | | % hCD45$^+$ (spleen) | % hCD45$^+$CD19$^+$ (spleen) |
|---|---|---|---|
| Protocol A | Mock | 19.27 ± 4.66 | 73.56 ± 4.18 |
| | Edited | 16.18 ± 3.42 | 70.59 ± 2.84 |
| Protocol B | Mock | 18.58 ± 2.92 | 76.97 ± 3.28 |
| | edited | 11.88 ± 2.25 | 70.96 ± 2.83 |
| Protocol A | Mock | 9.62 ± 1.6 | 0.26 ± 0.08 |
| | Edited | 9.16 ± 1.06 | 3.56 ± 0.65** |
| Protocol B | Mock | 11.16 ± 1.97 | 0.51 ± 0.23 |
| | edited | 12.77 ± 1.49 | 10.58 ± 2.09**** |

**P value = 0.0021 (edited Protocol B vs. edited Protocol A)
****P value < 0.0001 (edited Protocol B vs. mock in either experiment)

| Treatment | | % hCD19$^+$GFP$^+$ (spleen) | % hCD33$^+$GFP$^+$ (spleen) |
|---|---|---|---|
| Protocol A | Mock | 0.05 ± 0.01 | 0.33 ± 0.09 |
| | Edited | 1.84 ± 0.39*** | 3.51 ± 0.35** |

-continued

| Treatment | | % hCD19⁺GFP⁺ (spleen) | % hCD33⁺GFP⁺ (spleen) |
|---|---|---|---|
| Protocol B | Mock | 0.28 ± 0.07 | 0.51 ± 0.11 |
| | edited | 9.90 ± 2.01**** | 11.79 ± 2.35**** |

**P value = 0.0021 (edited Protocol B vs. edited Protocol A)
***P value = 0.002 (edited Protocol B vs. edited Protocol A)
****P value < 0.0001 (edited Protocol B vs. mock in either experiment)

Additionally, the percent of human CD45⁺ hematopoietic stem cells engrafted within the bone marrow as defined by expression of $CD38^{low}$ $CD34^+$ was similar between mock and HDR-edited recipients as shown in the tables below. GFP⁺ cells were present within this population consistent with editing of a stem cell population capable of persisting long-term in vivo.

| Treatment | | % hCD45⁺CD34⁺CD38$^{low}$ (bone marrow) | % hCD45⁺CD34⁺CD38$^{low}$GFP⁺ (spleen) |
|---|---|---|---|
| Protocol A | Mock | 2.69 ± 0.68 | 0.12 ± 0.1 |
| | Edited | 2.58 ± 0.78 | 4.86 ± 2.27 |
| Protocol B | Mock | 5.28 ± 1.13 | 0.37 ± 0.05 |
| | edited | 5.6 ± 1.1 | 13.89 ± 5.07* |

*P value = 0.0332 compared to mock in protocol A

Methods

For protocol A, mobilized human CD34⁺ cells were cultured in SCGM media supplemented with TPO, SCF, FLT3L and IL6 (each at 100 ng/ml) plus 35 nm UM171 and 1 uM SR1 for 48 hours at a concentration of 1×10⁶ cells/ml, followed by nucleofection of 1 μg of RNP comprising SpyFi Cas9/T3 gRNA (1:1.2 Cas9:gRNA molar ratio) using Neon or Lonza. The cells were subsequently transduced with AAV donor template #3088 at the MOI of 50. Cells (mock or edited, 1.5-2×10⁶ per mouse) cultured with the above protocol were injected into NSGW41 recipient mice that were injected with 12.5 mg/kg busulfan 24 hours prior. The transplanted mice were sacrificed 12-16 weeks later, and bone marrow and spleens were analyzed For protocol B, CD34⁺ cells were cultured in SFEMII media containing the same supplements and concentrations as above. The cell density during pre-stimulation was 2.50× 10⁵/ml. Following the 48 hours pre-stimulation, the cells were nucleofected with Lonza and plated at a density of 1×10⁶ cells/ml prior to transduction with AAV donor template at MOI of 200. Cells (mock or edited, 1.5-2×10⁶ per mouse) cultured with the above protocol were injected into NSGW41 recipient mice that were injected with 12.5 mg/kg busulfan 24 hours prior. The transplanted mice were sacrificed 12-16 weeks later, and bone marrow and spleens were analyzed.

The gating strategy for analyzing cells harvested from the bone marrow of NSGW41 mice 16 weeks following cell transplantation is described below. Bone marrow was harvested from mice transplanted with mock untreated cells. In parallel, bone marrow was harvested from mice transplanted with cells treated with AAV plus RNP. In both cases, the degree of hCD45:mCD45 chimerism was determined, and human CD45-gated CD33⁺ and CD19⁺ staining was performed. GFP expression among hCD45⁺, CD33⁺ and CD19⁺ cells was determined.

These sorted cells were transfected with 1 ng of RNP comprising SpyFi Cas9/T3 gRNA (1:1.2 Cas9:gRNA ratio) and transduced with AAV donor template #3088 (SEQ ID NO: 35) at MOIs ranging from 50-200. The cells were transplanted into NSGW41 mice the following day. Mice were injected with 12.5 mg/kg busulfan one day prior to transplantation of cells. The mice were sacrificed 12-16 weeks post transplantation and analyzed for the presence of human cells. The tables shown above summarize the results of engraftment of the sorted cells. Both mock and RNP-edited cells engrafted at comparable rates in recipient mice.

The gating strategy for analyzing cells harvested from the spleen of NSGW41 mice 16 weeks following cell transplantation is described below. Spleens were harvested from mice transplanted with mock untreated cells. In parallel, spleens were harvested from mice transplanted with cells treated with AAV plus RNP. In each cohort, the degree of hCD45:mCD45 chimerism was determined, and human CD45-gated CD33⁺ and CD19⁺ staining performed: GFP expression among hCD45⁺, CD33⁺ and CD19⁺ cells was determined.

These sorted cells were transfected with 1 μg of RNP comprising SpyFi Cas9/T3 gRNA (1:1.2 Cas9:gRNA ratio) and transduced with AAV donor template #3088 (SEQ ID NO: 35) at MOIs ranging from 50-200 k. The cells were transplanted into NSGW41 mice the following day. Mice were injected with 12.5 mg/kg busulfan 1-2 days prior to transplantation of cells. The mice were sacrificed 12-16 weeks post transplantation and analyzed for the presence of human cells. Both mock and RNP-edited cells engrafted at comparable rates in recipient mice.

The gating strategy for analyzing GFP⁺ cells among human CD34⁺CD38$^{low}$ CD45⁺ cells recovered from the bone marrow of NSGW41 mice engrafted with mock or edited cells, is as follows. The degree of hCD45:mCD45 chimerism was determined, and human CD45-gated CD38$^{low}$CD34⁺ staining was performed. GFP⁺ cells among the CD38$^{low}$CD34⁺ population were isolated.

These cells were transfected with 1 μg of RNP comprising SpyFi Cas9/T3 gRNA (1:1.2 Cas9:gRNA ratio) and transduced with AAV donor template #3088 (SEQ ID NO: 35) at MOIs ranging from 50-200. The cells were transplanted into NSGW41 mice the following day. Mice were injected with 12.5 mg/kg busulfan 1-2 days prior to transplantation of cells. The mice were sacrificed 12-16 weeks post transplantation and analyzed for the presence of human cells.

SEQUENCES

In addition to sequences disclosed elsewhere in the present disclosure, the following sequences are provided as they are mentioned or used in various exemplary embodiments of the disclosures, which are provided for the purpose of illustration.

| SEQ ID NO | Sequence | Description |
|---|---|---|
| 1 | TTCCAGGGCCGAGATCTTCG | T1 spacer targeting human FOXP3 |
| 2 | CGCCTCGAAGATCTCGGCCC | T3 spacer targeting human FOXP3 |
| 3 | TCGAAGATCTCGGCCCTGGA | T4 spacer targeting human FOXP3 |
| 4 | GGCCCTGGAAGGTTCCCCCT | T7 spacer targeting human FOXP3 |
| 5 | TCCAGCTGGGCGAGGCTCCT | T9 spacer targeting human FOXP3 |
| 6 | TCAGACCTGCTGGGGGCCCG | T18 spacer targeting human FOXP3 |
| 7 | GAGCCCCGCCTCGAAGATCT | R1 spacer targeting human FOXP3 |
| 8 | AGG | PAM sequence |
| 9 | TGG | PAM sequence |
| 10 | AGG | PAM sequence |
| 11 | GGG | PAM sequence |
| 12 | GGG | PAM sequence |
| 13 | GGG | PAM sequence |
| 14 | CGG | PAM sequence |
| 15 | ATTCCCAGGGCCGGTTAATG | P1 spacer targeting human AAVS1 |
| 16 | GTCCCCTCCACCCCACAGTG | P3 spacer targeting human AAVS1 |
| 17 | ACCCCACAGTGGGGCCACTA | P4 spacer targeting human AAVS1 |
| 18 | CCTCTAAGGTTTGCTTACGA | N1 spacer targeting human AAVS1 |

-continued

| SEQ ID NO | Sequence | Description |
|---|---|---|
| 19 | TATAAGGTGGTCCCAGCTCG | N2 spacer targeting human AAVS1 |
| 20 | CCATCGTAAGCAAACCTTAG | N3 spacer targeting human AAVS1 |
| 21 | TGG | PAM sequence |
| 22 | GGG | PAM sequence |
| 23 | GGG | PAM sequence |
| 24 | TGG | PAM sequence |
| 25 | GGG | PAM sequence |
| 26 | AGG | PAM sequence |
| 27 | GACTCCTGGGGATGGGCCAA | mT20 spacer target murine FOXP3 |
| 28 | TTGGCCCTTGGCCCATCCCC | mT22 spacer target murine FOXP3 |
| 29 | CCAGCTTGGCAAGACTCCTG | mT23 spacer target murine FOXP3 |
| 30 | GGG | PAM sequence |
| 31 | AGG | PAM sequence |
| 32 | GGG | PAM sequence |
| 33 | GTAGAAAAGATCAAAGGATCTTCTTGAGATCCTTTTTTTCTGCGCGTAATCTGCTGCTTGC<br>AAACAAAAAAACCACCGCTACCAGCGGTGGTTTGTTTGCCGGATCAAGAGCTACCAACT<br>CTTTTTCCGAAGGTAACTGGCTTCAGCAGAGCGCAGATACCAAATACTGTCCTTCTAGTG<br>TAGCCGTAGTTAGGCCACCACTTCAAGAACTCTGTAGCACCGCCTACATACCTCGCTCTG<br>CTAATCCTGTTACCAGTGGCTGCTGCCAGTGGCGATAAGTCGTGTCTTACCGGGTTGGAC<br>TCAAGACGATAGTTACCGGATAAGGCGCAGCGGTCGGGCTGAACGGGGGGTTCGTGCAC<br>ACAGCCCAGCTTGGAGCGAACGACCTACACCGAACTGAGATACCTACAGCGTGAGCTAT<br>GAGAAAGCGCCACGCTTCCCGAAGGGAGAAAGGCGGACAGGTATCCGGTAAGCGGCAG<br>GGTCGGAACAGGAGAGCGCACGAGGGAGCTTCCAGGGGGAAACGCCTGGTATCTTTATA<br>GTCCTGTCGGGTTTCGCCACCTCTGACTTGAGCGTCGATTTTTGTGATGCTCGTCAGGGGG<br>GCGGAGCCTATGGAAAAACGCCAGCAACGCGGCCTTTTTACGGTTCCTGGCCTTTTGCTG<br>GCCTTTTGCTCACATGTTCTTTCCTGCGTTATCCCCTGATTCTGTGGATAACCGTATTACCG<br>CCTTTGAGTGAGCTGATACCGCTCGCCGCAGCCGAACGACCGAGCGCAGCGAGTCAGTG<br>AGCGAGGAAGCGGAAGAGCGCCCAATACGCAAACCGCCTCTCCCCGCGCGTTGGCCGAT<br>TCATTAATGCAGCTGCGCGCTCGCTCGCTCACTGAGGCCGCCCGGGCAAAGCCCGGGCGT<br>CGGGCGACCTTTGGTCGCCCGGCCTCAGTGAGCGAGCGAGCGCGCAGAGAGGGAGTGGC<br>CAACTCCATCACTAGGGGTTCCTTGTAGTTAATGATTAACCCGCCATGCTACTTATCTACG<br>TAGCGGCCGCTCAGAATCTACCCACTTCTCGCCTTCTCCACTGCCACCAGCCCATTCTGTG<br>CCAGCATCATCACTTGCCAGGACTGTTACAATAGCCTCCTCACTAGCCCCACTCACAGCA<br>GCCAGATGAATCTTTTGAGTCCATGCCTAGTCACTGGGGCAAAATAGGACTCCGAGGAG<br>AAAGTCCGAGACCAGCTCCGGCAAGATGAGCAAACACAGCCTGTGCAGGGTGCAGGGA<br>GGGCTAGAGGCCTGAGGCTTGAAACAGCTCTCAAGTGGAGGGGGAAACAACCATTGCCC<br>TCATAGAGGACACATCCACACCAGGGCTGTGCTAGCGTGGGCAGGCAAGCCAGGTGCTG<br>GACCTCTGCACGTGGGGCATGTGTGGGTATGTACATGTACCTGTGTTCTTGGTGTGTGTGT<br>GTGTGTGTGTGTGTGTGTGTGTCTAGAGCTGGGGTGCAACTATGGGGCCCCTCGGGACAT<br>GTCCCAGCCAATGCCTGCTTTGACCAGAGGAGTGTCCACGTGGCTCAGGTGGTCGAGTAT | #3008 pAAV_FoxP 3.0.6 kb.MN D.GFP.WPR E3.pA |

-continued

| SEQ ID NO | Sequence | Description |
|---|---|---|
| | CTCATACCGCCCTAGCACACGTGTGACTCCTTTCCCCTATTGTCTACGCAGCCTGCCCTTG | |
| | GACAAGGACCCGACGCGTAGGAACAGAGAAACAGGAGAATATGGGCCAAACAGGATAT | |
| | CTGTGGTAAGCAGTTCCTGCCCCGGCTCAGGGCCAAGAACAGTTGGAACAGCAGAATAT | |
| | GGGCCAAACAGGATATCTGTGGTAAGCAGTTCCTGCCCCGGCTCAGGGCCAAGAACAGA | |
| | TGGTCCCCAGATGCGGTCCCGCCCTCAGCAGTTTCTAGAGAACCATCAGATGTTTCCAGG | |
| | GTGCCCCAAGGACCTGAAATGACCCTGTGCCTTATTTGAACTAACCAATCAGTTCGCTTC | |
| | TCGCTTCTGTTCGCGCGCTTCTGCTCCCCGAGCTCTATATAAGCAGAGCTCGTTTAGTGAA | |
| | CCGTCAGATCGCCTGGAGACGCCATCCACGCTGTTTTGACTTCCATAGAAGGATCTCGAG | |
| | GCCACCATGGTGAGCAAGGGCGAGGAGCTGTTCACCGGGGTGGTGCCCATCCTGGTCGA | |
| | GCTGGACGGCGACGTAAACGGCCACAAGTTCAGCGTGTCCGGCGAGGGCGAGGGCGATG | |
| | CCACCTACGGCAAGCTGACCCTGAAGTTCATCTGCACCACCGGCAAGCTGCCCGTGCCCT | |
| | GGCCCACCCTCGTGACCACCCTGACCTACGGCGTGCAGTGCTTCAGCCGCTACCCCGACC | |
| | ACATGAAGCAGCACGACTTCTTCAAGTCCGCCATGCCCGAAGGCTACGTCCAGGAGCGC | |
| | ACCATCTTCTTCAAGGACGACGGCAACTACAAGACCCGCGCCGAGGTGAAGTTCGAGGG | |
| | CGACACCCTGGTGAACCGCATCGAGCTGAAGGGCATCGACTTCAAGGAGGACGGCAACA | |
| | TCCTGGGGCACAAGCTGGAGTACAACTACAACAGCCACAACGTCTATATCATGGCCGAC | |
| | AAGCAGAAGAACGGCATCAAGGTGAACTTCAAGATCCGCCACAACATCGAGGACGGCA | |
| | GCGTGCAGCTCGCCGACCACTACCAGCAGAACACCCCCATCGGCGACGGCCCCGTGCTG | |
| | CTGCCCGACAACCACTACCTGAGCACCCAGTCCGCCCTGAGCAAAGACCCCAACGAGAA | |
| | GCGCGATCACATGGTCCTGCTGGAGTTCGTGACCGCCGCCGGGATCACTCTCGGCATGGA | |
| | CGAGCTGTACAAGTAAAAGCTTGATAATCAACCTCTGGATTACAAAATTTGTGAAAGATT | |
| | GACTGGTATTCTTAACTATGTTGCTCCTTTTACGCTATGTGGATACGCTGCTTTAATGCCT | |
| | TTGTATCATGCTATTGCTTCCCGTATGGCTTTCATTTTCTCCTCCTTGTATAAATCCTGGTT | |
| | AGTTCTTGCCACGGCGGAACTCATCGCCGCCTGCCTTGCCCGCTGCTGGACAGGGGCTCG | |
| | GCTGTTGGGCACTGACAATTCCGTGGGTCGACTGCTTTATTTGTGAAATTTGTGATGCTAT | |
| | TGCTTTATTTGTAACCATTATAAGCTGCAATAAACAAGTTAACAACAACAATTGCATTCA | |
| | TTTTATGTTTCAGGTTCAGGGGGAGATGTGGGAGGTTTTTTAAAGCACTAGTGTGAGGCC | |
| | CTGGGCCCAGGATGGGGCAGGCAGGGTGGGGTACCTGGACCTACAGGTGCCGACCTTTA | |
| | CTGTGGCACTGGGCGGGAGGGGGGCTGGCTGGGGCACAGGAAGTGGTTTCTGGGTCCCA | |
| | GGCAAGTCTGTGACTTATGCAGATGTTGCAGGGCCAAGAAAATCCCCACCTGCCAGGCCT | |
| | CAGAGATTGGAGGCTCTCCCCGACCTCCCAATCCCTGTCTCAGGAGAGGAGGAGGCCGT | |
| | ATTGTAGTCCCATGAGCATAGCTATGTGTCCCCATCCCCATGTGACAAGAGAAGAGGACT | |
| | GGGGCCAAGTAGGTGAGGTGACAGGGCTGAGGCCAGCTCTGCAACTTATTAGCTGTTTG | |
| | ATCTTTAAAAAGTTACTCGATCTCCATGAGCCTCAGTTTCCATACGTGTAAAAGGGGGAT | |
| | GATCATAGCATCTACCATGTGGGCTTGCAGTGCAGAGTATTTGAATTAGACACAGAACAG | |
| | TGAGGATCAGGATGGCCTCTCACCCACCTGCCTTTCTGCCCAGCTGCCCACACTGCCCCT | |
| | AGTCATGGTGGCACCCTCCGGGGCACGGCTGGGCCCCTTGCCCCACTTACAGGCACCGCG | |
| | GCGCTACGTAGATAAGTAGCATGGCGGGTTAATCATTAACTACAAGGAACCCCTAGTGAT | |
| | GGAGTTGGCCACTCCCTCTCTGCGCGCTCGCTCGCTCACTGAGGCCGGGCGACCAAAGGT | |
| | CGCCCGACGCCCGGGCTTTGCCCGGGCGGCCTCAGTGAGCGAGCGAGCGCGCCAGCTGG | |
| | CGTAATAGCGAAGAGGCCCGCACCGATCGCCCTTCCCAACAGTTGCGCAGCCTGAATGG | |
| | CGAATGGCGATTCCGTTGCAATGGCTGGCGGTAATATTGTTCTGGATATTACCAGCAAGG | |
| | CCGATAGTTTGAGTTCTTCTACTCAGGCAAGTGATGTTATTACTAATCAAAGAAGTATTG | |
| | CGACAACGGTTAATTTGCGTGATGGACAGACTCTTTTACTCGGTGGCCTCACTGATTATA | |
| | AAAACACTTCTCAGGATTCTGGCGTACCGTTCCTGTCTAAAATCCCTTTAATCGGCCTCCT | |
| | GTTTAGCTCCCGCTCTGATTCTAACGAGGAAAGCACGTTATACGTGCTCGTCAAAGCAAC | |
| | CATAGTACGCGCCCTGTAGCGGCGCATTAAGCGCGGCGGGTGTGGTGGTTACGCGCAGC | |
| | GTGACCGCTACACTTGCCAGCGCCCTAGCGCCCGCTCCTTTCGCTTTCTTCCCTTCCTTTCT | |
| | CGCCACGTTCGCCGGCTTTCCCCGTCAAGCTCTAAATCGGGGGCTCCCTTTAGGGTTCCG | |
| | ATTTAGTGCTTTACGGCACCTCGACCCCAAAAAACTTGATTAGGGTGATGGTTCACGTAG | |
| | TGGGCCATCGCCCTGATAGACGGTTTTTCGCCCTTTGACGTTGGAGTCCACGTTCTTTAAT | |
| | AGTGGACTCTTGTTCCAAACTGGAACAACACTCAACCCTATCTCGGTCTATTCTTTTGATT | |
| | TATAAGGGATTTTGCCGATTTCGGCCTATTGGTTAAAAAATGAGCTGATTTAACAAAAAT | |
| | TTAACGCGAATTTTAACAAAATATTAACGTTTACAATTTAAATATTTGCTTATACAATCTT | |
| | CCTGTTTTTGGGGCTTTTCTGATTATCAACCGGGGTACATATGATTGACATGCTAGTTTTA | |
| | CGATTACCGTTCATCGATTCTCTTGTTTGCTCCAGACTCTCAGGCAATGACCTGATAGCCT | |
| | TTGTAGAGACCTCTCAAAAATAGCTACCCTCTCCGGCATGAATTTATCAGCTAGAACGGT | |
| | TGAATATCATATTGATGGTGATTTGACTGTCTCCGGCCTTTCTCACCCGTTTGAATCTTTA | |
| | CCTACACATTACTCAGGCATTGCATTTAAAATATATGAGGGTTCTAAAAATTTTTATCCTT | |
| | GCGTTGAAATAAAGGCTTCTCCCGCAAAAGTATTACAGGGTCATAATGTTTTTGGTACAA | |
| | CCGATTTAGCTTTATGCTCTGAGGCTTTATTGCTTAATTTTGCTAATTCTTTGCCTTGCCTG | |
| | TATGATTTATTGGATGTTGGAATCGCCTGATGCGGTATTTTCTCCTTACGCATCTGTGCGG | |
| | TATTTCACACCGCATATGGTGCACTCTCAGTACAATCTGCTCTGATGCCGCATAGTTAAG | |
| | CCAGCCCCGACACCCGCCAACACCCGCTGACGCGCCCTGACGGGCTTGTCTGCTCCCGGC | |
| | ATCCGCTTACAGACAAGCTGTGACCGTCTCCGGGAGCTGCATGTGTCAGAGGTTTTCACC | |
| | GTCATCACCGAAACGCGCGAGACGAAAGGGCCTCGTGATACGCCTATTTTTATAGGTTAA | |
| | TGTCATGATAATAATGGTTTCTTAGACGTCAGGTGGCACTTTTCGGGGAAATGTGCGCGG | |
| | AACCCCTATTTGTTTATTTTTCTAAATACATTCAAATATGTATCCGCTCATGAGACAATAA | |
| | CCCTGATAAATGCTTCAATAATATTGAAAAAGGAAGAGTATGAGTATTCAACATTTCCGT | |
| | GTCGCCCTTATTCCCTTTTTTGCGGCATTTTGCCTTCCTGTTTTTGCTCACCCAGAAACGCT | |
| | GGTGAAAGTAAAAGATGCTGAAGATCAGTTGGGTGCACGAGTGGGTTACATCGAACTGG | |
| | ATCTCAACAGCGGTAAGATCCTTGAGAGTTTTCGCCCCGAAGAACGTTTTCCAATGATGA | |
| | GCACTTTTAAAGTTCTGCTATGTGGCGCGGTATTATCCCGTATTGACGCCGGGCAAGAGC | |
| | AACTCGGTCGCCGCATACACTATTCTCAGAATGACTTGGTTGAGTACTCACCAGTCACAG | |
| | AAAAGCATCTTACGGATGGCATGACAGTAAGAGAATTATGCAGTGCTGCCATAACCATG | |

-continued

| SEQ ID NO | Sequence | Description |
|---|---|---|
| | AGTGATAACACTGCGGCCAACTTACTTCTGACAACGATCGGAGGACCGAAGGAGCTAAC<br>CGCTTTTTTGCACAACATGGGGGATCATGTAACTCGCCTTGATCGTTGGGAACCGGAGCT<br>GAATGAAGCCATACCAAACGACGAGCGTGACACCACGATGCCTGTAGCAATGGCAACAA<br>CGTTGCGCAAACTATTAACTGGCGAACTACTTACTCTAGCTTCCCGGCAACAATTAATAG<br>ACTGGATGGAGGCGGATAAAGTTGCAGGACCACTTCTGCGCTCGGCCCTTCCGGCTGGCT<br>GGTTTATTGCTGATAAATCTGGAGCCGGTGAGCGTGGGTCTCGCGGTATCATTGCAGCAC<br>TGGGGCCAGATGGTAAGCCCTCCCGTATCGTAGTTATCTACACGACGGGGAGTCAGGCA<br>ACTATGGATGAACGAAATAGACAGATCGCTGAGATAGGTGCCTCACTGATTAAGCATTG<br>GTAACTGTCAGACCAAGTTTACTCATATATACTTTAGATTGATTTAAAACTTCATTTTTAA<br>TTTAAAAGGATCTAGGTGAAGATCCTTTTTGATAATCTCATGACCAAAATCCCTTAACGT<br>GAGTTTTCGTTCCACTGAGCGTCAGACCCC | |
| 34 | GTAGAAAAGATCAAAGGATCTTCTTGAGATCCTTTTTTTCTGCGCGTAATCTGCTGCTTGC<br>AAACAAAAAAACCACCGCTACCAGCGGTGGTTTGTTTGCCGGATCAAGAGCTACCAACT<br>CTTTTTCCGAAGGTAACTGGCTTCAGCAGAGCGCAGATACCAAATACTGTCCTTCTAGTG<br>TAGCCGTAGTTAGGCCACCACTTCAAGAACTCTGTAGCACCGCCTACATACCTCGCTCTG<br>CTAATCCTGTTACCAGTGGCTGCTGCCAGTGGCGATAAGTCGTGTCTTACCGGGTTGGAC<br>TCAAGACGATAGTTACCGGATAAGGCGCAGCGGTCGGGCTGAACGGGGGGTTCGTGCAC<br>ACAGCCCAGCTTGGAGCGAACGACCTACACCGAACTGAGATACCTACAGCGTGAGCTAT<br>GAGAAAGCGCCACGCTTCCCGAAGGGAGAAAGGCGGACAGGTATCCGGTAAGCGGCAG<br>GGTCGGAACAGGAGAGCGCACGAGGGAGCTTCCAGGGGGAAACGCCTGGTATCTTTATA<br>GTCCTGTCGGGTTTCGCCACCTCTGACTTGAGCGTCGATTTTTGTGATGCTCGTCAGGGGG<br>GCGGAGCCTATGGAAAAACGCCAGCAACGCGGCCTTTTTACGGTTCCTGGCCTTTTGCTG<br>GCCTTTTGCTCACATGTTCTTTCCTGCGTTATCCCCTGATTCTGTGGATAACCGTATTACCG<br>CCTTTGAGTGAGCTGATACCGCTCGCCGCAGCCGAACGACCGAGCGCAGCGAGTCAGTG<br>AGCGAGGAAGCGGAAGAGCGCCCAATACGCAAACCGCCTCTCCCCGCGCGTTGGCCGAT<br>TCATTAATGCAGCTGCGCGCTCGCTCGCTCACTGAGGCCGCCCGGGCAAAGCCCGGGCGT<br>CGGGCGACCTTTGGTCGCCCGGCCTCAGTGAGCGAGCGAGCGCGCAGAGAGGGAGTGGC<br>CAACTCCATCACTAGGGGTTCCTTGTAGTTAATGATTAACCCGCCATGCTACTTATCTACG<br>TAGCGGCCGCTCAGAATCTACCCACTTCTCGCCTTCTCCACTGCCACCAGCCCATTCTGTG<br>CCAGCATCATCACTTGCCAGGACTGTTACAATAGCCTCCTCACTAGCCCCACTCACAGCA<br>GCCAGATGAATCTTTTGAGTCCATGCCTAGTCACTGGGGCAAAATAGGACTCCGAGGAG<br>AAAGTCCGAGACCAGCTCCGGCAAGATGAGCAAACACAGCCTGTGCAGGGTGCAGGGA<br>GGGCTAGAGGCCTGAGGCTTGAAACAGCTCTCAAGTGGAGGGGGAAACAACCATTGCCC<br>TCATAGAGGACACATCCACACCAGGGCTGTGCTAGCGTGGGCAGGCAAGCCAGGTGCTG<br>GACCTCTGCACGTGGGGCATGTGTGGGTATGTACATGTACCTGTGTTCTTGGTGTGTGTGT<br>GTGTGTGTGTGTGTGTGTGTGTCTAGAGCTGGGGTGCAACTATGGGGCCCCTCGGGACAT<br>GTCCCAGCCAATGCCTGCTTTGACCAGAGGAGTGTCCACGTGGCTCAGGTGGTCGAGTAT<br>CTCATACCGCCCTAGCACACGTGTGACTCCTTTCCCCTATTGTCTACGCAGCCTGCCCTTG<br>GACAAGGACCCGATGCCTAATCCTCGGCCTGGAAAGCCTAGCGCTCCTTCTCTTGCTCTG<br>GGACCTTCTCCTGGCGCCTCTCCATCTTGGAGAGCCGCTCCTAAAGCCAGCGATCTGCTG<br>GGAGCTAGAGGACCTGGCGGCACATTTCAGGGCAGAGATCTTAGAGGCGGAGCCCACGC<br>TAGCTCCTCCAGCCTTAATCCTATGCCTCCTAGCCAGCTCCAGCTGCCTACACTGCCTCTG<br>GTTATGGTGGCTCCTAGCGGAGCTAGACTGGGCCCTCTGCCTCATCTGCAAGCTCTGCTG<br>CAGGACAGACCCCACTTCATGCACCAGCTGAGCACCGTGGATGCCCACGCAAGAACACC<br>TGTGCTGCAGGTTCACCCTCTGGAATCCCCAGCCATGATCAGCCTGACACCTCCAACAAC<br>AGCCACCGGCGTGTTCAGCCTGAAAGCCAGACCTGGACTGCCTCCTGGCATCAATGTGGC<br>CAGCCTGGAATGGGTGTCCAGAGAACCTGCTCTGCTGTGCACATTCCCCAATCCAAGCGC<br>TCCCAGAAAGGACAGCACACTGTCTGCCGTGCCTCAGAGCAGCTATCCCCTGCTTGCTAA<br>CGGCGTGTGCAAGTGGCCTGGATGCGAGAAGGTGTTCGAGGAACCCGAGGACTTCCTGA<br>AGCACTGCCAGGCCGATCATCTGCTGGACGAGAAAGGCAGAGCCCAGTGTCTGCTCCAG<br>CGCGAGATGGTGCAGTCTCTGGAACAGCAGCTGGTCCTGGAAAAAGAAAAGCTGAGCGC<br>CATGCAGGCCCACCTGGCCGGAAAAATGGCCCTGACAAAGGCCAGCAGCGTGGCCTCTT<br>CTGATAAGGGCAGCTGCTGCATTGTGGCCGCTGGATCTCAGGGACCTGTGGTTCCTGCTT<br>GGAGCGGACCTAGAGAGGCCCCTGATTCTCTGTTTGCCGTGCGGAGACACCTGTGGGGCT<br>CTCACGGCAACTCTACTTTCCCCGAGTTCCTGCACAACATGGACTACTTCAAGTTCCACA<br>ACATGCGGCCTCCATTCACCTACGCCACACTGATCAGATGGGCCATTCTGGAAGCCCCTG<br>AGAAGCAGAGAACCCTGAACGAGATCTACCACTGGTTTACCCGGATGTTCGCCTTCTTCC<br>GGAATCACCCTGCCACCTGGAAGAACGCCATCCGGCACAATCTGAGCCTGCACAAGTGC<br>TTCGTGCGCGTGGAATCTGAGAAAGGCGCCGTGTGGACAGTGGACGAGCTGGAATTCAG<br>AAAGAAGAGAAGCCAGCGGCCTAGCCGGTGCAGCAATCCTACACCTGGACCTTGAAAGC<br>TTGATAATCAACCTCTGGATTACAAAATTTGTGAAAGATTGACTGGTATTCTTAACTATGT<br>TGCTCCTTTTACGCTATGTGGATACGCTGCTTTAATGCCTTTGTATCATGCTATTGCTTCCC<br>GTATGGCTTTCATTTTCTCCTCCTTGTATAAATCCTGGTTAGTTCTTGCCACGGCGGAACT<br>CATCGCCGCCTGCCTTGCCCGCTGCTGGACAGGGGCTCGGCTGTTGGGCACTGACAATTC<br>CGTGGGTCGACTGCTTTATTTGTGAAATTTGTGATGCTATTGCTTTATTTGTAACCATTAT<br>AAGCTGCAATAAACAAGTTAACAACAACAATTGCATTCATTTTATGTTTCAGGTTCAGGG<br>GGAGATGTGGGAGGTTTTTTAAAGCACTAGTGTGAGGCCCTGGGCCCAGGATGGGGCAG<br>GCAGGGTGGGGTACCTGGACCTACAGGTGCCGACCTTTACTGTGGCACTGGGCGGGAGG<br>GGGGCTGGCTGGGGCACAGGAAGTGGTTTCTGGGTCCCAGGCAAGTCTGTGACTTATGCA<br>GATGTTGCAGGGCCAAGAAAATCCCCACCTGCCAGGCCTCAGAGATTGGAGGCTCTCCC<br>CGACCTCCCAATCCCTGTCTCAGGAGAGGAGGAGGCCGTATTGTAGTCCCATGAGCATAG<br>CTATGTGTCCCCATCCCCATGTGACAAGAGAAGAGGACTGGGGCCAAGTAGGTGAGGTG<br>ACAGGGCTGAGGCCAGCTCTGCAACTTATTAGCTGTTTGATCTTTAAAAGTTACTCGAT<br>CTCCATGAGCCTCAGTTTCCATACGTGTAAAAGGGGGATGATCATAGCATCTACCATGTG | #3037<br>pAAV_FoxP<br>3.0.6 kb.FoxP<br>3cDNA.WPR<br>E3.pA |

-continued

| SEQ ID NO | Sequence | Description |
|---|---|---|
| | GGCTTGCAGTGCAGAGTATTTGAATTAGACACAGAACAGTGAGGATCAGGATGGCCTCT<br>CACCCACCTGCCTTTCTGCCCAGCTGCCCACACTGCCCCTAGTCATGGTGGCACCCTCCG<br>GGGCACGGCTGGGCCCCTTGCCCCACTTACAGGCACCGCGGCGCTACGTAGATAAGTAG<br>CATGGCGGGTTAATCATTAACTACAAGGAACCCCTAGTGATGGAGTTGGCCACTCCCTCT<br>CTGCGCGCTCGCTCGCTCACTGAGGCCGGGCGACCAAAGGTCGCCCGACGCCCGGGCTTT<br>GCCCGGGCGGCCTCAGTGAGCGAGCGAGCGCGCCAGCTGGCGTAATAGCGAAGAGGCCC<br>GCACCGATCGCCCTTCCCAACAGTTGCGCAGCCTGAATGGCGAATGGCGATTCCGTTGCA<br>ATGGCTGGCGGTAATATTGTTCTGGATATTACCAGCAAGGCCGATAGTTTGAGTTCTTCT<br>ACTCAGGCAAGTGATGTTATTACTAATCAAAGAAGTATTGCGACAACGGTTAATTTGCGT<br>GATGGACAGACTCTTTTACTCGGTGGCCTCACTGATTATAAAAACACTTCTCAGGATTCT<br>GGCGTACCGTTCCTGTCTAAAATCCCTTTAATCGGCCTCCTGTTTAGCTCCCGCTCTGATT<br>CTAACGAGGAAAGCACGTTATACGTGCTCGTCAAAGCAACCATAGTACGCGCCCTGTAG<br>CGGCGCATTAAGCGCGGCGGGTGTGGTGGTTACGCGCAGCGTGACCGCTACACTTGCCA<br>GCGCCCTAGCGCCCGCTCCTTTCGCTTTCTTCCCTTCCTTTCTCGCCACGTTCGCCGGCTTT<br>CCCCGTCAAGCTCTAAATCGGGGGCTCCCTTTAGGGTTCCGATTTAGTGCTTTACGGCAC<br>CTCGACCCCAAAAAACTTGATTAGGGTGATGGTTCACGTAGTGGGCCATCGCCCTGATAG<br>ACGGTTTTTCGCCCTTTGACGTTGGAGTCCACGTTCTTTAATAGTGGACTCTTGTTCCAAA<br>CTGGAACAACACTCAACCCTATCTCGGTCTATTCTTTTGATTTATAAGGGATTTTGCCGAT<br>TTCGGCCTATTGGTTAAAAAATGAGCTGATTTAACAAAAATTTAACGCGAATTTTAACAA<br>AATATTAACGTTTACAATTTAAATATTTGCTTATACAATCTTCCTGTTTTTGGGGCTTTTCT<br>GATTATCAACCGGGGTACATATGATTGACATGCTAGTTTTACGATTACCGTTCATCGATTC<br>TCTTGTTTGCTCCAGACTCTCAGGCAATGACCTGATAGCCTTTGTAGAGACCTCTCAAAA<br>ATAGCTACCCTCTCCGGCATGAATTTATCAGCTAGAACGGTTGAATATCATATTGATGGT<br>GATTTGACTGTCTCCGGCCTTTCTCACCCGTTTGAATCTTTACCTACACATTACTCAGGCA<br>TTGCATTTAAAATATATGAGGGTTCTAAAAATTTTTATCCTTGCGTTGAAATAAAGGCTTC<br>TCCCGCAAAAGTATTACAGGGTCATAATGTTTTTGGTACAACCGATTTAGCTTTATGCTCT<br>GAGGCTTTATTGCTTAATTTTGCTAATTCTTTGCCTTGCCTGTATGATTTATTGGATGTTGG<br>AATCGCCTGATGCGGTATTTTCTCCTTACGCATCTGTGCGGTATTTCACACCGCATATGGT<br>GCACTCTCAGTACAATCTGCTCTGATGCCGCATAGTTAAGCCAGCCCCGACACCCGCCAA<br>CACCCGCTGACGCGCCCTGACGGGCTTGTCTGCTCCCGGCATCCGCTTACAGACAAGCTG<br>TGACCGTCTCCGGGAGCTGCATGTGTCAGAGGTTTTCACCGTCATCACCGAAACGCGCGA<br>GACGAAAGGGCCTCGTGATACGCCTATTTTTATAGGTTAATGTCATGATAATAATGGTTT<br>CTTAGACGTCAGGTGGCACTTTTCGGGGAAATGTGCGCGGAACCCCTATTTGTTTATTTTT<br>CTAAATACATTCAAATATGTATCCGCTCATGAGACAATAACCCTGATAAATGCTTCAATA<br>ATATTGAAAAAGGAAGAGTATGAGTATTCAACATTTCCGTGTCGCCCTTATTCCCTTTTTT<br>GCGGCATTTTGCCTTCCTGTTTTTGCTCACCCAGAAACGCTGGTGAAAGTAAAAGATGCT<br>GAAGATCAGTTGGGTGCACGAGTGGGTTACATCGAACTGGATCTCAACAGCGGTAAGAT<br>CCTTGAGAGTTTTCGCCCCGAAGAACGTTTTCCAATGATGAGCACTTTTAAAGTTCTGCTA<br>TGTGGCGCGGTATTATCCCGTATTGACGCCGGGCAAGAGCAACTCGGTCGCCGCATACAC<br>TATTCTCAGAATGACTTGGTTGAGTACTCACCAGTCACAGAAAAGCATCTTACGGATGGC<br>ATGACAGTAAGAGAATTATGCAGTGCTGCCATAACCATGAGTGATAACACTGCGGCCAA<br>CTTACTTCTGACAACGATCGGAGGACCGAAGGAGCTAACCGCTTTTTTGCACAACATGGG<br>GGATCATGTAACTCGCCTTGATCGTTGGGAACCGGAGCTGAATGAAGCCATACCAAACG<br>ACGAGCGTGACACCACGATGCCTGTAGCAATGGCAACAACGTTGCGCAAACTATTAACT<br>GGCGAACTACTTACTCTAGCTTCCCGGCAACAATTAATAGACTGGATGGAGGCGGATAA<br>AGTTGCAGGACCACTTCTGCGCTCGGCCCTTCCGGCTGGCTGGTTTATTGCTGATAAATCT<br>GGAGCCGGTGAGCGTGGGTCTCGCGGTATCATTGCAGCACTGGGGCCAGATGGTAAGCC<br>CTCCCGTATCGTAGTTATCTACACGACGGGGAGTCAGGCAACTATGGATGAACGAAATA<br>GACAGATCGCTGAGATAGGTGCCTCACTGATTAAGCATTGGTAACTGTCAGACCAAGTTT<br>ACTCATATATACTTTAGATTGATTTAAAACTTCATTTTTAATTTAAAAGGATCTAGGTGAA<br>GATCCTTTTTGATAATCTCATGACCAAAATCCCTTAACGTGAGTTTTCGTTCCACTGAGCG<br>TCAGACCCC | |
| 35 | GTAGAAAAGATCAAAGGATCTTCTTGAGATCCTTTTTTTCTGCGCGTAATCTGCTGCTTGC<br>AAACAAAAAAACCACCGCTACCAGCGGTGGTTTGTTTGCCGGATCAAGAGCTACCAACT<br>CTTTTTCCGAAGGTAACTGGCTTCAGCAGAGCGCAGATACCAAATACTGTCCTTCTAGTG<br>TAGCCGTAGTTAGGCCACCACTTCAAGAACTCTGTAGCACCGCCTACATACCTCGCTCTG<br>CTAATCCTGTTACCAGTGGCTGCTGCCAGTGGCGATAAGTCGTGTCTTACCGGGTTGGAC<br>TCAAGACGATAGTTACCGGATAAGGCGCAGCGGTCGGGCTGAACGGGGGGTTCGTGCAC<br>ACAGCCCAGCTTGGAGCGAACGACCTACACCGAACTGAGATACCTACAGCGTGAGCTAT<br>GAGAAAGCGCCACGCTTCCCGAAGGGAGAAAGGCGGACAGGTATCCGGTAAGCGGCAG<br>GGTCGGAACAGGAGAGCGCACGAGGGAGCTTCCAGGGGGAAACGCCTGGTATCTTTATA<br>GTCCTGTCGGGTTTCGCCACCTCTGACTTGAGCGTCGATTTTTGTGATGCTCGTCAGGGGG<br>GCGGAGCCTATGGAAAAACGCCAGCAACGCGGCCTTTTTACGGTTCCTGGCCTTTTGCTG<br>GCCTTTTGCTCACATGTTCTTTCCTGCGTTATCCCCTGATTCTGTGGATAACCGTATTACCG<br>CCTTTGAGTGAGCTGATACCGCTCGCCGCAGCCGAACGACCGAGCGCAGCGAGTCAGTG<br>AGCGAGGAAGCGGAAGAGCGCCCAATACGCAAACCGCCTCTCCCCGCGCGTTGGCCGAT<br>TCATTAATGCAGCTGCGCGCTCGCTCGCTCACTGAGGCCGCCCGGGCAAAGCCCGGGCGT<br>CGGGCGACCTTTGGTCGCCCGGCCTCAGTGAGCGAGCGAGCGCGCAGAGAGGGAGTGGC<br>CAACTCCATCACTAGGGGTTCCTTGTAGTTAATGATTAACCCGCCATGCTACTTATCTACG<br>TAGCGGCCGCCTTGCCCACTACATCCAAGCTGCTAGCACTGCTCCTGATCCAGCTTCAGA<br>TTAAGTCTCAGAATCTACCCACTTCTCGCCTTCTCCACTGCCACCAGCCCATTCTGTGCCA<br>GCATCATCACTTGCCAGGACTGTTACAATAGCCTCCTCACTAGCCCCACTCACAGCAGCC<br>AGATGAATCTTTTGAGTCCATGCCTAGTCACTGGGGCAAAATAGGACTCCGAGGAGAAA<br>GTCCGAGACCAGCTCCGGCAAGATGAGCAAACACAGCCTGTGCAGGGTGCAGGGAGGGC | #3088<br>pAAV_FOX<br>P3.08_MND.<br>GFP 08_for<br>T3 |

-continued

| SEQ ID NO | Sequence | Description |
|---|---|---|
| | TAGAGGCCTGAGGCTTGAAACAGCTCTCAAGTGGAGGGGGAAACAACCATTGCCCTCAT AGAGGACACATCCACACCAGGGCTGTGCTAGCGTGGGCAGGCAAGCCAGGTGCTGGACC TCTGCACGTGGGGCATGTGTGGGTATGTACATGTACCTGTGTTCTTGGTGTGTGTGTGTGT GTGTGTGTGTGTGTGTGTCTAGAGCTGGGGTGCAACTATGGGGCCCCTCGGGACATGTCC CAGCCAATGCCTGCTTTGACCAGAGGAGTGTCCACGTGGCTCAGGTGGTCGAGTATCTCA TACCGCCCTAGCACACGTGTGACTCCTTTCCCCTATTGTCTACGCAGCCTGCCCTTGGACA AGGACCCGATGCCCAACCCCAGGCCTGGCAAGCCCTCGGCCCCTTCCTTGGCCCTTGGCC CATCCCCAGGAGCCTCGCCCAGCTGGAGGGCTGCACCCAAAGCCTCAGACCTGCTGGGG GCCCGGGGCCCAGGGGGAACCTTCCAACGCGTAGGAACAGAGAAACAGGAGAATATGG GCCAAACAGGATATCTGTGGTAAGCAGTTCCTGCCCCGGCTCAGGGCCAAGAACAGTTG GAACAGCAGAATATGGGCCAAACAGGATATCTGTGGTAAGCAGTTCCTGCCCCGGCTCA GGGCCAAGAACAGATGGTCCCCAGATGCGGTCCCGCCCTCAGCAGTTTCTAGAGAACCA TCAGATGTTTCCAGGGTGCCCCAAGGACCTGAAATGACCCTGTGCCTTATTTGAACTAAC CAATCAGTTCGCTTCTCGCTTCTGTTCGCGCGCTTCTGCTCCCCGAGCTCTATATAAGCAG AGCTCGTTTAGTGAACCGTCAGATCGCCTGGAGACGCCATCCACGCTGTTTTGACTTCCA TAGAAGGATCTCGAGGCCACCATGGTGAGCAAGGGCGAGGAGCTGTTCACCGGGGTGGT GCCCATCCTGGTCGAGCTGGACGGCGACGTAAACGGCCACAAGTTCAGCGTGTCCGGCG AGGGCGAGGGCGATGCCACCTACGGCAAGCTGACCCTGAAGTTCATCTGCACCACCGGC AAGCTGCCCGTGCCCTGGCCCACCCTCGTGACCACCCTGACCTACGGCGTGCAGTGCTTC AGCCGCTACCCCGACCACATGAAGCAGCACGACTTCTTCAAGTCCGCCATGCCCGAAGG CTACGTCCAGGAGCGCACCATCTTCTTCAAGGACGACGGCAACTACAAGACCCGCGCCG AGGTGAAGTTCGAGGGCGACACCCTGGTGAACCGCATCGAGCTGAAGGGCATCGACTTC AAGGAGGACGGCAACATCCTGGGGCACAAGCTGGAGTACAACTACAACAGCCACAACGT CTATATCATGGCCGACAAGCAGAAGAACGGCATCAAGGTGAACTTCAAGATCCGCCACA ACATCGAGGACGGCAGCGTGCAGCTCGCCGACCACTACCAGCAGAACACCCCCATCGGC GACGGCCCCGTGCTGCTGCCCGACAACCACTACCTGAGCACCCAGTCCGCCCTGAGCAA AGACCCCAACGAGAAGCGCGATCACATGGTCCTGCTGGAGTTCGTGACCGCCGCCGGGA TCACTCTCGGCATGGACGAGCTGTACAAGTAAAAGCTTGATAATCAACCTCTGGATTACA AAATTTGTGAAAGATTGACTGGTATTCTTAACTATGTTGCTCCTTTTACGCTATGTGGATA CGCTGCTTTAATGCCTTTGTATCATGCTATTGCTTCCCGTATGGCTTTCATTTTCTCCTCCT TGTATAAATCCTGGTTAGTTCTTGCCACGGCGGAACTCATCGCCGCCTGCCTTGCCCGCTG CTGGACAGGGGCTCGGCTGTTGGGCACTGACAATTCCGTGGGTCGACTGCTTTATTTGTG AAATTTGTGATGCTATTGCTTTATTTGTAACCATTATAAGCTGCAATAAACAAGTTAACA ACAACAATTGCATTCATTTTATGTTTCAGGTTCAGGGGGAGATGTGGGAGGTTTTTTAAA GCACTAGTCGAGATCTTCGAGGCGGGGCCCATGCCTCCTCTTCTTCCTTGAACCCCATGC CACCATCGCAGCTGCAGGTGAGGCCCTGGGCCCAGGATGGGGCAGGCAGGGTGGGGTAC CTGGACCTACAGGTGCCGACCTTTACTGTGGCACTGGGCGGGAGGGGGGCTGGCTGGGG CACAGGAAGTGGTTTCTGGGTCCCAGGCAAGTCTGTGACTTATGCAGATGTTGCAGGGCC AAGAAAATCCCCACCTGCCAGGCCTCAGAGATTGGAGGCTCTCCCCGACCTCCCAATCCC TGTCTCAGGAGAGGAGGAGGCCGTATTGTAGTCCCATGAGCATAGCTATGTGTCCCCATC CCCATGTGACAAGAGAAGAGGACTGGGGCCAAGTAGGTGAGGTGACAGGGCTGAGGCC AGCTCTGCAACTTATTAGCTGTTTGATCTTTAAAAAGTTACTCGATCTCCATGAGCCTCAG TTTCCATACGTGTAAAAGGGGGATGATCATAGCATCTACCATGTGGGCTTGCAGTGCAGA GTATTTGAATTAGACACAGAACAGTGAGGATCAGGATGGCCTCTCACCCACCTGCCTTTC TGCCCAGCTGCCCACACTGCCCCTAGTCATGGTGGCACCCTCCGGGGCACGGCTGGGCCC CTTGCCCCACTTACAGGCACTCCTCCAGGACAGGCCACATTTCATGCACCAGGTATGGAC GGTGAATGGGCAGGGAGGAGGGAGCAGGTGGGAGAACTGTGGGGAGGGGCCCCGAGTC AGGCTGAACCGGATCCTACGTAGATAAGTAGCATGGCGGGTTAATCATTAACTACAAGG AACCCCTAGTGATGGAGTTGGCCACTCCCTCTCTGCGCGCTCGCTCGCTCACTGAGGCCG GGCGACCAAAGGTCGCCCGACGCCCGGGCTTTGCCCGGGCGGCCTCAGTGAGCGAGCGA GCGCGCCAGCTGGCGTAATAGCGAAGAGGCCCGCACCGATCGCCCTTCCCAACAGTTGC GCAGCCTGAATGGCGAATGGCGATTCCGTTGCAATGGCTGGCGGTAATATTGTTCTGGAT ATTACCAGCAAGGCCGATAGTTTGAGTTCTTCTACTCAGGCAAGTGATGTTATTACTAAT CAAAGAAGTATTGCGACAACGGTTAATTTGCGTGATGGACAGACTCTTTTACTCGGTGGC CTCACTGATTATAAAAACACTTCTCAGGATTCTGGCGTACCGTTCCTGTCTAAAATCCCTT TAATCGGCCTCCTGTTTAGCTCCCGCTCTGATTCTAACGAGGAAAGCACGTTATACGTGC TCGTCAAAGCAACCATAGTACGCGCCCTGTAGCGGCGCATTAAGCGCGGCGGGTGTGGT GGTTACGCGCAGCGTGACCGCTACACTTGCCAGCGCCCTAGCGCCCGCTCCTTTCGCTTT CTTCCCTTCCTTTCTCGCCACGTTCGCCGGCTTTCCCCGTCAAGCTCTAAATCGGGGGCTC CCTTTAGGGTTCCGATTTAGTGCTTTACGGCACCTCGACCCCAAAAAACTTGATTAGGGT GATGGTTCACGTAGTGGGCCATCGCCCTGATAGACGGTTTTTCGCCCTTTGACGTTGGAG TCCACGTTCTTTAATAGTGGACTCTTGTTCCAAACTGGAACAACACTCAACCCTATCTCGG TCTATTCTTTTGATTTATAAGGGATTTTGCCGATTTCGGCCTATTGGTTAAAAAATGAGCT GATTTAACAAAAATTTAACGCGAATTTTAACAAAATATTAACGTTTACAATTTAAATATT TGCTTATACAATCTTCCTGTTTTTGGGGCTTTTCTGATTATCAACCGGGGTACATATGATT GACATGCTAGTTTTACGATTACCGTTCATCGATTCTCTTGTTTGCTCCAGACTCTCAGGCA ATGACCTGATAGCCTTTGTAGAGACCTCTCAAAAATAGCTACCCTCTCCGGCATGAATTT ATCAGCTAGAACGGTTGAATATCATATTGATGGTGATTTGACTGTCTCCGGCCTTTCTCAC CCGTTTGAATCTTTACCTACACATTACTCAGGCATTGCATTTAAAATATATGAGGGTTCTA AAAATTTTTATCCTTGCGTTGAAATAAAGGCTTCTCCCGCAAAAGTATTACAGGGTCATA ATGTTTTTGGTACAACCGATTTAGCTTTATGCTCTGAGGCTTTATTGCTTAATTTTGCTAAT TCTTTGCCTTGCCTGTATGATTTATTGGATGTTGGAATCGCCTGATGCGGTATTTTCTCCTT ACGCATCTGTGCGGTATTTCACACCGCATATGGTGCACTCTCAGTACAATCTGCTCTGAT GCCGCATAGTTAAGCCAGCCCCGACACCCGCCAACACCCGCTGACGCGCCCTGACGGGC TTGTCTGCTCCCGGCATCCGCTTACAGACAAGCTGTGACCGTCTCCGGGAGCTGCATGTG | |

-continued

| SEQ ID NO | Sequence | Description |
|---|---|---|
| | TCAGAGGTTTTCACCGTCATCACCGAAACGCGCGAGACGAAAGGGCCTCGTGATACGCC<br>TATTTTTATAGGTTAATGTCATGATAATAATGGTTTCTTAGACGTCAGGTGGCACTTTTCG<br>GGGAAATGTGCGCGGAACCCCTATTTGTTTATTTTTCTAAATACATTCAAATATGTATCCG<br>CTCATGAGACAATAACCCTGATAAATGCTTCAATAATATTGAAAAAGGAAGAGTATGAG<br>TATTCAACATTTCCGTGTCGCCCTTATTCCCTTTTTTGCGGCATTTTGCCTTCCTGTTTTTG<br>CTCACCCAGAAACGCTGGTGAAAGTAAAAGATGCTGAAGATCAGTTGGGTGCACGAGTG<br>GGTTACATCGAACTGGATCTCAACAGCGGTAAGATCCTTGAGAGTTTTCGCCCCGAAGAA<br>CGTTTTCCAATGATGAGCACTTTTAAAGTTCTGCTATGTGGCGCGGTATTATCCCGTATTG<br>ACGCCGGGCAAGAGCAACTCGGTCGCCGCATACACTATTCTCAGAATGACTTGGTTGAGT<br>ACTCACCAGTCACAGAAAAGCATCTTACGGATGGCATGACAGTAAGAGAATTATGCAGT<br>GCTGCCATAACCATGAGTGATAACACTGCGGCCAACTTACTTCTGACAACGATCGGAGG<br>ACCGAAGGAGCTAACCGCTTTTTTGCACAACATGGGGGATCATGTAACTCGCCTTGATCG<br>TTGGGAACCGGAGCTGAATGAAGCCATACCAAACGACGAGCGTGACACCACGATGCCTG<br>TAGCAATGGCAACAACGTTGCGCAAACTATTAACTGGCGAACTACTTACTCTAGCTTCCC<br>GGCAACAATTAATAGACTGGATGGAGGCGGATAAAGTTGCAGGACCACTTCTGCGCTCG<br>GCCCTTCCGGCTGGCTGGTTTATTGCTGATAAATCTGGAGCCGGTGAGCGTGGGTCTCGC<br>GGTATCATTGCAGCACTGGGGCCAGATGGTAAGCCCTCCCGTATCGTAGTTATCTACACG<br>ACGGGGAGTCAGGCAACTATGGATGAACGAAATAGACAGATCGCTGAGATAGGTGCCTC<br>ACTGATTAAGCATTGGTAACTGTCAGACCAAGTTTACTCATATATACTTTAGATTGATTTA<br>AAACTTCATTTTTAATTTAAAAGGATCTAGGTGAAGATCCTTTTTGATAATCTCATGACCA<br>AAATCCCTTAACGTGAGTTTTCGTTCCACTGAGCGTCAGACCCC | |
| 36 | GTAGAAAAGATCAAAGGATCTTCTTGAGATCCTTTTTTTCTGCGCGTAATCTGCTGCTTGC<br>AAACAAAAAAACCACCGCTACCAGCGGTGGTTTGTTTGCCGGATCAAGAGCTACCAACT<br>CTTTTTCCGAAGGTAACTGGCTTCAGCAGAGCGCAGATACCAAATACTGTCCTTCTAGTG<br>TAGCCGTAGTTAGGCCACCACTTCAAGAACTCTGTAGCACCGCCTACATACCTCGCTCTG<br>CTAATCCTGTTACCAGTGGCTGCTGCCAGTGGCGATAAGTCGTGTCTTACCGGGTTGGAC<br>TCAAGACGATAGTTACCGGATAAGGCGCAGCGGTCGGGCTGAACGGGGGGTTCGTGCAC<br>ACAGCCCAGCTTGGAGCGAACGACCTACACCGAACTGAGATACCTACAGCGTGAGCTAT<br>GAGAAAGCGCCACGCTTCCCGAAGGGAGAAAGGCGGACAGGTATCCGGTAAGCGGCAG<br>GGTCGGAACAGGAGAGCGCACGAGGGAGCTTCCAGGGGGAAACGCCTGGTATCTTTATA<br>GTCCTGTCGGGTTTCGCCACCTCTGACTTGAGCGTCGATTTTTGTGATGCTCGTCAGGGGG<br>GCGGAGCCTATGGAAAAACGCCAGCAACGCGGCCTTTTTACGGTTCCTGGCCTTTTGCTG<br>GCCTTTTGCTCACATGTTCTTTCCTGCGTTATCCCCTGATTCTGTGGATAACCGTATTACCG<br>CCTTTGAGTGAGCTGATACCGCTCGCCGCAGCCGAACGACCGAGCGCAGCGAGTCAGTG<br>AGCGAGGAAGCGGAAGAGCGCCCAATACGCAAACCGCCTCTCCCCGCGCGTTGGCCGAT<br>TCATTAATGCAGCTGCGCGCTCGCTCGCTCACTGAGGCCGCCCGGGCAAAGCCCGGGCGT<br>CGGGCGACCTTTGGTCGCCCGGCCTCAGTGAGCGAGCGAGCGCGCAGAGAGGGAGTGGC<br>CAACTCCATCACTAGGGGTTCCTTGTAGTTAATGATTAACCCGCCATGCTACTTATCTACG<br>TAGCGGCCGCATCTCAGGTAATGTCAGCTCGGTCCTTCCAGCTGCTCAAGCTAAAACCCA<br>TGTCACTTTGACTCTCCCTCTTGCCCACTACATCCAAGCTGCTAGCACTGCTCCTGATCCA<br>GCTTCAGATTAAGTCTCAGAATCTACCCACTTCTCGCCTTCTCCACTGCCACCAGCCCATT<br>CTGTGCCAGCATCATCACTTGCCAGGACTGTTACAATAGCCTCCTCACTAGCCCCACTCA<br>CAGCAGCCAGATGAATCTTTTGAGTCCATGCCTAGTCACTGGGGCAAAATAGGACTCCGA<br>GGAGAAAGTCCGAGACCAGCTCCGGCAAGATGAGCAAACACAGCCTGTGCAGGGTGCA<br>GGGAGGGCTAGAGGCCTGAGGCTTGAAACAGCTCTCAAGTGGAGGGGGAAACAACCATT<br>GCCCTCATAGAGGACACATCCACACCAGGGCTGTGCTAGCGTGGGCAGGCAAGCCAGGT<br>GCTGGACCTCTGCACGTGGGGCATGTGTGGGTATGTACATGTACCTGTGTTCTTGGTGTGT<br>GTGTGTGTGTGTGTGTGTGTGTGTCTAGAGCTGGGGTGCAACTATGGGGCCCCTCGGG<br>ACATGTCCCAGCCAATGCCTGCTTTGACCAGAGGAGTGTCCACGTGGCTCAGGTGGTCGA<br>GTATCTCATACCGCCCTAGCACACGTGTGACTCCTTTCCCCTATTGTCTACGCAGCCTGCC<br>CTTGGACAAGGACCCGATGCCCAACCCCAGGCCTGGCAAGCCCTCGGCCCCTTCCTTGGC<br>CCTTGGCCCATCCCCACGCGTAGGAACAGAGAAACAGGAGAATATGGGCCAAACAGGAT<br>ATCTGTGGTAAGCAGTTCCTGCCCCGGCTCAGGGCCAAGAACAGTTGGAACAGCAGAAT<br>ATGGGCCAAACAGGATATCTGTGGTAAGCAGTTCCTGCCCCGGCTCAGGGCCAAGAACA<br>GATGGTCCCCAGATGCGGTCCCGCCCTCAGCAGTTTCTAGAGAACCATCAGATGTTTCCA<br>GGGTGCCCCAAGGACCTGAAATGACCCTGTGCCTTATTTGAACTAACCAATCAGTTCGCT<br>TCTCGCTTCTGTTCGCGCGCTTCTGCTCCCCGAGCTCTATATAAGCAGAGCTCGTTTAGTG<br>AACCGTCAGATCGCCTGGAGACGCCATCCACGCTGTTTTGACTTCCATAGAAGGATCTCG<br>AGGCCACCATGGTGAGCAAGGGCGAGGAGCTGTTCACCGGGGTGGTGCCCATCCTGGTC<br>GAGCTGGACGGCGACGTAAACGGCCACAAGTTCAGCGTGTCCGGCGAGGGCGAGGGCG<br>ATGCCACCTACGGCAAGCTGACCCTGAAGTTCATCTGCACCACCGGCAAGCTGCCCGTGC<br>CCTGGCCCACCCTCGTGACCACCCTGACCTACGGCGTGCAGTGCTTCAGCCGCTACCCCG<br>ACCACATGAAGCAGCACGACTTCTTCAAGTCCGCCATGCCCGAAGGCTACGTCCAGGAG<br>CGCACCATCTTCTTCAAGGACGACGGCAACTACAAGACCCGCGCCGAGGTGAAGTTCGA<br>GGGCGACACCCTGGTGAACCGCATCGAGCTGAAGGGCATCGACTTCAAGGAGGACGGCA<br>ACATCCTGGGGCACAAGCTGGAGTACAACTACAACAGCCACAACGTCTATATCATGGCC<br>GACAAGCAGAAGAACGGCATCAAGGTGAACTTCAAGATCCGCCACAACATCGAGGACG<br>GCAGCGTGCAGCTCGCCGACCACTACCAGCAGAACACCCCCATCGGCGACGGCCCCGTG<br>CTGCTGCCCGACAACCACTACCTGAGCACCCAGTCCGCCCTGAGCAAAGACCCCAACGA<br>GAAGCGCGATCACATGGTCCTGCTGGAGTTCGTGACCGCCGCCGGGATCACTCTCGGCAT<br>GGACGAGCTGTACAAGTAAAAGCTTGATAATCAACCTCTGGATTACAAAATTTGTGAAA<br>GATTGACTGGTATTCTTAACTATGTTGCTCCTTTTACGCTATGTGGATACGCTGCTTTAAT<br>GCCTTTGTATCATGCTATTGCTTCCCGTATGGCTTTCATTTTCTCCTCCTTGTATAAATCCT<br>GGTTAGTTCTTGCCACGGCGGAACTCATCGCCGCCTGCCTTGCCCGCTGCTGGACAGGGG | #3089<br>pAAV_FOX<br>P3.08_MND.<br>GFP08_for<br>T9 |

-continued

| SEQ ID NO | Sequence | Description |
|---|---|---|
| | CTCGGCTGTTGGGCACTGACAATTCCGTGGGTCGACTGCTTTATTTGTGAAATTTGTGATG CTATTGCTTTATTTGTAACCATTATAAGCTGCAATAAACAAGTTAACAACAACAATTGCA TTCATTTTATGTTTCAGGTTCAGGGGGAGATGTGGGAGGTTTTTTAAAGCACTAGTGCCTC GCCCAGCTGGAGGGCTGCACCCAAAGCCTCAGACCTGCTGGGGGCCCGGGGCCCAGGGG GAACCTTCCAGGGCCGAGATCTTCGAGGCGGGGCCCATGCCTCCTCTTCTTCCTTGAACC CCATGCCACCATCGCAGCTGCAGGTGAGGCCCTGGGCCCAGGATGGGGCAGGCAGGGTG GGGTACCTGGACCTACAGGTGCCGACCTTTACTGTGGCACTGGGCGGGAGGGGGGCTGG CTGGGGCACAGGAAGTGGTTTCTGGGTCCCAGGCAAGTCTGTGACTTATGCAGATGTTGC AGGGCCAAGAAAATCCCCACCTGCCAGGCCTCAGAGATTGGAGGCTCTCCCCGACCTCC CAATCCCTGTCTCAGGAGAGGAGGAGGCCGTATTGTAGTCCCATGAGCATAGCTATGTGT CCCCATCCCCATGTGACAAGAGAAGAGGACTGGGGCCAAGTAGGTGAGGTGACAGGGCT GAGGCCAGCTCTGCAACTTATTAGCTGTTTGATCTTTAAAAAGTTACTCGATCTCCATGAG CCTCAGTTTCCATACGTGTAAAAGGGGGATGATCATAGCATCTACCATGTGGGCTTGCAG TGCAGAGTATTTGAATTAGACACAGAACAGTGAGGATCAGGATGGCCTCTCACCCACCT GCCTTTCTGCCCAGCTGCCCACACTGCCCCTAGTCATGGTGGCACCCTCCGGGGCACGGC TGGGCCCCTTGCCCCACTTACAGGCACTCCTCCAGGACAGGCCACATTTCATGCACCAGG TATGGACGGTGAATGGATCCTACGTAGATAAGTAGCATGGCGGGTTAATCATTAACTACA AGGAACCCCTAGTGATGGAGTTGGCCACTCCCTCTCTGCGCGCTCGCTCGCTCACTGAGG CCGGGCGACCAAAGGTCGCCCGACGCCCGGGCTTTGCCCGGGCGGCCTCAGTGAGCGAG CGAGCGCGCCAGCTGGCGTAATAGCGAAGAGGCCCGCACCGATCGCCCTTCCCAACAGT TGCGCAGCCTGAATGGCGAATGGCGATTCCGTTGCAATGGCTGGCGGTAATATTGTTCTG GATATTACCAGCAAGGCCGATAGTTTGAGTTCTTCTACTCAGGCAAGTGATGTTATTACT AATCAAAGAAGTATTGCGACAACGGTTAATTTGCGTGATGGACAGACTCTTTTACTCGGT GGCCTCACTGATTATAAAAACACTTCTCAGGATTCTGGCGTACCGTTCCTGTCTAAAATC CCTTTAATCGGCCTCCTGTTTAGCTCCCGCTCTGATTCTAACGAGGAAAGCACGTTATACG TGCTCGTCAAAGCAACCATAGTACGCGCCCTGTAGCGGCGCATTAAGCGCGGCGGGTGT GGTGGTTACGCGCAGCGTGACCGCTACACTTGCCAGCGCCCTAGCGCCCGCTCCTTTCGC TTTCTTCCCTTCCTTTCTCGCCACGTTCGCCGGCTTTCCCCGTCAAGCTCTAAATCGGGGG CTCCCTTTAGGGTTCCGATTTAGTGCTTTACGGCACCTCGACCCCAAAAAACTTGATTAG GGTGATGGTTCACGTAGTGGGCCATCGCCCTGATAGACGGTTTTTCGCCCTTTGACGTTG GAGTCCACGTTCTTTAATAGTGGACTCTTGTTCCAAACTGGAACAACACTCAACCCTATC TCGGTCTATTCTTTTGATTTATAAGGGATTTTGCCGATTTCGGCCTATTGGTTAAAAAATG AGCTGATTTAACAAAAATTTAACGCGAATTTTAACAAAATATTAACGTTTACAATTTAAA TATTTGCTTATACAATCTTCCTGTTTTTGGGGCTTTTCTGATTATCAACCGGGGTACATAT GATTGACATGCTAGTTTTACGATTACCGTTCATCGATTCTCTTGTTTGCTCCAGACTCTCA GGCAATGACCTGATAGCCTTTGTAGAGACCTCTCAAAAATAGCTACCCTCTCCGGCATGA ATTTATCAGCTAGAACGGTTGAATATCATATTGATGGTGATTTGACTGTCTCCGGCCTTTC TCACCCGTTTGAATCTTTACCTACACATTACTCAGGCATTGCATTTAAAATATATGAGGGT TCTAAAAATTTTTATCCTTGCGTTGAAATAAAGGCTTCTCCCGCAAAAGTATTACAGGGT CATAATGTTTTTGGTACAACCGATTTAGCTTTATGCTCTGAGGCTTTATTGCTTAATTTTGC TAATTCTTTGCCTTGCCTGTATGATTTATTGGATGTTGGAATCGCCTGATGCGGTATTTTCT CCTTACGCATCTGTGCGGTATTTCACACCGCATATGGTGCACTCTCAGTACAATCTGCTCT GATGCCGCATAGTTAAGCCAGCCCCGACACCCGCCAACACCCGCTGACGCGCCCTGACG GGCTTGTCTGCTCCCGGCATCCGCTTACAGACAAGCTGTGACCGTCTCCGGGAGCTGCAT GTGTCAGAGGTTTTCACCGTCATCACCGAAACGCGCGAGACGAAAGGGCCTCGTGATAC GCCTATTTTTATAGGTTAATGTCATGATAATAATGGTTTCTTAGACGTCAGGTGGCACTTT TCGGGGAAATGTGCGCGGAACCCCTATTTGTTTATTTTTCTAAATACATTCAAATATGTAT CCGCTCATGAGACAATAACCCTGATAAATGCTTCAATAATATTGAAAAAGGAAGAGTAT GAGTATTCAACATTTCCGTGTCGCCCTTATTCCCTTTTTTGCGGCATTTTGCCTTCCTGTTT TTGCTCACCCAGAAACGCTGGTGAAAGTAAAAGATGCTGAAGATCAGTTGGGTGCACGA GTGGGTTACATCGAACTGGATCTCAACAGCGGTAAGATCCTTGAGAGTTTTCGCCCCGAA GAACGTTTTCCAATGATGAGCACTTTTAAAGTTCTGCTATGTGGCGCGGTATTATCCCGTA TTGACGCCGGGCAAGAGCAACTCGGTCGCCGCATACACTATTCTCAGAATGACTTGGTTG AGTACTCACCAGTCACAGAAAAGCATCTTACGGATGGCATGACAGTAAGAGAATTATGC AGTGCTGCCATAACCATGAGTGATAACACTGCGGCCAACTTACTTCTGACAACGATCGGA GGACCGAAGGAGCTAACCGCTTTTTTGCACAACATGGGGGATCATGTAACTCGCCTTGAT CGTTGGGAACCGGAGCTGAATGAAGCCATACCAAACGACGAGCGTGACACCACGATGCC TGTAGCAATGGCAACAACGTTGCGCAAACTATTAACTGGCGAACTACTTACTCTAGCTTC CCGGCAACAATTAATAGACTGGATGGAGGCGGATAAAGTTGCAGGACCACTTCTGCGCT CGGCCCTTCCGGCTGGCTGGTTTATTGCTGATAAATCTGGAGCCGGTGAGCGTGGGTCTC GCGGTATCATTGCAGCACTGGGGCCAGATGGTAAGCCCTCCCGTATCGTAGTTATCTACA CGACGGGGAGTCAGGCAACTATGGATGAACGAAATAGACAGATCGCTGAGATAGGTGCC TCACTGATTAAGCATTGGTAACTGTCAGACCAAGTTTACTCATATATACTTTAGATTGATT TAAAACTTCATTTTTAATTTAAAAGGATCTAGGTGAAGATCCTTTTTGATAATCTCATGAC CAAAATCCCTTAACGTGAGTTTTCGTTCCACTGAGCGTCAGACCCC | |
| 39 | MEMWHEGLEEASRLYFGERNVKGMFEVLEPLHAMMERGPQTLKETSFNQAYGRDLMEAQE WCRKYMKSGNVKDLTQAWDLYYHVFRRISK | naked FRB wild-type polypeptide |
| 40 | MEMWHEGLEEASRLYFGERNVKGMFEVLEPLHAMMERGPQTLKETSFNQAYGRDLMEAQE WCRKYMKSGNVKDLLQAWDLYYHVFRRISK | naked FRB mutant polypeptide |

-continued

| SEQ ID NO | Sequence | Description |
|---|---|---|
| 41 | GAACAGAGAAACAGGAGAATATGGGCCAAACAGGATATCTGTGGTAAGCAGTTCCTGCC<br>CCGGCTCAGGGCCAAGAACAGTTGGAACAGCAGAATATGGGCCAAACAGGATATCTGTG<br>GTAAGCAGTTCCTGCCCCGGCTCAGGGCCAAGAACAGATGGTCCCCAGATGCGGTCCCG<br>CCCTCAGCAGTTTCTAGAGAACCATCAGATGTTTCCAGGGTGCCCCAAGGACCTGAAATG<br>ACCCTGTGCCTTATTTGAACTAACCAATCAGTTCGCTTCTCGCTTCTGTTCGCGCGCTTCT<br>GCTCCCCGAGCTCTATATAAGCAGAGCTCGTTTAGTGAACCGTCAGATCGCTAGCACCGG<br>TGCCGCCACCATGCCTCTGGGCCTGCTGTGGCTGGGCCTGGCCCTGCTGGGCGCCCTGCA<br>CGCCCAGGCCGGCGTGCAGGTGGAGACAATCTCCCCAGGCGACGGACGCACATTCCCTA<br>AGCGGGGCCAGACCTGCGTTGTGCACTATACAGGCATGCTGGAGGATGGCAAGAAGTTT<br>GACAGCTCCCGGGATAGAAACAAGCCATTCAAGTTTATGCTGGGCAAGCAGGAAGTGAT<br>CAGAGGCTGGGAGGAGGGCGTGGCCCAGATGTCTGTGGGCCAGAGGGCCAAGCTGACCA<br>TCAGCCCAGACTACGCCTATGGAGCAACAGGCCACCCAGGAATCATCCCACCTCACGCC<br>ACCCTGGTGTTCGATGTGGAGCTGCTGAAGCTGGGCGAGGGATCCAACACATCAAAAGA<br>GAACCCCTTTCTGTTCGCATTGGAGGCCGTAGTCATATCTGTTGGATCCATGGGACTTATT<br>ATCTCCCTGTTGTGTGTGTACTTCTGGCTGGAACGGACTATGCCCAGGATCCCCACGCTC<br>AAGAATCTGGAAGATCTCGTCACAGAATACCATGGTAATTTCAGCGCCTGGAGCGGAGT<br>CTCTAAGGGTCTGGCCGAATCCCTCCAACCCGATTATTCTGAACGGTTGTGCCTCGTATCC<br>GAAATACCACCAAAAGGCGGGGCTCTGGGTGAGGGCCCAGGGGCGAGTCCGTGCAATCA<br>ACACAGCCCGTATTGGGCCCCTCCTTGTTATACGTTGAAGCCCGAAACTGGAAGCGGAGC<br>TACTAACTTCAGCCTGCTGAAGCAGGCTGGAGACGTGGAGGAGAACCCTGGACCTATGG<br>CACTGCCCGTGACCGCCCTGCTGCTGCCTCTGGCCCTGCTGCTGCACGCAGCCCGGCCTA<br>TCCTGTGGCACGAGATGTGGCACGAGGGCCTGGAGGAGGCCAGCAGGCTGTATTTTGGC<br>GAGCGCAACGTGAAGGGCATGTTCGAGGTGCTGGAGCCTCTGCACGCCATGATGGAGAG<br>AGGCCCACAGACCCTGAAGGAGACATCCTTTAACCAGGCCTATGGACGGGACCTGATGG<br>AGGCACAGGAGTGGTGCAGAAAGTACATGAAGTCTGGCAATGTGAAGGACCTGCTGCAG<br>GCCTGGGATCTGTACTATCACGTGTTTCGGAGAATCTCCAAGGGCAAAGACACGATTCCG<br>TGGCTTGGGCATCTGCTCGTTGGGCTGAGTGGTGCGTTTGGTTTCATCATCTTGGTCTATC<br>TCTTGATCAATTGCAGAAATACAGGCCCTTGGCTGAAAAAAGTGCTCAAGTGTAATACCC<br>CCGACCCAAGCAAGTTCTTCTCCCAGCTTTCTTCAGAGCATGGAGGCGATGTGCAGAAAT<br>GGCTCTCTTCACCTTTTCCCTCCTCAAGCTTCTCCCCGGGAGGGCTGGCGCCCGAGATTTC<br>ACCTCTTGAGGTACTTGAACGAGACAAGGTTACCCAACTTCTCCTTCAACAGGATAAGGT<br>ACCCGAACCTGCGAGCCTTAGCTCCAACCACTCTCTTACGAGCTGCTTCACCAATCAGGG<br>ATACTTCTTTTTCCACCTTCCCGATGCGCTGGAAATCGAAGCTTGTCAAGTTTACTTTACC<br>TATGATCCATATAGCGAGGAAGATCCCGACGAAGGAGTCGCCGGTGCGCCCACGGGTTC<br>CTCACCCCAACCTCTCCAGCCTCTCTCAGGAGAAGATGATGCTTATTGCACTTTTCCCAGT<br>AGAGACGATCTCCTCCTCTTTTCTCCATCTCTTTTGGGGGGACCTTCCCCCCCTTCTACGG<br>CACCTGGCGGGTCTGGTGCTGGCGAGGAGCGGATGCCGCCGTCCCTCCAGGAGCGAGTA<br>CCACGAGATTGGGATCCCCAGCCACTTGGACCCCCCACCCCCGGCGTACCTGACCTTGTC<br>GATTTTCAACCTCCCCCTGAATTGGTGCTGCGAGAGGCTGGGGAGGAAGTTCCGGACGCT<br>GGGCCGAGGGAGGGCGTGTCCTTTCCATGGAGTAGGCCTCCAGGTCAAGGCGAGTTTAG<br>GGCTCTCAACGCGCGGCTGCCGTTGAATACAGACGCTTATCTCTCACTGCAGGAACTGCA<br>AGGTCAGGACCCAACACATCTTGTAGGATCTGGTGCTACTAATTTTTCTCTTTTGAAGCAA<br>GCTGGAGATGTTGAAGAGAACCCCGGTCCGGAGATGTGGCATGAGGGTCTGGAAGAAGC<br>GTCTCGACTGTACTTTGGTGAGCGCAATGTGAAGGGCATGTTTGAAGTCCTCGAACCCCT<br>TCATGCCATGATGGAACGCGGACCCCAGACCTTGAAGGAGACAAGTTTTAACCAAGCTT<br>ACGGAAGAGACCTGATGGAAGCCCAGGAATGGTGCAGGAAATACATGAAAAGCGGGAA<br>TGTGAAGGACTTGCTCCAAGCGTGGGACCTGTACTATCATGTCTTTAGGCGCATTAGTAA<br>GGGCAGCGGCGCCACCAACTTCAGCCTGCTGAAGCAGGCCGGCGACGTGGAGGAGAACC<br>CCGGCCCCGTGAGCAAGGGCGAGGAGGATAACATGGCCATCATCAAGGAGTTCATGCGC<br>TTCAAGGTGCACATGGAGGGCTCCGTGAACGGCCACGAGTTCGAGATCGAGGGCGAGGG<br>CGAGGGCCGCCCCTACGAGGGCACCCAGACCGCCAAGCTGAAGGTGACCAAGGGTGGCC<br>CCCTGCCCTTCGCCTGGGACATCCTGTCCCCTCAGTTCATGTACGGCTCCAAGGCCTACGT<br>GAAGCACCCCGCCGACATCCCCGACTACTTGAAGCTGTCCTTCCCCGAGGGCTTCAAGTG<br>GGAGCGCGTGATGAACTTCGAGGACGGCGGCGTGGTGACCGTGACCCAGGACTCCTCTC<br>TGCAGGACGGCGAGTTCATCTACAAGGTGAAGCTGCGCGGCACCAACTTCCCCTCCGAC<br>GGCCCCGTAATGCAGAAGAAGACCATGGGCTGGGAGGCCTCCTCCGAGCGGATGTACCC<br>CGAGGACGGCGCCCTGAAGGGCGAGATCAAGCAGAGGCTGAAGCTGAAGGACGGCGGC<br>CACTACGACGCTGAGGTCAAGACCACCTACAAGGCCAAGAAGCCCGTGCAGCTGCCCGG<br>CGCCTACAACGTCAACATCAAGTTGGACATCACCTCCCACAACGAGGACTACACCATCGT<br>GGAACAGTACGAACGCGCCGAGGGCCGCCACTCCACCGGCGGCATGGACGAGCTGTACA<br>AGTGAACTAGTGTCGACAATCAACCTCTGGATTACAAAATTTGTGAAAGATTGACTGGTA<br>TTCTTAACTATGTTGCTCCTTTTACGCTATGTGGATACGCTGCTTTAATGCCTTTGTATCAT<br>GCTATTGCTTCCCGTATGGCTTTCATTTTCTCCTCCTTGTATAAATCCTGGTTGCTGTCTCT<br>TTATGAGGAGTTGTGGCCCGTTGTCAGGCAACGTGGCGTGGTGTGCACTGTGTTTGCTGA<br>CGCAACCCCCACTGGTTGGGGCATTGCCACCACCTGTCAGCTCCTTTCCGGGACTTTCGCT<br>TTCCCCCTCCCTATTGCCACGGCGGAACTCATCGCCGCCTGCCTTGCCCGCTGCTGGACA<br>GGGGCTCGGCTGTTGGGCACTGACAATTCCGTGGTGTTGTCGGGGAAGCTGACGTCCTTT<br>CCATGGCTGCTCGCCTGTGTTGCCACCTGGATTCTGCGCGGGACGTCCTTCTGCTACGTCC<br>CTTCGGCCCTCAATCCAGCGGACCTTCCTTCCCGCGGCCTGCTGCCGGCTCTGCGGCCTCT<br>TCCGCGTCTTCGCCTTCGCCCTCAGACGAGTCGGATCTCCCTTTGGGCCGCCTCCCCGCCT<br>GGA | DISC vector DNA |
| 42 | CCAGCAGCTCTCGGCAAAGACACGATTCCGTGGCTTGGGCATCTGCTCGTTGGGCTGAGC<br>GGTGCGTTTGGTTTCATCATCTTGGTCTATCTCTTGATCAATTGCAGAAATACAGGCCCTT<br>GGCTGAAAAAAGTGCTCAAGTGTAATACCCCCGACCCAAGCAAGTTCTTCTCCCAGCTTT | µDISC DNA (cytoplasmic tail only; |

-continued

| SEQ ID NO | Sequence | Description |
|---|---|---|
| | CTTCAGAGCATGGAGGCGATGTGCAGAAATGGCTCTCTTCACCTTTTCCCTCCTCAAGCTT CTCCCCGGGAGGGCTGGCGCCCGAGATTTCACCTCTTGAGGTACTTGAACGAGACAAGGT TACCCAACTTCTCCTTCAACAGGATAAGGTACCCGAACCTGCGAGCCTTAGCTTGAATAC AGACGCTTATCTCTCACTGCAGGAACTGCAA | codon diverged) |
| 43 | PAALGKDTIPWLGHLLVGLSGAFGFIILVYLLINCRNTGPWLKKVLKCNTPDPSKFFSQLSSEH GGDVQKWLSSPFPSSSFSPGGLAPEISPLEVLERDKVTQLLLQQDKVPEPASLSLNTDAYLSLQ ELQ | μDISC polypeptide (cytoplasmic tail only) |
| 44 | GVQVETISPGDGRTFPKRGQTCVVHYTGMLEDGKKFDSSRDRNKPFKFMLGKQEVIRGWEE GVAQMSVGQRAKLTISPDYAYGATGHPGIIPPHATLVFDVELLKLGE | FKBP CISC domain |
| 45 | MALPVTALLLPLALLLHAARPILWHEMWHEGLEEASRLYFGERNVKGMFEVLEPLHAMMER GPQTLKETSFNQAYGRDLMEAQEWCRKYMKSGNVKDLLQAWDLYYHVFRRISKPAALGKD TIPWLGHLLVGLSGAFGFIILVYLLINCRNTGPWLKKVLKCNTPDPSKFFSQLSSEHGGDVQK WLSSPFPSSSFSPGGLAPEISPLEVLERDKVTQLLLQQDKVPEPASLSLNTDAYLSLQELQ | Entire μDISC polypeptide (FRB-truncated IL2Rβ) |
| 46 | GAACAGAGAAACAGGAGAATATGGGCCAAACAGGATATCTGTGGTAAGCAGTTCCTGCC CCGGCTCAGGGCCAAGAACAGTTGGAACAGCAGAATATGGGCCAAACAGGATATCTGTG GTAAGCAGTTCCTGCCCCGGCTCAGGGCCAAGAACAGATGGTCCCCAGATGCGGTCCCG CCCTCAGCAGTTTCTAGAGAACCATCAGATGTTTCCAGGGTGCCCCAAGGACCTGAAATG ACCCTGTGCCTTATTTGAACTAACCAATCAGTTCGCTTCTCGCTTCTGTTCGCGCGCTTCT GCTCCCCGAGCTCTATATAAGCAGAGCTCGTTTAGTGAACCGTCAGATCGCTAGCACCGG TGCCGCCACCATGCCTCTGGGCCTGCTGTGGCTGGGCCTGGCCCTGCTGGGCGCCCTGCA CGCCCAGGCCGGCGTGCAGGTGGAGACAATCTCCCCAGGCGACGGACGCACATTCCCTA AGCGGGGCCAGACCTGCGTTGTGCACTATACAGGCATGCTGGAGGATGGCAAGAAGTTT GACAGCTCCCGGGATAGAAACAAGCCATTCAAGTTTATGCTGGGCAAGCAGGAAGTGAT CAGAGGCTGGGAGGAGGGCGTGGCCCAGATGTCTGTGGGCCAGAGGGCCAAGCTGACCA TCAGCCCAGACTACGCCTATGGAGCAACAGGCCACCCAGGAATCATCCCACCTCACGCC ACCCTGGTGTTCGATGTGGAGCTGCTGAAGCTGGGCGAGGGATCCAACACATCAAAAGA GAACCCCTTTCTGTTCGCATTGGAGGCCGTAGTCATATCTGTTGGATCCATGGGACTTATT ATCTCCCTGTTGTGTGTGTACTTCTGGCTGGAACGGACTATGCCCAGGATCCCCACGCTC AAGAATCTGGAAGATCTCGTCACAGAATACCATGGTAATTTCAGCGCCTGGAGCGGAGT CTCTAAGGGTCTGGCCGAATCCCTCCAACCCGATTATTCTGAACGGTTGTGCCTCGTATCC GAAATACCACCAAAAGGCGGGGCTCTGGGTGAGGGCCCAGGGGCGAGTCCGTGCAATCA ACACAGCCCGTATTGGGCCCCTCCTTGTTATACGTTGAAGCCCGAAACTGGAAGCGGAGC TACTAACTTCAGCCTGCTGAAGCAGGCTGGAGACGTGGAGGAGAACCCTGGACCTATGG CACTGCCCGTGACCGCCCTGCTGCTGCCTCTGGCCCTGCTGCTGCACGCAGCCCGGCCTA TCCTGTGGCACGAGATGTGGCACGAGGGCCTGGAGGAGGCCAGCAGGCTGTATTTTGGC GAGCGCAACGTGAAGGGCATGTTCGAGGTGCTGGAGCCTCTGCACGCCATGATGGAGAG AGGCCCACAGACCCTGAAGGAGACATCCTTTAACCAGGCCTATGGACGGGACCTGATGG AGGCACAGGAGTGGTGCAGAAAGTACATGAAGTCTGGCAATGTGAAGGACCTGCTGCAG GCCTGGGATCTGTACTATCACGTGTTTCGGAGAATCTCCAAGGGCAAAGACACGATTCCG TGGCTTGGGCATCTGCTCGTTGGGCTGAGTGGTGCGTTTGGTTTCATCATCTTGGTCTATC TCTTGATCAATTGCAGAAATACAGGCCCTTGGCTGAAAAAAGTGCTCAAGTGTAATACCC CCGACCCAAGCAAGTTCTTCTCCCAGCTTTCTTCAGAGCATGGAGGCGATGTGCAGAAAT GGCTCTCTTCACCTTTTCCCTCCTCAAGCTTCTCCCCGGGAGGGCTGGCGCCCGAGATTTC ACCTCTTGAGGTACTTGAACGAGACAAGGTTACCCAACTTCTCCTTCAACAGGATAAGGT ACCCGAACCTGCGAGCCTTAGCTTGAATACAGACGCTTATCTCTCACTGCAGGAACTGCA AGGATCTGGTGCTACTAATTTTTCTCTTTTGAAGCAAGCTGGAGATGTTGAAGAGAACCC CGGTCCGGAGATGTGGCATGAGGGTCTGGAAGAAGCGTCTCGACTGTACTTTGGTGAGC GCAATGTGAAGGGCATGTTTGAAGTCCTCGAACCCCTTCATGCCATGATGGAACGCGGAC CCCAGACCTTGAAGGAGACAAGTTTTAACCAAGCTTACGGAAGAGACCTGATGGAAGCC CAGGAATGGTGCAGGAAATACATGAAAAGCGGGAATGTGAAGGACTTGCTCCAAGCGTG GGACCTGTACTATCATGTCTTTAGGCGCATTAGTAAGGGCAGCGGCGCCACCAACTTCAG CCTGCTGAAGCAGGCCGGCGACGTGGAGGAGAACCCCGGCCCCGTGAGCAAGGGCGAG GAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGC ACCCAGACCGCCAAGCTGAAGGTGACCAAGGGTGGCCCCCTGCCCTTCGCCTGGGACAT CCTGTCCCCTCAGTTCATGTACGGCTCCAAGGCCTACGTGAAGCACCCCGCCGACATCCC CGACTACTTGAAGCTGTCCTTCCCCGAGGGCTTCAAGTGGGAGCGCGTGATGAACTTCGA GGACGGCGGCGTGGTGACCGTGACCCAGGACTCCTCTCTGCAGGACGGCGAGTTCATCT ACAAGGTGAAGCTGCGCGGCACCAACTTCCCCTCCGACGGCCCCGTAATGCAGAAGAAG ACCATGGGCTGGGAGGCCTCCTCCGAGCGGATGTACCCCGAGGACGGCGCCCTGAAGGG CGAGATCAAGCAGAGGCTGAAGCTGAAGGACGGCGGCCACTACGACGCTGAGGTCAAG ACCACCTACAAGGCCAAGAAGCCCGTGCAGCTGCCCGGCGCCTACAACGTCAACATCAA GTTGGACATCACCTCCCACAACGAGGACTACACCATCGTGGAACAGTACGAACGCGCCG AGGGCCGCCACTCCACCGGCGGCATGGACGAGCTGTACAAGTGAACTAGTGTCGACAAT CAACCTCTGGATTACAAAATTTGTGAAAGATTGACTGGTATTCTTAACTATGTTGCTCCTT TTACGCTATGTGGATACGCTGCTTTAATGCCTTTGTATCATGCTATTGCTTCCCGTATGGC TTTCATTTTCTCCTCCTTGTATAAATCCTGGTTGCTGTCTCTTTATGAGGAGTTGTGGCCCG TTGTCAGGCAACGTGGCGTGGTGTGCACTGTGTTTGCTGACGCAACCCCCACTGGTTGGG GCATTGCCACCACCTGTCAGCTCCTTTCCGGGACTTTCGCTTTCCCCCTCCCTATTGCCAC | μDISC vector DNA |

-continued

| SEQ ID NO | Sequence | Description |
|---|---|---|
| | GGCGGAACTCATCGCCGCCTGCCTTGCCCGCTGCTGGACAGGGGCTCGGCTGTTGGGCAC TGACAATTCCGTGGTGTTGTCGGGGAAGCTGACGTCCTTTCCATGGCTGCTCGCCTGTGTT GCCACCTGGATTCTGCGCGGGACGTCCTTCTGCTACGTCCCTTCGGCCCTCAATCCAGCG GACCTTCCTTCCCGCGGCCTGCTGCCGGCTCTGCGGCCTCTTCCGCGTCTTCGCCTTCGCC CTCAGACGAGTCGGATCTCCCTTTGGGCCGCCTCCCCGCCTGGA | |
| 47 | MPLGLLWLGLALLGALHAQAGVQVETISPGDGRTFPKRGQTCVVHYTGMLEDGKKFDSSRD RNKPFKFMLGKQEVIRGWEEGVAQMSVGQRAKLTISPDYAYGATGHPGIIPPHATLVFDVEL LKLGEGSNTSKENPFLFALEAVVISVGSMGLIISLLCVYFWLERTMPRIPTLKNLEDLVTEYHG NFSAWSGVSKGLAESLQPDYSERLCLVSEIPPKGGALGEGPGASPCNQHSPYWAPPCYTLKPE T | IL2Rγ-CISC polypeptide |
| 48 | MPLGLLWLGLALLGALHAQAGVQVETISPGDGRTFPKRGQTCVVHYTGMLEDGKKFDSSRD RNKPFKFMLGKQEVIRGWEEGVAQMSVGQRAKLTISPDYAYGATGHPGIIPPHATLVFDVEL LKLEGGGSQNLVIPWAPENLTLHKLSESQLELNWNNRFLNHCLEHLVQYRTDWDHSWTEQS VDYRHKFSLPSVDGQKRYTFRVRSRFNPLCGSAQHWSEWSHPIHWGSNTSKENPFLFALEAV VISVGSMGLIISLLCVYFWLERTMPRIPTLKNLEDLVTEYHGNFSAWSGVSKGLAESLQPDYS ERLCLVSEIPPKGGALGEGPGASPCNQHSPYWAPPCYTLKPET | IL2Rγ-CISC polypeptide |
| 49 | MPLGLLWLGLALLGALHAQAGVQVETISPGDGRTFPKRGQTCVVHYTGMLEDGKKFDSSRD RNKPFKFMLGKQEVIRGWEEGVAQMSVGQRAKLTISPDYAYGATGHPGIIPPHATLVFDVEL LKLEGQNLVIPWAPENLTLHKLSESQLELNWNNRFLNHCLEHLVQYRTDWDHSWTEQSVDY RHKFSLPSVDGQKRYTFRVRSRFNPLCGSAQHWSEWSHPIHWGSNTSKENPFLFALEAVVISV GSMGLIISLLCVYFWLERTMPRIPTLKNLEDLVTEYHGNFSAWSGVSKGLAESLQPDYSERLC LVSEIPPKGGALGEGPGASPCNQHSPYWAPPCYTLKPET | IL2Rγ-CISC polypeptide |
| 50 | MPLGLLWLGLALLGALHAQAGVQVETISPGDGRTFPKRGQTCVVHYTGMLEDGKKFDSSRD RNKPFKFMLGKQEVIRGWEEGVAQMSVGQRAKLTISPDYAYGATGHPGIIPPHATLVFDVEL LKLEGGSNTSKENPFLFALEAVVISVGSMGLIISLLCVYFWLERTMPRIPTLKNLEDLVTEYHG NFSAWSGVSKGLAESLQPDYSERLCLVSEIPPKGGALGEGPGASPCNQHSPYWAPPCYTLKPE T | IL2Rγ-CISC polypeptide |
| 51 | MALPVTALLLPLALLLHAARPILWHEMWHEGLEEASRLYFGERNVKGMFEVLEPLHAMMER GPQTLKETSFNQAYGRDLMEAQEWCRKYMKSGNVKDLLQAWDLYYHVFRRISKGKDTIPW LGHLLVGLSGAFGFIILVYLLINCRNTGPWLKKVLKCNTPDPSKFFSQLSSEHGGDVQKWLSS PFPSSSFSPGGLAPEISPLEVLERDKVTQLLLQQDKVPEPASLSSNHSLTSCFTNQGYFFFHLPD ALEIEACQVYFTYDPYSEEDPDEGVAGAPTGSSPQPLQPLSGEDDAYCTFPSRDDLLLFSPSLL GGPSPPSTAPGGSGAGEERMPPSLQERVPRDWDPQPLGPPTPGVPDLVDFQPPPELVLREAGE EVPDAGPREGVSFPWSRPPGQGEFRALNARLPLNTDAYLSLQELQGQDPTHLV | IL2Rβ-CISC polypeptide |
| 52 | MALPVTALLLPLALLLHAARPILWHEMWHEGLEEASRLYFGERNVKGMFEVLEPLHAMMER GPQTLKETSFNQAYGRDLMEAQEWCRKYMKSGNVKDLLQAWDLYYHVFRRISKGGSKPFE NLRLMAPISLQVVHVETHRCNISWEISQASHYFERHLEFEARTLSPGHTWEEAPLLTLKQKQE WICLETLTPDTQYEFQVRVKPLQGEFTTWSPWSQPLAFRTKPAALGKDTIPWLGHLLVGLSG AFGFIILVYLLINCRNTGPWLKKVLKCNTPDPSKFFQLSSEHGGDVQKWLSSPFPSSSFSPGGL APEISPLEVLERDKVTQLLLQQDKVPEPASLSSNHSLTSCFTNQGYFFFHLPDALEIEACQVYF TYDPYSEEDPDEGVAGAPTGSSPQPLQPLSGEDDAYCTFPSRDDLLLFSPSLLGGPSPPSTAPG GSGAGEERMPPSLQERVPRDWDPQPLGPPTPGVPDLVDFQPPPELVLREAGEEVPDAGPREG VSFPWSRPPGQGEFRALNARLPLNTDAYLSLQELQGQDPTHLV | IL2Rβ-CISC polypeptide |
| 53 | MALPVTALLLPLALLLHAARPILWHEMWHEGLEEASRLYFGERNVKGMFEVLEPLHAMMER GPQTLKETSFNQAYGRDLMEAQEWCRKYMKSGNVKDLLQAWDLYYHVFRRISKKPFENLR LMAPISLQVVHVETHRCNISWEISQASHYFERHLEFEARTLSPGHTWEEAPLLTLKQKQEWIC LETLTPDTQYEFQVRVKPLQGEFTTWSPWSQPLAFRTKPAALGKDTIPWLGHLLVGLSGAFG FIILVYLLINCRNTGPWLKKVLKCNTPDPSKFFSQLSSEHGGDVQKWLSSPFPSSSFSPGGLAPE ISPLEVLERDKVTQLLLQQDKVPEPASLSSNHSLTSCFTNQGYFFFHLPDALEIEACQVYFTYD PYSEEDPDEGVAGAPTGSSPQPLQPLSGEDDAYCTFPSRDDLLLFSPSLLGGPSPPSTAPGGSG AGEERMPPSLQERVPRDWDPQPLGPPTPGVPDLVDFQPPPELVLREAGEEVPDAGPREGVSFP WSRPPGQGEFRALNARLPLNTDAYLSLQELQGQDPTHLV | IL2Rβ-CISC polypeptide |
| 54 | MALPVTALLLPLALLLHAARPILWHEMWHEGLEEASRLYFGERNVKGMFEVLEPLHAMMER GPQTLKETSWLGHLLVGLSGAFGFIILVYLLINCRNTGPWLKKVLKCNTPDPSKFFSQLSSEH GGDVQKWLSSPFPSSSFSPGGLAPEISPLEVLERDKVTQLLLQQDKVPEPASLSSNHSLTSCFT NQGYFFFHLPDALEIEACQVYFTYDPYSEEDPDEGVAGAPTGSSPQPLQPLSGEDDAYCTFPS RDDLLLFSPSLLGGPSPPSTAPGGSGAGEERMPPSLQERVPRDWDPQPLGPPTPGVPDLVDFQ PPPELVLREAGEEVPDAGPREGVSFPWSRPPGQGEFRALNARLPLNTDAYLSLQELQGQDPTH LV | IL7Rα-CISC polypeptide |
| 55 | MALPVTALLLPLALLLHAARPILWHEMWHEGLEEASRLYFGERNVKGMFEVLEPLHAMMER GPQTLKETSFNQAYGRDLMEAQEWCRKYMKSGNVKDLLQAWDLYYHVFRRISKGEINNSS GEMDPILLTISILSFFSVALLVILACVLWKKRIKPIVWPSLPDHKKTLEHLCKKPRKNLNVSFNP ESFLDCQIHRVDDIQARDEVEGFLQDTFPQQLEESEKQRLGGDVQSPNCPSEDVVITPESFGRD SSLTCLAGNVSACDAPILSSSRSLDCRESGKNGPHVYQDLLLSLGTTNSTLPPPFSLQSGILTLN PVAQGQPILTSLGSNQEEAYVTMSSFYQNQ | IL7Rα-CISC polypeptide |

-continued

| SEQ ID NO | Sequence | Description |
|---|---|---|
| 56 | GGGS | Linker polypeptide |
| 57 | GGGSGGG | Linker polypeptide |
| 58 | GGG | Linker polypeptide |
| 59 | GGS | Linker polypeptide |
| 60 | GGSP | Linker polypeptide |
| 61 | MPLGLLWLGLALLGALHAQAGVQVETISPGDGRTFPKRGQTCVVHYTGMLEDGKKVDSSR DRNKPFKFMLGKQEVIRGWEEGVAQMSVGQRAKLTISPDYAYGATGHPGIIPPHATLVFDVE LLKLEGGSNTSKENPFLFALEAVVISVGSMGLIISLLCVYFWLERTMPRIPTLKNLEDLVTEYH GNFSAWSGVSKGLAESLQPDYSERLCLVSEIPPKGGALGEGPGASPCNQHSPYWAPPCYTLK PET | IL2Rγ-CISC polypeptide |
| 62 | MPLGLLWLGLALLGALHAQAGVQVETISPGDGRTFPKRGQTCVVHYTGMLEDGKKVDSSR DRNKPFKFMLGKQEVIRGWEEGVAQMSVGQRAKLTISPDYAYGATGHPGIIPPHATLVFDVE LLKLEGGKDTIPWLGHLLVGLSGAFGFIILVYLLINCRNTGPWLKKVLKCNTPDPSKFFSQLSS EHGGDVQKWLSSPFPSSSFSPGGLAPEISPLEVLERDKVTQLLLQQDKVPEPASLSSNHSLTSC FTNQGYFFFHLPDALEIEACQVYFTYDPYSEEDPDEGVAGAPTGSSPQPLQPLSGEDDAYCTF PSRDDLLLFSPSLLGGPSPPSTAPGGSGAGEERMPPSLQERVPRDWDPQPLGPPTPGVPDLVDF QPPPELVLREAGEEVPDAGPREGVSFPWSRPPGQGEFRALNARLPLNTDAYLSLQELQGQDPT HLV | IL2Rβ-CISC polypeptide |
| 63 | MPLGLLWLGLALLGALHAQAGVQVETISPGDGRTFPKRGQTCVVHYTGMLEDGKKVDSSR DRNKPFKFMLGKQEVIRGWEEGVAQMSVGQRAKLTISPDYAYGATGHPGIIPPHATLVFDVE LLKLEGEINNSSGEMDPILLTISILSFFSVALLVILACVLWKKRIKPIVWPSLPDHKKTLEHLCK KPRKNLNVSFNPESFLDCQIHRVDDIQARDEVEGFLQDTFPQQLEESEKQRLGGDVQSPNCPS EDVVITPESFGRDSSLTCLAGNVSACDAPILSSSRSLDCRESGKNGPHVYQDLLLSLGTTNSTL PPPFSLQSGILTLNPVAQGQPILTSLGSNQEEAYVTMSSFYQNQ | IL2Rα-CISC polypeptide |
| 64 | MPLGLLWLGLALLGALHAQAGVQVETISPGDGRTFPKRGQTCVVHYTGMLEDGKKVDSSR DRNKPFKFMLGKQEVIRGWEEGVAQMSVGQRAKLTISPDYAYGATGHPGIIPPHATLVFDVE LLKLEGEINNSSGEMDPILLTISILSFFSVALLVILACVLWKKRIKPIVWPSLPDHKKTLEHLCK KPRKNLNVSFNPESFLDCQIHRVDDIQARDEVEGFLQDTFPQQLEESEKQRLGGDVQSPNCPS EDVVITPESFGRDSSLTCLAGNVSACDAPILSSSRSLDCRESGKNGPHVYQDLLLSLGTTNSTL PPPFSLQSGILTLNPVAQGQPILTSLGSNQEEAYVTMSSFYQNQ | IL7Rα-CISC polypeptide |
| 65 | MPLGLLWLGLALLGALHAQAGVQVETISPGDGRTFPKRGQTCVVHYTGMLEDGKKVDSSR DRNKPFKFMLGKQEVIRGWEEGVAQMSVGQRAKLTISPDYAYGATGHPGIIPPHATLVFDVE LLKLGEETAWISLVTALHLVLGLSAVLGLLLLRWQFPAHYRRLRHALWPSLPDLHRVLGQYL RDTAALSPPKATVSDTCEEVEPSLLEILPKSSERTPLPLCSSQAQMDYRRLQPSCLGTMPLSVC PPMAESGSCCTTHIANHSYLPLSYWQQP | MPL-CISC polypeptide |
| 66 | AGCTTAATGTAGTCTTATGCAATACTCTTGTAGTCTTGCAACATGGTAACGATGAGTTAG CAACATGCCTTACAAGGAGAGAAAAAGCACCGTGCATGCCGATTGGTGGAAGTAAGGTG GTACGATCGTGCCTTATTAGGAAGGCAACAGACGGGTCTGACATGGATTGGACGAACCA CTGAATTGCCGCATTGCAGAGATATTGTATTTAAGTGCCTAGCTCGATACAATAAACGGG TCTCTCTGGTTAGACCAGATCTGAGCCTGGGAGCTCTCTGGCTAACTAGGGAACCCACTG CTTAAGCCTCAATAAAGCTTGCCTTGAGTGCTTCAAGTAGTGTGTGCCCGTCTGTTGTGTG ACTCTGGTAACTAGAGATCCCTCAGACCCTTTTAGTCAGTGTGGAAAATCTCTAGCAGTG GCGCCCGAACAGGGACTTGAAAGCGAAAGGGAAACCAGAGGAGCTCTCTCGACGCAGG ACTCGGCTTGCTGAAGCGCGCACGGCAAGAGGCGAGGGGCGGCGACTGGTGAGTACGCC AAAAATTTTGACTAGCGGAGGCTAGAAGGAGAGAGATGGGTGCGAGAGCGTCAGTATTA AGCGGGGGAGAATTAGATCGCGATGGGAAAAAATTCGGTTAAGGCCAGGGGGAAAGAA AAAATATAAATTAAAACATATAGTATGGGCAAGCAGGGAGCTAGAACGATTCGCAGTTA ATCCTGGCCTGTTAGAAACATCAGAAGGCTGTAGACAAATACTGGGACAGCTACAACCA TCCCTTCAGACAGGATCAGAAGAACTTAGATCATTATATAATACAGTAGCAACCCTCTAT TGTGTGCATCAAAGGATAGAGATAAAAGACACCAAGGAAGCTTTAGACAAGATAGAGGA AGAGCAAAACAAAAGTAAGACCACCGCACAGCAAGCGGCCGCTGATCTTCAGACCTGGA GGAGGAGATATGAGGGACAATTGGAGAAGTGAATTATATAAATATAAAGTAGTAAAAAT TGAACCATTAGGAGTAGCACCCACCAAGGCAAAGAGAAGAGTGGTGCAGAGAGAAAAA AGAGCAGTGGGAATAGGAGCTTTGTTCCTTGGGTTCTTGGGAGCAGCAGGAAGCACTAT GGGCGCAGCCTCAATGACGCTGACGGTACAGGCCAGACAATTATTGTCTGGTATAGTGC AGCAGCAGAACAATTTGCTGAGGGCTATTGAGGCGCAACAGCATCTGTTGCAACTCACA GTCTGGGGCATCAAGCAGCTCCAGGCAAGAATCCTGGCTGTGGAAAGATACCTAAAGGA TCAACAGCTCCTGGGGATTTGGGGTTGCTCTGGAAAACTCATTTGCACCACTGCTGTGCC TTGGAATGCTAGTTGGAGTAATAAATCTCTGGAACAGATTTGGAATCACACGACCTGGAT GGAGTGGGACAGAGAAATTAACAATTACACAAGCTTAATACACTCCTTAATTGAAGAAT | CISC vector DNA |

-continued

| SEQ ID NO | Sequence | Description |
|---|---|---|
| | CGCAAAACCAGCAAGAAAAGAATGAACAAGAATTATTGGAATTAGATAAATGGGCAAGT<br>TTGTGGAATTGGTTTAACATAACAAATTGGCTGTGGTATATAAAATTATTCATAATGATA<br>GTAGGAGGCTTGGTAGGTTTAAGAATAGTTTTTGCTGTACTTTCTATAGTGAATAGAGTT<br>AGGCAGGGATATTCACCATTATCGTTTCAGACCCACCTCCCAACCCCGAGGGGACCCGAC<br>AGGCCCGAAGGAATAGAAGAAGAAGGTGGAGAGAGAGACAGAGACAGATCCATTCGAT<br>TAGTGAACGGATCTCGACGGTATCGGTTAACTTTTAAAAGAAAAGGGGGGATTGGGGGG<br>TACAGTGCAGGGGAAAGAATAGTAGACATAATAGCAACAGACATACAAACTAAAGAATT<br>ACAAAAACAAATTACAAAAATTCAAAATTTTATCGATCACGAGACTAGCCTCGAGAAGC<br>TTGATATCGAATTCCCACGGGGTTGGACGCGTAGGAACAGAGAAACAGGAGAATATGGG<br>CCAAACAGGATATCTGTGGTAAGCAGTTCCTGCCCCGGCTCAGGGCCAAGAACAGTTGG<br>AACAGCAGAATATGGGCCAAACAGGATATCTGTGGTAAGCAGTTCCTGCCCCGGCTCAG<br>GGCCAAGAACAGATGGTCCCCAGATGCGGTCCCGCCCTCAGCAGTTTCTAGAGAACCAT<br>CAGATGTTTCCAGGGTGCCCCAAGGACCTGAAATGACCCTGTGCCTTATTTGAACTAACC<br>AATCAGTTCGCTTCTCGCTTCTGTTCGCGCGCTTCTGCTCCCCGAGCTCTATATAAGCAGA<br>GCTCGTTTAGTGAACCGTCAGATCGCTAGCACCGGTGCCGCCACCATGCCTCTGGGCCTG<br>CTGTGGCTGGGCCTGGCCCTGCTGGGCGCCCTGCACGCCCAGGCCGGCGTGCAGGTGGA<br>GACAATCTCCCCAGGCGACGGACGCACATTCCCTAAGCGGGGCCAGACCTGCGTGGTGC<br>ACTATACAGGCATGCTGGAGGATGGCAAGAAGTTTGACAGCTCCCGGGATAGAAACAAG<br>CCATTCAAGTTTATGCTGGGCAAGCAGGAAGTGATCAGAGGCTGGGAGGAGGGCGTGGC<br>CCAGATGTCTGTGGGCCAGAGGGCCAAGCTGACCATCAGCCCAGACTACGCCTATGGAG<br>CAACAGGCCACCCAGGAATCATCCCACCTCACGCCACCCTGGTGTTCGATGTGGAGCTGC<br>TGAAGCTGGGCGAGGGATCCAACACATCAAAAGAGAACCCCTTTCTGTTCGCATTGGAG<br>GCCGTAGTCATATCTGTTGGATCCATGGGACTTATTATCTCCCTGTTGTGTGTGTACTTCT<br>GGCTGGAACGGACTATGCCCAGGATCCCCACGCTCAAGAATCTGGAAGATCTCGTCACA<br>GAATACCATGGTAATTTCAGCGCCTGGAGCGGAGTCTCTAAGGGTCTGGCCGAATCCCTC<br>CAACCCGATTATTCTGAACGGTTGTGCCTCGTATCCGAAATACCACCAAAAGGCGGGGCT<br>CTGGGTGAGGGCCCAGGGGCGAGTCCGTGCAATCAACACAGCCCGTATTGGGCCCCTCC<br>TTGTTATACGTTGAAGCCCGAAACTGGAAGCGGAGCTACTAACTTCAGCCTGCTGAAGCA<br>GGCTGGAGACGTGGAGGAGAACCCTGGACCTATGGCACTGCCCGTGACCGCCCTGCTGC<br>TGCCTCTGGCCCTGCTGCTGCACGCAGCCCGGCCTATCCTGTGGCACGAGATGTGGCACG<br>AGGGCCTGGAGGAGGCCAGCAGGCTGTATTTTGGCGAGCGCAACGTGAAGGGCATGTTC<br>GAGGTGCTGGAGCCTCTGCACGCCATGATGGAGAGAGGCCCACAGACCCTGAAGGAGAC<br>ATCCTTTAACCAGGCCTATGGACGGGACCTGATGGAGGCACAGGAGTGGTGCAGAAAGT<br>ACATGAAGTCTGGCAATGTGAAGGACCTGCTGCAGGCCTGGGATCTGTACTATCACGTGT<br>TTCGGAGAATCTCCAAGGGCAAAGACACGATTCCGTGGCTTGGGCATCTGCTCGTTGGGC<br>TGAGTGGTGCGTTTGGTTTCATCATCTTGGTCTATCTCTTGATCAATTGCAGAAATACAGG<br>CCCTTGGCTGAAAAAAGTGCTCAAGTGTAATACCCCCGACCCAAGCAAGTTCTTCTCCCA<br>GCTTTCTTCAGAGCATGGAGGCGATGTGCAGAAATGGCTCTCTTCACCTTTTCCCTCCTCA<br>AGCTTCTCCCCGGGAGGGCTGGCGCCCGAGATTTCACCTCTTGAGGTACTTGAACGAGAC<br>AAGGTTACCCAACTTCTCCTTCAACAGGATAAGGTACCCGAACCTGCGAGCCTTAGCTCC<br>AACCACTCTCTTACGAGCTGCTTCACCAATCAGGGATACTTCTTTTTCCACCTTCCCGATG<br>CGCTGGAAATCGAAGCTTGTCAAGTTTACTTTACCTATGATCCATATAGCGAGGAAGATC<br>CCGACGAAGGAGTCGCCGGTGCGCCCACGGGTTCCTCACCCCAACCTCTCCAGCCTCTCT<br>CAGGAGAAGATGATGCTTATTGCACTTTTCCCAGTAGAGACGATCTCCTCCTCTTTTCTCC<br>ATCTCTTTTGGGGGGACCTTCCCCCCCTTCTACGGCACCTGGCGGGTCTGGTGCTGGCGA<br>GGAGCGGATGCCGCCGTCCCTCCAGGAGCGAGTACCACGAGATTGGGATCCCCAGCCAC<br>TTGGACCCCCCACCCCCGGCGTACCTGACCTTGTCGATTTTCAACCTCCCCCTGAATTGGT<br>GCTGCGAGAGGCTGGGGAGGAAGTTCCGGACGCTGGGCCGAGGGAGGGCGTGTCCTTTC<br>CATGGAGTAGGCCTCCAGGTCAAGGCGAGTTTAGGGCTCTCAACGCGCGGCTGCCGTTG<br>AATACAGACGCTTATCTCTCACTGCAGGAACTGCAAGGTCAGGACCCAACACATCTTGTA<br>GGATCTGGTGCTACTAATTTTTCTCTTTTGAAGCAAGCTGGAGATGTTGAAGAGAACCCT<br>GGTCCAGTGAGCAAGGGCGAGGAGCTGTTCACCGGGGTGGTGCCCATCCTGGTCGAGCT<br>GGACGGCGACGTAAACGGCCACAAGTTCAGCGTGTCCGGCGAGGGCGAGGGCGATGCCA<br>CCTACGGCAAGCTGACCCTGAAGTTCATCTGCACCACCGGCAAGCTGCCCGTGCCCTGGC<br>CCACCCTCGTGACCACCCTGACCTACGGCGTGCAGTGCTTCAGCCGCTACCCCGACCACA<br>TGAAGCAGCACGACTTCTTCAAGTCCGCCATGCCCGAAGGCTACGTCCAGGAGCGCACC<br>ATCTTCTTCAAGGACGACGGCAACTACAAGACCCGCGCCGAGGTGAAGTTCGAGGGCGA<br>CACCCTGGTGAACCGCATCGAGCTGAAGGGCATCGACTTCAAGGAGGACGGCAACATCC<br>TGGGGCACAAGCTGGAGTACAACTACAACAGCCACAACGTCTATATCATGGCCGACAAG<br>CAGAAGAACGGCATCAAGGTGAACTTCAAGATCCGCCACAACATCGAGGACGGCAGCGT<br>GCAGCTCGCCGACCACTACCAGCAGAACACCCCCATCGGCGACGGCCCCGTGCTGCTGC<br>CCGACAACCACTACCTGAGCACCCAGTCCGCCCTGAGCAAAGACCCCAACGAGAAGCGC<br>GATCACATGGTCCTGCTGGAGTTCGTGACCGCCGCCGGGATCACTCTCGGCATGGACGAG<br>CTGTACAAGTAAACTAGTGTCGACAATCAACCTCTGGATTACAAAATTTGTGAAAGATTG<br>ACTGGTATTCTTAACTATGTTGCTCCTTTTACGCTATGTGGATACGCTGCTTTAATGCCTTT<br>GTATCATGCTATTGCTTCCCGTATGGCTTTCATTTTCTCCTCCTTGTATAAATCCTGGTTGC<br>TGTCTCTTTATGAGGAGTTGTGGCCCGTTGTCAGGCAACGTGGCGTGGTGTGCACTGTGTT<br>TGCTGACGCAACCCCCACTGGTTGGGGCATTGCCACCACCTGTCAGCTCCTTTCCGGGAC<br>TTTCGCTTTCCCCCTCCCTATTGCCACGGCGGAACTCATCGCCGCCTGCCTTGCCCGCTGC<br>TGGACAGGGGCTCGGCTGTTGGGCACTGACAATTCCGTGGTGTTGTCGGGGAAGCTGACG<br>TCCTTTCCATGGCTGCTCGCCTGTGTTGCCACCTGGATTCTGCGCGGGACGTCCTTCTGCT<br>ACGTCCCTTCGGCCCTCAATCCAGCGGACCTTCCTTCCCGCGGCCTGCTGCCGGCTCTGCG<br>GCCTCTTCCGCGTCTTCGCCTTCGCCCTCAGACGAGTCGGATCTCCCTTTGGGCCGCCTCC<br>CCGCCTGGAATTCGAGCTCGGTACCTTTAAGACCAATGACTTACAAGGCAGCTGTAGATC<br>TTAGCCACTTTTTAAAAGAAAAGGGGGGACTGGAAGGGCTAATTCACTCCCAACGAAGA | |

-continued

| SEQ ID NO | Sequence | Description |
|---|---|---|
| | CAAGATCTGCTTTTTGCTTGTACTGGGTCTCTCTGGTTAGACCAGATCTGAGCCTGGGAGC<br>TCTCTGGCTAACTAGGGAACCCACTGCTTAAGCCTCAATAAAGCTTGCCTTGAGTGCTTC<br>AAGTAGTGTGTGCCCGTCTGTTGTGTGACTCTGGTAACTAGAGATCCCTCAGACCCTTTTA<br>GTCAGTGTGGAAAATCTCTAGCAGTAGTAGTTCATGTCATCTTATTATTCAGTATTTATAA<br>CTTGCAAAGAAATGAATATCAGAGAGTGAGAGGAACTTGTTTATTGCAGCTTATAATGGT<br>TACAAATAAAGCAATAGCATCACAAATTTCACAAATAAAGCATTTTTTTCACTGCATTCT<br>AGTTGTGGTTTGTCCAAACTCATCAATGTATCTTATCATGTCTGGCTCTAGCTATCCCGCC<br>CCTAACTCCGCCCAGTTCCGCCCATTCTCCGCCCCATGGCTGACTAATTTTTTTTATTTAT<br>GCAGAGGCCGAGGCCGCCTCGGCCTCTGAGCTATTCCAGAAGTAGTGAGGAGGCTTTTTT<br>GGAGGCCTAGGCTTTTGCGTCGAGACGTACCCAATTCGCCCTATAGTGAGTCGTATTACG<br>CGCGCTCACTGGCCGTCGTTTTACAACGTCGTGACTGGGAAAACCCTGGCGTTACCCAAC<br>TTAATCGCCTTGCAGCACATCCCCCTTTCGCCAGCTGGCGTAATAGCGAAGAGGCCCGCA<br>CCGATCGCCCTTCCCAACAGTTGCGCAGCCTGAATGGCGAATGGCGCGACGCGCCCTGTA<br>GCGGCGCATTAAGCGCGGCGGGTGTGGTGGTTACGCGCAGCGTGACCGCTACACTTGCC<br>AGCGCCCTAGCGCCCGCTCCTTTCGCTTTCTTCCCTTCCTTTCTCGCCACGTTCGCCGGCTT<br>TCCCCGTCAAGCTCTAAATCGGGGGCTCCCTTTAGGGTTCCGATTTAGTGCTTTACGGCAC<br>CTCGACCCCAAAAAACTTGATTAGGGTGATGGTTCACGTAGTGGGCCATCGCCCTGATAG<br>ACGGTTTTTCGCCCTTTGACGTTGGAGTCCACGTTCTTTAATAGTGGACTCTTGTTCCAAA<br>CTGGAACAACACTCAACCCTATCTCGGTCTATTCTTTTGATTTATAAGGGATTTTGCCGAT<br>TTCGGCCTATTGGTTAAAAAATGAGCTGATTTAACAAAAATTTAACGCGAATTTTAACAA<br>AATATTAACGTTTACAATTTCCCAGGTGGCACTTTTCGGGGAAATGTGCGCGGAACCCCT<br>ATTTGTTTATTTTTCTAAATACATTCAAATATGTATCCGCTCATGAGACAATAACCCTGAT<br>AAATGCTTCAATAATATTGAAAAAGGAAGAGTATGAGTATTCAACATTTCCGTGTCGCCC<br>TTATTCCCTTTTTTGCGGCATTTTGCCTTCCTGTTTTTGCTCACCCAGAAACGCTGGTGAAA<br>GTAAAAGATGCTGAAGATCAGTTGGGTGCACGAGTGGGTTACATCGAACTGGATCTCAA<br>CAGCGGTAAGATCCTTGAGAGTTTTCGCCCCGAAGAACGTTTTCCAATGATGAGCACTTT<br>TAAAGTTCTGCTATGTGGCGCGGTATTATCCCGTATTGACGCCGGGCAAGAGCAACTCGG<br>TCGCCGCATACACTATTCTCAGAATGACTTGGTTGAGTACTCACCAGTCACAGAAAAGCA<br>TCTTACGGATGGCATGACAGTAAGAGAATTATGCAGTGCTGCCATAACCATGAGTGATAA<br>CACTGCGGCCAACTTACTTCTGACAACGATCGGAGGACCGAAGGAGCTAACCGCTTTTTT<br>GCACAACATGGGGGATCATGTAACTCGCCTTGATCGTTGGGAACCGGAGCTGAATGAAG<br>CCATACCAAACGACGAGCGTGACACCACGATGCCTGTAGCAATGGCAACAACGTTGCGC<br>AAACTATTAACTGGCGAACTACTTACTCTAGCTTCCCGGCAACAATTAATAGACTGGATG<br>GAGGCGGATAAAGTTGCAGGACCACTTCTGCGCTCGGCCCTTCCGGCTGGCTGGTTTATT<br>GCTGATAAATCTGGAGCCGGTGAGCGTGGGTCTCGCGGTATCATTGCAGCACTGGGGCC<br>AGATGGTAAGCCCTCCCGTATCGTAGTTATCTACACGACGGGGAGTCAGGCAACTATGG<br>ATGAACGAAATAGACAGATCGCTGAGATAGGTGCCTCACTGATTAAGCATTGGTAACTGT<br>CAGACCAAGTTTACTCATATATACTTTAGATTGATTTAAAACTTCATTTTTAATTTAAAAG<br>GATCTAGGTGAAGATCCTTTTTGATAATCTCATGACCAAAATCCCTTAACGTGAGTTTTCG<br>TTCCACTGAGCGTCAGACCCCGTAGAAAAGATCAAAGGATCTTCTTGAGATCCTTTTTTTC<br>TGCGCGTAATCTGCTGCTTGCAAACAAAAAAACCACCGCTACCAGCGGTGGTTTGTTTGC<br>CGGATCAAGAGCTACCAACTCTTTTTCCGAAGGTAACTGGCTTCAGCAGAGCGCAGATAC<br>CAAATACTGTCCTTCTAGTGTAGCCGTAGTTAGGCCACCACTTCAAGAACTCTGTAGCAC<br>CGCCTACATACCTCGCTCTGCTAATCCTGTTACCAGTGGCTGCTGCCAGTGGCGATAAGT<br>CGTGTCTTACCGGGTTGGACTCAAGACGATAGTTACCGGATAAGGCGCAGCGGTCGGGC<br>TGAACGGGGGGTTCGTGCACACAGCCCAGCTTGGAGCGAACGACCTACACCGAACTGAG<br>ATACCTACAGCGTGAGCTATGAGAAAGCGCCACGCTTCCCGAAGGGAGAAAGGCGGACA<br>GGTATCCGGTAAGCGGCAGGGTCGGAACAGGAGAGCGCACGAGGGAGCTTCCAGGGGG<br>AAACGCCTGGTATCTTTATAGTCCTGTCGGGTTTCGCCACCTCTGACTTGAGCGTCGATTT<br>TTGTGATGCTCGTCAGGGGGGCGGAGCCTATGGAAAAACGCCAGCAACGCGGCCTTTTT<br>ACGGTTCCTGGCCTTTTGCTGGCCTTTTGCTCACATGTTCTTTCCTGCGTTATCCCCTGATT<br>CTGTGGATAACCGTATTACCGCCTTTGAGTGAGCTGATACCGCTCGCCGCAGCCGAACGA<br>CCGAGCGCAGCGAGTCAGTGAGCGAGGAAGCGGAAGAGCGCCCAATACGCAAACCGCC<br>TCTCCCCGCGCGTTGGCCGATTCATTAATGCAGCTGGCACGACAGGTTTCCCGACTGGAA<br>AGCGGGCAGTGAGCGCAACGCAATTAATGTGAGTTAGCTCACTCATTAGGCACCCCAGG<br>CTTTACACTTTATGCTTCCGGCTCGTATGTTGTGTGGAATTGTGAGCGGATAACAATTTCA<br>CACAGGAAACAGCTATGACCATGATTACGCCAAGCGCGCAATTAACCCTCACTAAAGGG<br>AACAAAAGCTGGAGCTGCA | |
| 67 | AGCTTAATGTAGTCTTATGCAATACTCTTGTAGTCTTGCAACATGGTAACGATGAGTTAG<br>CAACATGCCTTACAAGGAGAGAAAAAGCACCGTGCATGCCGATTGGTGGAAGTAAGGTG<br>GTACGATCGTGCCTTATTAGGAAGGCAACAGACGGGTCTGACATGGATTGGACGAACCA<br>CTGAATTGCCGCATTGCAGAGATATTGTATTTAAGTGCCTAGCTCGATACAATAAACGGG<br>TCTCTCTGGTTAGACCAGATCTGAGCCTGGGAGCTCTCTGGCTAACTAGGGAACCCACTG<br>CTTAAGCCTCAATAAAGCTTGCCTTGAGTGCTTCAAGTAGTGTGTGCCCGTCTGTTGTGTG<br>ACTCTGGTAACTAGAGATCCCTCAGACCCTTTTAGTCAGTGTGGAAAATCTCTAGCAGTG<br>GCGCCCGAACAGGGACTTGAAAGCGAAAGGGAAACCAGAGGAGCTCTCTCGACGCAGG<br>ACTCGGCTTGCTGAAGCGCGCACGGCAAGAGGCGAGGGGCGGCGACTGGTGAGTACGCC<br>AAAAATTTTGACTAGCGGAGGCTAGAAGGAGAGAGATGGGTGCGAGAGCGTCAGTATTA<br>AGCGGGGGAGAATTAGATCGCGATGGGAAAAAATTCGGTTAAGGCCAGGGGGAAAGAA<br>AAAATATAAATTAAAACATATAGTATGGGCAAGCAGGGAGCTAGAACGATTCGCAGTTA<br>ATCCTGGCCTGTTAGAAACATCAGAAGGCTGTAGACAAATACTGGGACAGCTACAACCA<br>TCCCTTCAGACAGGATCAGAAGAACTTAGATCATTATATAATACAGTAGCAACCCTCTAT<br>TGTGTGCATCAAAGGATAGAGATAAAAGACACCAAGGAAGCTTTAGACAAGATAGAGGA<br>AGAGCAAAACAAAAGTAAGACCACCGCACAGCAAGCGGCCGCTGATCTTCAGACCTGGA | CISC vector DNA |

-continued

| SEQ ID NO | Sequence | Description |
|---|---|---|
| | GGAGGAGATATGAGGGACAATTGGAGAAGTGAATTATATAAATATAAAGTAGTAAAAT<br>TGAACCATTAGGAGTAGCACCCACCAAGGCAAAGAGAAGAGTGGTGCAGAGAGAAAAA<br>AGAGCAGTGGGAATAGGAGCTTTGTTCCTTGGGTTCTTGGGAGCAGCAGGAAGCACTAT<br>GGGCGCAGCCTCAATGACGCTGACGGTACAGGCCAGACAATTATTGTCTGGTATAGTGC<br>AGCAGCAGAACAATTTGCTGAGGGCTATTGAGGCGCAACAGCATCTGTTGCAACTCACA<br>GTCTGGGGCATCAAGCAGCTCCAGGCAAGAATCCTGGCTGTGGAAAGATACCTAAAGGA<br>TCAACAGCTCCTGGGGATTTGGGGTTGCTCTGGAAAACTCATTTGCACCACTGCTGTGCC<br>TTGGAATGCTAGTTGGAGTAATAAATCTCTGGAACAGATTTGGAATCACACGACCTGGAT<br>GGAGTGGGACAGAGAAATTAACAATTACACAAGCTTAATACACTCCTTAATTGAAGAAT<br>CGCAAAACCAGCAAGAAAAGAATGAACAAGAATTATTGGAATTAGATAAATGGGCAAGT<br>TTGTGGAATTGGTTTAACATAACAAATTGGCTGTGGTATATAAAATTATTCATAATGATA<br>GTAGGAGGCTTGGTAGGTTTAAGAATAGTTTTTGCTGTACTTTCTATAGTGAATAGAGTT<br>AGGCAGGGATATTCACCATTATCGTTTCAGACCCACCTCCCAACCCCGAGGGGACCCGAC<br>AGGCCCGAAGGAATAGAAGAAGAAGGTGGAGAGAGAGACAGAGACAGATCCATTCGAT<br>TAGTGAACGGATCTCGACGGTATCGGTTAACTTTTAAAAGAAAAGGGGGGATTGGGGGG<br>TACAGTGCAGGGGAAAGAATAGTAGACATAATAGCAACAGACATACAAACTAAAGAATT<br>ACAAAAACAAATTACAAAAATTCAAAATTTTATCGATCACGAGACTAGCCTCGAGAAGC<br>TTGATATCGAATTCCCACGGGGTTGGACGCGTAGGAACAGAGAAACAGGAGAATATGGG<br>CCAAACAGGATATCTGTGGTAAGCAGTTCCTGCCCCGGCTCAGGGCCAAGAACAGTTGG<br>AACAGCAGAATATGGGCCAAACAGGATATCTGTGGTAAGCAGTTCCTGCCCCGGCTCAG<br>GGCCAAGAACAGATGGTCCCCAGATGCGGTCCCGCCCTCAGCAGTTTCTAGAGAACCAT<br>CAGATGTTTCCAGGGTGCCCCAAGGACCTGAAATGACCCTGTGCCTTATTTGAACTAACC<br>AATCAGTTCGCTTCTCGCTTCTGTTCGCGCGCTTCTGCTCCCCGAGCTCTATATAAGCAGA<br>GCTCGTTTAGTGAACCGTCAGATCGCTAGCACCGGTGCCGCCACCATGCCTCTGGGCCTG<br>CTGTGGCTGGGCCTGGCCCTGCTGGGCGCCCTGCACGCCCAGGCCGGCGTGCAGGTGGA<br>GACAATCTCCCCAGGCGACGGACGCACATTCCCTAAGCGGGGCCAGACCTGCGTGGTGC<br>ACTATACAGGCATGCTGGAGGATGGCAAGAAGTTTGACAGCTCCCGGGATAGAAACAAG<br>CCATTCAAGTTTATGCTGGGCAAGCAGGAAGTGATCAGAGGCTGGGAGGAGGGCGTGGC<br>CCAGATGTCTGTGGGCCAGAGGGCCAAGCTGACCATCAGCCCAGACTACGCCTATGGAG<br>CAACAGGCCACCCAGGAATCATCCCACCTCACGCCACCCTGGTGTTCGATGTGGAGCTGC<br>TGAAGCTGGGCGAGGGCGGTAGTCAGAACCTTGTGATACCATGGGCCCCAGAAAATCTC<br>ACACTTCATAAACTTTCCGAATCACAACTCGAACTCAACTGGAATAACCGGTTCCTGAAT<br>CACTGTCTTGAACACCTGGTACAATATCGGACCGACTGGGATCACTCATGGACAGAACA<br>ATCTGTGGACTATAGGCACAAATTCTCACTCCCAAGCGTAGACGGCCAAAAAAGATACA<br>CTTTTCGCGTACGATCCCGCTTTAATCCTCTCTGCGGCTCTGCTCAGCACTGGAGTGAATG<br>GTCCCATCCCATTCATTGGGGATCCAACACATCAAAAGAGAACCCCTTTCTGTTCGCATT<br>GGAGGCCGTAGTCATATCTGTTGGATCCATGGGACTTATTATCTCCCTGTTGTGTGTGTAC<br>TTCTGGCTGGAACGGACTATGCCCAGGATCCCCACGCTCAAGAATCTGGAAGATCTCGTC<br>ACAGAATACCATGGTAATTTCAGCGCCTGGAGCGGAGTCTCTAAGGGTCTGGCCGAATCC<br>CTCCAACCCGATTATTCTGAACGGTTGTGCCTCGTATCCGAAATACCACCAAAAGGCGGG<br>GCTCTGGGTGAGGGCCCAGGGGCGAGTCCGTGCAATCAACACAGCCCGTATTGGGCCCC<br>TCCTTGTTATACGTTGAAGCCCGAAACTGGAAGCGGAGCTACTAACTTCAGCCTGCTGAA<br>GCAGGCTGGAGACGTGGAGGAGAACCCTGGACCTATGGCACTGCCCGTGACCGCCCTGC<br>TGCTGCCTCTGGCCCTGCTGCTGCACGCAGCCCGGCCTATCCTGTGGCACGAGATGTGGC<br>ACGAGGGCCTGGAGGAGGCCAGCAGGCTGTATTTTGGCGAGCGCAACGTGAAGGGCATG<br>TTCGAGGTGCTGGAGCCTCTGCACGCCATGATGGAGAGAGGCCCACAGACCCTGAAGGA<br>GACATCCTTTAACCAGGCCTATGGACGGGACCTGATGGAGGCACAGGAGTGGTGCAGAA<br>AGTACATGAAGTCTGGCAATGTGAAGGACCTGCTGCAGGCCTGGGATCTGTACTATCACG<br>TGTTTCGGAGAATCTCCAAGGGAGGTTCAAAACCTTTTGAGAACCTTAGACTGATGGCGC<br>CCATCTCTCTGCAGGTAGTTCACGTTGAGACCCATAGATGCAATATAAGCTGGGAAATCT<br>CACAAGCCAGCCATTACTTTGAACGGCATTTGGAATTCGAGGCCCGAACACTTTCCCCCG<br>GTCATACGTGGGAAGAAGCTCCTCTCTTGACGCTGAAGCAGAAGCAGGAGTGGATTTGTC<br>TGGAGACTTTGACTCCTGATACTCAGTATGAGTTCCAAGTTCGGGTGAAACCACTCCAAG<br>GCGAGTTCACGACGTGGTCTCCGTGGAGTCAACCGTTGGCGTTCCGCACGAAGCCCGCTG<br>CCCTTGGCAAAGACACGATTCCGTGGCTTGGGCATCTGCTCGTTGGGCTGAGTGGTGCGT<br>TTGGTTTCATCATCTTGGTCTATCTCTTGATCAATTGCAGAAATACAGGCCCTTGGCTGAA<br>AAAAGTGCTCAAGTGTAATACCCCCGACCCAAGCAAGTTCTTCTCCCAGCTTTCTTCAGA<br>GCATGGAGGCGATGTGCAGAAATGGCTCTCTTCACCTTTTCCCTCCTCAAGCTTCTCCCCG<br>GGAGGGCTGGCGCCCGAGATTTCACCTCTTGAGGTACTTGAACGAGACAAGGTTACCCA<br>ACTTCTCCTTCAACAGGATAAGGTACCCGAACCTGCGAGCCTTAGCTCCAACCACTCTCT<br>TACGAGCTGCTTCACCAATCAGGGATACTTCTTTTTCCACCTTCCCGATGCGCTGGAAATC<br>GAAGCTTGTCAAGTTTACTTTACCTATGATCCATATAGCGAGGAAGATCCCGACGAAGGA<br>GTCGCCGGTGCGCCCACGGGTTCCTCACCCCAACCTCTCCAGCCTCTCTCAGGAGAAGAT<br>GATGCTTATTGCACTTTTCCCAGTAGAGACGATCTCCTCCTCTTTTCTCCATCTCTTTTGGG<br>GGGACCTTCCCCCCCTTCTACGGCACCTGGCGGGTCTGGTGCTGGCGAGGAGCGGATGCC<br>GCCGTCCCTCCAGGAGCGAGTACCACGAGATTGGGATCCCCAGCCACTTGGACCCCCCAC<br>CCCCGGCGTACCTGACCTTGTCGATTTTCAACCTCCCCCTGAATTGGTGCTGCGAGAGGC<br>TGGGGAGGAAGTTCCGGACGCTGGGCCGAGGGAGGGCGTGTCCTTTCCATGGAGTAGGC<br>CTCCAGGTCAAGGCGAGTTTAGGGCTCTCAACGCGCGGCTGCCGTTGAATACAGACGCTT<br>ATCTCTCACTGCAGGAACTGCAAGGTCAGGACCCAACACATCTTGTAGGATCTGGTGCTA<br>CTAATTTTTCTCTTTTGAAGCAAGCTGGAGATGTTGAAGAGAACCCTGGTCCAGTGAGCA<br>AGGGCGAGGAGCTGTTCACCGGGGTGGTGCCCATCCTGGTCGAGCTGGACGGCGACGTA<br>AACGGCCACAAGTTCAGCGTGTCCGGCGAGGGCGAGGGCGATGCCACCTACGGCAAGCT<br>GACCCTGAAGTTCATCTGCACCACCGGCAAGCTGCCCGTGCCCTGGCCCACCCTCGTGAC<br>CACCCTGACCTACGGCGTGCAGTGCTTCAGCCGCTACCCCGACCACATGAAGCAGCACG | |

-continued

| SEQ ID NO | Sequence | Description |
|---|---|---|
| | ACTTCTTCAAGTCCGCCATGCCCGAAGGCTACGTCCAGGAGCGCACCATCTTCTTCAAGG | |
| | ACGACGGCAACTACAAGACCCGCGCCGAGGTGAAGTTCGAGGGCGACACCCTGGTGAAC | |
| | CGCATCGAGCTGAAGGGCATCGACTTCAAGGAGGACGGCAACATCCTGGGGCACAAGCT | |
| | GGAGTACAACTACAACAGCCACAACGTCTATATCATGGCCGACAAGCAGAAGAACGGCA | |
| | TCAAGGTGAACTTCAAGATCCGCCACAACATCGAGGACGGCAGCGTGCAGCTCGCCGAC | |
| | CACTACCAGCAGAACACCCCCATCGGCGACGGCCCCGTGCTGCTGCCCGACAACCACTA | |
| | CCTGAGCACCCAGTCCGCCCTGAGCAAAGACCCCAACGAGAAGCGCGATCACATGGTCC | |
| | TGCTGGAGTTCGTGACCGCCGCCGGGATCACTCTCGGCATGGACGAGCTGTACAAGTAA | |
| | ACTAGTGTCGACAATCAACCTCTGGATTACAAAATTTGTGAAAGATTGACTGGTATTCTT | |
| | AACTATGTTGCTCCTTTTACGCTATGTGGATACGCTGCTTTAATGCCTTTGTATCATGCTA | |
| | TTGCTTCCCGTATGGCTTTCATTTTCTCCTCCTTGTATAAATCCTGGTTGCTGTCTCTTTAT | |
| | GAGGAGTTGTGGCCCGTTGTCAGGCAACGTGGCGTGGTGTGCACTGTGTTTGCTGACGCA | |
| | ACCCCCACTGGTTGGGGCATTGCCACCACCTGTCAGCTCCTTTCCGGGACTTTCGCTTTCC | |
| | CCCTCCCTATTGCCACGGCGGAACTCATCGCCGCCTGCCTTGCCCGCTGCTGGACAGGGG | |
| | CTCGGCTGTTGGGCACTGACAATTCCGTGGTGTTGTCGGGGAAGCTGACGTCCTTTCCAT | |
| | GGCTGCTCGCCTGTGTTGCCACCTGGATTCTGCGCGGGACGTCCTTCTGCTACGTCCCTTC | |
| | GGCCCTCAATCCAGCGGACCTTCCTTCCCGCGGCCTGCTGCCGGCTCTGCGGCCTCTTCCG | |
| | CGTCTTCGCCTTCGCCCTCAGACGAGTCGGATCTCCCTTTGGGCCGCCTCCCCGCCTGGAA | |
| | TTCGAGCTCGGTACCTTTAAGACCAATGACTTACAAGGCAGCTGTAGATCTTAGCCACTT | |
| | TTTAAAAGAAAAGGGGGGACTGGAAGGGCTAATTCACTCCCAACGAAGACAAGATCTGC | |
| | TTTTTGCTTGTACTGGGTCTCTCTGGTTAGACCAGATCTGAGCCTGGGAGCTCTCTGGCTA | |
| | ACTAGGGAACCCACTGCTTAAGCCTCAATAAAGCTTGCCTTGAGTGCTTCAAGTAGTGTG | |
| | TGCCCGTCTGTTGTGTGACTCTGGTAACTAGAGATCCCTCAGACCCTTTTAGTCAGTGTGG | |
| | AAAATCTCTAGCAGTAGTAGTTCATGTCATCTTATTATTCAGTATTTATAACTTGCAAAGA | |
| | AATGAATATCAGAGAGTGAGAGGAACTTGTTTATTGCAGCTTATAATGGTTACAAATAAA | |
| | GCAATAGCATCACAAATTTCACAAATAAAGCATTTTTTTCACTGCATTCTAGTTGTGGTTT | |
| | GTCCAAACTCATCAATGTATCTTATCATGTCTGGCTCTAGCTATCCCGCCCCTAACTCCGC | |
| | CCAGTTCCGCCCATTCTCCGCCCCATGGCTGACTAATTTTTTTTATTTATGCAGAGGCCGA | |
| | GGCCGCCTCGGCCTCTGAGCTATTCCAGAAGTAGTGAGGAGGCTTTTTTGGAGGCCTAGG | |
| | CTTTTGCGTCGAGACGTACCCAATTCGCCCTATAGTGAGTCGTATTACGCGCGCTCACTG | |
| | GCCGTCGTTTTACAACGTCGTGACTGGGAAAACCCTGGCGTTACCCAACTTAATCGCCTT | |
| | GCAGCACATCCCCCTTTCGCCAGCTGGCGTAATAGCGAAGAGGCCCGCACCGATCGCCCT | |
| | TCCCAACAGTTGCGCAGCCTGAATGGCGAATGGCGCGACGCGCCCTGTAGCGGCGCATT | |
| | AAGCGCGGCGGGTGTGGTGGTTACGCGCAGCGTGACCGCTACACTTGCCAGCGCCCTAG | |
| | CGCCCGCTCCTTTCGCTTTCTTCCCTTCCTTTCTCGCCACGTTCGCCGGCTTTCCCCGTCAA | |
| | GCTCTAAATCGGGGGCTCCCTTTAGGGTTCCGATTTAGTGCTTTACGGCACCTCGACCCC | |
| | AAAAAACTTGATTAGGGTGATGGTTCACGTAGTGGGCCATCGCCCTGATAGACGGTTTTT | |
| | CGCCCTTTGACGTTGGAGTCCACGTTCTTTAATAGTGGACTCTTGTTCCAAACTGGAACAA | |
| | CACTCAACCCTATCTCGGTCTATTCTTTTGATTTATAAGGGATTTTGCCGATTTCGGCCTA | |
| | TTGGTTAAAAAATGAGCTGATTTAACAAAAATTTAACGCGAATTTTAACAAAATATTAAC | |
| | GTTTACAATTTCCCAGGTGGCACTTTTCGGGGAAATGTGCGCGGAACCCCTATTTGTTTAT | |
| | TTTTCTAAATACATTCAAATATGTATCCGCTCATGAGACAATAACCCTGATAAATGCTTCA | |
| | ATAATATTGAAAAAGGAAGAGTATGAGTATTCAACATTTCCGTGTCGCCCTTATTCCCTTT | |
| | TTTGCGGCATTTTGCCTTCCTGTTTTTGCTCACCCAGAAACGCTGGTGAAAGTAAAAGATG | |
| | CTGAAGATCAGTTGGGTGCACGAGTGGGTTACATCGAACTGGATCTCAACAGCGGTAAG | |
| | ATCCTTGAGAGTTTTCGCCCCGAAGAACGTTTTCCAATGATGAGCACTTTTAAAGTTCTGC | |
| | TATGTGGCGCGGTATTATCCCGTATTGACGCCGGGCAAGAGCAACTCGGTCGCCGCATAC | |
| | ACTATTCTCAGAATGACTTGGTTGAGTACTCACCAGTCACAGAAAAGCATCTTACGGATG | |
| | GCATGACAGTAAGAGAATTATGCAGTGCTGCCATAACCATGAGTGATAACACTGCGGCC | |
| | AACTTACTTCTGACAACGATCGGAGGACCGAAGGAGCTAACCGCTTTTTTGCACAACATG | |
| | GGGGATCATGTAACTCGCCTTGATCGTTGGGAACCGGAGCTGAATGAAGCCATACCAAA | |
| | CGACGAGCGTGACACCACGATGCCTGTAGCAATGGCAACAACGTTGCGCAAACTATTAA | |
| | CTGGCGAACTACTTACTCTAGCTTCCCGGCAACAATTAATAGACTGGATGGAGGCGGATA | |
| | AAGTTGCAGGACCACTTCTGCGCTCGGCCCTTCCGGCTGGCTGGTTTATTGCTGATAAAT | |
| | CTGGAGCCGGTGAGCGTGGGTCTCGCGGTATCATTGCAGCACTGGGGCCAGATGGTAAG | |
| | CCCTCCCGTATCGTAGTTATCTACACGACGGGGAGTCAGGCAACTATGGATGAACGAAAT | |
| | AGACAGATCGCTGAGATAGGTGCCTCACTGATTAAGCATTGGTAACTGTCAGACCAAGTT | |
| | TACTCATATATACTTTAGATTGATTTAAAACTTCATTTTTAATTTAAAAGGATCTAGGTGA | |
| | AGATCCTTTTTGATAATCTCATGACCAAAATCCCTTAACGTGAGTTTTCGTTCCACTGAGC | |
| | GTCAGACCCCGTAGAAAAGATCAAAGGATCTTCTTGAGATCCTTTTTTTCTGCGCGTAAT | |
| | CTGCTGCTTGCAAACAAAAAAACCACCGCTACCAGCGGTGGTTTGTTTGCCGGATCAAGA | |
| | GCTACCAACTCTTTTTCCGAAGGTAACTGGCTTCAGCAGAGCGCAGATACCAAATACTGT | |
| | CCTTCTAGTGTAGCCGTAGTTAGGCCACCACTTCAAGAACTCTGTAGCACCGCCTACATA | |
| | CCTCGCTCTGCTAATCCTGTTACCAGTGGCTGCTGCCAGTGGCGATAAGTCGTGTCTTACC | |
| | GGGTTGGACTCAAGACGATAGTTACCGGATAAGGCGCAGCGGTCGGGCTGAACGGGGGG | |
| | TTCGTGCACACAGCCCAGCTTGGAGCGAACGACCTACACCGAACTGAGATACCTACAGC | |
| | GTGAGCTATGAGAAAGCGCCACGCTTCCCGAAGGGAGAAAGGCGGACAGGTATCCGGTA | |
| | AGCGGCAGGGTCGGAACAGGAGAGCGCACGAGGGAGCTTCCAGGGGGAAACGCCTGGT | |
| | ATCTTTATAGTCCTGTCGGGTTTCGCCACCTCTGACTTGAGCGTCGATTTTTGTGATGCTC | |
| | GTCAGGGGGGCGGAGCCTATGGAAAAACGCCAGCAACGCGGCCTTTTTACGGTTCCTGG | |
| | CCTTTTGCTGGCCTTTTGCTCACATGTTCTTTCCTGCGTTATCCCCTGATTCTGTGGATAAC | |
| | CGTATTACCGCCTTTGAGTGAGCTGATACCGCTCGCCGCAGCCGAACGACCGAGCGCAGC | |
| | GAGTCAGTGAGCGAGGAAGCGGAAGAGCGCCCAATACGCAAACCGCCTCTCCCCGCGCG | |
| | TTGGCCGATTCATTAATGCAGCTGGCACGACAGGTTTCCCGACTGGAAAGCGGGCAGTG | |
| | AGCGCAACGCAATTAATGTGAGTTAGCTCACTCATTAGGCACCCCAGGCTTTACACTTTA | |

-continued

| SEQ ID NO | Sequence | Description |
|---|---|---|
| | TGCTTCCGGCTCGTATGTTGTGTGGAATTGTGAGCGGATAACAATTTCACACAGGAAACA<br>GCTATGACCATGATTACGCCAAGCGCGCAATTAACCCTCACTAAAGGGAACAAAAGCTG<br>GAGCTGCA | |
| 68 | AGCTTAATGTAGTCTTATGCAATACTCTTGTAGTCTTGCAACATGGTAACGATGAGTTAG<br>CAACATGCCTTACAAGGAGAGAAAAAGCACCGTGCATGCCGATTGGTGGAAGTAAGGTG<br>GTACGATCGTGCCTTATTAGGAAGGCAACAGACGGGTCTGACATGGATTGGACGAACCA<br>CTGAATTGCCGCATTGCAGAGATATTGTATTTAAGTGCCTAGCTCGATACAATAAACGGG<br>TCTCTCTGGTTAGACCAGATCTGAGCCTGGGAGCTCTCTGGCTAACTAGGGAACCCACTG<br>CTTAAGCCTCAATAAAGCTTGCCTTGAGTGCTTCAAGTAGTGTGTGCCCGTCTGTTGTGTG<br>ACTCTGGTAACTAGAGATCCCTCAGACCCTTTTAGTCAGTGTGGAAAATCTCTAGCAGTG<br>GCGCCCGAACAGGGACTTGAAAGCGAAAGGGAAACCAGAGGAGCTCTCTCGACGCAGG<br>ACTCGGCTTGCTGAAGCGCGCACGGCAAGAGGCGAGGGGCGGCGACTGGTGAGTACGCC<br>AAAAATTTTGACTAGCGGAGGCTAGAAGGAGAGAGATGGGTGCGAGAGCGTCAGTATTA<br>AGCGGGGGAGAATTAGATCGCGATGGGAAAAAATTCGGTTAAGGCCAGGGGGAAAGAA<br>AAAATATAAATTAAAACATATAGTATGGGCAAGCAGGGAGCTAGAACGATTCGCAGTTA<br>ATCCTGGCCTGTTAGAAACATCAGAAGGCTGTAGACAAATACTGGGACAGCTACAACCA<br>TCCCTTCAGACAGGATCAGAAGAACTTAGATCATTATATAATACAGTAGCAACCCTCTAT<br>TGTGTGCATCAAAGGATAGAGATAAAAGACACCAAGGAAGCTTTAGACAAGATAGAGGA<br>AGAGCAAAACAAAAGTAAGACCACCGCACAGCAAGCGGCCGCTGATCTTCAGACCTGGA<br>GGAGGAGATATGAGGGACAATTGGAGAAGTGAATTATATAAATATAAAGTAGTAAAAAT<br>TGAACCATTAGGAGTAGCACCCACCAAGGCAAAGAGAAGAGTGGTGCAGAGAGAAAAA<br>AGAGCAGTGGGAATAGGAGCTTTGTTCCTTGGGTTCTTGGGAGCAGCAGGAAGCACTAT<br>GGGCGCAGCCTCAATGACGCTGACGGTACAGGCCAGACAATTATTGTCTGGTATAGTGC<br>AGCAGCAGAACAATTTGCTGAGGGCTATTGAGGCGCAACAGCATCTGTTGCAACTCACA<br>GTCTGGGGCATCAAGCAGCTCCAGGCAAGAATCCTGGCTGTGGAAAGATACCTAAAGGA<br>TCAACAGCTCCTGGGGATTTGGGGTTGCTCTGGAAAACTCATTTGCACCACTGCTGTGCC<br>TTGGAATGCTAGTTGGAGTAATAAATCTCTGGAACAGATTTGGAATCACACGACCTGGAT<br>GGAGTGGGACAGAGAAATTAACAATTACACAAGCTTAATACACTCCTTAATTGAAGAAT<br>CGCAAAACCAGCAAGAAAAGAATGAACAAGAATTATTGGAATTAGATAAATGGGCAAGT<br>TTGTGGAATTGGTTTAACATAACAAATTGGCTGTGGTATATAAAATTATTCATAATGATA<br>GTAGGAGGCTTGGTAGGTTTAAGAATAGTTTTTGCTGTACTTTCTATAGTGAATAGAGTT<br>AGGCAGGGATATTCACCATTATCGTTTCAGACCCACCTCCCAACCCCGAGGGGACCCGAC<br>AGGCCCGAAGGAATAGAAGAAGAAGGTGGAGAGAGAGACAGAGACAGATCCATTCGAT<br>TAGTGAACGGATCTCGACGGTATCGGTTAACTTTTAAAAGAAAAGGGGGGATTGGGGGG<br>TACAGTGCAGGGGAAAGAATAGTAGACATAATAGCAACAGACATACAAACTAAAGAATT<br>ACAAAAACAAATTACAAAAATTCAAAATTTTATCGATCACGAGACTAGCCTCGAGAAGC<br>TTGATATCGAATTCCCACGGGGTTGGACGCGTAGGAACAGAGAAACAGGAGAATATGGG<br>CCAAACAGGATATCTGTGGTAAGCAGTTCCTGCCCCGGCTCAGGGCCAAGAACAGTTGG<br>AACAGCAGAATATGGGCCAAACAGGATATCTGTGGTAAGCAGTTCCTGCCCCGGCTCAG<br>GGCCAAGAACAGATGGTCCCCAGATGCGGTCCCGCCCTCAGCAGTTTCTAGAGAACCAT<br>CAGATGTTTCCAGGGTGCCCCAAGGACCTGAAATGACCCTGTGCCTTATTTGAACTAACC<br>AATCAGTTCGCTTCTCGCTTCTGTTCGCGCGCTTCTGCTCCCCGAGCTCTATATAAGCAGA<br>GCTCGTTTAGTGAACCGTCAGATCGCTAGCACCGGTGCCGCCACCATGCCTCTGGGCCTG<br>CTGTGGCTGGGCCTGGCCCTGCTGGGCGCCCTGCACGCCCAGGCCGGCGTGCAGGTGGA<br>GACAATCTCCCCAGGCGACGGACGCACATTCCCTAAGCGGGGCCAGACCTGCGTGGTGC<br>ACTATACAGGCATGCTGGAGGATGGCAAGAAGTTTGACAGCTCCCGGGATAGAAACAAG<br>CCATTCAAGTTTATGCTGGGCAAGCAGGAAGTGATCAGAGGCTGGGAGGAGGGCGTGGC<br>CCAGATGTCTGTGGGCCAGAGGGCCAAGCTGACCATCAGCCCAGACTACGCCTATGGAG<br>CAACAGGCCACCCAGGAATCATCCCACCTCACGCCACCCTGGTGTTCGATGTGGAGCTGC<br>TGAAGCTGGGCGAGCAAAACTTGGTGATTCCTTGGGCCCCAGAAAATCTCACGCTTCACA<br>AGTTGTCCGAATCCCAGCTCGAGCTCAACTGGAATAATAGATTTCTTAATCATTGTTTGG<br>AACACCTGGTTCAATATAGAACGGATTGGGACCACTCATGGACCGAGCAGTCAGTTGAC<br>TACCGCCACAAATTTTCACTTCCCAGCGTAGATGGGCAGAAGAGGTACACATTTAGGGTC<br>AGATCCAGGTTTAATCCTCTGTGTGGTTCTGCTCAACACTGGTCTGAGTGGAGCCATCCG<br>ATCCACTGGGGCTCAAATACCTCTAAAGAAAATCCGTTCCTCTTTGCGCTCGAAGCCGTT<br>GTTATCAGCGTCGGAAGCATGGGACTTATCATTTCCCTTCTCTGCGTGTACTTCTGGCTGG<br>AGCGGACGATGCCGCGGATTCCGACGCTCAAAAACCTGGAGGACCTTGTAACAGAATAT<br>CACGGTAATTTCTCCGCTTGGAGTGGCGTATCAAAGGGGCTTGCTGAGTCCCTTCAACCG<br>GATTACTCTGAGCGCCTCTGCTTGGTGTCCGAGATACCTCCCAAAGGAGGTGCACTTGGG<br>GAGGGGCCAGGCGCGTCCCCTTGCAATCAGCATAGTCCGTATTGGGCGCCCCCCTGTTAT<br>ACCCTCAAACCGGAAACGGGAAGCGGAGCTACTAACTTCAGCCTGCTGAAGCAGGCTGG<br>AGACGTGGAGGAGAACCCTGGACCTATGGCACTGCCCGTGACCGCCCTGCTGCTGCCTCT<br>GGCCCTGCTGCTGCACGCAGCCCGGCCTATCCTGTGGCACGAGATGTGGCACGAGGGCCT<br>GGAGGAGGCCAGCAGGCTGTATTTTGGCGAGCGCAACGTGAAGGGCATGTTCGAGGTGC<br>TGGAGCCTCTGCACGCCATGATGGAGAGAGGCCCACAGACCCTGAAGGAGACATCCTTT<br>AACCAGGCCTATGGACGGGACCTGATGGAGGCACAGGAGTGGTGCAGAAAGTACATGA<br>AGTCTGGCAATGTGAAGGACCTGCTGCAGGCCTGGGATCTGTACTATCACGTGTTTCGGA<br>GAATCTCCAAGAAACCTTTTGAGAACCTTAGACTGATGGCGCCCATCTCTCTGCAGGTAG<br>TTCACGTTGAGACCCATAGATGCAATATAAGCTGGGAAATCTCACAAGCCAGCCATTACT<br>TTGAACGGCATTTGGAATTCGAGGCCCGAACACTTTCCCCCGGTCATACGTGGGAAGAAG<br>CTCCTCTCTTGACGCTGAAGCAGAAGCAGGAGTGGATTTGTCTGGAGACTTTGACTCCTG<br>ATACTCAGTATGAGTTCCAAGTTCGGGTGAAACCACTCCAAGGCGAGTTCACGACGTGGT<br>CTCCGTGGAGTCAACCGTTGGCGTTCCGCACGAAGCCCGCTGCCCTTGGCAAAGACACGA<br>TTCCGTGGCTTGGGCATCTGCTCGTTGGGCTGAGTGGTGCGTTTGGTTTCATCATCTTGGT | CISC vector DNA |

-continued

| SEQ ID NO | Sequence | Description |
|---|---|---|
| | CTATCTCTTGATCAATTGCAGAAATACAGGCCCTTGGCTGAAAAAAGTGCTCAAGTGTAA | |
| | TACCCCCGACCCAAGCAAGTTCTTCTCCCAGCTTTCTTCAGAGCATGGAGGCGATGTGCA | |
| | GAAATGGCTCTCTTCACCTTTTCCCTCCTCAAGCTTCTCCCCGGGAGGGCTGGCGCCCGA | |
| | GATTTCACCTCTTGAGGTACTTGAACGAGACAAGGTTACCCAACTTCTCCTTCAACAGGA | |
| | TAAGGTACCCGAACCTGCGAGCCTTAGCTCCAACCACTCTCTTACGAGCTGCTTCACCAA | |
| | TCAGGGATACTTCTTTTTCCACCTTCCCGATGCGCTGGAAATCGAAGCTTGTCAAGTTTAC | |
| | TTTACCTATGATCCATATAGCGAGGAAGATCCCGACGAAGGAGTCGCCGGTGCGCCCAC | |
| | GGGTTCCTCACCCCAACCTCTCCAGCCTCTCTCAGGAGAAGATGATGCTTATTGCACTTTT | |
| | CCCAGTAGAGACGATCTCCTCCTCTTTTCTCCATCTCTTTTGGGGGGACCTTCCCCCCCTT | |
| | CTACGGCACCTGGCGGGTCTGGTGCTGGCGAGGAGCGGATGCCGCCGTCCCTCCAGGAG | |
| | CGAGTACCACGAGATTGGGATCCCCAGCCACTTGGACCCCCCACCCCCGGCGTACCTGAC | |
| | CTTGTCGATTTTCAACCTCCCCCTGAATTGGTGCTGCGAGAGGCTGGGGAGGAAGTTCCG | |
| | GACGCTGGGCCGAGGGAGGGCGTGTCCTTTCCATGGAGTAGGCCTCCAGGTCAAGGCGA | |
| | GTTTAGGGCTCTCAACGCGCGGCTGCCGTTGAATACAGACGCTTATCTCTCACTGCAGGA | |
| | ACTGCAAGGTCAGGACCCAACACATCTTGTAGGATCTGGTGCTACTAATTTTTCTCTTTTG | |
| | AAGCAAGCTGGAGATGTTGAAGAGAACCCTGGTCCAGTGAGCAAGGGCGAGGAGCTGTT | |
| | CACCGGGGTGGTGCCCATCCTGGTCGAGCTGGACGGCGACGTAAACGGCCACAAGTTCA | |
| | GCGTGTCCGGCGAGGGCGAGGGCGATGCCACCTACGGCAAGCTGACCCTGAAGTTCATC | |
| | TGCACCACCGGCAAGCTGCCCGTGCCCTGGCCCACCCTCGTGACCACCCTGACCTACGGC | |
| | GTGCAGTGCTTCAGCCGCTACCCCGACCACATGAAGCAGCACGACTTCTTCAAGTCCGCC | |
| | ATGCCCGAAGGCTACGTCCAGGAGCGCACCATCTTCTTCAAGGACGACGGCAACTACAA | |
| | GACCCGCGCCGAGGTGAAGTTCGAGGGCGACACCCTGGTGAACCGCATCGAGCTGAAGG | |
| | GCATCGACTTCAAGGAGGACGGCAACATCCTGGGGCACAAGCTGGAGTACAACTACAAC | |
| | AGCCACAACGTCTATATCATGGCCGACAAGCAGAAGAACGGCATCAAGGTGAACTTCAA | |
| | GATCCGCCACAACATCGAGGACGGCAGCGTGCAGCTCGCCGACCACTACCAGCAGAACA | |
| | CCCCCATCGGCGACGGCCCCGTGCTGCTGCCCGACAACCACTACCTGAGCACCCAGTCCG | |
| | CCCTGAGCAAAGACCCCAACGAGAAGCGCGATCACATGGTCCTGCTGGAGTTCGTGACC | |
| | GCCGCCGGGATCACTCTCGGCATGGACGAGCTGTACAAGTAAACTAGTGTCGACAATCA | |
| | ACCTCTGGATTACAAAATTTGTGAAAGATTGACTGGTATTCTTAACTATGTTGCTCCTTTT | |
| | ACGCTATGTGGATACGCTGCTTTAATGCCTTTGTATCATGCTATTGCTTCCCGTATGGCTT | |
| | TCATTTTCTCCTCCTTGTATAAATCCTGGTTGCTGTCTCTTTATGAGGAGTTGTGGCCCGTT | |
| | GTCAGGCAACGTGGCGTGGTGTGCACTGTGTTTGCTGACGCAACCCCCACTGGTTGGGGC | |
| | ATTGCCACCACCTGTCAGCTCCTTTCCGGGACTTTCGCTTTCCCCCTCCCTATTGCCACGG | |
| | CGGAACTCATCGCCGCCTGCCTTGCCCGCTGCTGGACAGGGGCTCGGCTGTTGGGCACTG | |
| | ACAATTCCGTGGTGTTGTCGGGGAAGCTGACGTCCTTTCCATGGCTGCTCGCCTGTGTTGC | |
| | CACCTGGATTCTGCGCGGGACGTCCTTCTGCTACGTCCCTTCGGCCCTCAATCCAGCGGA | |
| | CCTTCCTTCCCGCGGCCTGCTGCCGGCTCTGCGGCCTCTTCCGCGTCTTCGCCTTCGCCCT | |
| | CAGACGAGTCGGATCTCCCTTTGGGCCGCCTCCCCGCCTGGAATTCGAGCTCGGTACCTT | |
| | TAAGACCAATGACTTACAAGGCAGCTGTAGATCTTAGCCACTTTTTAAAAGAAAAGGGG | |
| | GGACTGGAAGGGCTAATTCACTCCCAACGAAGACAAGATCTGCTTTTTGCTTGTACTGGG | |
| | TCTCTCTGGTTAGACCAGATCTGAGCCTGGGAGCTCTCTGGCTAACTAGGGAACCCACTG | |
| | CTTAAGCCTCAATAAAGCTTGCCTTGAGTGCTTCAAGTAGTGTGTGCCCGTCTGTTGTGTG | |
| | ACTCTGGTAACTAGAGATCCCTCAGACCCTTTTAGTCAGTGTGGAAAATCTCTAGCAGTA | |
| | GTAGTTCATGTCATCTTATTATTCAGTATTTATAACTTGCAAAGAAATGAATATCAGAGA | |
| | GTGAGAGGAACTTGTTTATTGCAGCTTATAATGGTTACAAATAAAGCAATAGCATCACAA | |
| | ATTTCACAAATAAAGCATTTTTTTCACTGCATTCTAGTTGTGGTTTGTCCAAACTCATCAA | |
| | TGTATCTTATCATGTCTGGCTCTAGCTATCCCGCCCCTAACTCCGCCCAGTTCCGCCCATT | |
| | CTCCGCCCCATGGCTGACTAATTTTTTTTATTTATGCAGAGGCCGAGGCCGCCTCGGCCTC | |
| | TGAGCTATTCCAGAAGTAGTGAGGAGGCTTTTTTGGAGGCCTAGGCTTTTGCGTCGAGAC | |
| | GTACCCAATTCGCCCTATAGTGAGTCGTATTACGCGCGCTCACTGGCCGTCGTTTTACAA | |
| | CGTCGTGACTGGGAAAACCCTGGCGTTACCCAACTTAATCGCCTTGCAGCACATCCCCCT | |
| | TTCGCCAGCTGGCGTAATAGCGAAGAGGCCCGCACCGATCGCCCTTCCCAACAGTTGCGC | |
| | AGCCTGAATGGCGAATGGCGCGACGCGCCCTGTAGCGGCGCATTAAGCGCGGCGGGTGT | |
| | GGTGGTTACGCGCAGCGTGACCGCTACACTTGCCAGCGCCCTAGCGCCCGCTCCTTTCGC | |
| | TTTCTTCCCTTCCTTTCTCGCCACGTTCGCCGGCTTTCCCCGTCAAGCTCTAAATCGGGGG | |
| | CTCCCTTTAGGGTTCCGATTTAGTGCTTTACGGCACCTCGACCCCAAAAAACTTGATTAG | |
| | GGTGATGGTTCACGTAGTGGGCCATCGCCCTGATAGACGGTTTTTCGCCCTTTGACGTTG | |
| | GAGTCCACGTTCTTTAATAGTGGACTCTTGTTCCAAACTGGAACAACACTCAACCCTATC | |
| | TCGGTCTATTCTTTTGATTTATAAGGGATTTTGCCGATTTCGGCCTATTGGTTAAAAAATG | |
| | AGCTGATTTAACAAAAATTTAACGCGAATTTTAACAAAATATTAACGTTTACAATTTCCC | |
| | AGGTGGCACTTTTCGGGGAAATGTGCGCGGAACCCCTATTTGTTTATTTTTCTAAATACAT | |
| | TCAAATATGTATCCGCTCATGAGACAATAACCCTGATAAATGCTTCAATAATATTGAAAA | |
| | AGGAAGAGTATGAGTATTCAACATTTCCGTGTCGCCCTTATTCCCTTTTTTGCGGCATTTT | |
| | GCCTTCCTGTTTTTGCTCACCCAGAAACGCTGGTGAAAGTAAAAGATGCTGAAGATCAGT | |
| | TGGGTGCACGAGTGGGTTACATCGAACTGGATCTCAACAGCGGTAAGATCCTTGAGAGTT | |
| | TTCGCCCCGAAGAACGTTTTCCAATGATGAGCACTTTTAAAGTTCTGCTATGTGGCGCGG | |
| | TATTATCCCGTATTGACGCCGGGCAAGAGCAACTCGGTCGCCGCATACACTATTCTCAGA | |
| | ATGACTTGGTTGAGTACTCACCAGTCACAGAAAAGCATCTTACGGATGGCATGACAGTAA | |
| | GAGAATTATGCAGTGCTGCCATAACCATGAGTGATAACACTGCGGCCAACTTACTTCTGA | |
| | CAACGATCGGAGGACCGAAGGAGCTAACCGCTTTTTTGCACAACATGGGGGATCATGTA | |
| | ACTCGCCTTGATCGTTGGGAACCGGAGCTGAATGAAGCCATACCAAACGACGAGCGTGA | |
| | CACCACGATGCCTGTAGCAATGGCAACAACGTTGCGCAAACTATTAACTGGCGAACTACT | |
| | TACTCTAGCTTCCCGGCAACAATTAATAGACTGGATGGAGGCGGATAAAGTTGCAGGAC | |
| | CACTTCTGCGCTCGGCCCTTCCGGCTGGCTGGTTTATTGCTGATAAATCTGGAGCCGGTG | |
| | AGCGTGGGTCTCGCGGTATCATTGCAGCACTGGGGCCAGATGGTAAGCCCTCCCGTATCG | |

-continued

| SEQ ID NO | Sequence | Description |
|---|---|---|
| | TAGTTATCTACACGACGGGGAGTCAGGCAACTATGGATGAACGAAATAGACAGATCGCT<br>GAGATAGGTGCCTCACTGATTAAGCATTGGTAACTGTCAGACCAAGTTTACTCATATATA<br>CTTTAGATTGATTTAAAACTTCATTTTTAATTTAAAAGGATCTAGGTGAAGATCCTTTTTG<br>ATAATCTCATGACCAAAATCCCTTAACGTGAGTTTTCGTTCCACTGAGCGTCAGACCCCG<br>TAGAAAAGATCAAAGGATCTTCTTGAGATCCTTTTTTTCTGCGCGTAATCTGCTGCTTGCA<br>AACAAAAAAACCACCGCTACCAGCGGTGGTTTGTTTGCCGGATCAAGAGCTACCAACTCT<br>TTTTCCGAAGGTAACTGGCTTCAGCAGAGCGCAGATACCAAATACTGTCCTTCTAGTGTA<br>GCCGTAGTTAGGCCACCACTTCAAGAACTCTGTAGCACCGCCTACATACCTCGCTCTGCT<br>AATCCTGTTACCAGTGGCTGCTGCCAGTGGCGATAAGTCGTGTCTTACCGGGTTGGACTC<br>AAGACGATAGTTACCGGATAAGGCGCAGCGGTCGGGCTGAACGGGGGGTTCGTGCACAC<br>AGCCCAGCTTGGAGCGAACGACCTACACCGAACTGAGATACCTACAGCGTGAGCTATGA<br>GAAAGCGCCACGCTTCCCGAAGGGAGAAAGGCGGACAGGTATCCGGTAAGCGGCAGGG<br>TCGGAACAGGAGAGCGCACGAGGGAGCTTCCAGGGGGAAACGCCTGGTATCTTTATAGT<br>CCTGTCGGGTTTCGCCACCTCTGACTTGAGCGTCGATTTTTGTGATGCTCGTCAGGGGGGC<br>GGAGCCTATGGAAAAACGCCAGCAACGCGGCCTTTTTACGGTTCCTGGCCTTTTGCTGGC<br>CTTTTGCTCACATGTTCTTTCCTGCGTTATCCCCTGATTCTGTGGATAACCGTATTACCGCC<br>TTTGAGTGAGCTGATACCGCTCGCCGCAGCCGAACGACCGAGCGCAGCGAGTCAGTGAG<br>CGAGGAAGCGGAAGAGCGCCCAATACGCAAACCGCCTCTCCCCGCGCGTTGGCCGATTC<br>ATTAATGCAGCTGGCACGACAGGTTTCCCGACTGGAAAGCGGGCAGTGAGCGCAACGCA<br>ATTAATGTGAGTTAGCTCACTCATTAGGCACCCCAGGCTTTACACTTTATGCTTCCGGCTC<br>GTATGTTGTGTGGAATTGTGAGCGGATAACAATTTCACACAGGAAACAGCTATGACCATG<br>ATTACGCCAAGCGCGCAATTAACCCTCACTAAAGGGAACAAAAGCTGGAGCTGCA | |
| 69 | PAAL | Linker/spacer polypeptide |
| 70 | GAGATGTGGCATGAGGGTCTGGAAGAAGCGTCTCGACTGTACTTTGGTGAGCGCAATGT<br>GAAGGGCATGTTTGAAGTCCTCGAACCCCTTCATGCCATGATGGAACGCGGACCCCAGA<br>CCTTGAAGGAGACAAGTTTTAACCAAGCTTACGGAAGAGACCTGATGGAAGCCCAGGAA<br>TGGTGCAGGAAATACATGAAAAGCGGGAATGTGAAGGACTTGACCCAAGCGTGGGACCT<br>GTACTATCATGTCTTTAGGCGCATTAGTAAG | Naked FRB domain nucleic acid sequence |
| 71 | GAACAGAGAAACAGGAGAATATGGGCCAAACAGGATATCTGTGGTAAGCAGTTCCTGCC<br>CCGGCTCAGGGCCAAGAACAGTTGGAACAGCAGAATATGGGCCAAACAGGATATCTGTG<br>GTAAGCAGTTCCTGCCCCGGCTCAGGGCCAAGAACAGATGGTCCCCAGATGCGGTCCCG<br>CCCTCAGCAGTTTCTAGAGAACCATCAGATGTTTCCAGGGTGCCCCAAGGACCTGAAATG<br>ACCCTGTGCCTTATTTGAACTAACCAATCAGTTCGCTTCTCGCTTCTGTTCGCGCGCTTCT<br>GCTCCCCGAGCTCTATATAAGCAGAGCTCGTTTAGTGAACCGTCAGATCGCTAGC | MND promoter |
| 72 | GCCACCATGCCTAATCCTCGGCCTGGAAAGCCTAGCGCTCCTTCTCTTGCTCTGGGACCTT<br>CTCCTGGCGCCTCTCCATCTTGGAGAGCCGCTCCTAAAGCCAGCGATCTGCTGGGAGCTA<br>GAGGACCTGGCGGCACATTTCAGGGCAGAGATCTTAGAGGCGGAGCCCACGCTAGCTCC<br>TCCAGCCTTAATCCTATGCCTCCTAGCCAGCTCCAGCTGCCTACACTGCCTCTGGTTATGG<br>TGGCTCCTAGCGGAGCTAGACTGGGCCCTCTGCCTCATCTGCAAGCTCTGCTGCAGGACA<br>GACCCCACTTCATGCACCAGCTGAGCACCGTGGATGCCCACGCAAGAACACCTGTGCTGC<br>AGGTTCACCCTCTGGAATCCCCAGCCATGATCAGCCTGACACCTCCAACAACAGCCACCG<br>GCGTGTTCAGCCTGAAAGCCAGACCTGGACTGCCTCCTGGCATCAATGTGGCCAGCCTGG<br>AATGGGTGTCCAGAGAACCTGCTCTGCTGTGCACATTCCCCAATCCAAGCGCTCCCAGAA<br>AGGACAGCACACTGTCTGCCGTGCCTCAGAGCAGCTATCCCCTGCTTGCTAACGGCGTGT<br>GCAAGTGGCCTGGATGCGAGAAGGTGTTCGAGGAACCCGAGGACTTCCTGAAGCACTGC<br>CAGGCCGATCATCTGCTGGACGAGAAAGGCAGAGCCCAGTGTCTGCTCCAGCGCGAGAT<br>GGTGCAGTCTCTGGAACAGCAGCTGGTCCTGGAAAAAGAAAAGCTGAGCGCCATGCAGG<br>CCCACCTGGCCGGAAAAATGGCCCTGACAAAGGCCAGCAGCGTGGCCTCTTCTGATAAG<br>GGCAGCTGCTGCATTGTGGCCGCTGGATCTCAGGGACCTGTGGTTCCTGCTTGGAGCGGA<br>CCTAGAGAGGCCCCTGATTCTCTGTTTGCCGTGCGGAGACACCTGTGGGGCTCTCACGGC<br>AACTCTACTTTCCCCGAGTTCCTGCACAACATGGACTACTTCAAGTTCCACAACATGCGG<br>CCTCCATTCACCTACGCCACACTGATCAGATGGGCCATTCTGGAAGCCCCTGAGAAGCAG<br>AGAACCCTGAACGAGATCTACCACTGGTTTACCCGGATGTTCGCCTTCTTCCGGAATCAC<br>CCTGCCACCTGGAAGAACGCCATCCGGCACAATCTGAGCCTGCACAAGTGCTTCGTGCGC<br>GTGGAATCTGAGAAAGGCGCCGTGTGGACAGTGGACGAGCTGGAATTCAGAAAGAAGA<br>GAAGCCAGCGGCCTAGCCGGTGCAGCAATCCTACACCTGGACCTGGAAGCGGAGCGACT<br>AACTTCAGCCTGCTGAAGCAGGCCGGAGATGTGGAGGAAAACCCTGGACCGATGGGGGC<br>AGGTGCCACCGGACGAGCCATGGACGGGCCGCGCCTGCTGCTGTTGCTGCTTCTGGGGGT<br>GTCCCTTGGAGGTGCCAAGGAGGCATGCCCCACAGGCCTGTACACACACAGCGGTGAGT<br>GCTGCAAAGCCTGCAACCTGGGCGAGGGTGTGGCCCAGCCTTGTGGAGCCAACCAGACC<br>GTGTGTGAGCCCTGCCTGGACAGCGTGACGTTCTCCGACGTGGTGAGCGCGACCGAGCC<br>GTGCAAGCCGTGCACCGAGTGCGTGGGGCTCCAGAGCATGTCGGCGCCGTGCGTGGAGG<br>CCGACGACGCCGTGTGCCGCTGCGCCTACGGCTACTACCAGGATGAGACGACTGGGCGC<br>TGCGAGGCGTGCCGCGTGTGCGAGGCGGGCTCGGGCCTCGTGTTCTCCTGCCAGGACAA<br>GCAGAACACCGTGTGCGAGGAGTGCCCCGACGGCACGTATTCCGACGAGGCCAACCACG | FOXP3cDNA-P2A-LNGFR (kozak-start codon-FOXP3cDNA-P2A-LNGFR-stop codon) |

-continued

| SEQ ID NO | Sequence | Description |
|---|---|---|
| | TGGACCCGTGCCTGCCCTGCACCGTGTGCGAGGACACCGAGCGCCAGCTCCGCGAGTGC<br>ACACGCTGGGCCGACGCCGAGTGCGAGGAGATCCCTGGCCGTTGGATTACACGGTCCAC<br>ACCCCCAGAGGGCTCGGACAGCACAGCCCCCAGCACCCAGGAGCCTGAGGCACCTCCAG<br>AACAAGACCTCATAGCCAGCACGGTGGCAGGTGTGGTGACCACAGTGATGGGCAGCTCC<br>CAGCCCGTGGTGACCCGAGGCACCACCGACAACCTCATCCCTGTCTATTGCTCCATCCTG<br>GCTGCTGTGGTTGTGGGTCTTGTGGCCTACATAGCCTTCAAGAGGTGA | |
| 73 | GCCACCATGGGGGCAGGTGCCACCGGACGAGCCATGGACGGGCCGCGCCTGCTGCTGTT<br>GCTGCTTCTGGGGGTGTCCCTTGGAGGTGCCAAGGAGGCATGCCCCACAGGCCTGTACAC<br>ACACAGCGGTGAGTGCTGCAAAGCCTGCAACCTGGGCGAGGGTGTGGCCCAGCCTTGTG<br>GAGCCAACCAGACCGTGTGTGAGCCCTGCCTGGACAGCGTGACGTTCTCCGACGTGGTG<br>AGCGCGACCGAGCCGTGCAAGCCGTGCACCGAGTGCGTGGGGCTCCAGAGCATGTCGGC<br>GCCGTGCGTGGAGGCCGACGACGCCGTGTGCCGCTGCGCCTACGGCTACTACCAGGATG<br>AGACGACTGGGCGCTGCGAGGCGTGCCGCGTGTGCGAGGCGGGCTCGGGCCTCGTGTTC<br>TCCTGCCAGGACAAGCAGAACACCGTGTGCGAGGAGTGCCCCGACGGCACGTATTCCGA<br>CGAGGCCAACCACGTGGACCCGTGCCTGCCCTGCACCGTGTGCGAGGACACCGAGCGCC<br>AGCTCCGCGAGTGCACACGCTGGGCCGACGCCGAGTGCGAGGAGATCCCTGGCCGTTGG<br>ATTACACGGTCCACACCCCCAGAGGGCTCGGACAGCACAGCCCCCAGCACCCAGGAGCC<br>TGAGGCACCTCCAGAACAAGACCTCATAGCCAGCACGGTGGCAGGTGTGGTGACCACAG<br>TGATGGGCAGCTCCCAGCCCGTGGTGACCCGAGGCACCACCGACAACCTCATCCCTGTCT<br>ATTGCTCCATCCTGGCTGCTGTGGTTGTGGGTCTTGTGGCCTACATAGCCTTCAAGAGGG<br>GAAGCGGAGCGACTAACTTCAGCCTGCTGAAGCAGGCCGGAGATGTGGAGGAAAACCCT<br>GGACCGATGCCTAATCCTCGGCCTGGAAAGCCTAGCGCTCCTTCTCTTGCTCTGGGACCT<br>TCTCCTGGCGCCTCTCCATCTTGGAGAGCCGCTCCTAAAGCCAGCGATCTGCTGGGAGCT<br>AGAGGACCTGGCGGCACATTTCAGGGCAGAGATCTTAGAGGCGGAGCCCACGCTAGCTC<br>CTCCAGCCTTAATCCTATGCCTCCTAGCCAGCTCCAGCTGCCTACACTGCCTCTGGTTATG<br>GTGGCTCCTAGCGGAGCTAGACTGGGCCCTCTGCCTCATCTGCAAGCTCTGCTGCAGGAC<br>AGACCCCACTTCATGCACCAGCTGAGCACCGTGGATGCCCACGCAAGAACACCTGTGCT<br>GCAGGTTCACCCTCTGGAATCCCCAGCCATGATCAGCCTGACACCTCCAACAACAGCCAC<br>CGGCGTGTTCAGCCTGAAAGCCAGACCTGGACTGCCTCCTGGCATCAATGTGGCCAGCCT<br>GGAATGGGTGTCCAGAGAACCTGCTCTGCTGTGCACATTCCCCAATCCAAGCGCTCCCAG<br>AAAGGACAGCACACTGTCTGCCGTGCCTCAGAGCAGCTATCCCCTGCTTGCTAACGGCGT<br>GTGCAAGTGGCCTGGATGCGAGAAGGTGTTCGAGGAACCCGAGGACTTCCTGAAGCACT<br>GCCAGGCCGATCATCTGCTGGACGAGAAAGGCAGAGCCCAGTGTCTGCTCCAGCGCGAG<br>ATGGTGCAGTCTCTGGAACAGCAGCTGGTCCTGGAAAAAGAAAAGCTGAGCGCCATGCA<br>GGCCCACCTGGCCGGAAAAATGGCCCTGACAAAGGCCAGCAGCGTGGCCTCTTCTGATA<br>AGGGCAGCTGCTGCATTGTGGCCGCTGGATCTCAGGGACCTGTGGTTCCTGCTTGGAGCG<br>GACCTAGAGAGGCCCCTGATTCTCTGTTTGCCGTGCGGAGACACCTGTGGGGCTCTCACG<br>GCAACTCTACTTTCCCCGAGTTCCTGCACAACATGGACTACTTCAAGTTCCACAACATGC<br>GGCCTCCATTCACCTACGCCACACTGATCAGATGGGCCATTCTGGAAGCCCCTGAGAAGC<br>AGAGAACCCTGAACGAGATCTACCACTGGTTTACCCGGATGTTCGCCTTCTTCCGGAATC<br>ACCCTGCCACCTGGAAGAACGCCATCCGGCACAATCTGAGCCTGCACAAGTGCTTCGTGC<br>GCGTGGAATCTGAGAAAGGCGCCGTGTGGACAGTGGACGAGCTGGAATTCAGAAAGAAG<br>AGAAGCCAGCGGCCTAGCCGGTGCAGCAATCCTACACCTGGACCTTGA | LNGFR-<br>P2A-<br>FOXP3cDN<br>A (kozak-<br>start codon-<br>LNGFR-<br>P2A-<br>FOXP3cDN<br>A-stop<br>codon) |
| 74 | ATGCCTAATCCTCGGCCTGGAAAGCCTAGCGCTCCTTCTCTTGCTCTGGGACCTTCTCCTG<br>GCGCCTCTCCATCTTGGAGAGCCGCTCCTAAAGCCAGCGATCTGCTGGGAGCTAGAGGAC<br>CTGGCGGCACATTTCAGGGCAGAGATCTTAGAGGCGGAGCCCACGCTAGCTCCTCCAGC<br>CTTAATCCTATGCCTCCTAGCCAGCTCCAGCTGCCTACACTGCCTCTGGTTATGGTGGCTC<br>CTAGCGGAGCTAGACTGGGCCCTCTGCCTCATCTGCAAGCTCTGCTGCAGGACAGACCCC<br>ACTTCATGCACCAGCTGAGCACCGTGGATGCCCACGCAAGAACACCTGTGCTGCAGGTTC<br>ACCCTCTGGAATCCCCAGCCATGATCAGCCTGACACCTCCAACAACAGCCACCGGCGTGT<br>TCAGCCTGAAAGCCAGACCTGGACTGCCTCCTGGCATCAATGTGGCCAGCCTGGAATGG<br>GTGTCCAGAGAACCTGCTCTGCTGTGCACATTCCCCAATCCAAGCGCTCCCAGAAAGGAC<br>AGCACACTGTCTGCCGTGCCTCAGAGCAGCTATCCCCTGCTTGCTAACGGCGTGTGCAAG<br>TGGCCTGGATGCGAGAAGGTGTTCGAGGAACCCGAGGACTTCCTGAAGCACTGCCAGGC<br>CGATCATCTGCTGGACGAGAAAGGCAGAGCCCAGTGTCTGCTCCAGCGCGAGATGGTGC<br>AGTCTCTGGAACAGCAGCTGGTCCTGGAAAAAGAAAAGCTGAGCGCCATGCAGGCCCAC<br>CTGGCCGGAAAAATGGCCCTGACAAAGGCCAGCAGCGTGGCCTCTTCTGATAAGGGCAG<br>CTGCTGCATTGTGGCCGCTGGATCTCAGGGACCTGTGGTTCCTGCTTGGAGCGGACCTAG<br>AGAGGCCCCTGATTCTCTGTTTGCCGTGCGGAGACACCTGTGGGGCTCTCACGGCAACTC<br>TACTTTCCCCGAGTTCCTGCACAACATGGACTACTTCAAGTTCCACAACATGCGGCCTCC<br>ATTCACCTACGCCACACTGATCAGATGGGCCATTCTGGAAGCCCCTGAGAAGCAGAGAA<br>CCCTGAACGAGATCTACCACTGGTTTACCCGGATGTTCGCCTTCTTCCGGAATCACCCTGC<br>CACCTGGAAGAACGCCATCCGGCACAATCTGAGCCTGCACAAGTGCTTCGTGCGCGTGG<br>AATCTGAGAAAGGCGCCGTGTGGACAGTGGACGAGCTGGAATTCAGAAAGAAGAGAAG<br>CCAGCGGCCTAGCCGGTGCAGCAATCCTACACCTGGACCTGGAAGCGGAGCGACTAACT<br>TCAGCCTGCTTAAGCAGGCCGGAGATGTGGAGGAAAACCCTGGACCGATGCCTCTGGGC<br>CTGCTGTGGCTGGGCCTGGCCCTGCTGGGCGCCCTGCACGCCCAGGCCGGCGTGCAGGTG<br>GAGACAATCTCCCCAGGCGACGGACGCACATTCCCTAAGCGGGGCCAGACCTGCGTGGT<br>GCACTATACAGGCATGCTGGAGGATGGCAAGAAGTTTGACAGCTCCCGGGATAGAAACA<br>AGCCATTCAAGTTTATGCTGGGCAAGCAGGAAGTGATCAGAGGCTGGGAGGAGGGCGTG<br>GCCCAGATGTCTGTGGGCCAGAGGGCCAAGCTGACCATCAGCCCAGACTACGCCTATGG<br>AGCAACAGGCCACCCAGGAATCATCCCACCTCACGCCACCCTGGTGTTCGATGTGGAGCT<br>GCTGAAGCTGGGCGAGGGAGGGTCACCTGGATCCAACACATCAAAAGAGAACCCCTTTC | FOXP3cDN<br>A-μDISC<br>nucleotide<br>sequence<br>(coding<br>sequence<br>only; codon-<br>optimized;<br>our DISC<br>architecture<br>version 6) |

-continued

| SEQ ID NO | Sequence | Description |
|---|---|---|
| | TGTTCGCATTGGAGGCCGTAGTCATATCTGTTGGATCCATGGGACTTATTATCTCCCTGTT<br>GTGTGTGTACTTCTGGCTGGAACGGACTATGCCCAGGATCCCCACGCTCAAGAATCTGGA<br>AGATCTCGTCACAGAATACCATGGTAATTTCAGCGCCTGGAGCGGAGTCTCTAAGGGTCT<br>GGCCGAATCCCTCCAACCCGATTATTCTGAACGGTTGTGCCTCGTATCCGAAATACCACC<br>AAAAGGCGGGGCTCTGGGTGAGGGCCCAGGGGCGAGTCCGTGCAATCAACACAGCCCGT<br>ATTGGGCCCCTCCTTGTTATACGTTGAAGCCCGAAACTGGAAGCGGAGCTACTAACTTCA<br>GCCTGCTGAAGCAGGCTGGAGACGTGGAGGAGAACCCTGGACCTATGGCACTGCCCGTG<br>ACCGCCCTGCTGCTGCCTCTGGCCCTGCTGCTGCACGCAGCCCGGCCTATCCTGTGGCAC<br>GAGATGTGGCACGAGGGCCTGGAGGAGGCCAGCAGGCTGTATTTTGGCGAGCGCAACGT<br>GAAGGGCATGTTCGAGGTGCTGGAGCCTCTGCACGCCATGATGGAGAGAGGCCCACAGA<br>CCCTGAAGGAGACATCCTTTAACCAGGCCTATGGACGGGACCTGATGGAGGCACAGGAG<br>TGGTGCAGAAAGTACATGAAGTCTGGCAATGTGAAGGACCTGCTGCAGGCCTGGGATCT<br>GTACTATCACGTGTTTCGGAGAATCTCCAAGCCAGCAGCTCTCGGCAAAGACACGATTCC<br>GTGGCTTGGGCATCTGCTCGTTGGGCTGAGCGGTGCGTTTGGTTTCATCATCTTGGTCTAT<br>CTCTTGATCAATTGCAGAAATACAGGCCCTTGGCTGAAAAAAGTGCTCAAGTGTAATACC<br>CCCGACCCAAGCAAGTTCTTCTCCCAGCTTTCTTCAGAGCATGGAGGCGATGTGCAGAAA<br>TGGCTCTCTTCACCTTTTCCCTCCTCAAGCTTCTCCCCGGGAGGGCTGGCGCCCGAGATTT<br>CACCTCTTGAGGTACTTGAACGAGACAAGGTTACCCAACTTCTCCTTCAACAGGATAAGG<br>TACCCGAACCTGCGAGCCTTAGCTTGAATACAGACGCTTATCTCTCACTGCAGGAACTGC<br>AAGGATCTGGTGCTACTAATTTTTCTCTTTTGAAGCAAGCTGGAGATGTTGAAGAGAACC<br>CCGGTCCGGAGATGTGGCATGAGGGTCTGGAAGAAGCGTCTCGACTGTACTTTGGTGAGC<br>GCAATGTGAAGGGCATGTTTGAAGTCCTCGAACCCCTTCATGCCATGATGGAACGCGGAC<br>CCCAGACCTTGAAGGAGACAAGTTTTAACCAAGCTTACGGAAGAGACCTGATGGAAGCC<br>CAGGAATGGTGCAGGAAATACATGAAAAGCGGGAATGTGAAGGACTTGCTCCAAGCGTG<br>GGACCTGTACTATCATGTCTTTAGGCGCATTAGTAAGTGA | |
| 75 | GAACAGAGAAACAGGAGAATATGGGCCAAACAGGATATCTGTGGTAAGCAGTTCCTGCC<br>CCGGCTCAGGGCCAAGAACAGTTGGAACAGCAGAATATGGGCCAAACAGGATATCTGTG<br>GTAAGCAGTTCCTGCCCCGGCTCAGGGCCAAGAACAGATGGTCCCCAGATGCGGTCCCG<br>CCCTCAGCAGTTTCTAGAGAACCATCAGATGTTTCCAGGGTGCCCCAAGGACCTGAAATG<br>ACCCTGTGCCTTATTTGAACTAACCAATCAGTTCGCTTCTCGCTTCTGTTCGCGCGCTTCT<br>GCTCCCCGAGCTCTATATAAGCAGAGCTCGTTTAGTGAACCGTCAGATCGCCTGGAGACG<br>CCATCCACGCTGTTTTGACTTCCATAGAAGGATCTCGAGGCCACCATGCCTAATCCTCGG<br>CCTGGAAAGCCTAGCGCTCCTTCTCTTGCTCTGGGACCTTCTCCTGGCGCCTCTCCATCTT<br>GGAGAGCCGCTCCTAAAGCCAGCGATCTGCTGGGAGCTAGAGGACCTGGCGGCACATTT<br>CAGGGCAGAGATCTTAGAGGCGGAGCCCACGCTAGCTCCTCCAGCCTTAATCCTATGCCT<br>CCTAGCCAGCTCCAGCTGCCTACACTGCCTCTGGTTATGGTGGCTCCTAGCGGAGCTAGA<br>CTGGGCCCTCTGCCTCATCTGCAAGCTCTGCTGCAGGACAGACCCCACTTCATGCACCAG<br>CTGAGCACCGTGGATGCCCACGCAAGAACACCTGTGCTGCAGGTTCACCCTCTGGAATCC<br>CCAGCCATGATCAGCCTGACACCTCCAACAACAGCCACCGGCGTGTTCAGCCTGAAAGC<br>CAGACCTGGACTGCCTCCTGGCATCAATGTGGCCAGCCTGGAATGGGTGTCCAGAGAAC<br>CTGCTCTGCTGTGCACATTCCCCAATCCAAGCGCTCCCAGAAAGGACAGCACACTGTCTG<br>CCGTGCCTCAGAGCAGCTATCCCCTGCTTGCTAACGGCGTGTGCAAGTGGCCTGGATGCG<br>AGAAGGTGTTCGAGGAACCCGAGGACTTCCTGAAGCACTGCCAGGCCGATCATCTGCTG<br>GACGAGAAAGGCAGAGCCCAGTGTCTGCTCCAGCGCGAGATGGTGCAGTCTCTGGAACA<br>GCAGCTGGTCCTGGAAAAAGAAAAGCTGAGCGCCATGCAGGCCCACCTGGCCGGAAAAA<br>TGGCCCTGACAAAGGCCAGCAGCGTGGCCTCTTCTGATAAGGGCAGCTGCTGCATTGTGG<br>CCGCTGGATCTCAGGGACCTGTGGTTCCTGCTTGGAGCGGACCTAGAGAGGCCCCTGATT<br>CTCTGTTTGCCGTGCGGAGACACCTGTGGGGCTCTCACGGCAACTCTACTTTCCCCGAGTT<br>CCTGCACAACATGGACTACTTCAAGTTCCACAACATGCGGCCTCCATTCACCTACGCCAC<br>ACTGATCAGATGGGCCATTCTGGAAGCCCCTGAGAAGCAGAGAACCCTGAACGAGATCT<br>ACCACTGGTTTACCCGGATGTTCGCCTTCTTCCGGAATCACCCTGCCACCTGGAAGAACG<br>CCATCCGGCACAATCTGAGCCTGCACAAGTGCTTCGTGCGCGTGGAATCTGAGAAAGGC<br>GCCGTGTGGACAGTGGACGAGCTGGAATTCAGAAAGAAGAGAAGCCAGCGGCCTAGCC<br>GGTGCAGCAATCCTACACCTGGACCTGGAAGCGGAGCGACTAACTTCAGCCTGCTTAAG<br>CAGGCCGGAGATGTGGAGGAAAACCCTGGACCGATGCCTCTGGGCCTGCTGTGGCTGGG<br>CCTGGCCCTGCTGGGCGCCCTGCACGCCCAGGCCGGCGTGCAGGTGGAGACAATCTCCCC<br>AGGCGACGGACGCACATTCCCTAAGCGGGGCCAGACCTGCGTGGTGCACTATACAGGCA<br>TGCTGGAGGATGGCAAGAAGTTTGACAGCTCCCGGGATAGAAACAAGCCATTCAAGTTT<br>ATGCTGGGCAAGCAGGAAGTGATCAGAGGCTGGGAGGAGGGCGTGGCCCAGATGTCTGT<br>GGGCCAGAGGGCCAAGCTGACCATCAGCCCAGACTACGCCTATGGAGCAACAGGCCACC<br>CAGGAATCATCCCACCTCACGCCACCCTGGTGTTCGATGTGGAGCTGCTGAAGCTGGGCG<br>AGGGAGGGTCACCTGGATCCAACACATCAAAAGAGAACCCCTTTCTGTTCGCATTGGAG<br>GCCGTAGTCATATCTGTTGGATCCATGGGACTTATTATCTCCCTGTTGTGTGTGTACTTCT<br>GGCTGGAACGGACTATGCCCAGGATCCCCACGCTCAAGAATCTGGAAGATCTCGTCACA<br>GAATACCATGGTAATTTCAGCGCCTGGAGCGGAGTCTCTAAGGGTCTGGCCGAATCCCTC<br>CAACCCGATTATTCTGAACGGTTGTGCCTCGTATCCGAAATACCACCAAAAGGCGGGGCT<br>CTGGGTGAGGGCCCAGGGGCGAGTCCGTGCAATCAACACAGCCCGTATTGGGCCCCTCC<br>TTGTTATACGTTGAAGCCCGAAACTGGAAGCGGAGCTACTAACTTCAGCCTGCTGAAGCA<br>GGCTGGAGACGTGGAGGAGAACCCTGGACCTATGGCACTGCCCGTGACCGCCCTGCTGC<br>TGCCTCTGGCCCTGCTGCTGCACGCAGCCCGGCCTATCCTGTGGCACGAGATGTGGCACG<br>AGGGCCTGGAGGAGGCCAGCAGGCTGTATTTTGGCGAGCGCAACGTGAAGGGCATGTTC<br>GAGGTGCTGGAGCCTCTGCACGCCATGATGGAGAGAGGCCCACAGACCCTGAAGGAGAC<br>ATCCTTTAACCAGGCCTATGGACGGGACCTGATGGAGGCACAGGAGTGGTGCAGAAAGT<br>ACATGAAGTCTGGCAATGTGAAGGACCTGCTGCAGGCCTGGGATCTGTACTATCACGTGT | MND-FOXP3cDNA-μDISC-SV40 polyA nucleotide sequence (codon optimized; this is our expression cassette part of the donor template; does not include homology arms (e.g. targeting to FoxP3, AAVS1, etc) nor AAV vector sequences) |

-continued

| SEQ ID NO | Sequence | Description |
|---|---|---|
| | TTCGGAGAATCTCCAAGCCAGCAGCTCTCGGCAAAGACACGATTCCGTGGCTTGGGCATC<br>TGCTCGTTGGGCTGAGCGGTGCGTTTGGTTTCATCATCTTGGTCTATCTCTTGATCAATTG<br>CAGAAATACAGGCCCTTGGCTGAAAAAGTGCTCAAGTGTAATACCCCCGACCCAAGCA<br>AGTTCTTCTCCCAGCTTTCTTCAGAGCATGGAGGCGATGTGCAGAAATGGCTCTCTTCAC<br>CTTTTCCCTCCTCAAGCTTCTCCCCGGGAGGGCTGGCGCCCGAGATTTCACCTCTTGAGGT<br>ACTTGAACGAGACAAGGTTACCCAACTTCTCCTTCAACAGGATAAGGTACCCGAACCTGC<br>GAGCCTTAGCTTGAATACAGACGCTTATCTCTCACTGCAGGAACTGCAAGGATCTGGTGC<br>TACTAATTTTTCTCTTTTGAAGCAAGCTGGAGATGTTGAAGAGAACCCCGGTCCGGAGAT<br>GTGGCATGAGGGTCTGGAAGAAGCGTCTCGACTGTACTTTGGTGAGCGCAATGTGAAGG<br>GCATGTTTGAAGTCCTCGAACCCCTTCATGCCATGATGGAACGCGGACCCCAGACCTTGA<br>AGGAGACAAGTTTTAACCAAGCTTACGGAAGAGACCTGATGGAAGCCCAGGAATGGTGC<br>AGGAAATACATGAAAAGCGGGAATGTGAAGGACTTGCTCCAAGCGTGGGACCTGTACTA<br>TCATGTCTTTAGGCGCATTAGTAAGTGAGTCGACTGCTTTATTTGTGAAATTTGTGATGCT<br>ATTGCTTTATTTGTAACCATTATAAGCTGCAATAAACAAGTTAACAACAACAATTGCATT<br>CATTTTATGTTTCAGGTTCAGGGGGAGATGTGGGAGGTTTTTTAAAGC | |
| 76 | MPNPRPGKPSAPSLALGPSPGASPSWRAAPKASDLLGARGPGGTFQGRDLRGGAHASSSSLN<br>PMPPSQLQLPTLPLVMVAPSGARLGPLPHLQALLQDRPHFMHQLSTVDAHARTPVLQVHPLE<br>SPAMISLTPPTTATGVFSLKARPGLPPGINVASLEWVSREPALLCTFPNPSAPRKDSTLSAVPQS<br>SYPLLANGVCKWPGCEKVFEEPEDFLKHCQADHLLDEKGRAQCLLQREMVQSLEQQLVLEK<br>EKLSAMQAHLAGKMALTKASSVASSDKGSCCIVAAGSQGPVVPAWSGPREAPDSLFAVRRH<br>LWGSHGNSTFPEFLHNMDYFKFHNMRPPFTYATLIRWAILEAPEKQRTLNEIYHWFTRMFAF<br>FRNHPATWKNAIRHNLSLHKCFVRVESEKGAVWTVDELEFRKKRSQRPSRCSNPTPGPGSGA<br>TNFSLLKQAGDVEENPGPMPLGLLWLGLALLGALHAQAGVQVETISPGDGRTFPKRGQTCV<br>VHYTGMLEDGKKFDSSRDRNKPFKFMLGKQEVIRGWEEGVAQMSVGQRAKLTISPDYAYG<br>ATGHPGIIPPHATLVFDVELLKLGEGGSPGSNTSKENPFLFALEAVVISVGSMGLIISLLCVYFW<br>LERTMPRIPTLKNLEDLVTEYHGNFSAWSGVSKGLAESLQPDYSERLCLVSEIPPKGGALGEG<br>PGASPCNQHSPYWAPPCYTLKPETGSGATNFSLLKQAGDVEENPGPMALPVTALLLPLALLL<br>HAARPILWHEMWHEGLEEASRLYFGERNVKGMFEVLEPLHAMMERGPQTLKETSFNQAYG<br>RDLMEAQEWCRKYMKSGNVKDLLQAWDLYYHVFRRISKPAALGKDTIPWLGHLLVGLSGA<br>FGFIILVYLLINCRNTGPWLKKVLKCNTPDPSKFFSQLSSEHGGDVQKWLSSPFPSSSFSPGGL<br>APEISPLEVLERDKVTQLLLQQDKVPEPASLSLNTDAYLSLQELQGSGATNFSLLKQAGDVEE<br>NPGPEMWHEGLEEASRLYFGERNVKGMFEVLEPLHAMMERGPQTLKETSFNQAYGRDLME<br>AQEWCRKYMKSGNVKDLLQAWDLYYHVFRRISK* | FOXP3cDNA-μDISC amino acid sequence |
| 77 | ATGCCTAATCCTCGGCCTGGAAAGCCTAGCGCTCCTTCTCTTGCTCTGGGACCTTCTCCTG<br>GCGCCTCTCCATCTTGGAGAGCCGCTCCTAAAGCCAGCGATCTGCTGGGAGCTAGAGGAC<br>CTGGCGGCACATTTCAGGGCAGAGATCTTAGAGGCGGAGCCCACGCTAGCTCCTCCAGC<br>CTTAATCCTATGCCTCCTAGCCAGCTCCAGCTGCCTACACTGCCTCTGGTTATGGTGGCTC<br>CTAGCGGAGCTAGACTGGGCCCTCTGCCTCATCTGCAAGCTCTGCTGCAGGACAGACCCC<br>ACTTCATGCACCAGCTGAGCACCGTGGATGCCCACGCAAGAACACCTGTGCTGCAGGTTC<br>ACCCTCTGGAATCCCCAGCCATGATCAGCCTGACACCTCCAACAACAGCCACCGGCGTGT<br>TCAGCCTGAAAGCCAGACCTGGACTGCCTCCTGGCATCAATGTGGCCAGCCTGGAATGG<br>GTGTCCAGAGAACCTGCTCTGCTGTGCACATTCCCCAATCCAAGCGCTCCCAGAAAGGAC<br>AGCACACTGTCTGCCGTGCCTCAGAGCAGCTATCCCCTGCTTGCTAACGGCGTGTGCAAG<br>TGGCCTGGATGCGAGAAGGTGTTCGAGGAACCCGAGGACTTCCTGAAGCACTGCCAGGC<br>CGATCATCTGCTGGACGAGAAAGGCAGAGCCCAGTGTCTGCTCCAGCGCGAGATGGTGC<br>AGTCTCTGGAACAGCAGCTGGTCCTGGAAAAAGAAAAGCTGAGCGCCATGCAGGCCCAC<br>CTGGCCGGAAAAATGGCCCTGACAAAGGCCAGCAGCGTGGCCTCTTCTGATAAGGGCAG<br>CTGCTGCATTGTGGCCGCTGGATCTCAGGGACCTGTGGTTCCTGCTTGGAGCGGACCTAG<br>AGAGGCCCCTGATTCTCTGTTTGCCGTGCGGAGACACCTGTGGGGCTCTCACGGCAACTC<br>TACTTTCCCCGAGTTCCTGCACAACATGGACTACTTCAAGTTCCACAACATGCGGCCTCC<br>ATTCACCTACGCCACACTGATCAGATGGGCCATTCTGGAAGCCCCTGAGAAGCAGAGAA<br>CCCTGAACGAGATCTACCACTGGTTTACCCGGATGTTCGCCTTCTTCCGGAATCACCCTGC<br>CACCTGGAAGAACGCCATCCGGCACAATCTGAGCCTGCACAAGTGCTTCGTGCGCGTGG<br>AATCTGAGAAAGGCGCCGTGTGGACAGTGGACGAGCTGGAATTCAGAAAGAAGAGAAG<br>CCAGCGGCCTAGCCGGTGCAGCAATCCTACACCTGGACCTGGAAGCGGAGCGACTAACT<br>TCAGCCTGCTTAAGCAGGCCGGAGATGTGGAGGAAAACCCTGGACCGATGCCTCTGGGC<br>CTGCTGTGGCTGGGCCTGGCCCTGCTGGGCGCCCTGCACGCCCAGGCCATGGGGGCAGGT<br>GCCACCGGACGAGCCATGGACGGGCCGCGCCTGCTGCTGTTGCTGCTTCTGGGGGTGTCC<br>CTTGGAGGTGCCAAGGAGGCATGCCCCACAGGCCTGTACACACACAGCGGTGAGTGCTG<br>CAAAGCCTGCAACCTGGGCGAGGGTGTGGCCCAGCCTTGTGGAGCCAACCAGACCGTGT<br>GTGAGCCCTGCCTGGACAGCGTGACGTTCTCCGACGTGGTGAGCGCGACCGAGCCGTGC<br>AAGCCGTGCACCGAGTGCGTGGGGCTCCAGAGCATGTCGGCGCCGTGCGTGGAGGCCGA<br>CGACGCCGTGTGCCGCTGCGCCTACGGCTACTACCAGGATGAGACGACTGGGCGCTGCG<br>AGGCGTGCCGCGTGTGCGAGGCGGGCTCGGGCCTCGTGTTCTCCTGCCAGGACAAGCAG<br>AACACCGTGTGCGAGGAGTGCCCCGACGGCACGTATTCCGACGAGGCCAACCACGTGGA<br>CCCGTGCCTGCCCTGCACCGTGTGCGAGGACACCGAGCGCCAGCTCCGCGAGTGCACAC<br>GCTGGGCCGACGCCGAGTGCGAGGAGATCCCTGGCCGTTGGATTACACGGTCCACACCC<br>CCAGAGGGCTCGGACAGCACAGCCCCCAGCACCCAGGAGCCTGAGGCACCTCCAGAACA<br>AGACCTCATAGCCAGCACGGTGGCAGGTGTGGTGACCACAGTGATGGGCAGCTCCCAGC<br>CCGTGGTGACCCGAGGCACCACCGACAACCTCATCCCTGTCTATTGCTCCATCCTGGCTG<br>CTGTGGTTGTGGGTCTTGTGGCCTACATAGCCTTCAAGAGGGGCGTGCAGGTGGAGACAA<br>TCTCCCCAGGCGACGGACGCACATTCCCTAAGCGGGGCCAGACCTGCGTGGTGCACTATA<br>CAGGCATGCTGGAGGATGGCAAGAAGTTTGACAGCTCCCGGGATAGAAACAAGCCATTC | FOXP3cDNA-LNGFRe-μDISC nucleotide sequence (coding sequence only; codon-optimized; our DISC architecture version 6) |

-continued

| SEQ ID NO | Sequence | Description |
|---|---|---|
| | AAGTTTATGCTGGGCAAGCAGGAAGTGATCAGAGGCTGGGAGGAGGGCGTGGCCCAGAT<br>GTCTGTGGGCCAGAGGGCCAAGCTGACCATCAGCCCAGACTACGCCTATGGAGCAACAG<br>GCCACCCAGGAATCATCCCACCTCACGCCACCCTGGTGTTCGATGTGGAGCTGCTGAAGC<br>TGGGCGAGGGAGGGTCACCTGGATCCAACACATCAAAAGAGAACCCCTTTCTGTTCGCA<br>TTGGAGGCCGTAGTCATATCTGTTGGATCCATGGGACTTATTATCTCCCTGTTGTGTGTGT<br>ACTTCTGGCTGGAACGGACTATGCCCAGGATCCCCACGCTCAAGAATCTGGAAGATCTCG<br>TCACAGAATACCATGGTAATTTCAGCGCCTGGAGCGGAGTCTCTAAGGGTCTGGCCGAAT<br>CCCTCCAACCCGATTATTCTGAACGGTTGTGCCTCGTATCCGAAATACCACCAAAAGGCG<br>GGGCTCTGGGTGAGGGCCCAGGGGCGAGTCCGTGCAATCAACACAGCCCGTATTGGGCC<br>CCTCCTTGTTATACGTTGAAGCCCGAAACTGGAAGCGGAGCTACTAACTTCAGCCTGCTG<br>AAGCAGGCTGGAGACGTGGAGGAGAACCCTGGACCTATGGCACTGCCCGTGACCGCCCT<br>GCTGCTGCCTCTGGCCCTGCTGCTGCACGCAGCCCGGCCTATCCTGTGGCACGAGATGTG<br>GCACGAGGGCCTGGAGGAGGCCAGCAGGCTGTATTTTGGCGAGCGCAACGTGAAGGGCA<br>TGTTCGAGGTGCTGGAGCCTCTGCACGCCATGATGGAGAGAGGCCCACAGACCCTGAAG<br>GAGACATCCTTTAACCAGGCCTATGGACGGGACCTGATGGAGGCACAGGAGTGGTGCAG<br>AAAGTACATGAAGTCTGGCAATGTGAAGGACCTGCTGCAGGCCTGGGATCTGTACTATCA<br>CGTGTTTCGGAGAATCTCCAAGCCAGCAGCTCTCGGCAAAGACACGATTCCGTGGCTTGG<br>GCATCTGCTCGTTGGGCTGAGCGGTGCGTTTGGTTTCATCATCTTGGTCTATCTCTTGATC<br>AATTGCAGAAATACAGGCCCTTGGCTGAAAAAAGTGCTCAAGTGTAATACCCCCGACCC<br>AAGCAAGTTCTTCTCCCAGCTTTCTTCAGAGCATGGAGGCGATGTGCAGAAATGGCTCTC<br>TTCACCTTTTCCCTCCTCAAGCTTCTCCCCGGGAGGGCTGGCGCCCGAGATTTCACCTCTT<br>GAGGTACTTGAACGAGACAAGGTTACCCAACTTCTCCTTCAACAGGATAAGGTACCCGA<br>ACCTGCGAGCCTTAGCTTGAATACAGACGCTTATCTCTCACTGCAGGAACTGCAAGGATC<br>TGGTGCTACTAATTTTTCTCTTTTGAAGCAAGCTGGAGATGTTGAAGAGAACCCCGGTCC<br>GGAGATGTGGCATGAGGGTCTGGAAGAAGCGTCTCGACTGTACTTTGGTGAGCGCAATG<br>TGAAGGGCATGTTTGAAGTCCTCGAACCCCTTCATGCCATGATGGAACGCGGACCCCAGA<br>CCTTGAAGGAGACAAGTTTTAACCAAGCTTACGGAAGAGACCTGATGGAAGCCCAGGAA<br>TGGTGCAGGAAATACATGAAAAGCGGGAATGTGAAGGACTTGCTCCAAGCGTGGGACCT<br>GTACTATCATGTCTTTAGGCGCATTAGTAAG | |
| 78 | SEQ ID NO: 78: FOXP3cDNA-LNGFRe-μDISC amino acid sequence:<br>MPNPRPGKPSAPSLALGPSPGASPSWRAAPKASDLLGARGPGGTFQGRDLRGGAHASSSSLN<br>PMPPSQLQLPTLPLVMVAPSGARLGPLPHLQALLQDRPHFMHQLSTVDAHARTPVLQVHPLE<br>SPAMISLTPPTTATGVFSLKARPGLPPGINVASLEWVSREPALLCTFPNPSAPRKDSTLSAVPQS<br>SYPLLANGVCKWPGCEKVFEEPEDFLKHCQADHLLDEKGRAQCLLQREMVQSLEQQLVLEK<br>EKLSAMQAHLAGKMALTKASSVASSDKGSCCIVAAGSQGPVVPAWSGPREAPDSLFAVRRH<br>LWGSHGNSTFPEFLHNMDYFKFHNMRPPFTYATLIRWAILEAPEKQRTLNEIYHWFTRMFAF<br>FRNHPATWKNAIRHNLSLHKCFVRVESEKGAVWTVDELEFRKKRSQRPSRCSNPTPGPGSGA<br>TNFSLLKQAGDVEENPGPMPLGLLWLGLALLGALHAQAMGAGATGRAMDGPRLLLLLLLG<br>VSLGGAKEACPTGLYTHSGECCKACNLGEGVAQPCGANQTVCEPCLDSVTFSDVVSATEPC<br>KPCTECVGLQSMSAPCVEADDAVCRCAYGYYQDETTGRCEACRVCEAGSGLVFSCQDKQN<br>TVCEECPDGTYSDEANHVDPCLPCTVCEDTERQLRECTRWADAECEEIPGRWITRSTPPEGSD<br>STAPSTQEPEAPPEQDLIASTVAGVVTTVMGSSQPVVTRGTTDNUPVYCSILAAVVVGLVAYI<br>AFKRGVQVETISPGDGRTFPKRGQTCVVHYTGMLEDGKKFDSSRDRNKPFKFMLGKQEVIR<br>GWEEGVAQMSVGQRAKLTISPDYAYGATGHPGIIPPHATLVFDVELLKLGEGGSPGSNTSKE<br>NPFLFALEAVVISVGSMGLIISLLCVYFWLERTMPRIPTLKNLEDLVTEYHGNFSAWSGVSKG<br>LAESLQPDYSERLCLVSEIPPKGGALGEGPGASPCNQHSPYWAPPCYTLKPETGSGATNFSLL<br>KQAGDVEENPGPMALPVTALLLPLALLLHAARPILWHEMWHEGLEEASRLYFGERNVKGMF<br>EVLEPLHAMMERGPQTLKETSFNQAYGRDLMEAQEWCRKYMKSGNVKDLLQAWDLYYHV<br>FRRISKPAALGKDTIPWLGHLLVGLSGAFGFIILVYLLINCRNTGPWLKKVLKCNTPDPSKFFS<br>QLSSEHGGDVQKWLSSPFPSSSFSPGGLAPEISPLEVLERDKVTQLLLQQDKVPEPASLSLNTD<br>AYLSLQELQGSGATNFSLLKQAGDVEENPGPEMWHEGLEEASRLYFGERNVKGMFEVLEPL<br>HAMMERGPQTLKETSFNQAYGRDLMEAQEWCRKYMKSGNVKDLLQAWDLYYHVFRRISK | |
| 79 | ATGCCTCTGGGCCTGCTGTGGCTGGGCCTGGCCCTGCTGGGCGCCCTGCACGCCCAGGCC<br>GGCGTGCAGGTGGAGACAATCTCCCCAGGCGACGGACGCACATTCCCTAAGCGGGGCCA<br>GACCTGCGTGGTGCACTATACAGGCATGCTGGAGGATGGCAAGAAGTTTGACAGCTCCC<br>GGGATAGAAACAAGCCATTCAAGTTTATGCTGGGCAAGCAGGAAGTGATCAGAGGCTGG<br>GAGGAGGGCGTGGCCCAGATGTCTGTGGGCCAGAGGGCCAAGCTGACCATCAGCCCAGA<br>CTACGCCTATGGAGCAACAGGCCACCCAGGAATCATCCCACCTCACGCCACCCTGGTGTT<br>CGATGTGGAGCTGCTGAAGCTGGGCGAGGGAGGGTCACCTGGATCCAACACATCAAAAG<br>AGAACCCCTTTCTGTTCGCATTGGAGGCCGTAGTCATATCTGTTGGATCCATGGGACTTAT<br>TATCTCCCTGTTGTGTGTGTACTTCTGGCTGGAACGGACTATGCCCAGGATCCCCACGCTC<br>AAGAATCTGGAAGATCTCGTCACAGAATACCATGGTAATTTCAGCGCCTGGAGCGGAGT<br>CTCTAAGGGTCTGGCCGAATCCCTCCAACCCGATTATTCTGAACGGTTGTGCCTCGTATCC<br>GAAATACCACCAAAAGGCGGGGCTCTGGGTGAGGGCCCAGGGGCGAGTCCGTGCAATCA<br>ACACAGCCCGTATTGGGCCCCTCCTTGTTATACGTTGAAGCCCGAAACTGGAAGCGGAGC<br>TACTAACTTCAGCCTGCTGAAGCAGGCTGGAGACGTGGAGGAGAACCCTGGACCTATGG<br>CACTGCCCGTGACCGCCCTGCTGCTGCCTCTGGCCCTGCTGCTGCACGCAGCCCGGCCTA<br>TCCTGTGGCACGAGATGTGGCACGAGGGCCTGGAGGAGGCCAGCAGGCTGTATTTTGGC<br>GAGCGCAACGTGAAGGGCATGTTCGAGGTGCTGGAGCCTCTGCACGCCATGATGGAGAG<br>AGGCCCACAGACCCTGAAGGAGACATCCTTTAACCAGGCCTATGGACGGGACCTGATGG<br>AGGCACAGGAGTGGTGCAGAAAGTACATGAAGTCTGGCAATGTGAAGGACCTGCTGCAG<br>GCCTGGGATCTGTACTATCACGTGTTTCGGAGAATCTCCAAGCCAGCAGCTCTCGGCAAA<br>GACACGATTCCGTGGCTTGGGCATCTGCTCGTTGGGCTGAGCGGTGCGTTTGGTTTCATC | μDISC-FOXP3cDNA nucleotide sequence (coding sequence only; codon-optimized; our DISC architecture version 6) |

-continued

| SEQ ID NO | Sequence | Description |
|---|---|---|
| | ATCTTGGTCTATCTCTTGATCAATTGCAGAAATACAGGCCCTTGGCTGAAAAAAGTGCTC<br>AAGTGTAATACCCCCGACCCAAGCAAGTTCTTCTCCCAGCTTTCTTCAGAGCATGGAGGC<br>GATGTGCAGAAATGGCTCTCTTCACCTTTTCCCTCCTCAAGCTTCTCCCCGGGAGGGCTGG<br>CGCCCGAGATTTCACCTCTTGAGGTACTTGAACGAGACAAGGTTACCCAACTTCTCCTTC<br>AACAGGATAAGGTACCCGAACCTGCGAGCCTTAGCTTGAATACAGACGCTTATCTCTCAC<br>TGCAGGAACTGCAAGGATCTGGTGCTACTAATTTTTCTCTTTTGAAGCAAGCTGGAGATG<br>TTGAAGAGAACCCCGGTCCGGAGATGTGGCATGAGGGTCTGGAAGAAGCGTCTCGACTG<br>TACTTTGGTGAGCGCAATGTGAAGGGCATGTTTGAAGTCCTCGAACCCCTTCATGCCATG<br>ATGGAACGCGGACCCCAGACCTTGAAGGAGACAAGTTTTAACCAAGCTTACGGAAGAGA<br>CCTGATGGAAGCCCAGGAATGGTGCAGGAAATACATGAAAAGCGGGAATGTGAAGGACT<br>TGCTCCAAGCGTGGGACCTGTACTATCATGTCTTTAGGCGCATTAGTAAGGGAAGCGGAG<br>CGACTAACTTCAGCCTGCTTAAGCAGGCCGGAGATGTGGAGGAAAACCCTGGACCGATG<br>CCTAATCCTCGGCCTGGAAAGCCTAGCGCTCCTTCTCTTGCTCTGGGACCTTCTCCTGGCG<br>CCTCTCCATCTTGGAGAGCCGCTCCTAAAGCCAGCGATCTGCTGGGAGCTAGAGGACCTG<br>GCGGCACATTTCAGGGCAGAGATCTTAGAGGCGGAGCCCACGCTAGCTCCTCCAGCCTTA<br>ATCCTATGCCTCCTAGCCAGCTCCAGCTGCCTACACTGCCTCTGGTTATGGTGGCTCCTAG<br>CGGAGCTAGACTGGGCCCTCTGCCTCATCTGCAAGCTCTGCTGCAGGACAGACCCCACTT<br>CATGCACCAGCTGAGCACCGTGGATGCCCACGCAAGAACACCTGTGCTGCAGGTTCACC<br>CTCTGGAATCCCCAGCCATGATCAGCCTGACACCTCCAACAACAGCCACCGGCGTGTTCA<br>GCCTGAAAGCCAGACCTGGACTGCCTCCTGGCATCAATGTGGCCAGCCTGGAATGGGTGT<br>CCAGAGAACCTGCTCTGCTGTGCACATTCCCCAATCCAAGCGCTCCCAGAAAGGACAGC<br>ACACTGTCTGCCGTGCCTCAGAGCAGCTATCCCCTGCTTGCTAACGGCGTGTGCAAGTGG<br>CCTGGATGCGAGAAGGTGTTCGAGGAACCCGAGGACTTCCTGAAGCACTGCCAGGCCGA<br>TCATCTGCTGGACGAGAAAGGCAGAGCCCAGTGTCTGCTCCAGCGCGAGATGGTGCAGT<br>CTCTGGAACAGCAGCTGGTCCTGGAAAAAGAAAAGCTGAGCGCCATGCAGGCCCACCTG<br>GCCGGAAAAATGGCCCTGACAAAGGCCAGCAGCGTGGCCTCTTCTGATAAGGGCAGCTG<br>CTGCATTGTGGCCGCTGGATCTCAGGGACCTGTGGTTCCTGCTTGGAGCGGACCTAGAGA<br>GGCCCCTGATTCTCTGTTTGCCGTGCGGAGACACCTGTGGGGCTCTCACGGCAACTCTAC<br>TTTCCCCGAGTTCCTGCACAACATGGACTACTTCAAGTTCCACAACATGCGGCCTCCATTC<br>ACCTACGCCACACTGATCAGATGGGCCATTCTGGAAGCCCCTGAGAAGCAGAGAACCCT<br>GAACGAGATCTACCACTGGTTTACCCGGATGTTCGCCTTCTTCCGGAATCACCCTGCCAC<br>CTGGAAGAACGCCATCCGGCACAATCTGAGCCTGCACAAGTGCTTCGTGCGCGTGGAAT<br>CTGAGAAAGGCGCCGTGTGGACAGTGGACGAGCTGGAATTCAGAAAGAAGAGAAGCCA<br>GCGGCCTAGCCGGTGCAGCAATCCTACACCTGGACCT | |
| 80 | MPLGLLWLGLALLGALHAQAGVQVETISPGDGRTFPKRGQTCVVHYTGMLEDGKKFDSSRD<br>RNKPFKFMLGKQEVIRGWEEGVAQMSVGQRAKLTISPDYAYGATGHPGIIPPHATLVFDVEL<br>LKLGEGGSPGSNTSKENPFLFALEAVVISVGSMGLIISLLCVYFWLERTMPRIPTLKNLEDLVT<br>EYHGNFSAWSGVSKGLAESLQPDYSERLCLVSEIPPKGGALGEGPGASPCNQHSPYWAPPCY<br>TLKPETGSGATNFSLLKQAGDVEENPGPMALPVTALLLPLALLLHAARPILWHEMWHEGLEE<br>ASRLYFGERNVKGMFEVLEPLHAMMERGPQTLKETSFNQAYGRDLMEAQEWCRKYMKSG<br>NVKDLLQAWDLYYHVFRRISKPAALGKDTIPWLGHLLVGLSGAFGFIILVYLLINCRNTGPWL<br>KKVLKCNTPDPSKFFSQLSSEHGGDVQKWLSSPFPSSSFSPGGLAPEISPLEVLERDKVTQLLL<br>QQDKVPEPASLSLNTDAYLSLQELQGSGATNFSLLKQAGDVEENPGPEMWHEGLEEASRLYF<br>GERNVKGMFEVLEPLHAMMERGPQTLKETSFNQAYGRDLMEAQEWCRKYMKSGNVKDLL<br>QAWDLYYHVFRRISKGSGATNFSLLKQAGDVEENPGPMPNPRPGKPSAPSLALGPSPGASPS<br>WRAAPKASDLLGARGPGGTFQGRDLRGGAHASSSSLNPMPPSQLQLPTLPLVMVAPSGARL<br>GPLPHLQALLQDRPHFMHQLSTVDAHARTPVLQVHPLESPAMISLTPPTTATGVFSLKARPGL<br>PPGINVASLEWVSREPALLCTFPNPSAPRKDSTLSAVPQSSYPLLANGVCKWPGCEKVFEEPE<br>DFLKHCQADHLLDEKGRAQCLLQREMVQSLEQQLVLEKEKLSAMQAHLAGKMALTKASSV<br>ASSDKGSCCIVAAGSQGPVVPAWSGPREAPDSLFAVRRHLWGSHGNSTFPEFLHNMDYFKFH<br>NMRPPFTYATLIRWAILEAPEKQRTLNEIYHWFTRMFAFFRNHPATWKNAIRHNLSLHKCFV<br>RVESEKGAVWTVDELEFRKKRSQRPSRCSNPTPGP | µDISC-<br>FOXP3cDN<br>A amino acid<br>sequence |
| 81 | ATGCCTCTGGGCCTGCTGTGGCTGGGCCTGGCCCTGCTGGGCGCCCTGCACGCCCAGGCC<br>ATGGGGGCAGGTGCCACCGGACGAGCCATGGACGGGCCGCGCCTGCTGCTGTTGCTGCT<br>TCTGGGGGTGTCCCTTGGAGGTGCCAAGGAGGCATGCCCCACAGGCCTGTACACACACA<br>GCGGTGAGTGCTGCAAAGCCTGCAACCTGGGCGAGGGTGTGGCCCAGCCTTGTGGAGCC<br>AACCAGACCGTGTGTGAGCCCTGCCTGGACAGCGTGACGTTCTCCGACGTGGTGAGCGC<br>GACCGAGCCGTGCAAGCCGTGCACCGAGTGCGTGGGGCTCCAGAGCATGTCGGCGCCGT<br>GCGTGGAGGCCGACGACGCCGTGTGCCGCTGCGCCTACGGCTACTACCAGGATGAGACG<br>ACTGGGCGCTGCGAGGCGTGCCGCGTGTGCGAGGCGGGCTCGGGCCTCGTGTTCTCCTGC<br>CAGGACAAGCAGAACACCGTGTGCGAGGAGTGCCCCGACGGCACGTATTCCGACGAGGC<br>CAACCACGTGGACCCGTGCCTGCCCTGCACCGTGTGCGAGGACACCGAGCGCCAGCTCC<br>GCGAGTGCACACGCTGGGCCGACGCCGAGTGCGAGGAGATCCCTGGCCGTTGGATTACA<br>CGGTCCACACCCCCAGAGGGCTCGGACAGCACAGCCCCCAGCACCCAGGAGCCTGAGGC<br>ACCTCCAGAACAAGACCTCATAGCCAGCACGGTGGCAGGTGTGGTGACCACAGTGATGG<br>GCAGCTCCCAGCCCGTGGTGACCCGAGGCACCACCGACAACCTCATCCCTGTCTATTGCT<br>CCATCCTGGCTGCTGTGGTTGTGGGTCTTGTGGCCTACATAGCCTTCAAGAGGGGCGTGC<br>AGGTGGAGACAATCTCCCCAGGCGACGGACGCACATTCCCTAAGCGGGGCCAGACCTGC<br>GTGGTGCACTATACAGGCATGCTGGAGGATGGCAAGAAGTTTGACAGCTCCCGGGATAG<br>AAACAAGCCATTCAAGTTTATGCTGGGCAAGCAGGAAGTGATCAGAGGCTGGGAGGAGG<br>GCGTGGCCCAGATGTCTGTGGGCCAGAGGGCCAAGCTGACCATCAGCCCAGACTACGCC<br>TATGGAGCAACAGGCCACCCAGGAATCATCCCACCTCACGCCACCCTGGTGTTCGATGTG<br>GAGCTGCTGAAGCTGGGCGAGGGAGGGTCACCTGGATCCAACACATCAAAAGAGAACCC | LNGFRe-<br>µDISC -<br>FOXP3cDN<br>A nucleotide<br>sequence<br>(coding<br>sequence<br>only; codon-<br>optimized;<br>our DISC<br>architecture<br>version 6) |

-continued

| SEQ ID NO | Sequence | Description |
|---|---|---|
| | CTTTCTGTTCGCATTGGAGGCCGTAGTCATATCTGTTGGATCCATGGACTTATTATCTCC<br>CTGTTGTGTGTGTACTTCTGGCTGGAACGGACTATGCCCAGGATCCCCACGCTCAAGAAT<br>CTGGAAGATCTCGTCACAGAATACCATGGTAATTTCAGCGCCTGGAGCGGAGTCTCTAAG<br>GGTCTGGCCGAATCCCTCCAACCCGATTATTCTGAACGGTTGTGCCTCGTATCCGAAATA<br>CCACCAAAAGGCGGGGCTCTGGGTGAGGGCCCAGGGGCGAGTCCGTGCAATCAACACAG<br>CCCGTATTGGGCCCCTCCTTGTTATACGTTGAAGCCCGAAACTGGAAGCGGAGCTACTAA<br>CTTCAGCCTGCTGAAGCAGGCTGGAGACGTGGAGGAGAACCCTGGACCTATGGCACTGC<br>CCGTGACCGCCCTGCTGCTGCCTCTGGCCCTGCTGCTGCACGCAGCCCGGCCTATCCTGT<br>GGCACGAGATGTGGCACGAGGGCCTGGAGGAGGCCAGCAGGCTGTATTTTGGCGAGCGC<br>AACGTGAAGGGCATGTTCGAGGTGCTGGAGCCTCTGCACGCCATGATGGAGAGAGGCCC<br>ACAGACCCTGAAGGAGACATCCTTTAACCAGGCCTATGGACGGGACCTGATGGAGGCAC<br>AGGAGTGGTGCAGAAAGTACATGAAGTCTGGCAATGTGAAGGACCTGCTGCAGGCCTGG<br>GATCTGTACTATCACGTGTTTCGGAGAATCTCCAAGCCAGCAGCTCTCGGCAAAGACACG<br>ATTCCGTGGCTTGGGCATCTGCTCGTTGGGCTGAGCGGTGCGTTTGGTTTCATCATCTTGG<br>TCTATCTCTTGATCAATTGCAGAAATACAGGCCCTTGGCTGAAAAAGTGCTCAAGTGTA<br>ATACCCCCGACCCAAGCAAGTTCTTCTCCCAGCTTTCTTCAGAGCATGGAGGCGATGTGC<br>AGAAATGGCTCTCTTCACCTTTTCCCTCCTCAAGCTTCTCCCCGGGAGGGCTGGCGCCCG<br>AGATTTCACCTCTTGAGGTACTTGAACGAGACAAGGTTACCCAACTTCTCCTTCAACAGG<br>ATAAGGTACCCGAACCTGCGAGCCTTAGCTTGAATACAGACGCTTATCTCTCACTGCAGG<br>AACTGCAAGGATCTGGTGCTACTAATTTTTCTCTTTTGAAGCAAGCTGGAGATGTTGAAG<br>AGAACCCCGGTCCGGAGATGTGGCATGAGGGTCTGGAAGAAGCGTCTCGACTGTACTTT<br>GGTGAGCGCAATGTGAAGGGCATGTTTGAAGTCCTCGAACCCCTTCATGCCATGATGGAA<br>CGCGGACCCCAGACCTTGAAGGAGACAAGTTTTAACCAAGCTTACGGAAGAGACCTGAT<br>GGAAGCCCAGGAATGGTGCAGGAAATACATGAAAAGCGGGAATGTGAAGGACTTGCTCC<br>AAGCGTGGGACCTGTACTATCATGTCTTTAGGCGCATTAGTAAGGGAAGCGGAGCGACT<br>AACTTCAGCCTGCTTAAGCAGGCCGGAGATGTGGAGGAAAACCCTGGACCGATGCCTAA<br>TCCTCGGCCTGGAAAGCCTAGCGCTCCTTCTCTTGCTCTGGGACCTTCTCCTGGCGCCTCT<br>CCATCTTGGAGAGCCGCTCCTAAAGCCAGCGATCTGCTGGGAGCTAGAGGACCTGGCGG<br>CACATTTCAGGGCAGAGATCTTAGAGGCGGAGCCCACGCTAGCTCCTCCAGCCTTAATCC<br>TATGCCTCCTAGCCAGCTCCAGCTGCCTACACTGCCTCTGGTTATGGTGGCTCCTAGCGG<br>AGCTAGACTGGGCCCTCTGCCTCATCTGCAAGCTCTGCTGCAGGACAGACCCCACTTCAT<br>GCACCAGCTGAGCACCGTGGATGCCCACGCAAGAACACCTGTGCTGCAGGTTCACCCTCT<br>GGAATCCCCAGCCATGATCAGCCTGACACCTCCAACAACAGCCACCGGCGTGTTCAGCCT<br>GAAAGCCAGACCTGGACTGCCTCCTGGCATCAATGTGGCCAGCCTGGAATGGGTGTCCA<br>GAGAACCTGCTCTGCTGTGCACATTCCCCAATCCAAGCGCTCCCAGAAAGGACAGCACA<br>CTGTCTGCCGTGCCTCAGAGCAGCTATCCCCTGCTTGCTAACGGCGTGTGCAAGTGGCCT<br>GGATGCGAGAAGGTGTTCGAGGAACCCGAGGACTTCCTGAAGCACTGCCAGGCCGATCA<br>TCTGCTGGACGAGAAAGGCAGAGCCCAGTGTCTGCTCCAGCGCGAGATGGTGCAGTCTC<br>TGGAACAGCAGCTGGTCCTGGAAAAAGAAAAGCTGAGCGCCATGCAGGCCCACCTGGCC<br>GGAAAAATGGCCCTGACAAAGGCCAGCAGCGTGGCCTCTTCTGATAAGGGCAGCTGCTG<br>CATTGTGGCCGCTGGATCTCAGGGACCTGTGGTTCCTGCTTGGAGCGGACCTAGAGAGGC<br>CCCTGATTCTCTGTTTGCCGTGCGGAGACACCTGTGGGGCTCTCACGGCAACTCTACTTTC<br>CCCGAGTTCCTGCACAACATGGACTACTTCAAGTTCCACAACATGCGGCCTCCATTCACC<br>TACGCCACACTGATCAGATGGGCCATTCTGGAAGCCCCTGAGAAGCAGAGAACCCTGAA<br>CGAGATCTACCACTGGTTTACCCGGATGTTCGCCTTCTTCCGGAATCACCCTGCCACCTGG<br>AAGAACGCCATCCGGCACAATCTGAGCCTGCACAAGTGCTTCGTGCGCGTGGAATCTGA<br>GAAAGGCGCCGTGTGGACAGTGGACGAGCTGGAATTCAGAAAGAAGAGAAGCCAGCGG<br>CCTAGCCGGTGCAGCAATCCTACACCTGGACCTTGA | |
| 82 | MPLGLLWLGLALLGALHAQAMGAGATGRAMDGPRLLLLLLLGVSLGGAKEACPTGLYTHS<br>GECCKACNLGEGVAQPCGANQTVCEPCLDSVTFSDVVSATEPCKPCTECVGLQSMSAPCVE<br>ADDAVCRCAYGYYQDETTGRCEACRVCEAGSGLVFSCQDKQNTVCEECPDGTYSDEANHV<br>DPCLPCTVCEDTERQLRECTRWADAECEEIPGRWITRSTPPEGSDSTAPSTQEPEAPPEQDLIA<br>STVAGVVTTVMGSSQPVVTRGTTDNLIPVYCSILAAVVVGLVAYIAFKRGVQVETISPGDGRT<br>FPKRGQTCVVHYTGMLEDGKKFDSSRDRNKPFKFMLGKQEVIRGWEEGVAQMSVGQRAKL<br>TISPDYAYGATGHPGIIPPHATLVFDVELLKLGEGGSPGSNTSKENPFLFALEAVVISVGSMGLI<br>ISLLCVYFWLERTMPRIPTLKNLEDLVTEYHGNFSAWSGVSKGLAESLQPDYSERLCLVSEIPP<br>KGGALGEGPGASPCNQHSPYWAPPCYTLKPETGSGATNFSLLKQAGDVEENPGPMALPVTA<br>LLLPLALLLHAARPILWHEMWHEGLEEASRLYFGERNVKGMFEVLEPLHAMMERGPQTLKE<br>TSFNQAYGRDLMEAQEWCRKYMKSGNVKDLLQAWDLYYHVFRRISKPAALGKDTIPWLGH<br>LLVGLSGAFGFIILVYLLINCRNTGPWLKKVLKCNTPDPSKFFSQLSSEHGGDVQKWLSSPFPS<br>SSFSPGGLAPEISPLEVLERDKVTQLLLQQDKVPEPASLSLNTDAYLSLQELQGSGATNFSLLK<br>QAGDVEENPGPEMWHEGLEEASRLYFGERNVKGMFEVLEPLHAMMERGPQTLKETSFNQA<br>YGRDLMEAQEWCRKYMKSGNVKDLLQAWDLYYHVFRRISKGSGATNFSLLKQAGDVEENP<br>GPMPNPRPGKPSAPSLALGPSPGASPSWRAAPKASDLLGARGPGGTFQGRDLRGGAHASSSS<br>LNPMPPSQLQLPTLPLVMVAPSGARLGPLPHLQALLQDRPHFMHQLSTVDAHARTPVLQVHP<br>LESPAMISLTPPTTATGVFSLKARPGLPPGINVASLEWVSREPALLCTFPNPSAPRKDSTLSAVP<br>QSSYPLLANGVCKWPGCEKVFEEPEDFLKHCQADHLLDEKGRAQCLLQREMVQSLEQQLVL<br>EKEKLSAMQAHLAGKMALTKASSVASSDKGSCCIVAAGSQGPVVPAWSGPREAPDSLFAVR<br>RHLWGSHGNSTFPEFLHNMDYFKFHNMRPPFTYATLIRWAILEAPEKQRTLNEIYHWFTRMF<br>AFFRNHPATWKNAIRHNLSLHKCFVRVESEKGAVWTVDELEFRKKRSQRPSRCSNPTPGP* | LNGFRe-<br>µDISC-<br>FOXP3cDN<br>A amino acid<br>sequence |
| 83 | ATGCCTCTGGGCCTGCTGTGGCTGGGCCTGGCCCTGCTGGGCGCCCTGCACGCCCAGGCC<br>GGCGTGCAGGTGGAGACAATCTCCCCAGGCGACGGACGCACATTCCCTAAGCGGGGCCA<br>GACCTGCGTGGTGCACTATACAGGCATGCTGGAGGATGGCAAGAAGTTTGACAGCTCCC | DISC<br>nucleotide<br>sequence |

-continued

| SEQ ID NO | Sequence | Description |
|---|---|---|
| | GGGATAGAAACAAGCCATTCAAGTTTATGCTGGGCAAGCAGGAAGTGATCAGAGGCTGG<br>GAGGAGGGCGTGGCCCAGATGTCTGTGGGCCAGAGGGCCAAGCTGACCATCAGCCCAGA<br>CTACGCCTATGGAGCAACAGGCCACCCAGGAATCATCCCACCTCACGCCACCCTGGTGTT<br>CGATGTGGAGCTGCTGAAGCTGGGCGAGGGAGGGTCACCTGGATCCAACACATCAAAAG<br>AGAACCCCTTTCTGTTCGCATTGGAGGCCGTAGTCATATCTGTTGGATCCATGGGACTTAT<br>TATCTCCCTGTTGTGTGTGTACTTCTGGCTGGAACGGACTATGCCCAGGATCCCCACGCTC<br>AAGAATCTGGAAGATCTCGTCACAGAATACCATGGTAATTTCAGCGCCTGGAGCGGAGT<br>CTCTAAGGGTCTGGCCGAATCCCTCCAACCCGATTATTCTGAACGGTTGTGCCTCGTATCC<br>GAAATACCACCAAAAGGCGGGGCTCTGGGTGAGGGCCCAGGGGCGAGTCCGTGCAATCA<br>ACACAGCCCGTATTGGGCCCCTCCTTGTTATACGTTGAAGCCCGAAACTGGAAGCGGAGC<br>TACTAACTTCAGCCTGCTGAAGCAGGCTGGAGACGTGGAGGAGAACCCTGGACCTATGG<br>CACTGCCCGTGACCGCCCTGCTGCTGCCTCTGGCCCTGCTGCTGCACGCAGCCCGGCCTA<br>TCCTGTGGCACGAGATGTGGCACGAGGGCCTGGAGGAGGCCAGCAGGCTGTATTTTGGC<br>GAGCGCAACGTGAAGGGCATGTTCGAGGTGCTGGAGCCTCTGCACGCCATGATGGAGAG<br>AGGCCCACAGACCCTGAAGGAGACATCCTTTAACCAGGCCTATGGACGGGACCTGATGG<br>AGGCACAGGAGTGGTGCAGAAAGTACATGAAGTCTGGCAATGTGAAGGACCTGCTGCAG<br>GCCTGGGATCTGTACTATCACGTGTTTCGGAGAATCTCCAAGCCAGCAGCTCTCGGCAAA<br>GACACGATTCCGTGGCTTGGGCATCTGCTCGTTGGGCTGAGCGGTGCGTTTGGTTTCATC<br>ATCTTGGTCTATCTCTTGATCAATTGCAGAAATACAGGCCCTTGGCTGAAAAAGTGCTC<br>AAGTGTAATACCCCCGACCCAAGCAAGTTCTTCTCCCAGCTTTCTTCAGAGCATGGAGGC<br>GATGTGCAGAAATGGCTCTCTTCACCTTTTCCCTCCTCAAGCTTCTCCCCGGGAGGGCTGG<br>CGCCCGAGATTTCACCTCTTGAGGTACTTGAACGAGACAAGGTTACCCAACTTCTCCTTC<br>AACAGGATAAGGTACCCGAACCTGCGAGCCTTAGCTCCAACCACTCTCTTACGAGCTGCT<br>TCACCAATCAGGGATACTTCTTTTTCCACCTTCCCGATGCGCTGGAAATCGAAGCTTGTCA<br>AGTTTACTTTACCTATGATCCATATAGCGAGGAAGATCCCGACGAAGGAGTCGCCGGTGC<br>GCCCACGGGTTCCTCACCCCAACCTCTCCAGCCTCTCTCAGGAGAAGATGATGCTTATTG<br>CACTTTTCCCAGTAGAGACGATCTCCTCCTCTTTTCTCCATCTCTTTTGGGGGGACCTTCC<br>CCCCCTTCTACGGCACCTGGCGGGTCTGGTGCTGGCGAGGAGCGGATGCCGCCGTCCCTC<br>CAGGAGCGAGTACCACGAGATTGGGATCCCCAGCCACTTGGACCCCCCACCCCCGGCGT<br>ACCTGACCTTGTCGATTTTCAACCTCCCCCTGAATTGGTGCTGCGAGAGGCTGGGGAGGA<br>AGTTCCGGACGCTGGGCCGAGGGAGGGCGTGTCCTTTCCATGGAGTAGGCCTCCAGGTC<br>AAGGCGAGTTTAGGGCTCTCAACGCGCGGCTGCCGTTGAATACAGACGCTTATCTCTCAC<br>TGCAGGAACTGCAAGGTCAGGACCCAACACATCTTGTAGGATCTGGTGCTACTAATTTTT<br>CTCTTTTGAAGCAAGCTGGAGATGTTGAAGAGAACCCCGGTCCGGAGATGTGGCATGAG<br>GGTCTGGAAGAAGCGTCTCGACTGTACTTTGGTGAGCGCAATGTGAAGGGCATGTTTGAA<br>GTCCTCGAACCCCTTCATGCCATGATGGAACGCGGACCCCAGACCTTGAAGGAGACAAG<br>TTTTAACCAAGCTTACGGAAGAGACCTGATGGAAGCCCAGGAATGGTGCAGGAAATACA<br>TGAAAAGCGGGAATGTGAAGGACTTGCTCCAAGCGTGGGACCTGTACTATCATGTCTTTA<br>GGCGCATTAGTAAG | (coding sequence only; codon-optimized; our DISC architecture version 6) |
| 84 | MPLGLLWLGLALLGALHAQAGVQVETISPGDGRTFPKRGQTCVVHYTGMLEDGKKFDSSRD<br>RNKPFKFMLGKQEVIRGWEEGVAQMSVGQRAKLTISPDYAYGATGHPGIIPPHATLVFDVEL<br>LKLGEGGSPGSNTSKENPFLFALEAVVISVGSMGLIISLLCVYFWLERTMPRIPTLKNLEDLVT<br>EYHGNFSAWSGVSKGLAESLQPDYSERLCLVSEIPPKGGALGEGPGASPCNQHSPYWAPPCY<br>TLKPETGSGATNFSLLKQAGDVEENPGPMALPVTALLLPLALLLHAARPILWHEMWHEGLEE<br>ASRLYFGERNVKGMFEVLEPLHAMMERGPQTLKETSFNQAYGRDLMEAQEWCRKYMKSG<br>NVKDLLQAWDLYYHVFRRISKPAALGKDTIPWLGHLLVGLSGAFGFIILVYLLINCRNTGPWL<br>KKVLKCNTPDPSKFFSQLSSEHGGDVQKWLSSPFPSSSFSPGGLAPEISPLEVLERDKVTQLLL<br>QQDKVPEPASLSSNHSLTSCFTNQGYFFFHLPDALEIEACQVYFTYDPYSEEDPDEGVAGAPT<br>GSSPQPLQPLSGEDDAYCTFPSRDDLLLFSPSLLGGPSPPSTAPGGSGAGEERMPPSLQERVPR<br>DWDPQPLGPPTPGVPDLVDFQPPPELVLREAGEEVPDAGPREGVSFPWSRPPGQGEFRALNA<br>RLPLNTDAYLSLQELQGQDPTHLVGSGATNFSLLKQAGDVEENPGPEMWHEGLEEASRLYF<br>GERNVKGMFEVLEPLHAMMERGPQTLKETSFNQAYGRDLMEAQEWCRKYMKSGNVKDLL<br>QAWDLYYHVFRRISK | DISC amino acid sequence |
| 85 | ATGCCTCTGGGCCTGCTGTGGCTGGGCCTGGCCCTGCTGGGCGCCCTGCACGCCCAGGCC<br>GGCGTGCAGGTGGAGACAATCTCCCCAGGCGACGGACGCACATTCCCTAAGCGGGGCCA<br>GACCTGCGTGGTGCACTATACAGGCATGCTGGAGGATGGCAAGAAGTTTGACAGCTCCC<br>GGGATAGAAACAAGCCATTCAAGTTTATGCTGGGCAAGCAGGAAGTGATCAGAGGCTGG<br>GAGGAGGGCGTGGCCCAGATGTCTGTGGGCCAGAGGGCCAAGCTGACCATCAGCCCAGA<br>CTACGCCTATGGAGCAACAGGCCACCCAGGAATCATCCCACCTCACGCCACCCTGGTGTT<br>CGATGTGGAGCTGCTGAAGCTGGGCGAGGGAGGGTCACCTGGATCCAACACATCAAAAG<br>AGAACCCCTTTCTGTTCGCATTGGAGGCCGTAGTCATATCTGTTGGATCCATGGGACTTAT<br>TATCTCCCTGTTGTGTGTGTACTTCTGGCTGGAACGGACTATGCCCAGGATCCCCACGCTC<br>AAGAATCTGGAAGATCTCGTCACAGAATACCATGGTAATTTCAGCGCCTGGAGCGGAGT<br>CTCTAAGGGTCTGGCCGAATCCCTCCAACCCGATTATTCTGAACGGTTGTGCCTCGTATCC<br>GAAATACCACCAAAAGGCGGGGCTCTGGGTGAGGGCCCAGGGGCGAGTCCGTGCAATCA<br>ACACAGCCCGTATTGGGCCCCTCCTTGTTATACGTTGAAGCCCGAAACTGGAAGCGGAGC<br>TACTAACTTCAGCCTGCTGAAGCAGGCTGGAGACGTGGAGGAGAACCCTGGACCTATGG<br>CACTGCCCGTGACCGCCCTGCTGCTGCCTCTGGCCCTGCTGCTGCACGCAGCCCGGCCTA<br>TCCTGTGGCACGAGATGTGGCACGAGGGCCTGGAGGAGGCCAGCAGGCTGTATTTTGGC<br>GAGCGCAACGTGAAGGGCATGTTCGAGGTGCTGGAGCCTCTGCACGCCATGATGGAGAG<br>AGGCCCACAGACCCTGAAGGAGACATCCTTTAACCAGGCCTATGGACGGGACCTGATGG<br>AGGCACAGGAGTGGTGCAGAAAGTACATGAAGTCTGGCAATGTGAAGGACCTGCTGCAG<br>GCCTGGGATCTGTACTATCACGTGTTTCGGAGAATCTCCAAGCCAGCAGCTCTCGGCAAA | µDISC nucleotide sequence (coding sequence only; codon-optimized; our DISC architecture version 6) |

-continued

| SEQ ID NO | Sequence | Description |
|---|---|---|
| | GACACGATTCCGTGGCTTGGGCATCTGCTCGTTGGGCTGAGCGGTGCGTTTGGTTTCATC<br>ATCTTGGTCTATCTCTTGATCAATTGCAGAAATACAGGCCCTTGGCTGAAAAAAGTGCTC<br>AAGTGTAATACCCCCGACCCAAGCAAGTTCTTCTCCCAGCTTTCTTCAGAGCATGGAGGC<br>GATGTGCAGAAATGGCTCTCTTCACCTTTTCCCTCCTCAAGCTTCTCCCCGGGAGGGCTGG<br>CGCCCGAGATTTCACCTCTTGAGGTACTTGAACGAGACAAGGTTACCCAACTTCTCCTTC<br>AACAGGATAAGGTACCCGAACCTGCGAGCCTTAGCTTGAATACAGACGCTTATCTCTCAC<br>TGCAGGAACTGCAAGGATCTGGTGCTACTAATTTTTCTCTTTTGAAGCAAGCTGGAGATG<br>TTGAAGAGAACCCCGGTCCGGAGATGTGGCATGAGGGTCTGGAAGAAGCGTCTCGACTG<br>TACTTTGGTGAGCGCAATGTGAAGGGCATGTTTGAAGTCCTCGAACCCCTTCATGCCATG<br>ATGGAACGCGGACCCCAGACCTTGAAGGAGACAAGTTTTAACCAAGCTTACGGAAGAGA<br>CCTGATGGAAGCCCAGGAATGGTGCAGGAAATACATGAAAAGCGGGAATGTGAAGGACT<br>TGCTCCAAGCGTGGGACCTGTACTATCATGTCTTTAGGCGCATTAGTAAG | |
| 86 | MPLGLLWLGLALLGALHAQAGVQVETISPGDGRTFPKRGQTCVVHYTGMLEDGKKFDSSRD<br>RNKPFKFMLGKQEVIRGWEEGVAQMSVGQRAKLTISPDYAYGATGHPGIIPPHATLVFDVEL<br>LKLGEGGSPGSNTSKENPFLFALEAVVISVGSMGLIISLLCVYFWLERTMPRIPTLKNLEDLVT<br>EYHGNFSAWSGVSKGLAESLQPDYSERLCLVSEIPPKGGALGEGPGASPCNQHSPYWAPPCY<br>TLKPETGSGATNFSLLKQAGDVEENPGPMALPVTALLLPLALLLHAARPILWHEMWHEGLEE<br>ASRLYFGERNVKGMFEVLEPLHAMMERGPQTLKETSFNQAYGRDLMEAQEWCRKYMKSG<br>NVKDLLQAWDLYYHVFRRISKPAALGKDTIPWLGHLLVGLSGAFGFIILVYLLINCRNTGPWL<br>KKVLKCNTPDPSKFFSQLSSEHGGDVQKWLSSPFPSSSFSPGGLAPEISPLEVLERDKVTQLLL<br>QQDKVPEPASLSLNTDAYLSLQELQGSGATNFSLLKQAGDVEENPGPEMWHEGLEEASRLYF<br>GERNVKGMFEVLEPLHAMMERGPQTLKETSFNQAYGRDLMEAQEWCRKYMKSGNVKDLL<br>QAWDLYYHVFRRISK | µDISC amino acid sequence |
| 87 | ATGGCACTGCCCGTGACCGCCCTGCTGCTGCCTCTGGCCCTGCTGCTGCACGCAGCCCGG<br>CCTATCCTGTGGCACGAGATGTGGCACGAGGGCCTGGAGGAGGCCAGCAGGCTGTATTT<br>TGGCGAGCGCAACGTGAAGGGCATGTTCGAGGTGCTGGAGCCTCTGCACGCCATGATGG<br>AGAGAGGCCCACAGACCCTGAAGGAGACATCCTTTAACCAGGCCTATGGACGGGACCTG<br>ATGGAGGCACAGGAGTGGTGCAGAAAGTACATGAAGTCTGGCAATGTGAAGGACCTGCT<br>GCAGGCCTGGGATCTGTACTATCACGTGTTTCGGAGAATCTCCAAGCCAGCAGCTCTCGG<br>CAAAGACACGATTCCGTGGCTTGGGCATCTGCTCGTTGGGCTGAGCGGTGCGTTTGGTTT<br>CATCATCTTGGTCTATCTCTTGATCAATTGCAGAAATACAGGCCCTTGGCTGAAAAAAGT<br>GCTCAAGTGTAATACCCCCGACCCAAGCAAGTTCTTCTCCCAGCTTTCTTCAGAGCATGG<br>AGGCGATGTGCAGAAATGGCTCTCTTCACCTTTTCCCTCCTCAAGCTTCTCCCCGGGAGG<br>GCTGGCGCCCGAGATTTCACCTCTTGAGGTACTTGAACGAGACAAGGTTACCCAACTTCT<br>CCTTCAACAGGATAAGGTACCCGAACCTGCGAGCCTTAGCTCCAACCACTCTCTTACGAG<br>CTGCTTCACCAATCAGGGATACTTCTTTTTCCACCTTCCCGATGCGCTGGAAATCGAAGCT<br>TGTCAAGTTTACTTTACCTATGATCCATATAGCGAGGAAGATCCCGACGAAGGAGTCGCC<br>GGTGCGCCCACGGGTTCCTCACCCCAACCTCTCCAGCCTCTCTCAGGAGAAGATGATGCT<br>TATTGCACTTTTCCCAGTAGAGACGATCTCCTCCTCTTTTCTCCATCTCTTTTGGGGGGAC<br>CTTCCCCCCCTTCTACGGCACCTGGCGGGTCTGGTGCTGGCGAGGAGCGGATGCCGCCGT<br>CCCTCCAGGAGCGAGTACCACGAGATTGGGATCCCCAGCCACTTGGACCCCCCACCCCCG<br>GCGTACCTGACCTTGTCGATTTTCAACCTCCCCCTGAATTGGTGCTGCGAGAGGCTGGGG<br>AGGAAGTTCCGGACGCTGGGCCGAGGGAGGGCGTGTCCTTTCCATGGAGTAGGCCTCCA<br>GGTCAAGGCGAGTTTAGGGCTCTCAACGCGCGGCTGCCGTTGAATACAGACGCTTATCTC<br>TCACTGCAGGAACTGCAAGGTCAGGACCCAACACATCTTGTAGGATCTGGTGCTACTAAT<br>TTTTCTCTTTTGAAGCAAGCTGGAGATGTTGAAGAGAACCCCGGTCCGGAGATGTGGCAT<br>GAGGGTCTGGAAGAAGCGTCTCGACTGTACTTTGGTGAGCGCAATGTGAAGGGCATGTTT<br>GAAGTCCTCGAACCCCTTCATGCCATGATGGAACGCGGACCCCAGACCTTGAAGGAGAC<br>AAGTTTTAACCAAGCTTACGGAAGAGACCTGATGGAAGCCCAGGAATGGTGCAGGAAAT<br>ACATGAAAAGCGGGAATGTGAAGGACTTGCTCCAAGCGTGGGACCTGTACTATCATGTCT<br>TTAGGCGCATTAGTAAG | CISCβ-DN nucleotide sequence (coding sequence only; codon-optimized; our DISC architecture version 6 |
| 88 | MALPVTALLLPLALLLHAARPILWHEMWHEGLEEASRLYFGERNVKGMFEVLEPLHAMMER<br>GPQTLKETSFNQAYGRDLMEAQEWCRKYMKSGNVKDLLQAWDLYYHVFRRISKPAALGKD<br>TIPWLGHLLVGLSGAFGFIILVYLLINCRNTGPWLKKVLKCNTPDPSKFFSQLSSEHGGDVQK<br>WLSSPFPSSSFSPGGLAPEISPLEVLERDKVTQLLLQQDKVPEPASLSSNHSLTSCFTNQGYFFF<br>HLPDALEIEACQVYFTYDPYSEEDPDEGVAGAPTGSSPQPLQPLSGEDDAYCTFPSRDDLLLFS<br>PSLLGGPSPPSTAPGGSGAGEERMPPSLQERVPRDWDPQPLGPPTPGVPDLVDFQPPPELVLRE<br>AGEEVPDAGPREGVSFPWSRPPGQGEFRALNARLPLNTDAYLSLQELQGQDPTHLVGSGATN<br>FSLLKQAGDVEENPGPEMWHEGLEEASRLYFGERNVKGMFEVLEPLHAMMERGPQTLKETS<br>FNQAYGRDLMEAQEWCRKYMKSGNVKDLLQAWDLYYHVFRRISK | CISCβ-DN amino acid sequence |
| 89 | ATGCCTCTGGGCCTGCTGTGGCTGGGCCTGGCCCTGCTGGGCGCCCTGCACGCCCAGGCC<br>GGCGTGCAGGTGGAGACAATCTCCCCAGGCGACGGACGCACATTCCCTAAGCGGGGCCA<br>GACCTGCGTGGTGCACTATACAGGCATGCTGGAGGATGGCAAGAAGTTTGACAGCTCCC<br>GGGATAGAAACAAGCCATTCAAGTTTATGCTGGGCAAGCAGGAAGTGATCAGAGGCTGG<br>GAGGAGGGCGTGGCCCAGATGTCTGTGGGCCAGAGGGCCAAGCTGACCATCAGCCCAGA<br>CTACGCCTATGGAGCAACAGGCCACCCAGGAATCATCCCACCTCACGCCACCCTGGTGTT<br>CGATGTGGAGCTGCTGAAGCTGGGCGAGGGAGGGTCACCTGGATCCAACACATCAAAAG<br>AGAACCCCTTTCTGTTCGCATTGGAGGCCGTAGTCATATCTGTTGGATCCATGGGACTTAT<br>TATCTCCCTGTTGTGTGTGTACTTCTGGCTGGAACGGACTATGCCCAGGATCCCCACGCTC<br>AAGAATCTGGAAGATCTCGTCACAGAATACCATGGTAATTTCAGCGCCTGGAGCGGAGT<br>CTCTAAGGGTCTGGCCGAATCCCTCCAACCCGATTATTCTGAACGGTTGTGCCTCGTATCC | CISCγ-FOXP3 cDNA-LNGFR nucleotide sequence (coding sequence only; codon-optimized; our DISC |

-continued

| SEQ ID NO | Sequence | Description |
|---|---|---|
| | GAAATACCACCAAAAGGCGGGGCTCTGGGTGAGGGCCCAGGGGCGAGTCCGTGCAATCA ACACAGCCCGTATTGGGCCCCTCCTTGTTATACGTTGAAGCCCGAAACTGGAAGCGGAGC GACTAACTTCAGCCTGCTTAAGCAGGCCGGAGATGTGGAGGAAAACCCTGGACCGATGC CTAATCCTCGGCCTGGAAAGCCTAGCGCTCCTTCTCTTGCTCTGGGACCTTCTCCTGGCGC CTCTCCATCTTGGAGAGCCGCTCCTAAAGCCAGCGATCTGCTGGGAGCTAGAGGACCTGG CGGCACATTTCAGGGCAGAGATCTTAGAGGCGGAGCCCACGCTAGCTCCTCCAGCCTTAA TCCTATGCCTCCTAGCCAGCTCCAGCTGCCTACACTGCCTCTGGTTATGGTGGCTCCTAGC GGAGCTAGACTGGGCCCTCTGCCTCATCTGCAAGCTCTGCTGCAGGACAGACCCCACTTC ATGCACCAGCTGAGCACCGTGGATGCCCACGCAAGAACACCTGTGCTGCAGGTTCACCCT CTGGAATCCCCAGCCATGATCAGCCTGACACCTCCAACAACAGCCACCGGCGTGTTCAGC CTGAAAGCCAGACCTGGACTGCCTCCTGGCATCAATGTGGCCAGCCTGGAATGGGTGTCC AGAGAACCTGCTCTGCTGTGCACATTCCCCAATCCAAGCGCTCCCAGAAAGGACAGCAC ACTGTCTGCCGTGCCTCAGAGCAGCTATCCCCTGCTTGCTAACGGCGTGTGCAAGTGGCC TGGATGCGAGAAGGTGTTCGAGGAACCCGAGGACTTCCTGAAGCACTGCCAGGCCGATC ATCTGCTGGACGAGAAAGGCAGAGCCCAGTGTCTGCTCCAGCGCGAGATGGTGCAGTCT CTGGAACAGCAGCTGGTCCTGGAAAAAGAAAAGCTGAGCGCCATGCAGGCCCACCTGGC CGGAAAAATGGCCCTGACAAAGGCCAGCAGCGTGGCCTCTTCTGATAAGGGCAGCTGCT GCATTGTGGCCGCTGGATCTCAGGGACCTGTGGTTCCTGCTTGGAGCGGACCTAGAGAGG CCCCTGATTCTCTGTTTGCCGTGCGGAGACACCTGTGGGGCTCTCACGGCAACTCTACTTT CCCCGAGTTCCTGCACAACATGGACTACTTCAAGTTCCACAACATGCGGCCTCCATTCAC CTACGCCACACTGATCAGATGGGCCATTCTGGAAGCCCCTGAGAAGCAGAGAACCCTGA ACGAGATCTACCACTGGTTTACCCGGATGTTCGCCTTCTTCCGGAATCACCCTGCCACCTG GAAGAACGCCATCCGGCACAATCTGAGCCTGCACAAGTGCTTCGTGCGCGTGGAATCTG AGAAAGGCGCCGTGTGGACAGTGGACGAGCTGGAATTCAGAAAGAAGAGAAGCCAGCG GCCTAGCCGGTGCAGCAATCCTACACCTGGACCTGGAAGCGGAGCGACTAACTTCAGCC TGCTGAAGCAGGCCGGAGATGTGGAGGAAAACCCTGGACCGATGGGGGCAGGTGCCACC GGACGAGCCATGGACGGGCCGCGCCTGCTGCTGTTGCTGCTTCTGGGGGTGTCCCTTGGA GGTGCCAAGGAGGCATGCCCCACAGGCCTGTACACACACAGCGGTGAGTGCTGCAAAGC CTGCAACCTGGGCGAGGGTGTGGCCCAGCCTTGTGGAGCCAACCAGACCGTGTGTGAGC CCTGCCTGGACAGCGTGACGTTCTCCGACGTGGTGAGCGCGACCGAGCCGTGCAAGCCG TGCACCGAGTGCGTGGGGCTCCAGAGCATGTCGGCGCCGTGCGTGGAGGCCGACGACGC CGTGTGCCGCTGCGCCTACGGCTACTACCAGGATGAGACGACTGGGCGCTGCGAGGCGT GCCGCGTGTGCGAGGCGGGCTCGGGCCTCGTGTTCTCCTGCCAGGACAAGCAGAACACC GTGTGCGAGGAGTGCCCCGACGGCACGTATTCCGACGAGGCCAACCACGTGGACCCGTG CCTGCCCTGCACCGTGTGCGAGGACACCGAGCGCCAGCTCCGCGAGTGCACACGCTGGG CCGACGCCGAGTGCGAGGAGATCCCTGGCCGTTGGATTACACGGTCCACACCCCCAGAG GGCTCGGACAGCACAGCCCCCAGCACCCAGGAGCCTGAGGCACCTCCAGAACAAGACCT CATAGCCAGCACGGTGGCAGGTGTGGTGACCACAGTGATGGGCAGCTCCCAGCCCGTGG TGACCCGAGGCACCACCGACAACCTCATCCCTGTCTATTGCTCCATCCTGGCTGCTGTGG TTGTGGGTCTTGTGGCCTACATAGCCTTCAAGAGGTGA | architecture version 6) |
| 90 | MPLGLLWLGLALLGALHAQAGVQVETISPGDGRTFPKRGQTCVVHYTGMLEDGKKFDSSRD RNKPFKFMLGKQEVIRGWEEGVAQMSVGQRAKLTISPDYAYGATGHPGIIPPHATLVFDVEL LKLGEGGSPGSNTSKENPFLFALEAVVISVGSMGLIISLLCVYFWLERTMPRIPTLKNLEDLVT EYHGNFSAWSGVSKGLAESLQPDYSERLCLVSEIPPKGGALGEGPGASPCNQHSPYWAPPCY TLKPETGSGATNFSLLKQAGDVEENPGPMPNPRPGKPSAPSLALGPSPGASPSWRAAPKASDL LGARGPGGTFQGRDLRGGAHASSSSLNPMPPSQLQLPTLPLVMVAPSGARLGPLPHLQALLQ DRPHFMHQLSTVDAHARTPVLQVHPLESPAMISLTPPTTATGVFSLKARPGLPPGINVASLEW VSREPALLCTFPNPSAPRKDSTLSAVPQSSYPLLANGVCKWPGCEKVFEEPEDFLKHCQADHL LDEKGRAQCLLQREMVQSLEQQLVLEKEKLSAMQAHLAGKMALTKASSVASSDKGSCCIVA AGSQGPVVPAWSGPREAPDSLFAVRRHLWGSHGNSTFPEFLHNMDYFKFHNMRPPFTYATLI RWAILEAPEKQRTLNEIYHWFTRMFAFFRNHPATWKNAIRHNLSLHKCFVRVESEKGAVWT VDELEFRKKRSQRPSRCSNPTPGPGSGATNFSLLKQAGDVEENPGPMGAGATGRAMDGPRLL LLLLLGVSLGGAKEACPTGLYTHSGECCKACNLGEGVAQPCGANQTVCEPCLDSVTFSDVVS ATEPCKPCTECVGLQSMSAPCVEADDAVCRCAYGYYQDETTGRCEACRVCEAGSGLVFSCQ DKQNTVCEECPDGTYSDEANHVDPCLPCTVCEDTERQLRECTRWADAECEEIPGRWITRSTP PEGSDSTAPSTQEPEAPPEQDLIASTVAGVVTTVMGSSQPVVTRGTTDNLIPVYCSILAAVVV GLVAYIAFKR* | CISCγ-FOXP3 cDNA-LNGFR amino acid sequence |
| 91 | ATGCCTCTGGGCCTGCTGTGGCTGGGCCTGGCCCTGCTGGGCGCCCTGCACGCCCAGGCC GGCGTGCAGGTGGAGACAATCTCCCCAGGCGACGGACGCACATTCCCTAAGCGGGGCCA GACCTGCGTGGTGCACTATACAGGCATGCTGGAGGATGGCAAGAAGTTTGACAGCTCCC GGGATAGAAACAAGCCATTCAAGTTTATGCTGGGCAAGCAGGAAGTGATCAGAGGCTGG GAGGAGGGCGTGGCCCAGATGTCTGTGGGCCAGAGGGCCAAGCTGACCATCAGCCCAGA CTACGCCTATGGAGCAACAGGCCACCCAGGAATCATCCCACCTCACGCCACCCTGGTGTT CGATGTGGAGCTGCTGAAGCTGGGCGAGGGAGGGTCACCTGGATCCAACACATCAAAAG AGAACCCCTTTCTGTTCGCATTGGAGGCCGTAGTCATATCTGTTGGATCCATGGGACTTAT TATCTCCCTGTTGTGTGTGTACTTCTGGCTGGAACGGACTATGCCCAGGATCCCCACGCTC AAGAATCTGGAAGATCTCGTCACAGAATACCATGGTAATTTCAGCGCCTGGAGCGGAGT CTCTAAGGGTCTGGCCGAATCCCTCCAACCCGATTATTCTGAACGGTTGTGCCTCGTATCC GAAATACCACCAAAAGGCGGGGCTCTGGGTGAGGGCCCAGGGGCGAGTCCGTGCAATCA ACACAGCCCGTATTGGGCCCCTCCTTGTTATACGTTGAAGCCCGAAACTGGAAGCGGAGC GACTAACTTCAGCCTGCTTAAGCAGGCCGGAGATGTGGAGGAAAACCCTGGACCGATGG GGGCAGGTGCCACCGGACGAGCCATGGACGGGCCGCGCCTGCTGCTGTTGCTGCTTCTGG GGGTGTCCCTTGGAGGTGCCAAGGAGGCATGCCCCACAGGCCTGTACACACACAGCGGT | CISCγ-LNGFR-FOXP3 cDNA nucleotide sequence (coding sequence only; codon-optimized; our DISC architecture version 6) |

-continued

| SEQ ID NO | Sequence | Description |
|---|---|---|
| | GAGTGCTGCAAAGCCTGCAACCTGGGCGAGGGTGTGGCCCAGCCTTGTGGAGCCAACCA<br>GACCGTGTGTGAGCCCTGCCTGGACAGCGTGACGTTCTCCGACGTGGTGAGCGCGACCG<br>AGCCGTGCAAGCCGTGCACCGAGTGCGTGGGGCTCCAGAGCATGTCGGCGCCGTGCGTG<br>GAGGCCGACGACGCCGTGTGCCGCTGCGCCTACGGCTACTACCAGGATGAGACGACTGG<br>GCGCTGCGAGGCGTGCCGCGTGTGCGAGGCGGGCTCGGGCCTCGTGTTCTCCTGCCAGGA<br>CAAGCAGAACACCGTGTGCGAGGAGTGCCCCGACGGCACGTATTCCGACGAGGCCAACC<br>ACGTGGACCCGTGCCTGCCCTGCACCGTGTGCGAGGACACCGAGCGCCAGCTCCGCGAG<br>TGCACACGCTGGGCCGACGCCGAGTGCGAGGAGATCCCTGGCCGTTGGATTACACGGTC<br>CACACCCCCAGAGGGCTCGGACAGCACAGCCCCCAGCACCCAGGAGCCTGAGGCACCTC<br>CAGAACAAGACCTCATAGCCAGCACGGTGGCAGGTGTGGTGACCACAGTGATGGGCAGC<br>TCCCAGCCCGTGGTGACCCGAGGCACCACCGACAACCTCATCCCTGTCTATTGCTCCATC<br>CTGGCTGCTGTGGTTGTGGGTCTTGTGGCCTACATAGCCTTCAAGAGGGGAAGCGGAGCG<br>ACTAACTTCAGCCTGCTGAAGCAGGCCGGAGATGTGGAGGAAAACCCTGGACCGATGCC<br>TAATCCTCGGCCTGGAAAGCCTAGCGCTCCTTCTCTTGCTCTGGGACCTTCTCCTGGCGCC<br>TCTCCATCTTGGAGAGCCGCTCCTAAAGCCAGCGATCTGCTGGGAGCTAGAGGACCTGGC<br>GGCACATTTCAGGGCAGAGATCTTAGAGGCGGAGCCCACGCTAGCTCCTCCAGCCTTAAT<br>CCTATGCCTCCTAGCCAGCTCCAGCTGCCTACACTGCCTCTGGTTATGGTGGCTCCTAGCG<br>GAGCTAGACTGGGCCCTCTGCCTCATCTGCAAGCTCTGCTGCAGGACAGACCCCACTTCA<br>TGCACCAGCTGAGCACCGTGGATGCCCACGCAAGAACACCTGTGCTGCAGGTTCACCCTC<br>TGGAATCCCCAGCCATGATCAGCCTGACACCTCCAACAACAGCCACCGGCGTGTTCAGCC<br>TGAAAGCCAGACCTGGACTGCCTCCTGGCATCAATGTGGCCAGCCTGGAATGGGTGTCCA<br>GAGAACCTGCTCTGCTGTGCACATTCCCCAATCCAAGCGCTCCCAGAAAGGACAGCACA<br>CTGTCTGCCGTGCCTCAGAGCAGCTATCCCCTGCTTGCTAACGGCGTGTGCAAGTGGCCT<br>GGATGCGAGAAGGTGTTCGAGGAACCCGAGGACTTCCTGAAGCACTGCCAGGCCGATCA<br>TCTGCTGGACGAGAAAGGCAGAGCCCAGTGTCTGCTCCAGCGCGAGATGGTGCAGTCTC<br>TGGAACAGCAGCTGGTCCTGGAAAAAGAAAAGCTGAGCGCCATGCAGGCCCACCTGGCC<br>GGAAAAATGGCCCTGACAAAGGCCAGCAGCGTGGCCTCTTCTGATAAGGGCAGCTGCTG<br>CATTGTGGCCGCTGGATCTCAGGGACCTGTGGTTCCTGCTTGGAGCGGACCTAGAGAGGC<br>CCCTGATTCTCTGTTTGCCGTGCGGAGACACCTGTGGGGCTCTCACGGCAACTCTACTTTC<br>CCCGAGTTCCTGCACAACATGGACTACTTCAAGTTCCACAACATGCGGCCTCCATTCACC<br>TACGCCACACTGATCAGATGGGCCATTCTGGAAGCCCCTGAGAAGCAGAGAACCCTGAA<br>CGAGATCTACCACTGGTTTACCCGGATGTTCGCCTTCTTCCGGAATCACCCTGCCACCTGG<br>AAGAACGCCATCCGGCACAATCTGAGCCTGCACAAGTGCTTCGTGCGCGTGGAATCTGA<br>GAAAGGCGCCGTGTGGACAGTGGACGAGCTGGAATTCAGAAAGAAGAGAAGCCAGCGG<br>CCTAGCCGGTGCAGCAATCCTACACCTGGACCTTGA | |
| 92 | ATGCCTCTGGGCCTGCTGTGGCTGGGCCTGGCCCTGCTGGGCGCCCTGCACGCCCAGGCC<br>GGCGTGCAGGTGGAGACAATCTCCCCAGGCGACGGACGCACATTCCCTAAGCGGGGCCA<br>GACCTGCGTGGTGCACTATACAGGCATGCTGGAGGATGGCAAGAAGTTTGACAGCTCCC<br>GGGATAGAAACAAGCCATTCAAGTTTATGCTGGGCAAGCAGGAAGTGATCAGAGGCTGG<br>GAGGAGGGCGTGGCCCAGATGTCTGTGGGCCAGAGGGCCAAGCTGACCATCAGCCCAGA<br>CTACGCCTATGGAGCAACAGGCCACCCAGGAATCATCCCACCTCACGCCACCCTGGTGTT<br>CGATGTGGAGCTGCTGAAGCTGGGCGAGGGAGGGTCACCTGGATCCAACACATCAAAAG<br>AGAACCCCTTTCTGTTCGCATTGGAGGCCGTAGTCATATCTGTTGGATCCATGGGACTTAT<br>TATCTCCCTGTTGTGTGTGTACTTCTGGCTGGAACGGACTATGCCCAGGATCCCCACGCTC<br>AAGAATCTGGAAGATCTCGTCACAGAATACCATGGTAATTTCAGCGCCTGGAGCGGAGT<br>CTCTAAGGGTCTGGCCGAATCCCTCCAACCCGATTATTCTGAACGGTTGTGCCTCGTATCC<br>GAAATACCACCAAAAGGCGGGGCTCTGGGTGAGGGCCCAGGGGCGAGTCCGTGCAATCA<br>ACACAGCCCGTATTGGGCCCCTCCTTGTTATACGTTGAAGCCCGAAACTGGAAGCGGAGC<br>GACTAACTTCAGCCTGCTTAAGCAGGCCGGAGATGTGGAGGAAAACCCTGGACCGATGG<br>GGGCAGGTGCCACCGGACGAGCCATGGACGGGCCGCGCCTGCTGCTGTTGCTGCTTCTGG<br>GGGTGTCCCTTGGAGGTGCCAAGGAGGCATGCCCCACAGGCCTGTACACACACAGCGGT<br>GAGTGCTGCAAAGCCTGCAACCTGGGCGAGGGTGTGGCCCAGCCTTGTGGAGCCAACCA<br>GACCGTGTGTGAGCCCTGCCTGGACAGCGTGACGTTCTCCGACGTGGTGAGCGCGACCG<br>AGCCGTGCAAGCCGTGCACCGAGTGCGTGGGGCTCCAGAGCATGTCGGCGCCGTGCGTG<br>GAGGCCGACGACGCCGTGTGCCGCTGCGCCTACGGCTACTACCAGGATGAGACGACTGG<br>GCGCTGCGAGGCGTGCCGCGTGTGCGAGGCGGGCTCGGGCCTCGTGTTCTCCTGCCAGGA<br>CAAGCAGAACACCGTGTGCGAGGAGTGCCCCGACGGCACGTATTCCGACGAGGCCAACC<br>ACGTGGACCCGTGCCTGCCCTGCACCGTGTGCGAGGACACCGAGCGCCAGCTCCGCGAG<br>TGCACACGCTGGGCCGACGCCGAGTGCGAGGAGATCCCTGGCCGTTGGATTACACGGTC<br>CACACCCCCAGAGGGCTCGGACAGCACAGCCCCCAGCACCCAGGAGCCTGAGGCACCTC<br>CAGAACAAGACCTCATAGCCAGCACGGTGGCAGGTGTGGTGACCACAGTGATGGGCAGC<br>TCCCAGCCCGTGGTGACCCGAGGCACCACCGACAACCTCATCCCTGTCTATTGCTCCATC<br>CTGGCTGCTGTGGTTGTGGGTCTTGTGGCCTACATAGCCTTCAAGAGGGGAAGCGGAGCG<br>ACTAACTTCAGCCTGCTGAAGCAGGCCGGAGATGTGGAGGAAAACCCTGGACCGATGCC<br>TAATCCTCGGCCTGGAAAGCCTAGCGCTCCTTCTCTTGCTCTGGGACCTTCTCCTGGCGCC<br>TCTCCATCTTGGAGAGCCGCTCCTAAAGCCAGCGATCTGCTGGGAGCTAGAGGACCTGGC<br>GGCACATTTCAGGGCAGAGATCTTAGAGGCGGAGCCCACGCTAGCTCCTCCAGCCTTAAT<br>CCTATGCCTCCTAGCCAGCTCCAGCTGCCTACACTGCCTCTGGTTATGGTGGCTCCTAGCG<br>GAGCTAGACTGGGCCCTCTGCCTCATCTGCAAGCTCTGCTGCAGGACAGACCCCACTTCA<br>TGCACCAGCTGAGCACCGTGGATGCCCACGCAAGAACACCTGTGCTGCAGGTTCACCCTC<br>TGGAATCCCCAGCCATGATCAGCCTGACACCTCCAACAACAGCCACCGGCGTGTTCAGCC<br>TGAAAGCCAGACCTGGACTGCCTCCTGGCATCAATGTGGCCAGCCTGGAATGGGTGTCCA<br>GAGAACCTGCTCTGCTGTGCACATTCCCCAATCCAAGCGCTCCCAGAAAGGACAGCACA<br>CTGTCTGCCGTGCCTCAGAGCAGCTATCCCCTGCTTGCTAACGGCGTGTGCAAGTGGCCT | CISCγ-<br>LNGFR-<br>FOXP3<br>cDNA |

-continued

| SEQ ID NO | Sequence | Description |
|---|---|---|
| | GGATGCGAGAAGGTGTTCGAGGAACCCGAGGACTTCCTGAAGCACTGCCAGGCCGATCA TCTGCTGGACGAGAAAGGCAGAGCCCAGTGTCTGCTCCAGCGCGAGATGGTGCAGTCTC TGGAACAGCAGCTGGTCCTGGAAAAAGAAAAGCTGAGCGCCATGCAGGCCCACCTGGCC GGAAAAATGGCCCTGACAAAGGCCAGCAGCGTGGCCTCTTCTGATAAGGGCAGCTGCTG CATTGTGGCCGCTGGATCTCAGGGACCTGTGGTTCCTGCTTGGAGCGGACCTAGAGAGGC CCCTGATTCTCTGTTTGCCGTGCGGAGACACCTGTGGGGCTCTCACGGCAACTCTACTTTC CCCGAGTTCCTGCACAACATGGACTACTTCAAGTTCCACAACATGCGGCCTCCATTCACC TACGCCACACTGATCAGATGGGCCATTCTGGAAGCCCCTGAGAAGCAGAGAACCCTGAA CGAGATCTACCACTGGTTTACCCGGATGTTCGCCTTCTTCCGGAATCACCCTGCCACCTGG AAGAACGCCATCCGGCACAATCTGAGCCTGCACAAGTGCTTCGTGCGCGTGGAATCTGA GAAAGGCGCCGTGTGGACAGTGGACGAGCTGGAATTCAGAAAGAAGAGAAGCCAGCGG CCTAGCCGGTGCAGCAATCCTACACCTGGACCTTGA | |
| 93 | MPLGLLWLGLALLGALHAQAGVQVETISPGDGRTFPKRGQTCVVHYTGMLEDGKKFDSSRD RNKPFKFMLGKQEVIRGWEEGVAQMSVGQRAKLTISPDYAYGATGHPGIIPPHATLVFDVEL LKLGEGSNTSKENPFLFALEAVVISVGSMGLIISLLCVYFWLERTMPRIPTLKNLEDLVTEYHG NFSAWSGVSKGLAESLQPDYSERLCLVSEIPPKGGALGEGPGASPCNQHSPYWAPPCYTLKPE T | IL2Rγ-CISC amino acid sequence |
| 94 | (MALPVTALLLPLALLLHAARPILWHEMWHEGLEEASRLYFGERNVKGMFEVLEPLHAMME RGPQTLKETSFNQAYGRDLMEAQEWCRKYMKSGNVKDLLQAWDLYYHVFRRISKGKDTIP WLGHLLVGLSGAFGFIILVYLLINCRNTGPWLKKVLKCNTPDPSKFFSQLSSEHGGDVQKWL SSPFPSSSFSPGGLAPEISPLEVLERDKVTQLLLQQDKVPEPASLSSNHSLTSCFTNQGYFFFHLP DALEIEACQVYFTYDPYSEEDPDEGVAGAPTGSSPQPLQPLSGEDDAYCTFPSRDDLLLFSPSL LGGPSPPSTAPGGSGAGEERMPPSLQERVPRDWDPQPLGPPTPGVPDLVDFQPPPELVLREAG EEVPDAGPREGVSFPWSRPPGQGEFRALNARLPLNTDAYLSLQELQGQDPTHLV | IL2Rβ-CISC |
| 95 | (MPLGLLWLGLALLGALHAQAGVQVETISPGDGRTFPKRGQTCVVHYTGMLEDGKKFDSSR DRNKPFKFMLGKQEVIRGWEEGVAQMSVGQRAKLTISPDYAYGATGHPGIIPPHATLVFDVE LLKLEGGGSQNLVIPWAPENLTLHKLSESQLELNWNNRFLNHCLEHLVQYRTDWDHSWTEQ SVDYRHKFSLPSVDGQKRYTFRVRSRFNPLCGSAQHWSEWSHPIHWGSNTSKENPFLFALEA VVISVGSMGLIISLLCVYFWLERTMPRIPTLKNLEDLVTEYHGNFSAWSGVSKGLAESLQPDY SERLCLVSEIPPKGGALGEGPGASPCNQHSPYWAPPCYTLKPET | IL2Rγ-CISC |
| 96 | (MALPVTALLLPLALLLHAARPILWHEMWHEGLEEASRLYFGERNVKGMFEVLEPLHAMME RGPQTLKETSFNQAYGRDLMEAQEWCRKYMKSGNVKDLLQAWDLYYHVFRRISKGGSKPF ENLRLMAPISLQVVHVETHRCNISWEISQASHYFERHLEFEARTLSPGHTWEEAPLLTLKQKQ EWICLETLTPDTQYEFQVRVKPLQGEFTTWSPWSQPLAFRTKPAALGKDTIPWLGHLLVGLS GAFGFIILVYLLINCRNTGPWLKKVLKCNTPDPSKFFQLSSEHGGDVQKWLSSPFPSSSFSPGG LAPEISPLEVLERDKVTQLLLQQDKVPEPASLSSNHSLTSCFTNQGYFFFHLPDALEIEACQVY FTYDPYSEEDPDEGVAGAPTGSSPQPLQPLSGEDDAYCTFPSRDDLLLFSPSLLGGPSPPSTAP GGSGAGEERMPPSLQERVPRDWDPQPLGPPTPGVPDLVDFQPPPELVLREAGEEVPDAGPRE GVSFPWSRPPGQGEFRALNARLPLNTDAYLSLQELQGQDPTHLV | IL2Rβ-CISC |
| 97 | (MPLGLLWLGLALLGALHAQAGVQVETISPGDGRTFPKRGQTCVVHYTGMLEDGKKFDSSR DRNKPFKFMLGKQEVIRGWEEGVAQMSVGQRAKLTISPDYAYGATGHPGIIPPHATLVFDVE LLKLEGQNLVIPWAPENLTLHKLSESQLELNWNNRFLNHCLEHLVQYRTDWDHSWTEQSVD YRHKFSLPSVDGQKRYTFRVRSRFNPLCGSAQHWSEWSHPIHWGSNTSKENPFLFALEAVVIS VGSMGLIISLLCVYFWLERTMPRIPTLKNLEDLVTEYHGNFSAWSGVSKGLAESLQPDYSERL CLVSEIPPKGGALGEGPGASPCNQHSPYWAPPCYTLKPET | IL2Rγ-CISC |
| 98 | (MALPVTALLLPLALLLHAARPILWHEMWHEGLEEASRLYFGERNVKGMFEVLEPLHAMME RGPQTLKETSFNQAYGRDLMEAQEWCRKYMKSGNVKDLLQAWDLYYHVFRRISKKPFENL RLMAPISLQVVHVETHRCNISWEISQASHYFERHLEFEARTLSPGHTWEEAPLLTLKQKQEWI CLETLTPDTQYEFQVRVKPLQGEFTTWSPWSQPLAFRTKPAALGKDTIPWLGHLLVGLSGAF GFIILVYLLINCRNTGPWLKKVLKCNTPDPSKFFSQLSSEHGGDVQKWLSSPFPSSSFSPGGLA PEISPLEVLERDKVTQLLLQQDKVPEPASLSSNHSLTSCFTNQGYFFFHLPDALEIEACQVYFT YDPYSEEDPDEGVAGAPTGSSPQPLQPLSGEDDAYCTFPSRDDLLLFSPSLLGGPSPPSTAPGG SGAGEERMPPSLQERVPRDWDPQPLGPPTPGVPDLVDFQPPPELVLREAGEEVPDAGPREGVS FPWSRPPGQGEFRALNARLPLNTDAYLSLQELQGQDPTHLV | IL2Rβ-CISC |
| 99 | (MPLGLLWLGLALLGALHAQAGVQVETISPGDGRTFPKRGQTCVVHYTGMLEDGKKFDSSR DRNKPFKFMLGKQEVIRGWEEGVAQMSVGQRAKLTISPDYAYGATGHPGIIPPHATLVFDVE LLKLEGGSNTSKENPFLFALEAVVISVGSMGLIISLLCVYFWLERTMPRIPTLKNLEDLVTEYH GNFSAWSGVSKGLAESLQPDYSERLCLVSEIPPKGGALGEGPGASPCNQHSPYWAPPCYTLK PET | IL2Rγ-CISC |
| 100 | (MALPVTALLLPLALLLHAARPILWHEMWHEGLEEASRLYFGERNVKGMFEVLEPLHAMME RGPQTLKETSWLGHLLVGLSGAFGFIILVYLLINCRNTGPWLKKVLKCNTPDPSKFFSQLSSEH GGDVQKWLSSPFPSSSFSPGGLAPEISPLEVLERDKVTQLLLQQDKVPEPASLSSNHSLTSCFT NQGYFFFHLPDALEIEACQVYFTYDPYSEEDPDEGVAGAPTGSSPQPLQPLSGEDDAYCTFPS RDDLLLFSPSLLGGPSPPSTAPGGSGAGEERMPPSLQERVPRDWDPQPLGPPTPGVPDLVDFQ PPPELVLREAGEEVPDAGPREGVSFPWSRPPGQGEFRALNARLPLNTDAYLSLQELQGQDPTH LV | IL2Rβ-CISC |

-continued

| SEQ ID NO | Sequence | Description |
|---|---|---|
| 101 | (MALPVTALLLPLALLLHAARPILWHEMWHEGLEEASRLYFGERNVKGMFEVLEPLHAMME<br>RGPQTLKETSFNQAYGRDLMEAQEWCRKYMKSGNVKDLLQAWDLYYHVFRRISKGEINNS<br>SGEMDPILLTISILSFFSVALLVILACVLWKKRIKPIVWPSLPDHKKTLEHLCKKPRKNLNVSFN<br>PESFLDCQIHRVDDIQARDEVEGFLQDTFPQQLEESEKQRLGGDVQSPNCPSEDVVITPESFGR<br>DSSLTCLAGNVSACDAPILSSSRSLDCRESGKNGPHVYQDLLLSLGTTNSTLPPPFSLQSGILTL<br>NPVAQGQPILTSLGSNQEEAYVTMSSFYQNQ | IL7Rα-CISC |
| 102 | (MPLGLLWLGLALLGALHAQAGVQVETISPGDGRTFPKRGQTCVVHYTGMLEDGKKVDSSR<br>DRNKPFKFMLGKQEVIRGWEEGVAQMSVGQRAKLTISPDYAYGATGHPGIIPPHATLVFDVE<br>LLKLEGGKDTIPWLGHLLVGLSGAFGFIILVYLLINCRNTGPWLKKVLKCNTPDPSKFFSQLSS<br>EHGGDVQKWLSSPFPSSSFSPGGLAPEISPLEVLERDKVTQLLLQQDKVPEPASLSSNHSLTSC<br>FTNQGYFFFHLPDALEIEACQVYFTYDPYSEEDPDEGVAGAPTGSSPQPLQPLSGEDDAYCTF<br>PSRDDLLLFSPSLLGGPSPPSTAPGGSGAGEERMPPSLQERVPRDWDPQPLGPPTPGVPDLVDF<br>QPPPELVLREAGEEVPDAGPREGVSFPWSRPPGQGEFRALNARLPLNTDAYLSLQELQGQDPT<br>HLV | IL2Rβ-CISC |
| 103 | (MPLGLLWLGLALLGALHAQAGVQVETISPGDGRTFPKRGQTCVVHYTGMLEDGKKVDSSR<br>DRNKPFKFMLGKQEVIRGWEEGVAQMSVGQRAKLTISPDYAYGATGHPGIIPPHATLVFDVE<br>LLKLEGGSNTSKENPFLFALEAVVISVGSMGLIISLLCVYFWLERTMPRIPTLKNLEDLVTEYH<br>GNFSAWSGVSKGLAESLQPDYSERLCLVSEIPPKGGALGEGPGASPCNQHSPYWAPPCYTLK<br>PET | IL2Rγ-CISC |
| 104 | (MPLGLLWLGLALLGALHAQAGVQVETISPGDGRTFPKRGQTCVVHYTGMLEDGKKVDSSR<br>DRNKPFKFMLGKQEVIRGWEEGVAQMSVGQRAKLTISPDYAYGATGHPGIIPPHATLVFDVE<br>LLKLEGEINNSSGEMDPILLTISILSFFSVALLVILACVLWKKRIKPIVWPSLPDHKKTLEHLCK<br>KPRKNLNVSFNPESFLDCQIHRVDDIQARDEVEGFLQDTFPQQLEESEKQRLGGDVQSPNCPS<br>EDVVITPESFGRDSSLTCLAGNVSACDAPILSSSRSLDCRESGKNGPHVYQDLLLSLGTTNSTL<br>PPPFSLQSGILTLNPVAQGQPILTSLGSNQEEAYVTMSSFYQNQ | IL2Rα-CISC |
| 105 | (MPLGLLWLGLALLGALHAQAGVQVETISPGDGRTFPKRGQTCVVHYTGMLEDGKKVDSSR<br>DRNKPFKFMLGKQEVIRGWEEGVAQMSVGQRAKLTISPDYAYGATGHPGIIPPHATLVFDVE<br>LLKLEGEINNSSGEMDPILLTISILSFFSVALLVILACVLWKKRIKPIVWPSLPDHKKTLEHLCK<br>KPRKNLNVSFNPESFLDCQIHRVDDIQARDEVEGFLQDTFPQQLEESEKQRLGGDVQSPNCPS<br>EDVVITPESFGRDSSLTCLAGNVSACDAPILSSSRSLDCRESGKNGPHVYQDLLLSLGTTNSTL<br>PPPFSLQSGILTLNPVAQGQPILTSLGSNQEEAYVTMSSFYQNQ | IL7Rα-CISC |
| 106 | ((MPLGLLWLGLALLGALHAQAGVQVETISPGDGRTFPKRGQTCVVHYTGMLEDGKKVDSSR<br>DRNKPFKFMLGKQEVIRGWEEGVAQMSVGQRAKLTISPDYAYGATGHPGIIPPHATLVFDVE<br>LLKLGEETAWISLVTALHLVLGLSAVLGLLLLRWQFPAHYRRLRHALWPSLPDLHRVLGQYL<br>RDTAALSPPKATVSDTCEEVEPSLLEILPKSSERTPLPLCSSQAQMDYRRLQPSCLGTMPLSVC<br>PPMAESGSCCTTHIANHSYLPLSYWQQP | MPL-CISC |
| 107 | ((AGCTTAATGTAGTCTTATGCAATACTCTTGTAGTCTTGCAACATGGTAACGATGAGTTA<br>GCAACATGCCTTACAAGGAGAGAAAAAGCACCGTGCATGCCGATTGGTGGAAGTAAGGT<br>GGTACGATCGTGCCTTATTAGGAAGGCAACAGACGGGTCTGACATGGATTGGACGAACC<br>ACTGAATTGCCGCATTGCAGAGATATTGTATTTAAGTGCCTAGCTCGATACAATAAACGG<br>GTCTCTCTGGTTAGACCAGATCTGAGCCTGGGAGCTCTCTGGCTAACTAGGGAACCCACT<br>GCTTAAGCCTCAATAAAGCTTGCCTTGAGTGCTTCAAGTAGTGTGTGCCCGTCTGTTGTGT<br>GACTCTGGTAACTAGAGATCCCTCAGACCCTTTTAGTCAGTGTGGAAAATCTCTAGCAGT<br>GGCGCCCGAACAGGGACTTGAAAGCGAAAGGGAAACCAGAGGAGCTCTCTCGACGCAG<br>GACTCGGCTTGCTGAAGCGCGCACGGCAAGAGGCGAGGGGCGGCGACTGGTGAGTACGC<br>CAAAAATTTTGACTAGCGGAGGCTAGAAGGAGAGAGATGGGTGCGAGAGCGTCAGTATT<br>AAGCGGGGGAGAATTAGATCGCGATGGGAAAAAATTCGGTTAAGGCCAGGGGGAAAGA<br>AAAAATATAAATTAAAACATATAGTATGGGCAAGCAGGGAGCTAGAACGATTCGCAGTT<br>AATCCTGGCCTGTTAGAAACATCAGAAGGCTGTAGACAAATACTGGGACAGCTACAACC<br>ATCCCTTCAGACAGGATCAGAAGAACTTAGATCATTATATAATACAGTAGCAACCCTCTA<br>TTGTGTGCATCAAAGGATAGAGATAAAAGACACCAAGGAAGCTTTAGACAAGATAGAGG<br>AAGAGCAAAACAAAAGTAAGACCACCGCACAGCAAGCGGCCGCTGATCTTCAGACCTGG<br>AGGAGGAGATATGAGGGACAATTGGAGAAGTGAATTATATAAATATAAAGTAGTAAAAA<br>TTGAACCATTAGGAGTAGCACCCACCAAGGCAAAGAGAAGAGTGGTGCAGAGAGAAAA<br>AAGAGCAGTGGGAATAGGAGCTTTGTTCCTTGGGTTCTTGGGAGCAGCAGGAAGCACTA<br>TGGGCGCAGCCTCAATGACGCTGACGGTACAGGCCAGACAATTATTGTCTGGTATAGTGC<br>AGCAGCAGAACAATTTGCTGAGGGCTATTGAGGCGCAACAGCATCTGTTGCAACTCACA<br>GTCTGGGGCATCAAGCAGCTCCAGGCAAGAATCCTGGCTGTGGAAAGATACCTAAAGGA<br>TCAACAGCTCCTGGGGATTTGGGGTTGCTCTGGAAAACTCATTTGCACCACTGCTGTGCC<br>TTGGAATGCTAGTTGGAGTAATAAATCTCTGGAACAGATTTGGAATCACACGACCTGGAT<br>GGAGTGGGACAGAGAAATTAACAATTACACAAGCTTAATACACTCCTTAATTGAAGAAT<br>CGCAAAACCAGCAAGAAAAGAATGAACAAGAATTATTGGAATTAGATAAATGGGCAAGT<br>TTGTGGAATTGGTTTAACATAACAAATTGGCTGTGGTATATAAAATTATTCATAATGATA<br>GTAGGAGGCTTGGTAGGTTTAAGAATAGTTTTTGCTGTACTTTCTATAGTGAATAGAGTT<br>AGGCAGGGATATTCACCATTATCGTTTCAGACCCACCTCCCAACCCCGAGGGGACCCGAC<br>AGGCCCGAAGGAATAGAAGAAGAAGGTGGAGAGAGAGACAGAGACAGATCCATTCGAT<br>TAGTGAACGGATCTCGACGGTATCGGTTAACTTTTAAAAGAAAAGGGGGGATTGGGGG<br>TACAGTGCAGGGGAAAGAATAGTAGACATAATAGCAACAGACATACAAACTAAAGAATT<br>ACAAAAACAAATTACAAAAATTCAAAATTTTATCGATCACGAGACTAGCCTCGAGAAGC | Expression vector |

-continued

| SEQ ID NO | Sequence | Description |
|---|---|---|
| | TTGATATCGAATTCCCACGGGGTTGGACGCGTAGGAACAGAGAAACAGGAGAATATGGG<br>CCAAACAGGATATCTGTGGTAAGCAGTTCCTGCCCCGGCTCAGGGCCAAGAACAGTTGG<br>AACAGCAGAATATGGGCCAAACAGGATATCTGTGGTAAGCAGTTCCTGCCCCGGCTCAG<br>GGCCAAGAACAGATGGTCCCCAGATGCGGTCCCGCCCTCAGCAGTTTCTAGAGAACCAT<br>CAGATGTTTCCAGGGTGCCCCAAGGACCTGAAATGACCCTGTGCCTTATTTGAACTAACC<br>AATCAGTTCGCTTCTCGCTTCTGTTCGCGCGCTTCTGCTCCCCGAGCTCTATATAAGCAGA<br>GCTCGTTTAGTGAACCGTCAGATCGCTAGCACCGGTGCCGCCACCATGCCTCTGGGCCTG<br>CTGTGGCTGGGCCTGGCCCTGCTGGGCGCCCTGCACGCCCAGGCCGGCGTGCAGGTGGA<br>GACAATCTCCCCAGGCGACGGACGCACATTCCCTAAGCGGGGCCAGACCTGCGTGGTGC<br>ACTATACAGGCATGCTGGAGGATGGCAAGAAGTTTGACAGCTCCCGGGATAGAAACAAG<br>CCATTCAAGTTTATGCTGGGCAAGCAGGAAGTGATCAGAGGCTGGGAGGAGGGCGTGGC<br>CCAGATGTCTGTGGGCCAGAGGGCCAAGCTGACCATCAGCCCAGACTACGCCTATGGAG<br>CAACAGGCCACCCAGGAATCATCCCACCTCACGCCACCCTGGTGTTCGATGTGGAGCTGC<br>TGAAGCTGGGCGAGGGCGGTAGTCAGAACCTTGTGATACCATGGGCCCCAGAAAATCTC<br>ACACTTCATAAACTTTCCGAATCACAACTCGAACTCAACTGGAATAACCGGTTCCTGAAT<br>CACTGTCTTGAACACCTGGTACAATATCGGACCGACTGGGATCACTCATGGACAGAACA<br>ATCTGTGGACTATAGGCACAAATTCTCACTCCCAAGCGTAGACGGCCAAAAAAGATACA<br>CTTTTCGCGTACGATCCCGCTTTAATCCTCTCTGCGGCTCTGCTCAGCACTGGAGTGAATG<br>GTCCCATCCCATTCATTGGGGATCCAACACATCAAAAGAGAACCCCTTTCTGTTCGCATT<br>GGAGGCCGTAGTCATATCTGTTGGATCCATGGGACTTATTATCTCCCTGTTGTGTGTGTAC<br>TTCTGGCTGGAACGGACTATGCCCAGGATCCCCACGCTCAAGAATCTGGAAGATCTCGTC<br>ACAGAATACCATGGTAATTTCAGCGCCTGGAGCGGAGTCTCTAAGGGTCTGGCCGAATCC<br>CTCCAACCCGATTATTCTGAACGGTTGTGCCTCGTATCCGAAATACCACCAAAAGGCGGG<br>GCTCTGGGTGAGGGCCCAGGGGCGAGTCCGTGCAATCAACACAGCCCGTATTGGGCCCC<br>TCCTTGTTATACGTTGAAGCCCGAAACTGGAAGCGGAGCTACTAACTTCAGCCTGCTGAA<br>GCAGGCTGGAGACGTGGAGGAGAACCCTGGACCTATGGCACTGCCCGTGACCGCCCTGC<br>TGCTGCCTCTGGCCCTGCTGCTGCACGCAGCCCGGCCTATCCTGTGGCACGAGATGTGGC<br>ACGAGGGCCTGGAGGAGGCCAGCAGGCTGTATTTTGGCGAGCGCAACGTGAAGGGCATG<br>TTCGAGGTGCTGGAGCCTCTGCACGCCATGATGGAGAGAGGCCCACAGACCCTGAAGGA<br>GACATCCTTTAACCAGGCCTATGGACGGGACCTGATGGAGGCACAGGAGTGGTGCAGAA<br>AGTACATGAAGTCTGGCAATGTGAAGGACCTGCTGCAGGCCTGGGATCTGTACTATCACG<br>TGTTTCGGAGAATCTCCAAGGGAGGTTCAAAACCTTTTGAGAACCTTAGACTGATGGCGC<br>CCATCTCTCTGCAGGTAGTTCACGTTGAGACCCATAGATGCAATATAAGCTGGGAAATCT<br>CACAAGCCAGCCATTACTTTGAACGGCATTTGGAATTCGAGGCCCGAACACTTTCCCCCG<br>GTCATACGTGGGAAGAAGCTCCTCTCTTGACGCTGAAGCAGAAGCAGGAGTGGATTTGTC<br>TGGAGACTTTGACTCCTGATACTCAGTATGAGTTCCAAGTTCGGGTGAAACCACTCCAAG<br>GCGAGTTCACGACGTGGTCTCCGTGGAGTCAACCGTTGGCGTTCCGCACGAAGCCCGCTG<br>CCCTTGGCAAAGACACGATTCCGTGGCTTGGGCATCTGCTCGTTGGGCTGAGTGGTGCGT<br>TTGGTTTCATCATCTTGGTCTATCTCTTGATCAATTGCAGAAATACAGGCCCTTGGCTGAA<br>AAAAGTGCTCAAGTGTAATACCCCCGACCCAAGCAAGTTCTTCTCCCAGCTTTCTTCAGA<br>GCATGGAGGCGATGTGCAGAAATGGCTCTCTTCACCTTTTCCCTCCTCAAGCTTCTCCCCG<br>GGAGGGCTGGCGCCCGAGATTTCACCTCTTGAGGTACTTGAACGAGACAAGGTTACCCA<br>ACTTCTCCTTCAACAGGATAAGGTACCCGAACCTGCGAGCCTTAGCTCCAACCACTCTCT<br>TACGAGCTGCTTCACCAATCAGGGATACTTCTTTTTCCACCTTCCCGATGCGCTGGAAATC<br>GAAGCTTGTCAAGTTTACTTTACCTATGATCCATATAGCGAGGAAGATCCCGACGAAGGA<br>GTCGCCGGTGCGCCCACGGGTTCCTCACCCCAACCTCTCCAGCCTCTCTCAGGAGAAGAT<br>GATGCTTATTGCACTTTTCCCAGTAGAGACGATCTCCTCCTCTTTTCTCCATCTCTTTTGGG<br>GGGACCTTCCCCCCCTTCTACGGCACCTGGCGGGTCTGGTGCTGGCGAGGAGCGGATGCC<br>GCCGTCCCTCCAGGAGCGAGTACCACGAGATTGGGATCCCCAGCCACTTGGACCCCCCAC<br>CCCCGGCGTACCTGACCTTGTCGATTTTCAACCTCCCCCTGAATTGGTGCTGCGAGAGGC<br>TGGGGAGGAAGTTCCGGACGCTGGGCCGAGGGAGGGCGTGTCCTTTCCATGGAGTAGGC<br>CTCCAGGTCAAGGCGAGTTTAGGGCTCTCAACGCGCGGCTGCCGTTGAATACAGACGCTT<br>ATCTCTCACTGCAGGAACTGCAAGGTCAGGACCCAACACATCTTGTAGGATCTGGTGCTA<br>CTAATTTTTCTCTTTTGAAGCAAGCTGGAGATGTTGAAGAGAACCCTGGTCCAGTGAGCA<br>AGGGCGAGGAGCTGTTCACCGGGGTGGTGCCCATCCTGGTCGAGCTGGACGGCGACGTA<br>AACGGCCACAAGTTCAGCGTGTCCGGCGAGGGCGAGGGCGATGCCACCTACGGCAAGCT<br>GACCCTGAAGTTCATCTGCACCACCGGCAAGCTGCCCGTGCCCTGGCCCACCCTCGTGAC<br>CACCCTGACCTACGGCGTGCAGTGCTTCAGCCGCTACCCCGACCACATGAAGCAGCACG<br>ACTTCTTCAAGTCCGCCATGCCCGAAGGCTACGTCCAGGAGCGCACCATCTTCTTCAAGG<br>ACGACGGCAACTACAAGACCCGCGCCGAGGTGAAGTTCGAGGGCGACACCCTGGTGAAC<br>CGCATCGAGCTGAAGGGCATCGACTTCAAGGAGGACGGCAACATCCTGGGGCACAAGCT<br>GGAGTACAACTACAACAGCCACAACGTCTATATCATGGCCGACAAGCAGAAGAACGGCA<br>TCAAGGTGAACTTCAAGATCCGCCACAACATCGAGGACGGCAGCGTGCAGCTCGCCGAC<br>CACTACCAGCAGAACACCCCCATCGGCGACGGCCCCGTGCTGCTGCCCGACAACCACTA<br>CCTGAGCACCCAGTCCGCCCTGAGCAAAGACCCCAACGAGAAGCGCGATCACATGGTCC<br>TGCTGGAGTTCGTGACCGCCGCCGGGATCACTCTCGGCATGGACGAGCTGTACAAGTAA<br>ACTAGTGTCGACAATCAACCTCTGGATTACAAAATTTGTGAAAGATTGACTGGTATTCTT<br>AACTATGTTGCTCCTTTTACGCTATGTGGATACGCTGCTTTAATGCCTTTGTATCATGCTA<br>TTGCTTCCCGTATGGCTTTCATTTTCTCCTCCTTGTATAAATCCTGGTTGCTGTCTCTTTAT<br>GAGGAGTTGTGGCCCGTTGTCAGGCAACGTGGCGTGGTGTGCACTGTGTTTGCTGACGCA<br>ACCCCCACTGGTTGGGGCATTGCCACCACCTGTCAGCTCCTTTCCGGGACTTTCGCTTTCC<br>CCCTCCCTATTGCCACGGCGGAACTCATCGCCGCCTGCCTTGCCCGCTGCTGGACAGGGG<br>CTCGGCTGTTGGGCACTGACAATTCCGTGGTGTTGTCGGGGAAGCTGACGTCCTTTCCAT<br>GGCTGCTCGCCTGTGTTGCCACCTGGATTCTGCGCGGGACGTCCTTCTGCTACGTCCCTTC<br>GGCCCTCAATCCAGCGGACCTTCCTTCCCGCGGCCTGCTGCCGGCTCTGCGGCCTCTTCCG | |

-continued

| SEQ ID NO | Sequence | Description |
|---|---|---|
| | CGTCTTCGCCTTCGCCCTCAGACGAGTCGGATCTCCCTTTGGGCCGCCTCCCCGCCTGGAA<br>TTCGAGCTCGGTACCTTTAAGACCAATGACTTACAAGGCAGCTGTAGATCTTAGCCACTT<br>TTTAAAAGAAAAGGGGGGACTGGAAGGGCTAATTCACTCCCAACGAAGACAAGATCTGC<br>TTTTTGCTTGTACTGGGTCTCTCTGGTTAGACCAGATCTGAGCCTGGGAGCTCTCTGGCTA<br>ACTAGGGAACCCACTGCTTAAGCCTCAATAAAGCTTGCCTTGAGTGCTTCAAGTAGTGTG<br>TGCCCGTCTGTTGTGTGACTCTGGTAACTAGAGATCCCTCAGACCCTTTTAGTCAGTGTGG<br>AAAATCTCTAGCAGTAGTAGTTCATGTCATCTTATTATTCAGTATTTATAACTTGCAAAGA<br>AATGAATATCAGAGAGTGAGAGGAACTTGTTTATTGCAGCTTATAATGGTTACAAATAAA<br>GCAATAGCATCACAAATTTCACAAATAAAGCATTTTTTTCACTGCATTCTAGTTGTGGTTT<br>GTCCAAACTCATCAATGTATCTTATCATGTCTGGCTCTAGCTATCCCGCCCCTAACTCCGC<br>CCAGTTCCGCCCATTCTCCGCCCCATGGCTGACTAATTTTTTTTATTTATGCAGAGGCCGA<br>GGCCGCCTCGGCCTCTGAGCTATTCCAGAAGTAGTGAGGAGGCTTTTTTGGAGGCCTAGG<br>CTTTTGCGTCGAGACGTACCCAATTCGCCCTATAGTGAGTCGTATTACGCGCGCTCACTG<br>GCCGTCGTTTTACAACGTCGTGACTGGGAAAACCCTGGCGTTACCCAACTTAATCGCCTT<br>GCAGCACATCCCCCTTTCGCCAGCTGGCGTAATAGCGAAGAGGCCCGCACCGATCGCCCT<br>TCCCAACAGTTGCGCAGCCTGAATGGCGAATGGCGCGACGCGCCCTGTAGCGGCGCATT<br>AAGCGCGGCGGGTGTGGTGGTTACGCGCAGCGTGACCGCTACACTTGCCAGCGCCCTAG<br>CGCCCGCTCCTTTCGCTTTCTTCCCTTCCTTTCTCGCCACGTTCGCCGGCTTTCCCCGTCAA<br>GCTCTAAATCGGGGGCTCCCTTTAGGGTTCCGATTTAGTGCTTTACGGCACCTCGACCCC<br>AAAAAACTTGATTAGGGTGATGGTTCACGTAGTGGGCCATCGCCCTGATAGACGGTTTTT<br>CGCCCTTTGACGTTGGAGTCCACGTTCTTTAATAGTGGACTCTTGTTCCAAACTGGAACAA<br>CACTCAACCCTATCTCGGTCTATTCTTTTGATTTATAAGGGATTTTGCCGATTTCGGCCTA<br>TTGGTTAAAAAATGAGCTGATTTAACAAAAATTTAACGCGAATTTTAACAAAATATTAAC<br>GTTTACAATTTCCCAGGTGGCACTTTTCGGGGAAATGTGCGCGGAACCCCTATTTGTTTAT<br>TTTTCTAAATACATTCAAATATGTATCCGCTCATGAGACAATAACCCTGATAAATGCTTCA<br>ATAATATTGAAAAAGGAAGAGTATGAGTATTCAACATTTCCGTGTCGCCCTTATTCCCTTT<br>TTTGCGGCATTTTGCCTTCCTGTTTTTGCTCACCCAGAAACGCTGGTGAAAGTAAAAGATG<br>CTGAAGATCAGTTGGGTGCACGAGTGGGTTACATCGAACTGGATCTCAACAGCGGTAAG<br>ATCCTTGAGAGTTTTCGCCCCGAAGAACGTTTTCCAATGATGAGCACTTTTAAAGTTCTGC<br>TATGTGGCGCGGTATTATCCCGTATTGACGCCGGGCAAGAGCAACTCGGTCGCCGCATAC<br>ACTATTCTCAGAATGACTTGGTTGAGTACTCACCAGTCACAGAAAAGCATCTTACGGATG<br>GCATGACAGTAAGAGAATTATGCAGTGCTGCCATAACCATGAGTGATAACACTGCGGCC<br>AACTTACTTCTGACAACGATCGGAGGACCGAAGGAGCTAACCGCTTTTTTGCACAACATG<br>GGGGATCATGTAACTCGCCTTGATCGTTGGGAACCGGAGCTGAATGAAGCCATACCAAA<br>CGACGAGCGTGACACCACGATGCCTGTAGCAATGGCAACAACGTTGCGCAAACTATTAA<br>CTGGCGAACTACTTACTCTAGCTTCCCGGCAACAATTAATAGACTGGATGGAGGCGGATA<br>AAGTTGCAGGACCACTTCTGCGCTCGGCCCTTCCGGCTGGCTGGTTTATTGCTGATAAAT<br>CTGGAGCCGGTGAGCGTGGGTCTCGCGGTATCATTGCAGCACTGGGGCCAGATGGTAAG<br>CCCTCCCGTATCGTAGTTATCTACACGACGGGGAGTCAGGCAACTATGGATGAACGAAAT<br>AGACAGATCGCTGAGATAGGTGCCTCACTGATTAAGCATTGGTAACTGTCAGACCAAGTT<br>TACTCATATATACTTTAGATTGATTTAAAACTTCATTTTTAATTTAAAAGGATCTAGGTGA<br>AGATCCTTTTTGATAATCTCATGACCAAAATCCCTTAACGTGAGTTTTCGTTCCACTGAGC<br>GTCAGACCCCGTAGAAAAGATCAAAGGATCTTCTTGAGATCCTTTTTTTCTGCGCGTAAT<br>CTGCTGCTTGCAAACAAAAAAACCACCGCTACCAGCGGTGGTTTGTTTGCCGGATCAAGA<br>GCTACCAACTCTTTTTCCGAAGGTAACTGGCTTCAGCAGAGCGCAGATACCAAATACTGT<br>CCTTCTAGTGTAGCCGTAGTTAGGCCACCACTTCAAGAACTCTGTAGCACCGCCTACATA<br>CCTCGCTCTGCTAATCCTGTTACCAGTGGCTGCTGCCAGTGGCGATAAGTCGTGTCTTACC<br>GGGTTGGACTCAAGACGATAGTTACCGGATAAGGCGCAGCGGTCGGGCTGAACGGGGGG<br>TTCGTGCACACAGCCCAGCTTGGAGCGAACGACCTACACCGAACTGAGATACCTACAGC<br>GTGAGCTATGAGAAAGCGCCACGCTTCCCGAAGGGAGAAAGGCGGACAGGTATCCGGTA<br>AGCGGCAGGGTCGGAACAGGAGAGCGCACGAGGGAGCTTCCAGGGGGAAACGCCTGGT<br>ATCTTTATAGTCCTGTCGGGTTTCGCCACCTCTGACTTGAGCGTCGATTTTTGTGATGCTC<br>GTCAGGGGGGCGGAGCCTATGGAAAAACGCCAGCAACGCGGCCTTTTTACGGTTCCTGG<br>CCTTTTGCTGGCCTTTTGCTCACATGTTCTTTCCTGCGTTATCCCCTGATTCTGTGGATAAC<br>CGTATTACCGCCTTTGAGTGAGCTGATACCGCTCGCCGCAGCCGAACGACCGAGCGCAGC<br>GAGTCAGTGAGCGAGGAAGCGGAAGAGCGCCCAATACGCAAACCGCCTCTCCCCGCGCG<br>TTGGCCGATTCATTAATGCAGCTGGCACGACAGGTTTCCCGACTGGAAAGCGGGCAGTG<br>AGCGCAACGCAATTAATGTGAGTTAGCTCACTCATTAGGCACCCCAGGCTTTACACTTTA<br>TGCTTCCGGCTCGTATGTTGTGTGGAATTGTGAGCGGATAACAATTTCACACAGGAAACA<br>GCTATGACCATGATTACGCCAAGCGCGCAATTAACCCTCACTAAAGGGAACAAAAGCTG<br>GAGCTGCA | |
| 108 | (AGCTTAATGTAGTCTTATGCAATACTCTTGTAGTCTTGCAACATGGTAACGATGAGTTAG<br>CAACATGCCTTACAAGGAGAGAAAAAGCACCGTGCATGCCGATTGGTGGAAGTAAGGTG<br>GTACGATCGTGCCTTATTAGGAAGGCAACAGACGGGTCTGACATGGATTGGACGAACCA<br>CTGAATTGCCGCATTGCAGAGATATTGTATTTAAGTGCCTAGCTCGATACAATAAACGGG<br>TCTCTCTGGTTAGACCAGATCTGAGCCTGGGAGCTCTCTGGCTAACTAGGGAACCCACTG<br>CTTAAGCCTCAATAAAGCTTGCCTTGAGTGCTTCAAGTAGTGTGTGCCCGTCTGTTGTGTG<br>ACTCTGGTAACTAGAGATCCCTCAGACCCTTTTAGTCAGTGTGGAAAATCTCTAGCAGTG<br>GCGCCCGAACAGGGACTTGAAAGCGAAAGGGAAACCAGAGGAGCTCTCTCGACGCAGG<br>ACTCGGCTTGCTGAAGCGCGCACGGCAAGAGGCGAGGGGCGGCGACTGGTGAGTACGCC<br>AAAAATTTTGACTAGCGGAGGCTAGAAGGAGAGAGATGGGTGCGAGAGCGTCAGTATTA<br>AGCGGGGGAGAATTAGATCGCGATGGGAAAAAATTCGGTTAAGGCCAGGGGGAAAGAA<br>AAAATATAAATTAAAACATATAGTATGGGCAAGCAGGGAGCTAGAACGATTCGCAGTTA<br>ATCCTGGCCTGTTAGAAACATCAGAAGGCTGTAGACAAATACTGGGACAGCTACAACCA | Expression vector |

-continued

| SEQ ID NO | Sequence | Description |
|---|---|---|

TCCCTTCAGACAGGATCAGAAGAACTTAGATCATTATATAATACAGTAGCAACCCTCTAT
TGTGTGCATCAAAGGATAGAGATAAAAGACACCAAGGAAGCTTTAGACAAGATAGAGGA
AGAGCAAAACAAAAGTAAGACCACCGCACAGCAAGCGGCCGCTGATCTTCAGACCTGGA
GGAGGAGATATGAGGGACAATTGGAGAAGTGAATTATATAAATATAAAGTAGTAAAAAT
TGAACCATTAGGAGTAGCACCCACCAAGGCAAAGAGAAGAGTGGTGCAGAGAGAAAAA
AGAGCAGTGGGAATAGGAGCTTTGTTCCTTGGGTTCTTGGGAGCAGCAGGAAGCACTAT
GGGCGCAGCCTCAATGACGCTGACGGTACAGGCCAGACAATTATTGTCTGGTATAGTGC
AGCAGCAGAACAATTTGCTGAGGGCTATTGAGGCGCAACAGCATCTGTTGCAACTCACA
GTCTGGGGCATCAAGCAGCTCCAGGCAAGAATCCTGGCTGTGGAAAGATACCTAAAGGA
TCAACAGCTCCTGGGGATTTGGGGTTGCTCTGGAAAACTCATTTGCACCACTGCTGTGCC
TTGGAATGCTAGTTGGAGTAATAAATCTCTGGAACAGATTTGGAATCACACGACCTGGAT
GGAGTGGGACAGAGAAATTAACAATTACACAAGCTTAATACACTCCTTAATTGAAGAAT
CGCAAAACCAGCAAGAAAAGAATGAACAAGAATTATTGGAATTAGATAAATGGGCAAGT
TTGTGGAATTGGTTTAACATAACAAATTGGCTGTGGTATATAAAATTATTCATAATGATA
GTAGGAGGCTTGGTAGGTTTAAGAATAGTTTTTGCTGTACTTTCTATAGTGAATAGAGTT
AGGCAGGGATATTCACCATTATCGTTTCAGACCCACCTCCCAACCCCGAGGGGACCCGAC
AGGCCCGAAGGAATAGAAGAAGAAGGTGGAGAGAGAGACAGAGACAGATCCATTCGAT
TAGTGAACGGATCTCGACGGTATCGGTTAACTTTTAAAAGAAAAGGGGGGATTGGGGGG
TACAGTGCAGGGGAAAGAATAGTAGACATAATAGCAACAGACATACAAACTAAAGAATT
ACAAAAACAAATTACAAAAATTCAAAATTTTATCGATCACGAGACTAGCCTCGAGAAGC
TTGATATCGAATTCCCACGGGGTTGGACGCGTAGGAACAGAGAAACAGGAGAATATGGG
CCAAACAGGATATCTGTGGTAAGCAGTTCCTGCCCCGGCTCAGGGCCAAGAACAGTTGG
AACAGCAGAATATGGGCCAAACAGGATATCTGTGGTAAGCAGTTCCTGCCCCGGCTCAG
GGCCAAGAACAGATGGTCCCCAGATGCGGTCCCGCCCTCAGCAGTTTCTAGAGAACCAT
CAGATGTTTCCAGGGTGCCCCAAGGACCTGAAATGACCCTGTGCCTTATTTGAACTAACC
AATCAGTTCGCTTCTCGCTTCTGTTCGCGCGCTTCTGCTCCCCGAGCTCTATATAAGCAGA
GCTCGTTTAGTGAACCGTCAGATCGCTAGCACCGGTGCCGCCACCATGCCTCTGGGCCTG
CTGTGGCTGGGCCTGGCCCTGCTGGGCGCCCTGCACGCCCAGGCCGGCGTGCAGGTGGA
GACAATCTCCCCAGGCGACGGACGCACATTCCCTAAGCGGGGCCAGACCTGCGTGGTGC
ACTATACAGGCATGCTGGAGGATGGCAAGAAGTTTGACAGCTCCCGGGATAGAAACAAG
CCATTCAAGTTTATGCTGGGCAAGCAGGAAGTGATCAGAGGCTGGGAGGAGGGCGTGGC
CCAGATGTCTGTGGGCCAGAGGGCCAAGCTGACCATCAGCCCAGACTACGCCTATGGAG
CAACAGGCCACCCAGGAATCATCCCACCTCACGCCACCCTGGTGTTCGATGTGGAGCTGC
TGAAGCTGGGCGAGCAAAACTTGGTGATTCCTTGGGCCCCAGAAAATCTCACGCTTCACA
AGTTGTCCGAATCCCAGCTCGAGCTCAACTGGAATAATAGATTTCTTAATCATTGTTTGG
AACACCTGGTTCAATATAGAACGGATTGGGACCACTCATGGACCGAGCAGTCAGTTGAC
TACCGCCACAAATTTTCACTTCCCAGCGTAGATGGGCAGAAGAGGTACACATTTAGGGTC
AGATCCAGGTTTAATCCTCTGTGTGGTTCTGCTCAACACTGGTCTGAGTGGAGCCATCCG
ATCCACTGGGGCTCAAATACCTCTAAAGAAAATCCGTTCCTCTTTGCGCTCGAAGCCGTT
GTTATCAGCGTCGGAAGCATGGGACTTATCATTTCCCTTCTCTGCGTGTACTTCTGGCTGG
AGCGGACGATGCCGCGGATTCCGACGCTCAAAAACCTGGAGGACCTTGTAACAGAATAT
CACGGTAATTTCTCCGCTTGGAGTGGCGTATCAAAGGGGCTTGCTGAGTCCCTTCAACCG
GATTACTCTGAGCGCCTCTGCTTGGTGTCCGAGATACCTCCCAAAGGAGGTGCACTTGGG
GAGGGGCCAGGCGCGTCCCCTTGCAATCAGCATAGTCCGTATTGGGCGCCCCCCTGTTAT
ACCCTCAAACCGGAAACGGGAAGCGGAGCTACTAACTTCAGCCTGCTGAAGCAGGCTGG
AGACGTGGAGGAGAACCCTGGACCTATGGCACTGCCCGTGACCGCCCTGCTGCTGCCTCT
GGCCCTGCTGCTGCACGCAGCCCGGCCTATCCTGTGGCACGAGATGTGGCACGAGGGCCT
GGAGGAGGCCAGCAGGCTGTATTTTGGCGAGCGCAACGTGAAGGGCATGTTCGAGGTGC
TGGAGCCTCTGCACGCCATGATGGAGAGAGGCCCACAGACCCTGAAGGAGACATCCTTT
AACCAGGCCTATGGACGGGACCTGATGGAGGCACAGGAGTGGTGCAGAAAGTACATGA
AGTCTGGCAATGTGAAGGACCTGCTGCAGGCCTGGGATCTGTACTATCACGTGTTTCGGA
GAATCTCCAAGAAACCTTTTGAGAACCTTAGACTGATGGCGCCCATCTCTCTGCAGGTAG
TTCACGTTGAGACCCATAGATGCAATATAAGCTGGGAAATCTCACAAGCCAGCCATTACT
TTGAACGGCATTTGGAATTCGAGGCCCGAACACTTTCCCCCGGTCATACGTGGGAAGAAG
CTCCTCTCTTGACGCTGAAGCAGAAGCAGGAGTGGATTTGTCTGGAGACTTTGACTCCTG
ATACTCAGTATGAGTTCCAAGTTCGGGTGAAACCACTCCAAGGCGAGTTCACGACGTGGT
CTCCGTGGAGTCAACCGTTGGCGTTCCGCACGAAGCCCGCTGCCCTTGGCAAAGACACGA
TTCCGTGGCTTGGGCATCTGCTCGTTGGGCTGAGTGGTGCGTTTGGTTTCATCATCTTGGT
CTATCTCTTGATCAATTGCAGAAATACAGGCCCTTGGCTGAAAAAAGTGCTCAAGTGTAA
TACCCCCGACCCAAGCAAGTTCTTCTCCCAGCTTTCTTCAGAGCATGGAGGCGATGTGCA
GAAATGGCTCTCTTCACCTTTTCCCTCCTCAAGCTTCTCCCCGGGAGGGCTGGCGCCCGA
GATTTCACCTCTTGAGGTACTTGAACGAGACAAGGTTACCCAACTTCTCCTTCAACAGGA
TAAGGTACCCGAACCTGCGAGCCTTAGCTCCAACCACTCTCTTACGAGCTGCTTCACCAA
TCAGGGATACTTCTTTTTCCACCTTCCCGATGCGCTGGAAATCGAAGCTTGTCAAGTTTAC
TTTACCTATGATCCATATAGCGAGGAAGATCCCGACGAAGGAGTCGCCGGTGCGCCCAC
GGGTTCCTCACCCCAACCTCTCCAGCCTCTCTCAGGAGAAGATGATGCTTATTGCACTTTT
CCCAGTAGAGACGATCTCCTCCTCTTTTCTCCATCTCTTTTGGGGGGACCTTCCCCCCCTT
CTACGGCACCTGGCGGGTCTGGTGCTGGCGAGGAGCGGATGCCGCCGTCCCTCCAGGAG
CGAGTACCACGAGATTGGGATCCCCAGCCACTTGGACCCCCCACCCCCGGCGTACCTGAC
CTTGTCGATTTTCAACCTCCCCCTGAATTGGTGCTGCGAGAGGCTGGGGAGGAAGTTCCG
GACGCTGGGCCGAGGGAGGGCGTGTCCTTTCCATGGAGTAGGCCTCCAGGTCAAGGCGA
GTTTAGGGCTCTCAACGCGCGGCTGCCGTTGAATACAGACGCTTATCTCTCACTGCAGGA
ACTGCAAGGTCAGGACCCAACACATCTTGTAGGATCTGGTGCTACTAATTTTTCTCTTTTG
AAGCAAGCTGGAGATGTTGAAGAGAACCCTGGTCCAGTGAGCAAGGGCGAGGAGCTGTT
CACCGGGGTGGTGCCCATCCTGGTCGAGCTGGACGGCGACGTAAACGGCCACAAGTTCA

-continued

| SEQ ID NO | Sequence | Description |
|---|---|---|
| | GCGTGTCCGGCGAGGGCGAGGGCGATGCCACCTACGGCAAGCTGACCCTGAAGTTCATC<br>TGCACCACCGGCAAGCTGCCCGTGCCCTGGCCCACCCTCGTGACCACCCTGACCTACGGC<br>GTGCAGTGCTTCAGCCGCTACCCCGACCACATGAAGCAGCACGACTTCTTCAAGTCCGCC<br>ATGCCCGAAGGCTACGTCCAGGAGCGCACCATCTTCTTCAAGGACGACGGCAACTACAA<br>GACCCGCGCCGAGGTGAAGTTCGAGGGCGACACCCTGGTGAACCGCATCGAGCTGAAGG<br>GCATCGACTTCAAGGAGGACGGCAACATCCTGGGGCACAAGCTGGAGTACAACTACAAC<br>AGCCACAACGTCTATATCATGGCCGACAAGCAGAAGAACGGCATCAAGGTGAACTTCAA<br>GATCCGCCACAACATCGAGGACGGCAGCGTGCAGCTCGCCGACCACTACCAGCAGAACA<br>CCCCCATCGGCGACGGCCCCGTGCTGCTGCCCGACAACCACTACCTGAGCACCCAGTCCG<br>CCCTGAGCAAAGACCCCAACGAGAAGCGCGATCACATGGTCCTGCTGGAGTTCGTGACC<br>GCCGCCGGGATCACTCTCGGCATGGACGAGCTGTACAAGTAAACTAGTGTCGACAATCA<br>ACCTCTGGATTACAAAATTTGTGAAAGATTGACTGGTATTCTTAACTATGTTGCTCCTTTT<br>ACGCTATGTGGATACGCTGCTTTAATGCCTTTGTATCATGCTATTGCTTCCCGTATGGCTT<br>TCATTTTCTCCTCCTTGTATAAATCCTGGTTGCTGTCTCTTTATGAGGAGTTGTGGCCCGTT<br>GTCAGGCAACGTGGCGTGGTGTGCACTGTGTTTGCTGACGCAACCCCCACTGGTTGGGGC<br>ATTGCCACCACCTGTCAGCTCCTTTCCGGGACTTTCGCTTTCCCCCTCCCTATTGCCACGG<br>CGGAACTCATCGCCGCCTGCCTTGCCCGCTGCTGGACAGGGGCTCGGCTGTTGGGCACTG<br>ACAATTCCGTGGTGTTGTCGGGGAAGCTGACGTCCTTTCCATGGCTGCTCGCCTGTGTTGC<br>CACCTGGATTCTGCGCGGGACGTCCTTCTGCTACGTCCCTTCGGCCCTCAATCCAGCGGA<br>CCTTCCTTCCCGCGGCCTGCTGCCGGCTCTGCGGCCTCTTCCGCGTCTTCGCCTTCGCCCT<br>CAGACGAGTCGGATCTCCCTTTGGGCCGCCTCCCCGCCTGGAATTCGAGCTCGGTACCTT<br>TAAGACCAATGACTTACAAGGCAGCTGTAGATCTTAGCCACTTTTTAAAAGAAAAGGGG<br>GGACTGGAAGGGCTAATTCACTCCCAACGAAGACAAGATCTGCTTTTTGCTTGTACTGGG<br>TCTCTCTGGTTAGACCAGATCTGAGCCTGGGAGCTCTCTGGCTAACTAGGGAACCCACTG<br>CTTAAGCCTCAATAAAGCTTGCCTTGAGTGCTTCAAGTAGTGTGTGCCCGTCTGTTGTGTG<br>ACTCTGGTAACTAGAGATCCCTCAGACCCTTTTAGTCAGTGTGGAAAATCTCTAGCAGTA<br>GTAGTTCATGTCATCTTATTATTCAGTATTTATAACTTGCAAAGAAATGAATATCAGAGA<br>GTGAGAGGAACTTGTTTATTGCAGCTTATAATGGTTACAAATAAAGCAATAGCATCACAA<br>ATTTCACAAATAAAGCATTTTTTTCACTGCATTCTAGTTGTGGTTTGTCCAAACTCATCAA<br>TGTATCTTATCATGTCTGGCTCTAGCTATCCCGCCCCTAACTCCGCCCAGTTCCGCCCATT<br>CTCCGCCCCATGGCTGACTAATTTTTTTTATTTATGCAGAGGCCGAGGCCGCCTCGGCCTC<br>TGAGCTATTCCAGAAGTAGTGAGGAGGCTTTTTTGGAGGCCTAGGCTTTTGCGTCGAGAC<br>GTACCCAATTCGCCCTATAGTGAGTCGTATTACGCGCGCTCACTGGCCGTCGTTTTACAA<br>CGTCGTGACTGGGAAAACCCTGGCGTTACCCAACTTAATCGCCTTGCAGCACATCCCCCT<br>TTCGCCAGCTGGCGTAATAGCGAAGAGGCCCGCACCGATCGCCCTTCCCAACAGTTGCGC<br>AGCCTGAATGGCGAATGGCGCGACGCGCCCTGTAGCGGCGCATTAAGCGCGGCGGGTGT<br>GGTGGTTACGCGCAGCGTGACCGCTACACTTGCCAGCGCCCTAGCGCCCGCTCCTTTCGC<br>TTTCTTCCCTTCCTTTCTCGCCACGTTCGCCGGCTTTCCCCGTCAAGCTCTAAATCGGGGG<br>CTCCCTTTAGGGTTCCGATTTAGTGCTTTACGGCACCTCGACCCCAAAAAACTTGATTAG<br>GGTGATGGTTCACGTAGTGGGCCATCGCCCTGATAGACGGTTTTTCGCCCTTTGACGTTG<br>GAGTCCACGTTCTTTAATAGTGGACTCTTGTTCCAAACTGGAACAACACTCAACCCTATC<br>TCGGTCTATTCTTTTGATTTATAAGGGATTTTGCCGATTTCGGCCTATTGGTTAAAAAATG<br>AGCTGATTTAACAAAAATTTAACGCGAATTTTAACAAAATATTAACGTTTACAATTTCCC<br>AGGTGGCACTTTTCGGGGAAATGTGCGCGGAACCCCTATTTGTTTATTTTTCTAAATACAT<br>TCAAATATGTATCCGCTCATGAGACAATAACCCTGATAAATGCTTCAATAATATTGAAAA<br>AGGAAGAGTATGAGTATTCAACATTTCCGTGTCGCCCTTATTCCCTTTTTTGCGGCATTTT<br>GCCTTCCTGTTTTTGCTCACCCAGAAACGCTGGTGAAAGTAAAAGATGCTGAAGATCAGT<br>TGGGTGCACGAGTGGGTTACATCGAACTGGATCTCAACAGCGGTAAGATCCTTGAGAGTT<br>TTCGCCCCGAAGAACGTTTTCCAATGATGAGCACTTTTAAAGTTCTGCTATGTGGCGCGG<br>TATTATCCCGTATTGACGCCGGGCAAGAGCAACTCGGTCGCCGCATACACTATTCTCAGA<br>ATGACTTGGTTGAGTACTCACCAGTCACAGAAAAGCATCTTACGGATGGCATGACAGTAA<br>GAGAATTATGCAGTGCTGCCATAACCATGAGTGATAACACTGCGGCCAACTTACTTCTGA<br>CAACGATCGGAGGACCGAAGGAGCTAACCGCTTTTTTGCACAACATGGGGGATCATGTA<br>ACTCGCCTTGATCGTTGGGAACCGGAGCTGAATGAAGCCATACCAAACGACGAGCGTGA<br>CACCACGATGCCTGTAGCAATGGCAACAACGTTGCGCAAACTATTAACTGGCGAACTACT<br>TACTCTAGCTTCCCGGCAACAATTAATAGACTGGATGGAGGCGGATAAAGTTGCAGGAC<br>CACTTCTGCGCTCGGCCCTTCCGGCTGGCTGGTTTATTGCTGATAAATCTGGAGCCGGTG<br>AGCGTGGGTCTCGCGGTATCATTGCAGCACTGGGGCCAGATGGTAAGCCCTCCCGTATCG<br>TAGTTATCTACACGACGGGGAGTCAGGCAACTATGGATGAACGAAATAGACAGATCGCT<br>GAGATAGGTGCCTCACTGATTAAGCATTGGTAACTGTCAGACCAAGTTTACTCATATATA<br>CTTTAGATTGATTTAAAACTTCATTTTTAATTTAAAAGGATCTAGGTGAAGATCCTTTTTG<br>ATAATCTCATGACCAAAATCCCTTAACGTGAGTTTTCGTTCCACTGAGCGTCAGACCCCG<br>TAGAAAAGATCAAAGGATCTTCTTGAGATCCTTTTTTTCTGCGCGTAATCTGCTGCTTGCA<br>AACAAAAAAACCACCGCTACCAGCGGTGGTTTGTTTGCCGGATCAAGAGCTACCAACTCT<br>TTTTCCGAAGGTAACTGGCTTCAGCAGAGCGCAGATACCAAATACTGTCCTTCTAGTGTA<br>GCCGTAGTTAGGCCACCACTTCAAGAACTCTGTAGCACCGCCTACATACCTCGCTCTGCT<br>AATCCTGTTACCAGTGGCTGCTGCCAGTGGCGATAAGTCGTGTCTTACCGGGTTGGACTC<br>AAGACGATAGTTACCGGATAAGGCGCAGCGGTCGGGCTGAACGGGGGGTTCGTGCACAC<br>AGCCCAGCTTGGAGCGAACGACCTACACCGAACTGAGATACCTACAGCGTGAGCTATGA<br>GAAAGCGCCACGCTTCCCGAAGGGAGAAAGGCGGACAGGTATCCGGTAAGCGGCAGGG<br>TCGGAACAGGAGAGCGCACGAGGGAGCTTCCAGGGGGAAACGCCTGGTATCTTTATAGT<br>CCTGTCGGGTTTCGCCACCTCTGACTTGAGCGTCGATTTTTGTGATGCTCGTCAGGGGGGC<br>GGAGCCTATGGAAAAACGCCAGCAACGCGGCCTTTTTACGGTTCCTGGCCTTTTGCTGGC<br>CTTTTGCTCACATGTTCTTTCCTGCGTTATCCCCTGATTCTGTGGATAACCGTATTACCGCC<br>TTTGAGTGAGCTGATACCGCTCGCCGCAGCCGAACGACCGAGCGCAGCGAGTCAGTGAG | |

-continued

| SEQ ID NO | Sequence | Description |
|---|---|---|
| | CGAGGAAGCGGAAGAGCGCCCAATACGCAAACCGCCTCTCCCCGCGCGTTGGCCGATTC | |
| | ATTAATGCAGCTGGCACGACAGGTTTCCCGACTGGAAAGCGGGCAGTGAGCGCAACGCA | |
| | ATTAATGTGAGTTAGCTCACTCATTAGGCACCCCAGGCTTTACACTTTATGCTTCCGGCTC | |
| | GTATGTTGTGTGGAATTGTGAGCGGATAACAATTTCACACAGGAAACAGCTATGACCATG | |
| | ATTACGCCAAGCGCGCAATTAACCCTCACTAAAGGGAACAAAAGCTGGAGCTGCA | |
| 109 | (AGCTTAATGTAGTCTTATGCAATACTCTTGTAGTCTTGCAACATGGTAACGATGAGTTAG | Expression vector |
| | CAACATGCCTTACAAGGAGAGAAAAAGCACCGTGCATGCCGATTGGTGGAAGTAAGGTG | |
| | GTACGATCGTGCCTTATTAGGAAGGCAACAGACGGGTCTGACATGGATTGGACGAACCA | |
| | CTGAATTGCCGCATTGCAGAGATATTGTATTTAAGTGCCTAGCTCGATACAATAAACGGG | |
| | TCTCTCTGGTTAGACCAGATCTGAGCCTGGGAGCTCTCTGGCTAACTAGGGAACCCACTG | |
| | CTTAAGCCTCAATAAAGCTTGCCTTGAGTGCTTCAAGTAGTGTGTGCCCGTCTGTTGTGTG | |
| | ACTCTGGTAACTAGAGATCCCTCAGACCCTTTTAGTCAGTGTGGAAAATCTCTAGCAGTG | |
| | GCGCCCGAACAGGGACTTGAAAGCGAAAGGGAAACCAGAGGAGCTCTCTCGACGCAGG | |
| | ACTCGGCTTGCTGAAGCGCGCACGGCAAGAGGCGAGGGGCGGCGACTGGTGAGTACGCC | |
| | AAAAATTTTGACTAGCGGAGGCTAGAAGGAGAGAGATGGGTGCGAGAGCGTCAGTATTA | |
| | AGCGGGGGAGAATTAGATCGCGATGGGAAAAAATTCGGTTAAGGCCAGGGGGAAAGAA | |
| | AAAATATAAATTAAAACATATAGTATGGGCAAGCAGGGAGCTAGAACGATTCGCAGTTA | |
| | ATCCTGGCCTGTTAGAAACATCAGAAGGCTGTAGACAAATACTGGGACAGCTACAACCA | |
| | TCCCTTCAGACAGGATCAGAAGAACTTAGATCATTATATAATACAGTAGCAACCCTCTAT | |
| | TGTGTGCATCAAAGGATAGAGATAAAAGACACCAAGGAAGCTTTAGACAAGATAGAGGA | |
| | AGAGCAAAACAAAAGTAAGACCACCGCACAGCAAGCGGCCGCTGATCTTCAGACCTGGA | |
| | GGAGGAGATATGAGGGACAATTGGAGAAGTGAATTATATAAATATAAAGTAGTAAAAAT | |
| | TGAACCATTAGGAGTAGCACCCACCAAGGCAAAGAGAAGAGTGGTGCAGAGAGAAAAA | |
| | AGAGCAGTGGGAATAGGAGCTTTGTTCCTTGGGTTCTTGGGAGCAGCAGGAAGCACTAT | |
| | GGGCGCAGCCTCAATGACGCTGACGGTACAGGCCAGACAATTATTGTCTGGTATAGTGC | |
| | AGCAGCAGAACAATTTGCTGAGGGCTATTGAGGCGCAACAGCATCTGTTGCAACTCACA | |
| | GTCTGGGGCATCAAGCAGCTCCAGGCAAGAATCCTGGCTGTGGAAAGATACCTAAAGGA | |
| | TCAACAGCTCCTGGGGATTTGGGGTTGCTCTGGAAAACTCATTTGCACCACTGCTGTGCC | |
| | TTGGAATGCTAGTTGGAGTAATAAATCTCTGGAACAGATTTGGAATCACACGACCTGGAT | |
| | GGAGTGGGACAGAGAAATTAACAATTACACAAGCTTAATACACTCCTTAATTGAAGAAT | |
| | CGCAAAACCAGCAAGAAAAGAATGAACAAGAATTATTGGAATTAGATAAATGGGCAAGT | |
| | TTGTGGAATTGGTTTAACATAACAAATTGGCTGTGGTATATAAAATTATTCATAATGATA | |
| | GTAGGAGGCTTGGTAGGTTTAAGAATAGTTTTTGCTGTACTTTCTATAGTGAATAGAGTT | |
| | AGGCAGGGATATTCACCATTATCGTTTCAGACCCACCTCCCAACCCCGAGGGGACCCGAC | |
| | AGGCCCGAAGGAATAGAAGAAGAAGGTGGAGAGAGAGACAGAGACAGATCCATTCGAT | |
| | TAGTGAACGGATCTCGACGGTATCGGTTAACTTTTAAAAGAAAAGGGGGGATTGGGGGG | |
| | TACAGTGCAGGGGAAAGAATAGTAGACATAATAGCAACAGACATACAAACTAAAGAATT | |
| | ACAAAAACAAATTACAAAAATTCAAAATTTTATCGATCACGAGACTAGCCTCGAGAAGC | |
| | TTGATATCGAATTCCCACGGGGTTGGACGCGTAGGAACAGAGAAACAGGAGAATATGGG | |
| | CCAAACAGGATATCTGTGGTAAGCAGTTCCTGCCCCGGCTCAGGGCCAAGAACAGTTGG | |
| | AACAGCAGAATATGGGCCAAACAGGATATCTGTGGTAAGCAGTTCCTGCCCCGGCTCAG | |
| | GGCCAAGAACAGATGGTCCCCAGATGCGGTCCCGCCCTCAGCAGTTTCTAGAGAACCAT | |
| | CAGATGTTTCCAGGGTGCCCCAAGGACCTGAAATGACCCTGTGCCTTATTTGAACTAACC | |
| | AATCAGTTCGCTTCTCGCTTCTGTTCGCGCGCTTCTGCTCCCCGAGCTCTATATAAGCAGA | |
| | GCTCGTTTAGTGAACCGTCAGATCGCTAGCACCGGTGCCGCCACCATGCCTCTGGGCCTG | |
| | CTGTGGCTGGGCCTGGCCCTGCTGGGCGCCCTGCACGCCCAGGCCGGCGTGCAGGTGGA | |
| | GACAATCTCCCCAGGCGACGGACGCACATTCCCTAAGCGGGGCCAGACCTGCGTGGTGC | |
| | ACTATACAGGCATGCTGGAGGATGGCAAGAAGTTTGACAGCTCCCGGGATAGAAACAAG | |
| | CCATTCAAGTTTATGCTGGGCAAGCAGGAAGTGATCAGAGGCTGGGAGGAGGGCGTGGC | |
| | CCAGATGTCTGTGGGCCAGAGGGCCAAGCTGACCATCAGCCCAGACTACGCCTATGGAG | |
| | CAACAGGCCACCCAGGAATCATCCCACCTCACGCCACCCTGGTGTTCGATGTGGAGCTGC | |
| | TGAAGCTGGGCGAGGGATCCAACACATCAAAAGAGAACCCCTTTCTGTTCGCATTGGAG | |
| | GCCGTAGTCATATCTGTTGGATCCATGGGACTTATTATCTCCCTGTTGTGTGTGTACTTCT | |
| | GGCTGGAACGGACTATGCCCAGGATCCCCACGCTCAAGAATCTGGAAGATCTCGTCACA | |
| | GAATACCATGGTAATTTCAGCGCCTGGAGCGGAGTCTCTAAGGGTCTGGCCGAATCCCTC | |
| | CAACCCGATTATTCTGAACGGTTGTGCCTCGTATCCGAAATACCACCAAAAGGCGGGGCT | |
| | CTGGGTGAGGGCCCAGGGGCGAGTCCGTGCAATCAACACAGCCCGTATTGGGCCCCTCC | |
| | TTGTTATACGTTGAAGCCCGAAACTGGAAGCGGAGCTACTAACTTCAGCCTGCTGAAGCA | |
| | GGCTGGAGACGTGGAGGAGAACCCTGGACCTATGGCACTGCCCGTGACCGCCCTGCTGC | |
| | TGCCTCTGGCCCTGCTGCTGCACGCAGCCCGGCCTATCCTGTGGCACGAGATGTGGCACG | |
| | AGGGCCTGGAGGAGGCCAGCAGGCTGTATTTTGGCGAGCGCAACGTGAAGGGCATGTTC | |
| | GAGGTGCTGGAGCCTCTGCACGCCATGATGGAGAGAGGCCCACAGACCCTGAAGGAGAC | |
| | ATCCTTTAACCAGGCCTATGGACGGGACCTGATGGAGGCACAGGAGTGGTGCAGAAAGT | |
| | ACATGAAGTCTGGCAATGTGAAGGACCTGCTGCAGGCCTGGGATCTGTACTATCACGTGT | |
| | TTCGGAGAATCTCCAAGGGCAAAGACACGATTCCGTGGCTTGGGCATCTGCTCGTTGGGC | |
| | TGAGTGGTGCGTTTGGTTTCATCATCTTGGTCTATCTCTTGATCAATTGCAGAAATACAGG | |
| | CCCTTGGCTGAAAAAAGTGCTCAAGTGTAATACCCCCGACCCAAGCAAGTTCTTCTCCCA | |
| | GCTTTCTTCAGAGCATGGAGGCGATGTGCAGAAATGGCTCTCTTCACCTTTTCCCTCCTCA | |
| | AGCTTCTCCCCGGGAGGGCTGGCGCCCGAGATTTCACCTCTTGAGGTACTTGAACGAGAC | |
| | AAGGTTACCCAACTTCTCCTTCAACAGGATAAGGTACCCGAACCTGCGAGCCTTAGCTCC | |
| | AACCACTCTCTTACGAGCTGCTTCACCAATCAGGGATACTTCTTTTTCCACCTTCCCGATG | |
| | CGCTGGAAATCGAAGCTTGTCAAGTTTACTTTACCTATGATCCATATAGCGAGGAAGATC | |
| | CCGACGAAGGAGTCGCCGGTGCGCCCACGGGTTCCTCACCCCAACCTCTCCAGCCTCTCT | |
| | CAGGAGAAGATGATGCTTATTGCACTTTTCCCAGTAGAGACGATCTCCTCCTCTTTTCTCC | |

-continued

| SEQ ID NO | Sequence | Description |
|---|---|---|
| | ATCTCTTTTGGGGGGACCTTCCCCCCCTTCTACGGCACCTGGCGGGTCTGGTGCTGGCGA<br>GGAGCGGATGCCGCCGTCCCTCCAGGAGCGAGTACCACGAGATTGGGATCCCCAGCCAC<br>TTGGACCCCCCACCCCCGGCGTACCTGACCTTGTCGATTTTCAACCTCCCCCTGAATTGGT<br>GCTGCGAGAGGCTGGGGAGGAAGTTCCGGACGCTGGGCCGAGGGAGGGCGTGTCCTTTC<br>CATGGAGTAGGCCTCCAGGTCAAGGCGAGTTTAGGGCTCTCAACGCGCGGCTGCCGTTG<br>AATACAGACGCTTATCTCTCACTGCAGGAACTGCAAGGTCAGGACCCAACACATCTTGTA<br>GGATCTGGTGCTACTAATTTTTCTCTTTTGAAGCAAGCTGGAGATGTTGAAGAGAACCCT<br>GGTCCAGTGAGCAAGGGCGAGGAGCTGTTCACCGGGGTGGTGCCCATCCTGGTCGAGCT<br>GGACGGCGACGTAAACGGCCACAAGTTCAGCGTGTCCGGCGAGGGCGAGGGCGATGCCA<br>CCTACGGCAAGCTGACCCTGAAGTTCATCTGCACCACCGGCAAGCTGCCCGTGCCCTGGC<br>CCACCCTCGTGACCACCCTGACCTACGGCGTGCAGTGCTTCAGCCGCTACCCCGACCACA<br>TGAAGCAGCACGACTTCTTCAAGTCCGCCATGCCCGAAGGCTACGTCCAGGAGCGCACC<br>ATCTTCTTCAAGGACGACGGCAACTACAAGACCCGCGCCGAGGTGAAGTTCGAGGGCGA<br>CACCCTGGTGAACCGCATCGAGCTGAAGGGCATCGACTTCAAGGAGGACGGCAACATCC<br>TGGGGCACAAGCTGGAGTACAACTACAACAGCCACAACGTCTATATCATGGCCGACAAG<br>CAGAAGAACGGCATCAAGGTGAACTTCAAGATCCGCCACAACATCGAGGACGGCAGCGT<br>GCAGCTCGCCGACCACTACCAGCAGAACACCCCCATCGGCGACGGCCCCGTGCTGCTGC<br>CCGACAACCACTACCTGAGCACCCAGTCCGCCCTGAGCAAAGACCCCAACGAGAAGCGC<br>GATCACATGGTCCTGCTGGAGTTCGTGACCGCCGCCGGGATCACTCTCGGCATGGACGAG<br>CTGTACAAGTAAACTAGTGTCGACAATCAACCTCTGGATTACAAAATTTGTGAAAGATTG<br>ACTGGTATTCTTAACTATGTTGCTCCTTTTACGCTATGTGGATACGCTGCTTTAATGCCTTT<br>GTATCATGCTATTGCTTCCCGTATGGCTTTCATTTTCTCCTCCTTGTATAAATCCTGGTTGC<br>TGTCTCTTTATGAGGAGTTGTGGCCCGTTGTCAGGCAACGTGGCGTGGTGTGCACTGTGTT<br>TGCTGACGCAACCCCCACTGGTTGGGGCATTGCCACCACCTGTCAGCTCCTTTCCGGGAC<br>TTTCGCTTTCCCCCTCCCTATTGCCACGGCGGAACTCATCGCCGCCTGCCTTGCCCGCTGC<br>TGGACAGGGGCTCGGCTGTTGGGCACTGACAATTCCGTGGTGTTGTCGGGGAAGCTGACG<br>TCCTTTCCATGGCTGCTCGCCTGTGTTGCCACCTGGATTCTGCGCGGGACGTCCTTCTGCT<br>ACGTCCCTTCGGCCCTCAATCCAGCGGACCTTCCTTCCCGCGGCCTGCTGCCGGCTCTGCG<br>GCCTCTTCCGCGTCTTCGCCTTCGCCCTCAGACGAGTCGGATCTCCCTTTGGGCCGCCTCC<br>CCGCCTGGAATTCGAGCTCGGTACCTTTAAGACCAATGACTTACAAGGCAGCTGTAGATC<br>TTAGCCACTTTTTAAAAGAAAAGGGGGGACTGGAAGGGCTAATTCACTCCCAACGAAGA<br>CAAGATCTGCTTTTTGCTTGTACTGGGTCTCTCTGGTTAGACCAGATCTGAGCCTGGGAGC<br>TCTCTGGCTAACTAGGGAACCCACTGCTTAAGCCTCAATAAAGCTTGCCTTGAGTGCTTC<br>AAGTAGTGTGTGCCCGTCTGTTGTGTGACTCTGGTAACTAGAGATCCCTCAGACCCTTTTA<br>GTCAGTGTGGAAAATCTCTAGCAGTAGTAGTTCATGTCATCTTATTATTCAGTATTTATAA<br>CTTGCAAAGAAATGAATATCAGAGAGTGAGAGGAACTTGTTTATTGCAGCTTATAATGGT<br>TACAAATAAAGCAATAGCATCACAAATTTCACAAATAAAGCATTTTTTTCACTGCATTCT<br>AGTTGTGGTTTGTCCAAACTCATCAATGTATCTTATCATGTCTGGCTCTAGCTATCCCGCC<br>CCTAACTCCGCCCAGTTCCGCCCATTCTCCGCCCCATGGCTGACTAATTTTTTTTATTTAT<br>GCAGAGGCCGAGGCCGCCTCGGCCTCTGAGCTATTCCAGAAGTAGTGAGGAGGCTTTTTT<br>GGAGGCCTAGGCTTTTGCGTCGAGACGTACCCAATTCGCCCTATAGTGAGTCGTATTACG<br>CGCGCTCACTGGCCGTCGTTTTACAACGTCGTGACTGGGAAAACCCTGGCGTTACCCAAC<br>TTAATCGCCTTGCAGCACATCCCCCTTTCGCCAGCTGGCGTAATAGCGAAGAGGCCCGCA<br>CCGATCGCCCTTCCCAACAGTTGCGCAGCCTGAATGGCGAATGGCGCGACGCGCCCTGTA<br>GCGGCGCATTAAGCGCGGCGGGTGTGGTGGTTACGCGCAGCGTGACCGCTACACTTGCC<br>AGCGCCCTAGCGCCCGCTCCTTTCGCTTTCTTCCCTTCCTTTCTCGCCACGTTCGCCGGCTT<br>TCCCCGTCAAGCTCTAAATCGGGGGCTCCCTTTAGGGTTCCGATTTAGTGCTTTACGGCAC<br>CTCGACCCCAAAAAACTTGATTAGGGTGATGGTTCACGTAGTGGGCCATCGCCCTGATAG<br>ACGGTTTTTCGCCCTTTGACGTTGGAGTCCACGTTCTTTAATAGTGGACTCTTGTTCCAAA<br>CTGGAACAACACTCAACCCTATCTCGGTCTATTCTTTTGATTTATAAGGGATTTTGCCGAT<br>TTCGGCCTATTGGTTAAAAAATGAGCTGATTTAACAAAAATTTAACGCGAATTTTAACAA<br>AATATTAACGTTTACAATTTCCCAGGTGGCACTTTTCGGGGAAATGTGCGCGGAACCCCT<br>ATTTGTTTATTTTTCTAAATACATTCAAATATGTATCCGCTCATGAGACAATAACCCTGAT<br>AAATGCTTCAATAATATTGAAAAAGGAAGAGTATGAGTATTCAACATTTCCGTGTCGCCC<br>TTATTCCCTTTTTTGCGGCATTTTGCCTTCCTGTTTTTGCTCACCCAGAAACGCTGGTGAAA<br>GTAAAAGATGCTGAAGATCAGTTGGGTGCACGAGTGGGTTACATCGAACTGGATCTCAA<br>CAGCGGTAAGATCCTTGAGAGTTTTCGCCCCGAAGAACGTTTTCCAATGATGAGCACTTT<br>TAAAGTTCTGCTATGTGGCGCGGTATTATCCCGTATTGACGCCGGGCAAGAGCAACTCGG<br>TCGCCGCATACACTATTCTCAGAATGACTTGGTTGAGTACTCACCAGTCACAGAAAAGCA<br>TCTTACGGATGGCATGACAGTAAGAGAATTATGCAGTGCTGCCATAACCATGAGTGATAA<br>CACTGCGGCCAACTTACTTCTGACAACGATCGGAGGACCGAAGGAGCTAACCGCTTTTTT<br>GCACAACATGGGGGATCATGTAACTCGCCTTGATCGTTGGGAACCGGAGCTGAATGAAG<br>CCATACCAAACGACGAGCGTGACACCACGATGCCTGTAGCAATGGCAACAACGTTGCGC<br>AAACTATTAACTGGCGAACTACTTACTCTAGCTTCCCGGCAACAATTAATAGACTGGATG<br>GAGGCGGATAAAGTTGCAGGACCACTTCTGCGCTCGGCCCTTCCGGCTGGCTGGTTTATT<br>GCTGATAAATCTGGAGCCGGTGAGCGTGGGTCTCGCGGTATCATTGCAGCACTGGGGCC<br>AGATGGTAAGCCCTCCCGTATCGTAGTTATCTACACGACGGGGAGTCAGGCAACTATGG<br>ATGAACGAAATAGACAGATCGCTGAGATAGGTGCCTCACTGATTAAGCATTGGTAACTGT<br>CAGACCAAGTTTACTCATATATACTTTAGATTGATTTAAAACTTCATTTTTAATTTAAAAG<br>GATCTAGGTGAAGATCCTTTTTGATAATCTCATGACCAAAATCCCTTAACGTGAGTTTTCG<br>TTCCACTGAGCGTCAGACCCCGTAGAAAAGATCAAAGGATCTTCTTGAGATCCTTTTTTTC<br>TGCGCGTAATCTGCTGCTTGCAAACAAAAAAACCACCGCTACCAGCGGTGGTTTGTTTGC<br>CGGATCAAGAGCTACCAACTCTTTTTCCGAAGGTAACTGGCTTCAGCAGAGCGCAGATAC<br>CAAATACTGTCCTTCTAGTGTAGCCGTAGTTAGGCCACCACTTCAAGAACTCTGTAGCAC<br>CGCCTACATACCTCGCTCTGCTAATCCTGTTACCAGTGGCTGCTGCCAGTGGCGATAAGT | |

-continued

| SEQ ID NO | Sequence | Description |
|---|---|---|
| | CGTGTCTTACCGGGTTGGACTCAAGACGATAGTTACCGGATAAGGCGCAGCGGTCGGGC TGAACGGGGGGTTCGTGCACACAGCCCAGCTTGGAGCGAACGACCTACACCGAACTGAG ATACCTACAGCGTGAGCTATGAGAAAGCGCCACGCTTCCCGAAGGGAGAAAGGCGGACA GGTATCCGGTAAGCGGCAGGGTCGGAACAGGAGAGCGCACGAGGGAGCTTCCAGGGGG AAACGCCTGGTATCTTTATAGTCCTGTCGGGTTTCGCCACCTCTGACTTGAGCGTCGATTT TTGTGATGCTCGTCAGGGGGGCGGAGCCTATGGAAAAACGCCAGCAACGCGGCCTTTTT ACGGTTCCTGGCCTTTTGCTGGCCTTTTGCTCACATGTTCTTTCCTGCGTTATCCCCTGATT CTGTGGATAACCGTATTACCGCCTTTGAGTGAGCTGATACCGCTCGCCGCAGCCGAACGA CCGAGCGCAGCGAGTCAGTGAGCGAGGAAGCGGAAGAGCGCCCAATACGCAAACCGCC TCTCCCCGCGCGTTGGCCGATTCATTAATGCAGCTGGCACGACAGGTTTCCCGACTGGAA AGCGGGCAGTGAGCGCAACGCAATTAATGTGAGTTAGCTCACTCATTAGGCACCCCAGG CTTTACACTTTATGCTTCCGGCTCGTATGTTGTGTGGAATTGTGAGCGGATAACAATTTCA CACAGGAAACAGCTATGACCATGATTACGCCAAGCGCGCAATTAACCCTCACTAAAGGG AACAAAAGCTGGAGCTGCA | |
| 110 | (ATGCCTAATCCTCGGCCTGGAAAGCCTAGCGCTCCTTCTCTTGCTCTGGGACCTTCTCCT GGCGCCTCTCCATCTTGGAGAGCCGCTCCTAAAGCCAGCGATCTGCTGGGAGCTAGAGG ACCTGGCGGCACATTTCAGGGCAGAGATCTTAGAGGCGGAGCCCACGCTAGCTCCTCCA GCCTTAATCCTATGCCTCCTAGCCAGCTCCAGCTGCCTACACTGCCTCTGGTTATGGTGGC TCCTAGCGGAGCTAGACTGGGCCCTCTGCCTCATCTGCAAGCTCTGCTGCAGGACAGACC CCACTTCATGCACCAGCTGAGCACCGTGGATGCCCACGCAAGAACACCTGTGCTGCAGGT TCACCCTCTGGAATCCCCAGCCATGATCAGCCTGACACCTCCAACAACAGCCACCGGCGT GTTCAGCCTGAAAGCCAGACCTGGACTGCCTCCTGGCATCAATGTGGCCAGCCTGGAATG GGTGTCCAGAGAACCTGCTCTGCTGTGCACATTCCCCAATCCAAGCGCTCCCAGAAAGGA CAGCACACTGTCTGCCGTGCCTCAGAGCAGCTATCCCCTGCTTGCTAACGGCGTGTGCAA GTGGCCTGGATGCGAGAAGGTGTTCGAGGAACCCGAGGACTTCCTGAAGCACTGCCAGG CCGATCATCTGCTGGACGAGAAAGGCAGAGCCCAGTGTCTGCTCCAGCGCGAGATGGTG CAGTCTCTGGAACAGCAGCTGGTCCTGGAAAAAGAAAAGCTGAGCGCCATGCAGGCCCA CCTGGCCGGAAAAATGGCCCTGACAAAGGCCAGCAGCGTGGCCTCTTCTGATAAGGGCA GCTGCTGCATTGTGGCCGCTGGATCTCAGGGACCTGTGGTTCCTGCTTGGAGCGGACCTA GAGAGGCCCCTGATTCTCTGTTTGCCGTGCGGAGACACCTGTGGGGCTCTCACGGCAACT CTACTTTCCCCGAGTTCCTGCACAACATGGACTACTTCAAGTTCCACAACATGCGGCCTC CATTCACCTACGCCACACTGATCAGATGGGCCATTCTGGAAGCCCCTGAGAAGCAGAGA ACCCTGAACGAGATCTACCACTGGTTTACCCGGATGTTCGCCTTCTTCCGGAATCACCCT GCCACCTGGAAGAACGCCATCCGGCACAATCTGAGCCTGCACAAGTGCTTCGTGCGCGT GGAATCTGAGAAAGGCGCCGTGTGGACAGTGGACGAGCTGGAATTCAGAAAGAAGAGA AGCCAGCGGCCTAGCCGGTGCAGCAATCCTACACCTGGACCT) | Codon-optimized human FOXP3 cDNA, Without stop codon |
| 111 | (ATGCCTAATCCTCGGCCTGGAAAGCCTAGCGCTCCTTCTCTTGCTCTGGGACCTTCTCCT GGCGCCTCTCCATCTTGGAGAGCCGCTCCTAAAGCCAGCGATCTGCTGGGAGCTAGAGG ACCTGGCGGCACATTTCAGGGCAGAGATCTTAGAGGCGGAGCCCACGCTAGCTCCTCCA GCCTTAATCCTATGCCTCCTAGCCAGCTCCAGCTGCCTACACTGCCTCTGGTTATGGTGGC TCCTAGCGGAGCTAGACTGGGCCCTCTGCCTCATCTGCAAGCTCTGCTGCAGGACAGACC CCACTTCATGCACCAGCTGAGCACCGTGGATGCCCACGCAAGAACACCTGTGCTGCAGGT TCACCCTCTGGAATCCCCAGCCATGATCAGCCTGACACCTCCAACAACAGCCACCGGCGT GTTCAGCCTGAAAGCCAGACCTGGACTGCCTCCTGGCATCAATGTGGCCAGCCTGGAATG GGTGTCCAGAGAACCTGCTCTGCTGTGCACATTCCCCAATCCAAGCGCTCCCAGAAAGGA CAGCACACTGTCTGCCGTGCCTCAGAGCAGCTATCCCCTGCTTGCTAACGGCGTGTGCAA GTGGCCTGGATGCGAGAAGGTGTTCGAGGAACCCGAGGACTTCCTGAAGCACTGCCAGG CCGATCATCTGCTGGACGAGAAAGGCAGAGCCCAGTGTCTGCTCCAGCGCGAGATGGTG CAGTCTCTGGAACAGCAGCTGGTCCTGGAAAAAGAAAAGCTGAGCGCCATGCAGGCCCA CCTGGCCGGAAAAATGGCCCTGACAAAGGCCAGCAGCGTGGCCTCTTCTGATAAGGGCA GCTGCTGCATTGTGGCCGCTGGATCTCAGGGACCTGTGGTTCCTGCTTGGAGCGGACCTA GAGAGGCCCCTGATTCTCTGTTTGCCGTGCGGAGACACCTGTGGGGCTCTCACGGCAACT CTACTTTCCCCGAGTTCCTGCACAACATGGACTACTTCAAGTTCCACAACATGCGGCCTC CATTCACCTACGCCACACTGATCAGATGGGCCATTCTGGAAGCCCCTGAGAAGCAGAGA ACCCTGAACGAGATCTACCACTGGTTTACCCGGATGTTCGCCTTCTTCCGGAATCACCCT GCCACCTGGAAGAACGCCATCCGGCACAATCTGAGCCTGCACAAGTGCTTCGTGCGCGT GGAATCTGAGAAAGGCGCCGTGTGGACAGTGGACGAGCTGGAATTCAGAAAGAAGAGA AGCCAGCGGCCTAGCCGGTGCAGCAATCCTACACCTGGACCTTGA | Codon-optimized human FOXP3 cDNA, With stop codon |
| 112 | MEMWHEGLEEASRLYFGERNVKGMFEVLEPLHAMMERGPQTLKETSFNQAYGRDLMEAQE WCRKYMKSGNVKDLTQAWDLYYHVFRRISK | Naked FRB domain |
| 113 | MEMWHEGLEEASRLYFGERNVKGMFEVLEPLHAMMERGPQTLKETSFNQAYGRDLMEAQE WCRKYMKSGNVKDLLQAWDLYYHVFRRISK | Naked FRB domain |
| 114 | ATGGCACTGCCCGTGACCGCCCTGCTGCTGCCTCTGGCCCTGCTGCTGCACGCAGCCCGG CCTATCCTGTGGCACGAGATGTGGCACGAGGGCCTGGAGGAGGCCAGCAGGCTGTATTT TGGCGAGCGCAACGTGAAGGGCATGTTCGAGGTGCTGGAGCCTCTGCACGCCATGATGG AGAGAGGCCCACAGACCCTGAAGGAGACATCCTTTAACCAGGCCTATGGACGGGACCTG ATGGAGGCACAGGAGTGGTGCAGAAAGTACATGAAGTCTGGCAATGTGAAGGACCTGCT GCAGGCCTGGGATCTGTACTATCACGTGTTTCGGAGAATCTCCAAGCCAGCAGCTCTCGG CAAAGACACGATTCCGTGGCTTGGGCATCTGCTCGTTGGGCTGAGCGGTGCGTTTGGTTT CATCATCTTGGTCTATCTCTTGATCAATTGCAGAAATACAGGCCCTTGGCTGAAAAAAGT | CISCβ: FRB-IL2Rβ; nucleotide sequence |

-continued

| SEQ ID NO | Sequence | Description |
|---|---|---|
| | GCTCAAGTGTAATACCCCCGACCCAAGCAAGTTCTTCTCCCAGCTTTCTTCAGAGCATGG<br>AGGCGATGTGCAGAAATGGCTCTCTTCACCTTTTCCCTCCTCAAGCTTCTCCCCGGGAGG<br>GCTGGCGCCCGAGATTTCACCTCTTGAGGTACTTGAACGAGACAAGGTTACCCAACTTCT<br>CCTTCAACAGGATAAGGTACCCGAACCTGCGAGCCTTAGCTCCAACCACTCTCTTACGAG<br>CTGCTTCACCAATCAGGGATACTTCTTTTTCCACCTTCCCGATGCGCTGGAAATCGAAGCT<br>TGTCAAGTTTACTTTACCTATGATCCATATAGCGAGGAAGATCCCGACGAAGGAGTCGCC<br>GGTGCGCCCACGGGTTCCTCACCCCAACCTCTCCAGCCTCTCTCAGGAGAAGATGATGCT<br>TATTGCACTTTTCCCAGTAGAGACGATCTCCTCCTCTTTTCTCCATCTCTTTTGGGGGGAC<br>CTTCCCCCCCTTCTACGGCACCTGGCGGGTCTGGTGCTGGCGAGGAGCGGATGCCGCCGT<br>CCCTCCAGGAGCGAGTACCACGAGATTGGGATCCCCAGCCACTTGGACCCCCCACCCCCG<br>GCGTACCTGACCTTGTCGATTTTCAACCTCCCCCTGAATTGGTGCTGCGAGAGGCTGGGG<br>AGGAAGTTCCGGACGCTGGGCCGAGGGAGGGCGTGTCCTTTCCATGGAGTAGGCCTCCA<br>GGTCAAGGCGAGTTTAGGGCTCTCAACGCGCGGCTGCCGTTGAATACAGACGCTTATCTC<br>TCACTGCAGGAACTGCAAGGTCAGGACCCAACACATCTTGTA | |
| 115 | MALPVTALLLPLALLLHAARPILWHEMWHEGLEEASRLYFGERNVKGMFEVLEPLHAMMER<br>GPQTLKETSFNQAYGRDLMEAQEWCRKYMKSGNVKDLLQAWDLYYHVFRRISKPAALGKD<br>TIPWLGHLLVGLSGAFGFIILVYLLINCRNTGPWLKKVLKCNTPDPSKFFSQLSSEHGGDVQK<br>WLSSPFPSSSFSPGGLAPEISPLEVLERDKVTQLLLQQDKVPEPASLSSNHSLTSCFTNQGYFFF<br>HLPDALEIEACQVYFTYDPYSEEDPDEGVAGAPTGSSPQPLQPLSGEDDAYCTFPSRDDLLLFS<br>PSLLGGPSPPSTAPGGSGAGEERMPPSLQERVPRDWDPQPLGPPTPGVPDLVDFQPPPELVLRE<br>AGEEVPDAGPREGVSFPWSRPPGQGEFRALNARLPLNTDAYLSLQELQGQDPTHLV | CISCβ: FRB-IL2Rβ amino acid sequence |
| 116 | ATGCCTCTGGGCCTGCTGTGGCTGGGCCTGGCCCTGCTGGGCGCCCTGCACGCCCAGGCC<br>GGCGTGCAGGTGGAGACAATCTCCCCAGGCGACGGACGCACATTCCCTAAGCGGGGCCA<br>GACCTGCGTGGTGCACTATACAGGCATGCTGGAGGATGGCAAGAAGTTTGACAGCTCCC<br>GGGATAGAAACAAGCCATTCAAGTTTATGCTGGGCAAGCAGGAAGTGATCAGAGGCTGG<br>GAGGAGGGCGTGGCCCAGATGTCTGTGGGCCAGAGGGCCAAGCTGACCATCAGCCCAGA<br>CTACGCCTATGGAGCAACAGGCCACCCAGGAATCATCCCACCTCACGCCACCCTGGTGTT<br>CGATGTGGAGCTGCTGAAGCTGGGCGAGGGAGGGTCACCTGGATCCAACACATCAAAAG<br>AGAACCCCTTTCTGTTCGCATTGGAGGCCGTAGTCATATCTGTTGGATCCATGGGACTTAT<br>TATCTCCCTGTTGTGTGTGTACTTCTGGCTGGAACGGACTATGCCCAGGATCCCCACGCTC<br>AAGAATCTGGAAGATCTCGTCACAGAATACCATGGTAATTTCAGCGCCTGGAGCGGAGT<br>CTCTAAGGGTCTGGCCGAATCCCTCCAACCCGATTATTCTGAACGGTTGTGCCTCGTATCC<br>GAAATACCACCAAAAGGCGGGGCTCTGGGTGAGGGCCCAGGGGCGAGTCCGTGCAATCA<br>ACACAGCCCGTATTGGGCCCCTCCTTGTTATACGTTGAAGCCCGAAACT | CISCγ: FKBP-IL2Rγ; nucleotide sequence |
| 117 | MPLGLLWLGLALLGALHAQAGVQVETISPGDGRTFPKRGQTCVVHYTGMLEDGKKFDSSRD<br>RNKPFKFMLGKQEVIRGWEEGVAQMSVGQRAKLTISPDYAYGATGHPGIIPPHATLVFDVEL<br>LKLGEGGSPGSNTSKENPFLFALEAVVISVGSMGLIISLLCVYFWLERTMPRIPTLKNLEDLVT<br>EYHGNFSAWSGVSKGLAESLQPDYSERLCLVSEIPPKGGALGEGPGASPCNQHSPYWAPPCY<br>TLKPET | CISCγ: FKBP-IL2Rγ amino acid sequence |
| 118 | ATGCCTCTGGGCCTGCTGTGGCTGGGCCTGGCCCTGCTGGGCGCCCTGCACGCCCAGGCC<br>GGCGTGCAGGTGGAGACAATCTCCCCAGGCGACGGACGCACATTCCCTAAGCGGGGCCA<br>GACCTGCGTGGTGCACTATACAGGCATGCTGGAGGATGGCAAGAAGTTTGACAGCTCCC<br>GGGATAGAAACAAGCCATTCAAGTTTATGCTGGGCAAGCAGGAAGTGATCAGAGGCTGG<br>GAGGAGGGCGTGGCCCAGATGTCTGTGGGCCAGAGGGCCAAGCTGACCATCAGCCCAGA<br>CTACGCCTATGGAGCAACAGGCCACCCAGGAATCATCCCACCTCACGCCACCCTGGTGTT<br>CGATGTGGAGCTGCTGAAGCTGGGCGAGGGAGGGTCACCTGGATCCAACACATCAAAAG<br>AGAACCCCTTTCTGTTCGCATTGGAGGCCGTAGTCATATCTGTTGGATCCATGGGACTTAT<br>TATCTCCCTGTTGTGTGTGTACTTCTGGCTGGAACGGACTATGCCCAGGATCCCCACGCTC<br>AAGAATCTGGAAGATCTCGTCACAGAATACCATGGTAATTTCAGCGCCTGGAGCGGAGT<br>CTCTAAGGGTCTGGCCGAATCCCTCCAACCCGATTATTCTGAACGGTTGTGCCTCGTATCC<br>GAAATACCACCAAAAGGCGGGGCTCTGGGTGAGGGCCCAGGGGCGAGTCCGTGCAATCA<br>ACACAGCCCGTATTGGGCCCCTCCTTGTTATACGTTGAAGCCCGAAACTGGAAGCGGAGC<br>TACTAACTTCAGCCTGCTGAAGCAGGCTGGAGACGTGGAGGAGAACCCTGGACCTATGG<br>CACTGCCCGTGACCGCCCTGCTGCTGCCTCTGGCCCTGCTGCTGCACGCAGCCCGGCCTA<br>TCCTGTGGCACGAGATGTGGCACGAGGGCCTGGAGGAGGCCAGCAGGCTGTATTTTGGC<br>GAGCGCAACGTGAAGGGCATGTTCGAGGTGCTGGAGCCTCTGCACGCCATGATGGAGAG<br>AGGCCCACAGACCCTGAAGGAGACATCCTTTAACCAGGCCTATGGACGGGACCTGATGG<br>AGGCACAGGAGTGGTGCAGAAAGTACATGAAGTCTGGCAATGTGAAGGACCTGCTGCAG<br>GCCTGGGATCTGTACTATCACGTGTTTCGGAGAATCTCCAAGCCAGCAGCTCTCGGCAAA<br>GACACGATTCCGTGGCTTGGGCATCTGCTCGTTGGGCTGAGCGGTGCGTTTGGTTTCATC<br>ATCTTGGTCTATCTCTTGATCAATTGCAGAAATACAGGCCCTTGGCTGAAAAAAGTGCTC<br>AAGTGTAATACCCCCGACCCAAGCAAGTTCTTCTCCCAGCTTTCTTCAGAGCATGGAGGC<br>GATGTGCAGAAATGGCTCTCTTCACCTTTTCCCTCCTCAAGCTTCTCCCCGGGAGGGCTGG<br>CGCCCGAGATTTCACCTCTTGAGGTACTTGAACGAGACAAGGTTACCCAACTTCTCCTTC<br>AACAGGATAAGGTACCCGAACCTGCGAGCCTTAGCTCCAACCACTCTCTTACGAGCTGCT<br>TCACCAATCAGGGATACTTCTTTTTCCACCTTCCCGATGCGCTGGAAATCGAAGCTTGTCA<br>AGTTTACTTTACCTATGATCCATATAGCGAGGAAGATCCCGACGAAGGAGTCGCCGGTGC<br>GCCCACGGGTTCCTCACCCCAACCTCTCCAGCCTCTCTCAGGAGAAGATGATGCTTATTG<br>CACTTTTCCCAGTAGAGACGATCTCCTCCTCTTTTCTCCATCTCTTTTGGGGGGACCTTCC<br>CCCCCTTCTACGGCACCTGGCGGGTCTGGTGCTGGCGAGGAGCGGATGCCGCCGTCCCTC<br>CAGGAGCGAGTACCACGAGATTGGGATCCCCAGCCACTTGGACCCCCCACCCCCGGCGT | DISC: CISC-FRB; μDISC: μCISC-FRB DISC: CISC-FRB; nucleotide sequence |

-continued

| SEQ ID NO | Sequence | Description |
|---|---|---|
| | ACCTGACCTTGTCGATTTTCAACCTCCCCCTGAATTGGTGCTGCGAGAGGCTGGGGAGGA AGTTCCGGACGCTGGGCCGAGGGAGGGCGTGTCCTTTCCATGGAGTAGGCCTCCAGGTC AAGGCGAGTTTAGGGCTCTCAACGCGCGGCTGCCGTTGAATACAGACGCTTATCTCTCAC TGCAGGAACTGCAAGGTCAGGACCCAACACATCTTGTAGGATCTGGTGCTACTAATTTTT CTCTTTTGAAGCAAGCTGGAGATGTTGAAGAGAACCCCGGTCCGGAGATGTGGCATGAG GGTCTGGAAGAAGCGTCTCGACTGTACTTTGGTGAGCGCAATGTGAAGGGCATGTTTGAA GTCCTCGAACCCCTTCATGCCATGATGGAACGCGGACCCCAGACCTTGAAGGAGACAAG TTTTAACCAAGCTTACGGAAGAGACCTGATGGAAGCCCAGGAATGGTGCAGGAAATACA TGAAAAGCGGGAATGTGAAGGACTTGCTCCAAGCGTGGGACCTGTACTATCATGTCTTTA GGCGCATTAGTAAG | |
| 119 | MPLGLLWLGLALLGALHAQAGVQVETISPGDGRTFPKRGQTCVVHYTGMLEDGKKFDSSRD RNKPFKFMLGKQEVIRGWEEGVAQMSVGQRAKLTISPDYAYGATGHPGIIPPHATLVFDVEL LKLGEGGSPGSNTSKENPFLFALEAVVISVGSMGLIISLLCVYFWLERTMPRIPTLKNLEDLVT EYHGNFSAWSGVSKGLAESLQPDYSERLCLVSEIPPKGGALGEGPGASPCNQHSPYWAPPCY TLKPETGSGATNFSLLKQAGDVEENPGPMALPVTALLLPLALLLHAARPILWHEMWHEGLEE ASRLYFGERNVKGMFEVLEPLHAMMERGPQTLKETSFNQAYGRDLMEAQEWCRKYMKSG NVKDLLQAWDLYYHVFRRISKPAALGKDTIPWLGHLLVGLSGAFGFIILVYLLINCRNTGPWL KKVLKCNTPDPSKFFSQLSSEHGGDVQKWLSSPFPSSSFSPGGLAPEISPLEVLERDKVTQLLL QQDKVPEPASLSSNHSLTSCFTNQGYFFFHLPDALEIEACQVYFTYDPYSEEDPDEGVAGAPT GSSPQPLQPLSGEDDAYCTFPSRDDLLLFSPSLLGGPSPPSTAPGGSGAGEERMPPSLQERVPR DWDPQPLGPPTPGVPDLVDFQPPPELVLREAGEEVPDAGPREGVSFPWSRPPGQGEFRALNA RLPLNTDAYLSLQELQGQDPTHLVGSGATNFSLLKQAGDVEENPGPEMWHEGLEEASRLYF GERNVKGMFEVLEPLHAMMERGPQTLKETSFNQAYGRDLMEAQEWCRKYMKSGNVKDLL QAWDLYYHVFRRISK | DISC: CISC-FRB; µDISC amino acid sequence |
| 120 | GAGATGTGGCATGAGGGTCTGGAAGAAGCGTCTCGACTGTACTTTGGTGAGCGCAATGT GAAGGGCATGTTTGAAGTCCTCGAACCCCTTCATGCCATGATGGAACGCGGACCCCAGA CCTTGAAGGAGACAAGTTTTAACCAAGCTTACGGAAGAGACCTGATGGAAGCCCAGGAA TGGTGCAGGAAATACATGAAAAGCGGGAATGTGAAGGACTTGACCCAAGCGTGGGACCT GTACTATCATGTCTTTAGGCGCATTAGTAAG | FRB: express intracellularly to function as a decoy for rapamycin: FRB; nucleotide sequence |
| 121 | EMWHEGLEEASRLYFGERNVKGMFEVLEPLHAMMERGPQTLKETSFNQAYGRDLMEAQE WCRKYMKSGNVKDLTQAWDLYYHVFRRISK | FRB amino acid sequence |
| 122 | ATGGGGGCAGGTGCCACCGGACGAGCCATGGACGGGCCGCGCCTGCTGCTGTTGCTGCT TCTGGGGGTGTCCCTTGGAGGTGCCAAGGAGGCATGCCCCACAGGCCTGTACACACACA GCGGTGAGTGCTGCAAAGCCTGCAACCTGGGCGAGGGTGTGGCCCAGCCTTGTGGAGCC AACCAGACCGTGTGTGAGCCCTGCCTGGACAGCGTGACGTTCTCCGACGTGGTGAGCGC GACCGAGCCGTGCAAGCCGTGCACCGAGTGCGTGGGGCTCCAGAGCATGTCGGCGCCGT GCGTGGAGGCCGACGACGCCGTGTGCCGCTGCGCCTACGGCTACTACCAGGATGAGACG ACTGGGCGCTGCGAGGCGTGCCGCGTGTGCGAGGCGGGCTCGGGCCTCGTGTTCTCCTGC CAGGACAAGCAGAACACCGTGTGCGAGGAGTGCCCCGACGGCACGTATTCCGACGAGGC CAACCACGTGGACCCGTGCCTGCCCTGCACCGTGTGCGAGGACACCGAGCGCCAGCTCC GCGAGTGCACACGCTGGGCCGACGCCGAGTGCGAGGAGATCCCTGGCCGTTGGATTACA CGGTCCACACCCCCAGAGGGCTCGGACAGCACAGCCCCCAGCACCCAGGAGCCTGAGGC ACCTCCAGAACAAGACCTCATAGCCAGCACGGTGGCAGGTGTGGTGACCACAGTGATGG GCAGCTCCCAGCCCGTGGTGACCCGAGGCACCACCGACAACCTCATCCCTGTCTATTGCT CCATCCTGGCTGCTGTGGTTGTGGGTCTTGTGGCCTACATAGCCTTCAAGAGGTGA | LNGFR coding sequence with stop codon |
| 123 | GGAAGCGGAGCGACTAACTTCAGCCTGCTGAAGCAGGCCGGAGATGTGGAGGAAAACCC TGGACCG | LNGFRe: LNGFR epitope coding sequence 2A: P2A self-cleaving peptide |
| 124 | TGCTAGCGTGGGCAGGCAAGCCAGGTGCTGGACCTCTGCACGTGGGGCATGTGTGGGTA TGTACATGTACCTGTGTTCTTGGTGTGTGTGTGTGTGTGTGTGTGTGTGTGTGTCTAGAGC TGGGGTGCAACTATGGGGCCCCTCGGGACATGTCCCAGCCAATGCCTGCTTTGACCAGAG GAGTGTCCACGTGGCTCAGGTGGTCGAGTATCTCATACCGCCCTAGCACACGTGTGACTC CTTTCCCCTATTGTCTAC | 0.25 kb human FOXP3 5'HA designed for both TALEN and Cas9 approache |
| 125 | CATGTGTGGGTATGTACATGTACCTGTGTTCTTGGTGTGTGTGTGTGTGTGTGTGTGTG TGTGTCTAGAGCTGGGGTGCAACTATGGGGCCCCTCGGGACATGTCCCAGCCAATGCCTG | 0.3 kb human FOXP3 |

-continued

| SEQ ID NO | Sequence | Description |
|---|---|---|
| | CTTTGACCAGAGGAGTGTCCACGTGGCTCAGGTGGTCGAGTATCTCATACCGCCCTAGCA<br>CACGTGTGACTCCTTTCCCCTATTGTCTACGCAGCCTGCCCTTGGACAAGGACCCGATGC<br>CCAACCCCAGGCCTGGCAAGCCCTCGGCCCCTTCCTTGGCCCTTGGCCCATCCCC | 5'HA for Cas9-T9 |
| 126 | AGCCTGTGCAGGGTGCAGGGAGGGCTAGAGGCCTGAGGCTTGAAACAGCTCTCAAGTGG<br>AGGGGGAAACAACCATTGCCCTCATAGAGGACACATCCACACCAGGGCTGTGCTAGCGT<br>GGGCAGGCAAGCCAGGTGCTGGACCTCTGCACGTGGGGCATGTGTGGGTATGTACATGT<br>ACCTGTGTTCTTGGTGTGTGTGTGTGTGTGTGTGTGTGTGTGTCTAGAGCTGGGGTGCA<br>ACTATGGGGCCCCTCGGGACATGTCCCAGCCAATGCCTGCTTTGACCAGAGGAGTGTCCA<br>CGTGGCTCAGGTGGTCGAGTATCTCATACCGCCCTAGCACACGTGTGACTCCTTTCCCCT<br>ATTGTCTACGCAGCCTGCCCTTGGACAAGGACCCGATGCCCAACCCCAGGCCTGGCAAGC<br>CCTCGGCCCCTTCCTTGGCCCTTGGCCCATCCCC | 0.45 kb human FOXP3 5'HA for Cas9-T9 |
| 127 | ATCACTTGCCAGGACTGTTACAATAGCCTCCTCACTAGCCCCACTCACAGCAGCCAGATG<br>AATCTTTTGAGTCCATGCCTAGTCACTGGGGCAAAATAGGACTCCGAGGAGAAAGTCCG<br>AGACCAGCTCCGGCAAGATGAGCAAACACAGCCTGTGCAGGGTGCAGGGAGGGCTAGA<br>GGCCTGAGGCTTGAAACAGCTCTCAAGTGGAGGGGGAAACAACCATTGCCCTCATAGAG<br>GACACATCCACACCAGGGCTGTGCTAGCGTGGGCAGGCAAGCCAGGTGCTGGACCTCTG<br>CACGTGGGGCATGTGTGGGTATGTACATGTACCTGTGTTCTTGGTGTGTGTGTGTGTGT<br>GTGTGTGTGTGTGTCTAGAGCTGGGGTGCAACTATGGGGCCCCTCGGGACATGTCCCAGC<br>CAATGCCTGCTTTGACCAGAGGAGTGTCCACGTGGCTCAGGTGGTCGAGTATCTCATACC<br>GCCCTAGCACACGTGTGACTCCTTTCCCCTATTGTCTACGCAGCCTGCCCTTGGACAAGG<br>ACCCGATGCCCAACCCCAGGCCTGGCAAGCCCTCGGCCCCTTCCTTGGCCCTTGGCCCAT<br>CCCC | 0.6 kb human FOXP3 5'HA for Cas9-T9 |
| 128 | ATCTCAGGTAATGTCAGCTCGGTCCTTCCAGCTGCTCAAGCTAAAACCCATGTCACTTTG<br>ACTCTCCCTCTTGCCCACTACATCCAAGCTGCTAGCACTGCTCCTGATCCAGCTTCAGATT<br>AAGTCTCAGAATCTACCCACTTCTCGCCTTCTCCACTGCCACCAGCCCATTCTGTGCCAGC<br>ATCATCACTTGCCAGGACTGTTACAATAGCCTCCTCACTAGCCCCACTCACAGCAGCCAG<br>ATGAATCTTTTGAGTCCATGCCTAGTCACTGGGGCAAAATAGGACTCCGAGGAGAAAGTC<br>CGAGACCAGCTCCGGCAAGATGAGCAAACACAGCCTGTGCAGGGTGCAGGGAGGGCTA<br>GAGGCCTGAGGCTTGAAACAGCTCTCAAGTGGAGGGGGAAACAACCATTGCCCTCATAG<br>AGGACACATCCACACCAGGGCTGTGCTAGCGTGGGCAGGCAAGCCAGGTGCTGGACCTC<br>TGCACGTGGGGCATGTGTGGGTATGTACATGTACCTGTGTTCTTGGTGTGTGTGTGTGT<br>GTGTGTGTGTGTGTGTCTAGAGCTGGGGTGCAACTATGGGGCCCCTCGGGACATGTCCCA<br>GCCAATGCCTGCTTTGACCAGAGGAGTGTCCACGTGGCTCAGGTGGTCGAGTATCTCATA<br>CCGCCCTAGCACACGTGTGACTCCTTTCCCCTATTGTCTACGCAGCCTGCCCTTGGACAAG<br>GACCCGATGCCCAACCCCAGGCCTGGCAAGCCCTCGGCCCCTTCCTTGGCCCTTGGCCCA<br>TCCCC | 0.8 kb human FOXP3 5'HA for Cas9-T9 |
| 129 | GACATGTCCCAGCCAATGCCTGCTTTGACCAGAGGAGTGTCCACGTGGCTCAGGTGGTCG<br>AGTATCTCATACCGCCCTAGCACACGTGTGACTCCTTTCCCCTATTGTCTACGCAGCCTGC<br>CCTTGGACAAGGACCCGATGCCCAACCCCAGGCCTGGCAAGCCCTCGGCCCCTTCCTTGG<br>CCCTTGGCCCATCCCCAGGAGCCTCGCCCAGCTGGAGGGCTGCACCCAAAGCCTCAGACC<br>TGCTGGGGGCCCGGGGCCCAGGGGGAACCTTCCA | 0.3 kb human FOXP3 5'HA for Cas9-T3 |
| 130 | CATAGAGGACACATCCACACCAGGGCTGTGCTAGCGTGGGCAGGCAAGCCAGGTGCTGG<br>ACCTCTGCACGTGGGGCATGTGTGGGTATGTACATGTACCTGTGTTCTTGGTGTGTGTGTG<br>TGTGTGTGTGTGTGTGTGTGTCTAGAGCTGGGGTGCAACTATGGGGCCCCTCGGGACATG<br>TCCCAGCCAATGCCTGCTTTGACCAGAGGAGTGTCCACGTGGCTCAGGTGGTCGAGTATC<br>TCATACCGCCCTAGCACACGTGTGACTCCTTTCCCCTATTGTCTACGCAGCCTGCCCTTGG<br>ACAAGGACCCGATGCCCAACCCCAGGCCTGGCAAGCCCTCGGCCCCTTCCTTGGCCCTTG<br>GCCCATCCCCAGGAGCCTCGCCCAGCTGGAGGGCTGCACCCAAAGCCTCAGACCTGCTG<br>GGGGCCCGGGGCCCAGGGGGAACCTTCCA | 0.45 kb human FOXP3 5'HA for Cas9-T3 |
| 131 | CTAGTCACTGGGGCAAAATAGGACTCCGAGGAGAAAGTCCGAGACCAGCTCCGGCAAGA<br>TGAGCAAACACAGCCTGTGCAGGGTGCAGGGAGGGCTAGAGGCCTGAGGCTTGAAACAG<br>CTCTCAAGTGGAGGGGGAAACAACCATTGCCCTCATAGAGGACACATCCACACCAGGGC<br>TGTGCTAGCGTGGGCAGGCAAGCCAGGTGCTGGACCTCTGCACGTGGGGCATGTGTGGG<br>TATGTACATGTACCTGTGTTCTTGGTGTGTGTGTGTGTGTGTGTGTGTGTGTGTGTCTAGA<br>GCTGGGGTGCAACTATGGGGCCCCTCGGGACATGTCCCAGCCAATGCCTGCTTTGACCAG<br>AGGAGTGTCCACGTGGCTCAGGTGGTCGAGTATCTCATACCGCCCTAGCACACGTGTGAC<br>TCCTTTCCCCTATTGTCTACGCAGCCTGCCCTTGGACAAGGACCCGATGCCCAACCCCAG<br>GCCTGGCAAGCCCTCGGCCCCTTCCTTGGCCCTTGGCCCATCCCCAGGAGCCTCGCCCAG<br>CTGGAGGGCTGCACCCAAAGCCTCAGACCTGCTGGGGGCCCGGGGCCCAGGGGGAACCT<br>TCCA | 0.6 kb human FOXP3 5'HA for Cas9-T3 |
| 132 | GTGAGGCCCTGGGCCCAGGATGGGGCAGGCAGGGTGGGGTACCTGGACCTACAGGTGCC<br>GACCTTTACTGTGGCACTGGGCGGGAGGGGGGCTGGCTGGGGCACAGGAAGTGGTTTCT<br>GGGTCCCAGGCAAGTCTGTGACTTATGCAGATGTTGCAGGGCCAAGAAAATCCCCACCT<br>GCCAGGCCTCAGAGATTGGAGGCTCTCCCCGACCTCCCAATCCCTGTCTCAGGAGAGGAG<br>GAGGCCGT | 0.25 kb human FOXP3 3'HA designed for both TALEN and Cas9 approaches: |

-continued

| SEQ ID NO | Sequence | Description |
|---|---|---|
| 133 | GCCTCGCCCAGCTGGAGGGCTGCACCCAAAGCCTCAGACCTGCTGGGGGCCCGGGGCCC<br>AGGGGGAACCTTCCAGGGCCGAGATCTTCGAGGCGGGGCCCATGCCTCCTCTTCTTCCTT<br>GAACCCCATGCCACCATCGCAGCTGCAGGTGAGGCCCTGGGCCCAGGATGGGGCAGGCA<br>GGGTGGGGTACCTGGACCTACAGGTGCCGACCTTTACTGTGGCACTGGGCGGGAGGGGG<br>GCTGGCTGGGGCACAGGAAGTGGTTTCTGGGTCCCAGGCAAGTCTGTGACTTATGCAGAT<br>GTT | 0.3 kb human FOXP3 3'HA for Cas9-T9 |
| 134 | GCCTCGCCCAGCTGGAGGGCTGCACCCAAAGCCTCAGACCTGCTGGGGGCCCGGGGCCC<br>AGGGGGAACCTTCCAGGGCCGAGATCTTCGAGGCGGGGCCCATGCCTCCTCTTCTTCCTT<br>GAACCCCATGCCACCATCGCAGCTGCAGGTGAGGCCCTGGGCCCAGGATGGGGCAGGCA<br>GGGTGGGGTACCTGGACCTACAGGTGCCGACCTTTACTGTGGCACTGGGCGGGAGGGGG<br>GCTGGCTGGGGCACAGGAAGTGGTTTCTGGGTCCCAGGCAAGTCTGTGACTTATGCAGAT<br>GTTGCAGGGCCAAGAAAATCCCCACCTGCCAGGCCTCAGAGATTGGAGGCTCTCCCCGA<br>CCTCCCAATCCCTGTCTCAGGAGAGGAGGAGGCCGTATTGTAGTCCCATGAGCATAGCTA<br>TGTGTCCCCATCCCCATGTGACAAGAGAAGAGGA | 0.45 kb human FOXP3 3'HA for Cas9-T9 |
| 135 | GCCTCGCCCAGCTGGAGGGCTGCACCCAAAGCCTCAGACCTGCTGGGGGCCCGGGGCCC<br>AGGGGGAACCTTCCAGGGCCGAGATCTTCGAGGCGGGGCCCATGCCTCCTCTTCTTCCTT<br>GAACCCCATGCCACCATCGCAGCTGCAGGTGAGGCCCTGGGCCCAGGATGGGGCAGGCA<br>GGGTGGGGTACCTGGACCTACAGGTGCCGACCTTTACTGTGGCACTGGGCGGGAGGGGG<br>GCTGGCTGGGGCACAGGAAGTGGTTTCTGGGTCCCAGGCAAGTCTGTGACTTATGCAGAT<br>GTTGCAGGGCCAAGAAAATCCCCACCTGCCAGGCCTCAGAGATTGGAGGCTCTCCCCGA<br>CCTCCCAATCCCTGTCTCAGGAGAGGAGGAGGCCGTATTGTAGTCCCATGAGCATAGCTA<br>TGTGTCCCCATCCCCATGTGACAAGAGAAGAGGACTGGGGCCAAGTAGGTGAGGTGACA<br>GGGCTGAGGCCAGCTCTGCAACTTATTAGCTGTTTGATCTTTAAAAAGTTACTCGATCTCC<br>ATGAGCCTCAGTTTCCATACGTGTAAAAGGGGGATGATCATAGCATCTACCATGTGGGCT<br>TGCA | 0.6 kb human FOXF3 3'HA for Cas9-T9 |
| 136 | GCCTCGCCCAGCTGGAGGGCTGCACCCAAAGCCTCAGACCTGCTGGGGGCCCGGGGCCC<br>AGGGGGAACCTTCCAGGGCCGAGATCTTCGAGGCGGGGCCCATGCCTCCTCTTCTTCCTT<br>GAACCCCATGCCACCATCGCAGCTGCAGGTGAGGCCCTGGGCCCAGGATGGGGCAGGCA<br>GGGTGGGGTACCTGGACCTACAGGTGCCGACCTTTACTGTGGCACTGGGCGGGAGGGGG<br>GCTGGCTGGGGCACAGGAAGTGGTTTCTGGGTCCCAGGCAAGTCTGTGACTTATGCAGAT<br>GTTGCAGGGCCAAGAAAATCCCCACCTGCCAGGCCTCAGAGATTGGAGGCTCTCCCCGA<br>CCTCCCAATCCCTGTCTCAGGAGAGGAGGAGGCCGTATTGTAGTCCCATGAGCATAGCTA<br>TGTGTCCCCATCCCCATGTGACAAGAGAAGAGGACTGGGGCCAAGTAGGTGAGGTGACA<br>GGGCTGAGGCCAGCTCTGCAACTTATTAGCTGTTTGATCTTTAAAAAGTTACTCGATCTCC<br>ATGAGCCTCAGTTTCCATACGTGTAAAAGGGGGATGATCATAGCATCTACCATGTGGGCT<br>TGCAGTGCAGAGTATTTGAATTAGACACAGAACAGTGAGGATCAGGATGGCCTCTCACC<br>CACCTGCCTTTCTGCCCAGCTGCCCACACTGCCCCTAGTCATGGTGGCACCCTCCGGGGC<br>ACGGCTGGGCCCCTTGCCCCACTTACAGGCACTCCTCCAGGACAGGCCACATTTCATGCA<br>CCAGGTATGGACGGTGAAT | 0.8 kb human FOXF3 3'HA for Cas9-T9 |
| 137 | CGAGATCTTCGAGGCGGGGCCCATGCCTCCTCTTCTTCCTTGAACCCCATGCCACCATCG<br>CAGCTGCAGGTGAGGCCCTGGGCCCAGGATGGGGCAGGCAGGGTGGGGTACCTGGACCT<br>ACAGGTGCCGACCTTTACTGTGGCACTGGGCGGGAGGGGGGCTGGCTGGGGCACAGGAA<br>GTGGTTTCTGGGTCCCAGGCAAGTCTGTGACTTATGCAGATGTTGCAGGGCCAAGAAAAT<br>CCCCACCTGCCAGGCCTCAGAGATTGGAGGCTCTCCCCGACCTCCCAATCCCTGTCTCAG<br>GA | 0.3 kb human FOXP3 3'HA for Cas9-T3 |
| 138 | CGAGATCTTCGAGGCGGGGCCCATGCCTCCTCTTCTTCCTTGAACCCCATGCCACCATCG<br>CAGCTGCAGGTGAGGCCCTGGGCCCAGGATGGGGCAGGCAGGGTGGGGTACCTGGACCT<br>ACAGGTGCCGACCTTTACTGTGGCACTGGGCGGGAGGGGGGCTGGCTGGGGCACAGGAA<br>GTGGTTTCTGGGTCCCAGGCAAGTCTGTGACTTATGCAGATGTTGCAGGGCCAAGAAAAT<br>CCCCACCTGCCAGGCCTCAGAGATTGGAGGCTCTCCCCGACCTCCCAATCCCTGTCTCAG<br>GAGAGGAGGAGGCCGTATTGTAGTCCCATGAGCATAGCTATGTGTCCCCATCCCCATGTG<br>ACAAGAGAAGAGGACTGGGGCCAAGTAGGTGAGGTGACAGGGCTGAGGCCAGCTCTGC<br>AACTTATTAGCTGTTTGATCTTTAAAAAGTTACTC | 0.45 kb human FOXP3 3'HA for Cas9-T3 |
| 139 | CGAGATCTTCGAGGCGGGGCCCATGCCTCCTCTTCTTCCTTGAACCCCATGCCACCATCG<br>CAGCTGCAGGTGAGGCCCTGGGCCCAGGATGGGGCAGGCAGGGTGGGGTACCTGGACCT<br>ACAGGTGCCGACCTTTACTGTGGCACTGGGCGGGAGGGGGGCTGGCTGGGGCACAGGAA<br>GTGGTTTCTGGGTCCCAGGCAAGTCTGTGACTTATGCAGATGTTGCAGGGCCAAGAAAAT<br>CCCCACCTGCCAGGCCTCAGAGATTGGAGGCTCTCCCCGACCTCCCAATCCCTGTCTCAG<br>GAGAGGAGGAGGCCGTATTGTAGTCCCATGAGCATAGCTATGTGTCCCCATCCCCATGTG<br>ACAAGAGAAGAGGACTGGGGCCAAGTAGGTGAGGTGACAGGGCTGAGGCCAGCTCTGC<br>AACTTATTAGCTGTTTGATCTTTAAAAAGTTACTCGATCTCCATGAGCCTCAGTTTCCATA<br>CGTGTAAAAGGGGGATGATCATAGCATCTACCATGTGGGCTTGCAGTGCAGAGTATTTGA<br>ATTAGACACAGAACAGTGAGGATCAGGATGGCCTCTCACCCACCTGCCTTTCTGCCCAGC<br>TGC | 0.6 kb human FOXP3 3'HA for Cas9-T3 |

-continued

| SEQ ID NO | Sequence | Description |
|---|---|---|
| 140 | TAGCCACCTCTCCATCCTCTTGCTTTCTTTGCCTGGACACCCCGTTCTCCTGTGGATTCGG GTCACCTCTCACTCCTTTCATTTGGGCAGCTCCCCTACCCCCCTTACCTCTCTAGTCTGTGC TAGCTCTTCCAGCCCCCTGTCATGGCATCTTCCAGGGGTCCGAGAGCTCAGCTAGTCTTCT TCCTCCAACCCGGGCCCCTATGTCCACTTCAGGACAGCATGTTTGCTGCCTCCAGGGATC CTGTGT | 0.25 kb AAVS1 5'HA for Cas9-P1 and Cas9-N2 |
| 141 | AGGTTCCGTCTTCCTCCACTCCCTCTTCCCCTTGCTCTCTGCTGTGTTGCTGCCCAAGGAT GCTCTTTCCGGAGCACTTCCTTCTCGGCGCTGCACCACGTGATGTCCTCTGAGCGGATCCT CCCCGTGTCTGGGTCCTCTCCGGGCATCTCTCCTCCCTCACCCAACCCCATGCCGTCTTCA CTCGCTGGGTTCCCTTTTCCTTCTCCTTCTGGGGCCTGTGCCATCTCTCGTTTCTTAGGATG GCCTTCTCCGACGGATGTCTCCCTTGCGTCCCGCCTCCCCTTCTTGTAGGCCTGCATCATC ACCGTTTTTCTGGACAACCCCAAAGTACCCCGTCTCCCTGGCTTTAGCCACCTCTCCATCC TCTTGCTTTCTTTGCCTGGACACCCCGTTCTCCTGTGGATTCGGGTCACCTCTCACTCCTTT CATTTGGGCAGCTCCCCTACCCCCCTTACCTCTCTAGTCTGTGCTAGCTCTTCCAGCCCCC TGTCATGGCATCTTCCAGGGGTCCGAGAGCTCAGCTAGTCTTCTTCCTCCAACCCGGGCC CCTATGTCCACTTCAGGACAGCATGTTTGCTGCCTCCAGGGATCCTGTGT | 0.6 kb AAVS1 5'HA for Cas9-P1 and Cas9-N2 |
| 142 | CTCTGGTTCTGGGTACTTTTATCTGTCCCCTCCACCCCACAGTGGGGCCACTAGGGACAG GATTGGTGACAGAAAAGCCCCATCCTTAGGCCTCCTCCTTCCTAGTCTCCTGATATTGGGT CTAACCCCCACCTCCTGTTAGGCAGATTCCTTATCTGGTGACACACCCCCATTTCCTGGAG CCATCTCTCTCCTTGCCAGAACCTCTAAGGTTTGCTTACGATGGAGCCAGAGAGGATCCT GGGAGGGA | 0.25 kb AAVS1 3'HA for Cas9-P1 and Cas9-N2 |
| 143 | CTCTGGTTCTGGGTACTTTTATCTGTCCCCTCCACCCCACAGTGGGGCCACTAGGGACAG GATTGGTGACAGAAAAGCCCCATCCTTAGGCCTCCTCCTTCCTAGTCTCCTGATATTGGGT CTAACCCCCACCTCCTGTTAGGCAGATTCCTTATCTGGTGACACACCCCCATTTCCTGGAG CCATCTCTCTCCTTGCCAGAACCTCTAAGGTTTGCTTACGATGGAGCCAGAGAGGATCCT GGGAGGGAGAGCTTGGCAGGGGGTGGGAGGGAAGGGGGGGATGCGTGACCTGCCCGGT TCTCAGTGGCCACCCTGCGCTACCCTCTCCCAGAACCTGAGCTGCTCTGACGCGGCCGTC TGGTGCGTTTCACTGATCCTGGTGCTGCAGCTTCCTTACACTTCCCAAGAGGAGAAGCAG TTTGGAAAAACAAAATCAGAATAAGTTGGTCCTGAGTTCTAACTTTGGCTCTTCACCTTTC TAGTCCCCAATTTATATTGTTCCTCCGTGCGTCAGTTTTACCTGTGAGATAAGGCCAGTAG CCAGCCCCGTCCTGGCAGGGCTGTGGTGAGGAGGGGGGTGTCCGTGTGGAAAACTCCC | 0.6 kb AAVS1 3'HA for Cas9-P1 and Cas9-N2 |
| 144 | MGAGATGRAMDGPRLLLLLLLGVSLGGAKEACPTGLYTHSGECCKACNLGEGVAQPCGAN QTVCEPCLDSVTFSDVVSATEPCKPCTECVGLQSMSAPCVEADDAVCRCAYGYYQDETTGR CEACRVCEAGSGLVFSCQDKQNTVCEECPDGTYSDEANHVDPCLPCTVCEDTERQLRECTR WADAECEEIPGRWITRSTPPEGSDSTAPSTQEPEAPPEQDLIASTVAGVVTTVMGSSQPVVTR GTTDNLIPVYCSILAAVVVGLVAYIAFKR | LNGFRt protein sequence |
| 145 | MGTSLLCWMALCLLGADHADACPYSNPSLCSGGGGSELPTQGTFSNVSTNVSPAKPTTTACP YSNPSLCSGGGGSPAPRPPTPAPTIASQPLSLRPEACRPAAGGAVHTRGLDFACDIYIWAPLAG TCGVLLLSLVITLYCNHRNRRRVCKCPRPVV | RQR8 protein sequence |
| 146 | MLLLVTSLLLCELPHPAFLLIPRKVCNGIGIGEFKDSLSINATNIKHFKNCTSISGDLHILPVAFR GDSFTHTPPLDPQELDILKTVKEITGFLLIQAWPENRTDLHAFENLEIIRGRTKQHGQFSLAVVS LNITSLGLRSLKEISDGDVIISGNKNLCYANTINWKKLFGTSGQKTKIISNRGENSCKATGQVC HALCSPEGCWGPEPRDCVSCRNVSRGRECVDKCNLLEGEPREFVENSECIQCHPECLPQAMNI TCTGRGPDNCIQCAHYIDGPHCVKTCPAGVMGENNTLVWKYADAGHVCHLCHPNCTYGCT GPGLEGCPTNGPKIPSIATGMVGALLLLLVVALGIGLFM | EGFRt with GM-CSFR signal peptide |
| 147 | GAACAGAGAAACAGGAGAATATGGGCCAAACAGGATATCTGTGGTAAGCAGTTCCTGCC CCGGCTCAGGGCCAAGAACAGTTGGAACAGCAGAATATGGGCCAAACAGGATATCTGTG GTAAGCAGTTCCTGCCCCGGCTCAGGGCCAAGAACAGATGGTCCCCAGATGCGGTCCCG CCCTCAGCAGTTTCTAGAGAACCATCAGATGTTTCCAGGGTGCCCCAAGGACCTGAAATG ACCCTGTGCCTTATTTGAACTAACCAATCAGTTCGCTTCTCGCTTCTGTTCGCGCGCTTCT GCTCCCCGAGCTCTATATAAGCAGAGCTCGTTTAGTGAACCGTCAGATC | MND promoter |
| 148 | CCACGGGGTTGGGGTTGCGCCTTTTCCAAGGCAGCCCTGGGTTTGCGCAGGGACGCGGCT GCTCTGGGCGTGGTTCCGGGAAACGCAGCGGCGCCGACCCTGGGTCTCGCACATTCTTCA CGTCCGTTCGCAGCGTCACCCGGATCTTCGCCGCTACCCTTGTGGGCCCCCCGGCGACGC TTCCTGCTCCGCCCCTAAGTCGGGAAGGTTCCTTGCGGTTCGCGGCGTGCCGGACGTGAC AAACGGAAGCCGCACGTCTCACTAGTACCCTCGCAGACGGACAGCGCCAGGGAGCAATG GCAGCGCGCCGACCGCGATGGGCTGTGGCCAATAGCGGCTGCTCAGCGGGGCGCGCCGA GAGCAGCGGCCGGGAAGGGGCGGTGCGGGAGGCGGGGTGTGGGGCGGTAGTGTGGGCC CTGTTCCTGCCCGCGCGGTGTTCCGCATTCTGCAAGCCTCCGGAGCGCACGTCGGCAGTC GGCTCCCTCGTTGACCGAATCACCGACCTCTCTCCCCAGGGGGATCC | PGK promoter |
| 149 | AGGCTCCGGTGCCCGTCAGTGGGCAGAGCGCACATCGCCCACAGTCCCCGAGAAGTTGG GGGGAGGGGTCGGCAATTGAACCGGTGCCTAGAGAAGGTGGCGCGGGGTAAACTGGGA AAGTGATGTCGTGTACTGGCTCCGCCTTTTTCCCGAGGGTGGGGGAGAACCGTATATAAG TGCAGTAGTCGCCGTGAACGTTCTTTTTCGCAACGGGTTTGCCGCCAGAACACA | EF1 promoter |

-continued

| SEQ ID NO | Sequence | Description |
|---|---|---|
| 150 | TGCTTTATTTGTGAAATTTGTGATGCTATTGCTTTATTTGTAACCATTATAAGCTGCAATA AACAAGTTAACAACAACAATTGCATTCATTTTATGTTTCAGGTTCAGGGGGAGATGTGGG AGGTTTTTTAAAGC | SV40 poly A |
| 151 | CCTCAAGATCAAGGAAAGGAGGATGGACGAACAGGGGCCAAACTGGTGGGAGGCAGAG GTGGTGGGGGCAGGGATGATAGGCCCTGGATGTGCCCACAGGGACCAAGAAGTGAGGTT TCCACTGTCTTGCCTGCCAGGGCCCCTGTTCCCCCGCTGGCAGCCACCCCCTCCCCCATCA TATCCTTTGCCCCAAGGCTGCTCAGAGGGGCCCCGGTCCTGGCCCCAGCCCCCACCTCCG CCCCAGACACACCCCCCAGTCGAGCCCTGCAGCCAAACAGAGCCTTCACAACCAGCCAC ACAGAGCCTGCCTCAGCTGCTCGCACAGATTACTTCAGGGCTGGAAAAGTCACACAGAC ACACAAAATGTCACAATCCTGTCCCTCACTCAACACAAACCCCAAAACACAGAGAGCCT GCCTCAGTACACTCAAACAACCTCAAAGCTGCATCATCACACAATCACACACAAGCACA GCCCTGACAACCCACACACCCCAAGGCACGCACCCACAGCCAGCCTCAGGGCCCACAGG GGCACTGTCAACACAGGGGTGTGCCCAGAGGCCTACACAGAAGCAGCGTCAGTACCCTC AGGATCTGAGGTCCCAACACGTGCTCGCTCACACACACGGCCTGTTAGAATTCACCTGTG TATCTCACGCATATGCACACGCACAGCCCCCCAGTGGGTCTCTTGAGTCCCGTGCAGACA CACACAGCCACACACACTGCCTTGCCAAAAATACCCCGTGTCTCCCCTGCCACTCACCTC ACTCCCATTCCCTGAGCCCTGATCCATGCCTCAGCTTAGACTGCAGAGGAACTACTCATT TATTTGGGATCCAAGGCCCCCAACCCACAGTACCGTCCCCAATAAACTGCAGCCGAGCTC CCCACA | 3'UTR of FOXP3 |
| 152 | ATGGGGGCAGGTGCCACCGGACGAGCCATGGACGGGCCGCGCCTGCTGCTGTTGCTGCT TCTGGGGGTGTCCCTTGGAGGTGCCAAGGAGGCATGCCCCACAGGCCTGTACACACACA GCGGTGAGTGCTGCAAAGCCTGCAACCTGGGCGAGGGTGTGGCCCAGCCTTGTGGAGCC AACCAGACCGTGTGTGAGCCCTGCCTGGACAGCGTGACGTTCTCCGACGTGGTGAGCGC GACCGAGCCGTGCAAGCCGTGCACCGAGTGCGTGGGGCTCCAGAGCATGTCGGCGCCGT GCGTGGAGGCCGACGACGCCGTGTGCCGCTGCGCCTACGGCTACTACCAGGATGAGACG ACTGGGCGCTGCGAGGCGTGCCGCGTGTGCGAGGCGGGCTCGGGCCTCGTGTTCTCCTGC CAGGACAAGCAGAACACCGTGTGCGAGGAGTGCCCCGACGGCACGTATTCCGACGAGGC CAACCACGTGGACCCGTGCCTGCCCTGCACCGTGTGCGAGGACACCGAGCGCCAGCTCC GCGAGTGCACACGCTGGGCCGACGCCGAGTGCGAGGAGATCCCTGGCCGTTGGATTACA CGGTCCACACCCCCAGAGGGCTCGGACAGCACAGCCCCCAGCACCCAGGAGCCTGAGGC ACCTCCAGAACAAGACCTCATAGCCAGCACGGTGGCAGGTGTGGTGACCACAGTGATGG GCAGCTCCCAGCCCGTGGTGACCCGAGGCACCACCGACAACCTCATCCCTGTCTATTGCT CCATCCTGGCTGCTGTGGTTGTGGGTCTTGTGGCCTACATAGCCTTCAAGAGG | LNGFR coding sequence without stop codon |
| 153 | ATGCCTCTGGGCCTGCTGTGGCTGGGCCTGGCCCTGCTGGGCGCCCTGCACGCCCAGGCC GGCGTGCAGGTGGAGACAATCTCCCCAGGCGACGGACGCACATTCCCTAAGCGGGGCCA GACCTGCGTGGTGCACTATACAGGCATGCTGGAGGATGGCAAGAAGTTTGACAGCTCCC GGGATAGAAACAAGCCATTCAAGTTTATGCTGGGCAAGCAGGAAGTGATCAGAGGCTGG GAGGAGGGCGTGGCCCAGATGTCTGTGGGCCAGAGGGCCAAGCTGACCATCAGCCCAGA CTACGCCTATGGAGCAACAGGCCACCCAGGAATCATCCCACCTCACGCCACCCTGGTGTT CGATGTGGAGCTGCTGAAGCTGGGCGAGGGAGGGTCACCTGGATCCAACACATCAAAAG AGAACCCCTTTCTGTTCGCATTGGAGGCCGTAGTCATATCTGTTGGATCCATGGGACTTAT TATCTCCCTGTTGTGTGTGTACTTCTGGCTGGAACGGACTATGCCCAGGATCCCCACGCTC AAGAATCTGGAAGATCTCGTCACAGAATACCATGGTAATTTCAGCGCCTGGAGCGGAGT CTCTAAGGGTCTGGCCGAATCCCTCCAACCCGATTATTCTGAACGGTTGTGCCTCGTATCC GAAATACCACCAAAAGGCGGGGCTCTGGGTGAGGGCCCAGGGGCGAGTCCGTGCAATCA ACACAGCCCGTATTGGGCCCCTCCTTGTTATACGTTGAAGCCCGAAACTGGAAGCGGAGC TACTAACTTCAGCCTGCTGAAGCAGGCTGGAGACGTGGAGGAGAACCCTGGACCTATGG CACTGCCCGTGACCGCCCTGCTGCTGCCTCTGGCCCTGCTGCTGCACGCAGCCCGGCCTA TCCTGTGGCACGAGATGTGGCACGAGGGCCTGGAGGAGGCCAGCAGGCTGTATTTTGGC GAGCGCAACGTGAAGGGCATGTTCGAGGTGCTGGAGCCTCTGCACGCCATGATGGAGAG AGGCCCACAGACCCTGAAGGAGACATCCTTTAACCAGGCCTATGGACGGGACCTGATGG AGGCACAGGAGTGGTGCAGAAAGTACATGAAGTCTGGCAATGTGAAGGACCTGCTGCAG GCCTGGGATCTGTACTATCACGTGTTTCGGAGAATCTCCAAGCCAGCAGCTCTCGGCAAA GACACGATTCCGTGGCTTGGGCATCTGCTCGTTGGGCTGAGCGGTGCGTTTGGTTTCATC ATCTTGGTCTATCTCTTGATCAATTGCAGAAATACAGGCCCTTGGCTGAAAAAAGTGCTC AAGTGTAATACCCCCGACCCAAGCAAGTTCTTCTCCCAGCTTTCTTCAGAGCATGGAGGC GATGTGCAGAAATGGCTCTCTTCACCTTTTCCCTCCTCAAGCTTCTCCCCGGGAGGGCTGG CGCCCGAGATTTCACCTCTTGAGGTACTTGAACGAGACAAGGTTACCCAACTTCTCCTTC AACAGGATAAGGTACCCGAACCTGCGAGCCTTAGCTTGAATACAGACGCTTATCTCTCAC TGCAGGAACTGCAAGGATCTGGTGCTACTAATTTTTCTCTTTTGAAGCAAGCTGGAGATG TTGAAGAGAACCCCGGTCCGGAGATGTGGCATGAGGGTCTGGAAGAAGCGTCTCGACTG TACTTTGGTGAGCGCAATGTGAAGGGCATGTTTGAAGTCCTCGAACCCCTTCATGCCATG ATGGAACGCGGACCCCAGACCTTGAAGGAGACAAGTTTTAACCAAGCTTACGGAAGAGA CCTGATGGAAGCCCAGGAATGGTGCAGGAAATACATGAAAAGCGGGAATGTGAAGGACT TGCTCCAAGCGTGGGACCTGTACTATCATGTCTTTAGGCGCATTAGTAAG | μDISC: μCISC-FRB; nucleotide sequence |
| 154 | MPLGLLWLGLALLGALHAQAGVQVETISPGDGRTFPKRGQTCVVHYTGMLEDGKKFDSSRD RNKPFKFMLGKQEVIRGWEEGVAQMSVGQRAKLTISPDYAYGATGHPGIIPPHATLVFDVEL LKLGEGGSPGSNTSKENPFLFALEAVVISVGSMGLIISLLCVYFWLERTMPRIPTLKNLEDLVT EYHGNFSAWSGVSKGLAESLQPDYSERLCLVSEIPPKGGALGEGPGASPCNQHSPYWAPPCY TLKPETGSGATNFSLLKQAGDVEENPGPMALPVTALLLPLALLLHAARPILWHEMWHEGLEE ASRLYFGERNVKGMFEVLEPLHAMMERGPQTLKETSFNQAYGRDLMEAQEWCRKYMKSG | μDISC: μCISC-FRB amino acid sequence |

-continued

| SEQ ID NO | Sequence | Description |
|---|---|---|
| | NVKDLLQAWDLYYHVFRRISKPAALGKDTIPWLGHLLVGLSGAFGFIILVYLLINCRNTGPWL KKVLKCNTPDPSKFFSQLSSEHGGDVQKWLSSPFPSSSFSPGGLAPEISPLEVLERDKVTQLLL QQDKVPEPASLSLNTDAYLSLQELQGSGATNFSLLKQAGDVEENPGPEMWHEGLEEASRLYF GERNVKGMFEVLEPLHAMMERGPQTLKETSFNQAYGRDLMEAQEWCRKYMKSGNVKDLL QAWDLYYHVFRRISK | |
| 155 | CACGTGTGACTCCTTTCCC | NHEJ_F |
| 156 | CCCAGTGCCACAGTAAAGGT | NHEJ_R |
| 157 | AGGGCCGAGATCTTCGAGGC | FAM_NHEJ probe |
| 158 | CGACACTTCACCCCTTTTCT | Control_F |
| 159 | CTCCCCAATGTGCCTATGAG | Control_R |
| 160 | GTGGCGGTGACTGGGATGGC | HEXControl probe |
| 161 | GTAGAAAAGATCAAAGGATCTTCTTGAGATCCTTTTTTTCTGCGCGTAATCTGCTGCTTGC AAACAAAAAAACCACCGCTACCAGCGGTGGTTTGTTTGCCGGATCAAGAGCTACCAACT CTTTTTCCGAAGGTAACTGGCTTCAGCAGAGCGCAGATACCAAATACTGTCCTTCTAGTG TAGCCGTAGTTAGGCCACCACTTCAAGAACTCTGTAGCACCGCCTACATACCTCGCTCTG CTAATCCTGTTACCAGTGGCTGCTGCCAGTGGCGATAAGTCGTGTCTTACCGGGTTGGAC TCAAGACGATAGTTACCGGATAAGGCGCAGCGGTCGGGCTGAACGGGGGGTTCGTGCAC ACAGCCCAGCTTGGAGCGAACGACCTACACCGAACTGAGATACCTACAGCGTGAGCTAT GAGAAAGCGCCACGCTTCCCGAAGGGAGAAAGGCGGACAGGTATCCGGTAAGCGGCAG GGTCGGAACAGGAGAGCGCACGAGGGAGCTTCCAGGGGGAAACGCCTGGTATCTTTATA GTCCTGTCGGGTTTCGCCACCTCTGACTTGAGCGTCGATTTTTGTGATGCTCGTCAGGGGG GCGGAGCCTATGGAAAAACGCCAGCAACGCGGCCTTTTTACGGTTCCTGGCCTTTTGCTG GCCTTTTGCTCACATGTTCTTTCCTGCGTTATCCCCTGATTCTGTGGATAACCGTATTACCG CCTTTGAGTGAGCTGATACCGCTCGCCGCAGCCGAACGACCGAGCGCAGCGAGTCAGTG AGCGAGGAAGCGGAAGAGCGCCCAATACGCAAACCGCCTCTCCCCGCGCGTTGGCCGAT TCATTAATGCAGCTGCGCGCTCGCTCGCTCACTGAGGCCGCCCGGGCAAAGCCCGGGCGT CGGGCGACCTTTGGTCGCCCGGCCTCAGTGAGCGAGCGAGCGCGCAGAGAGGGAGTGGC CAACTCCATCACTAGGGGTTCCTTGTAGTTAATGATTAACCCGCCATGCTACTTATCTACG TAGCGGCCGCATTTAATGCCAGACTCTTCATGTCTATCTACACCTGCACTTTTGCACCCAA TCCAACTCCCCGCCATGTCCCCCATCTCAGGTAATGTCAGCTCGGTCCTTCCAGCTGCTCA AGCTAAAACCCATGTCACTTTGACTCTCCCTCTTGCCCACTACATCCAAGCTGCTAGCACT GCTCCTGATCCAGCTTCAGATTAAGTCTCAGAATCTACCCACTTCTCGCCTTCTCCACTGC CACCAGCCCATTCTGTGCCAGCATCATCACTTGCCAGGACTGTTACAATAGCCTCCTCAC TAGCCCCACTCACAGCAGCCAGATGAATCTTTTGAGTCCATGCCTAGTCACTGGGGCAAA ATAGGACTCCGAGGAGAAAGTCCGAGACCAGCTCCGGCAAGATGAGCAAACACAGCCTG TGCAGGGTGCAGGGAGGGCTAGAGGCCTGAGGCTTGAAACAGCTCTCAAGTGGAGGGGG AAACAACCATTGCCCTCATAGAGGACACATCCACACCAGGGCTGTGCTAGCGTGGGCAG GCAAGCCAGGTGCTGGACCTCTGCACGTGGGGCATGTGTGGGTATGTACATGTACCTGTG TTCTTGGTGTGTGTGTGTGTGTGTGTGTGTGTGTGTGTCTAGAGCTGGGGTGCAACTATGG GGCCCCTCGGGACATGTCCCAGCCAATGCCTGCTTTGACCAGAGGAGTGTCCACGTGGCT CAGGTGGTCGAGTATCTCATACCGCCCTAGCACACGTGTGACTCCTTTCCCCTATTGTCTA CGCAGCCTGCCCTTGGACAAGGACCCGATGCCTAATCCTCGGCCTGGAAAGCCTAGCGCT CCTTCTCTTGCTCTGGGACCTTCTCCTGGCGCCTCTCCATCTTGGAGAGCCGCTCCTAAAG CCAGCGATCTGCTGGGAGCTAGAGGACCTGGCGGCACATTTCAGGGCAGAGATCTTAGA GGCGGAGCCCACGCTAGCTCCTCCAGCCTTAATCCTATGCCTCCTAGCCAGCTCCAGCTG CCTACACTGCCTCTGGTTATGGTGGCTCCTAGCGGAGCTAGACTGGGCCCTCTGCCTCAT CTGCAAGCTCTGCTGCAGGACAGACCCCACTTCATGCACCAGCTGAGCACCGTGGATGCC CACGCAAGAACACCTGTGCTGCAGGTTCACCCTCTGGAATCCCCAGCCATGATCAGCCTG ACACCTCCAACAACAGCCACCGGCGTGTTCAGCCTGAAAGCCAGACCTGGACTGCCTCCT GGCATCAATGTGGCCAGCCTGGAATGGGTGTCCAGAGAACCTGCTCTGCTGTGCACATTC CCCAATCCAAGCGCTCCCAGAAAGGACAGCACACTGTCTGCCGTGCCTCAGAGCAGCTA TCCCCTGCTTGCTAACGGCGTGTGCAAGTGGCCTGGATGCGAGAAGGTGTTCGAGGAACC CGAGGACTTCCTGAAGCACTGCCAGGCCGATCATCTGCTGGACGAGAAAGGCAGAGCCC AGTGTCTGCTCCAGCGCGAGATGGTGCAGTCTCTGGAACAGCAGCTGGTCCTGGAAAAA GAAAAGCTGAGCGCCATGCAGGCCCACCTGGCCGGAAAAATGGCCCTGACAAAGGCCAG CAGCGTGGCCTCTTCTGATAAGGGCAGCTGCTGCATTGTGGCCGCTGGATCTCAGGGACC TGTGGTTCCTGCTTGGAGCGGACCTAGAGAGGCCCCTGATTCTCTGTTTGCCGTGCGGAG ACACCTGTGGGGCTCTCACGGCAACTCTACTTTCCCCGAGTTCCTGCACAACATGGACTA CTTCAAGTTCCACAACATGCGGCCTCCATTCACCTACGCCACACTGATCAGATGGGCCAT TCTGGAAGCCCCTGAGAAGCAGAGAACCCTGAACGAGATCTACCACTGGTTTACCCGGA TGTTCGCCTTCTTCCGGAATCACCCTGCCACCTGGAAGAACGCCATCCGGCACAATCTGA GCCTGCACAAGTGCTTCGTGCGCGTGGAATCTGAGAAAGGCGCCGTGTGGACAGTGGAC GAGCTGGAATTCAGAAAGAAGAGAAAGCCAGCGGCCTAGCCGGTGCAGCAATCCTACACC TGGACCTTGAAAGCTTGATAATCAACCTCTGGATTACAAAATTTGTGAAAGATTGACTGG TATTCTTAACTATGTTGCTCCTTTTACGCTATGTGGATACGCTGCTTTAATGCCTTTGTATC ATGCTATTGCTTCCCGTATGGCTTTCATTTTCTCCTCCTTGTATAAATCCTGGTTAGTTCTT | #3232_pAAV. FOXP3.0.8H A.ATG.FOX P3cDNA.WP RE3.pA_T3 specific |

-continued

| SEQ ID NO | Sequence | Description |
|---|---|---|
| | GCCACGGCGGAACTCATCGCCGCCTGCCTTGCCCGCTGCTGGACAGGGGCTCGGCTGTTG<br>GGCACTGACAATTCCGTGGGTCGACTGCTTTATTTGTGAAATTTGTGATGCTATTGCTTTA<br>TTTGTAACCATTATAAGCTGCAATAAACAAGTTAACAACAACAATTGCATTCATTTTATG<br>TTTCAGGTTCAGGGGGAGATGTGGGAGGTTTTTTAAAGCACTAGTCGAGATCTTCGAGGC<br>GGGGCCCATGCCTCCTCTTCTTCCTTGAACCCCATGCCACCATCGCAGCTGCAGGTGAGG<br>CCCTGGGCCCAGGATGGGGCAGGCAGGGTGGGGTACCTGGACCTACAGGTGCCGACCTT<br>TACTGTGGCACTGGGCGGGAGGGGGGCTGGCTGGGGCACAGGAAGTGGTTTCTGGGTCC<br>CAGGCAAGTCTGTGACTTATGCAGATGTTGCAGGGCCAAGAAAATCCCCACCTGCCAGG<br>CCTCAGAGATTGGAGGCTCTCCCCGACCTCCCAATCCCTGTCTCAGGAGAGGAGGAGGCC<br>GTATTGTAGTCCCATGAGCATAGCTATGTGTCCCCATCCCCATGTGACAAGAGAAGAGGA<br>CTGGGGCCAAGTAGGTGAGGTGACAGGGCTGAGGCCAGCTCTGCAACTTATTAGCTGTTT<br>GATCTTTAAAAAGTTACTCGATCTCCATGAGCCTCAGTTTCCATACGTGTAAAAGGGGGA<br>TGATCATAGCATCTACCATGTGGGCTTGCAGTGCAGAGTATTTGAATTAGACACAGAACA<br>GTGAGGATCAGGATGGCCTCTCACCCACCTGCCTTTCTGCCCAGCTGCCCACACTGCCCC<br>TAGTCATGGTGGCACCCTCCGGGGCACGGCTGGGCCCCTTGCCCCACTTACAGGCACTCC<br>TCCAGGACAGGCCACATTTCATGCACCAGGTATGGACGGTGAATGGGCAGGGAGGAGGG<br>AGCAGGTGGGAGAACTGTGGGGAGGGGCCCCGAGTCAGGCTGAACCGGATCCTACGTAG<br>ATAAGTAGCATGGCGGGTTAATCATTAACTACAAGGAACCCCTAGTGATGGAGTTGGCC<br>ACTCCCTCTCTGCGCGCTCGCTCGCTCACTGAGGCCGGGCGACCAAAGGTCGCCCGACGC<br>CCGGGCTTTGCCCGGGCGGCCTCAGTGAGCGAGCGAGCGCGCCAGCTGGCGTAATAGCG<br>AAGAGGCCCGCACCGATCGCCCTTCCCAACAGTTGCGCAGCCTGAATGGCGAATGGCGA<br>TTCCGTTGCAATGGCTGGCGGTAATATTGTTCTGGATATTACCAGCAAGGCCGATAGTTT<br>GAGTTCTTCTACTCAGGCAAGTGATGTTATTACTAATCAAAGAAGTATTGCGACAACGGT<br>TAATTTGCGTGATGGACAGACTCTTTTACTCGGTGGCCTCACTGATTATAAAAACACTTCT<br>CAGGATTCTGGCGTACCGTTCCTGTCTAAAATCCCTTTAATCGGCCTCCTGTTTAGCTCCC<br>GCTCTGATTCTAACGAGGAAAGCACGTTATACGTGCTCGTCAAAGCAACCATAGTACGCG<br>CCCTGTAGCGGCGCATTAAGCGCGGCGGGTGTGGTGGTTACGCGCAGCGTGACCGCTAC<br>ACTTGCCAGCGCCCTAGCGCCCGCTCCTTTCGCTTTCTTCCCTTCCTTTCTCGCCACGTTCG<br>CCGGCTTTCCCCGTCAAGCTCTAAATCGGGGGCTCCCTTTAGGGTTCCGATTTAGTGCTTT<br>ACGGCACCTCGACCCCAAAAAACTTGATTAGGGTGATGGTTCACGTAGTGGGCCATCGCC<br>CTGATAGACGGTTTTTCGCCCTTTGACGTTGGAGTCCACGTTCTTTAATAGTGGACTCTTG<br>TTCCAAACTGGAACAACACTCAACCCTATCTCGGTCTATTCTTTTGATTTATAAGGGATTT<br>TGCCGATTTCGGCCTATTGGTTAAAAAATGAGCTGATTTAACAAAAATTTAACGCGAATT<br>TTAACAAAATATTAACGTTTACAATTTAAATATTTGCTTATACAATCTTCCTGTTTTTGGG<br>GCTTTTCTGATTATCAACCGGGGTACATATGATTGACATGCTAGTTTTACGATTACCGTTC<br>ATCGATTCTCTTGTTTGCTCCAGACTCTCAGGCAATGACCTGATAGCCTTTGTAGAGACCT<br>CTCAAAAATAGCTACCCTCTCCGGCATGAATTTATCAGCTAGAACGGTTGAATATCATAT<br>TGATGGTGATTTGACTGTCTCCGGCCTTTCTCACCCGTTTGAATCTTTACCTACACATTAC<br>TCAGGCATTGCATTTAAAATATATGAGGGTTCTAAAAATTTTTATCCTTGCGTTGAAATAA<br>AGGCTTCTCCCGCAAAAGTATTACAGGGTCATAATGTTTTTGGTACAACCGATTTAGCTTT<br>ATGCTCTGAGGCTTTATTGCTTAATTTTGCTAATTCTTTGCCTTGCCTGTATGATTTATTGG<br>ATGTTGGAATCGCCTGATGCGGTATTTTCTCCTTACGCATCTGTGCGGTATTTCACACCGC<br>ATATGGTGCACTCTCAGTACAATCTGCTCTGATGCCGCATAGTTAAGCCAGCCCCGACAC<br>CCGCCAACACCCGCTGACGCGCCCTGACGGGCTTGTCTGCTCCCGGCATCCGCTTACAGA<br>CAAGCTGTGACCGTCTCCGGGAGCTGCATGTGTCAGAGGTTTTCACCGTCATCACCGAAA<br>CGCGCGAGACGAAAGGGCCTCGTGATACGCCTATTTTTATAGGTTAATGTCATGATAATA<br>ATGGTTTCTTAGACGTCAGGTGGCACTTTTCGGGGAAATGTGCGCGGAACCCCTATTTGT<br>TTATTTTTCTAAATACATTCAAATATGTATCCGCTCATGAGACAATAACCCTGATAAATGC<br>TTCAATAATATTGAAAAAGGAAGAGTATGAGTATTCAACATTTCCGTGTCGCCCTTATTC<br>CCTTTTTTGCGGCATTTTGCCTTCCTGTTTTTGCTCACCCAGAAACGCTGGTGAAAGTAAA<br>AGATGCTGAAGATCAGTTGGGTGCACGAGTGGGTTACATCGAACTGGATCTCAACAGCG<br>GTAAGATCCTTGAGAGTTTTCGCCCCGAAGAACGTTTTCCAATGATGAGCACTTTTAAAG<br>TTCTGCTATGTGGCGCGGTATTATCCCGTATTGACGCCGGGCAAGAGCAACTCGGTCGCC<br>GCATACACTATTCTCAGAATGACTTGGTTGAGTACTCACCAGTCACAGAAAAGCATCTTA<br>CGGATGGCATGACAGTAAGAGAATTATGCAGTGCTGCCATAACCATGAGTGATAACACT<br>GCGGCCAACTTACTTCTGACAACGATCGGAGGACCGAAGGAGCTAACCGCTTTTTTGCAC<br>AACATGGGGGATCATGTAACTCGCCTTGATCGTTGGGAACCGGAGCTGAATGAAGCCAT<br>ACCAAACGACGAGCGTGACACCACGATGCCTGTAGCAATGGCAACAACGTTGCGCAAAC<br>TATTAACTGGCGAACTACTTACTCTAGCTTCCCGGCAACAATTAATAGACTGGATGGAGG<br>CGGATAAAGTTGCAGGACCACTTCTGCGCTCGGCCCTTCCGGCTGGCTGGTTTATTGCTG<br>ATAAATCTGGAGCCGGTGAGCGTGGGTCTCGCGGTATCATTGCAGCACTGGGGCCAGAT<br>GGTAAGCCCTCCCGTATCGTAGTTATCTACACGACGGGGAGTCAGGCAACTATGGATGA<br>ACGAAATAGACAGATCGCTGAGATAGGTGCCTCACTGATTAAGCATTGGTAACTGTCAG<br>ACCAAGTTTACTCATATATACTTTAGATTGATTTAAAACTTCATTTTTAATTTAAAAGGAT<br>CTAGGTGAAGATCCTTTTTGATAATCTCATGACCAAAATCCCTTAACGTGAGTTTTCGTTC<br>CACTGAGCGTCAGACCCC | |

What is claimed is:

1. A method of making a genetically modified CD34+ cell, the method comprising delivering to a CD34+ cell a donor template comprising:

a) a first homology arm having homology to a sequence in a forkhead box protein P3 (FOXP3) gene, adeno-associated virus site 1 (AAVS 1) locus, or T cell receptor alpha (TRA) gene in the CD34+ cell;

b) a second homology arm having homology to a sequence in the same gene or locus as the first homology arm;

c) a promoter; and d) a FOXP3 cDNA sequence comprising at least 90% sequence identity to the nucleic acid sequence of SEQ ID NO: 110, wherein the FOXP3 cDNA sequence is codon-optimized for expression in the cell, wherein the promoter and the FOXP3 cDNA sequence are located between the first homology arm and second homology arm.

2. The method of claim 1, further comprising delivering to the cell a DNA endonuclease or a nucleic acid encoding the DNA endonuclease.

3. The method of claim 2, further comprising delivering to the cell a gRNA comprising a spacer sequence that is complementary to the FOXP3 gene, AAVS1 locus, or TRA gene.

4. The method of claim 3, wherein the gRNA comprises:

i) the spacer sequence from any one of SEQ ID NOs: 1-7, 15-20, and 27-29 or a variant thereof having no more than 3 mismatches compared to any one of SEQ ID NOs: 1-7, 15-20, and 27-29;

ii) the spacer sequence from any one of SEQ ID NOs: 1-7 or a variant thereof having no more than 3 mismatches compared to any one of SEQ ID NOs: 1-7; or iii) the spacer sequence from any one of SEQ ID NOs: 2, 3, and 5 or a variant thereof having no more than 3 mismatches compared to any one of SEQ ID NOs: 2, 3, and 5.

5. The method of claim 1, wherein the first homology arm has homology to a sequence in the FOXP3 gene, and the second homology arm has homology to another sequence in the FOXP3 gene.

6. The method of claim 1, wherein:

a) the donor template is encoded in an adeno-associated virus (AAV) vector; and/or b) the promoter is a myeloproliferative sarcoma virus MPSV enhancer, negative control region NCR deletion, d1587rev primer binding site replacement (MND) promoter, phosphoglycerate kinase (PGK) promoter, elongation factor-1 alpha (EF-1$\alpha$) promoter, or E2 factor (E2F) promoter.

7. The method of claim 1, wherein the donor template further comprises a sequence encoding a selectable marker, and the method further comprises separating cells expressing the selectable marker from cells that do not express the selectable marker.

8. A genetically modified CD34+ cell made by the method of claim 1, wherein the donor template is integrated within a FOXP3 gene, AAVS1 locus, or TRA gene in the genome of the CD34+ cell.

9. A pharmaceutical composition comprising the genetically modified CD34+ cell of claim 8 and a pharmaceutically acceptable excipient.

10. A nucleic acid comprising:

a) a first homology arm having homology to a sequence in a FOXP3 gene, AAVS1 locus, or TRA gene in a CD34+ cell;

b) a second homology arm having homology to another sequence in the same gene or locus as the first homology arm;

c) a promoter; and d) a FOXP3 cDNA sequence comprising at least 90% sequence identity to the nucleic acid sequence of SEQ ID NO: 110, wherein the FOXP3 cDNA sequence is codon-optimized for expression in the cell, wherein the promoter and the FOXP3 cDNA sequence are located between the first homology arm and second homology arm.

* * * * *

UNITED STATES PATENT AND TRADEMARK OFFICE

CERTIFICATE OF CORRECTION

PATENT NO. : 11,713,459 B2
APPLICATION NO. : 16/981223
DATED : August 1, 2023
INVENTOR(S) : David J. Rawlings It is certified that error appears in the above-identified patent and that said Letters Patent is hereby corrected as shown below:

On the Title Page

Column 1, Line 1, under Title, delete "CD34+" and insert --$CD34^{+}$--.

Column 2, Line 4, item (56) under Other Publications, delete "FPXP3" and insert --FOXP3--.

Column 2, Line 5, item (56) under Other Publications, delete "FPXP3+" and insert --$FOXP3^{+}$--.

Column 2, Line 6, item (56) under Other Publications, delete "ceils," and insert --cells,--.

On Page 2, Column 1, Line 15, item (56) under Other Publications, delete "glomerulopephritis," and insert --glomerulonephritis,--.

In the Specification

In Column 1, Line 1, delete "CD34+" and insert --$CD34^{+}$--.

In Column 11, Line 36, delete "mellitis" and insert --mellitus--.

In Column 17, Line 48, delete "FKBPS;" and insert --FKBP5;--.

In Column 18, Line 14, delete "D L" and insert --DL--.

In Column 18, Line 19, delete "D L" and insert --DL--.

In Column 19, Lines 13-16, delete ""IL-2/15R" refers to a receptor signaling subunit that is shared by IL-2 and IL-15, and may include a subunit alpha (IL2/15Ra or IL2/15Rα), beta (IL2/15Rb or IL2/15Rβ, or gamma (IL2/15Rg or IL2/15Rγ)." and insert the same on Column 19, Line 12, as a continuation of the same paragraph.

Signed and Sealed this
Second Day of April, 2024

Katherine Kelly Vidal

Katherine Kelly Vidal
*Director of the United States Patent and Trademark Office*

In Column 19, Lines 25-26, delete “heterodimizeration” and insert --heterodimerization--.

In Column 22, Line 5, delete “subject;” and insert --subject.--.

In Column 22, Line 6, delete “same);” and insert --same).--.

In Column 37, Line 25, delete “and” and insert --and HDR.--.

In Column 43, Lines 1-2, delete “endonucelases” and insert --endonucleases--.

In Column 61, Line 56, delete “and or” and insert --and/or--.

In Column 61, Lines 58-59, delete “and or” and insert --and/or--.

In Column 67, Line 1, delete “intracerobrospinal,” and insert --intracerebrospinal,--.

In Column 72, Line 33, delete “and or” and insert --and/or--.

In Column 72, Lines 35-36, delete “and or” and insert --and/or--.

In Column 73, Line 65, delete “and or” and insert --and/or--.

In Column 76, Line 5, delete “and or” and insert --and/or--.

In Column 76, Line 8, delete “and or” and insert --and/or--.

In Column 79, Line 33, delete “FOXP3 cDNA.” and insert --FOXP3cDNA.--.

In Column 80, Line 10, delete “ng” and insert --μg--.

In Column 89, Line 42 (approx.), delete “analyzed” and insert --analyzed.--.

In Column 89, Line 65, delete “ng” and insert --μg--.

In Column 90, Line 16, delete “performed:” and insert --performed.--.

In Columns 143-144, Line 37, delete “version 6” and insert --version 6)--.

In Columns 149-150, Line 22, delete “(M” and insert --M--.

In Columns 149-150, Line 29, delete “(M” and insert --M--.

In Columns 149-150, Line 35, delete “(M” and insert --M--.

In Columns 149-150, Line 44, delete “(M” and insert --M--.

In Columns 149-150, Line 50, delete "(M" and insert --M--.

In Columns 149-150, Line 59, delete "(M" and insert --M--.

In Columns 149-150, Line 64, delete "(M" and insert --M--.

In Columns 151-152, Line 5, delete "(M" and insert --M--.

In Columns 151-152, Line 11, delete "(M" and insert --M--.

In Columns 151-152, Line 19, delete "(M" and insert --M--.

In Columns 151-152, Line 24, delete "(M" and insert --M--.

In Columns 151-152, Line 30, delete "(M" and insert --M--.

In Columns 151-152, Line 36, delete "((M" and insert --M--.

In Columns 151-152, Line 41, delete "((A" and insert --A--.

In Columns 155-156, Line 66, delete "(A" and insert --A--.

In Columns 161-162, Line 10, delete "(A" and insert --A--.

In Columns 165-166, Line 19, delete "(A" and insert --A--.

In Columns 165-166, Line 40, delete "T)" and insert --T--.

In Columns 165-166, Line 41, delete "(A" and insert --A--.

In the Claims

In Column 485, Claim 1, Line 17, delete "(AAVS 1)" and insert --(AAVS1)--.

SEQUENCE LISTING

<160> NUMBER OF SEQ ID NOS: 161

<210> SEQ ID NO 1
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T1 Guide sequence

<400> SEQUENCE: 1
ttccagggcc gagatcttcg 20

<210> SEQ ID NO 2
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T3 Guide sequence

<400> SEQUENCE: 2
cgcctcgaag atctcggccc 20

<210> SEQ ID NO 3
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T4 Guide sequence

<400> SEQUENCE: 3
tcgaagatct cggccctgga 20

<210> SEQ ID NO 4
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T7 Guide sequence

<400> SEQUENCE: 4
ggccctggaa ggttccccct 20

<210> SEQ ID NO 5
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T9 Guide sequence

<400> SEQUENCE: 5
tccagctggg cgaggctcct 20

<210> SEQ ID NO 6

<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T18 Guide sequence

<400> SEQUENCE: 6
tcagacctgc tgggggcccg 20

<210> SEQ ID NO 7
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R1 Guide sequence

<400> SEQUENCE: 7
gagccccgcc tcgaagatct 20

<210> SEQ ID NO 8
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T1 PAM sequence

<400> SEQUENCE: 8 agg 3

<210> SEQ ID NO 9
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T3 PAM sequence

<400> SEQUENCE: 9 tgg 3

<210> SEQ ID NO 10
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T4 PAM sequence

<400> SEQUENCE: 10 agg 3

<210> SEQ ID NO 11
<211> LENGTH: 3
<212> TYPE: DNA
<213> ORGANISM: Artificial sequence
<220> FEATURE:

<223> OTHER INFORMATION: Synthetic polynucleotide
<220> FEATURE:
<221> NAME/KEY: misc_feature
<223> OTHER INFORMATION: T7 PAM sequence

<400> SEQUENCE: 11 ggg 3

<210> SEQ ID NO 12
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T9 PAM sequence

<400> SEQUENCE: 12 ggg 3

<210> SEQ ID NO 13
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T18 PAM sequence

<400> SEQUENCE: 13 ggg 3

<210> SEQ ID NO 14
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R1 PAM sequence

<400> SEQUENCE: 14 cgg 3

<210> SEQ ID NO 15
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P1 Guide sequence

<400> SEQUENCE: 15
attcccaggg ccggttaatg 20

<210> SEQ ID NO 16
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P3 Guide sequence

<400> SEQUENCE: 16
gtcccctcca ccccacagtg 20

<210> SEQ ID NO 17
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P4 Guide sequence

<400> SEQUENCE: 17
accccacagt ggggccacta 20

<210> SEQ ID NO 18
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: N1 Guide sequence

<400> SEQUENCE: 18
cctctaaggt ttgcttacga 20

<210> SEQ ID NO 19
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: N2 Guide sequence

<400> SEQUENCE: 19
tataaggtgg tcccagctcg 20

<210> SEQ ID NO 20
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: N3 Guide sequence

<400> SEQUENCE: 20
ccatcgtaag caaaccttag 20

<210> SEQ ID NO 21
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P1 PAM sequence

<400> SEQUENCE: 21 tgg 3

<210> SEQ ID NO 22
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P3 PAM sequence

<400> SEQUENCE: 22 ggg 3

<210> SEQ ID NO 23
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P4 PAM sequence

<400> SEQUENCE: 23 ggg 3

<210> SEQ ID NO 24
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: N1 PAM sequence

<400> SEQUENCE: 24 tgg 3

<210> SEQ ID NO 25
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: N2 PAM sequence

<400> SEQUENCE: 25 ggg 3

<210> SEQ ID NO 26
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: N3 PAM sequence

<400> SEQUENCE: 26 agg 3

<210> SEQ ID NO 27
<211> LENGTH: 20

<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: m T20 Guide sequence

<400> SEQUENCE: 27
gactcctggg gatgggccaa 20

<210> SEQ ID NO 28
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: m T22 Guide sequence

<400> SEQUENCE: 28
ttggcccttg gcccatcccc 20

<210> SEQ ID NO 29
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: m T23 Guide sequence

<400> SEQUENCE: 29
ccagcttggc aagactcctg 20

<210> SEQ ID NO 30
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: m T20 PAM sequence

<400> SEQUENCE: 30 ggg 3

<210> SEQ ID NO 31
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: m T22 PAM sequence

<400> SEQUENCE: 31 agg 3

<210> SEQ ID NO 32
<211> LENGTH: 3
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: m T23 PAM sequence

<400> SEQUENCE: 32 ggg 3

<210> SEQ ID NO 33
<211> LENGTH: 6679
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 3008 pAAV_FoxP3_0_6kb_MND_GFP_WPRE3_pA

<400> SEQUENCE: 33
gtagaaaaga tcaaaggatc ttcttgagat cctttttttc tgcgcgtaat ctgctgcttg 60
caaacaaaaa aaccaccgct accagcggtg gtttgtttgc cggatcaaga gctaccaact 120
ctttttccga aggtaactgg cttcagcaga gcgcagatac caaatactgt ccttctagtg 180
tagccgtagt taggccacca cttcaagaac tctgtagcac cgcctacata cctcgctctg 240
ctaatcctgt taccagtggc tgctgccagt ggcgataagt cgtgtcttac cgggttggac 300
tcaagacgat agttaccgga taaggcgcag cggtcgggct gaacgggggg ttcgtgcaca 360
cagcccagct tggagcgaac gacctacacc gaactgagat acctacagcg tgagctatga 420
gaaagcgcca cgcttcccga agggagaaag gcggacaggt atccggtaag cggcagggtc 480
ggaacaggag agcgcacgag ggagcttcca gggggaaacg cctggtatct ttatagtcct 540
gtcgggtttc gccacctctg acttgagcgt cgatttttgt gatgctcgtc aggggggcgg 600
agcctatgga aaaacgccag caacgcggcc tttttacggt tcctggcctt ttgctggcct 660
tttgctcaca tgttctttcc tgcgttatcc cctgattctg tggataaccg tattaccgcc 720
tttgagtgag ctgataccgc tcgccgcagc cgaacgaccg agcgcagcga gtcagtgagc 780
gaggaagcgg aagagcgccc aatacgcaaa ccgcctctcc ccgcgcgttg gccgattcat 840
taatgcagct gcgcgctcgc tcgctcactg aggccgcccg ggcaaagccc gggcgtcggg 900
cgacctttgg tcgcccggcc tcagtgagcg agcgagcgcg cagagaggga gtggccaact 960
ccatcactag gggttccttg tagttaatga ttaacccgcc atgctactta tctacgtagc 1020
ggccgctcag aatctaccca cttctcgcct tctccactgc caccagccca ttctgtgcca 1080
gcatcatcac ttgccaggac tgttacaata gcctcctcac tagccccact cacagcagcc 1140
agatgaatct tttgagtcca tgcctagtca ctggggcaaa ataggactcc gaggagaaag 1200
tccgagacca gctccggcaa gatgagcaaa cacagcctgt gcagggtgca gggagggcta 1260
gaggcctgag gcttgaaaca gctctcaagt ggagggggaa acaaccattg ccctcataga 1320
ggacacatcc acaccagggc tgtgctagcg tgggcaggca agccaggtgc tggacctctg 1380
cacgtggggc atgtgtgggt atgtacatgt acctgtgttc ttggtgtgtg tgtgtgtgtg 1440
tgtgtgtgtg tgtgtctaga gctggggtgc aactatgggg cccctcggga catgtcccag 1500
ccaatgcctg ctttgaccag aggagtgtcc acgtggctca ggtggtcgag tatctcatac 1560
cgccctagca cacgtgtgac tcctttcccc tattgtctac gcagcctgcc cttggacaag 1620
gacccgacgc gtaggaacag agaaacagga gaatatgggc caaacaggat atctgtggta 1680
agcagttcct gccccggctc agggccaaga acagttggaa cagcagaata tgggccaaac 1740
aggatatctg tggtaagcag ttcctgcccc ggctcagggc caagaacaga tggtccccag 1800
atgcggtccc gccctcagca gtttctagag aaccatcaga tgtttccagg gtgccccaag 1860
gacctgaaat gaccctgtgc cttatttgaa ctaaccaatc agttcgcttc tcgcttctgt 1920
tcgcgcgctt ctgctccccg agctctatat aagcagagct cgtttagtga accgtcagat 1980
cgcctggaga cgccatccac gctgttttga cttccataga aggatctcga ggccaccatg 2040
gtgagcaagg gcgaggagct gttcaccggg gtggtgccca tcctggtcga gctggacggc 2100
gacgtaaacg gccacaagtt cagcgtgtcc ggcgagggcg agggcgatgc cacctacggc 2160
aagctgaccc tgaagttcat ctgcaccacc ggcaagctgc ccgtgccctg gcccaccctc 2220
gtgaccaccc tgacctacgg cgtgcagtgc ttcagccgct accccgacca catgaagcag 2280
cacgacttct tcaagtccgc catgcccgaa ggctacgtcc aggagcgcac catcttcttc 2340
aaggacgacg gcaactacaa gacccgcgcc gaggtgaagt tcgagggcga caccctggtg 2400
aaccgcatcg agctgaaggg catcgacttc aaggaggacg gcaacatcct ggggcacaag 2460
ctggagtaca actacaacag ccacaacgtc tatatcatgg ccgacaagca gaagaacggc 2520
atcaaggtga acttcaagat ccgccacaac atcgaggacg gcagcgtgca gctcgccgac 2580
cactaccagc agaacacccc catcggcgac ggccccgtgc tgctgcccga caaccactac 2640
ctgagcaccc agtccgccct gagcaaagac cccaacgaga agcgcgatca catggtcctg 2700
ctggagttcg tgaccgccgc cgggatcact ctcggcatgg acgagctgta caagtaaaag 2760
cttgataatc aacctctgga ttacaaaatt tgtgaaagat tgactggtat tcttaactat 2820
gttgctcctt ttacgctatg tggatacgct gctttaatgc ctttgtatca tgctattgct 2880
tcccgtatgg ctttcatttt ctcctccttg tataaatcct ggttagttct tgccacggcg 2940
gaactcatcg ccgcctgcct tgcccgctgc tggacagggg ctcggctgtt gggcactgac 3000
aattccgtgg gtcgactgct ttatttgtga aatttgtgat gctattgctt tatttgtaac 3060
cattataagc tgcaataaac aagttaacaa caacaattgc attcatttta tgtttcaggt 3120
tcagggggag atgtgggagg tttttttaaag cactagtgtg aggccctggg cccaggatgg 3180
ggcaggcagg gtggggtacc tggacctaca ggtgccgacc tttactgtgg cactgggcgg 3240
gaggggggct ggctggggca caggaagtgg tttctgggtc ccaggcaagt ctgtgactta 3300
tgcagatgtt gcagggccaa gaaaatcccc acctgccagg cctcagagat tggaggctct 3360
ccccgacctc ccaatccctg tctcaggaga ggaggaggcc gtattgtagt cccatgagca 3420
tagctatgtg tccccatccc catgtgacaa gagaagagga ctggggccaa gtaggtgagg 3480
tgacagggct gaggccagct ctgcaactta ttagctgttt gatctttaaa aagttactcg 3540
atctccatga gcctcagttt ccatacgtgt aaaaggggga tgatcatagc atctaccatg 3600
tgggcttgca gtgcagagta tttgaattag acacagaaca gtgaggatca ggatggcctc 3660
tcacccacct gcctttctgc ccagctgccc acactgcccc tagtcatggt ggcaccctcc 3720
ggggcacggc tgggcccctt gccccactta caggcaccgc ggcgctacgt agataagtag 3780
catggcgggt taatcattaa ctacaaggaa cccctagtga tggagttggc cactccctct 3840
ctgcgcgctc gctcgctcac tgaggccggg cgaccaaagg tcgcccgacg cccgggcttt 3900
gcccgggcgg cctcagtgag cgagcgagcg cgccagctgg cgtaatagcg aagaggcccg 3960
caccgatcgc ccttcccaac agttgcgcag cctgaatggc gaatggcgat tccgttgcaa 4020
tggctggcgg taatattgtt ctggatatta ccagcaaggc cgatagtttg agttcttcta 4080
ctcaggcaag tgatgttatt actaatcaaa gaagtattgc gacaacggtt aatttgcgtg 4140
atggacagac tcttttactc ggtggcctca ctgattataa aaacacttct caggattctg 4200
gcgtaccgtt cctgtctaaa atccctttaa tcggcctcct gtttagctcc cgctctgatt 4260
ctaacgagga aagcacgtta tacgtgctcg tcaaagcaac catagtacgc gccctgtagc 4320
ggcgcattaa gcgcggcggg tgtggtggtt acgcgcagcg tgaccgctac acttgccagc 4380
gccctagcgc ccgctccttt cgctttcttc ccttcctttc tcgccacgtt cgccggcttt 4440
ccccgtcaag ctctaaatcg ggggctccct ttagggttcc gatttagtgc tttacggcac 4500
ctcgacccca aaaaacttga ttagggtgat ggttcacgta gtgggccatc gccctgatag 4560
acggtttttc gccctttgac gttggagtcc acgttcttta atagtggact cttgttccaa 4620
actggaacaa cactcaaccc tatctcggtc tattcttttg atttataagg gattttgccg 4680
atttcggcct attggttaaa aaatgagctg atttaacaaa aatttaacgc gaattttaac 4740
aaaatattaa cgtttacaat ttaaatattt gcttatacaa tcttcctgtt tttggggctt 4800
ttctgattat caaccggggt acatatgatt gacatgctag ttttacgatt accgttcatc 4860
gattctcttg tttgctccag actctcaggc aatgacctga tagcctttgt agagacctct 4920
caaaaatagc taccctctcc ggcatgaatt tatcagctag aacggttgaa tatcatattg 4980
atggtgattt gactgtctcc ggcctttctc acccgtttga atctttacct acacattact 5040
caggcattgc atttaaaata tatgagggtt ctaaaaattt ttatccttgc gttgaaataa 5100
aggcttctcc cgcaaaagta ttacagggtc ataatgtttt tggtacaacc gatttagctt 5160
tatgctctga ggctttattg cttaattttg ctaattcttt gccttgcctg tatgatttat 5220
tggatgttgg aatcgcctga tgcggtattt tctccttacg catctgtgcg gtatttcaca 5280
ccgcatatgg tgcactctca gtacaatctg ctctgatgcc gcatagttaa gccagccccg 5340
acacccgcca acacccgctg acgcgccctg acgggcttgt ctgctcccgg catccgctta 5400
cagacaagct gtgaccgtct ccgggagctg catgtgtcag aggttttcac cgtcatcacc 5460
gaaacgcgcg agacgaaagg gcctcgtgat acgcctattt ttataggtta atgtcatgat 5520
aataatggtt tcttagacgt caggtggcac ttttcgggga aatgtgcgcg gaacccctat 5580
ttgtttattt ttctaaatac attcaaatat gtatccgctc atgagacaat aaccctgata 5640
aatgcttcaa taatattgaa aaaggaagag tatgagtatt caacatttcc gtgtcgccct 5700
tattcccttt tttgcggcat tttgccttcc tgtttttgct cacccagaaa cgctggtgaa 5760
agtaaaagat gctgaagatc agttgggtgc acgagtgggt tacatcgaac tggatctcaa 5820
cagcggtaag atccttgaga gttttcgccc cgaagaacgt tttccaatga tgagcacttt 5880
taaagttctg ctatgtggcg cggtattatc ccgtattgac gccgggcaag agcaactcgg 5940
tcgccgcata cactattctc agaatgactt ggttgagtac tcaccagtca cagaaaagca 6000
tcttacggat ggcatgacag taagagaatt atgcagtgct gccataacca tgagtgataa 6060
cactgcggcc aacttacttc tgacaacgat cggaggaccg aaggagctaa ccgctttttt 6120
gcacaacatg ggggatcatg taactcgcct tgatcgttgg gaaccggagc tgaatgaagc 6180
cataccaaac gacgagcgtg acaccacgat gcctgtagca atggcaacaa cgttgcgcaa 6240
actattaact ggcgaactac ttactctagc ttcccggcaa caattaatag actggatgga 6300
ggcggataaa gttgcaggac cacttctgcg ctcggccctt ccggctggct ggtttattgc 6360
tgataaatct ggagccggtg agcgtgggtc tcgcggtatc attgcagcac tggggccaga 6420
tggtaagccc tcccgtatcg tagttatcta cacgacgggg agtcaggcaa ctatggatga 6480

-continued acgaaataga cagatcgctg agataggtgc ctcactgatt aagcattggt aactgtcaga 6540
ccaagtttac tcatatatac tttagattga tttaaaactt catttttaat ttaaaaggat 6600
ctaggtgaag atcctttttg ataatctcat gaccaaaatc ccttaacgtg agttttcgtt 6660
ccactgagcg tcagaccc 6679

<210> SEQ ID NO 34
<211> LENGTH: 6844
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 3037 pAAV_FoxP3_0_6kb_FoxP3cDNA_WPRE3_pA

<400> SEQUENCE: 34
gtagaaaaga tcaaaggatc ttcttgagat cctttttttc tgcgcgtaat ctgctgcttg 60
caaacaaaaa aaccaccgct accagcggtg gtttgtttgc cggatcaaga gctaccaact 120
ctttttccga aggtaactgg cttcagcaga gcgcagatac caaatactgt ccttctagtg 180
tagccgtagt taggccacca cttcaagaac tctgtagcac cgcctacata cctcgctctg 240
ctaatcctgt taccagtggc tgctgccagt ggcgataagt cgtgtcttac cgggttggac 300
tcaagacgat agttaccgga taaggcgcag cggtcgggct gaacgggggg ttcgtgcaca 360
cagcccagct tggagcgaac gacctacacc gaactgagat acctacagcg tgagctatga 420
gaaagcgcca cgcttcccga agggagaaag gcggacaggt atccggtaag cggcagggtc 480
ggaacaggag agcgcacgag ggagcttcca gggggaaacg cctggtatct ttatagtcct 540
gtcgggtttc gccacctctg acttgagcgt cgatttttgt gatgctcgtc aggggggcgg 600
agcctatgga aaaacgccag caacgcggcc tttttacggt tcctggcctt ttgctggcct 660
tttgctcaca tgttctttcc tgcgttatcc cctgattctg tggataaccg tattaccgcc 720
tttgagtgag ctgataccgc tcgccgcagc cgaacgaccg agcgcagcga gtcagtgagc 780
gaggaagcgg aagagcgccc aatacgcaaa ccgcctctcc ccgcgcgttg gccgattcat 840
taatgcagct gcgcgctcgc tcgctcactg aggccgcccg ggcaaagccc gggcgtcggg 900
cgacctttgg tcgcccggcc tcagtgagcg agcgagcgcg cagagaggga gtggccaact 960
ccatcactag gggttccttg tagttaatga ttaacccgcc atgctactta tctacgtagc 1020
ggccgctcag aatctaccca cttctcgcct tctccactgc caccagccca ttctgtgcca 1080
gcatcatcac ttgccaggac tgttacaata gcctcctcac tagccccact cacagcagcc 1140
agatgaatct tttgagtcca tgcctagtca ctggggcaaa ataggactcc gaggagaaag 1200
tccgagacca gctccggcaa gatgagcaaa cacagcctgt gcagggtgca gggagggcta 1260
gaggcctgag gcttgaaaca gctctcaagt ggagggggaa acaaccattg ccctcataga 1320
ggacacatcc acaccagggc tgtgctagcg tgggcaggca agccaggtgc tggacctctg 1380
cacgtggggc atgtgtgggt atgtacatgt acctgtgttc ttggtgtgtg tgtgtgtgtg 1440
tgtgtgtgtg tgtgtctaga gctggggtgc aactatgggg cccctcggga catgtcccag 1500
ccaatgcctg ctttgaccag aggagtgtcc acgtggctca ggtggtcgag tatctcatac 1560
cgccctagca cacgtgtgac tcctttcccc tattgtctac gcagcctgcc cttggacaag 1620
gacccgatgc ctaatcctcg gcctggaaag cctagcgctc cttctcttgc tctgggacct 1680
tctcctggcg cctctccatc ttggagagcc gctcctaaag ccagcgatct gctgggagct 1740
agaggacctg gcggcacatt tcagggcaga gatcttagag gcggagccca cgctagctcc 1800
tccagcctta atcctatgcc tcctagccag ctccagctgc ctacactgcc tctggttatg 1860
gtggctccta gcggagctag actgggccct ctgcctcatc tgcaagctct gctgcaggac 1920
agaccccact tcatgcacca gctgagcacc gtggatgccc acgcaagaac acctgtgctg 1980
caggttcacc ctctggaatc cccagccatg atcagcctga cacctccaac aacagccacc 2040
ggcgtgttca gcctgaaagc cagacctgga ctgcctcctg gcatcaatgt ggccagcctg 2100
gaatgggtgt ccagagaacc tgctctgctg tgcacattcc ccaatccaag cgctcccaga 2160
aaggacagca cactgtctgc cgtgcctcag agcagctatc ccctgcttgc taacggcgtg 2220
tgcaagtggc ctggatgcga gaaggtgttc gaggaacccg aggacttcct gaagcactgc 2280
caggccgatc atctgctgga cgagaaaggc agagcccagt gtctgctcca gcgcgagatg 2340
gtgcagtctc tggaacagca gctggtcctg gaaaaagaaa agctgagcgc catgcaggcc 2400
cacctggccg gaaaaatggc cctgacaaag gccagcagcg tggcctcttc tgataagggc 2460
agctgctgca ttgtggccgc tggatctcag ggacctgtgg ttcctgcttg gagcggacct 2520
agagaggccc ctgattctct gtttgccgtg cggagacacc tgtggggctc tcacggcaac 2580
tctactttcc ccgagttcct gcacaacatg gactacttca agttccacaa catgcggcct 2640
ccattcacct acgccacact gatcagatgg gccattctgg aagcccctga gaagcagaga 2700
accctgaacg agatctacca ctggtttacc cggatgttcg ccttcttccg gaatcaccct 2760
gccacctgga agaacgccat ccggcacaat ctgagcctgc acaagtgctt cgtgcgcgtg 2820
gaatctgaga aaggcgccgt gtggacagtg gacgagctgg aattcagaaa gaagagaagc 2880
cagcggccta gccggtgcag caatcctaca cctggacctt gaaagcttga taatcaacct 2940
ctggattaca aaatttgtga aagattgact ggtattctta actatgttgc tccttttacg 3000
ctatgtggat acgctgcttt aatgcctttg tatcatgcta ttgcttcccg tatggctttc 3060
attttctcct ccttgtataa atcctggtta gttcttgcca cggcggaact catcgccgcc 3120
tgccttgccc gctgctggac aggggctcgg ctgttgggca ctgacaattc cgtgggtcga 3180
ctgctttatt tgtgaaattt gtgatgctat tgctttattt gtaaccatta taagctgcaa 3240
taaacaagtt aacaacaaca attgcattca ttttatgttt caggttcagg gggagatgtg 3300
ggaggttttt taaagcacta gtgtgaggcc ctgggcccag gatggggcag gcagggtggg 3360
gtacctggac ctacaggtgc cgacctttac tgtggcactg ggcgggaggg gggctggctg 3420
gggcacagga agtggtttct gggtcccagg caagtctgtg acttatgcag atgttgcagg 3480
gccaagaaaa tccccacctg ccaggcctca gagattggag gctctccccg acctcccaat 3540
ccctgtctca ggagaggagg aggccgtatt gtagtcccat gagcatagct atgtgtcccc 3600
atccccatgt gacaagagaa gaggactggg gccaagtagg tgaggtgaca gggctgaggc 3660
cagctctgca acttattagc tgtttgatct ttaaaaagtt actcgatctc catgagcctc 3720
agtttccata cgtgtaaaag gggatgatc atagcatcta ccatgtgggc ttgcagtgca 3780
gagtatttga attagacaca gaacagtgag gatcaggatg gcctctcacc cacctgcctt 3840
tctgcccagc tgcccacact gcccctagtc atggtggcac cctccggggc acggctgggc 3900
cccttgcccc acttacaggc accgcggcgc tacgtagata agtagcatgg cgggttaatc 3960
attaactaca aggaacccct agtgatggag ttggccactc cctctctgcg cgctcgctcg 4020
ctcactgagg ccgggcgacc aaaggtcgcc cgacgcccgg gctttgcccg ggcggcctca 4080
gtgagcgagc gagcgcgcca gctggcgtaa tagcgaagag gcccgcaccg atcgcccttc 4140

-continued

```
ccaacagttg cgcagcctga atggcgaatg gcgattccgt tgcaatggct ggcggtaata   4200
ttgttctgga tattaccagc aaggccgata gtttgagttc ttctactcag gcaagtgatg   4260
ttattactaa tcaaagaagt attgcgacaa cggttaattt gcgtgatgga cagactcttt   4320
tactcggtgg cctcactgat tataaaaaca cttctcagga ttctggcgta ccgttcctgt   4380
ctaaaatccc tttaatcggc ctcctgttta gctcccgctc tgattctaac gaggaaagca   4440
cgttatacgt gctcgtcaaa gcaaccatag tacgcgccct gtagcggcgc attaagcgcg   4500
gcgggtgtgg tggttacgcg cagcgtgacc gctacacttg ccagcgccct agcgcccgct   4560
cctttcgctt tcttcccttc ctttctcgcc acgttcgccg gctttccccg tcaagctcta   4620
aatcgggggc tccctttagg gttccgattt agtgctttac ggcacctcga ccccaaaaaa   4680
cttgattagg gtgatggttc acgtagtggg ccatcgccct gatagacggt ttttcgccct   4740
ttgacgttgg agtccacgtt ctttaatagt ggactcttgt tccaaactgg aacaacactc   4800
aaccctatct cggtctattc ttttgattta taagggattt tgccgatttc ggcctattgg   4860
ttaaaaaatg agctgattta acaaaaattt aacgcgaatt ttaacaaaat attaacgttt   4920
acaatttaaa tatttgctta tacaatcttc ctgtttttgg ggcttttctg attatcaacc   4980
ggggtacata tgattgacat gctagtttta cgattaccgt tcatcgattc tcttgtttgc   5040
tccagactct caggcaatga cctgatagcc tttgtagaga cctctcaaaa atagctaccc   5100
tctccggcat gaatttatca gctagaacgg ttgaatatca tattgatggt gatttgactg   5160
tctccggcct ttctcacccg tttgaatctt tacctacaca ttactcaggc attgcattta   5220
aaatatatga gggttctaaa aatttttatc cttgcgttga aataaaggct tctcccgcaa   5280
aagtattaca gggtcataat gtttttggta caaccgattt agctttatgc tctgaggctt   5340
tattgcttaa ttttgctaat tctttgcctt gcctgtatga tttattggat gttggaatcg   5400
cctgatgcgg tattttctcc ttacgcatct gtgcggtatt tcacaccgca tatggtgcac   5460
tctcagtaca atctgctctg atgccgcata gttaagccag ccccgacacc cgccaacacc   5520
cgctgacgcg ccctgacggg cttgtctgct cccggcatcc gcttacagac aagctgtgac   5580
cgtctccggg agctgcatgt gtcagaggtt ttcaccgtca tcaccgaaac gcgcgagacg   5640
aaagggcctc gtgatacgcc tatttttata ggttaatgtc atgataataa tggtttctta   5700
gacgtcaggt ggcacttttc ggggaaatgt gcgcggaacc cctatttgtt tatttttcta   5760
aatacattca aatatgtatc cgctcatgag acaataaccc tgataaatgc ttcaataata   5820
ttgaaaaagg aagagtatga gtattcaaca tttccgtgtc gcccttattc ccttttttgc   5880
ggcattttgc cttcctgttt ttgctcaccc agaaacgctg gtgaaagtaa aagatgctga   5940
agatcagttg ggtgcacgag tgggttacat cgaactggat ctcaacagcg gtaagatcct   6000
tgagagtttt cgccccgaag aacgttttcc aatgatgagc acttttaaag ttctgctatg   6060
tggcgcggta ttatcccgta ttgacgccgg gcaagagcaa ctcggtcgcc gcatacacta   6120
ttctcagaat gacttggttg agtactcacc agtcacagaa aagcatctta cggatggcat   6180
gacagtaaga gaattatgca gtgctgccat aaccatgagt gataacactg cggccaactt   6240
acttctgaca acgatcggag gaccgaagga gctaaccgct tttttgcaca acatggggga   6300
tcatgtaact cgccttgatc gttgggaacc ggagctgaat gaagccatac caaacgacga   6360
gcgtgacacc acgatgcctg tagcaatggc aacaacgttg cgcaaactat taactggcga   6420
actacttact ctagcttccc ggcaacaatt aatagactgg atggaggcgg ataaagttgc   6480
```

```
aggaccactt ctgcgctcgg cccttccggc tggctggttt attgctgata aatctggagc   6540

cggtgagcgt gggtctcgcg gtatcattgc agcactgggg ccagatggta agccctcccg   6600

tatcgtagtt atctacacga cggggagtca ggcaactatg gatgaacgaa atagacagat   6660

cgctgagata ggtgcctcac tgattaagca ttggtaactg tcagaccaag tttactcata   6720

tatactttag attgatttaa aacttcattt ttaatttaaa aggatctagg tgaagatcct   6780

ttttgataat ctcatgacca aaatccctta acgtgagttt tcgttccact gagcgtcaga   6840

cccc                                                                6844


<210> SEQ ID NO 35
<211> LENGTH: 7048
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 3088 pAAV_FOXP3_08_MND_GFP 08_for T3

<400> SEQUENCE: 35

gtagaaaaga tcaaaggatc ttcttgagat cctttttttc tgcgcgtaat ctgctgcttg     60

caaacaaaaa aaccaccgct accagcggtg gtttgtttgc cggatcaaga gctaccaact    120

ctttttccga aggtaactgg cttcagcaga gcgcagatac caaatactgt ccttctagtg    180

tagccgtagt taggccacca cttcaagaac tctgtagcac cgcctacata cctcgctctg    240

ctaatcctgt taccagtggc tgctgccagt ggcgataagt cgtgtcttac cgggttggac    300

tcaagacgat agttaccgga taaggcgcag cggtcgggct gaacgggggg ttcgtgcaca    360

cagcccagct tggagcgaac gacctacacc gaactgagat acctacagcg tgagctatga    420

gaaagcgcca cgcttcccga agggagaaag gcggacaggt atccggtaag cggcagggtc    480

ggaacaggag agcgcacgag ggagcttcca gggggaaacg cctggtatct ttatagtcct    540

gtcgggtttc gccacctctg acttgagcgt cgatttttgt gatgctcgtc aggggggcgg    600

agcctatgga aaaacgccag caacgcggcc tttttacggt tcctggcctt ttgctggcct    660

tttgctcaca tgttctttcc tgcgttatcc cctgattctg tggataaccg tattaccgcc    720

tttgagtgag ctgataccgc tcgccgcagc cgaacgaccg agcgcagcga gtcagtgagc    780

gaggaagcgg aagagcgccc aatacgcaaa ccgcctctcc ccgcgcgttg gccgattcat    840

taatgcagct gcgcgctcgc tcgctcactg aggccgcccg ggcaaagccc gggcgtcggg    900

cgacctttgg tcgcccggcc tcagtgagcg agcgagcgcg cagagaggga gtggccaact    960

ccatcactag gggttccttg tagttaatga ttaacccgcc atgctactta tctacgtagc   1020

ggccgccttg cccactacat ccaagctgct agcactgctc ctgatccagc ttcagattaa   1080

gtctcagaat ctacccactt ctcgccttct ccactgccac cagcccattc tgtgccagca   1140

tcatcacttg ccaggactgt tacaatagcc tcctcactag ccccactcac agcagccaga   1200

tgaatctttt gagtccatgc ctagtcactg ggcaaaaata ggactccgag gagaaagtcc   1260

gagaccagct ccggcaagat gagcaaacac agcctgtgca gggtgcaggg agggctagag   1320

gcctgaggct tgaaacagct ctcaagtgga gggggaaaca accattgccc tcatagagga   1380

cacatccaca ccagggctgt gctagcgtgg gcaggcaagc caggtgctgg acctctgcac   1440

gtggggcatg tgtgggtatg tacatgtacc tgtgttcttg gtgtgtgtgt gtgtgtgtgt   1500

gtgtgtgtgt gtctagagct ggggtgcaac tatggggccc ctcgggacat gtcccagcca   1560
```

-continued

```
atgcctgctt tgaccagagg agtgtccacg tggctcaggt ggtcgagtat ctcataccgc   1620
cctagcacac gtgtgactcc tttcccctat tgtctacgca gcctgccctt ggacaaggac   1680
ccgatgccca accccaggcc tggcaagccc tcggcccctt ccttggccct tggcccatcc   1740
ccaggagcct cgcccagctg gagggctgca cccaaagcct cagacctgct gggggcccgg   1800
ggcccagggg gaaccttcca acgcgtagga acagagaaac aggagaatat gggccaaaca   1860
ggatatctgt ggtaagcagt tcctgccccg gctcagggcc aagaacagtt ggaacagcag   1920
aatatgggcc aaacaggata tctgtggtaa gcagttcctg ccccggctca gggccaagaa   1980
cagatggtcc ccagatgcgg tcccgccctc agcagtttct agagaaccat cagatgtttc   2040
cagggtgccc caaggacctg aaatgaccct gtgccttatt tgaactaacc aatcagttcg   2100
cttctcgctt ctgttcgcgc gcttctgctc cccgagctct atataagcag agctcgttta   2160
gtgaaccgtc agatcgcctg gagacgccat ccacgctgtt ttgacttcca tagaaggatc   2220
tcgaggccac catggtgagc aagggcgagg agctgttcac cggggtggtg cccatcctgg   2280
tcgagctgga cggcgacgta aacggccaca agttcagcgt gtccggcgag ggcgagggcg   2340
atgccaccta cggcaagctg accctgaagt tcatctgcac caccggcaag ctgcccgtgc   2400
cctggcccac cctcgtgacc accctgacct acggcgtgca gtgcttcagc cgctaccccg   2460
accacatgaa gcagcacgac ttcttcaagt ccgccatgcc cgaaggctac gtccaggagc   2520
gcaccatctt cttcaaggac gacggcaact acaagacccg cgccgaggtg aagttcgagg   2580
gcgacaccct ggtgaaccgc atcgagctga agggcatcga cttcaaggag gacggcaaca   2640
tcctggggca caagctggag tacaactaca acagccacaa cgtctatatc atggccgaca   2700
agcagaagaa cggcatcaag gtgaacttca agatccgcca caacatcgag gacggcagcg   2760
tgcagctcgc cgaccactac cagcagaaca cccccatcgg cgacggcccc gtgctgctgc   2820
ccgacaacca ctacctgagc acccagtccg ccctgagcaa agaccccaac gagaagcgcg   2880
atcacatggt cctgctggag ttcgtgaccg ccgccgggat cactctcggc atggacgagc   2940
tgtacaagta aaagcttgat aatcaacctc tggattacaa aatttgtgaa agattgactg   3000
gtattcttaa ctatgttgct ccttttacgc tatgtggata cgctgcttta atgcctttgt   3060
atcatgctat tgcttcccgt atggctttca ttttctcctc cttgtataaa tcctggttag   3120
ttcttgccac ggcggaactc atcgccgcct gccttgcccg ctgctggaca ggggctcggc   3180
tgttgggcac tgacaattcc gtgggtcgac tgctttattt gtgaaatttg tgatgctatt   3240
gctttatttg taaccattat aagctgcaat aaacaagtta acaacaacaa ttgcattcat   3300
tttatgtttc aggttcaggg ggagatgtgg gaggtttttt aaagcactag tcgagatctt   3360
cgaggcgggg cccatgcctc ctcttcttcc ttgaacccca tgccaccatc gcagctgcag   3420
gtgaggccct gggcccagga tggggcaggc agggtggggt acctggacct acaggtgccg   3480
acctttactg tggcactggg cgggaggggg gctggctggg gcacaggaag tggtttctgg   3540
gtcccaggca agtctgtgac ttatgcagat gttgcagggc caagaaaatc cccacctgcc   3600
aggcctcaga gattggaggc tctccccgac ctcccaatcc ctgtctcagg agaggaggag   3660
gccgtattgt agtcccatga gcatagctat gtgtccccat ccccatgtga caagagaaga   3720
ggactggggc caagtaggtg aggtgacagg gctgaggcca gctctgcaac ttattagctg   3780
tttgatcttt aaaaagttac tcgatctcca tgagcctcag tttccatacg tgtaaaaggg   3840
ggatgatcat agcatctacc atgtgggctt gcagtgcaga gtatttgaat tagacacaga   3900
acagtgagga tcaggatggc ctctcaccca cctgcctttc tgcccagctg cccacactgc   3960
```

ccctagtcat ggtggcaccc tccggggcac ggctgggccc cttgccccac ttacaggcac 4020
tcctccagga caggccacat ttcatgcacc aggtatggac ggtgaatggg cagggaggag 4080
ggagcaggtg ggagaactgt ggggaggggc cccgagtcag gctgaaccgg atcctacgta 4140
gataagtagc atggcgggtt aatcattaac tacaaggaac ccctagtgat ggagttggcc 4200
actccctctc tgcgcgctcg ctcgctcact gaggccgggc gaccaaaggt cgcccgacgc 4260
ccgggctttg cccgggcggc ctcagtgagc gagcgagcgc gccagctggc gtaatagcga 4320
agaggcccgc accgatcgcc cttcccaaca gttgcgcagc ctgaatggcg aatggcgatt 4380
ccgttgcaat ggctggcggt aatattgttc tggatattac cagcaaggcc gatagtttga 4440
gttcttctac tcaggcaagt gatgttatta ctaatcaaag aagtattgcg acaacggtta 4500
atttgcgtga tggacagact cttttactcg gtggcctcac tgattataaa aacacttctc 4560
aggattctgg cgtaccgttc ctgtctaaaa tccctttaat cggcctcctg tttagctccc 4620
gctctgattc taacgaggaa agcacgttat acgtgctcgt caaagcaacc atagtacgcg 4680
ccctgtagcg gcgcattaag cgcggcgggt gtggtggtta cgcgcagcgt gaccgctaca 4740
cttgccagcg ccctagcgcc cgctcctttc gctttcttcc cttcctttct cgccacgttc 4800
gccggctttc cccgtcaagc tctaaatcgg gggctccctt tagggttccg atttagtgct 4860
ttacggcacc tcgaccccaa aaaacttgat tagggtgatg gttcacgtag tgggccatcg 4920
ccctgataga cggtttttcg ccctttgacg ttggagtcca cgttctttaa tagtggactc 4980
ttgttccaaa ctggaacaac actcaaccct atctcggtct attcttttga tttataaggg 5040
attttgccga tttcggccta ttggttaaaa aatgagctga tttaacaaaa atttaacgcg 5100
aattttaaca aaatattaac gtttacaatt taaatatttg cttatacaat cttcctgttt 5160
ttggggcttt tctgattatc aaccggggta catatgattg acatgctagt tttacgatta 5220
ccgttcatcg attctcttgt ttgctccaga ctctcaggca atgacctgat agcctttgta 5280
gagacctctc aaaaatagct accctctccg gcatgaattt atcagctaga acggttgaat 5340
atcatattga tggtgatttg actgtctccg gcctttctca cccgtttgaa tctttaccta 5400
cacattactc aggcattgca tttaaaatat atgagggttc taaaaatttt tatccttgcg 5460
ttgaaataaa ggcttctccc gcaaaagtat tacagggtca taatgttttt ggtacaaccg 5520
atttagcttt atgctctgag gctttattgc ttaattttgc taattctttg ccttgcctgt 5580
atgatttatt ggatgttgga atcgcctgat gcggtatttt ctccttacgc atctgtgcgg 5640
tatttcacac cgcatatggt gcactctcag tacaatctgc tctgatgccg catagttaag 5700
ccagccccga cacccgccaa cacccgctga cgcgccctga cgggcttgtc tgctcccggc 5760
atccgcttac agacaagctg tgaccgtctc cgggagctgc atgtgtcaga ggttttcacc 5820
gtcatcaccg aaacgcgcga gacgaaaggg cctcgtgata cgcctatttt tataggttaa 5880
tgtcatgata ataatggttt cttagacgtc aggtggcact tttcggggaa atgtgcgcgg 5940
aacccctatt tgtttatttt tctaaataca ttcaaatatg tatccgctca tgagacaata 6000
accctgataa atgcttcaat aatattgaaa aaggaagagt atgagtattc aacatttccg 6060
tgtcgccctt attccctttt ttgcggcatt ttgccttcct gtttttgctc acccagaaac 6120
gctggtgaaa gtaaaagatg ctgaagatca gttgggtgca cgagtgggtt acatcgaact 6180
ggatctcaac agcggtaaga tccttgagag ttttcgcccc gaagaacgtt ttccaatgat 6240
gagcactttt aaagttctgc tatgtggcgc ggtattatcc cgtattgacg ccgggcaaga 6300
gcaactcggt cgccgcatac actattctca gaatgacttg gttgagtact caccagtcac 6360
agaaaagcat cttacggatg gcatgacagt aagagaatta tgcagtgctg ccataaccat 6420
gagtgataac actgcggcca acttacttct gacaacgatc ggaggaccga aggagctaac 6480
cgcttttttg cacaacatgg gggatcatgt aactcgcctt gatcgttggg aaccggagct 6540
gaatgaagcc ataccaaacg acgagcgtga caccacgatg cctgtagcaa tggcaacaac 6600
gttgcgcaaa ctattaactg gcgaactact tactctagct tcccggcaac aattaataga 6660
ctggatggag gcggataaag ttgcaggacc acttctgcgc tcggcccttc cggctggctg 6720
gtttattgct gataaatctg gagccggtga gcgtgggtct cgcggtatca ttgcagcact 6780
ggggccagat ggtaagccct cccgtatcgt agttatctac acgacgggga gtcaggcaac 6840
tatggatgaa cgaaatagac agatcgctga gataggtgcc tcactgatta agcattggta 6900
actgtcagac caagtttact catatatact ttagattgat ttaaaacttc atttttaatt 6960
taaaaggatc taggtgaaga tcctttttga taatctcatg accaaaatcc cttaacgtga 7020
gttttcgttc cactgagcgt cagacccc 7048

<210> SEQ ID NO 36
<211> LENGTH: 7056
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 3089 pAAV_FOXP3_08_MND_GFP08_for T9

<400> SEQUENCE: 36
gtagaaaaga tcaaaggatc ttcttgagat cctttttttc tgcgcgtaat ctgctgcttg 60
caaacaaaaa aaccaccgct accagcggtg gtttgtttgc cggatcaaga gctaccaact 120
ctttttccga aggtaactgg cttcagcaga gcgcagatac caaatactgt ccttctagtg 180
tagccgtagt taggccacca cttcaagaac tctgtagcac cgcctacata cctcgctctg 240
ctaatcctgt taccagtggc tgctgccagt ggcgataagt cgtgtcttac cgggttggac 300
tcaagacgat agttaccgga taaggcgcag cggtcgggct gaacgggggg ttcgtgcaca 360
cagcccagct tggagcgaac gacctacacc gaactgagat acctacagcg tgagctatga 420
gaaagcgcca cgcttcccga agggagaaag gcggacaggt atccggtaag cggcagggtc 480
ggaacaggag agcgcacgag ggagcttcca gggggaaacg cctggtatct ttatagtcct 540
gtcgggtttc gccacctctg acttgagcgt cgatttttgt gatgctcgtc aggggggcgg 600
agcctatgga aaaacgccag caacgcggcc tttttacggt tcctggcctt ttgctggcct 660
tttgctcaca tgttctttcc tgcgttatcc cctgattctg tggataaccg tattaccgcc 720
tttgagtgag ctgataccgc tcgccgcagc cgaacgaccg agcgcagcga gtcagtgagc 780
gaggaagcgg aagagcgccc aatacgcaaa ccgcctctcc ccgcgcgttg gccgattcat 840
taatgcagct gcgcgctcgc tcgctcactg aggccgcccg ggcaaagccc gggcgtcggg 900
cgacctttgg tcgcccggcc tcagtgagcg agcgagcgcg cagagaggga gtggccaact 960
ccatcactag gggttccttg tagttaatga ttaacccgcc atgctactta tctacgtagc 1020
ggccgcatct caggtaatgt cagctcggtc cttccagctg ctcaagctaa aacccatgtc 1080
actttgactc tccctcttgc ccactacatc caagctgcta gcactgctcc tgatccagct 1140
tcagattaag tctcagaatc tacccacttc tcgccttctc cactgccacc agcccattct 1200

-continued

```
gtgccagcat catcacttgc caggactgtt acaatagcct cctcactagc cccactcaca   1260
gcagccagat gaatcttttg agtccatgcc tagtcactgg ggcaaaatag gactccgagg   1320
agaaagtccg agaccagctc cggcaagatg agcaaacaca gcctgtgcag ggtgcaggga   1380
gggctagagg cctgaggctt gaaacagctc tcaagtggag ggggaaacaa ccattgccct   1440
catagaggac acatccacac cagggctgtg ctagcgtggg caggcaagcc aggtgctgga   1500
cctctgcacg tggggcatgt gtgggtatgt acatgtacct gtgttcttgg tgtgtgtgtg   1560
tgtgtgtgtg tgtgtgtgtg tctagagctg gggtgcaact atggggcccc tcgggacatg   1620
tcccagccaa tgcctgcttt gaccagagga gtgtccacgt ggctcaggtg gtcgagtatc   1680
tcataccgcc ctagcacacg tgtgactcct ttcccctatt gtctacgcag cctgcccttg   1740
gacaaggacc cgatgcccaa ccccaggcct ggcaagccct cggccccttc cttggccctt   1800
ggcccatccc cacgcgtagg aacagagaaa caggagaata tgggccaaac aggatatctg   1860
tggtaagcag ttcctgcccc ggctcagggc caagaacagt tggaacagca gaatatgggc   1920
caaacaggat atctgtggta agcagttcct gccccggctc agggccaaga acagatggtc   1980
cccagatgcg gtcccgccct cagcagtttc tagagaacca tcagatgttt ccagggtgcc   2040
ccaaggacct gaaatgaccc tgtgccttat ttgaactaac caatcagttc gcttctcgct   2100
tctgttcgcg cgcttctgct ccccgagctc tatataagca gagctcgttt agtgaaccgt   2160
cagatcgcct ggagacgcca tccacgctgt tttgacttcc atagaaggat ctcgaggcca   2220
ccatggtgag caagggcgag gagctgttca ccggggtggt gcccatcctg gtcgagctgg   2280
acggcgacgt aaacggccac aagttcagcg tgtccggcga gggcgagggc gatgccacct   2340
acggcaagct gaccctgaag ttcatctgca ccaccggcaa gctgcccgtg ccctggccca   2400
ccctcgtgac caccctgacc tacggcgtgc agtgcttcag ccgctacccc gaccacatga   2460
agcagcacga cttcttcaag tccgccatgc ccgaaggcta cgtccaggag cgcaccatct   2520
tcttcaagga cgacggcaac tacaagaccc gcgccgaggt gaagttcgag ggcgacaccc   2580
tggtgaaccg catcgagctg aagggcatcg acttcaagga ggacggcaac atcctggggc   2640
acaagctgga gtacaactac aacagccaca acgtctatat catggccgac aagcagaaga   2700
acggcatcaa ggtgaacttc aagatccgcc acaacatcga ggacggcagc gtgcagctcg   2760
ccgaccacta ccagcagaac acccccatcg gcgacggccc cgtgctgctg cccgacaacc   2820
actacctgag cacccagtcc gccctgagca aagaccccaa cgagaagcgc gatcacatgg   2880
tcctgctgga gttcgtgacc gccgccggga tcactctcgg catggacgag ctgtacaagt   2940
aaaagcttga taatcaacct ctggattaca aaatttgtga aagattgact ggtattctta   3000
actatgttgc tccttttacg ctatgtggat acgctgcttt aatgcctttg tatcatgcta   3060
ttgcttcccg tatggctttc attttctcct ccttgtataa atcctggtta gttcttgcca   3120
cggcggaact catcgccgcc tgccttgccc gctgctggac aggggctcgg ctgttgggca   3180
ctgacaattc cgtgggtcga ctgctttatt tgtgaaattt gtgatgctat tgctttattt   3240
gtaaccatta taagctgcaa taaacaagtt aacaacaaca attgcattca ttttatgttt   3300
caggttcagg gggagatgtg ggaggttttt taaagcacta gtgcctcgcc cagctggagg   3360
gctgcaccca aagcctcaga cctgctgggg gcccggggcc cagggggaac cttccagggc   3420
cgagatcttc gaggcggggc ccatgcctcc tcttcttcct tgaaccccat gccaccatcg   3480
cagctgcagg tgaggccctg ggcccaggat ggggcaggca gggtggggta cctggaccta   3540
caggtgccga cctttactgt ggcactgggc gggagggggg ctggctgggg cacaggaagt   3600
```

-continued

```
ggtttctggg tcccaggcaa gtctgtgact tatgcagatg ttgcagggcc aagaaaatcc   3660
ccacctgcca ggcctcagag attggaggct ctccccgacc tcccaatccc tgtctcagga   3720
gaggaggagg ccgtattgta gtcccatgag catagctatg tgtccccatc cccatgtgac   3780
aagagaagag gactggggcc aagtaggtga ggtgacaggg ctgaggccag ctctgcaact   3840
tattagctgt ttgatcttta aaaagttact cgatctccat gagcctcagt ttccatacgt   3900
gtaaaagggg gatgatcata gcatctacca tgtgggcttg cagtgcagag tatttgaatt   3960
agacacagaa cagtgaggat caggatggcc tctcacccac ctgcctttct gcccagctgc   4020
ccacactgcc cctagtcatg gtggcaccct ccggggcacg gctgggcccc ttgccccact   4080
tacaggcact cctccaggac aggccacatt tcatgcacca ggtatggacg gtgaatggat   4140
cctacgtaga taagtagcat ggcgggttaa tcattaacta caaggaaccc ctagtgatgg   4200
agttggccac tccctctctg cgcgctcgct cgctcactga ggccgggcga ccaaaggtcg   4260
cccgacgccc gggctttgcc cgggcggcct cagtgagcga gcgagcgcgc cagctggcgt   4320
aatagcgaag aggcccgcac cgatcgccct tcccaacagt tgcgcagcct gaatggcgaa   4380
tggcgattcc gttgcaatgg ctggcggtaa tattgttctg gatattacca gcaaggccga   4440
tagtttgagt tcttctactc aggcaagtga tgttattact aatcaaagaa gtattgcgac   4500
aacggttaat ttgcgtgatg gacagactct tttactcggt ggcctcactg attataaaaa   4560
cacttctcag gattctggcg taccgttcct gtctaaaatc cctttaatcg gcctcctgtt   4620
tagctcccgc tctgattcta acgaggaaag cacgttatac gtgctcgtca aagcaaccat   4680
agtacgcgcc ctgtagcggc gcattaagcg cggcgggtgt ggtggttacg cgcagcgtga   4740
ccgctacact tgccagcgcc ctagcgcccg ctcctttcgc tttcttccct tcctttctcg   4800
ccacgttcgc cggctttccc cgtcaagctc taaatcgggg gctcccttta gggttccgat   4860
ttagtgcttt acggcacctc gaccccaaaa aacttgatta gggtgatggt tcacgtagtg   4920
ggccatcgcc ctgatagacg gtttttcgcc ctttgacgtt ggagtccacg ttctttaata   4980
gtggactctt gttccaaact ggaacaacac tcaaccctat ctcggtctat tcttttgatt   5040
tataagggat tttgccgatt tcggcctatt ggttaaaaaa tgagctgatt taacaaaaat   5100
ttaacgcgaa ttttaacaaa atattaacgt ttacaattta aatatttgct tatacaatct   5160
tcctgttttt ggggcttttc tgattatcaa ccggggtaca tatgattgac atgctagttt   5220
tacgattacc gttcatcgat tctcttgttt gctccagact ctcaggcaat gacctgatag   5280
cctttgtaga gacctctcaa aaatagctac cctctccggc atgaatttat cagctagaac   5340
ggttgaatat catattgatg gtgatttgac tgtctccggc ctttctcacc cgtttgaatc   5400
tttacctaca cattactcag gcattgcatt taaaatatat gagggttcta aaaattttta   5460
tccttgcgtt gaaataaagg cttctcccgc aaaagtatta cagggtcata atgtttttgg   5520
tacaaccgat ttagctttat gctctgaggc tttattgctt aattttgcta attctttgcc   5580
ttgcctgtat gatttattgg atgttggaat cgcctgatgc ggtattttct ccttacgcat   5640
ctgtgcggta tttcacaccg catatggtgc actctcagta caatctgctc tgatgccgca   5700
tagttaagcc agccccgaca cccgccaaca cccgctgacg cgccctgacg ggcttgtctg   5760
ctcccggcat ccgcttacag acaagctgtg accgtctccg ggagctgcat gtgtcagagg   5820
ttttcaccgt catcaccgaa acgcgcgaga cgaaagggcc tcgtgatacg cctattttta   5880
taggttaatg tcatgataat aatggtttct tagacgtcag gtggcacttt tcggggaaat   5940
```

-continued

```
gtgcgcggaa cccctatttg tttatttttc taaatacatt caaatatgta tccgctcatg   6000

agacaataac cctgataaat gcttcaataa tattgaaaaa ggaagagtat gagtattcaa   6060

catttccgtg tcgcccttat tccctttttt gcggcatttt gccttcctgt ttttgctcac   6120

ccagaaacgc tggtgaaagt aaaagatgct gaagatcagt tgggtgcacg agtgggttac   6180

atcgaactgg atctcaacag cggtaagatc cttgagagtt ttcgccccga agaacgtttt   6240

ccaatgatga gcacttttaa agttctgcta tgtggcgcgg tattatcccg tattgacgcc   6300

gggcaagagc aactcggtcg ccgcatacac tattctcaga atgacttggt tgagtactca   6360

ccagtcacag aaaagcatct tacggatggc atgacagtaa gagaattatg cagtgctgcc   6420

ataaccatga gtgataacac tgcggccaac ttacttctga caacgatcgg aggaccgaag   6480

gagctaaccg cttttttgca caacatgggg gatcatgtaa ctcgccttga tcgttgggaa   6540

ccggagctga atgaagccat accaaacgac gagcgtgaca ccacgatgcc tgtagcaatg   6600

gcaacaacgt tgcgcaaact attaactggc gaactactta ctctagcttc ccggcaacaa   6660

ttaatagact ggatggaggc ggataaagtt gcaggaccac ttctgcgctc ggcccttccg   6720

gctggctggt ttattgctga taaatctgga gccggtgagc gtgggtctcg cggtatcatt   6780

gcagcactgg ggccagatgg taagccctcc cgtatcgtag ttatctacac gacggggagt   6840

caggcaacta tggatgaacg aaatagacag atcgctgaga taggtgcctc actgattaag   6900

cattggtaac tgtcagacca agtttactca tatatacttt agattgattt aaaacttcat   6960

ttttaattta aaaggatcta ggtgaagatc ctttttgata atctcatgac caaaatccct   7020

taacgtgagt tttcgttcca ctgagcgtca gacccc                             7056
```

<210> SEQ ID NO 37
<211> LENGTH: 90
<212> TYPE: PRT
<213> ORGANISM: Artificial sequence
<220> FEATURE:
<223> OTHER INFORMATION: Synthetic polypeptide

<400> SEQUENCE: 37

```
Met Glu Met Trp His Glu Gly Leu Glu Glu Ala Ser Arg Leu Tyr Phe
1               5                   10                  15

Gly Glu Arg Asn Val Lys Gly Met Phe Glu Val Leu Glu Pro Leu His
            20                  25                  30

Ala Met Met Glu Arg Gly Pro Gln Thr Leu Lys Glu Thr Ser Phe Asn
        35                  40                  45

Gln Ala Tyr Gly Arg Asp Leu Met Glu Ala Gln Glu Trp Cys Arg Lys
    50                  55                  60

Tyr Met Lys Ser Gly Asn Val Lys Asp Leu Thr Gln Ala Trp Asp Leu
65                  70                  75                  80

Tyr Tyr His Val Phe Arg Arg Ile Ser Lys
                85                  90
```

<210> SEQ ID NO 38
<211> LENGTH: 90
<212> TYPE: PRT
<213> ORGANISM: Artificial sequence
<220> FEATURE:
<223> OTHER INFORMATION: Synthetic polypeptide

<400> SEQUENCE: 38

```
Met Glu Met Trp His Glu Gly Leu Glu Glu Ala Ser Arg Leu Tyr Phe
1               5                   10                  15
```

Gly Glu Arg Asn Val Lys Gly Met Phe Glu Val Leu Glu Pro Leu His
            20                  25                  30

Ala Met Met Glu Arg Gly Pro Gln Thr Leu Lys Glu Thr Ser Phe Asn
        35                  40                  45

Gln Ala Tyr Gly Arg Asp Leu Met Glu Ala Gln Glu Trp Cys Arg Lys
    50                  55                  60

Tyr Met Lys Ser Gly Asn Val Lys Asp Leu Leu Gln Ala Trp Asp Leu
65                  70                  75                  80

Tyr Tyr His Val Phe Arg Arg Ile Ser Lys
                85                  90

<210> SEQ ID NO 39
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: naked FRB wild type polypeptide

<400> SEQUENCE: 39

Met Glu Met Trp His Glu Gly Leu Glu Glu Ala Ser Arg Leu Tyr Phe
1               5                   10                  15

Gly Glu Arg Asn Val Lys Gly Met Phe Glu Val Leu Glu Pro Leu His
            20                  25                  30

Ala Met Met Glu Arg Gly Pro Gln Thr Leu Lys Glu Thr Ser Phe Asn
        35                  40                  45

Gln Ala Tyr Gly Arg Asp Leu Met Glu Ala Gln Glu Trp Cys Arg Lys
    50                  55                  60

Tyr Met Lys Ser Gly Asn Val Lys Asp Leu Thr Gln Ala Trp Asp Leu
65                  70                  75                  80

Tyr Tyr His Val Phe Arg Arg Ile Ser Lys
                85                  90

<210> SEQ ID NO 40
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: naked FRB mutant polypeptide

<400> SEQUENCE: 40

Met Glu Met Trp His Glu Gly Leu Glu Glu Ala Ser Arg Leu Tyr Phe
1               5                   10                  15

Gly Glu Arg Asn Val Lys Gly Met Phe Glu Val Leu Glu Pro Leu His
            20                  25                  30

Ala Met Met Glu Arg Gly Pro Gln Thr Leu Lys Glu Thr Ser Phe Asn
        35                  40                  45

Gln Ala Tyr Gly Arg Asp Leu Met Glu Ala Gln Glu Trp Cys Arg Lys
    50                  55                  60

Tyr Met Lys Ser Gly Asn Val Lys Asp Leu Leu Gln Ala Trp Asp Leu
65                  70                  75                  80

Tyr Tyr His Val Phe Arg Arg Ile Ser Lys
                85                  90

<210> SEQ ID NO 41

<211> LENGTH: 4187
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DISC vector DNA

<400> SEQUENCE: 41
gaacagagaa acaggagaat atgggccaaa caggatatct gtggtaagca gttcctgccc 60
cggctcaggg ccaagaacag ttggaacagc agaatatggg ccaaacagga tatctgtggt 120
aagcagttcc tgccccggct cagggccaag aacagatggt ccccagatgc ggtcccgccc 180
tcagcagttt ctagagaacc atcagatgtt tccagggtgc cccaaggacc tgaaatgacc 240
ctgtgcctta tttgaactaa ccaatcagtt cgcttctcgc ttctgttcgc gcgcttctgc 300
tccccgagct ctatataagc agagctcgtt tagtgaaccg tcagatcgct agcaccggtg 360
ccgccaccat gcctctgggc ctgctgtggc tgggcctggc cctgctgggc gccctgcacg 420
cccaggccgg cgtgcaggtg gagacaatct ccccaggcga cggacgcaca ttccctaagc 480
ggggccagac ctgcgttgtg cactatacag gcatgctgga ggatggcaag aagtttgaca 540
gctcccggga tagaaacaag ccattcaagt ttatgctggg caagcaggaa gtgatcagag 600
gctgggagga gggcgtggcc cagatgtctg tgggccagag ggccaagctg accatcagcc 660
cagactacgc ctatggagca acaggccacc caggaatcat cccacctcac gccaccctgg 720
tgttcgatgt ggagctgctg aagctgggcg agggatccaa cacatcaaaa gagaacccct 780
ttctgttcgc attggaggcc gtagtcatat ctgttggatc catgggactt attatctccc 840
tgttgtgtgt gtacttctgg ctggaacgga ctatgcccag gatccccacg ctcaagaatc 900
tggaagatct cgtcacagaa taccatggta atttcagcgc ctggagcgga gtctctaagg 960
gtctggccga atccctccaa cccgattatt ctgaacggtt gtgcctcgta tccgaaatac 1020
caccaaaagg cggggctctg ggtgagggcc caggggcgag tccgtgcaat caacacagcc 1080
cgtattgggc ccctccttgt tatacgttga agcccgaaac tggaagcgga gctactaact 1140
tcagcctgct gaagcaggct ggagacgtgg aggagaaccc tggacctatg gcactgcccg 1200
tgaccgccct gctgctgcct ctggccctgc tgctgcacgc agcccggcct atcctgtggc 1260
acgagatgtg gcacgagggc ctggaggagg ccagcaggct gtattttggc gagcgcaacg 1320
tgaagggcat gttcgaggtg ctggagcctc tgcacgccat gatggagaga ggcccacaga 1380
ccctgaagga gacatccttt aaccaggcct atggacggga cctgatggag gcacaggagt 1440
ggtgcagaaa gtacatgaag tctggcaatg tgaaggacct gctgcaggcc tgggatctgt 1500
actatcacgt gtttcggaga atctccaagg gcaaagacac gattccgtgg cttgggcatc 1560
tgctcgttgg gctgagtggt gcgtttggtt tcatcatctt ggtctatctc ttgatcaatt 1620
gcagaaatac aggcccttgg ctgaaaaaag tgctcaagtg taatacccccc gacccaagca 1680 agttcttctc ccagctttct tcagagcatg gaggcgatgt gcagaaatgg ctctcttcac 1740
cttttccctc ctcaagcttc tccccgggag ggctggcgcc cgagatttca cctcttgagg 1800
tacttgaacg agacaaggtt acccaacttc tccttcaaca ggataaggta cccgaacctg 1860
cgagccttag ctccaaccac tctcttacga gctgcttcac caatcaggga tacttctttt 1920
tccaccttcc cgatgcgctg gaaatcgaag cttgtcaagt ttactttacc tatgatccat 1980
atagcgagga agatcccgac gaaggagtcg ccggtgcgcc cacgggttcc tcaccccaac 2040

-continued

```
ctctccagcc tctctcagga gaagatgatg cttattgcac ttttcccagt agagacgatc   2100
tcctcctctt ttctccatct cttttggggg gaccttcccc cccttctacg gcacctggcg   2160
ggtctggtgc tggcgaggag cggatgccgc cgtccctcca ggagcgagta ccacgagatt   2220
gggatcccca gccacttgga ccccccaccc ccggcgtacc tgaccttgtc gattttcaac   2280
ctccccctga attggtgctg cgagaggctg gggaggaagt tccggacgct gggccgaggg   2340
agggcgtgtc ctttccatgg agtaggcctc caggtcaagg cgagtttagg gctctcaacg   2400
cgcggctgcc gttgaataca gacgcttatc tctcactgca ggaactgcaa ggtcaggacc   2460
caacacatct tgtaggatct ggtgctacta atttttctct tttgaagcaa gctggagatg   2520
ttgaagagaa ccccggtccg gagatgtggc atgagggtct ggaagaagcg tctcgactgt   2580
actttggtga gcgcaatgtg aagggcatgt ttgaagtcct cgaacccctt catgccatga   2640
tggaacgcgg accccagacc ttgaaggaga caagttttaa ccaagcttac ggaagagacc   2700
tgatggaagc ccaggaatgg tgcaggaaat acatgaaaag cgggaatgtg aaggacttgc   2760
tccaagcgtg ggacctgtac tatcatgtct ttaggcgcat tagtaagggc agcggcgcca   2820
ccaacttcag cctgctgaag caggccggcg acgtggagga gaaccccggc cccgtgagca   2880
agggcgagga ggataacatg gccatcatca aggagttcat gcgcttcaag gtgcacatgg   2940
agggctccgt gaacggccac gagttcgaga tcgagggcga gggcgagggc cgcccctacg   3000
agggcaccca gaccgccaag ctgaaggtga ccaagggtgg cccccctgccc ttcgcctggg   3060
acatcctgtc ccctcagttc atgtacggct ccaaggccta cgtgaagcac cccgccgaca   3120
tccccgacta cttgaagctg tccttccccg agggcttcaa gtgggagcgc gtgatgaact   3180
tcgaggacgg cggcgtggtg accgtgaccc aggactcctc tctgcaggac ggcgagttca   3240
tctacaaggt gaagctgcgc ggcaccaact tcccctccga cggccccgta atgcagaaga   3300
agaccatggg ctgggaggcc tcctccgagc ggatgtaccc cgaggacggc gccctgaagg   3360
gcgagatcaa gcagaggctg aagctgaagg acggcggcca ctacgacgct gaggtcaaga   3420
ccacctacaa ggccaagaag cccgtgcagc tgcccggcgc ctacaacgtc aacatcaagt   3480
tggacatcac ctcccacaac gaggactaca ccatcgtgga acagtacgaa cgcgccgagg   3540
gccgccactc caccggcggc atggacgagc tgtacaagtg aactagtgtc gacaatcaac   3600
ctctggatta caaaatttgt gaaagattga ctggtattct taactatgtt gctcctttta   3660
cgctatgtgg atacgctgct ttaatgcctt tgtatcatgc tattgcttcc cgtatggctt   3720
tcattttctc ctccttgtat aaatcctggt tgctgtctct ttatgaggag ttgtggcccg   3780
ttgtcaggca acgtggcgtg gtgtgcactg tgtttgctga cgcaaccccc actggttggg   3840
gcattgccac cacctgtcag ctcctttccg ggactttcgc tttccccctc cctattgcca   3900
cggcggaact catcgccgcc tgccttgccc gctgctggac aggggctcgg ctgttgggca   3960
ctgacaattc cgtggtgttg tcggggaagc tgacgtcctt tccatggctg ctcgcctgtg   4020
ttgccacctg gattctgcgc gggacgtcct tctgctacgt cccttcggcc ctcaatccag   4080
cggaccttcc ttcccgcggc ctgctgccgg ctctgcggcc tcttccgcgt cttcgccttc   4140
gccctcagac gagtcggatc tccctttggg ccgcctcccc gcctgga                4187
```

<210> SEQ ID NO 42
<211> LENGTH: 393
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: uDISC DNA cytoplasmic tail only codon diverged

<400> SEQUENCE: 42
ccagcagctc tcggcaaaga cacgattccg tggcttgggc atctgctcgt tgggctgagc 60
ggtgcgtttg gtttcatcat cttggtctat ctcttgatca attgcagaaa tacaggccct 120
tggctgaaaa aagtgctcaa gtgtaatacc cccgacccaa gcaagttctt ctcccagctt 180
tcttcagagc atggaggcga tgtgcagaaa tggctctctt caccttttcc ctcctcaagc 240
ttctccccgg gagggctggc gcccgagatt tcacctcttg aggtacttga acgagacaag 300
gttacccaac ttctccttca acaggataag gtacccgaac ctgcgagcct tagcttgaat 360
acagacgctt atctctcact gcaggaactg caa 393

<210> SEQ ID NO 43
<211> LENGTH: 131
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: uDISC polypeptide cytoplasmic tail only

<400> SEQUENCE: 43

Pro Ala Ala Leu Gly Lys Asp Thr Ile Pro Trp Leu Gly His Leu Leu
1               5                   10                  15

Val Gly Leu Ser Gly Ala Phe Gly Phe Ile Ile Leu Val Tyr Leu Leu
            20                  25                  30

Ile Asn Cys Arg Asn Thr Gly Pro Trp Leu Lys Lys Val Leu Lys Cys
        35                  40                  45

Asn Thr Pro Asp Pro Ser Lys Phe Phe Ser Gln Leu Ser Ser Glu His
    50                  55                  60

Gly Gly Asp Val Gln Lys Trp Leu Ser Ser Pro Phe Pro Ser Ser Ser
65                  70                  75                  80

Phe Ser Pro Gly Gly Leu Ala Pro Glu Ile Ser Pro Leu Glu Val Leu
                85                  90                  95

Glu Arg Asp Lys Val Thr Gln Leu Leu Leu Gln Gln Asp Lys Val Pro
            100                 105                 110

Glu Pro Ala Ser Leu Ser Leu Asn Thr Asp Ala Tyr Leu Ser Leu Gln
        115                 120                 125

Glu Leu Gln
    130

<210> SEQ ID NO 44
<211> LENGTH: 108
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: FKBP CISC domain

<400> SEQUENCE: 44

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

-continued

```
Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Gly Glu
            100                 105


<210> SEQ ID NO 45
<211> LENGTH: 245
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Entire uDISC polypeptide FRB truncated IL2Rbeta

<400> SEQUENCE: 45

Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Pro Ala Ala Leu Gly Lys Asp Thr Ile Pro Trp Leu Gly His
        115                 120                 125

Leu Leu Val Gly Leu Ser Gly Ala Phe Gly Phe Ile Ile Leu Val Tyr
    130                 135                 140

Leu Leu Ile Asn Cys Arg Asn Thr Gly Pro Trp Leu Lys Lys Val Leu
145                 150                 155                 160

Lys Cys Asn Thr Pro Asp Pro Ser Lys Phe Phe Ser Gln Leu Ser Ser
                165                 170                 175

Glu His Gly Gly Asp Val Gln Lys Trp Leu Ser Ser Pro Phe Pro Ser
            180                 185                 190

Ser Ser Phe Ser Pro Gly Gly Leu Ala Pro Glu Ile Ser Pro Leu Glu
        195                 200                 205

Val Leu Glu Arg Asp Lys Val Thr Gln Leu Leu Leu Gln Gln Asp Lys
    210                 215                 220

Val Pro Glu Pro Ala Ser Leu Ser Leu Asn Thr Asp Ala Tyr Leu Ser
225                 230                 235                 240

Leu Gln Glu Leu Gln
                245


<210> SEQ ID NO 46
<211> LENGTH: 3623
```

<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: uDISC vector DNA

<400> SEQUENCE: 46
gaacagagaa acaggagaat atgggccaaa caggatatct gtggtaagca gttcctgccc 60
cggctcaggg ccaagaacag ttggaacagc agaatatggg ccaaacagga tatctgtggt 120
aagcagttcc tgccccggct cagggccaag aacagatggt ccccagatgc ggtcccgccc 180
tcagcagttt ctagagaacc atcagatgtt tccagggtgc cccaaggacc tgaaatgacc 240
ctgtgcctta tttgaactaa ccaatcagtt cgcttctcgc ttctgttcgc gcgcttctgc 300
tccccgagct ctatataagc agagctcgtt tagtgaaccg tcagatcgct agcaccggtg 360
ccgccaccat gcctctgggc ctgctgtggc tgggcctggc cctgctgggc gccctgcacg 420
cccaggccgg cgtgcaggtg gagacaatct ccccaggcga cggacgcaca ttccctaagc 480
ggggccagac ctgcgttgtg cactatacag gcatgctgga ggatggcaag aagtttgaca 540
gctcccggga tagaaacaag ccattcaagt ttatgctggg caagcaggaa gtgatcagag 600
gctgggagga gggcgtggcc cagatgtctg tgggccagag ggccaagctg accatcagcc 660
cagactacgc ctatggagca acaggccacc caggaatcat cccacctcac gccaccctgg 720
tgttcgatgt ggagctgctg aagctgggcg agggatccaa cacatcaaaa gagaacccct 780
ttctgttcgc attggaggcc gtagtcatat ctgttggatc catgggactt attatctccc 840
tgttgtgtgt gtacttctgg ctggaacgga ctatgcccag gatccccacg ctcaagaatc 900
tggaagatct cgtcacagaa taccatggta atttcagcgc ctggagcgga gtctctaagg 960
gtctggccga atccctccaa cccgattatt ctgaacggtt gtgcctcgta tccgaaatac 1020
caccaaaagg cggggctctg ggtgagggcc caggggcgag tccgtgcaat caacacagcc 1080
cgtattgggc ccctccttgt tatacgttga agcccgaaac tggaagcgga gctactaact 1140
tcagcctgct gaagcaggct ggagacgtgg aggagaaccc tggacctatg gcactgcccg 1200
tgaccgccct gctgctgcct ctggccctgc tgctgcacgc agcccggcct atcctgtggc 1260
acgagatgtg gcacgagggc ctggaggagg ccagcaggct gtattttggc gagcgcaacg 1320
tgaagggcat gttcgaggtg ctggagcctc tgcacgccat gatggagaga ggcccacaga 1380
ccctgaagga gacatccttt aaccaggcct atggacggga cctgatggag gcacaggagt 1440
ggtgcagaaa gtacatgaag tctggcaatg tgaaggacct gctgcaggcc tgggatctgt 1500
actatcacgt gtttcggaga atctccaagg gcaaagacac gattccgtgg cttgggcatc 1560
tgctcgttgg gctgagtggt gcgtttggtt tcatcatctt ggtctatctc ttgatcaatt 1620
gcagaaatac aggcccttgg ctgaaaaaag tgctcaagtg taataccccc gacccaagca 1680
agttcttctc ccagctttct tcagagcatg gaggcgatgt gcagaaatgg ctctcttcac 1740
cttttccctc ctcaagcttc tccccgggag ggctggcgcc cgagatttca cctcttgagg 1800
tacttgaacg agacaaggtt acccaacttc tccttcaaca ggataaggta cccgaacctg 1860
cgagccttag cttgaataca gacgcttatc tctcactgca ggaactgcaa ggatctggtg 1920
ctactaattt ttctcttttg aagcaagctg gagatgttga agagaacccc ggtccggaga 1980
tgtggcatga gggtctggaa gaagcgtctc gactgtactt tggtgagcgc aatgtgaagg 2040
gcatgtttga agtcctcgaa ccccttcatg ccatgatgga acgcggaccc cagaccttga 2100

```
aggagacaag ttttaaccaa gcttacggaa gagacctgat ggaagcccag gaatggtgca   2160

ggaaatacat gaaaagcggg aatgtgaagg acttgctcca agcgtgggac ctgtactatc   2220

atgtctttag gcgcattagt aagggcagcg gcgccaccaa cttcagcctg ctgaagcagg   2280

ccggcgacgt ggaggagaac cccggccccg tgagcaaggg cgaggaggat aacatggcca   2340

tcatcaagga gttcatgcgc ttcaaggtgc acatggaggg ctccgtgaac ggccacgagt   2400

tcgagatcga gggcgagggc gagggccgcc cctacgaggg cacccagacc gccaagctga   2460

aggtgaccaa gggtggcccc ctgcccttcg cctgggacat cctgtcccct cagttcatgt   2520

acggctccaa ggcctacgtg aagcaccccg ccgacatccc cgactacttg aagctgtcct   2580

tccccgaggg cttcaagtgg gagcgcgtga tgaacttcga ggacggcggc gtggtgaccg   2640

tgacccagga ctcctctctg caggacggcg agttcatcta caaggtgaag ctgcgcggca   2700

ccaacttccc ctccgacggc cccgtaatgc agaagaagac catgggctgg gaggcctcct   2760

ccgagcggat gtaccccgag gacggcgccc tgaagggcga gatcaagcag aggctgaagc   2820

tgaaggacgg cggccactac gacgctgagg tcaagaccac ctacaaggcc aagaagcccg   2880

tgcagctgcc cggcgcctac aacgtcaaca tcaagttgga catcacctcc cacaacgagg   2940

actacaccat cgtggaacag tacgaacgcg ccgagggccg ccactccacc ggcggcatgg   3000

acgagctgta caagtgaact agtgtcgaca atcaacctct ggattacaaa atttgtgaaa   3060

gattgactgg tattcttaac tatgttgctc cttttacgct atgtggatac gctgctttaa   3120

tgcctttgta tcatgctatt gcttcccgta tggctttcat tttctcctcc ttgtataaat   3180

cctggttgct gtctctttat gaggagttgt ggcccgttgt caggcaacgt ggcgtggtgt   3240

gcactgtgtt tgctgacgca acccccactg gttggggcat tgccaccacc tgtcagctcc   3300

tttccgggac tttcgctttc cccctcccta ttgccacggc ggaactcatc gccgcctgcc   3360

ttgcccgctg ctggacaggg gctcggctgt tgggcactga caattccgtg gtgttgtcgg   3420

ggaagctgac gtcctttcca tggctgctcg cctgtgttgc cacctggatt ctgcgcggga   3480

cgtccttctg ctacgtccct tcggccctca atccagcgga ccttccttcc cgcggcctgc   3540

tgccggctct gcggcctctt ccgcgtcttc gccttcgccc tcagacgagt cggatctccc   3600

tttgggccgc ctccccgcct gga                                            3623
```

<210> SEQ ID NO 47
<211> LENGTH: 251
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rgamma_CISC polypeptide

<400> SEQUENCE: 47

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
```

```
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Gly Ser Asn Thr Ser Lys Glu Asn Pro Phe Leu Phe Ala Leu Glu Ala
    130                 135                 140

Val Val Ile Ser Val Gly Ser Met Gly Leu Ile Ile Ser Leu Leu Cys
145                 150                 155                 160

Val Tyr Phe Trp Leu Glu Arg Thr Met Pro Arg Ile Pro Thr Leu Lys
                165                 170                 175

Asn Leu Glu Asp Leu Val Thr Glu Tyr His Gly Asn Phe Ser Ala Trp
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
    210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr
                245                 250


<210> SEQ ID NO 48
<211> LENGTH: 352
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rgamma_CISC polypeptide

<400> SEQUENCE: 48

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Gly Ser Gln Asn Leu Val Ile Pro Trp Ala Pro Glu Asn Leu Thr
    130                 135                 140

Leu His Lys Leu Ser Glu Ser Gln Leu Glu Leu Asn Trp Asn Asn Arg
145                 150                 155                 160

Phe Leu Asn His Cys Leu Glu His Leu Val Gln Tyr Arg Thr Asp Trp
```

```
                165                 170                 175

Asp His Ser Trp Thr Glu Gln Ser Val Asp Tyr Arg His Lys Phe Ser
            180                 185                 190

Leu Pro Ser Val Asp Gly Gln Lys Arg Tyr Thr Phe Arg Val Arg Ser
        195                 200                 205

Arg Phe Asn Pro Leu Cys Gly Ser Ala Gln His Trp Ser Glu Trp Ser
    210                 215                 220

His Pro Ile His Trp Gly Ser Asn Thr Ser Lys Glu Asn Pro Phe Leu
225                 230                 235                 240

Phe Ala Leu Glu Ala Val Val Ile Ser Val Gly Ser Met Gly Leu Ile
                245                 250                 255

Ile Ser Leu Leu Cys Val Tyr Phe Trp Leu Glu Arg Thr Met Pro Arg
            260                 265                 270

Ile Pro Thr Leu Lys Asn Leu Glu Asp Leu Val Thr Glu Tyr His Gly
        275                 280                 285

Asn Phe Ser Ala Trp Ser Gly Val Ser Lys Gly Leu Ala Glu Ser Leu
    290                 295                 300

Gln Pro Asp Tyr Ser Glu Arg Leu Cys Leu Val Ser Glu Ile Pro Pro
305                 310                 315                 320

Lys Gly Gly Ala Leu Gly Glu Gly Pro Gly Ala Ser Pro Cys Asn Gln
                325                 330                 335

His Ser Pro Tyr Trp Ala Pro Pro Cys Tyr Thr Leu Lys Pro Glu Thr
            340                 345                 350


<210> SEQ ID NO 49
<211> LENGTH: 349
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rgamma_CISC polypeptide

<400> SEQUENCE: 49

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gln Asn Leu Val Ile Pro Trp Ala Pro Glu Asn Leu Thr Leu His Lys
    130                 135                 140

Leu Ser Glu Ser Gln Leu Glu Leu Asn Trp Asn Asn Arg Phe Leu Asn
145                 150                 155                 160

His Cys Leu Glu His Leu Val Gln Tyr Arg Thr Asp Trp Asp His Ser
```

```
                165                 170                 175

Trp Thr Glu Gln Ser Val Asp Tyr Arg His Lys Phe Ser Leu Pro Ser
            180                 185                 190

Val Asp Gly Gln Lys Arg Tyr Thr Phe Arg Val Arg Ser Arg Phe Asn
        195                 200                 205

Pro Leu Cys Gly Ser Ala Gln His Trp Ser Glu Trp Ser His Pro Ile
    210                 215                 220

His Trp Gly Ser Asn Thr Ser Lys Glu Asn Pro Phe Leu Phe Ala Leu
225                 230                 235                 240

Glu Ala Val Val Ile Ser Val Gly Ser Met Gly Leu Ile Ile Ser Leu
                245                 250                 255

Leu Cys Val Tyr Phe Trp Leu Glu Arg Thr Met Pro Arg Ile Pro Thr
            260                 265                 270

Leu Lys Asn Leu Glu Asp Leu Val Thr Glu Tyr His Gly Asn Phe Ser
        275                 280                 285

Ala Trp Ser Gly Val Ser Lys Gly Leu Ala Glu Ser Leu Gln Pro Asp
    290                 295                 300

Tyr Ser Glu Arg Leu Cys Leu Val Ser Glu Ile Pro Pro Lys Gly Gly
305                 310                 315                 320

Ala Leu Gly Glu Gly Pro Gly Ala Ser Pro Cys Asn Gln His Ser Pro
                325                 330                 335

Tyr Trp Ala Pro Pro Cys Tyr Thr Leu Lys Pro Glu Thr
            340                 345
```

<210> SEQ ID NO 50
<211> LENGTH: 251
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rgamma_CISC polypeptide

<400> SEQUENCE: 50

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Ser Asn Thr Ser Lys Glu Asn Pro Phe Leu Phe Ala Leu Glu Ala
    130                 135                 140

Val Val Ile Ser Val Gly Ser Met Gly Leu Ile Ile Ser Leu Leu Cys
145                 150                 155                 160

Val Tyr Phe Trp Leu Glu Arg Thr Met Pro Arg Ile Pro Thr Leu Lys
```

```
                165                 170                 175

Asn Leu Glu Asp Leu Val Thr Glu Tyr His Gly Asn Phe Ser Ala Trp
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
    210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr
                245                 250


<210> SEQ ID NO 51
<211> LENGTH: 429
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta_CISC polypeptide

<400> SEQUENCE: 51

Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Gly Lys Asp Thr Ile Pro Trp Leu Gly His Leu Leu Val Gly
        115                 120                 125

Leu Ser Gly Ala Phe Gly Phe Ile Ile Leu Val Tyr Leu Leu Ile Asn
    130                 135                 140

Cys Arg Asn Thr Gly Pro Trp Leu Lys Lys Val Leu Lys Cys Asn Thr
145                 150                 155                 160

Pro Asp Pro Ser Lys Phe Phe Ser Gln Leu Ser Ser Glu His Gly Gly
                165                 170                 175

Asp Val Gln Lys Trp Leu Ser Ser Pro Phe Pro Ser Ser Ser Phe Ser
            180                 185                 190

Pro Gly Gly Leu Ala Pro Glu Ile Ser Pro Leu Glu Val Leu Glu Arg
        195                 200                 205

Asp Lys Val Thr Gln Leu Leu Leu Gln Gln Asp Lys Val Pro Glu Pro
    210                 215                 220

Ala Ser Leu Ser Ser Asn His Ser Leu Thr Ser Cys Phe Thr Asn Gln
225                 230                 235                 240

Gly Tyr Phe Phe Phe His Leu Pro Asp Ala Leu Glu Ile Glu Ala Cys
                245                 250                 255

Gln Val Tyr Phe Thr Tyr Asp Pro Tyr Ser Glu Glu Asp Pro Asp Glu
```

```
            260                 265                 270

Gly Val Ala Gly Ala Pro Thr Gly Ser Ser Pro Gln Pro Leu Gln Pro
        275                 280                 285

Leu Ser Gly Glu Asp Asp Ala Tyr Cys Thr Phe Pro Ser Arg Asp Asp
    290                 295                 300

Leu Leu Leu Phe Ser Pro Ser Leu Leu Gly Gly Pro Ser Pro Pro Ser
305                 310                 315                 320

Thr Ala Pro Gly Gly Ser Gly Ala Gly Glu Glu Arg Met Pro Pro Ser
                325                 330                 335

Leu Gln Glu Arg Val Pro Arg Asp Trp Asp Pro Gln Pro Leu Gly Pro
            340                 345                 350

Pro Thr Pro Gly Val Pro Asp Leu Val Asp Phe Gln Pro Pro Pro Glu
        355                 360                 365

Leu Val Leu Arg Glu Ala Gly Glu Glu Val Pro Asp Ala Gly Pro Arg
    370                 375                 380

Glu Gly Val Ser Phe Pro Trp Ser Arg Pro Pro Gly Gln Gly Glu Phe
385                 390                 395                 400

Arg Ala Leu Asn Ala Arg Leu Pro Leu Asn Thr Asp Ala Tyr Leu Ser
                405                 410                 415

Leu Gln Glu Leu Gln Gly Gln Asp Pro Thr His Leu Val
            420                 425


<210> SEQ ID NO 52
<211> LENGTH: 543
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta_CISC polypeptide

<400> SEQUENCE: 52

Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Gly Gly Ser Lys Pro Phe Glu Asn Leu Arg Leu Met Ala Pro
        115                 120                 125

Ile Ser Leu Gln Val Val His Val Glu Thr His Arg Cys Asn Ile Ser
    130                 135                 140

Trp Glu Ile Ser Gln Ala Ser His Tyr Phe Glu Arg His Leu Glu Phe
145                 150                 155                 160

Glu Ala Arg Thr Leu Ser Pro Gly His Thr Trp Glu Glu Ala Pro Leu
                165                 170                 175

Leu Thr Leu Lys Gln Lys Gln Glu Trp Ile Cys Leu Glu Thr Leu Thr
```

```
            180                 185                 190

Pro Asp Thr Gln Tyr Glu Phe Gln Val Arg Val Lys Pro Leu Gln Gly
        195                 200                 205

Glu Phe Thr Thr Trp Ser Pro Trp Ser Gln Pro Leu Ala Phe Arg Thr
    210                 215                 220

Lys Pro Ala Ala Leu Gly Lys Asp Thr Ile Pro Trp Leu Gly His Leu
225                 230                 235                 240

Leu Val Gly Leu Ser Gly Ala Phe Gly Phe Ile Ile Leu Val Tyr Leu
                245                 250                 255

Leu Ile Asn Cys Arg Asn Thr Gly Pro Trp Leu Lys Lys Val Leu Lys
            260                 265                 270

Cys Asn Thr Pro Asp Pro Ser Lys Phe Phe Gln Leu Ser Ser Glu His
        275                 280                 285

Gly Gly Asp Val Gln Lys Trp Leu Ser Ser Pro Phe Pro Ser Ser Ser
    290                 295                 300

Phe Ser Pro Gly Gly Leu Ala Pro Glu Ile Ser Pro Leu Glu Val Leu
305                 310                 315                 320

Glu Arg Asp Lys Val Thr Gln Leu Leu Leu Gln Gln Asp Lys Val Pro
                325                 330                 335

Glu Pro Ala Ser Leu Ser Ser Asn His Ser Leu Thr Ser Cys Phe Thr
            340                 345                 350

Asn Gln Gly Tyr Phe Phe Phe His Leu Pro Asp Ala Leu Glu Ile Glu
        355                 360                 365

Ala Cys Gln Val Tyr Phe Thr Tyr Asp Pro Tyr Ser Glu Glu Asp Pro
    370                 375                 380

Asp Glu Gly Val Ala Gly Ala Pro Thr Gly Ser Ser Pro Gln Pro Leu
385                 390                 395                 400

Gln Pro Leu Ser Gly Glu Asp Asp Ala Tyr Cys Thr Phe Pro Ser Arg
                405                 410                 415

Asp Asp Leu Leu Leu Phe Ser Pro Ser Leu Leu Gly Gly Pro Ser Pro
            420                 425                 430

Pro Ser Thr Ala Pro Gly Gly Ser Gly Ala Gly Glu Glu Arg Met Pro
        435                 440                 445

Pro Ser Leu Gln Glu Arg Val Pro Arg Asp Trp Asp Pro Gln Pro Leu
    450                 455                 460

Gly Pro Pro Thr Pro Gly Val Pro Asp Leu Val Asp Phe Gln Pro Pro
465                 470                 475                 480

Pro Glu Leu Val Leu Arg Glu Ala Gly Glu Glu Val Pro Asp Ala Gly
                485                 490                 495

Pro Arg Glu Gly Val Ser Phe Pro Trp Ser Arg Pro Pro Gly Gln Gly
            500                 505                 510

Glu Phe Arg Ala Leu Asn Ala Arg Leu Pro Leu Asn Thr Asp Ala Tyr
        515                 520                 525

Leu Ser Leu Gln Glu Leu Gln Gly Gln Asp Pro Thr His Leu Val
    530                 535                 540
```

<210> SEQ ID NO 53
<211> LENGTH: 541
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta_CISC polypeptide

<400> SEQUENCE: 53

```
Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Lys Pro Phe Glu Asn Leu Arg Leu Met Ala Pro Ile Ser Leu
        115                 120                 125

Gln Val Val His Val Glu Thr His Arg Cys Asn Ile Ser Trp Glu Ile
    130                 135                 140

Ser Gln Ala Ser His Tyr Phe Glu Arg His Leu Glu Phe Glu Ala Arg
145                 150                 155                 160

Thr Leu Ser Pro Gly His Thr Trp Glu Glu Ala Pro Leu Leu Thr Leu
                165                 170                 175

Lys Gln Lys Gln Glu Trp Ile Cys Leu Glu Thr Leu Thr Pro Asp Thr
            180                 185                 190

Gln Tyr Glu Phe Gln Val Arg Val Lys Pro Leu Gln Gly Glu Phe Thr
        195                 200                 205

Thr Trp Ser Pro Trp Ser Gln Pro Leu Ala Phe Arg Thr Lys Pro Ala
    210                 215                 220

Ala Leu Gly Lys Asp Thr Ile Pro Trp Leu Gly His Leu Leu Val Gly
225                 230                 235                 240

Leu Ser Gly Ala Phe Gly Phe Ile Ile Leu Val Tyr Leu Leu Ile Asn
                245                 250                 255

Cys Arg Asn Thr Gly Pro Trp Leu Lys Lys Val Leu Lys Cys Asn Thr
            260                 265                 270

Pro Asp Pro Ser Lys Phe Phe Ser Gln Leu Ser Ser Glu His Gly Gly
        275                 280                 285

Asp Val Gln Lys Trp Leu Ser Ser Pro Phe Pro Ser Ser Ser Phe Ser
    290                 295                 300

Pro Gly Gly Leu Ala Pro Glu Ile Ser Pro Leu Glu Val Leu Glu Arg
305                 310                 315                 320

Asp Lys Val Thr Gln Leu Leu Leu Gln Gln Asp Lys Val Pro Glu Pro
                325                 330                 335

Ala Ser Leu Ser Ser Asn His Ser Leu Thr Ser Cys Phe Thr Asn Gln
            340                 345                 350

Gly Tyr Phe Phe Phe His Leu Pro Asp Ala Leu Glu Ile Glu Ala Cys
        355                 360                 365

Gln Val Tyr Phe Thr Tyr Asp Pro Tyr Ser Glu Glu Asp Pro Asp Glu
    370                 375                 380

Gly Val Ala Gly Ala Pro Thr Gly Ser Ser Pro Gln Pro Leu Gln Pro
385                 390                 395                 400

Leu Ser Gly Glu Asp Asp Ala Tyr Cys Thr Phe Pro Ser Arg Asp Asp
                405                 410                 415
```

```
Leu Leu Leu Phe Ser Pro Ser Leu Leu Gly Gly Pro Ser Pro Pro Ser
            420                 425                 430

Thr Ala Pro Gly Gly Ser Gly Ala Gly Glu Glu Arg Met Pro Pro Ser
        435                 440                 445

Leu Gln Glu Arg Val Pro Arg Asp Trp Asp Pro Gln Pro Leu Gly Pro
    450                 455                 460

Pro Thr Pro Gly Val Pro Asp Leu Val Asp Phe Gln Pro Pro Pro Glu
465                 470                 475                 480

Leu Val Leu Arg Glu Ala Gly Glu Glu Val Pro Asp Ala Gly Pro Arg
                485                 490                 495

Glu Gly Val Ser Phe Pro Trp Ser Arg Pro Pro Gly Gln Gly Glu Phe
            500                 505                 510

Arg Ala Leu Asn Ala Arg Leu Pro Leu Asn Thr Asp Ala Tyr Leu Ser
        515                 520                 525

Leu Gln Glu Leu Gln Gly Gln Asp Pro Thr His Leu Val
    530                 535                 540


<210> SEQ ID NO 54
<211> LENGTH: 379
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL7Ralpha_CISC polypeptide

<400> SEQUENCE: 54

Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Trp Leu Gly His Leu Leu Val Gly Leu Ser
65                  70                  75                  80

Gly Ala Phe Gly Phe Ile Ile Leu Val Tyr Leu Leu Ile Asn Cys Arg
                85                  90                  95

Asn Thr Gly Pro Trp Leu Lys Lys Val Leu Lys Cys Asn Thr Pro Asp
            100                 105                 110

Pro Ser Lys Phe Phe Ser Gln Leu Ser Ser Glu His Gly Gly Asp Val
        115                 120                 125

Gln Lys Trp Leu Ser Ser Pro Phe Pro Ser Ser Ser Phe Ser Pro Gly
    130                 135                 140

Gly Leu Ala Pro Glu Ile Ser Pro Leu Glu Val Leu Glu Arg Asp Lys
145                 150                 155                 160

Val Thr Gln Leu Leu Leu Gln Gln Asp Lys Val Pro Glu Pro Ala Ser
                165                 170                 175

Leu Ser Ser Asn His Ser Leu Thr Ser Cys Phe Thr Asn Gln Gly Tyr
            180                 185                 190

Phe Phe Phe His Leu Pro Asp Ala Leu Glu Ile Glu Ala Cys Gln Val
        195                 200                 205

Tyr Phe Thr Tyr Asp Pro Tyr Ser Glu Glu Asp Pro Asp Glu Gly Val
    210                 215                 220
```

Ala Gly Ala Pro Thr Gly Ser Ser Pro Gln Pro Leu Gln Pro Leu Ser
225 230 235 240

Gly Glu Asp Asp Ala Tyr Cys Thr Phe Pro Ser Arg Asp Asp Leu Leu
245 250 255

Leu Phe Ser Pro Ser Leu Leu Gly Gly Pro Ser Pro Pro Ser Thr Ala
260 265 270

Pro Gly Gly Ser Gly Ala Gly Glu Glu Arg Met Pro Pro Ser Leu Gln
275 280 285

Glu Arg Val Pro Arg Asp Trp Asp Pro Gln Pro Leu Gly Pro Pro Thr
290 295 300

Pro Gly Val Pro Asp Leu Val Asp Phe Gln Pro Pro Pro Glu Leu Val
305 310 315 320

Leu Arg Glu Ala Gly Glu Glu Val Pro Asp Ala Gly Pro Arg Glu Gly
325 330 335

Val Ser Phe Pro Trp Ser Arg Pro Pro Gly Gln Gly Glu Phe Arg Ala
340 345 350

Leu Asn Ala Arg Leu Pro Leu Asn Thr Asp Ala Tyr Leu Ser Leu Gln
355 360 365

Glu Leu Gln Gly Gln Asp Pro Thr His Leu Val
370 375

<210> SEQ ID NO 55
<211> LENGTH: 345
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL7Ralpha_CISC polypeptide

<400> SEQUENCE: 55

Met Ala Leu Pro Val Thr Ala Leu Leu Leu Pro Leu Ala Leu Leu Leu
1 5 10 15

His Ala Ala Arg Pro Ile Leu Trp His Glu Met Trp His Glu Gly Leu
20 25 30

Glu Glu Ala Ser Arg Leu Tyr Phe Gly Glu Arg Asn Val Lys Gly Met
35 40 45

Phe Glu Val Leu Glu Pro Leu His Ala Met Met Glu Arg Gly Pro Gln
50 55 60

Thr Leu Lys Glu Thr Ser Phe Asn Gln Ala Tyr Gly Arg Asp Leu Met
65 70 75 80

Glu Ala Gln Glu Trp Cys Arg Lys Tyr Met Lys Ser Gly Asn Val Lys
85 90 95

Asp Leu Leu Gln Ala Trp Asp Leu Tyr Tyr His Val Phe Arg Arg Ile
100 105 110

Ser Lys Gly Glu Ile Asn Asn Ser Ser Gly Glu Met Asp Pro Ile Leu
115 120 125

Leu Thr Ile Ser Ile Leu Ser Phe Phe Ser Val Ala Leu Leu Val Ile
130 135 140

Leu Ala Cys Val Leu Trp Lys Lys Arg Ile Lys Pro Ile Val Trp Pro
145 150 155 160

Ser Leu Pro Asp His Lys Lys Thr Leu Glu His Leu Cys Lys Lys Pro
165 170 175

Arg Lys Asn Leu Asn Val Ser Phe Asn Pro Glu Ser Phe Leu Asp Cys
180 185 190

```
Gln Ile His Arg Val Asp Asp Ile Gln Ala Arg Asp Glu Val Glu Gly
        195                 200                 205

Phe Leu Gln Asp Thr Phe Pro Gln Gln Leu Glu Glu Ser Glu Lys Gln
    210                 215                 220

Arg Leu Gly Gly Asp Val Gln Ser Pro Asn Cys Pro Ser Glu Asp Val
225                 230                 235                 240

Val Ile Thr Pro Glu Ser Phe Gly Arg Asp Ser Ser Leu Thr Cys Leu
                245                 250                 255

Ala Gly Asn Val Ser Ala Cys Asp Ala Pro Ile Leu Ser Ser Ser Arg
            260                 265                 270

Ser Leu Asp Cys Arg Glu Ser Gly Lys Asn Gly Pro His Val Tyr Gln
        275                 280                 285

Asp Leu Leu Leu Ser Leu Gly Thr Thr Asn Ser Thr Leu Pro Pro Pro
    290                 295                 300

Phe Ser Leu Gln Ser Gly Ile Leu Thr Leu Asn Pro Val Ala Gln Gly
305                 310                 315                 320

Gln Pro Ile Leu Thr Ser Leu Gly Ser Asn Gln Glu Glu Ala Tyr Val
                325                 330                 335

Thr Met Ser Ser Phe Tyr Gln Asn Gln
            340                 345


<210> SEQ ID NO 56
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: linker polypeptide

<400> SEQUENCE: 56

Gly Gly Gly Ser
1


<210> SEQ ID NO 57
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: linker polypeptide

<400> SEQUENCE: 57

Gly Gly Gly Ser Gly Gly Gly
1               5


<210> SEQ ID NO 58
<211> LENGTH: 3
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: linker polypeptide

<400> SEQUENCE: 58

Gly Gly Gly
1
```

<210> SEQ ID NO 59
<211> LENGTH: 3
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: linker polypeptide

<400> SEQUENCE: 59

Gly Gly Ser
1

<210> SEQ ID NO 60
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: linker polypeptide

<400> SEQUENCE: 60

Gly Gly Ser Pro
1

<210> SEQ ID NO 61
<211> LENGTH: 251
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rgamma_CISC polypeptide

<400> SEQUENCE: 61

Met Pro Leu Gly Leu Leu Trp Leu Gly Leu Ala Leu Leu Gly Ala Leu
1 5 10 15

His Ala Gln Ala Gly Val Gln Val Glu Thr Ile Ser Pro Gly Asp Gly
20 25 30

Arg Thr Phe Pro Lys Arg Gly Gln Thr Cys Val Val His Tyr Thr Gly
35 40 45

Met Leu Glu Asp Gly Lys Lys Val Asp Ser Ser Arg Asp Arg Asn Lys
50 55 60

Pro Phe Lys Phe Met Leu Gly Lys Gln Glu Val Ile Arg Gly Trp Glu
65 70 75 80

Glu Gly Val Ala Gln Met Ser Val Gly Gln Arg Ala Lys Leu Thr Ile
85 90 95

Ser Pro Asp Tyr Ala Tyr Gly Ala Thr Gly His Pro Gly Ile Ile Pro
100 105 110

Pro His Ala Thr Leu Val Phe Asp Val Glu Leu Leu Lys Leu Glu Gly
115 120 125

Gly Ser Asn Thr Ser Lys Glu Asn Pro Phe Leu Phe Ala Leu Glu Ala
130 135 140

Val Val Ile Ser Val Gly Ser Met Gly Leu Ile Ile Ser Leu Leu Cys
145 150 155 160

Val Tyr Phe Trp Leu Glu Arg Thr Met Pro Arg Ile Pro Thr Leu Lys
165 170 175

Asn Leu Glu Asp Leu Val Thr Glu Tyr His Gly Asn Phe Ser Ala Trp

```
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
    210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr
                245                 250


<210> SEQ ID NO 62
<211> LENGTH: 443
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta_CISC polypeptide

<400> SEQUENCE: 62

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Lys Asp Thr Ile Pro Trp Leu Gly His Leu Leu Val Gly Leu Ser
    130                 135                 140

Gly Ala Phe Gly Phe Ile Ile Leu Val Tyr Leu Leu Ile Asn Cys Arg
145                 150                 155                 160

Asn Thr Gly Pro Trp Leu Lys Lys Val Leu Lys Cys Asn Thr Pro Asp
                165                 170                 175

Pro Ser Lys Phe Phe Ser Gln Leu Ser Ser Glu His Gly Gly Asp Val
            180                 185                 190

Gln Lys Trp Leu Ser Ser Pro Phe Pro Ser Ser Ser Phe Ser Pro Gly
        195                 200                 205

Gly Leu Ala Pro Glu Ile Ser Pro Leu Glu Val Leu Glu Arg Asp Lys
    210                 215                 220

Val Thr Gln Leu Leu Leu Gln Gln Asp Lys Val Pro Glu Pro Ala Ser
225                 230                 235                 240

Leu Ser Ser Asn His Ser Leu Thr Ser Cys Phe Thr Asn Gln Gly Tyr
                245                 250                 255

Phe Phe Phe His Leu Pro Asp Ala Leu Glu Ile Glu Ala Cys Gln Val
            260                 265                 270

Tyr Phe Thr Tyr Asp Pro Tyr Ser Glu Glu Asp Pro Asp Glu Gly Val
```

```
        275                 280                 285

Ala Gly Ala Pro Thr Gly Ser Ser Pro Gln Pro Leu Gln Pro Leu Ser
    290                 295                 300

Gly Glu Asp Asp Ala Tyr Cys Thr Phe Pro Ser Arg Asp Asp Leu Leu
305                 310                 315                 320

Leu Phe Ser Pro Ser Leu Leu Gly Gly Pro Ser Pro Pro Ser Thr Ala
                325                 330                 335

Pro Gly Gly Ser Gly Ala Gly Glu Glu Arg Met Pro Pro Ser Leu Gln
            340                 345                 350

Glu Arg Val Pro Arg Asp Trp Asp Pro Gln Pro Leu Gly Pro Pro Thr
        355                 360                 365

Pro Gly Val Pro Asp Leu Val Asp Phe Gln Pro Pro Pro Glu Leu Val
    370                 375                 380

Leu Arg Glu Ala Gly Glu Glu Val Pro Asp Ala Gly Pro Arg Glu Gly
385                 390                 395                 400

Val Ser Phe Pro Trp Ser Arg Pro Pro Gly Gln Gly Glu Phe Arg Ala
                405                 410                 415

Leu Asn Ala Arg Leu Pro Leu Asn Thr Asp Ala Tyr Leu Ser Leu Gln
            420                 425                 430

Glu Leu Gln Gly Gln Asp Pro Thr His Leu Val
        435                 440
```

<210> SEQ ID NO 63
<211> LENGTH: 358
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Ralpha_CISC polypeptide

<400> SEQUENCE: 63

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Glu Ile Asn Asn Ser Ser Gly Glu Met Asp Pro Ile Leu Leu Thr Ile
    130                 135                 140

Ser Ile Leu Ser Phe Phe Ser Val Ala Leu Leu Val Ile Leu Ala Cys
145                 150                 155                 160

Val Leu Trp Lys Lys Arg Ile Lys Pro Ile Val Trp Pro Ser Leu Pro
                165                 170                 175

Asp His Lys Lys Thr Leu Glu His Leu Cys Lys Lys Pro Arg Lys Asn
```

```
            180                 185                 190

Leu Asn Val Ser Phe Asn Pro Glu Ser Phe Leu Asp Cys Gln Ile His
        195                 200                 205

Arg Val Asp Asp Ile Gln Ala Arg Asp Glu Val Glu Gly Phe Leu Gln
    210                 215                 220

Asp Thr Phe Pro Gln Gln Leu Glu Glu Ser Glu Lys Gln Arg Leu Gly
225                 230                 235                 240

Gly Asp Val Gln Ser Pro Asn Cys Pro Ser Glu Asp Val Val Ile Thr
                245                 250                 255

Pro Glu Ser Phe Gly Arg Asp Ser Ser Leu Thr Cys Leu Ala Gly Asn
            260                 265                 270

Val Ser Ala Cys Asp Ala Pro Ile Leu Ser Ser Ser Arg Ser Leu Asp
        275                 280                 285

Cys Arg Glu Ser Gly Lys Asn Gly Pro His Val Tyr Gln Asp Leu Leu
    290                 295                 300

Leu Ser Leu Gly Thr Thr Asn Ser Thr Leu Pro Pro Pro Phe Ser Leu
305                 310                 315                 320

Gln Ser Gly Ile Leu Thr Leu Asn Pro Val Ala Gln Gly Gln Pro Ile
                325                 330                 335

Leu Thr Ser Leu Gly Ser Asn Gln Glu Glu Ala Tyr Val Thr Met Ser
            340                 345                 350

Ser Phe Tyr Gln Asn Gln
        355
```

<210> SEQ ID NO 64
<211> LENGTH: 358
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL7Ralpha_CISC polypeptide

<400> SEQUENCE: 64

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Glu Ile Asn Asn Ser Ser Gly Glu Met Asp Pro Ile Leu Leu Thr Ile
    130                 135                 140

Ser Ile Leu Ser Phe Phe Ser Val Ala Leu Leu Val Ile Leu Ala Cys
145                 150                 155                 160

Val Leu Trp Lys Lys Arg Ile Lys Pro Ile Val Trp Pro Ser Leu Pro
```

```
                165                 170                 175

Asp His Lys Lys Thr Leu Glu His Leu Cys Lys Lys Pro Arg Lys Asn
            180                 185                 190

Leu Asn Val Ser Phe Asn Pro Glu Ser Phe Leu Asp Cys Gln Ile His
        195                 200                 205

Arg Val Asp Asp Ile Gln Ala Arg Asp Glu Val Glu Gly Phe Leu Gln
    210                 215                 220

Asp Thr Phe Pro Gln Gln Leu Glu Glu Ser Glu Lys Gln Arg Leu Gly
225                 230                 235                 240

Gly Asp Val Gln Ser Pro Asn Cys Pro Ser Glu Asp Val Val Ile Thr
                245                 250                 255

Pro Glu Ser Phe Gly Arg Asp Ser Ser Leu Thr Cys Leu Ala Gly Asn
            260                 265                 270

Val Ser Ala Cys Asp Ala Pro Ile Leu Ser Ser Ser Arg Ser Leu Asp
        275                 280                 285

Cys Arg Glu Ser Gly Lys Asn Gly Pro His Val Tyr Gln Asp Leu Leu
    290                 295                 300

Leu Ser Leu Gly Thr Thr Asn Ser Thr Leu Pro Pro Pro Phe Ser Leu
305                 310                 315                 320

Gln Ser Gly Ile Leu Thr Leu Asn Pro Val Ala Gln Gly Gln Pro Ile
                325                 330                 335

Leu Thr Ser Leu Gly Ser Asn Gln Glu Glu Ala Tyr Val Thr Met Ser
            340                 345                 350

Ser Phe Tyr Gln Asn Gln
        355
```

<210> SEQ ID NO 65
<211> LENGTH: 276
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: MPL_CISC polypeptide

<400> SEQUENCE: 65

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Glu Thr Ala Trp Ile Ser Leu Val Thr Ala Leu His Leu Val Leu Gly
    130                 135                 140

Leu Ser Ala Val Leu Gly Leu Leu Leu Leu Arg Trp Gln Phe Pro Ala
```

-continued

```
145                 150                 155                 160

His Tyr Arg Arg Leu Arg His Ala Leu Trp Pro Ser Leu Pro Asp Leu
                165                 170                 175

His Arg Val Leu Gly Gln Tyr Leu Arg Asp Thr Ala Ala Leu Ser Pro
            180                 185                 190

Pro Lys Ala Thr Val Ser Asp Thr Cys Glu Glu Val Glu Pro Ser Leu
        195                 200                 205

Leu Glu Ile Leu Pro Lys Ser Ser Glu Arg Thr Pro Leu Pro Leu Cys
    210                 215                 220

Ser Ser Gln Ala Gln Met Asp Tyr Arg Arg Leu Gln Pro Ser Cys Leu
225                 230                 235                 240

Gly Thr Met Pro Leu Ser Val Cys Pro Pro Met Ala Glu Ser Gly Ser
                245                 250                 255

Cys Cys Thr Thr His Ile Ala Asn His Ser Tyr Leu Pro Leu Ser Tyr
            260                 265                 270

Trp Gln Gln Pro
        275


<210> SEQ ID NO 66
<211> LENGTH: 9405
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: CISC vector DNA

<400> SEQUENCE: 66

agcttaatgt agtcttatgc aatactcttg tagtcttgca acatggtaac gatgagttag     60

caacatgcct tacaaggaga gaaaaagcac cgtgcatgcc gattggtgga agtaaggtgg    120

tacgatcgtg ccttattagg aaggcaacag acgggtctga catggattgg acgaaccact    180

gaattgccgc attgcagaga tattgtattt aagtgcctag ctcgatacaa taaacgggtc    240

tctctggtta gaccagatct gagcctggga gctctctggc taactaggga acccactgct    300

taagcctcaa taaagcttgc cttgagtgct tcaagtagtg tgtgcccgtc tgttgtgtga    360

ctctggtaac tagagatccc tcagaccctt ttagtcagtg tggaaaatct ctagcagtgg    420

cgcccgaaca gggacttgaa agcgaaaggg aaaccagagg agctctctcg acgcaggact    480

cggcttgctg aagcgcgcac ggcaagaggc gaggggcggc gactggtgag tacgccaaaa    540

attttgacta gcggaggcta gaaggagaga gatgggtgcg agagcgtcag tattaagcgg    600

gggagaatta gatcgcgatg ggaaaaaatt cggttaaggc cagggggaaa gaaaaaatat    660

aaattaaaac atatagtatg ggcaagcagg gagctagaac gattcgcagt taatcctggc    720

ctgttagaaa catcagaagg ctgtagacaa atactgggac agctacaacc atcccttcag    780

acaggatcag aagaacttag atcattatat aatacagtag caaccctcta ttgtgtgcat    840

caaaggatag agataaaaga caccaaggaa gctttagaca agatagagga agagcaaaac    900

aaaagtaaga ccaccgcaca gcaagcggcc gctgatcttc agacctggag gaggagatat    960

gagggacaat tggagaagtg aattatataa atataaagta gtaaaaattg aaccattagg   1020

agtagcaccc accaaggcaa agagaagagt ggtgcagaga gaaaaaagag cagtgggaat   1080

aggagctttg ttccttgggt tcttgggagc agcaggaagc actatgggcg cagcctcaat   1140

gacgctgacg gtacaggcca gacaattatt gtctggtata gtgcagcagc agaacaattt   1200
```

-continued

```
gctgagggct attgaggcgc aacagcatct gttgcaactc acagtctggg gcatcaagca   1260
gctccaggca agaatcctgg ctgtggaaag atacctaaag gatcaacagc tcctggggat   1320
ttggggttgc tctggaaaac tcatttgcac cactgctgtg ccttggaatg ctagttggag   1380
taataaatct ctggaacaga tttggaatca cacgacctgg atggagtggg acagagaaat   1440
taacaattac acaagcttaa tacactcctt aattgaagaa tcgcaaaacc agcaagaaaa   1500
gaatgaacaa gaattattgg aattagataa atgggcaagt ttgtggaatt ggtttaacat   1560
aacaaattgg ctgtggtata taaaattatt cataatgata gtaggaggct tggtaggttt   1620
aagaatagtt tttgctgtac tttctatagt gaatagagtt aggcagggat attcaccatt   1680
atcgtttcag acccacctcc caaccccgag gggacccgac aggcccgaag gaatagaaga   1740
agaaggtgga gagagagaca gagacagatc cattcgatta gtgaacggat ctcgacggta   1800
tcggttaact tttaaaagaa aaggggggat tggggggtac agtgcagggg aaagaatagt   1860
agacataata gcaacagaca tacaaactaa agaattacaa aaacaaatta caaaaattca   1920
aaattttatc gatcacgaga ctagcctcga gaagcttgat atcgaattcc cacggggttg   1980
gacgcgtagg aacagagaaa caggagaata tgggccaaac aggatatctg tggtaagcag   2040
ttcctgcccc ggctcagggc caagaacagt tggaacagca gaatatgggc caaacaggat   2100
atctgtggta agcagttcct gccccggctc agggccaaga acagatggtc cccagatgcg   2160
gtcccgccct cagcagtttc tagagaacca tcagatgttt ccagggtgcc ccaaggacct   2220
gaaatgaccc tgtgccttat ttgaactaac caatcagttc gcttctcgct tctgttcgcg   2280
cgcttctgct ccccgagctc tatataagca gagctcgttt agtgaaccgt cagatcgcta   2340
gcaccggtgc cgccaccatg cctctgggcc tgctgtggct gggcctggcc ctgctgggcg   2400
ccctgcacgc ccaggccggc gtgcaggtgg agacaatctc cccaggcgac ggacgcacat   2460
tccctaagcg gggccagacc tgcgtggtgc actatacagg catgctggag gatggcaaga   2520
agtttgacag ctcccgggat agaaacaagc cattcaagtt tatgctgggc aagcaggaag   2580
tgatcagagg ctgggaggag ggcgtggccc agatgtctgt gggccagagg gccaagctga   2640
ccatcagccc agactacgcc tatggagcaa caggccaccc aggaatcatc ccacctcacg   2700
ccaccctggt gttcgatgtg gagctgctga agctgggcga gggatccaac acatcaaaag   2760
agaacccctt tctgttcgca ttggaggccg tagtcatatc tgttggatcc atgggactta   2820
ttatctccct gttgtgtgtg tacttctggc tggaacggac tatgcccagg atccccacgc   2880
tcaagaatct ggaagatctc gtcacagaat accatggtaa tttcagcgcc tggagcggag   2940
tctctaaggg tctggccgaa tccctccaac ccgattattc tgaacggttg tgcctcgtat   3000
ccgaaatacc accaaaaggc ggggctctgg gtgagggccc aggggcgagt ccgtgcaatc   3060
aacacagccc gtattgggcc cctccttgtt atacgttgaa gcccgaaact ggaagcggag   3120
ctactaactt cagcctgctg aagcaggctg gagacgtgga ggagaaccct ggacctatgg   3180
cactgcccgt gaccgccctg ctgctgcctc tggccctgct gctgcacgca gcccggccta   3240
tcctgtggca cgagatgtgg cacgagggcc tggaggaggc cagcaggctg tattttggcg   3300
agcgcaacgt gaagggcatg ttcgaggtgc tggagcctct gcacgccatg atggagagag   3360
gcccacagac cctgaaggag acatccttta accaggccta tggacgggac ctgatggagg   3420
cacaggagtg gtgcagaaag tacatgaagt ctggcaatgt gaaggacctg ctgcaggcct   3480
gggatctgta ctatcacgtg tttcggagaa tctccaaggg caaagacacg attccgtggc   3540
ttgggcatct gctcgttggg ctgagtggtg cgtttggttt catcatcttg gtctatctct   3600
```

```
tgatcaattg cagaaataca ggcccttggc tgaaaaaagt gctcaagtgt aatacccccg   3660
acccaagcaa gttcttctcc cagctttctt cagagcatgg aggcgatgtg cagaaatggc   3720
tctcttcacc ttttccctcc tcaagcttct ccccgggagg gctggcgccc gagatttcac   3780
ctcttgaggt acttgaacga gacaaggtta cccaacttct ccttcaacag gataaggtac   3840
ccgaacctgc gagccttagc tccaaccact ctcttacgag ctgcttcacc aatcagggat   3900
acttcttttt ccaccttccc gatgcgctgg aaatcgaagc ttgtcaagtt tactttacct   3960
atgatccata tagcgaggaa gatcccgacg aaggagtcgc cggtgcgccc acgggttcct   4020
caccccaacc tctccagcct ctctcaggag aagatgatgc ttattgcact tttcccagta   4080
gagacgatct cctcctcttt tctccatctc ttttgggggg accttccccc ccttctacgg   4140
cacctggcgg gtctggtgct ggcgaggagc ggatgccgcc gtccctccag gagcgagtac   4200
cacgagattg ggatccccag ccacttggac cccccacccc cggcgtacct gaccttgtcg   4260
attttcaacc tccccctgaa ttggtgctgc gagaggctgg ggaggaagtt ccggacgctg   4320
ggccgaggga gggcgtgtcc tttccatgga gtaggcctcc aggtcaaggc gagtttaggg   4380
ctctcaacgc gcggctgccg ttgaatacag acgcttatct ctcactgcag gaactgcaag   4440
gtcaggaccc aacacatctt gtaggatctg gtgctactaa tttttctctt ttgaagcaag   4500
ctggagatgt tgaagagaac cctggtccag tgagcaaggg cgaggagctg ttcaccgggg   4560
tggtgcccat cctggtcgag ctggacggcg acgtaaacgg ccacaagttc agcgtgtccg   4620
gcgagggcga gggcgatgcc acctacggca agctgaccct gaagttcatc tgcaccaccg   4680
gcaagctgcc cgtgccctgg cccaccctcg tgaccaccct gacctacggc gtgcagtgct   4740
tcagccgcta ccccgaccac atgaagcagc acgacttctt caagtccgcc atgcccgaag   4800
gctacgtcca ggagcgcacc atcttcttca aggacgacgg caactacaag acccgcgccg   4860
aggtgaagtt cgagggcgac accctggtga accgcatcga gctgaagggc atcgacttca   4920
aggaggacgg caacatcctg gggcacaagc tggagtacaa ctacaacagc cacaacgtct   4980
atatcatggc cgacaagcag aagaacggca tcaaggtgaa cttcaagatc cgccacaaca   5040
tcgaggacgg cagcgtgcag ctcgccgacc actaccagca gaacaccccc atcggcgacg   5100
gccccgtgct gctgcccgac aaccactacc tgagcaccca gtccgccctg agcaaagacc   5160
ccaacgagaa gcgcgatcac atggtcctgc tggagttcgt gaccgccgcc gggatcactc   5220
tcggcatgga cgagctgtac aagtaaacta gtgtcgacaa tcaacctctg gattacaaaa   5280
tttgtgaaag attgactggt attcttaact atgttgctcc ttttacgcta tgtggatacg   5340
ctgctttaat gcctttgtat catgctattg cttcccgtat ggctttcatt ttctcctcct   5400
tgtataaatc ctggttgctg tctctttatg aggagttgtg gcccgttgtc aggcaacgtg   5460
gcgtggtgtg cactgtgttt gctgacgcaa cccccactgg ttggggcatt gccaccacct   5520
gtcagctcct ttccgggact ttcgctttcc ccctccctat tgccacggcg gaactcatcg   5580
ccgcctgcct tgcccgctgc tggacagggg ctcggctgtt gggcactgac aattccgtgg   5640
tgttgtcggg gaagctgacg tcctttccat ggctgctcgc ctgtgttgcc acctggattc   5700
tgcgcgggac gtccttctgc tacgtccctt cggccctcaa tccagcggac cttccttccc   5760
gcggcctgct gccggctctg cggcctcttc cgcgtcttcg ccttcgccct cagacgagtc   5820
ggatctccct ttgggccgcc tccccgcctg gaattcgagc tcggtacctt taagaccaat   5880
gacttacaag gcagctgtag atcttagcca ctttttaaaa gaaaaggggg gactggaagg   5940
```

-continued

```
gctaattcac tcccaacgaa gacaagatct gctttttgct tgtactgggt ctctctggtt   6000
agaccagatc tgagcctggg agctctctgg ctaactaggg aacccactgc ttaagcctca   6060
ataaagcttg ccttgagtgc ttcaagtagt gtgtgcccgt ctgttgtgtg actctggtaa   6120
ctagagatcc ctcagaccct tttagtcagt gtggaaaatc tctagcagta gtagttcatg   6180
tcatcttatt attcagtatt tataacttgc aaagaaatga atatcagaga gtgagaggaa   6240
cttgtttatt gcagcttata atggttacaa ataaagcaat agcatcacaa atttcacaaa   6300
taaagcattt ttttcactgc attctagttg tggtttgtcc aaactcatca atgtatctta   6360
tcatgtctgg ctctagctat cccgccccta actccgccca gttccgccca ttctccgccc   6420
catggctgac taattttttt tatttatgca gaggccgagg ccgcctcggc ctctgagcta   6480
ttccagaagt agtgaggagg cttttttgga ggcctaggct tttgcgtcga gacgtaccca   6540
attcgcccta tagtgagtcg tattacgcgc gctcactggc cgtcgtttta caacgtcgtg   6600
actgggaaaa ccctggcgtt acccaactta atcgccttgc agcacatccc cctttcgcca   6660
gctggcgtaa tagcgaagag gcccgcaccg atcgcccttc ccaacagttg cgcagcctga   6720
atggcgaatg gcgcgacgcg ccctgtagcg gcgcattaag cgcggcgggt gtggtggtta   6780
cgcgcagcgt gaccgctaca cttgccagcg ccctagcgcc cgctcctttc gctttcttcc   6840
cttcctttct cgccacgttc gccggctttc cccgtcaagc tctaaatcgg gggctccctt   6900
tagggttccg atttagtgct ttacggcacc tcgaccccaa aaaacttgat tagggtgatg   6960
gttcacgtag tgggccatcg ccctgataga cggtttttcg ccctttgacg ttggagtcca   7020
cgttctttaa tagtggactc ttgttccaaa ctggaacaac actcaaccct atctcggtct   7080
attcttttga tttataaggg attttgccga tttcggccta ttggttaaaa aatgagctga   7140
tttaacaaaa atttaacgcg aattttaaca aaatattaac gtttacaatt tcccaggtgg   7200
cacttttcgg ggaaatgtgc gcggaacccc tatttgttta tttttctaaa tacattcaaa   7260
tatgtatccg ctcatgagac aataaccctg ataaatgctt caataatatt gaaaaaggaa   7320
gagtatgagt attcaacatt tccgtgtcgc ccttattccc ttttttgcgg cattttgcct   7380
tcctgttttt gctcacccag aaacgctggt gaaagtaaaa gatgctgaag atcagttggg   7440
tgcacgagtg ggttacatcg aactggatct caacagcggt aagatccttg agagttttcg   7500
ccccgaagaa cgttttccaa tgatgagcac ttttaaagtt ctgctatgtg gcgcggtatt   7560
atcccgtatt gacgccgggc aagagcaact cggtcgccgc atacactatt ctcagaatga   7620
cttggttgag tactcaccag tcacagaaaa gcatcttacg gatggcatga cagtaagaga   7680
attatgcagt gctgccataa ccatgagtga taacactgcg gccaacttac ttctgacaac   7740
gatcggagga ccgaaggagc taaccgcttt tttgcacaac atgggggatc atgtaactcg   7800
ccttgatcgt tgggaaccgg agctgaatga agccatacca aacgacgagc gtgacaccac   7860
gatgcctgta gcaatggcaa caacgttgcg caaactatta actggcgaac tacttactct   7920
agcttcccgg caacaattaa tagactggat ggaggcggat aaagttgcag gaccacttct   7980
gcgctcggcc cttccggctg gctggtttat tgctgataaa tctggagccg gtgagcgtgg   8040
gtctcgcggt atcattgcag cactggggcc agatggtaag ccctcccgta tcgtagttat   8100
ctacacgacg gggagtcagg caactatgga tgaacgaaat agacagatcg ctgagatagg   8160
tgcctcactg attaagcatt ggtaactgtc agaccaagtt tactcatata tactttagat   8220
tgatttaaaa cttcattttt aatttaaaag gatctaggtg aagatccttt ttgataatct   8280
catgaccaaa atcccttaac gtgagttttc gttccactga gcgtcagacc ccgtagaaaa   8340
```

gatcaaagga tcttcttgag atcctttttt tctgcgcgta atctgctgct tgcaaacaaa 8400
aaaaccaccg ctaccagcgg tggtttgttt gccggatcaa gagctaccaa ctctttttcc 8460
gaaggtaact ggcttcagca gagcgcagat accaaatact gtccttctag tgtagccgta 8520
gttaggccac cacttcaaga actctgtagc accgcctaca tacctcgctc tgctaatcct 8580
gttaccagtg gctgctgcca gtggcgataa gtcgtgtctt accgggttgg actcaagacg 8640
atagttaccg gataaggcgc agcggtcggg ctgaacgggg ggttcgtgca cacagcccag 8700
cttggagcga acgacctaca ccgaactgag atacctacag cgtgagctat gagaaagcgc 8760
cacgcttccc gaagggagaa aggcggacag gtatccggta agcggcaggg tcggaacagg 8820
agagcgcacg agggagcttc cagggggaaa cgcctggtat ctttatagtc ctgtcgggtt 8880
tcgccacctc tgacttgagc gtcgattttt gtgatgctcg tcaggggggc ggagcctatg 8940
gaaaaacgcc agcaacgcgg cctttttacg gttcctggcc ttttgctggc cttttgctca 9000
catgttcttt cctgcgttat cccctgattc tgtggataac cgtattaccg cctttgagtg 9060
agctgatacc gctcgccgca gccgaacgac cgagcgcagc gagtcagtga gcgaggaagc 9120
ggaagagcgc ccaatacgca aaccgcctct ccccgcgcgt tggccgattc attaatgcag 9180
ctggcacgac aggtttcccg actggaaagc gggcagtgag cgcaacgcaa ttaatgtgag 9240
ttagctcact cattaggcac cccaggcttt acactttatg cttccggctc gtatgttgtg 9300
tggaattgtg agcggataac aatttcacac aggaaacagc tatgaccatg attacgccaa 9360
gcgcgcaatt aaccctcact aaagggaaca aaagctggag ctgca 9405

<210> SEQ ID NO 67
<211> LENGTH: 10053
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: CISC vector DNA

<400> SEQUENCE: 67
agcttaatgt agtcttatgc aatactcttg tagtcttgca acatggtaac gatgagttag 60
caacatgcct tacaaggaga gaaaaagcac cgtgcatgcc gattggtgga agtaaggtgg 120
tacgatcgtg ccttattagg aaggcaacag acgggtctga catggattgg acgaaccact 180
gaattgccgc attgcagaga tattgtattt aagtgcctag ctcgatacaa taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc cagggggaaa gaaaaaatat 660
aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900

```
aaaagtaaga ccaccgcaca gcaagcggcc gctgatcttc agacctggag gaggagatat    960
gagggacaat tggagaagtg aattatataa atataaagta gtaaaaattg aaccattagg   1020
agtagcaccc accaaggcaa agagaagagt ggtgcagaga gaaaaaagag cagtgggaat   1080
aggagctttg ttccttgggt tcttgggagc agcaggaagc actatgggcg cagcctcaat   1140
gacgctgacg gtacaggcca gacaattatt gtctggtata gtgcagcagc agaacaattt   1200
gctgagggct attgaggcgc aacagcatct gttgcaactc acagtctggg gcatcaagca   1260
gctccaggca agaatcctgg ctgtggaaag atacctaaag gatcaacagc tcctggggat   1320
ttggggttgc tctggaaaac tcatttgcac cactgctgtg ccttggaatg ctagttggag   1380
taataaatct ctggaacaga tttggaatca cacgacctgg atggagtggg acagagaaat   1440
taacaattac acaagcttaa tacactcctt aattgaagaa tcgcaaaacc agcaagaaaa   1500
gaatgaacaa gaattattgg aattagataa atgggcaagt ttgtggaatt ggtttaacat   1560
aacaaattgg ctgtggtata taaaattatt cataatgata gtaggaggct tggtaggttt   1620
aagaatagtt tttgctgtac tttctatagt gaatagagtt aggcagggat attcaccatt   1680
atcgtttcag acccacctcc caaccccgag gggacccgac aggcccgaag gaatagaaga   1740
agaaggtgga gagagagaca gagacagatc cattcgatta gtgaacggat ctcgacggta   1800
tcggttaact tttaaaagaa aaggggggat tggggggtac agtgcagggg aaagaatagt   1860
agacataata gcaacagaca tacaaactaa agaattacaa aaacaaatta caaaaattca   1920
aaattttatc gatcacgaga ctagcctcga gaagcttgat atcgaattcc cacggggttg   1980
gacgcgtagg aacagagaaa caggagaata tgggccaaac aggatatctg tggtaagcag   2040
ttcctgcccc ggctcagggc caagaacagt tggaacagca gaatatgggc caaacaggat   2100
atctgtggta agcagttcct gccccggctc agggccaaga acagatggtc cccagatgcg   2160
gtcccgccct cagcagtttc tagagaacca tcagatgttt ccagggtgcc ccaaggacct   2220
gaaatgaccc tgtgccttat ttgaactaac caatcagttc gcttctcgct tctgttcgcg   2280
cgcttctgct ccccgagctc tatataagca gagctcgttt agtgaaccgt cagatcgcta   2340
gcaccggtgc cgccaccatg cctctgggcc tgctgtggct gggcctggcc ctgctgggcg   2400
ccctgcacgc ccaggccggc gtgcaggtgg agacaatctc cccaggcgac ggacgcacat   2460
tccctaagcg gggccagacc tgcgtggtgc actatacagg catgctggag gatggcaaga   2520
agtttgacag ctcccgggat agaaacaagc cattcaagtt tatgctgggc aagcaggaag   2580
tgatcagagg ctgggaggag ggcgtggccc agatgtctgt gggccagagg gccaagctga   2640
ccatcagccc agactacgcc tatggagcaa caggccaccc aggaatcatc ccacctcacg   2700
ccaccctggt gttcgatgtg gagctgctga agctgggcga gggcggtagt cagaaccttg   2760
tgataccatg ggccccagaa aatctcacac ttcataaact ttccgaatca caactcgaac   2820
tcaactggaa taaccggttc ctgaatcact gtcttgaaca cctggtacaa tatcggaccg   2880
actgggatca ctcatggaca gaacaatctg tggactatag gcacaaattc tcactcccaa   2940
gcgtagacgg ccaaaaaaga tacacttttc gcgtacgatc ccgctttaat cctctctgcg   3000
gctctgctca gcactggagt gaatggtccc atcccattca ttggggatcc aacacatcaa   3060
aagagaaccc ctttctgttc gcattggagg ccgtagtcat atctgttgga tccatgggac   3120
ttattatctc cctgttgtgt gtgtacttct ggctggaacg gactatgccc aggatcccca   3180
cgctcaagaa tctggaagat ctcgtcacag aataccatgg taatttcagc gcctggagcg   3240
```

-continued gagtctctaa gggtctggcc gaatccctcc aacccgatta ttctgaacgg ttgtgcctcg 3300
tatccgaaat accaccaaaa ggcggggctc tgggtgaggg cccaggggcg agtccgtgca 3360
atcaacacag cccgtattgg gcccctcctt gttatacgtt gaagcccgaa actggaagcg 3420
gagctactaa cttcagcctg ctgaagcagg ctggagacgt ggaggagaac cctggaccta 3480
tggcactgcc cgtgaccgcc ctgctgctgc ctctggccct gctgctgcac gcagcccggc 3540
ctatcctgtg gcacgagatg tggcacgagg gcctggagga ggccagcagg ctgtattttg 3600
gcgagcgcaa cgtgaagggc atgttcgagg tgctggagcc tctgcacgcc atgatggaga 3660
gaggcccaca gaccctgaag gagacatcct ttaaccaggc ctatggacgg gacctgatgg 3720
aggcacagga gtggtgcaga aagtacatga agtctggcaa tgtgaaggac ctgctgcagg 3780
cctgggatct gtactatcac gtgtttcgga gaatctccaa gggaggttca aaacctttttg 3840
agaaccttag actgatggcg cccatctctc tgcaggtagt tcacgttgag acccatagat 3900
gcaatataag ctgggaaatc tcacaagcca gccattactt tgaacggcat ttggaattcg 3960
aggcccgaac actttccccc ggtcatacgt gggaagaagc tcctctcttg acgctgaagc 4020
agaagcagga gtggatttgt ctggagactt tgactcctga tactcagtat gagttccaag 4080
ttcgggtgaa accactccaa ggcgagttca cgacgtggtc tccgtggagt caaccgttgg 4140
cgttccgcac gaagcccgct gcccttggca aagacacgat tccgtggctt gggcatctgc 4200
tcgttgggct gagtggtgcg tttggtttca tcatcttggt ctatctcttg atcaattgca 4260
gaaatacagg ccccttggctg aaaaaagtgc tcaagtgtaa tacccccgac ccaagcaagt 4320
tcttctccca gctttcttca gagcatggag gcgatgtgca gaaatggctc tcttcacctt 4380
ttccctcctc aagcttctcc ccgggagggc tggcgcccga gatttcacct cttgaggtac 4440
ttgaacgaga caaggttacc caacttctcc ttcaacagga taaggtaccc gaacctgcga 4500
gccttagctc caaccactct cttacgagct gcttcaccaa tcagggatac ttcttttttcc 4560
accttcccga tgcgctggaa atcgaagctt gtcaagttta ctttacctat gatccatata 4620
gcgaggaaga tcccgacgaa ggagtcgccg gtgcgcccac gggttcctca ccccaacctc 4680
tccagcctct ctcaggagaa gatgatgctt attgcacttt tcccagtaga gacgatctcc 4740
tcctcttttc tccatctctt ttgggggggac cttccccccc ttctacggca cctggcgggt 4800
ctggtgctgg cgaggagcgg atgccgccgt ccctccagga gcgagtacca cgagattggg 4860
atccccagcc acttggaccc cccacccccg gcgtacctga ccttgtcgat tttcaacctc 4920
cccctgaatt ggtgctgcga gaggctgggg aggaagttcc ggacgctggg ccgagggagg 4980
gcgtgtcctt tccatggagt aggcctccag gtcaaggcga gtttagggct ctcaacgcgc 5040
ggctgccgtt gaatacagac gcttatctct cactgcagga actgcaaggt caggacccaa 5100
cacatcttgt aggatctggt gctactaatt tttctctttt gaagcaagct ggagatgttg 5160
aagagaaccc tggtccagtg agcaagggcg aggagctgtt caccggggtg gtgcccatcc 5220
tggtcgagct ggacggcgac gtaaacggcc acaagttcag cgtgtccggc gagggcgagg 5280
gcgatgccac ctacggcaag ctgaccctga agttcatctg caccaccggc aagctgcccg 5340
tgccctggcc caccctcgtg accaccctga cctacggcgt gcagtgcttc agccgctacc 5400
ccgaccacat gaagcagcac gacttcttca agtccgccat gcccgaaggc tacgtccagg 5460
agcgcaccat cttcttcaag gacgacggca actacaagac ccgcgccgag gtgaagttcg 5520
agggcgacac cctggtgaac cgcatcgagc tgaagggcat cgacttcaag gaggacggca 5580
acatcctggg gcacaagctg gagtacaact acaacagcca caacgtctat atcatggccg 5640
acaagcagaa gaacggcatc aaggtgaact tcaagatccg ccacaacatc gaggacggca 5700
gcgtgcagct cgccgaccac taccagcaga acacccccat cggcgacggc cccgtgctgc 5760
tgcccgacaa ccactacctg agcacccagt ccgccctgag caaagacccc aacgagaagc 5820
gcgatcacat ggtcctgctg gagttcgtga ccgccgccgg gatcactctc ggcatggacg 5880
agctgtacaa gtaaactagt gtcgacaatc aacctctgga ttacaaaatt tgtgaaagat 5940
tgactggtat tcttaactat gttgctcctt ttacgctatg tggatacgct gctttaatgc 6000
ctttgtatca tgctattgct tcccgtatgg ctttcatttt ctcctccttg tataaatcct 6060
ggttgctgtc tctttatgag gagttgtggc ccgttgtcag gcaacgtggc gtggtgtgca 6120
ctgtgtttgc tgacgcaacc cccactggtt ggggcattgc caccacctgt cagctccttt 6180
ccgggacttt cgctttcccc ctccctattg ccacggcgga actcatcgcc gcctgccttg 6240
cccgctgctg gacaggggct cggctgttgg gcactgacaa ttccgtggtg ttgtcgggga 6300
agctgacgtc ctttccatgg ctgctcgcct gtgttgccac ctggattctg cgcgggacgt 6360
ccttctgcta cgtcccttcg gccctcaatc cagcggacct tccttcccgc ggcctgctgc 6420
cggctctgcg gcctcttccg cgtcttcgcc ttcgccctca gacgagtcgg atctcccttt 6480
gggccgcctc cccgcctgga attcgagctc ggtaccttta agaccaatga cttacaaggc 6540
agctgtagat cttagccact ttttaaaaga aaagggggga ctggaagggc taattcactc 6600
ccaacgaaga caagatctgc tttttgcttg tactgggtct ctctggttag accagatctg 6660
agcctgggag ctctctggct aactagggaa cccactgctt aagcctcaat aaagcttgcc 6720
ttgagtgctt caagtagtgt gtgcccgtct gttgtgtgac tctggtaact agagatccct 6780
cagacccttt tagtcagtgt ggaaaatctc tagcagtagt agttcatgtc atcttattat 6840
tcagtattta taacttgcaa agaaatgaat atcagagagt gagaggaact tgtttattgc 6900
agcttataat ggttacaaat aaagcaatag catcacaaat ttcacaaata aagcattttt 6960
ttcactgcat tctagttgtg gtttgtccaa actcatcaat gtatcttatc atgtctggct 7020
ctagctatcc cgcccctaac tccgcccagt tccgcccatt ctccgcccca tggctgacta 7080
atttttttta tttatgcaga ggccgaggcc gcctcggcct ctgagctatt ccagaagtag 7140
tgaggaggct tttttggagg cctaggcttt tgcgtcgaga cgtacccaat tcgccctata 7200
gtgagtcgta ttacgcgcgc tcactggccg tcgttttaca acgtcgtgac tgggaaaacc 7260
ctggcgttac ccaacttaat cgccttgcag cacatccccc tttcgccagc tggcgtaata 7320
gcgaagaggc ccgcaccgat cgcccttccc aacagttgcg cagcctgaat ggcgaatggc 7380
gcgacgcgcc ctgtagcggc gcattaagcg cggcgggtgt ggtggttacg cgcagcgtga 7440
ccgctacact tgccagcgcc ctagcgcccg ctcctttcgc tttcttccct tcctttctcg 7500
ccacgttcgc cggctttccc cgtcaagctc taaatcgggg gctcccttta gggttccgat 7560
ttagtgcttt acggcacctc gaccccaaaa aacttgatta gggtgatggt tcacgtagtg 7620
ggccatcgcc ctgatagacg gtttttcgcc ctttgacgtt ggagtccacg ttctttaata 7680
gtggactctt gttccaaact ggaacaacac tcaaccctat ctcggtctat tcttttgatt 7740
tataagggat tttgccgatt tcggcctatt ggttaaaaaa tgagctgatt taacaaaaat 7800
ttaacgcgaa ttttaacaaa atattaacgt ttacaatttc ccaggtggca cttttcgggg 7860
aaatgtgcgc ggaaccccta tttgtttatt tttctaaata cattcaaata tgtatccgct 7920
catgagacaa taaccctgat aaatgcttca ataatattga aaaaggaaga gtatgagtat 7980

-continued

```
tcaacatttc cgtgtcgccc ttattccctt ttttgcggca ttttgccttc ctgtttttgc   8040
tcacccagaa acgctggtga aagtaaaaga tgctgaagat cagttgggtg cacgagtggg   8100
ttacatcgaa ctggatctca acagcggtaa gatccttgag agttttcgcc ccgaagaacg   8160
ttttccaatg atgagcactt ttaaagttct gctatgtggc gcggtattat cccgtattga   8220
cgccgggcaa gagcaactcg gtcgccgcat acactattct cagaatgact tggttgagta   8280
ctcaccagtc acagaaaagc atcttacgga tggcatgaca gtaagagaat tatgcagtgc   8340
tgccataacc atgagtgata acactgcggc caacttactt ctgacaacga tcggaggacc   8400
gaaggagcta accgcttttt tgcacaacat gggggatcat gtaactcgcc ttgatcgttg   8460
ggaaccggag ctgaatgaag ccataccaaa cgacgagcgt gacaccacga tgcctgtagc   8520
aatggcaaca acgttgcgca aactattaac tggcgaacta cttactctag cttcccggca   8580
acaattaata gactggatgg aggcggataa agttgcagga ccacttctgc gctcggccct   8640
tccggctggc tggtttattg ctgataaatc tggagccggt gagcgtgggt ctcgcggtat   8700
cattgcagca ctggggccag atggtaagcc ctcccgtatc gtagttatct acacgacggg   8760
gagtcaggca actatggatg aacgaaatag acagatcgct gagataggtg cctcactgat   8820
taagcattgg taactgtcag accaagttta ctcatatata ctttagattg atttaaaact   8880
tcatttttaa tttaaaagga tctaggtgaa gatccttttt gataatctca tgaccaaaat   8940
cccttaacgt gagttttcgt tccactgagc gtcagacccc gtagaaaaga tcaaaggatc   9000
ttcttgagat cctttttttc tgcgcgtaat ctgctgcttg caaacaaaaa aaccaccgct   9060
accagcggtg gtttgtttgc cggatcaaga gctaccaact ctttttccga aggtaactgg   9120
cttcagcaga gcgcagatac caaatactgt ccttctagtg tagccgtagt taggccacca   9180
cttcaagaac tctgtagcac cgcctacata cctcgctctg ctaatcctgt taccagtggc   9240
tgctgccagt ggcgataagt cgtgtcttac cgggttggac tcaagacgat agttaccgga   9300
taaggcgcag cggtcgggct gaacgggggg ttcgtgcaca cagcccagct tggagcgaac   9360
gacctacacc gaactgagat acctacagcg tgagctatga gaaagcgcca cgcttcccga   9420
agggagaaag gcggacaggt atccggtaag cggcagggtc ggaacaggag agcgcacgag   9480
ggagcttcca gggggaaacg cctggtatct ttatagtcct gtcgggtttc gccacctctg   9540
acttgagcgt cgatttttgt gatgctcgtc aggggggcgg agcctatgga aaaacgccag   9600
caacgcggcc tttttacggt tcctggcctt ttgctggcct tttgctcaca tgttctttcc   9660
tgcgttatcc cctgattctg tggataaccg tattaccgcc tttgagtgag ctgataccgc   9720
tcgccgcagc cgaacgaccg agcgcagcga gtcagtgagc gaggaagcgg aagagcgccc   9780
aatacgcaaa ccgcctctcc ccgcgcgttg gccgattcat taatgcagct ggcacgacag   9840
gtttcccgac tggaaagcgg gcagtgagcg caacgcaatt aatgtgagtt agctcactca   9900
ttaggcaccc caggctttac actttatgct tccggctcgt atgttgtgtg gaattgtgag   9960
cggataacaa tttcacacag gaaacagcta tgaccatgat tacgccaagc gcgcaattaa  10020
ccctcactaa agggaacaaa agctggagct gca                               10053
```

```
<210> SEQ ID NO 68
<211> LENGTH: 10035
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

<223> OTHER INFORMATION: CISC vector DNA

<400> SEQUENCE: 68
agcttaatgt agtcttatgc aatactcttg tagtcttgca acatggtaac gatgagttag 60
caacatgcct tacaaggaga gaaaaagcac cgtgcatgcc gattggtgga agtaaggtgg 120
tacgatcgtg ccttattagg aaggcaacag acgggtctga catggattgg acgaaccact 180
gaattgccgc attgcagaga tattgtattt aagtgcctag ctcgatacaa taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc cagggggaaa gaaaaaatat 660
aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900
aaaagtaaga ccaccgcaca gcaagcggcc gctgatcttc agacctggag gaggagatat 960
gagggacaat tggagaagtg aattatataa atataaagta gtaaaaattg aaccattagg 1020
agtagcaccc accaaggcaa agagaagagt ggtgcagaga gaaaaaagag cagtgggaat 1080
aggagctttg ttccttgggt tcttgggagc agcaggaagc actatgggcg cagcctcaat 1140
gacgctgacg gtacaggcca gacaattatt gtctggtata gtgcagcagc agaacaattt 1200
gctgagggct attgaggcgc aacagcatct gttgcaactc acagtctggg gcatcaagca 1260
gctccaggca agaatcctgg ctgtggaaag atacctaaag gatcaacagc tcctggggat 1320
ttggggttgc tctggaaaac tcatttgcac cactgctgtg ccttggaatg ctagttggag 1380
taataaatct ctggaacaga tttggaatca cacgacctgg atggagtggg acagagaaat 1440
taacaattac acaagcttaa tacactcctt aattgaagaa tcgcaaaacc agcaagaaaa 1500
gaatgaacaa gaattattgg aattagataa atgggcaagt ttgtggaatt ggtttaacat 1560
aacaaattgg ctgtggtata taaaattatt cataatgata gtaggaggct tggtaggttt 1620
aagaatagtt tttgctgtac tttctatagt gaatagagtt aggcagggat attcaccatt 1680
atcgtttcag acccacctcc caaccccgag gggacccgac aggcccgaag gaatagaaga 1740
agaaggtgga gagagagaca gagacagatc cattcgatta gtgaacggat ctcgacggta 1800
tcggttaact tttaaaagaa aaggggggat tgggggggtac agtgcagggg aaagaatagt 1860
agacataata gcaacagaca tacaaactaa agaattacaa aaacaaatta caaaaattca 1920
aaattttatc gatcacgaga ctagcctcga gaagcttgat atcgaattcc cacggggttg 1980
gacgcgtagg aacagagaaa caggagaata tgggccaaac aggatatctg tggtaagcag 2040
ttcctgcccc ggctcagggc caagaacagt tggaacagca gaatatgggc caaacaggat 2100
atctgtggta agcagttcct gccccggctc agggccaaga acagatggtc cccagatgcg 2160
gtcccgccct cagcagtttc tagagaacca tcagatgttt ccagggtgcc ccaaggacct 2220
gaaatgaccc tgtgccttat ttgaactaac caatcagttc gcttctcgct tctgttcgcg 2280

```
cgcttctgct ccccgagctc tatataagca gagctcgttt agtgaaccgt cagatcgcta   2340
gcaccggtgc cgccaccatg cctctgggcc tgctgtggct gggcctggcc ctgctgggcg   2400
ccctgcacgc ccaggccggc gtgcaggtgg agacaatctc ccccaggcgac ggacgcacat   2460
tccctaagcg gggccagacc tgcgtggtgc actatacagg catgctggag gatggcaaga   2520
agtttgacag ctcccgggat agaaacaagc cattcaagtt tatgctgggc aagcaggaag   2580
tgatcagagg ctgggaggag ggcgtggccc agatgtctgt gggccagagg gccaagctga   2640
ccatcagccc agactacgcc tatggagcaa caggccaccc aggaatcatc ccacctcacg   2700
ccaccctggt gttcgatgtg gagctgctga agctgggcga gcaaaacttg gtgattcctt   2760
gggccccaga aaatctcacg cttcacaagt tgtccgaatc ccagctcgag ctcaactgga   2820
ataatagatt tcttaatcat tgtttggaac acctggttca atatagaacg gattgggacc   2880
actcatggac cgagcagtca gttgactacc gccacaaatt ttcacttccc agcgtagatg   2940
ggcagaagag gtacacattt agggtcagat ccaggtttaa tcctctgtgt ggttctgctc   3000
aacactggtc tgagtggagc catccgatcc actggggctc aaatacctct aaagaaaatc   3060
cgttcctctt tgcgctcgaa gccgttgtta tcagcgtcgg aagcatggga cttatcattt   3120
cccttctctg cgtgtacttc tggctggagc ggacgatgcc gcggattccg acgctcaaaa   3180
acctggagga ccttgtaaca gaatatcacg gtaatttctc cgcttggagt ggcgtatcaa   3240
aggggcttgc tgagtccctt caaccggatt actctgagcg cctctgcttg gtgtccgaga   3300
tacctcccaa aggaggtgca cttggggagg ggccaggcgc gtccccttgc aatcagcata   3360
gtccgtattg ggcgcccccc tgttataccc tcaaaccgga aacgggaagc ggagctacta   3420
acttcagcct gctgaagcag gctggagacg tggaggagaa ccctggacct atggcactgc   3480
ccgtgaccgc cctgctgctg cctctggccc tgctgctgca cgcagcccgg cctatcctgt   3540
ggcacgagat gtggcacgag ggcctggagg aggccagcag gctgtatttt ggcgagcgca   3600
acgtgaaggg catgttcgag gtgctggagc ctctgcacgc catgatggag agaggcccac   3660
agaccctgaa ggagacatcc tttaaccagg cctatggacg ggacctgatg gaggcacagg   3720
agtggtgcag aaagtacatg aagtctggca atgtgaagga cctgctgcag gcctgggatc   3780
tgtactatca cgtgtttcgg agaatctcca agaaaccttt tgagaacctt agactgatgg   3840
cgcccatctc tctgcaggta gttcacgttg agacccatag atgcaatata agctgggaaa   3900
tctcacaagc cagccattac tttgaacggc atttggaatt cgaggcccga acactttccc   3960
ccggtcatac gtgggaagaa gctcctctct tgacgctgaa gcagaagcag gagtggattt   4020
gtctggagac tttgactcct gatactcagt atgagttcca agttcgggtg aaaccactcc   4080
aaggcgagtt cacgacgtgg tctccgtgga gtcaaccgtt ggcgttccgc acgaagcccg   4140
ctgcccttgg caaagacacg attccgtggc ttgggcatct gctcgttggg ctgagtggtg   4200
cgtttggttt catcatcttg gtctatctct tgatcaattg cagaaataca ggcccttggc   4260
tgaaaaaagt gctcaagtgt aataccccccg acccaagcaa gttcttctcc cagctttctt   4320
cagagcatgg aggcgatgtg cagaaatggc tctcttcacc ttttccctcc tcaagcttct   4380
ccccgggagg gctggcgccc gagatttcac ctcttgaggt acttgaacga gacaaggtta   4440
cccaacttct ccttcaacag gataaggtac ccgaacctgc gagccttagc tccaaccact   4500
ctcttacgag ctgcttcacc aatcagggat acttcttttt ccaccttccc gatgcgctgg   4560
aaatcgaagc ttgtcaagtt tactttacct atgatccata tagcgaggaa gatcccgacg   4620
```

-continued

```
aaggagtcgc cggtgcgccc acgggttcct caccccaacc tctccagcct ctctcaggag   4680
aagatgatgc ttattgcact tttcccagta gagacgatct cctcctcttt tctccatctc   4740
ttttgggggg accttccccc ccttctacgg cacctggcgg gtctggtgct ggcgaggagc   4800
ggatgccgcc gtccctccag gagcgagtac cacgagattg ggatccccag ccacttggac   4860
cccccacccc cggcgtacct gaccttgtcg attttcaacc tccccctgaa ttggtgctgc   4920
gagaggctgg ggaggaagtt ccggacgctg ggccgaggga gggcgtgtcc tttccatgga   4980
gtaggcctcc aggtcaaggc gagtttaggg ctctcaacgc gcggctgccg ttgaatacag   5040
acgcttatct ctcactgcag gaactgcaag gtcaggaccc aacacatctt gtaggatctg   5100
gtgctactaa tttttctctt ttgaagcaag ctggagatgt tgaagagaac cctggtccag   5160
tgagcaaggg cgaggagctg ttcaccgggg tggtgcccat cctggtcgag ctggacggcg   5220
acgtaaacgg ccacaagttc agcgtgtccg gcgagggcga gggcgatgcc acctacggca   5280
agctgaccct gaagttcatc tgcaccaccg gcaagctgcc cgtgccctgg cccaccctcg   5340
tgaccaccct gacctacggc gtgcagtgct tcagccgcta ccccgaccac atgaagcagc   5400
acgacttctt caagtccgcc atgcccgaag gctacgtcca ggagcgcacc atcttcttca   5460
aggacgacgg caactacaag acccgcgccg aggtgaagtt cgagggcgac accctggtga   5520
accgcatcga gctgaagggc atcgacttca aggaggacgg caacatcctg gggcacaagc   5580
tggagtacaa ctacaacagc cacaacgtct atatcatggc cgacaagcag aagaacggca   5640
tcaaggtgaa cttcaagatc cgccacaaca tcgaggacgg cagcgtgcag ctcgccgacc   5700
actaccagca gaacaccccc atcggcgacg gccccgtgct gctgcccgac aaccactacc   5760
tgagcaccca gtccgccctg agcaaagacc ccaacgagaa gcgcgatcac atggtcctgc   5820
tggagttcgt gaccgccgcc gggatcactc tcggcatgga cgagctgtac aagtaaacta   5880
gtgtcgacaa tcaacctctg gattacaaaa tttgtgaaag attgactggt attcttaact   5940
atgttgctcc ttttacgcta tgtggatacg ctgctttaat gcctttgtat catgctattg   6000
cttcccgtat ggctttcatt ttctcctcct tgtataaatc ctggttgctg tctctttatg   6060
aggagttgtg gcccgttgtc aggcaacgtg gcgtggtgtg cactgtgttt gctgacgcaa   6120
cccccactgg ttggggcatt gccaccacct gtcagctcct ttccgggact ttcgctttcc   6180
ccctccctat tgccacggcg gaactcatcg ccgcctgcct tgcccgctgc tggacagggg   6240
ctcggctgtt gggcactgac aattccgtgg tgttgtcggg gaagctgacg tcctttccat   6300
ggctgctcgc ctgtgttgcc acctggattc tgcgcgggac gtccttctgc tacgtccctt   6360
cggccctcaa tccagcggac cttccttccc gcggcctgct gccggctctg cggcctcttc   6420
cgcgtcttcg ccttcgccct cagacgagtc ggatctccct ttgggccgcc tccccgcctg   6480
gaattcgagc tcggtacctt taagaccaat gacttacaag gcagctgtag atcttagcca   6540
ctttttaaaa gaaaaggggg gactggaagg gctaattcac tcccaacgaa gacaagatct   6600
gctttttgct tgtactgggt ctctctggtt agaccagatc tgagcctggg agctctctgg   6660
ctaactaggg aacccactgc ttaagcctca ataaagcttg ccttgagtgc ttcaagtagt   6720
gtgtgcccgt ctgttgtgtg actctggtaa ctagagatcc ctcagaccct tttagtcagt   6780
gtggaaaatc tctagcagta gtagttcatg tcatcttatt attcagtatt tataacttgc   6840
aaagaaatga atatcagaga gtgagaggaa cttgtttatt gcagcttata atggttacaa   6900
ataaagcaat agcatcacaa atttcacaaa taaagcattt ttttcactgc attctagttg   6960
tggtttgtcc aaactcatca atgtatctta tcatgtctgg ctctagctat cccgccccta   7020
```

actccgccca gttccgccca ttctccgccc catggctgac taattttttt tatttatgca 7080
gaggccgagg ccgcctcggc ctctgagcta ttccagaagt agtgaggagg cttttttgga 7140
ggcctaggct tttgcgtcga gacgtaccca attcgcccta tagtgagtcg tattacgcgc 7200
gctcactggc cgtcgtttta caacgtcgtg actgggaaaa ccctggcgtt acccaactta 7260
atcgccttgc agcacatccc cctttcgcca gctggcgtaa tagcgaagag gcccgcaccg 7320
atcgcccttc ccaacagttg cgcagcctga atggcgaatg gcgcgacgcg ccctgtagcg 7380
gcgcattaag cgcggcgggt gtggtggtta cgcgcagcgt gaccgctaca cttgccagcg 7440
ccctagcgcc cgctcctttc gctttcttcc cttcctttct cgccacgttc gccggctttc 7500
cccgtcaagc tctaaatcgg gggctccctt tagggttccg atttagtgct ttacggcacc 7560
tcgaccccaa aaaacttgat tagggtgatg gttcacgtag tgggccatcg ccctgataga 7620
cggtttttcg ccctttgacg ttggagtcca cgttctttaa tagtggactc ttgttccaaa 7680
ctggaacaac actcaaccct atctcggtct attcttttga tttataaggg attttgccga 7740
tttcggccta ttggttaaaa aatgagctga tttaacaaaa atttaacgcg aattttaaca 7800
aaatattaac gtttacaatt tcccaggtgg cacttttcgg ggaaatgtgc gcggaacccc 7860
tatttgttta tttttctaaa tacattcaaa tatgtatccg ctcatgagac aataaccctg 7920
ataaatgctt caataatatt gaaaaaggaa gagtatgagt attcaacatt tccgtgtcgc 7980
ccttattccc ttttttgcgg cattttgcct tcctgttttt gctcacccag aaacgctggt 8040
gaaagtaaaa gatgctgaag atcagttggg tgcacgagtg ggttacatcg aactggatct 8100
caacagcggt aagatccttg agagttttcg ccccgaagaa cgttttccaa tgatgagcac 8160
ttttaaagtt ctgctatgtg gcgcggtatt atcccgtatt gacgccgggc aagagcaact 8220
cggtcgccgc atacactatt ctcagaatga cttggttgag tactcaccag tcacagaaaa 8280
gcatcttacg gatggcatga cagtaagaga attatgcagt gctgccataa ccatgagtga 8340
taacactgcg gccaacttac ttctgacaac gatcggagga ccgaaggagc taaccgcttt 8400
tttgcacaac atgggggatc atgtaactcg ccttgatcgt tgggaaccgg agctgaatga 8460
agccatacca aacgacgagc gtgacaccac gatgcctgta gcaatggcaa caacgttgcg 8520
caaactatta actggcgaac tacttactct agcttcccgg caacaattaa tagactggat 8580
ggaggcggat aaagttgcag gaccacttct gcgctcggcc cttccggctg gctggtttat 8640
tgctgataaa tctggagccg gtgagcgtgg gtctcgcggt atcattgcag cactggggcc 8700
agatggtaag ccctcccgta tcgtagttat ctacacgacg gggagtcagg caactatgga 8760
tgaacgaaat agacagatcg ctgagatagg tgcctcactg attaagcatt ggtaactgtc 8820
agaccaagtt tactcatata tactttagat tgatttaaaa cttcattttt aatttaaaag 8880
gatctaggtg aagatccttt ttgataatct catgaccaaa atcccttaac gtgagttttc 8940
gttccactga gcgtcagacc ccgtagaaaa gatcaaagga tcttcttgag atcctttttt 9000
tctgcgcgta atctgctgct tgcaaacaaa aaaaccaccg ctaccagcgg tggtttgttt 9060
gccggatcaa gagctaccaa ctctttttcc gaaggtaact ggcttcagca gagcgcagat 9120
accaaatact gtccttctag tgtagccgta gttaggccac cacttcaaga actctgtagc 9180
accgcctaca tacctcgctc tgctaatcct gttaccagtg gctgctgcca gtggcgataa 9240
gtcgtgtctt accgggttgg actcaagacg atagttaccg gataaggcgc agcggtcggg 9300
ctgaacgggg ggttcgtgca cacagcccag cttggagcga acgacctaca ccgaactgag 9360

```
atacctacag cgtgagctat gagaaagcgc cacgcttccc gaagggagaa aggcggacag   9420

gtatccggta agcggcaggg tcggaacagg agagcgcacg agggagcttc caggggggaaa   9480

cgcctggtat ctttatagtc ctgtcgggtt tcgccacctc tgacttgagc gtcgattttt   9540

gtgatgctcg tcaggggggc ggagcctatg gaaaaacgcc agcaacgcgg cctttttacg   9600

gttcctggcc ttttgctggc cttttgctca catgttcttt cctgcgttat cccctgattc   9660

tgtggataac cgtattaccg cctttgagtg agctgatacc gctcgccgca gccgaacgac   9720

cgagcgcagc gagtcagtga gcgaggaagc ggaagagcgc ccaatacgca aaccgcctct   9780

ccccgcgcgt tggccgattc attaatgcag ctggcacgac aggtttcccg actggaaagc   9840

gggcagtgag cgcaacgcaa ttaatgtgag ttagctcact cattaggcac cccaggcttt   9900

acactttatg cttccggctc gtatgttgtg tggaattgtg agcggataac aatttcacac   9960

aggaaacagc tatgaccatg attacgccaa gcgcgcaatt aaccctcact aaagggaaca  10020

aaagctggag ctgca                                                   10035
```

<210> SEQ ID NO 69
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Linker spacer polypeptide

<400> SEQUENCE: 69

```
Pro Ala Ala Leu
1
```

<210> SEQ ID NO 70
<211> LENGTH: 267
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Naked FRB domain nucleic acid sequence

<400> SEQUENCE: 70

```
gagatgtggc atgagggtct ggaagaagcg tctcgactgt actttggtga gcgcaatgtg     60

aagggcatgt ttgaagtcct cgaacccctt catgccatga tggaacgcgg accccagacc    120

ttgaaggaga caagttttaa ccaagcttac ggaagagacc tgatggaagc ccaggaatgg    180

tgcaggaaat acatgaaaag cgggaatgtg aaggacttga cccaagcgtg ggacctgtac    240

tatcatgtct ttaggcgcat tagtaag                                        267
```

<210> SEQ ID NO 71
<211> LENGTH: 353
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: MND promoter

<400> SEQUENCE: 71

```
gaacagagaa acaggagaat atgggccaaa caggatatct gtggtaagca gttcctgccc     60

cggctcaggg ccaagaacag ttggaacagc agaatatggg ccaaacagga tatctgtggt    120
```

```
aagcagttcc tgccccggct cagggccaag aacagatggt ccccagatgc ggtcccgccc    180

tcagcagttt ctagagaacc atcagatgtt tccagggtgc cccaaggacc tgaaatgacc    240

ctgtgcctta tttgaactaa ccaatcagtt cgcttctcgc ttctgttcgc gcgcttctgc    300

tccccgagct ctatataagc agagctcgtt tagtgaaccg tcagatcgct agc           353
```

<210> SEQ ID NO 72
<211> LENGTH: 2190
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: FOXP3cDNA_P2A_LNGFR kozak_start codon_FOXP3cDNA_P2A_LNGFR_stop codon

<400> SEQUENCE: 72

```
gccaccatgc ctaatcctcg gcctggaaag cctagcgctc cttctcttgc tctgggacct     60

tctcctggcg cctctccatc ttggagagcc gctcctaaag ccagcgatct gctgggagct    120

agaggacctg gcggcacatt tcagggcaga gatcttagag gcggagccca cgctagctcc    180

tccagcctta atcctatgcc tcctagccag ctccagctgc ctacactgcc tctggttatg    240

gtggctccta gcggagctag actgggccct ctgcctcatc tgcaagctct gctgcaggac    300

agaccccact tcatgcacca gctgagcacc gtggatgccc acgcaagaac acctgtgctg    360

caggttcacc ctctggaatc cccagccatg atcagcctga cacctccaac aacagccacc    420

ggcgtgttca gcctgaaagc cagacctgga ctgcctcctg gcatcaatgt ggccagcctg    480

gaatgggtgt ccagagaacc tgctctgctg tgcacattcc ccaatccaag cgctcccaga    540

aaggacagca cactgtctgc cgtgcctcag agcagctatc cctgcttgc taacggcgtg    600

tgcaagtggc ctggatgcga gaaggtgttc gaggaacccg aggacttcct gaagcactgc    660

caggccgatc atctgctgga cgagaaaggc agagcccagt gtctgctcca gcgcgagatg    720

gtgcagtctc tggaacagca gctggtcctg gaaaaagaaa agctgagcgc catgcaggcc    780

cacctggccg gaaaaatggc cctgacaaag gccagcagcg tggcctcttc tgataagggc    840

agctgctgca ttgtggccgc tggatctcag ggacctgtgg ttcctgcttg gagcggacct    900

agagaggccc ctgattctct gtttgccgtg cggagacacc tgtggggctc tcacggcaac    960

tctactttcc ccgagttcct gcacaacatg gactacttca agttccacaa catgcggcct   1020

ccattcacct acgccacact gatcagatgg gccattctgg aagcccctga gaagcagaga   1080

accctgaacg agatctacca ctggtttacc cggatgttcg ccttcttccg gaatcaccct   1140

gccacctgga agaacgccat ccggcacaat ctgagcctgc acaagtgctt cgtgcgcgtg   1200

gaatctgaga aaggcgccgt gtggacagtg gacgagctgg aattcagaaa gaagagaagc   1260

cagcggccta gccggtgcag caatcctaca cctggacctg gaagcggagc gactaacttc   1320

agcctgctga agcaggccgg agatgtggag gaaaaccctg gaccgatggg ggcaggtgcc   1380

accggacgag ccatggacgg gccgcgcctg ctgctgttgc tgcttctggg ggtgtccctt   1440

ggaggtgcca aggaggcatg ccccacaggc ctgtacacac acagcggtga gtgctgcaaa   1500

gcctgcaacc tgggcgaggg tgtggcccag ccttgtggag ccaaccagac cgtgtgtgag   1560

ccctgcctgg acagcgtgac gttctccgac gtggtgagcg cgaccgagcc gtgcaagccg   1620

tgcaccgagt gcgtggggct ccagagcatg tcggcgccgt gcgtggaggc cgacgacgcc   1680
```

gtgtgccgct gcgcctacgg ctactaccag gatgagacga ctgggcgctg cgaggcgtgc 1740
cgcgtgtgcg aggcgggctc gggcctcgtg ttctcctgcc aggacaagca gaacaccgtg 1800
tgcgaggagt gccccgacgg cacgtattcc gacgaggcca accacgtgga cccgtgcctg 1860
ccctgcaccg tgtgcgagga caccgagcgc cagctccgcg agtgcacacg ctgggccgac 1920
gccgagtgcg aggagatccc tggccgttgg attacacggt ccacaccccc agagggctcg 1980
gacagcacag cccccagcac ccaggagcct gaggcacctc cagaacaaga cctcatagcc 2040
agcacggtgg caggtgtggt gaccacagtg atgggcagct cccagcccgt ggtgacccga 2100
ggcaccaccg acaacctcat ccctgtctat tgctccatcc tggctgctgt ggttgtgggt 2160
cttgtggcct acatagcctt caagaggtga 2190

<210> SEQ ID NO 73
<211> LENGTH: 2190
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: LNGFR_P2A_FOXP3cDNA kozak_start codon_LNGFR_P2A_FOXP3cDNA_stop codon

<400> SEQUENCE: 73
gccaccatgg gggcaggtgc caccggacga gccatggacg ggccgcgcct gctgctgttg 60
ctgcttctgg gggtgtccct tggaggtgcc aaggaggcat gccccacagg cctgtacaca 120
cacagcggtg agtgctgcaa agcctgcaac ctgggcgagg gtgtggccca gccttgtgga 180
gccaaccaga ccgtgtgtga gccctgcctg gacagcgtga cgttctccga cgtggtgagc 240
gcgaccgagc cgtgcaagcc gtgcaccgag tgcgtggggc tccagagcat gtcggcgccg 300
tgcgtggagg ccgacgacgc cgtgtgccgc tgcgcctacg gctactacca ggatgagacg 360
actgggcgct gcgaggcgtg ccgcgtgtgc gaggcgggct cgggcctcgt gttctcctgc 420
caggacaagc agaacaccgt gtgcgaggag tgccccgacg gcacgtattc cgacgaggcc 480
aaccacgtgg acccgtgcct gccctgcacc gtgtgcgagg acaccgagcg ccagctccgc 540
gagtgcacac gctgggccga cgccgagtgc gaggagatcc ctggccgttg gattacacgg 600
tccacacccc cagagggctc ggacagcaca gcccccagca cccaggagcc tgaggcacct 660
ccagaacaag acctcatagc cagcacggtg gcaggtgtgg tgaccacagt gatgggcagc 720
tcccagcccg tggtgacccg aggcaccacc gacaacctca tccctgtcta ttgctccatc 780
ctggctgctg tggttgtggg tcttgtggcc tacatagcct tcaagagggg aagcggagcg 840
actaacttca gcctgctgaa gcaggccgga gatgtggagg aaaaccctgg accgatgcct 900
aatcctcggc ctggaaagcc tagcgctcct tctcttgctc tgggaccttc tcctggcgcc 960
tctccatctt ggagagccgc tcctaaagcc agcgatctgc tgggagctag aggacctggc 1020
ggcacatttc agggcagaga tcttagaggc ggagcccacg ctagctcctc cagccttaat 1080
cctatgcctc ctagccagct ccagctgcct acactgcctc tggttatggt ggctcctagc 1140
ggagctagac tgggccctct gcctcatctg caagctctgc tgcaggacag accccacttc 1200
atgcaccagc tgagcaccgt ggatgcccac gcaagaacac ctgtgctgca ggttcaccct 1260
ctggaatccc cagccatgat cagcctgaca cctccaacaa cagccaccgg cgtgttcagc 1320
ctgaaagcca gacctggact gcctcctggc atcaatgtgg ccagcctgga atgggtgtcc 1380
agagaacctg ctctgctgtg cacattcccc aatccaagcg ctcccagaaa ggacagcaca 1440

```
ctgtctgccg tgcctcagag cagctatccc ctgcttgcta acggcgtgtg caagtggcct   1500

ggatgcgaga aggtgttcga ggaacccgag gacttcctga agcactgcca ggccgatcat   1560

ctgctggacg agaaaggcag agcccagtgt ctgctccagc gcgagatggt gcagtctctg   1620

gaacagcagc tggtcctgga aaaagaaaag ctgagcgcca tgcaggccca cctggccgga   1680

aaaatggccc tgacaaaggc cagcagcgtg gcctcttctg ataagggcag ctgctgcatt   1740

gtggccgctg gatctcaggg acctgtggtt cctgcttgga gcggacctag agaggcccct   1800

gattctctgt ttgccgtgcg gagacacctg tggggctctc acggcaactc tactttcccc   1860

gagttcctgc acaacatgga ctacttcaag ttccacaaca tgcggcctcc attcacctac   1920

gccacactga tcagatgggc cattctggaa gcccctgaga agcagagaac cctgaacgag   1980

atctaccact ggtttacccg gatgttcgcc ttcttccgga atcaccctgc cacctggaag   2040

aacgccatcc ggcacaatct gagcctgcac aagtgcttcg tgcgcgtgga atctgagaaa   2100

ggcgccgtgt ggacagtgga cgagctggaa ttcagaaaga agagaagcca gcggcctagc   2160

cggtgcagca atcctacacc tggaccttga                                    2190
```

<210> SEQ ID NO 74
<211> LENGTH: 3261
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: FOXP3cDNA_uDISC nucleotide sequence coding sequence only codon optimized our DISC architecture version 6

<400> SEQUENCE: 74

```
atgcctaatc ctcggcctgg aaagcctagc gctccttctc ttgctctggg accttctcct     60

ggcgcctctc catcttggag agccgctcct aaagccagcg atctgctggg agctagagga    120

cctggcggca catttcaggg cagagatctt agaggcggag cccacgctag ctcctccagc    180

cttaatccta tgcctcctag ccagctccag ctgcctacac tgcctctggt tatggtggct    240

cctagcggag ctagactggg ccctctgcct catctgcaag ctctgctgca ggacagaccc    300

cacttcatgc accagctgag caccgtggat gcccacgcaa gaacacctgt gctgcaggtt    360

caccctctgg aatccccagc catgatcagc ctgacacctc caacaacagc caccggcgtg    420

ttcagcctga aagccagacc tggactgcct cctggcatca atgtggccag cctggaatgg    480

gtgtccagag aacctgctct gctgtgcaca ttccccaatc caagcgctcc cagaaaggac    540

agcacactgt ctgccgtgcc tcagagcagc tatcccctgc ttgctaacgg cgtgtgcaag    600

tggcctggat gcgagaaggt gttcgaggaa cccgaggact tcctgaagca ctgccaggcc    660

gatcatctgc tggacgagaa aggcagagcc cagtgtctgc tccagcgcga gatggtgcag    720

tctctggaac agcagctggt cctggaaaaa gaaaagctga gcgccatgca ggcccacctg    780

gccggaaaaa tggccctgac aaaggccagc agcgtggcct cttctgataa gggcagctgc    840

tgcattgtgg ccgctggatc tcagggacct gtggttcctg cttggagcgg acctagagag    900

gcccctgatt ctctgtttgc cgtgcggaga cacctgtggg gctctcacgg caactctact    960

ttccccgagt tcctgcacaa catggactac ttcaagttcc acaacatgcg gcctccattc   1020

acctacgcca cactgatcag atgggccatt ctggaagccc ctgagaagca gagaaccctg   1080

aacgagatct accactggtt tacccggatg ttcgccttct tccggaatca ccctgccacc   1140
```

-continued

```
tggaagaacg ccatccggca caatctgagc ctgcacaagt gcttcgtgcg cgtggaatct   1200
gagaaaggcg ccgtgtggac agtggacgag ctggaattca gaaagaagag aagccagcgg   1260
cctagccggt gcagcaatcc tacacctgga cctggaagcg gagcgactaa cttcagcctg   1320
cttaagcagg ccggagatgt ggaggaaaac cctggaccga tgcctctggg cctgctgtgg   1380
ctgggcctgg ccctgctggg cgccctgcac gcccaggccg gcgtgcaggt ggagacaatc   1440
tccccaggcg acggacgcac attccctaag cggggccaga cctgcgtggt gcactataca   1500
ggcatgctgg aggatggcaa gaagtttgac agctcccggg atagaaacaa gccattcaag   1560
tttatgctgg gcaagcagga agtgatcaga ggctgggagg agggcgtggc ccagatgtct   1620
gtgggccaga gggccaagct gaccatcagc ccagactacg cctatggagc aacaggccac   1680
ccaggaatca tcccacctca cgccaccctg gtgttcgatg tggagctgct gaagctgggc   1740
gagggagggt cacctggatc caacacatca aaagagaacc cctttctgtt cgcattggag   1800
gccgtagtca tatctgttgg atccatggga cttattatct ccctgttgtg tgtgtacttc   1860
tggctggaac ggactatgcc caggatcccc acgctcaaga atctggaaga tctcgtcaca   1920
gaataccatg gtaatttcag cgcctggagc ggagtctcta agggtctggc cgaatccctc   1980
caacccgatt attctgaacg gttgtgcctc gtatccgaaa taccaccaaa aggcggggct   2040
ctgggtgagg gcccaggggc gagtccgtgc aatcaacaca gcccgtattg ggcccctcct   2100
tgttatacgt tgaagcccga aactggaagc ggagctacta acttcagcct gctgaagcag   2160
gctggagacg tggaggagaa ccctggacct atggcactgc ccgtgaccgc cctgctgctg   2220
cctctggccc tgctgctgca cgcagcccgg cctatcctgt ggcacgagat gtggcacgag   2280
ggcctggagg aggccagcag gctgtatttt ggcgagcgca acgtgaaggg catgttcgag   2340
gtgctggagc ctctgcacgc catgatggag agaggcccac agaccctgaa ggagacatcc   2400
tttaaccagg cctatggacg ggacctgatg gaggcacagg agtggtgcag aaagtacatg   2460
aagtctggca atgtgaagga cctgctgcag gcctgggatc tgtactatca cgtgtttcgg   2520
agaatctcca agccagcagc tctcggcaaa gacacgattc cgtggcttgg gcatctgctc   2580
gttgggctga gcggtgcgtt tggtttcatc atcttggtct atctcttgat caattgcaga   2640
aatacaggcc cttggctgaa aaaagtgctc aagtgtaata cccccgaccc aagcaagttc   2700
ttctcccagc tttcttcaga gcatggaggc gatgtgcaga aatggctctc ttcacctttt   2760
ccctcctcaa gcttctcccc gggagggctg gcgcccgaga tttcacctct tgaggtactt   2820
gaacgagaca aggttaccca acttctcctt caacaggata aggtacccga acctgcgagc   2880
cttagcttga atacagacgc ttatctctca ctgcaggaac tgcaaggatc tggtgctact   2940
aatttttctc ttttgaagca agctggagat gttgaagaga accccggtcc ggagatgtgg   3000
catgagggtc tggaagaagc gtctcgactg tactttggtg agcgcaatgt gaagggcatg   3060
tttgaagtcc tcgaacccct tcatgccatg atggaacgcg gaccccagac cttgaaggag   3120
acaagtttta accaagctta cggaagagac ctgatggaag cccaggaatg gtgcaggaaa   3180
tacatgaaaa gcgggaatgt gaaggacttg ctccaagcgt gggacctgta ctatcatgtc   3240
tttaggcgca ttagtaagtg a                                              3261
```

```
<210> SEQ ID NO 75
<211> LENGTH: 3805
<212> TYPE: DNA
<213> ORGANISM: Artificial sequence
<220> FEATURE:
<223> OTHER INFORMATION: Synthetic polynucleotide
```

<220> FEATURE:
<221> NAME/KEY: misc_feature
<223> OTHER INFORMATION: MND_FOXP3cDNA_uDISC_SV40 polyA nucleotide
sequence codon optimized

<400> SEQUENCE: 75
gaacagagaa acaggagaat atgggccaaa caggatatct gtggtaagca gttcctgccc 60
cggctcaggg ccaagaacag ttggaacagc agaatatggg ccaaacagga tatctgtggt 120
aagcagttcc tgccccggct cagggccaag aacagatggt ccccagatgc ggtcccgccc 180
tcagcagttt ctagagaacc atcagatgtt tccagggtgc cccaaggacc tgaaatgacc 240
ctgtgcctta tttgaactaa ccaatcagtt cgcttctcgc ttctgttcgc gcgcttctgc 300
tccccgagct ctatataagc agagctcgtt tagtgaaccg tcagatcgcc tggagacgcc 360
atccacgctg ttttgacttc catagaagga tctcgaggcc accatgccta atcctcggcc 420
tggaaagcct agcgctcctt ctcttgctct gggaccttct cctggcgcct ctccatcttg 480
gagagccgct cctaaagcca gcgatctgct gggagctaga ggacctggcg gcacatttca 540
gggcagagat cttagaggcg gagcccacgc tagctcctcc agccttaatc ctatgcctcc 600
tagccagctc cagctgccta cactgcctct ggttatggtg gctcctagcg gagctagact 660
gggccctctg cctcatctgc aagctctgct gcaggacaga ccccacttca tgcaccagct 720
gagcaccgtg gatgcccacg caagaacacc tgtgctgcag gttcaccctc tggaatcccc 780
agccatgatc agcctgacac ctccaacaac agccaccggc gtgttcagcc tgaaagccag 840
acctggactg cctcctggca tcaatgtggc cagcctggaa tgggtgtcca gagaacctgc 900
tctgctgtgc acattcccca atccaagcgc tcccagaaag gacagcacac tgtctgccgt 960
gcctcagagc agctatcccc tgcttgctaa cggcgtgtgc aagtggcctg gatgcgagaa 1020
ggtgttcgag gaacccgagg acttcctgaa gcactgccag gccgatcatc tgctggacga 1080
gaaaggcaga gcccagtgtc tgctccagcg cgagatggtg cagtctctgg aacagcagct 1140
ggtcctggaa aaagaaaagc tgagcgccat gcaggcccac ctggccggaa aaatggccct 1200
gacaaaggcc agcagcgtgg cctcttctga taagggcagc tgctgcattg tggccgctgg 1260
atctcaggga cctgtggttc ctgcttggag cggacctaga gaggcccctg attctctgtt 1320
tgccgtgcgg agacacctgt ggggctctca cggcaactct actttccccg agttcctgca 1380
caacatggac tacttcaagt tccacaacat gcggcctcca ttcacctacg ccacactgat 1440
cagatgggcc attctggaag cccctgagaa gcagagaacc ctgaacgaga tctaccactg 1500
gtttacccgg atgttcgcct tcttccggaa tcaccctgcc acctggaaga acgccatccg 1560
gcacaatctg agcctgcaca agtgcttcgt gcgcgtggaa tctgagaaag gcgccgtgtg 1620
gacagtggac gagctggaat tcagaaagaa gagaagccag cggcctagcc ggtgcagcaa 1680
tcctacacct ggacctggaa gcggagcgac taacttcagc ctgcttaagc aggccggaga 1740
tgtggaggaa aaccctggac cgatgcctct gggcctgctg tggctgggcc tggccctgct 1800
gggcgccctg cacgcccagg ccggcgtgca ggtggagaca atctccccag gcgacggacg 1860
cacattccct aagcggggcc agacctgcgt ggtgcactat acaggcatgc tggaggatgg 1920
caagaagttt gacagctccc gggatagaaa caagccattc aagtttatgc tgggcaagca 1980
ggaagtgatc agaggctggg aggagggcgt ggcccagatg tctgtgggcc agagggccaa 2040
gctgaccatc agcccagact acgcctatgg agcaacaggc cacccaggaa tcatcccacc 2100
tcacgccacc ctggtgttcg atgtggagct gctgaagctg ggcgagggag ggtcacctgg 2160

-continued

```
atccaacaca tcaaaagaga accccttttct gttcgcattg gaggccgtag tcatatctgt   2220
tggatccatg ggacttatta tctccctgtt gtgtgtgtac ttctggctgg aacggactat   2280
gcccaggatc cccacgctca agaatctgga agatctcgtc acagaatacc atggtaattt   2340
cagcgcctgg agcggagtct ctaagggtct ggccgaatcc ctccaacccg attattctga   2400
acggttgtgc ctcgtatccg aaataccacc aaaaggcggg gctctgggtg agggcccagg   2460
ggcgagtccg tgcaatcaac acagcccgta ttgggcccct ccttgttata cgttgaagcc   2520
cgaaactgga agcggagcta ctaacttcag cctgctgaag caggctggag acgtggagga   2580
gaaccctgga cctatggcac tgcccgtgac cgccctgctg ctgcctctgg ccctgctgct   2640
gcacgcagcc cggcctatcc tgtggcacga gatgtggcac gagggcctgg aggaggccag   2700
caggctgtat tttggcgagc gcaacgtgaa gggcatgttc gaggtgctgg agcctctgca   2760
cgccatgatg gagagaggcc cacagaccct gaaggagaca tcctttaacc aggcctatgg   2820
acgggacctg atggaggcac aggagtggtg cagaaagtac atgaagtctg gcaatgtgaa   2880
ggacctgctg caggcctggg atctgtacta tcacgtgttt cggagaatct ccaagccagc   2940
agctctcggc aaagacacga ttccgtggct tgggcatctg ctcgttgggc tgagcggtgc   3000
gtttggtttc atcatcttgg tctatctctt gatcaattgc agaaatacag gcccttggct   3060
gaaaaaagtg ctcaagtgta atacccccga cccaagcaag ttcttctccc agctttcttc   3120
agagcatgga ggcgatgtgc agaaatggct ctcttcacct tttccctcct caagcttctc   3180
cccgggaggg ctggcgcccg agatttcacc tcttgaggta cttgaacgag acaaggttac   3240
ccaacttctc cttcaacagg ataaggtacc cgaacctgcg agccttagct tgaatacaga   3300
cgcttatctc tcactgcagg aactgcaagg atctggtgct actaattttt ctcttttgaa   3360
gcaagctgga gatgttgaag agaaccccgg tccggagatg tggcatgagg gtctggaaga   3420
agcgtctcga ctgtactttg gtgagcgcaa tgtgaagggc atgtttgaag tcctcgaacc   3480
ccttcatgcc atgatggaac gcggacccca gaccttgaag gagacaagtt ttaaccaagc   3540
ttacggaaga gacctgatgg aagcccagga atggtgcagg aaatacatga aaagcgggaa   3600
tgtgaaggac ttgctccaag cgtgggacct gtactatcat gtctttaggc gcattagtaa   3660
gtgagtcgac tgctttattt gtgaaatttg tgatgctatt gctttatttg taaccattat   3720
aagctgcaat aaacaagtta acaacaacaa ttgcattcat tttatgtttc aggttcaggg   3780
ggagatgtgg gaggtttttt aaagc                                          3805
```

<210> SEQ ID NO 76
<211> LENGTH: 1086
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: FOXP3cDNA_uDISC amino acid sequence

<400> SEQUENCE: 76

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
```

```
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro Gly
            420                 425                 430

Ser Gly Ala Thr Asn Phe Ser Leu Leu Lys Gln Ala Gly Asp Val Glu
        435                 440                 445

Glu Asn Pro Gly Pro Met Pro Leu Gly Leu Leu Trp Leu Gly Leu Ala
    450                 455                 460

Leu Leu Gly Ala Leu His Ala Gln Ala Gly Val Gln Val Glu Thr Ile
465                 470                 475                 480
```

```
Ser Pro Gly Asp Gly Arg Thr Phe Pro Lys Arg Gly Gln Thr Cys Val
                485                 490                 495

Val His Tyr Thr Gly Met Leu Glu Asp Gly Lys Lys Phe Asp Ser Ser
            500                 505                 510

Arg Asp Arg Asn Lys Pro Phe Lys Phe Met Leu Gly Lys Gln Glu Val
        515                 520                 525

Ile Arg Gly Trp Glu Glu Gly Val Ala Gln Met Ser Val Gly Gln Arg
    530                 535                 540

Ala Lys Leu Thr Ile Ser Pro Asp Tyr Ala Tyr Gly Ala Thr Gly His
545                 550                 555                 560

Pro Gly Ile Ile Pro Pro His Ala Thr Leu Val Phe Asp Val Glu Leu
                565                 570                 575

Leu Lys Leu Gly Glu Gly Gly Ser Pro Gly Ser Asn Thr Ser Lys Glu
            580                 585                 590

Asn Pro Phe Leu Phe Ala Leu Glu Ala Val Val Ile Ser Val Gly Ser
        595                 600                 605

Met Gly Leu Ile Ile Ser Leu Leu Cys Val Tyr Phe Trp Leu Glu Arg
    610                 615                 620

Thr Met Pro Arg Ile Pro Thr Leu Lys Asn Leu Glu Asp Leu Val Thr
625                 630                 635                 640

Glu Tyr His Gly Asn Phe Ser Ala Trp Ser Gly Val Ser Lys Gly Leu
                645                 650                 655

Ala Glu Ser Leu Gln Pro Asp Tyr Ser Glu Arg Leu Cys Leu Val Ser
            660                 665                 670

Glu Ile Pro Pro Lys Gly Gly Ala Leu Gly Glu Gly Pro Gly Ala Ser
        675                 680                 685

Pro Cys Asn Gln His Ser Pro Tyr Trp Ala Pro Pro Cys Tyr Thr Leu
    690                 695                 700

Lys Pro Glu Thr Gly Ser Gly Ala Thr Asn Phe Ser Leu Leu Lys Gln
705                 710                 715                 720

Ala Gly Asp Val Glu Glu Asn Pro Gly Pro Met Ala Leu Pro Val Thr
                725                 730                 735

Ala Leu Leu Leu Pro Leu Ala Leu Leu Leu His Ala Ala Arg Pro Ile
            740                 745                 750

Leu Trp His Glu Met Trp His Glu Gly Leu Glu Glu Ala Ser Arg Leu
        755                 760                 765

Tyr Phe Gly Glu Arg Asn Val Lys Gly Met Phe Glu Val Leu Glu Pro
    770                 775                 780

Leu His Ala Met Met Glu Arg Gly Pro Gln Thr Leu Lys Glu Thr Ser
785                 790                 795                 800

Phe Asn Gln Ala Tyr Gly Arg Asp Leu Met Glu Ala Gln Glu Trp Cys
                805                 810                 815

Arg Lys Tyr Met Lys Ser Gly Asn Val Lys Asp Leu Leu Gln Ala Trp
            820                 825                 830

Asp Leu Tyr Tyr His Val Phe Arg Arg Ile Ser Lys Pro Ala Ala Leu
        835                 840                 845

Gly Lys Asp Thr Ile Pro Trp Leu Gly His Leu Leu Val Gly Leu Ser
    850                 855                 860

Gly Ala Phe Gly Phe Ile Ile Leu Val Tyr Leu Leu Ile Asn Cys Arg
865                 870                 875                 880

Asn Thr Gly Pro Trp Leu Lys Lys Val Leu Lys Cys Asn Thr Pro Asp
                885                 890                 895
```

```
Pro Ser Lys Phe Phe Ser Gln Leu Ser Ser Glu His Gly Gly Asp Val
            900                 905                 910

Gln Lys Trp Leu Ser Ser Pro Phe Pro Ser Ser Ser Phe Ser Pro Gly
        915                 920                 925

Gly Leu Ala Pro Glu Ile Ser Pro Leu Glu Val Leu Glu Arg Asp Lys
    930                 935                 940

Val Thr Gln Leu Leu Leu Gln Gln Asp Lys Val Pro Glu Pro Ala Ser
945                 950                 955                 960

Leu Ser Leu Asn Thr Asp Ala Tyr Leu Ser Leu Gln Glu Leu Gln Gly
                965                 970                 975

Ser Gly Ala Thr Asn Phe Ser Leu Leu Lys Gln Ala Gly Asp Val Glu
            980                 985                 990

Glu Asn Pro Gly Pro Glu Met Trp  His Glu Gly Leu Glu  Glu Ala Ser
        995                 1000                1005

Arg Leu  Tyr Phe Gly Glu Arg  Asn Val Lys Gly Met  Phe Glu Val
    1010                1015                1020

Leu Glu  Pro Leu His Ala Met  Met Glu Arg Gly Pro  Gln Thr Leu
    1025                1030                1035

Lys Glu  Thr Ser Phe Asn Gln  Ala Tyr Gly Arg Asp  Leu Met Glu
    1040                1045                1050

Ala Gln  Glu Trp Cys Arg Lys  Tyr Met Lys Ser Gly  Asn Val Lys
    1055                1060                1065

Asp Leu  Leu Gln Ala Trp Asp  Leu Tyr Tyr His Val  Phe Arg Arg
    1070                1075                1080

Ile Ser  Lys
    1085


<210> SEQ ID NO 77
<211> LENGTH: 4080
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: FOXP3cDNA_LNGFRe_uDISC nucleotide sequence
      coding sequence only

<400> SEQUENCE: 77

atgcctaatc ctcggcctgg aaagcctagc gctccttctc ttgctctggg accttctcct      60

ggcgcctctc catcttggag agccgctcct aaagccagcg atctgctggg agctagagga     120

cctggcggca catttcaggg cagagatctt agaggcggag cccacgctag ctcctccagc     180

cttaatccta tgcctcctag ccagctccag ctgcctacac tgcctctggt tatggtggct     240

cctagcggag ctagactggg ccctctgcct catctgcaag ctctgctgca ggacagaccc     300

cacttcatgc accagctgag caccgtggat gcccacgcaa gaacacctgt gctgcaggtt     360

cacccctctgg aatccccagc catgatcagc ctgacacctc caacaacagc caccggcgtg     420

ttcagcctga aagccagacc tggactgcct cctggcatca atgtggccag cctggaatgg     480

gtgtccagag aacctgctct gctgtgcaca ttccccaatc caagcgctcc cagaaaggac     540

agcacactgt ctgccgtgcc tcagagcagc tatcccctgc ttgctaacgg cgtgtgcaag     600

tggcctggat gcgagaaggt gttcgaggaa cccgaggact tcctgaagca ctgccaggcc     660

gatcatctgc tggacgagaa aggcagagcc cagtgtctgc tccagcgcga gatggtgcag     720

tctctggaac agcagctggt cctggaaaaa gaaaagctga gcgccatgca ggcccacctg     780
```

-continued

```
gccggaaaaa tggccctgac aaaggccagc agcgtggcct cttctgataa gggcagctgc    840
tgcattgtgg ccgctggatc tcagggacct gtggttcctg cttggagcgg acctagagag    900
gcccctgatt ctctgtttgc cgtgcggaga cacctgtggg gctctcacgg caactctact    960
ttccccgagt tcctgcacaa catggactac ttcaagttcc acaacatgcg gcctccattc   1020
acctacgcca cactgatcag atgggccatt ctggaagccc ctgagaagca gagaaccctg   1080
aacgagatct accactggtt tacccggatg ttcgccttct tccggaatca ccctgccacc   1140
tggaagaacg ccatccggca caatctgagc ctgcacaagt gcttcgtgcg cgtggaatct   1200
gagaaaggcg ccgtgtggac agtggacgag ctggaattca gaaagaagag aagccagcgg   1260
cctagccggt gcagcaatcc tacacctgga cctggaagcg gagcgactaa cttcagcctg   1320
cttaagcagg ccggagatgt ggaggaaaac cctggaccga tgcctctggg cctgctgtgg   1380
ctgggcctgg ccctgctggg cgccctgcac gcccaggcca tgggggcagg tgccaccgga   1440
cgagccatgg acgggccgcg cctgctgctg ttgctgcttc tgggggtgtc ccttggaggt   1500
gccaaggagg catgccccac aggcctgtac acacacagcg gtgagtgctg caaagcctgc   1560
aacctgggcg agggtgtggc ccagccttgt ggagccaacc agaccgtgtg tgagccctgc   1620
ctggacagcg tgacgttctc cgacgtggtg agcgcgaccg agccgtgcaa gccgtgcacc   1680
gagtgcgtgg ggctccagag catgtcggcg ccgtgcgtgg aggccgacga cgccgtgtgc   1740
cgctgcgcct acggctacta ccaggatgag acgactgggc gctgcgaggc gtgccgcgtg   1800
tgcgaggcgg gctcgggcct cgtgttctcc tgccaggaca agcagaacac cgtgtgcgag   1860
gagtgccccg acggcacgta ttccgacgag gccaaccacg tggacccgtg cctgccctgc   1920
accgtgtgcg aggacaccga gcgccagctc cgcgagtgca cacgctgggc cgacgccgag   1980
tgcgaggaga tccctggccg ttggattaca cggtccacac ccccagaggg ctcggacagc   2040
acagccccca gcacccagga gcctgaggca cctccagaac aagacctcat agccagcacg   2100
gtggcaggtg tggtgaccac agtgatgggc agctcccagc ccgtggtgac ccgaggcacc   2160
accgacaacc tcatccctgt ctattgctcc atcctggctg ctgtggttgt gggtcttgtg   2220
gcctacatag ccttcaagag gggcgtgcag gtggagacaa tctccccagg cgacggacgc   2280
acattcccta agcggggcca gacctgcgtg gtgcactata caggcatgct ggaggatggc   2340
aagaagtttg acagctcccg ggatagaaac aagccattca agtttatgct gggcaagcag   2400
gaagtgatca gaggctggga ggagggcgtg gcccagatgt ctgtgggcca gagggccaag   2460
ctgaccatca gcccagacta cgcctatgga gcaacaggcc acccaggaat catcccacct   2520
cacgccaccc tggtgttcga tgtggagctg ctgaagctgg gcgagggagg gtcacctgga   2580
tccaacacat caaaagagaa cccctttctg ttcgcattgg aggccgtagt catatctgtt   2640
ggatccatgg gacttattat ctccctgttg tgtgtgtact tctggctgga acggactatg   2700
cccaggatcc ccacgctcaa gaatctggaa gatctcgtca cagaatacca tggtaatttc   2760
agcgcctgga gcggagtctc taagggtctg gccgaatccc tccaacccga ttattctgaa   2820
cggttgtgcc tcgtatccga aataccacca aaaggcgggg ctctgggtga gggcccaggg   2880
gcgagtccgt gcaatcaaca cagcccgtat tgggcccctc cttgttatac gttgaagccc   2940
gaaactggaa gcggagctac taacttcagc ctgctgaagc aggctggaga cgtggaggag   3000
aaccctggac ctatggcact gcccgtgacc gccctgctgc tgcctctggc cctgctgctg   3060
cacgcagccc ggcctatcct gtggcacgag atgtggcacg agggcctgga ggaggccagc   3120
aggctgtatt ttggcgagcg caacgtgaag ggcatgttcg aggtgctgga gcctctgcac   3180
```

```
gccatgatgg agagaggccc acagaccctg aaggagacat cctttaacca ggcctatgga   3240

cgggacctga tggaggcaca ggagtggtgc agaaagtaca tgaagtctgg caatgtgaag   3300

gacctgctgc aggcctggga tctgtactat cacgtgtttc ggagaatctc caagccagca   3360

gctctcggca aagacacgat tccgtggctt gggcatctgc tcgttgggct gagcggtgcg   3420

tttggtttca tcatcttggt ctatctcttg atcaattgca gaaatacagg cccttggctg   3480

aaaaaagtgc tcaagtgtaa taccccccgac ccaagcaagt tcttctccca gctttcttca   3540

gagcatggag gcgatgtgca gaaatggctc tcttcacctt ttccctcctc aagcttctcc   3600

ccgggagggc tggcgcccga gatttcacct cttgaggtac ttgaacgaga caaggttacc   3660

caacttctcc ttcaacagga taaggtaccc gaacctgcga gccttagctt gaatacagac   3720

gcttatctct cactgcagga actgcaagga tctggtgcta ctaatttttc tcttttgaag   3780

caagctggag atgttgaaga gaaccccggt ccggagatgt ggcatgaggg tctggaagaa   3840

gcgtctcgac tgtactttgg tgagcgcaat gtgaagggca tgtttgaagt cctcgaaccc   3900

cttcatgcca tgatggaacg cggaccccag accttgaagg agacaagttt taaccaagct   3960

tacggaagag acctgatgga agcccaggaa tggtgcagga aatacatgaa aagcgggaat   4020

gtgaaggact tgctccaagc gtgggacctg tactatcatg tctttaggcg cattagtaag   4080
```

<210> SEQ ID NO 78
<211> LENGTH: 1360
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: FOXP3cDNA_LNGFRe_uDISC amino acid sequence

<400> SEQUENCE: 78

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190
```

```
Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro Gly
            420                 425                 430

Ser Gly Ala Thr Asn Phe Ser Leu Leu Lys Gln Ala Gly Asp Val Glu
        435                 440                 445

Glu Asn Pro Gly Pro Met Pro Leu Gly Leu Leu Trp Leu Gly Leu Ala
    450                 455                 460

Leu Leu Gly Ala Leu His Ala Gln Ala Met Gly Ala Gly Ala Thr Gly
465                 470                 475                 480

Arg Ala Met Asp Gly Pro Arg Leu Leu Leu Leu Leu Leu Leu Gly Val
                485                 490                 495

Ser Leu Gly Gly Ala Lys Glu Ala Cys Pro Thr Gly Leu Tyr Thr His
            500                 505                 510

Ser Gly Glu Cys Cys Lys Ala Cys Asn Leu Gly Glu Gly Val Ala Gln
        515                 520                 525

Pro Cys Gly Ala Asn Gln Thr Val Cys Glu Pro Cys Leu Asp Ser Val
    530                 535                 540

Thr Phe Ser Asp Val Val Ser Ala Thr Glu Pro Cys Lys Pro Cys Thr
545                 550                 555                 560

Glu Cys Val Gly Leu Gln Ser Met Ser Ala Pro Cys Val Glu Ala Asp
                565                 570                 575

Asp Ala Val Cys Arg Cys Ala Tyr Gly Tyr Tyr Gln Asp Glu Thr Thr
            580                 585                 590

Gly Arg Cys Glu Ala Cys Arg Val Cys Glu Ala Gly Ser Gly Leu Val
        595                 600                 605
```

-continued

```
Phe Ser Cys Gln Asp Lys Gln Asn Thr Val Cys Glu Glu Cys Pro Asp
    610                 615                 620

Gly Thr Tyr Ser Asp Glu Ala Asn His Val Asp Pro Cys Leu Pro Cys
625                 630                 635                 640

Thr Val Cys Glu Asp Thr Glu Arg Gln Leu Arg Glu Cys Thr Arg Trp
                645                 650                 655

Ala Asp Ala Glu Cys Glu Glu Ile Pro Gly Arg Trp Ile Thr Arg Ser
            660                 665                 670

Thr Pro Pro Glu Gly Ser Asp Ser Thr Ala Pro Ser Thr Gln Glu Pro
        675                 680                 685

Glu Ala Pro Pro Glu Gln Asp Leu Ile Ala Ser Thr Val Ala Gly Val
    690                 695                 700

Val Thr Thr Val Met Gly Ser Ser Gln Pro Val Val Thr Arg Gly Thr
705                 710                 715                 720

Thr Asp Asn Leu Ile Pro Val Tyr Cys Ser Ile Leu Ala Ala Val Val
                725                 730                 735

Val Gly Leu Val Ala Tyr Ile Ala Phe Lys Arg Gly Val Gln Val Glu
            740                 745                 750

Thr Ile Ser Pro Gly Asp Gly Arg Thr Phe Pro Lys Arg Gly Gln Thr
        755                 760                 765

Cys Val Val His Tyr Thr Gly Met Leu Glu Asp Gly Lys Lys Phe Asp
    770                 775                 780

Ser Ser Arg Asp Arg Asn Lys Pro Phe Lys Phe Met Leu Gly Lys Gln
785                 790                 795                 800

Glu Val Ile Arg Gly Trp Glu Glu Gly Val Ala Gln Met Ser Val Gly
                805                 810                 815

Gln Arg Ala Lys Leu Thr Ile Ser Pro Asp Tyr Ala Tyr Gly Ala Thr
            820                 825                 830

Gly His Pro Gly Ile Ile Pro Pro His Ala Thr Leu Val Phe Asp Val
        835                 840                 845

Glu Leu Leu Lys Leu Gly Glu Gly Gly Ser Pro Gly Ser Asn Thr Ser
    850                 855                 860

Lys Glu Asn Pro Phe Leu Phe Ala Leu Glu Ala Val Val Ile Ser Val
865                 870                 875                 880

Gly Ser Met Gly Leu Ile Ile Ser Leu Leu Cys Val Tyr Phe Trp Leu
                885                 890                 895

Glu Arg Thr Met Pro Arg Ile Pro Thr Leu Lys Asn Leu Glu Asp Leu
            900                 905                 910

Val Thr Glu Tyr His Gly Asn Phe Ser Ala Trp Ser Gly Val Ser Lys
        915                 920                 925

Gly Leu Ala Glu Ser Leu Gln Pro Asp Tyr Ser Glu Arg Leu Cys Leu
    930                 935                 940

Val Ser Glu Ile Pro Pro Lys Gly Gly Ala Leu Gly Glu Gly Pro Gly
945                 950                 955                 960

Ala Ser Pro Cys Asn Gln His Ser Pro Tyr Trp Ala Pro Pro Cys Tyr
                965                 970                 975

Thr Leu Lys Pro Glu Thr Gly Ser Gly Ala Thr Asn Phe Ser Leu Leu
            980                 985                 990

Lys Gln Ala Gly Asp Val Glu Glu  Asn Pro Gly Pro Met  Ala Leu Pro
        995                 1000                1005

Val Thr  Ala Leu Leu Leu Pro  Leu Ala Leu Leu Leu  His Ala Ala
    1010                1015                1020

Arg Pro  Ile Leu Trp His Glu  Met Trp His Glu Gly  Leu Glu Glu
```

```
    1025                1030                1035

Ala Ser  Arg Leu Tyr Phe Gly  Glu Arg Asn Val Lys  Gly Met Phe
    1040                1045                1050

Glu Val  Leu Glu Pro Leu His  Ala Met Met Glu Arg  Gly Pro Gln
    1055                1060                1065

Thr Leu  Lys Glu Thr Ser Phe  Asn Gln Ala Tyr Gly  Arg Asp Leu
    1070                1075                1080

Met Glu  Ala Gln Glu Trp Cys  Arg Lys Tyr Met Lys  Ser Gly Asn
    1085                1090                1095

Val Lys  Asp Leu Leu Gln Ala  Trp Asp Leu Tyr Tyr  His Val Phe
    1100                1105                1110

Arg Arg  Ile Ser Lys Pro Ala  Ala Leu Gly Lys Asp  Thr Ile Pro
    1115                1120                1125

Trp Leu  Gly His Leu Leu Val  Gly Leu Ser Gly Ala  Phe Gly Phe
    1130                1135                1140

Ile Ile  Leu Val Tyr Leu Leu  Ile Asn Cys Arg Asn  Thr Gly Pro
    1145                1150                1155

Trp Leu  Lys Lys Val Leu Lys  Cys Asn Thr Pro Asp  Pro Ser Lys
    1160                1165                1170

Phe Phe  Ser Gln Leu Ser Ser  Glu His Gly Gly Asp  Val Gln Lys
    1175                1180                1185

Trp Leu  Ser Ser Pro Phe Pro  Ser Ser Ser Phe Ser  Pro Gly Gly
    1190                1195                1200

Leu Ala  Pro Glu Ile Ser Pro  Leu Glu Val Leu Glu  Arg Asp Lys
    1205                1210                1215

Val Thr  Gln Leu Leu Leu Gln  Gln Asp Lys Val Pro  Glu Pro Ala
    1220                1225                1230

Ser Leu  Ser Leu Asn Thr Asp  Ala Tyr Leu Ser Leu  Gln Glu Leu
    1235                1240                1245

Gln Gly  Ser Gly Ala Thr Asn  Phe Ser Leu Leu Lys  Gln Ala Gly
    1250                1255                1260

Asp Val  Glu Glu Asn Pro Gly  Pro Glu Met Trp His  Glu Gly Leu
    1265                1270                1275

Glu Glu  Ala Ser Arg Leu Tyr  Phe Gly Glu Arg Asn  Val Lys Gly
    1280                1285                1290

Met Phe  Glu Val Leu Glu Pro  Leu His Ala Met Met  Glu Arg Gly
    1295                1300                1305

Pro Gln  Thr Leu Lys Glu Thr  Ser Phe Asn Gln Ala  Tyr Gly Arg
    1310                1315                1320

Asp Leu  Met Glu Ala Gln Glu  Trp Cys Arg Lys Tyr  Met Lys Ser
    1325                1330                1335

Gly Asn  Val Lys Asp Leu Leu  Gln Ala Trp Asp Leu  Tyr Tyr His
    1340                1345                1350

Val Phe  Arg Arg Ile Ser Lys
    1355                1360
```

<210> SEQ ID NO 79
<211> LENGTH: 3258
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: uDISC_FOXP3cDNA nucleotide sequence coding
sequence only

<400> SEQUENCE: 79
atgcctctgg gcctgctgtg gctgggcctg gccctgctgg gcgccctgca cgcccaggcc 60
ggcgtgcagg tggagacaat ctccccaggc gacggacgca cattccctaa gcggggccag 120
acctgcgtgg tgcactatac aggcatgctg gaggatggca agaagtttga cagctcccgg 180
gatagaaaca agccattcaa gtttatgctg ggcaagcagg aagtgatcag aggctgggag 240
gagggcgtgg cccagatgtc tgtgggccag agggccaagc tgaccatcag cccagactac 300
gcctatggag caacaggcca cccaggaatc atcccacctc acgccaccct ggtgttcgat 360
gtggagctgc tgaagctggg cgagggaggg tcacctggat ccaacacatc aaaagagaac 420
ccctttctgt tcgcattgga ggccgtagtc atatctgttg gatccatggg acttattatc 480
tccctgttgt gtgtgtactt ctggctggaa cggactatgc ccaggatccc cacgctcaag 540
aatctggaag atctcgtcac agaataccat ggtaatttca gcgcctggag cggagtctct 600
aagggtctgg ccgaatccct ccaacccgat tattctgaac ggttgtgcct cgtatccgaa 660
ataccaccaa aaggcggggc tctgggtgag ggcccagggg cgagtccgtg caatcaacac 720
agcccgtatt gggcccctcc ttgttatacg ttgaagcccg aaactggaag cggagctact 780
aacttcagcc tgctgaagca ggctggagac gtggaggaga accctggacc tatggcactg 840
cccgtgaccg ccctgctgct gcctctggcc ctgctgctgc acgcagcccg gcctatcctg 900
tggcacgaga tgtggcacga gggcctggag gaggccagca ggctgtattt tggcgagcgc 960
aacgtgaagg gcatgttcga ggtgctggag cctctgcacg ccatgatgga gagaggccca 1020
cagaccctga aggagacatc ctttaaccag gcctatggac gggacctgat ggaggcacag 1080
gagtggtgca gaaagtacat gaagtctggc aatgtgaagg acctgctgca ggcctgggat 1140
ctgtactatc acgtgtttcg gagaatctcc aagccagcag ctctcggcaa agacacgatt 1200
ccgtggcttg ggcatctgct cgttgggctg agcggtgcgt ttggtttcat catcttggtc 1260
tatctcttga tcaattgcag aaatacaggc ccttggctga aaaaagtgct caagtgtaat 1320
acccccgacc caagcaagtt cttctcccag ctttcttcag agcatggagg cgatgtgcag 1380
aaatggctct cttcaccttt tccctcctca agcttctccc cgggagggct ggcgcccgag 1440
atttcacctc ttgaggtact tgaacgagac aaggttaccc aacttctcct tcaacaggat 1500
aaggtacccg aacctgcgag ccttagcttg aatacagacg cttatctctc actgcaggaa 1560
ctgcaaggat ctggtgctac taatttttct cttttgaagc aagctggaga tgttgaagag 1620
aaccccggtc cggagatgtg gcatgagggt ctggaagaag cgtctcgact gtactttggt 1680
gagcgcaatg tgaagggcat gtttgaagtc ctcgaacccc ttcatgccat gatggaacgc 1740
ggaccccaga ccttgaagga gacaagtttt aaccaagctt acggaagaga cctgatggaa 1800
gcccaggaat ggtgcaggaa atacatgaaa agcgggaatg tgaaggactt gctccaagcg 1860
tgggacctgt actatcatgt ctttaggcgc attagtaagg gaagcggagc gactaacttc 1920
agcctgctta agcaggccgg agatgtggag gaaaaccctg gaccgatgcc taatcctcgg 1980
cctggaaagc ctagcgctcc ttctcttgct ctgggacctt ctcctggcgc ctctccatct 2040
tggagagccg ctcctaaagc cagcgatctg ctgggagcta gaggacctgg cggcacattt 2100
cagggcagag atcttagagg cggagcccac gctagctcct ccagccttaa tcctatgcct 2160
cctagccagc tccagctgcc tacactgcct ctggttatgg tggctcctag cggagctaga 2220
ctgggccctc tgcctcatct gcaagctctg ctgcaggaca gaccccactt catgcaccag 2280

```
ctgagcaccg tggatgccca cgcaagaaca cctgtgctgc aggttcaccc tctggaatcc   2340

ccagccatga tcagcctgac acctccaaca acagccaccg gcgtgttcag cctgaaagcc   2400

agacctggac tgcctcctgg catcaatgtg gccagcctgg aatgggtgtc cagagaacct   2460

gctctgctgt gcacattccc caatccaagc gctcccagaa aggacagcac actgtctgcc   2520

gtgcctcaga gcagctatcc cctgcttgct aacggcgtgt gcaagtggcc tggatgcgag   2580

aaggtgttcg aggaacccga ggacttcctg aagcactgcc aggccgatca tctgctggac   2640

gagaaaggca gagcccagtg tctgctccag cgcgagatgg tgcagtctct ggaacagcag   2700

ctggtcctgg aaaaagaaaa gctgagcgcc atgcaggccc acctggccgg aaaaatggcc   2760

ctgacaaagg ccagcagcgt ggcctcttct gataagggca gctgctgcat tgtggccgct   2820

ggatctcagg gacctgtggt tcctgcttgg agcggaccta gagaggcccc tgattctctg   2880

tttgccgtgc ggagacacct gtggggctct cacggcaact ctactttccc cgagttcctg   2940

cacaacatgg actacttcaa gttccacaac atgcggcctc cattcaccta cgccacactg   3000

atcagatggg ccattctgga agcccctgag aagcagagaa ccctgaacga gatctaccac   3060

tggtttaccc ggatgttcgc cttcttccgg aatcaccctg ccacctggaa gaacgccatc   3120

cggcacaatc tgagcctgca caagtgcttc gtgcgcgtgg aatctgagaa aggcgccgtg   3180

tggacagtgg acgagctgga attcagaaag aagagaagcc agcggcctag ccggtgcagc   3240

aatcctacac ctggacct                                                 3258
```

<210> SEQ ID NO 80
<211> LENGTH: 1086
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: uDISC_FOXP3cDNA amino acid sequence

<400> SEQUENCE: 80

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Gly Gly Ser Pro Gly Ser Asn Thr Ser Lys Glu Asn Pro Phe Leu Phe
    130                 135                 140

Ala Leu Glu Ala Val Val Ile Ser Val Gly Ser Met Gly Leu Ile Ile
145                 150                 155                 160

Ser Leu Leu Cys Val Tyr Phe Trp Leu Glu Arg Thr Met Pro Arg Ile
                165                 170                 175
```

```
Pro Thr Leu Lys Asn Leu Glu Asp Leu Val Thr Glu Tyr His Gly Asn
            180                 185                 190

Phe Ser Ala Trp Ser Gly Val Ser Lys Gly Leu Ala Glu Ser Leu Gln
        195                 200                 205

Pro Asp Tyr Ser Glu Arg Leu Cys Leu Val Ser Glu Ile Pro Pro Lys
    210                 215                 220

Gly Gly Ala Leu Gly Glu Gly Pro Gly Ala Ser Pro Cys Asn Gln His
225                 230                 235                 240

Ser Pro Tyr Trp Ala Pro Pro Cys Tyr Thr Leu Lys Pro Glu Thr Gly
                245                 250                 255

Ser Gly Ala Thr Asn Phe Ser Leu Leu Lys Gln Ala Gly Asp Val Glu
            260                 265                 270

Glu Asn Pro Gly Pro Met Ala Leu Pro Val Thr Ala Leu Leu Leu Pro
        275                 280                 285

Leu Ala Leu Leu Leu His Ala Ala Arg Pro Ile Leu Trp His Glu Met
    290                 295                 300

Trp His Glu Gly Leu Glu Glu Ala Ser Arg Leu Tyr Phe Gly Glu Arg
305                 310                 315                 320

Asn Val Lys Gly Met Phe Glu Val Leu Glu Pro Leu His Ala Met Met
                325                 330                 335

Glu Arg Gly Pro Gln Thr Leu Lys Glu Thr Ser Phe Asn Gln Ala Tyr
            340                 345                 350

Gly Arg Asp Leu Met Glu Ala Gln Glu Trp Cys Arg Lys Tyr Met Lys
        355                 360                 365

Ser Gly Asn Val Lys Asp Leu Leu Gln Ala Trp Asp Leu Tyr Tyr His
    370                 375                 380

Val Phe Arg Arg Ile Ser Lys Pro Ala Ala Leu Gly Lys Asp Thr Ile
385                 390                 395                 400

Pro Trp Leu Gly His Leu Leu Val Gly Leu Ser Gly Ala Phe Gly Phe
                405                 410                 415

Ile Ile Leu Val Tyr Leu Leu Ile Asn Cys Arg Asn Thr Gly Pro Trp
            420                 425                 430

Leu Lys Lys Val Leu Lys Cys Asn Thr Pro Asp Pro Ser Lys Phe Phe
        435                 440                 445

Ser Gln Leu Ser Ser Glu His Gly Gly Asp Val Gln Lys Trp Leu Ser
    450                 455                 460

Ser Pro Phe Pro Ser Ser Ser Phe Ser Pro Gly Gly Leu Ala Pro Glu
465                 470                 475                 480

Ile Ser Pro Leu Glu Val Leu Glu Arg Asp Lys Val Thr Gln Leu Leu
                485                 490                 495

Leu Gln Gln Asp Lys Val Pro Glu Pro Ala Ser Leu Ser Leu Asn Thr
            500                 505                 510

Asp Ala Tyr Leu Ser Leu Gln Glu Leu Gln Gly Ser Gly Ala Thr Asn
        515                 520                 525

Phe Ser Leu Leu Lys Gln Ala Gly Asp Val Glu Glu Asn Pro Gly Pro
    530                 535                 540

Glu Met Trp His Glu Gly Leu Glu Glu Ala Ser Arg Leu Tyr Phe Gly
545                 550                 555                 560

Glu Arg Asn Val Lys Gly Met Phe Glu Val Leu Glu Pro Leu His Ala
                565                 570                 575

Met Met Glu Arg Gly Pro Gln Thr Leu Lys Glu Thr Ser Phe Asn Gln
            580                 585                 590
```

-continued

```
Ala Tyr Gly Arg Asp Leu Met Glu Ala Gln Glu Trp Cys Arg Lys Tyr
        595                 600                 605

Met Lys Ser Gly Asn Val Lys Asp Leu Leu Gln Ala Trp Asp Leu Tyr
    610                 615                 620

Tyr His Val Phe Arg Arg Ile Ser Lys Gly Ser Gly Ala Thr Asn Phe
625                 630                 635                 640

Ser Leu Leu Lys Gln Ala Gly Asp Val Glu Glu Asn Pro Gly Pro Met
                645                 650                 655

Pro Asn Pro Arg Pro Gly Lys Pro Ser Ala Pro Ser Leu Ala Leu Gly
            660                 665                 670

Pro Ser Pro Gly Ala Ser Pro Ser Trp Arg Ala Ala Pro Lys Ala Ser
        675                 680                 685

Asp Leu Leu Gly Ala Arg Gly Pro Gly Gly Thr Phe Gln Gly Arg Asp
    690                 695                 700

Leu Arg Gly Gly Ala His Ala Ser Ser Ser Ser Leu Asn Pro Met Pro
705                 710                 715                 720

Pro Ser Gln Leu Gln Leu Pro Thr Leu Pro Leu Val Met Val Ala Pro
                725                 730                 735

Ser Gly Ala Arg Leu Gly Pro Leu Pro His Leu Gln Ala Leu Leu Gln
            740                 745                 750

Asp Arg Pro His Phe Met His Gln Leu Ser Thr Val Asp Ala His Ala
        755                 760                 765

Arg Thr Pro Val Leu Gln Val His Pro Leu Glu Ser Pro Ala Met Ile
    770                 775                 780

Ser Leu Thr Pro Pro Thr Thr Ala Thr Gly Val Phe Ser Leu Lys Ala
785                 790                 795                 800

Arg Pro Gly Leu Pro Pro Gly Ile Asn Val Ala Ser Leu Glu Trp Val
                805                 810                 815

Ser Arg Glu Pro Ala Leu Leu Cys Thr Phe Pro Asn Pro Ser Ala Pro
            820                 825                 830

Arg Lys Asp Ser Thr Leu Ser Ala Val Pro Gln Ser Ser Tyr Pro Leu
        835                 840                 845

Leu Ala Asn Gly Val Cys Lys Trp Pro Gly Cys Glu Lys Val Phe Glu
    850                 855                 860

Glu Pro Glu Asp Phe Leu Lys His Cys Gln Ala Asp His Leu Leu Asp
865                 870                 875                 880

Glu Lys Gly Arg Ala Gln Cys Leu Leu Gln Arg Glu Met Val Gln Ser
                885                 890                 895

Leu Glu Gln Gln Leu Val Leu Glu Lys Glu Lys Leu Ser Ala Met Gln
            900                 905                 910

Ala His Leu Ala Gly Lys Met Ala Leu Thr Lys Ala Ser Ser Val Ala
        915                 920                 925

Ser Ser Asp Lys Gly Ser Cys Cys Ile Val Ala Ala Gly Ser Gln Gly
    930                 935                 940

Pro Val Val Pro Ala Trp Ser Gly Pro Arg Glu Ala Pro Asp Ser Leu
945                 950                 955                 960

Phe Ala Val Arg Arg His Leu Trp Gly Ser His Gly Asn Ser Thr Phe
                965                 970                 975

Pro Glu Phe Leu His Asn Met Asp Tyr Phe Lys Phe His Asn Met Arg
            980                 985                 990

Pro Pro Phe Thr Tyr Ala Thr Leu  Ile Arg Trp Ala Ile  Leu Glu Ala
        995                 1000                1005

Pro Glu  Lys Gln Arg Thr Leu  Asn Glu Ile Tyr His  Trp Phe Thr
```

```
    1010                1015                1020

Arg Met  Phe Ala Phe Phe Arg  Asn His Pro Ala Thr  Trp Lys Asn
    1025                1030                1035

Ala Ile  Arg His Asn Leu Ser  Leu His Lys Cys Phe  Val Arg Val
    1040                1045                1050

Glu Ser  Glu Lys Gly Ala Val  Trp Thr Val Asp Glu  Leu Glu Phe
    1055                1060                1065

Arg Lys  Lys Arg Ser Gln Arg  Pro Ser Arg Cys Ser  Asn Pro Thr
    1070                1075                1080

Pro Gly  Pro
    1085


<210> SEQ ID NO 81
<211> LENGTH: 4083
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: LNGFRe_uDISC _FOXP3cDNA nucleotide sequence
      coding sequence only

<400> SEQUENCE: 81

atgcctctgg gcctgctgtg gctgggcctg gccctgctgg gcgccctgca cgcccaggcc     60

atgggggcag gtgccaccgg acgagccatg gacgggccgc gcctgctgct gttgctgctt    120

ctgggggtgt cccttggagg tgccaaggag gcatgcccca caggcctgta cacacacagc    180

ggtgagtgct gcaaagcctg caacctgggc gagggtgtgg cccagccttg tggagccaac    240

cagaccgtgt gtgagccctg cctggacagc gtgacgttct ccgacgtggt gagcgcgacc    300

gagccgtgca agccgtgcac cgagtgcgtg gggctccaga gcatgtcggc gccgtgcgtg    360

gaggccgacg acgccgtgtg ccgctgcgcc tacggctact accaggatga gacgactggg    420

cgctgcgagg cgtgccgcgt gtgcgaggcg ggctcgggcc tcgtgttctc ctgccaggac    480

aagcagaaca ccgtgtgcga ggagtgcccc gacggcacgt attccgacga ggccaaccac    540

gtggacccgt gcctgccctg caccgtgtgc gaggacaccg agcgccagct ccgcgagtgc    600

acacgctggg ccgacgccga gtgcgaggag atccctggcc gttggattac acggtccaca    660

cccccagagg gctcggacag cacagccccc agcacccagg agcctgaggc acctccagaa    720

caagacctca tagccagcac ggtggcaggt gtggtgacca cagtgatggg cagctcccag    780

cccgtggtga cccgaggcac caccgacaac ctcatccctg tctattgctc catcctggct    840

gctgtggttg tgggtcttgt ggcctacata gccttcaaga ggggcgtgca ggtggagaca    900

atctccccag gcgacggacg cacattccct aagcggggcc agacctgcgt ggtgcactat    960

acaggcatgc tggaggatgg caagaagttt gacagctccc gggatagaaa caagccattc   1020

aagtttatgc tgggcaagca ggaagtgatc agaggctggg aggagggcgt ggcccagatg   1080

tctgtgggcc agagggccaa gctgaccatc agcccagact acgcctatgg agcaacaggc   1140

cacccaggaa tcatcccacc tcacgccacc ctggtgttcg atgtggagct gctgaagctg   1200

ggcgagggag ggtcacctgg atccaacaca tcaaaagaga accccttttct gttcgcattg   1260

gaggccgtag tcatatctgt tggatccatg ggacttatta tctccctgtt gtgtgtgtac   1320

ttctggctgg aacggactat gcccaggatc cccacgctca agaatctgga agatctcgtc   1380

acagaatacc atggtaattt cagcgcctgg agcggagtct ctaagggtct ggccgaatcc   1440
```

-continued ctccaacccg attattctga acggttgtgc ctcgtatccg aaataccacc aaaaggcggg 1500
gctctgggtg agggcccagg ggcgagtccg tgcaatcaac acagcccgta ttgggcccct 1560
ccttgttata cgttgaagcc cgaaactgga agcggagcta ctaacttcag cctgctgaag 1620
caggctggag acgtggagga gaaccctgga cctatggcac tgcccgtgac cgccctgctg 1680
ctgcctctgg ccctgctgct gcacgcagcc cggcctatcc tgtggcacga gatgtggcac 1740
gagggcctgg aggaggccag caggctgtat tttggcgagc gcaacgtgaa gggcatgttc 1800
gaggtgctgg agcctctgca cgccatgatg gagagaggcc cacagaccct gaaggagaca 1860
tcctttaacc aggcctatgg acgggacctg atggaggcac aggagtggtg cagaaagtac 1920
atgaagtctg gcaatgtgaa ggacctgctg caggcctggg atctgtacta tcacgtgttt 1980
cggagaatct ccaagccagc agctctcggc aaagacacga ttccgtggct tgggcatctg 2040
ctcgttgggc tgagcggtgc gtttggtttc atcatcttgg tctatctctt gatcaattgc 2100
agaaatacag gcccttggct gaaaaaagtg ctcaagtgta ataccccga cccaagcaag 2160 ttcttctccc agctttcttc agagcatgga ggcgatgtgc agaaatggct ctcttcacct 2220
tttccctcct caagcttctc cccgggaggg ctggcgcccg agatttcacc tcttgaggta 2280
cttgaacgag acaaggttac ccaacttctc cttcaacagg ataaggtacc cgaacctgcg 2340
agccttagct tgaatacaga cgcttatctc tcactgcagg aactgcaagg atctggtgct 2400
actaattttt ctcttttgaa gcaagctgga gatgttgaag agaaccccgg tccggagatg 2460
tggcatgagg gtctggaaga agcgtctcga ctgtactttg gtgagcgcaa tgtgaagggc 2520
atgtttgaag tcctcgaacc ccttcatgcc atgatggaac gcggacccca gaccttgaag 2580
gagacaagtt ttaaccaagc ttacggaaga gacctgatgg aagcccagga atggtgcagg 2640
aaatacatga aaagcgggaa tgtgaaggac ttgctccaag cgtgggacct gtactatcat 2700
gtctttaggc gcattagtaa gggaagcgga gcgactaact tcagcctgct taagcaggcc 2760
ggagatgtgg aggaaaaccc tggaccgatg cctaatcctc ggcctggaaa gcctagcgct 2820
ccttctcttg ctctgggacc ttctcctggc gcctctccat cttggagagc cgctcctaaa 2880
gccagcgatc tgctgggagc tagaggacct ggcggcacat ttcagggcag agatcttaga 2940
ggcggagccc acgctagctc ctccagcctt aatcctatgc ctcctagcca gctccagctg 3000
cctacactgc ctctggttat ggtggctcct agcggagcta gactgggccc tctgcctcat 3060
ctgcaagctc tgctgcagga cagaccccac ttcatgcacc agctgagcac cgtggatgcc 3120
cacgcaagaa cacctgtgct gcaggttcac cctctggaat ccccagccat gatcagcctg 3180
acacctccaa caacagccac cggcgtgttc agcctgaaag ccagacctgg actgcctcct 3240
ggcatcaatg tggccagcct ggaatgggtg tccagagaac ctgctctgct gtgcacattc 3300
cccaatccaa gcgctcccag aaaggacagc acactgtctg ccgtgcctca gagcagctat 3360
cccctgcttg ctaacggcgt gtgcaagtgg cctggatgcg agaaggtgtt cgaggaaccc 3420
gaggacttcc tgaagcactg ccaggccgat catctgctgg acgagaaagg cagagcccag 3480
tgtctgctcc agcgcgagat ggtgcagtct ctggaacagc agctggtcct ggaaaaagaa 3540
aagctgagcg ccatgcaggc ccacctggcc ggaaaaatgg ccctgacaaa ggccagcagc 3600
gtggcctctt ctgataaggg cagctgctgc attgtggccg ctggatctca gggacctgtg 3660
gttcctgctt ggagcggacc tagagaggcc cctgattctc tgtttgccgt gcggagacac 3720
ctgtggggct ctcacggcaa ctctactttc cccgagttcc tgcacaacat ggactacttc 3780
aagttccaca acatgcggcc tccattcacc tacgccacac tgatcagatg ggccattctg 3840

```
gaagcccctg agaagcagag aaccctgaac gagatctacc actggtttac ccggatgttc   3900

gccttcttcc ggaatcaccc tgccacctgg aagaacgcca tccggcacaa tctgagcctg   3960

cacaagtgct tcgtgcgcgt ggaatctgag aaaggcgccg tgtggacagt ggacgagctg   4020

gaattcagaa agaagagaag ccagcggcct agccggtgca gcaatcctac acctggacct   4080

tga                                                                 4083


<210> SEQ ID NO 82
<211> LENGTH: 1360
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: LNGFRe_uDISC_FOXP3cDNA amino acid sequence

<400> SEQUENCE: 82

Met Pro Leu Gly Leu Leu Trp Leu Gly Leu Ala Leu Leu Gly Ala Leu
1               5                   10                  15

His Ala Gln Ala Met Gly Ala Gly Ala Thr Gly Arg Ala Met Asp Gly
            20                  25                  30

Pro Arg Leu Leu Leu Leu Leu Leu Leu Gly Val Ser Leu Gly Gly Ala
        35                  40                  45

Lys Glu Ala Cys Pro Thr Gly Leu Tyr Thr His Ser Gly Glu Cys Cys
    50                  55                  60

Lys Ala Cys Asn Leu Gly Glu Gly Val Ala Gln Pro Cys Gly Ala Asn
65                  70                  75                  80

Gln Thr Val Cys Glu Pro Cys Leu Asp Ser Val Thr Phe Ser Asp Val
                85                  90                  95

Val Ser Ala Thr Glu Pro Cys Lys Pro Cys Thr Glu Cys Val Gly Leu
            100                 105                 110

Gln Ser Met Ser Ala Pro Cys Val Glu Ala Asp Asp Ala Val Cys Arg
        115                 120                 125

Cys Ala Tyr Gly Tyr Tyr Gln Asp Glu Thr Thr Gly Arg Cys Glu Ala
    130                 135                 140

Cys Arg Val Cys Glu Ala Gly Ser Gly Leu Val Phe Ser Cys Gln Asp
145                 150                 155                 160

Lys Gln Asn Thr Val Cys Glu Glu Cys Pro Asp Gly Thr Tyr Ser Asp
                165                 170                 175

Glu Ala Asn His Val Asp Pro Cys Leu Pro Cys Thr Val Cys Glu Asp
            180                 185                 190

Thr Glu Arg Gln Leu Arg Glu Cys Thr Arg Trp Ala Asp Ala Glu Cys
        195                 200                 205

Glu Glu Ile Pro Gly Arg Trp Ile Thr Arg Ser Thr Pro Pro Glu Gly
    210                 215                 220

Ser Asp Ser Thr Ala Pro Ser Thr Gln Glu Pro Glu Ala Pro Pro Glu
225                 230                 235                 240

Gln Asp Leu Ile Ala Ser Thr Val Ala Gly Val Val Thr Thr Val Met
                245                 250                 255

Gly Ser Ser Gln Pro Val Val Thr Arg Gly Thr Thr Asp Asn Leu Ile
            260                 265                 270

Pro Val Tyr Cys Ser Ile Leu Ala Ala Val Val Val Gly Leu Val Ala
        275                 280                 285

Tyr Ile Ala Phe Lys Arg Gly Val Gln Val Glu Thr Ile Ser Pro Gly
```

290 295 300

Asp Gly Arg Thr Phe Pro Lys Arg Gly Gln Thr Cys Val Val His Tyr
305 310 315 320

Thr Gly Met Leu Glu Asp Gly Lys Lys Phe Asp Ser Ser Arg Asp Arg
325 330 335

Asn Lys Pro Phe Lys Phe Met Leu Gly Lys Gln Glu Val Ile Arg Gly
340 345 350

Trp Glu Glu Gly Val Ala Gln Met Ser Val Gly Gln Arg Ala Lys Leu
355 360 365

Thr Ile Ser Pro Asp Tyr Ala Tyr Gly Ala Thr Gly His Pro Gly Ile
370 375 380

Ile Pro Pro His Ala Thr Leu Val Phe Asp Val Glu Leu Leu Lys Leu
385 390 395 400

Gly Glu Gly Gly Ser Pro Gly Ser Asn Thr Ser Lys Glu Asn Pro Phe
405 410 415

Leu Phe Ala Leu Glu Ala Val Val Ile Ser Val Gly Ser Met Gly Leu
420 425 430

Ile Ile Ser Leu Leu Cys Val Tyr Phe Trp Leu Glu Arg Thr Met Pro
435 440 445

Arg Ile Pro Thr Leu Lys Asn Leu Glu Asp Leu Val Thr Glu Tyr His
450 455 460

Gly Asn Phe Ser Ala Trp Ser Gly Val Ser Lys Gly Leu Ala Glu Ser
465 470 475 480

Leu Gln Pro Asp Tyr Ser Glu Arg Leu Cys Leu Val Ser Glu Ile Pro
485 490 495

Pro Lys Gly Gly Ala Leu Gly Glu Gly Pro Gly Ala Ser Pro Cys Asn
500 505 510

Gln His Ser Pro Tyr Trp Ala Pro Pro Cys Tyr Thr Leu Lys Pro Glu
515 520 525

Thr Gly Ser Gly Ala Thr Asn Phe Ser Leu Leu Lys Gln Ala Gly Asp
530 535 540

Val Glu Glu Asn Pro Gly Pro Met Ala Leu Pro Val Thr Ala Leu Leu
545 550 555 560

Leu Pro Leu Ala Leu Leu Leu His Ala Ala Arg Pro Ile Leu Trp His
565 570 575

Glu Met Trp His Glu Gly Leu Glu Glu Ala Ser Arg Leu Tyr Phe Gly
580 585 590

Glu Arg Asn Val Lys Gly Met Phe Glu Val Leu Glu Pro Leu His Ala
595 600 605

Met Met Glu Arg Gly Pro Gln Thr Leu Lys Glu Thr Ser Phe Asn Gln
610 615 620

Ala Tyr Gly Arg Asp Leu Met Glu Ala Gln Glu Trp Cys Arg Lys Tyr
625 630 635 640

Met Lys Ser Gly Asn Val Lys Asp Leu Leu Gln Ala Trp Asp Leu Tyr
645 650 655

Tyr His Val Phe Arg Arg Ile Ser Lys Pro Ala Ala Leu Gly Lys Asp
660 665 670

Thr Ile Pro Trp Leu Gly His Leu Leu Val Gly Leu Ser Gly Ala Phe
675 680 685

Gly Phe Ile Ile Leu Val Tyr Leu Leu Ile Asn Cys Arg Asn Thr Gly
690 695 700

Pro Trp Leu Lys Lys Val Leu Lys Cys Asn Thr Pro Asp Pro Ser Lys
705 710 715 720

```
Phe Phe Ser Gln Leu Ser Ser Glu His Gly Gly Asp Val Gln Lys Trp
                725                 730                 735

Leu Ser Ser Pro Phe Pro Ser Ser Ser Phe Ser Pro Gly Gly Leu Ala
            740                 745                 750

Pro Glu Ile Ser Pro Leu Glu Val Leu Glu Arg Asp Lys Val Thr Gln
        755                 760                 765

Leu Leu Leu Gln Gln Asp Lys Val Pro Glu Pro Ala Ser Leu Ser Leu
    770                 775                 780

Asn Thr Asp Ala Tyr Leu Ser Leu Gln Glu Leu Gln Gly Ser Gly Ala
785                 790                 795                 800

Thr Asn Phe Ser Leu Leu Lys Gln Ala Gly Asp Val Glu Glu Asn Pro
                805                 810                 815

Gly Pro Glu Met Trp His Glu Gly Leu Glu Glu Ala Ser Arg Leu Tyr
            820                 825                 830

Phe Gly Glu Arg Asn Val Lys Gly Met Phe Glu Val Leu Glu Pro Leu
        835                 840                 845

His Ala Met Met Glu Arg Gly Pro Gln Thr Leu Lys Glu Thr Ser Phe
    850                 855                 860

Asn Gln Ala Tyr Gly Arg Asp Leu Met Glu Ala Gln Glu Trp Cys Arg
865                 870                 875                 880

Lys Tyr Met Lys Ser Gly Asn Val Lys Asp Leu Leu Gln Ala Trp Asp
                885                 890                 895

Leu Tyr Tyr His Val Phe Arg Arg Ile Ser Lys Gly Ser Gly Ala Thr
            900                 905                 910

Asn Phe Ser Leu Leu Lys Gln Ala Gly Asp Val Glu Glu Asn Pro Gly
        915                 920                 925

Pro Met Pro Asn Pro Arg Pro Gly Lys Pro Ser Ala Pro Ser Leu Ala
    930                 935                 940

Leu Gly Pro Ser Pro Gly Ala Ser Pro Ser Trp Arg Ala Ala Pro Lys
945                 950                 955                 960

Ala Ser Asp Leu Leu Gly Ala Arg Gly Pro Gly Gly Thr Phe Gln Gly
                965                 970                 975

Arg Asp Leu Arg Gly Gly Ala His Ala Ser Ser Ser Ser Leu Asn Pro
            980                 985                 990

Met Pro Pro Ser Gln Leu Gln Leu  Pro Thr Leu Pro Leu  Val Met Val
        995                 1000                 1005

Ala Pro  Ser Gly Ala Arg Leu  Gly Pro Leu Pro His  Leu Gln Ala
    1010                 1015                 1020

Leu Leu  Gln Asp Arg Pro His  Phe Met His Gln Leu  Ser Thr Val
    1025                 1030                 1035

Asp Ala  His Ala Arg Thr Pro  Val Leu Gln Val His  Pro Leu Glu
    1040                 1045                 1050

Ser Pro  Ala Met Ile Ser Leu  Thr Pro Pro Thr Thr  Ala Thr Gly
    1055                 1060                 1065

Val Phe  Ser Leu Lys Ala Arg  Pro Gly Leu Pro Pro  Gly Ile Asn
    1070                 1075                 1080

Val Ala  Ser Leu Glu Trp Val  Ser Arg Glu Pro Ala  Leu Leu Cys
    1085                 1090                 1095

Thr Phe  Pro Asn Pro Ser Ala  Pro Arg Lys Asp Ser  Thr Leu Ser
    1100                 1105                 1110

Ala Val  Pro Gln Ser Ser Tyr  Pro Leu Leu Ala Asn  Gly Val Cys
    1115                 1120                 1125
```

-continued

```
Lys Trp  Pro Gly Cys Glu Lys  Val Phe Glu Glu Pro  Glu Asp Phe
    1130                 1135                 1140

Leu Lys  His Cys Gln Ala Asp  His Leu Leu Asp Glu  Lys Gly Arg
    1145                 1150                 1155

Ala Gln  Cys Leu Leu Gln Arg  Glu Met Val Gln Ser  Leu Glu Gln
    1160                 1165                 1170

Gln Leu  Val Leu Glu Lys Glu  Lys Leu Ser Ala Met  Gln Ala His
    1175                 1180                 1185

Leu Ala  Gly Lys Met Ala Leu  Thr Lys Ala Ser Ser  Val Ala Ser
    1190                 1195                 1200

Ser Asp  Lys Gly Ser Cys Cys  Ile Val Ala Ala Gly  Ser Gln Gly
    1205                 1210                 1215

Pro Val  Val Pro Ala Trp Ser  Gly Pro Arg Glu Ala  Pro Asp Ser
    1220                 1225                 1230

Leu Phe  Ala Val Arg Arg His  Leu Trp Gly Ser His  Gly Asn Ser
    1235                 1240                 1245

Thr Phe  Pro Glu Phe Leu His  Asn Met Asp Tyr Phe  Lys Phe His
    1250                 1255                 1260

Asn Met  Arg Pro Pro Phe Thr  Tyr Ala Thr Leu Ile  Arg Trp Ala
    1265                 1270                 1275

Ile Leu  Glu Ala Pro Glu Lys  Gln Arg Thr Leu Asn  Glu Ile Tyr
    1280                 1285                 1290

His Trp  Phe Thr Arg Met Phe  Ala Phe Phe Arg Asn  His Pro Ala
    1295                 1300                 1305

Thr Trp  Lys Asn Ala Ile Arg  His Asn Leu Ser Leu  His Lys Cys
    1310                 1315                 1320

Phe Val  Arg Val Glu Ser Glu  Lys Gly Ala Val Trp  Thr Val Asp
    1325                 1330                 1335

Glu Leu  Glu Phe Arg Lys Lys  Arg Ser Gln Arg Pro  Ser Arg Cys
    1340                 1345                 1350

Ser Asn  Pro Thr Pro Gly Pro
    1355                 1360
```

<210> SEQ ID NO 83
<211> LENGTH: 2463
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DISC nucleotide sequence coding sequence only
codon optimized

<400> SEQUENCE: 83

```
atgcctctgg gcctgctgtg gctgggcctg gccctgctgg gcgccctgca cgcccaggcc     60

ggcgtgcagg tggagacaat ctccccaggc gacggacgca cattccctaa gcggggccag    120

acctgcgtgg tgcactatac aggcatgctg gaggatggca agaagtttga cagctcccgg    180

gatagaaaca agccattcaa gtttatgctg ggcaagcagg aagtgatcag aggctgggag    240

gagggcgtgg cccagatgtc tgtgggccag agggccaagc tgaccatcag cccagactac    300

gcctatggag caacaggcca cccaggaatc atcccacctc acgccaccct ggtgttcgat    360

gtggagctgc tgaagctggg cgagggaggg tcacctggat ccaacacatc aaaagagaac    420

ccctttctgt tcgcattgga ggccgtagtc atatctgttg gatccatggg acttattatc    480

tccctgttgt gtgtgtactt ctggctggaa cggactatgc ccaggatccc cacgctcaag    540
```

aatctggaag atctcgtcac agaataccat ggtaatttca gcgcctggag cggagtctct 600
aagggtctgg ccgaatccct ccaacccgat tattctgaac ggttgtgcct cgtatccgaa 660
ataccaccaa aaggcggggc tctgggtgag ggcccagggg cgagtccgtg caatcaacac 720
agcccgtatt gggcccctcc ttgttatacg ttgaagcccg aaactggaag cggagctact 780
aacttcagcc tgctgaagca ggctggagac gtggaggaga accctggacc tatggcactg 840
cccgtgaccg ccctgctgct gcctctggcc ctgctgctgc acgcagcccg gcctatcctg 900
tggcacgaga tgtggcacga gggcctggag gaggccagca ggctgtattt tggcgagcgc 960
aacgtgaagg gcatgttcga ggtgctggag cctctgcacg ccatgatgga gagaggccca 1020
cagaccctga aggagacatc ctttaaccag gcctatggac gggacctgat ggaggcacag 1080
gagtggtgca gaaagtacat gaagtctggc aatgtgaagg acctgctgca ggcctgggat 1140
ctgtactatc acgtgtttcg gagaatctcc aagccagcag ctctcggcaa agacacgatt 1200
ccgtggcttg ggcatctgct cgttgggctg agcggtgcgt ttggtttcat catcttggtc 1260
tatctcttga tcaattgcag aaatacaggc ccttggctga aaaaagtgct caagtgtaat 1320 accccccgacc caagcaagtt cttctcccag ctttcttcag agcatggagg cgatgtgcag 1380
aaatggctct cttcaccttt tccctcctca agcttctccc cgggagggct ggcgcccgag 1440
atttcacctc ttgaggtact tgaacgagac aaggttaccc aacttctcct tcaacaggat 1500
aaggtacccg aacctgcgag ccttagctcc aaccactctc ttacgagctg cttcaccaat 1560
cagggatact tctttttcca ccttcccgat gcgctggaaa tcgaagcttg tcaagtttac 1620
tttacctatg atccatatag cgaggaagat cccgacgaag gagtcgccgg tgcgcccacg 1680
ggttcctcac cccaacctct ccagcctctc tcaggagaag atgatgctta ttgcactttt 1740
cccagtagag acgatctcct cctcttttct ccatctcttt tggggggacc ttcccccccct 1800 tctacggcac ctggcgggtc tggtgctggc gaggagcgga tgccgccgtc cctccaggag 1860
cgagtaccac gagattggga tccccagcca cttggacccc ccacccccgg cgtacctgac 1920
cttgtcgatt ttcaacctcc ccctgaattg gtgctgcgag aggctgggga ggaagttccg 1980
gacgctgggc cgagggaggg cgtgtccttt ccatggagta ggcctccagg tcaaggcgag 2040
tttagggctc tcaacgcgcg gctgccgttg aatacagacg cttatctctc actgcaggaa 2100
ctgcaaggtc aggacccaac acatcttgta ggatctggtg ctactaattt ttctcttttg 2160
aagcaagctg gagatgttga agagaacccc ggtccggaga tgtggcatga gggtctggaa 2220
gaagcgtctc gactgtactt tggtgagcgc aatgtgaagg gcatgtttga agtcctcgaa 2280
ccccttcatg ccatgatgga acgcggaccc cagaccttga aggagacaag ttttaaccaa 2340
gcttacggaa gagacctgat ggaagcccag gaatggtgca ggaaatacat gaaaagcggg 2400
aatgtgaagg acttgctcca agcgtgggac ctgtactatc atgtctttag gcgcattagt 2460
aag 2463

<210> SEQ ID NO 84
<211> LENGTH: 821
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: DISC amino acid sequence

<400> SEQUENCE: 84

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Gly Gly Ser Pro Gly Ser Asn Thr Ser Lys Glu Asn Pro Phe Leu Phe
    130                 135                 140

Ala Leu Glu Ala Val Val Ile Ser Val Gly Ser Met Gly Leu Ile Ile
145                 150                 155                 160

Ser Leu Leu Cys Val Tyr Phe Trp Leu Glu Arg Thr Met Pro Arg Ile
                165                 170                 175

Pro Thr Leu Lys Asn Leu Glu Asp Leu Val Thr Glu Tyr His Gly Asn
            180                 185                 190

Phe Ser Ala Trp Ser Gly Val Ser Lys Gly Leu Ala Glu Ser Leu Gln
        195                 200                 205

Pro Asp Tyr Ser Glu Arg Leu Cys Leu Val Ser Glu Ile Pro Pro Lys
    210                 215                 220

Gly Gly Ala Leu Gly Glu Gly Pro Gly Ala Ser Pro Cys Asn Gln His
225                 230                 235                 240

Ser Pro Tyr Trp Ala Pro Pro Cys Tyr Thr Leu Lys Pro Glu Thr Gly
                245                 250                 255

Ser Gly Ala Thr Asn Phe Ser Leu Leu Lys Gln Ala Gly Asp Val Glu
            260                 265                 270

Glu Asn Pro Gly Pro Met Ala Leu Pro Val Thr Ala Leu Leu Leu Pro
        275                 280                 285

Leu Ala Leu Leu Leu His Ala Ala Arg Pro Ile Leu Trp His Glu Met
    290                 295                 300

Trp His Glu Gly Leu Glu Glu Ala Ser Arg Leu Tyr Phe Gly Glu Arg
305                 310                 315                 320

Asn Val Lys Gly Met Phe Glu Val Leu Glu Pro Leu His Ala Met Met
                325                 330                 335

Glu Arg Gly Pro Gln Thr Leu Lys Glu Thr Ser Phe Asn Gln Ala Tyr
            340                 345                 350

Gly Arg Asp Leu Met Glu Ala Gln Glu Trp Cys Arg Lys Tyr Met Lys
        355                 360                 365

Ser Gly Asn Val Lys Asp Leu Leu Gln Ala Trp Asp Leu Tyr Tyr His
    370                 375                 380

Val Phe Arg Arg Ile Ser Lys Pro Ala Ala Leu Gly Lys Asp Thr Ile
385                 390                 395                 400

Pro Trp Leu Gly His Leu Leu Val Gly Leu Ser Gly Ala Phe Gly Phe
                405                 410                 415
```

-continued

```
Ile Ile Leu Val Tyr Leu Leu Ile Asn Cys Arg Asn Thr Gly Pro Trp
            420                 425                 430

Leu Lys Lys Val Leu Lys Cys Asn Thr Pro Asp Pro Ser Lys Phe Phe
        435                 440                 445

Ser Gln Leu Ser Ser Glu His Gly Gly Asp Val Gln Lys Trp Leu Ser
    450                 455                 460

Ser Pro Phe Pro Ser Ser Ser Phe Ser Pro Gly Gly Leu Ala Pro Glu
465                 470                 475                 480

Ile Ser Pro Leu Glu Val Leu Glu Arg Asp Lys Val Thr Gln Leu Leu
                485                 490                 495

Leu Gln Gln Asp Lys Val Pro Glu Pro Ala Ser Leu Ser Ser Asn His
            500                 505                 510

Ser Leu Thr Ser Cys Phe Thr Asn Gln Gly Tyr Phe Phe Phe His Leu
        515                 520                 525

Pro Asp Ala Leu Glu Ile Glu Ala Cys Gln Val Tyr Phe Thr Tyr Asp
    530                 535                 540

Pro Tyr Ser Glu Glu Asp Pro Asp Glu Gly Val Ala Gly Ala Pro Thr
545                 550                 555                 560

Gly Ser Ser Pro Gln Pro Leu Gln Pro Leu Ser Gly Glu Asp Asp Ala
                565                 570                 575

Tyr Cys Thr Phe Pro Ser Arg Asp Asp Leu Leu Leu Phe Ser Pro Ser
            580                 585                 590

Leu Leu Gly Gly Pro Ser Pro Pro Ser Thr Ala Pro Gly Gly Ser Gly
        595                 600                 605

Ala Gly Glu Glu Arg Met Pro Pro Ser Leu Gln Glu Arg Val Pro Arg
    610                 615                 620

Asp Trp Asp Pro Gln Pro Leu Gly Pro Pro Thr Pro Gly Val Pro Asp
625                 630                 635                 640

Leu Val Asp Phe Gln Pro Pro Pro Glu Leu Val Leu Arg Glu Ala Gly
                645                 650                 655

Glu Glu Val Pro Asp Ala Gly Pro Arg Glu Gly Val Ser Phe Pro Trp
            660                 665                 670

Ser Arg Pro Pro Gly Gln Gly Glu Phe Arg Ala Leu Asn Ala Arg Leu
        675                 680                 685

Pro Leu Asn Thr Asp Ala Tyr Leu Ser Leu Gln Glu Leu Gln Gly Gln
    690                 695                 700

Asp Pro Thr His Leu Val Gly Ser Gly Ala Thr Asn Phe Ser Leu Leu
705                 710                 715                 720

Lys Gln Ala Gly Asp Val Glu Glu Asn Pro Gly Pro Glu Met Trp His
                725                 730                 735

Glu Gly Leu Glu Glu Ala Ser Arg Leu Tyr Phe Gly Glu Arg Asn Val
            740                 745                 750

Lys Gly Met Phe Glu Val Leu Glu Pro Leu His Ala Met Met Glu Arg
        755                 760                 765

Gly Pro Gln Thr Leu Lys Glu Thr Ser Phe Asn Gln Ala Tyr Gly Arg
    770                 775                 780

Asp Leu Met Glu Ala Gln Glu Trp Cys Arg Lys Tyr Met Lys Ser Gly
785                 790                 795                 800

Asn Val Lys Asp Leu Leu Gln Ala Trp Asp Leu Tyr Tyr His Val Phe
                805                 810                 815

Arg Arg Ile Ser Lys
            820
```

<210> SEQ ID NO 85
<211> LENGTH: 1899
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: uDISC nucleotide sequence coding sequence only
codon optimized

<400> SEQUENCE: 85

```
atgcctctgg gcctgctgtg gctgggcctg gccctgctgg gcgccctgca cgcccaggcc     60

ggcgtgcagg tggagacaat ctccccaggc gacggacgca cattccctaa gcggggccag    120

acctgcgtgg tgcactatac aggcatgctg gaggatggca agaagtttga cagctcccgg    180

gatagaaaca agccattcaa gtttatgctg ggcaagcagg aagtgatcag aggctgggag    240

gagggcgtgg cccagatgtc tgtgggccag agggccaagc tgaccatcag cccagactac    300

gcctatggag caacaggcca cccaggaatc atcccacctc acgccaccct ggtgttcgat    360

gtggagctgc tgaagctggg cgagggaggg tcacctggat ccaacacatc aaaagagaac    420

ccctttctgt tcgcattgga ggccgtagtc atatctgttg gatccatggg acttattatc    480

tccctgttgt gtgtgtactt ctggctggaa cggactatgc ccaggatccc cacgctcaag    540

aatctggaag atctcgtcac agaataccat ggtaatttca gcgcctggag cggagtctct    600

aagggtctgg ccgaatccct ccaacccgat tattctgaac ggttgtgcct cgtatccgaa    660

ataccaccaa aaggcggggc tctgggtgag ggcccagggg cgagtccgtg caatcaacac    720

agcccgtatt gggcccctcc ttgttatacg ttgaagcccg aaactggaag cggagctact    780

aacttcagcc tgctgaagca ggctggagac gtggaggaga accctggacc tatggcactg    840

cccgtgaccg ccctgctgct gcctctggcc ctgctgctgc acgcagcccg gcctatcctg    900

tggcacgaga tgtggcacga gggcctggag gaggccagca ggctgtattt tggcgagcgc    960

aacgtgaagg gcatgttcga ggtgctggag cctctgcacg ccatgatgga gagaggccca   1020

cagaccctga aggagacatc ctttaaccag gcctatggac gggacctgat ggaggcacag   1080

gagtggtgca gaaagtacat gaagtctggc aatgtgaagg acctgctgca ggcctgggat   1140

ctgtactatc acgtgtttcg gagaatctcc aagccagcag ctctcggcaa agacacgatt   1200

ccgtggcttg ggcatctgct cgttgggctg agcggtgcgt ttggtttcat catcttggtc   1260

tatctcttga tcaattgcag aaatacaggc ccttggctga aaaaagtgct caagtgtaat   1320

acccccgacc caagcaagtt cttctcccag ctttcttcag agcatggagg cgatgtgcag   1380

aaatggctct cttcaccttt tccctcctca agcttctccc cgggagggct ggcgcccgag   1440

atttcacctc ttgaggtact tgaacgagac aaggttaccc aacttctcct tcaacaggat   1500

aaggtacccg aacctgcgag ccttagcttg aatacagacg cttatctctc actgcaggaa   1560

ctgcaaggat ctggtgctac taatttttct cttttgaagc aagctggaga tgttgaagag   1620

aaccccggtc cggagatgtg gcatgagggt ctggaagaag cgtctcgact gtactttggt   1680

gagcgcaatg tgaagggcat gtttgaagtc ctcgaacccc ttcatgccat gatggaacgc   1740

ggaccccaga ccttgaagga gacaagtttt aaccaagctt acggaagaga cctgatggaa   1800

gcccaggaat ggtgcaggaa atacatgaaa agcgggaatg tgaaggactt gctccaagcg   1860

tgggacctgt actatcatgt ctttaggcgc attagtaag                           1899
```

<210> SEQ ID NO 86

<211> LENGTH: 633
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: uDISC amino acid sequence

<400> SEQUENCE: 86

Met Pro Leu Gly Leu Leu Trp Leu Gly Leu Ala Leu Leu Gly Ala Leu
1 5 10 15

His Ala Gln Ala Gly Val Gln Val Glu Thr Ile Ser Pro Gly Asp Gly
20 25 30

Arg Thr Phe Pro Lys Arg Gly Gln Thr Cys Val Val His Tyr Thr Gly
35 40 45

Met Leu Glu Asp Gly Lys Lys Phe Asp Ser Ser Arg Asp Arg Asn Lys
50 55 60

Pro Phe Lys Phe Met Leu Gly Lys Gln Glu Val Ile Arg Gly Trp Glu
65 70 75 80

Glu Gly Val Ala Gln Met Ser Val Gly Gln Arg Ala Lys Leu Thr Ile
85 90 95

Ser Pro Asp Tyr Ala Tyr Gly Ala Thr Gly His Pro Gly Ile Ile Pro
100 105 110

Pro His Ala Thr Leu Val Phe Asp Val Glu Leu Leu Lys Leu Gly Glu
115 120 125

Gly Gly Ser Pro Gly Ser Asn Thr Ser Lys Glu Asn Pro Phe Leu Phe
130 135 140

Ala Leu Glu Ala Val Val Ile Ser Val Gly Ser Met Gly Leu Ile Ile
145 150 155 160

Ser Leu Leu Cys Val Tyr Phe Trp Leu Glu Arg Thr Met Pro Arg Ile
165 170 175

Pro Thr Leu Lys Asn Leu Glu Asp Leu Val Thr Glu Tyr His Gly Asn
180 185 190

Phe Ser Ala Trp Ser Gly Val Ser Lys Gly Leu Ala Glu Ser Leu Gln
195 200 205

Pro Asp Tyr Ser Glu Arg Leu Cys Leu Val Ser Glu Ile Pro Pro Lys
210 215 220

Gly Gly Ala Leu Gly Glu Gly Pro Gly Ala Ser Pro Cys Asn Gln His
225 230 235 240

Ser Pro Tyr Trp Ala Pro Pro Cys Tyr Thr Leu Lys Pro Glu Thr Gly
245 250 255

Ser Gly Ala Thr Asn Phe Ser Leu Leu Lys Gln Ala Gly Asp Val Glu
260 265 270

Glu Asn Pro Gly Pro Met Ala Leu Pro Val Thr Ala Leu Leu Leu Pro
275 280 285

Leu Ala Leu Leu Leu His Ala Ala Arg Pro Ile Leu Trp His Glu Met
290 295 300

Trp His Glu Gly Leu Glu Glu Ala Ser Arg Leu Tyr Phe Gly Glu Arg
305 310 315 320

Asn Val Lys Gly Met Phe Glu Val Leu Glu Pro Leu His Ala Met Met
325 330 335

Glu Arg Gly Pro Gln Thr Leu Lys Glu Thr Ser Phe Asn Gln Ala Tyr
340 345 350

Gly Arg Asp Leu Met Glu Ala Gln Glu Trp Cys Arg Lys Tyr Met Lys
355 360 365

Ser Gly Asn Val Lys Asp Leu Leu Gln Ala Trp Asp Leu Tyr Tyr His
    370                 375                 380

Val Phe Arg Arg Ile Ser Lys Pro Ala Ala Leu Gly Lys Asp Thr Ile
385                 390                 395                 400

Pro Trp Leu Gly His Leu Leu Val Gly Leu Ser Gly Ala Phe Gly Phe
                405                 410                 415

Ile Ile Leu Val Tyr Leu Leu Ile Asn Cys Arg Asn Thr Gly Pro Trp
            420                 425                 430

Leu Lys Lys Val Leu Lys Cys Asn Thr Pro Asp Pro Ser Lys Phe Phe
        435                 440                 445

Ser Gln Leu Ser Ser Glu His Gly Gly Asp Val Gln Lys Trp Leu Ser
    450                 455                 460

Ser Pro Phe Pro Ser Ser Ser Phe Ser Pro Gly Gly Leu Ala Pro Glu
465                 470                 475                 480

Ile Ser Pro Leu Glu Val Leu Glu Arg Asp Lys Val Thr Gln Leu Leu
                485                 490                 495

Leu Gln Gln Asp Lys Val Pro Glu Pro Ala Ser Leu Ser Leu Asn Thr
            500                 505                 510

Asp Ala Tyr Leu Ser Leu Gln Glu Leu Gln Gly Ser Gly Ala Thr Asn
        515                 520                 525

Phe Ser Leu Leu Lys Gln Ala Gly Asp Val Glu Glu Asn Pro Gly Pro
    530                 535                 540

Glu Met Trp His Glu Gly Leu Glu Glu Ala Ser Arg Leu Tyr Phe Gly
545                 550                 555                 560

Glu Arg Asn Val Lys Gly Met Phe Glu Val Leu Glu Pro Leu His Ala
                565                 570                 575

Met Met Glu Arg Gly Pro Gln Thr Leu Lys Glu Thr Ser Phe Asn Gln
            580                 585                 590

Ala Tyr Gly Arg Asp Leu Met Glu Ala Gln Glu Trp Cys Arg Lys Tyr
        595                 600                 605

Met Lys Ser Gly Asn Val Lys Asp Leu Leu Gln Ala Trp Asp Leu Tyr
    610                 615                 620

Tyr His Val Phe Arg Arg Ile Ser Lys
625                 630

<210> SEQ ID NO 87
<211> LENGTH: 1632
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: CISCbeta_DN nucleotide sequence coding
      sequence only

<400> SEQUENCE: 87
atggcactgc ccgtgaccgc cctgctgctg cctctggccc tgctgctgca cgcagcccgg 60
cctatcctgt ggcacgagat gtggcacgag ggcctggagg aggccagcag gctgtatttt 120
ggcgagcgca acgtgaaggg catgttcgag gtgctggagc ctctgcacgc catgatggag 180
agaggcccac agaccctgaa ggagacatcc tttaaccagg cctatggacg ggacctgatg 240
gaggcacagg agtggtgcag aaagtacatg aagtctggca atgtgaagga cctgctgcag 300
gcctgggatc tgtactatca cgtgtttcgg agaatctcca agccagcagc tctcggcaaa 360
gacacgattc cgtggcttgg gcatctgctc gttgggctga gcggtgcgtt tggtttcatc 420

```
atcttggtct atctcttgat caattgcaga aatacaggcc cttggctgaa aaaagtgctc    480

aagtgtaata cccccgaccc aagcaagttc ttctcccagc tttcttcaga gcatggaggc    540

gatgtgcaga aatggctctc ttcacctttt ccctcctcaa gcttctcccc gggagggctg    600

gcgcccgaga tttcacctct tgaggtactt gaacgagaca aggttaccca acttctcctt    660

caacaggata aggtacccga acctgcgagc cttagctcca accactctct tacgagctgc    720

ttcaccaatc agggatactt ctttttccac cttcccgatg cgctggaaat cgaagcttgt    780

caagtttact ttacctatga tccatatagc gaggaagatc ccgacgaagg agtcgccggt    840

gcgcccacgg gttcctcacc ccaacctctc cagcctctct caggagaaga tgatgcttat    900

tgcacttttc ccagtagaga cgatctcctc ctcttttctc catctctttt gggggggacct    960

tcccccctt ctacggcacc tggcgggtct ggtgctggcg aggagcggat gccgccgtcc   1020

ctccaggagc gagtaccacg agattgggat ccccagccac ttggaccccc cacccccggc   1080

gtacctgacc ttgtcgattt tcaacctccc cctgaattgg tgctgcgaga ggctggggag   1140

gaagttccgg acgctgggcc gagggagggc gtgtcctttc catggagtag gcctccaggt   1200

caaggcgagt ttagggctct caacgcgcgg ctgccgttga atacagacgc ttatctctca   1260

ctgcaggaac tgcaaggtca ggacccaaca catcttgtag gatctggtgc tactaatttt   1320

tctcttttga agcaagctgg agatgttgaa gagaaccccg gtccggagat gtggcatgag   1380

ggtctggaag aagcgtctcg actgtacttt ggtgagcgca atgtgaaggg catgtttgaa   1440

gtcctcgaac cccttcatgc catgatggaa cgcggacccc agaccttgaa ggagacaagt   1500

tttaaccaag cttacggaag agacctgatg gaagcccagg aatggtgcag gaaatacatg   1560

aaaagcggga atgtgaagga cttgctccaa gcgtgggacc tgtactatca tgtctttagg   1620

cgcattagta ag                                                       1632
```

<210> SEQ ID NO 88
<211> LENGTH: 544
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: CISCbeta_DN amino acid sequence

<400> SEQUENCE: 88

```
Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Pro Ala Ala Leu Gly Lys Asp Thr Ile Pro Trp Leu Gly His
        115                 120                 125
```

-continued

```
Leu Leu Val Gly Leu Ser Gly Ala Phe Gly Phe Ile Ile Leu Val Tyr
    130                 135                 140

Leu Leu Ile Asn Cys Arg Asn Thr Gly Pro Trp Leu Lys Lys Val Leu
145                 150                 155                 160

Lys Cys Asn Thr Pro Asp Pro Ser Lys Phe Phe Ser Gln Leu Ser Ser
                165                 170                 175

Glu His Gly Gly Asp Val Gln Lys Trp Leu Ser Ser Pro Phe Pro Ser
            180                 185                 190

Ser Ser Phe Ser Pro Gly Gly Leu Ala Pro Glu Ile Ser Pro Leu Glu
        195                 200                 205

Val Leu Glu Arg Asp Lys Val Thr Gln Leu Leu Leu Gln Gln Asp Lys
    210                 215                 220

Val Pro Glu Pro Ala Ser Leu Ser Ser Asn His Ser Leu Thr Ser Cys
225                 230                 235                 240

Phe Thr Asn Gln Gly Tyr Phe Phe Phe His Leu Pro Asp Ala Leu Glu
                245                 250                 255

Ile Glu Ala Cys Gln Val Tyr Phe Thr Tyr Asp Pro Tyr Ser Glu Glu
            260                 265                 270

Asp Pro Asp Glu Gly Val Ala Gly Ala Pro Thr Gly Ser Ser Pro Gln
        275                 280                 285

Pro Leu Gln Pro Leu Ser Gly Glu Asp Asp Ala Tyr Cys Thr Phe Pro
    290                 295                 300

Ser Arg Asp Asp Leu Leu Leu Phe Ser Pro Ser Leu Leu Gly Gly Pro
305                 310                 315                 320

Ser Pro Pro Ser Thr Ala Pro Gly Gly Ser Gly Ala Gly Glu Glu Arg
                325                 330                 335

Met Pro Pro Ser Leu Gln Glu Arg Val Pro Arg Asp Trp Asp Pro Gln
            340                 345                 350

Pro Leu Gly Pro Pro Thr Pro Gly Val Pro Asp Leu Val Asp Phe Gln
        355                 360                 365

Pro Pro Pro Glu Leu Val Leu Arg Glu Ala Gly Glu Glu Val Pro Asp
    370                 375                 380

Ala Gly Pro Arg Glu Gly Val Ser Phe Pro Trp Ser Arg Pro Pro Gly
385                 390                 395                 400

Gln Gly Glu Phe Arg Ala Leu Asn Ala Arg Leu Pro Leu Asn Thr Asp
                405                 410                 415

Ala Tyr Leu Ser Leu Gln Glu Leu Gln Gly Gln Asp Pro Thr His Leu
            420                 425                 430

Val Gly Ser Gly Ala Thr Asn Phe Ser Leu Leu Lys Gln Ala Gly Asp
        435                 440                 445

Val Glu Glu Asn Pro Gly Pro Glu Met Trp His Glu Gly Leu Glu Glu
    450                 455                 460

Ala Ser Arg Leu Tyr Phe Gly Glu Arg Asn Val Lys Gly Met Phe Glu
465                 470                 475                 480

Val Leu Glu Pro Leu His Ala Met Met Glu Arg Gly Pro Gln Thr Leu
                485                 490                 495

Lys Glu Thr Ser Phe Asn Gln Ala Tyr Gly Arg Asp Leu Met Glu Ala
            500                 505                 510

Gln Glu Trp Cys Arg Lys Tyr Met Lys Ser Gly Asn Val Lys Asp Leu
        515                 520                 525

Leu Gln Ala Trp Asp Leu Tyr Tyr His Val Phe Arg Arg Ile Ser Lys
    530                 535                 540
```

<210> SEQ ID NO 89
<211> LENGTH: 3015
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: CISCgamma_FOXP3cDNA_LNGFR nucleotide sequence
coding sequence only codon optimized

<400> SEQUENCE: 89
atgcctctgg gcctgctgtg gctgggcctg gccctgctgg gcgccctgca cgcccaggcc 60
ggcgtgcagg tggagacaat ctccccaggc gacggacgca cattccctaa gcggggccag 120
acctgcgtgg tgcactatac aggcatgctg gaggatggca agaagtttga cagctcccgg 180
gatagaaaca agccattcaa gtttatgctg ggcaagcagg aagtgatcag aggctgggag 240
gagggcgtgg cccagatgtc tgtgggccag agggccaagc tgaccatcag cccagactac 300
gcctatggag caacaggcca cccaggaatc atcccacctc acgccaccct ggtgttcgat 360
gtggagctgc tgaagctggg cgagggaggg tcacctggat ccaacacatc aaaagagaac 420
ccctttctgt tcgcattgga ggccgtagtc atatctgttg gatccatggg acttattatc 480
tccctgttgt gtgtgtactt ctggctggaa cggactatgc ccaggatccc cacgctcaag 540
aatctggaag atctcgtcac agaataccat ggtaatttca gcgcctggag cggagtctct 600
aagggtctgg ccgaatccct ccaacccgat tattctgaac ggttgtgcct cgtatccgaa 660
ataccaccaa aaggcggggc tctgggtgag ggcccagggg cgagtccgtg caatcaacac 720
agcccgtatt gggcccctcc ttgttatacg ttgaagcccg aaactggaag cggagcgact 780
aacttcagcc tgcttaagca ggccggagat gtggaggaaa accctggacc gatgcctaat 840
cctcggcctg gaaagcctag cgctccttct cttgctctgg gaccttctcc tggcgcctct 900
ccatcttgga gagccgctcc taaagccagc gatctgctgg gagctagagg acctggcggc 960
acatttcagg gcagagatct tagaggcgga gcccacgcta gctcctccag ccttaatcct 1020
atgcctccta gccagctcca gctgcctaca ctgcctctgg ttatggtggc tcctagcgga 1080
gctagactgg gccctctgcc tcatctgcaa gctctgctgc aggacagacc ccacttcatg 1140
caccagctga gcaccgtgga tgcccacgca agaacacctg tgctgcaggt tcaccctctg 1200
gaatccccag ccatgatcag cctgacacct ccaacaacag ccaccggcgt gttcagcctg 1260
aaagccagac ctggactgcc tcctggcatc aatgtggcca gcctggaatg ggtgtccaga 1320
gaacctgctc tgctgtgcac attccccaat ccaagcgctc ccagaaagga cagcacactg 1380
tctgccgtgc ctcagagcag ctatcccctg cttgctaacg gcgtgtgcaa gtggcctgga 1440
tgcgagaagg tgttcgagga acccgaggac ttcctgaagc actgccaggc cgatcatctg 1500
ctggacgaga aaggcagagc ccagtgtctg ctccagcgcg agatggtgca gtctctggaa 1560
cagcagctgg tcctggaaaa agaaaagctg agcgccatgc aggcccacct ggccggaaaa 1620
atggccctga caaaggccag cagcgtggcc tcttctgata agggcagctg ctgcattgtg 1680
gccgctggat ctcagggacc tgtggttcct gcttggagcg gacctagaga ggcccctgat 1740
tctctgtttg ccgtgcggag acacctgtgg ggctctcacg gcaactctac tttccccgag 1800
ttcctgcaca acatggacta cttcaagttc cacaacatgc ggcctccatt cacctacgcc 1860
acactgatca gatgggccat tctggaagcc cctgagaagc agagaaccct gaacgagatc 1920
taccactggt ttacccggat gttcgccttc ttccggaatc accctgccac ctggaagaac 1980

```
gccatccggc acaatctgag cctgcacaag tgcttcgtgc gcgtggaatc tgagaaaggc   2040

gccgtgtgga cagtggacga gctggaattc agaaagaaga gaagccagcg gcctagccgg   2100

tgcagcaatc ctacacctgg acctggaagc ggagcgacta acttcagcct gctgaagcag   2160

gccggagatg tggaggaaaa ccctggaccg atgggggcag gtgccaccgg acgagccatg   2220

gacgggccgc gcctgctgct gttgctgctt ctgggggtgt cccttggagg tgccaaggag   2280

gcatgcccca caggcctgta cacacacagc ggtgagtgct gcaaagcctg caacctgggc   2340

gagggtgtgg cccagccttg tggagccaac cagaccgtgt gtgagccctg cctggacagc   2400

gtgacgttct ccgacgtggt gagcgcgacc gagccgtgca agccgtgcac cgagtgcgtg   2460

gggctccaga gcatgtcggc gccgtgcgtg gaggccgacg acgccgtgtg ccgctgcgcc   2520

tacggctact accaggatga gacgactggg cgctgcgagg cgtgccgcgt gtgcgaggcg   2580

ggctcgggcc tcgtgttctc ctgccaggac aagcagaaca ccgtgtgcga ggagtgcccc   2640

gacggcacgt attccgacga ggccaaccac gtggacccgt gcctgccctg caccgtgtgc   2700

gaggacaccg agcgccagct ccgcgagtgc acacgctggg ccgacgccga gtgcgaggag   2760

atccctggcc gttggattac acggtccaca cccccagagg gctcggacag cacagccccc   2820

agcacccagg agcctgaggc acctccagaa caagacctca tagccagcac ggtggcaggt   2880

gtggtgacca cagtgatggg cagctcccag cccgtggtga cccgaggcac caccgacaac   2940

ctcatccctg tctattgctc catcctggct gctgtggttg tgggtcttgt ggcctacata   3000

gccttcaaga ggtga                                                    3015
```

<210> SEQ ID NO 90
<211> LENGTH: 1004
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: CISCgamma_FOXP3cDNA_LNGFR amino acid sequence

<400> SEQUENCE: 90

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Gly Gly Ser Pro Gly Ser Asn Thr Ser Lys Glu Asn Pro Phe Leu Phe
    130                 135                 140

Ala Leu Glu Ala Val Val Ile Ser Val Gly Ser Met Gly Leu Ile Ile
145                 150                 155                 160
```

-continued

```
Ser Leu Leu Cys Val Tyr Phe Trp Leu Glu Arg Thr Met Pro Arg Ile
                165                 170                 175

Pro Thr Leu Lys Asn Leu Glu Asp Leu Val Thr Glu Tyr His Gly Asn
            180                 185                 190

Phe Ser Ala Trp Ser Gly Val Ser Lys Gly Leu Ala Glu Ser Leu Gln
        195                 200                 205

Pro Asp Tyr Ser Glu Arg Leu Cys Leu Val Ser Glu Ile Pro Pro Lys
    210                 215                 220

Gly Gly Ala Leu Gly Glu Gly Pro Gly Ala Ser Pro Cys Asn Gln His
225                 230                 235                 240

Ser Pro Tyr Trp Ala Pro Pro Cys Tyr Thr Leu Lys Pro Glu Thr Gly
                245                 250                 255

Ser Gly Ala Thr Asn Phe Ser Leu Leu Lys Gln Ala Gly Asp Val Glu
            260                 265                 270

Glu Asn Pro Gly Pro Met Pro Asn Pro Arg Pro Gly Lys Pro Ser Ala
        275                 280                 285

Pro Ser Leu Ala Leu Gly Pro Ser Pro Gly Ala Ser Pro Ser Trp Arg
    290                 295                 300

Ala Ala Pro Lys Ala Ser Asp Leu Leu Gly Ala Arg Gly Pro Gly Gly
305                 310                 315                 320

Thr Phe Gln Gly Arg Asp Leu Arg Gly Gly Ala His Ala Ser Ser Ser
                325                 330                 335

Ser Leu Asn Pro Met Pro Pro Ser Gln Leu Gln Leu Pro Thr Leu Pro
            340                 345                 350

Leu Val Met Val Ala Pro Ser Gly Ala Arg Leu Gly Pro Leu Pro His
        355                 360                 365

Leu Gln Ala Leu Leu Gln Asp Arg Pro His Phe Met His Gln Leu Ser
    370                 375                 380

Thr Val Asp Ala His Ala Arg Thr Pro Val Leu Gln Val His Pro Leu
385                 390                 395                 400

Glu Ser Pro Ala Met Ile Ser Leu Thr Pro Pro Thr Thr Ala Thr Gly
                405                 410                 415

Val Phe Ser Leu Lys Ala Arg Pro Gly Leu Pro Pro Gly Ile Asn Val
            420                 425                 430

Ala Ser Leu Glu Trp Val Ser Arg Glu Pro Ala Leu Leu Cys Thr Phe
        435                 440                 445

Pro Asn Pro Ser Ala Pro Arg Lys Asp Ser Thr Leu Ser Ala Val Pro
    450                 455                 460

Gln Ser Ser Tyr Pro Leu Leu Ala Asn Gly Val Cys Lys Trp Pro Gly
465                 470                 475                 480

Cys Glu Lys Val Phe Glu Glu Pro Glu Asp Phe Leu Lys His Cys Gln
                485                 490                 495

Ala Asp His Leu Leu Asp Glu Lys Gly Arg Ala Gln Cys Leu Leu Gln
            500                 505                 510

Arg Glu Met Val Gln Ser Leu Glu Gln Gln Leu Val Leu Glu Lys Glu
        515                 520                 525

Lys Leu Ser Ala Met Gln Ala His Leu Ala Gly Lys Met Ala Leu Thr
    530                 535                 540

Lys Ala Ser Ser Val Ala Ser Ser Asp Lys Gly Ser Cys Cys Ile Val
545                 550                 555                 560

Ala Ala Gly Ser Gln Gly Pro Val Val Pro Ala Trp Ser Gly Pro Arg
                565                 570                 575
```

-continued

```
Glu Ala Pro Asp Ser Leu Phe Ala Val Arg Arg His Leu Trp Gly Ser
            580                 585                 590

His Gly Asn Ser Thr Phe Pro Glu Phe Leu His Asn Met Asp Tyr Phe
        595                 600                 605

Lys Phe His Asn Met Arg Pro Pro Phe Thr Tyr Ala Thr Leu Ile Arg
    610                 615                 620

Trp Ala Ile Leu Glu Ala Pro Glu Lys Gln Arg Thr Leu Asn Glu Ile
625                 630                 635                 640

Tyr His Trp Phe Thr Arg Met Phe Ala Phe Phe Arg Asn His Pro Ala
                645                 650                 655

Thr Trp Lys Asn Ala Ile Arg His Asn Leu Ser Leu His Lys Cys Phe
            660                 665                 670

Val Arg Val Glu Ser Glu Lys Gly Ala Val Trp Thr Val Asp Glu Leu
        675                 680                 685

Glu Phe Arg Lys Lys Arg Ser Gln Arg Pro Ser Arg Cys Ser Asn Pro
    690                 695                 700

Thr Pro Gly Pro Gly Ser Gly Ala Thr Asn Phe Ser Leu Leu Lys Gln
705                 710                 715                 720

Ala Gly Asp Val Glu Glu Asn Pro Gly Pro Met Gly Ala Gly Ala Thr
                725                 730                 735

Gly Arg Ala Met Asp Gly Pro Arg Leu Leu Leu Leu Leu Leu Leu Gly
            740                 745                 750

Val Ser Leu Gly Gly Ala Lys Glu Ala Cys Pro Thr Gly Leu Tyr Thr
        755                 760                 765

His Ser Gly Glu Cys Cys Lys Ala Cys Asn Leu Gly Glu Gly Val Ala
    770                 775                 780

Gln Pro Cys Gly Ala Asn Gln Thr Val Cys Glu Pro Cys Leu Asp Ser
785                 790                 795                 800

Val Thr Phe Ser Asp Val Val Ser Ala Thr Glu Pro Cys Lys Pro Cys
                805                 810                 815

Thr Glu Cys Val Gly Leu Gln Ser Met Ser Ala Pro Cys Val Glu Ala
            820                 825                 830

Asp Asp Ala Val Cys Arg Cys Ala Tyr Gly Tyr Tyr Gln Asp Glu Thr
        835                 840                 845

Thr Gly Arg Cys Glu Ala Cys Arg Val Cys Glu Ala Gly Ser Gly Leu
    850                 855                 860

Val Phe Ser Cys Gln Asp Lys Gln Asn Thr Val Cys Glu Glu Cys Pro
865                 870                 875                 880

Asp Gly Thr Tyr Ser Asp Glu Ala Asn His Val Asp Pro Cys Leu Pro
                885                 890                 895

Cys Thr Val Cys Glu Asp Thr Glu Arg Gln Leu Arg Glu Cys Thr Arg
            900                 905                 910

Trp Ala Asp Ala Glu Cys Glu Glu Ile Pro Gly Arg Trp Ile Thr Arg
        915                 920                 925

Ser Thr Pro Pro Glu Gly Ser Asp Ser Thr Ala Pro Ser Thr Gln Glu
    930                 935                 940

Pro Glu Ala Pro Pro Glu Gln Asp Leu Ile Ala Ser Thr Val Ala Gly
945                 950                 955                 960

Val Val Thr Thr Val Met Gly Ser Ser Gln Pro Val Val Thr Arg Gly
                965                 970                 975

Thr Thr Asp Asn Leu Ile Pro Val Tyr Cys Ser Ile Leu Ala Ala Val
            980                 985                 990

Val Val Gly Leu Val Ala Tyr Ile  Ala Phe Lys Arg
```

995 1000

<210> SEQ ID NO 91
<211> LENGTH: 3015
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: CISCgamma_LNGFR_FOXP3cDNA nucleotide sequence
coding sequence only codon optimized

<400> SEQUENCE: 91
atgcctctgg gcctgctgtg gctgggcctg gccctgctgg gcgccctgca cgcccaggcc 60
ggcgtgcagg tggagacaat ctccccaggc gacggacgca cattccctaa gcggggccag 120
acctgcgtgg tgcactatac aggcatgctg gaggatggca agaagtttga cagctcccgg 180
gatagaaaca agccattcaa gtttatgctg ggcaagcagg aagtgatcag aggctgggag 240
gagggcgtgg cccagatgtc tgtgggccag agggccaagc tgaccatcag cccagactac 300
gcctatggag caacaggcca cccaggaatc atcccacctc acgccaccct ggtgttcgat 360
gtggagctgc tgaagctggg cgagggaggg tcacctggat ccaacacatc aaaagagaac 420
ccctttctgt tcgcattgga ggccgtagtc atatctgttg gatccatggg acttattatc 480
tccctgttgt gtgtgtactt ctggctggaa cggactatgc ccaggatccc cacgctcaag 540
aatctggaag atctcgtcac agaataccat ggtaatttca gcgcctggag cggagtctct 600
aagggtctgg ccgaatccct ccaacccgat tattctgaac ggttgtgcct cgtatccgaa 660
ataccaccaa aaggcggggc tctgggtgag ggcccagggg cgagtccgtg caatcaacac 720
agcccgtatt gggcccctcc ttgttatacg ttgaagcccg aaactggaag cggagcgact 780
aacttcagcc tgcttaagca ggccggagat gtggaggaaa accctggacc gatgggggca 840
ggtgccaccg gacgagccat ggacgggccg cgcctgctgc tgttgctgct tctgggggtg 900
tcccttggag gtgccaagga ggcatgcccc acaggcctgt acacacacag cggtgagtgc 960
tgcaaagcct gcaacctggg cgagggtgtg gcccagcctt gtggagccaa ccagaccgtg 1020
tgtgagccct gcctggacag cgtgacgttc tccgacgtgg tgagcgcgac cgagccgtgc 1080
aagccgtgca ccgagtgcgt ggggctccag agcatgtcgg cgccgtgcgt ggaggccgac 1140
gacgccgtgt gccgctgcgc ctacggctac taccaggatg agacgactgg gcgctgcgag 1200
gcgtgccgcg tgtgcgaggc gggctcgggc ctcgtgttct cctgccagga caagcagaac 1260
accgtgtgcg aggagtgccc cgacggcacg tattccgacg aggccaacca cgtggacccg 1320
tgcctgccct gcaccgtgtg cgaggacacc gagcgccagc tccgcgagtg cacacgctgg 1380
gccgacgccg agtgcgagga gatccctggc cgttggatta cacggtccac acccccagag 1440
ggctcggaca gcacagcccc cagcacccag gagcctgagg cacctccaga acaagacctc 1500
atagccagca cggtggcagg tgtggtgacc acagtgatgg gcagctccca gcccgtggtg 1560
acccgaggca ccaccgacaa cctcatccct gtctattgct ccatcctggc tgctgtggtt 1620
gtgggtcttg tggcctacat agccttcaag aggggaagcg gagcgactaa cttcagcctg 1680
ctgaagcagg ccggagatgt ggaggaaaac cctggaccga tgcctaatcc tcggcctgga 1740
aagcctagcg ctccttctct tgctctggga ccttctcctg gcgcctctcc atcttggaga 1800
gccgctccta aagccagcga tctgctggga gctagaggac ctggcggcac atttcagggc 1860
agagatctta gaggcggagc ccacgctagc tcctccagcc ttaatcctat gcctcctagc 1920
cagctccagc tgcctacact gcctctggtt atggtggctc ctagcggagc tagactgggc 1980
cctctgcctc atctgcaagc tctgctgcag gacagacccc acttcatgca ccagctgagc 2040
accgtggatg cccacgcaag aacacctgtg ctgcaggttc accctctgga atccccagcc 2100
atgatcagcc tgacacctcc aacaacagcc accggcgtgt tcagcctgaa agccagacct 2160
ggactgcctc ctggcatcaa tgtggccagc ctggaatggg tgtccagaga acctgctctg 2220
ctgtgcacat tccccaatcc aagcgctccc agaaaggaca gcacactgtc tgccgtgcct 2280
cagagcagct atcccctgct tgctaacggc gtgtgcaagt ggcctggatg cgagaaggtg 2340
ttcgaggaac ccgaggactt cctgaagcac tgccaggccg atcatctgct ggacgagaaa 2400
ggcagagccc agtgtctgct ccagcgcgag atggtgcagt ctctggaaca gcagctggtc 2460
ctggaaaaag aaaagctgag cgccatgcag gcccacctgg ccggaaaaat ggccctgaca 2520
aaggccagca gcgtggcctc ttctgataag ggcagctgct gcattgtggc cgctggatct 2580
cagggacctg tggttcctgc ttggagcgga cctagagagg cccctgattc tctgtttgcc 2640
gtgcggagac acctgtgggg ctctcacggc aactctactt tccccgagtt cctgcacaac 2700
atggactact tcaagttcca caacatgcgg cctccattca cctacgccac actgatcaga 2760
tgggccattc tggaagcccc tgagaagcag agaaccctga acgagatcta ccactggttt 2820
acccggatgt tcgccttctt ccggaatcac cctgccacct ggaagaacgc catccggcac 2880
aatctgagcc tgcacaagtg cttcgtgcgc gtggaatctg agaaaggcgc cgtgtggaca 2940
gtggacgagc tggaattcag aaagaagaga agccagcggc ctagccggtg cagcaatcct 3000
acacctggac cttga 3015

<210> SEQ ID NO 92
<211> LENGTH: 3015
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: CISCgamma_LNGFR_FOXP3cDNA amino acid sequence

<400> SEQUENCE: 92
atgcctctgg gcctgctgtg gctgggcctg gccctgctgg gcgccctgca cgcccaggcc 60
ggcgtgcagg tggagacaat ctccccaggc gacggacgca cattccctaa gcggggccag 120
acctgcgtgg tgcactatac aggcatgctg gaggatggca agaagtttga cagctcccgg 180
gatagaaaca agccattcaa gtttatgctg ggcaagcagg aagtgatcag aggctgggag 240
gagggcgtgg cccagatgtc tgtgggccag agggccaagc tgaccatcag cccagactac 300
gcctatggag caacaggcca cccaggaatc atcccacctc acgccaccct ggtgttcgat 360
gtggagctgc tgaagctggg cgagggaggg tcacctggat ccaacacatc aaaagagaac 420
ccctttctgt tcgcattgga ggccgtagtc atatctgttg gatccatggg acttattatc 480
tccctgttgt gtgtgtactt ctggctggaa cggactatgc ccaggatccc cacgctcaag 540
aatctggaag atctcgtcac agaataccat ggtaatttca gcgcctggag cggagtctct 600
aagggtctgg ccgaatccct ccaacccgat tattctgaac ggttgtgcct cgtatccgaa 660
ataccaccaa aaggcggggc tctgggtgag ggcccagggg cgagtccgtg caatcaacac 720
agcccgtatt gggcccctcc ttgttatacg ttgaagcccg aaactggaag cggagcgact 780
aacttcagcc tgcttaagca ggccggagat gtggaggaaa accctggacc gatgggggca 840

```
ggtgccaccg gacgagccat ggacgggccg cgcctgctgc tgttgctgct tctgggggtg    900
tcccttggag gtgccaagga ggcatgcccc acaggcctgt acacacacag cggtgagtgc    960
tgcaaagcct gcaacctggg cgagggtgtg gcccagcctt gtggagccaa ccagaccgtg   1020
tgtgagccct gcctggacag cgtgacgttc tccgacgtgg tgagcgcgac cgagccgtgc   1080
aagccgtgca ccgagtgcgt ggggctccag agcatgtcgg cgccgtgcgt ggaggccgac   1140
gacgccgtgt gccgctgcgc ctacggctac taccaggatg agacgactgg gcgctgcgag   1200
gcgtgccgcg tgtgcgaggc gggctcgggc ctcgtgttct cctgccagga caagcagaac   1260
accgtgtgcg aggagtgccc cgacggcacg tattccgacg aggccaacca cgtggacccg   1320
tgcctgccct gcaccgtgtg cgaggacacc gagcgccagc tccgcgagtg cacacgctgg   1380
gccgacgccg agtgcgagga gatccctggc cgttggatta cacggtccac acccccagag   1440
ggctcggaca gcacagcccc cagcacccag gagcctgagg cacctccaga acaagacctc   1500
atagccagca cggtggcagg tgtggtgacc acagtgatgg gcagctccca gcccgtggtg   1560
acccgaggca ccaccgacaa cctcatccct gtctattgct ccatcctggc tgctgtggtt   1620
gtgggtcttg tggcctacat agccttcaag aggggaagcg gagcgactaa cttcagcctg   1680
ctgaagcagg ccggagatgt ggaggaaaac cctggaccga tgcctaatcc tcggcctgga   1740
aagcctagcg ctccttctct tgctctggga ccttctcctg gcgcctctcc atcttggaga   1800
gccgctccta aagccagcga tctgctggga gctagaggac ctggcggcac atttcagggc   1860
agagatctta gaggcggagc ccacgctagc tcctccagcc ttaatcctat gcctcctagc   1920
cagctccagc tgcctacact gcctctggtt atggtggctc ctagcggagc tagactgggc   1980
cctctgcctc atctgcaagc tctgctgcag gacagacccc acttcatgca ccagctgagc   2040
accgtggatg cccacgcaag aacacctgtg ctgcaggttc accctctgga atccccagcc   2100
atgatcagcc tgacacctcc aacaacagcc accggcgtgt tcagcctgaa agccagacct   2160
ggactgcctc ctggcatcaa tgtggccagc ctggaatggg tgtccagaga acctgctctg   2220
ctgtgcacat tccccaatcc aagcgctccc agaaaggaca gcacactgtc tgccgtgcct   2280
cagagcagct atcccctgct tgctaacggc gtgtgcaagt ggcctggatg cgagaaggtg   2340
ttcgaggaac ccgaggactt cctgaagcac tgccaggccg atcatctgct ggacgagaaa   2400
ggcagagccc agtgtctgct ccagcgcgag atggtgcagt ctctggaaca gcagctggtc   2460
ctggaaaaag aaaagctgag cgccatgcag gcccacctgg ccggaaaaat ggccctgaca   2520
aaggccagca gcgtggcctc ttctgataag ggcagctgct gcattgtggc cgctggatct   2580
cagggacctg tggttcctgc ttggagcgga cctagagagg cccctgattc tctgtttgcc   2640
gtgcggagac acctgtgggg ctctcacggc aactctactt tccccgagtt cctgcacaac   2700
atggactact tcaagttcca caacatgcgg cctccattca cctacgccac actgatcaga   2760
tgggccattc tggaagcccc tgagaagcag agaaccctga acgagatcta ccactggttt   2820
acccggatgt tcgccttctt ccggaatcac cctgccacct ggaagaacgc catccggcac   2880
aatctgagcc tgcacaagtg cttcgtgcgc gtggaatctg agaaaggcgc cgtgtggaca   2940
gtggacgagc tggaattcag aaagaagaga agccagcggc ctagccggtg cagcaatcct   3000
acacctggac cttga                                                    3015
```

<210> SEQ ID NO 93
<211> LENGTH: 251
<212> TYPE: PRT

<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rgamma_CISC amino acid sequence

<400> SEQUENCE: 93

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Gly Ser Asn Thr Ser Lys Glu Asn Pro Phe Leu Phe Ala Leu Glu Ala
    130                 135                 140

Val Val Ile Ser Val Gly Ser Met Gly Leu Ile Ile Ser Leu Leu Cys
145                 150                 155                 160

Val Tyr Phe Trp Leu Glu Arg Thr Met Pro Arg Ile Pro Thr Leu Lys
                165                 170                 175

Asn Leu Glu Asp Leu Val Thr Glu Tyr His Gly Asn Phe Ser Ala Trp
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
    210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr
                245                 250
```

<210> SEQ ID NO 94
<211> LENGTH: 429
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta_CISC

<400> SEQUENCE: 94

```
Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45
```

```
Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Gly Lys Asp Thr Ile Pro Trp Leu Gly His Leu Leu Val Gly
        115                 120                 125

Leu Ser Gly Ala Phe Gly Phe Ile Ile Leu Val Tyr Leu Leu Ile Asn
    130                 135                 140

Cys Arg Asn Thr Gly Pro Trp Leu Lys Lys Val Leu Lys Cys Asn Thr
145                 150                 155                 160

Pro Asp Pro Ser Lys Phe Phe Ser Gln Leu Ser Ser Glu His Gly Gly
                165                 170                 175

Asp Val Gln Lys Trp Leu Ser Ser Pro Phe Pro Ser Ser Ser Phe Ser
            180                 185                 190

Pro Gly Gly Leu Ala Pro Glu Ile Ser Pro Leu Glu Val Leu Glu Arg
        195                 200                 205

Asp Lys Val Thr Gln Leu Leu Leu Gln Gln Asp Lys Val Pro Glu Pro
    210                 215                 220

Ala Ser Leu Ser Ser Asn His Ser Leu Thr Ser Cys Phe Thr Asn Gln
225                 230                 235                 240

Gly Tyr Phe Phe Phe His Leu Pro Asp Ala Leu Glu Ile Glu Ala Cys
                245                 250                 255

Gln Val Tyr Phe Thr Tyr Asp Pro Tyr Ser Glu Glu Asp Pro Asp Glu
            260                 265                 270

Gly Val Ala Gly Ala Pro Thr Gly Ser Ser Pro Gln Pro Leu Gln Pro
        275                 280                 285

Leu Ser Gly Glu Asp Asp Ala Tyr Cys Thr Phe Pro Ser Arg Asp Asp
    290                 295                 300

Leu Leu Leu Phe Ser Pro Ser Leu Leu Gly Gly Pro Ser Pro Pro Ser
305                 310                 315                 320

Thr Ala Pro Gly Gly Ser Gly Ala Gly Glu Glu Arg Met Pro Pro Ser
                325                 330                 335

Leu Gln Glu Arg Val Pro Arg Asp Trp Asp Pro Gln Pro Leu Gly Pro
            340                 345                 350

Pro Thr Pro Gly Val Pro Asp Leu Val Asp Phe Gln Pro Pro Pro Glu
        355                 360                 365

Leu Val Leu Arg Glu Ala Gly Glu Glu Val Pro Asp Ala Gly Pro Arg
    370                 375                 380

Glu Gly Val Ser Phe Pro Trp Ser Arg Pro Pro Gly Gln Gly Glu Phe
385                 390                 395                 400

Arg Ala Leu Asn Ala Arg Leu Pro Leu Asn Thr Asp Ala Tyr Leu Ser
                405                 410                 415

Leu Gln Glu Leu Gln Gly Gln Asp Pro Thr His Leu Val
            420                 425
```

<210> SEQ ID NO 95
<211> LENGTH: 352
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rgamma_CISC

<400> SEQUENCE: 95

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Gly Ser Gln Asn Leu Val Ile Pro Trp Ala Pro Glu Asn Leu Thr
    130                 135                 140

Leu His Lys Leu Ser Glu Ser Gln Leu Glu Leu Asn Trp Asn Asn Arg
145                 150                 155                 160

Phe Leu Asn His Cys Leu Glu His Leu Val Gln Tyr Arg Thr Asp Trp
                165                 170                 175

Asp His Ser Trp Thr Glu Gln Ser Val Asp Tyr Arg His Lys Phe Ser
            180                 185                 190

Leu Pro Ser Val Asp Gly Gln Lys Arg Tyr Thr Phe Arg Val Arg Ser
        195                 200                 205

Arg Phe Asn Pro Leu Cys Gly Ser Ala Gln His Trp Ser Glu Trp Ser
    210                 215                 220

His Pro Ile His Trp Gly Ser Asn Thr Ser Lys Glu Asn Pro Phe Leu
225                 230                 235                 240

Phe Ala Leu Glu Ala Val Val Ile Ser Val Gly Ser Met Gly Leu Ile
                245                 250                 255

Ile Ser Leu Leu Cys Val Tyr Phe Trp Leu Glu Arg Thr Met Pro Arg
            260                 265                 270

Ile Pro Thr Leu Lys Asn Leu Glu Asp Leu Val Thr Glu Tyr His Gly
        275                 280                 285

Asn Phe Ser Ala Trp Ser Gly Val Ser Lys Gly Leu Ala Glu Ser Leu
    290                 295                 300

Gln Pro Asp Tyr Ser Glu Arg Leu Cys Leu Val Ser Glu Ile Pro Pro
305                 310                 315                 320

Lys Gly Gly Ala Leu Gly Glu Gly Pro Gly Ala Ser Pro Cys Asn Gln
                325                 330                 335

His Ser Pro Tyr Trp Ala Pro Pro Cys Tyr Thr Leu Lys Pro Glu Thr
            340                 345                 350
```

<210> SEQ ID NO 96
<211> LENGTH: 543
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta_CISC

<400> SEQUENCE: 96

```
Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Gly Gly Ser Lys Pro Phe Glu Asn Leu Arg Leu Met Ala Pro
        115                 120                 125

Ile Ser Leu Gln Val Val His Val Glu Thr His Arg Cys Asn Ile Ser
    130                 135                 140

Trp Glu Ile Ser Gln Ala Ser His Tyr Phe Glu Arg His Leu Glu Phe
145                 150                 155                 160

Glu Ala Arg Thr Leu Ser Pro Gly His Thr Trp Glu Glu Ala Pro Leu
                165                 170                 175

Leu Thr Leu Lys Gln Lys Gln Glu Trp Ile Cys Leu Glu Thr Leu Thr
            180                 185                 190

Pro Asp Thr Gln Tyr Glu Phe Gln Val Arg Val Lys Pro Leu Gln Gly
        195                 200                 205

Glu Phe Thr Thr Trp Ser Pro Trp Ser Gln Pro Leu Ala Phe Arg Thr
    210                 215                 220

Lys Pro Ala Ala Leu Gly Lys Asp Thr Ile Pro Trp Leu Gly His Leu
225                 230                 235                 240

Leu Val Gly Leu Ser Gly Ala Phe Gly Phe Ile Ile Leu Val Tyr Leu
                245                 250                 255

Leu Ile Asn Cys Arg Asn Thr Gly Pro Trp Leu Lys Lys Val Leu Lys
            260                 265                 270

Cys Asn Thr Pro Asp Pro Ser Lys Phe Phe Gln Leu Ser Ser Glu His
        275                 280                 285

Gly Gly Asp Val Gln Lys Trp Leu Ser Ser Pro Phe Pro Ser Ser Ser
    290                 295                 300

Phe Ser Pro Gly Gly Leu Ala Pro Glu Ile Ser Pro Leu Glu Val Leu
305                 310                 315                 320

Glu Arg Asp Lys Val Thr Gln Leu Leu Leu Gln Gln Asp Lys Val Pro
                325                 330                 335

Glu Pro Ala Ser Leu Ser Ser Asn His Ser Leu Thr Ser Cys Phe Thr
            340                 345                 350

Asn Gln Gly Tyr Phe Phe Phe His Leu Pro Asp Ala Leu Glu Ile Glu
        355                 360                 365

Ala Cys Gln Val Tyr Phe Thr Tyr Asp Pro Tyr Ser Glu Glu Asp Pro
    370                 375                 380

Asp Glu Gly Val Ala Gly Ala Pro Thr Gly Ser Ser Pro Gln Pro Leu
```

```
385                 390                 395                 400

Gln Pro Leu Ser Gly Glu Asp Asp Ala Tyr Cys Thr Phe Pro Ser Arg
                405                 410                 415

Asp Asp Leu Leu Leu Phe Ser Pro Ser Leu Leu Gly Gly Pro Ser Pro
            420                 425                 430

Pro Ser Thr Ala Pro Gly Gly Ser Gly Ala Gly Glu Glu Arg Met Pro
        435                 440                 445

Pro Ser Leu Gln Glu Arg Val Pro Arg Asp Trp Asp Pro Gln Pro Leu
    450                 455                 460

Gly Pro Pro Thr Pro Gly Val Pro Asp Leu Val Asp Phe Gln Pro Pro
465                 470                 475                 480

Pro Glu Leu Val Leu Arg Glu Ala Gly Glu Glu Val Pro Asp Ala Gly
                485                 490                 495

Pro Arg Glu Gly Val Ser Phe Pro Trp Ser Arg Pro Pro Gly Gln Gly
            500                 505                 510

Glu Phe Arg Ala Leu Asn Ala Arg Leu Pro Leu Asn Thr Asp Ala Tyr
        515                 520                 525

Leu Ser Leu Gln Glu Leu Gln Gly Gln Asp Pro Thr His Leu Val
    530                 535                 540


<210> SEQ ID NO 97
<211> LENGTH: 349
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rgamma_CISC

<400> SEQUENCE: 97

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gln Asn Leu Val Ile Pro Trp Ala Pro Glu Asn Leu Thr Leu His Lys
    130                 135                 140

Leu Ser Glu Ser Gln Leu Glu Leu Asn Trp Asn Asn Arg Phe Leu Asn
145                 150                 155                 160

His Cys Leu Glu His Leu Val Gln Tyr Arg Thr Asp Trp Asp His Ser
                165                 170                 175

Trp Thr Glu Gln Ser Val Asp Tyr Arg His Lys Phe Ser Leu Pro Ser
            180                 185                 190

Val Asp Gly Gln Lys Arg Tyr Thr Phe Arg Val Arg Ser Arg Phe Asn
```

```
        195                 200                 205

Pro Leu Cys Gly Ser Ala Gln His Trp Ser Glu Trp Ser His Pro Ile
    210                 215                 220

His Trp Gly Ser Asn Thr Ser Lys Glu Asn Pro Phe Leu Phe Ala Leu
225                 230                 235                 240

Glu Ala Val Val Ile Ser Val Gly Ser Met Gly Leu Ile Ile Ser Leu
                245                 250                 255

Leu Cys Val Tyr Phe Trp Leu Glu Arg Thr Met Pro Arg Ile Pro Thr
            260                 265                 270

Leu Lys Asn Leu Glu Asp Leu Val Thr Glu Tyr His Gly Asn Phe Ser
        275                 280                 285

Ala Trp Ser Gly Val Ser Lys Gly Leu Ala Glu Ser Leu Gln Pro Asp
    290                 295                 300

Tyr Ser Glu Arg Leu Cys Leu Val Ser Glu Ile Pro Pro Lys Gly Gly
305                 310                 315                 320

Ala Leu Gly Glu Gly Pro Gly Ala Ser Pro Cys Asn Gln His Ser Pro
                325                 330                 335

Tyr Trp Ala Pro Pro Cys Tyr Thr Leu Lys Pro Glu Thr
            340                 345
```

<210> SEQ ID NO 98
<211> LENGTH: 541
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta_CISC

<400> SEQUENCE: 98

```
Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Lys Pro Phe Glu Asn Leu Arg Leu Met Ala Pro Ile Ser Leu
        115                 120                 125

Gln Val Val His Val Glu Thr His Arg Cys Asn Ile Ser Trp Glu Ile
    130                 135                 140

Ser Gln Ala Ser His Tyr Phe Glu Arg His Leu Glu Phe Glu Ala Arg
145                 150                 155                 160

Thr Leu Ser Pro Gly His Thr Trp Glu Glu Ala Pro Leu Leu Thr Leu
                165                 170                 175

Lys Gln Lys Gln Glu Trp Ile Cys Leu Glu Thr Leu Thr Pro Asp Thr
            180                 185                 190

Gln Tyr Glu Phe Gln Val Arg Val Lys Pro Leu Gln Gly Glu Phe Thr
```

```
        195                 200                 205

Thr Trp Ser Pro Trp Ser Gln Pro Leu Ala Phe Arg Thr Lys Pro Ala
    210                 215                 220

Ala Leu Gly Lys Asp Thr Ile Pro Trp Leu Gly His Leu Leu Val Gly
225                 230                 235                 240

Leu Ser Gly Ala Phe Gly Phe Ile Ile Leu Val Tyr Leu Leu Ile Asn
                245                 250                 255

Cys Arg Asn Thr Gly Pro Trp Leu Lys Lys Val Leu Lys Cys Asn Thr
            260                 265                 270

Pro Asp Pro Ser Lys Phe Phe Ser Gln Leu Ser Ser Glu His Gly Gly
        275                 280                 285

Asp Val Gln Lys Trp Leu Ser Ser Pro Phe Pro Ser Ser Ser Phe Ser
    290                 295                 300

Pro Gly Gly Leu Ala Pro Glu Ile Ser Pro Leu Glu Val Leu Glu Arg
305                 310                 315                 320

Asp Lys Val Thr Gln Leu Leu Leu Gln Gln Asp Lys Val Pro Glu Pro
                325                 330                 335

Ala Ser Leu Ser Ser Asn His Ser Leu Thr Ser Cys Phe Thr Asn Gln
            340                 345                 350

Gly Tyr Phe Phe Phe His Leu Pro Asp Ala Leu Glu Ile Glu Ala Cys
        355                 360                 365

Gln Val Tyr Phe Thr Tyr Asp Pro Tyr Ser Glu Glu Asp Pro Asp Glu
    370                 375                 380

Gly Val Ala Gly Ala Pro Thr Gly Ser Ser Pro Gln Pro Leu Gln Pro
385                 390                 395                 400

Leu Ser Gly Glu Asp Asp Ala Tyr Cys Thr Phe Pro Ser Arg Asp Asp
                405                 410                 415

Leu Leu Leu Phe Ser Pro Ser Leu Leu Gly Gly Pro Ser Pro Pro Ser
            420                 425                 430

Thr Ala Pro Gly Gly Ser Gly Ala Gly Glu Glu Arg Met Pro Pro Ser
        435                 440                 445

Leu Gln Glu Arg Val Pro Arg Asp Trp Asp Pro Gln Pro Leu Gly Pro
    450                 455                 460

Pro Thr Pro Gly Val Pro Asp Leu Val Asp Phe Gln Pro Pro Pro Glu
465                 470                 475                 480

Leu Val Leu Arg Glu Ala Gly Glu Glu Val Pro Asp Ala Gly Pro Arg
                485                 490                 495

Glu Gly Val Ser Phe Pro Trp Ser Arg Pro Pro Gly Gln Gly Glu Phe
            500                 505                 510

Arg Ala Leu Asn Ala Arg Leu Pro Leu Asn Thr Asp Ala Tyr Leu Ser
        515                 520                 525

Leu Gln Glu Leu Gln Gly Gln Asp Pro Thr His Leu Val
    530                 535                 540


<210> SEQ ID NO 99
<211> LENGTH: 251
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rgamma_CISC

<400> SEQUENCE: 99

Met Pro Leu Gly Leu Leu Trp Leu Gly Leu Ala Leu Leu Gly Ala Leu
```

```
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Ser Asn Thr Ser Lys Glu Asn Pro Phe Leu Phe Ala Leu Glu Ala
    130                 135                 140

Val Val Ile Ser Val Gly Ser Met Gly Leu Ile Ile Ser Leu Leu Cys
145                 150                 155                 160

Val Tyr Phe Trp Leu Glu Arg Thr Met Pro Arg Ile Pro Thr Leu Lys
                165                 170                 175

Asn Leu Glu Asp Leu Val Thr Glu Tyr His Gly Asn Phe Ser Ala Trp
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
    210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr
                245                 250


<210> SEQ ID NO 100
<211> LENGTH: 379
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta_CISC

<400> SEQUENCE: 100

Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Trp Leu Gly His Leu Leu Val Gly Leu Ser
65                  70                  75                  80

Gly Ala Phe Gly Phe Ile Ile Leu Val Tyr Leu Leu Ile Asn Cys Arg
                85                  90                  95

Asn Thr Gly Pro Trp Leu Lys Lys Val Leu Lys Cys Asn Thr Pro Asp
```

```
            100                 105                 110

Pro Ser Lys Phe Phe Ser Gln Leu Ser Ser Glu His Gly Gly Asp Val
        115                 120                 125

Gln Lys Trp Leu Ser Ser Pro Phe Pro Ser Ser Ser Phe Ser Pro Gly
    130                 135                 140

Gly Leu Ala Pro Glu Ile Ser Pro Leu Glu Val Leu Glu Arg Asp Lys
145                 150                 155                 160

Val Thr Gln Leu Leu Leu Gln Gln Asp Lys Val Pro Glu Pro Ala Ser
                165                 170                 175

Leu Ser Ser Asn His Ser Leu Thr Ser Cys Phe Thr Asn Gln Gly Tyr
            180                 185                 190

Phe Phe Phe His Leu Pro Asp Ala Leu Glu Ile Glu Ala Cys Gln Val
        195                 200                 205

Tyr Phe Thr Tyr Asp Pro Tyr Ser Glu Glu Asp Pro Asp Glu Gly Val
    210                 215                 220

Ala Gly Ala Pro Thr Gly Ser Ser Pro Gln Pro Leu Gln Pro Leu Ser
225                 230                 235                 240

Gly Glu Asp Asp Ala Tyr Cys Thr Phe Pro Ser Arg Asp Asp Leu Leu
                245                 250                 255

Leu Phe Ser Pro Ser Leu Leu Gly Gly Pro Ser Pro Pro Ser Thr Ala
            260                 265                 270

Pro Gly Gly Ser Gly Ala Gly Glu Glu Arg Met Pro Pro Ser Leu Gln
        275                 280                 285

Glu Arg Val Pro Arg Asp Trp Asp Pro Gln Pro Leu Gly Pro Pro Thr
    290                 295                 300

Pro Gly Val Pro Asp Leu Val Asp Phe Gln Pro Pro Pro Glu Leu Val
305                 310                 315                 320

Leu Arg Glu Ala Gly Glu Glu Val Pro Asp Ala Gly Pro Arg Glu Gly
                325                 330                 335

Val Ser Phe Pro Trp Ser Arg Pro Pro Gly Gln Gly Glu Phe Arg Ala
            340                 345                 350

Leu Asn Ala Arg Leu Pro Leu Asn Thr Asp Ala Tyr Leu Ser Leu Gln
        355                 360                 365

Glu Leu Gln Gly Gln Asp Pro Thr His Leu Val
    370                 375
```

<210> SEQ ID NO 101
<211> LENGTH: 345
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL7Ralpha_CISC

<400> SEQUENCE: 101

```
Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
```

65 70 75 80

Glu Ala Gln Glu Trp Cys Arg Lys Tyr Met Lys Ser Gly Asn Val Lys
85 90 95

Asp Leu Leu Gln Ala Trp Asp Leu Tyr Tyr His Val Phe Arg Arg Ile
100 105 110

Ser Lys Gly Glu Ile Asn Asn Ser Ser Gly Glu Met Asp Pro Ile Leu
115 120 125

Leu Thr Ile Ser Ile Leu Ser Phe Phe Ser Val Ala Leu Leu Val Ile
130 135 140

Leu Ala Cys Val Leu Trp Lys Lys Arg Ile Lys Pro Ile Val Trp Pro
145 150 155 160

Ser Leu Pro Asp His Lys Lys Thr Leu Glu His Leu Cys Lys Lys Pro
165 170 175

Arg Lys Asn Leu Asn Val Ser Phe Asn Pro Glu Ser Phe Leu Asp Cys
180 185 190

Gln Ile His Arg Val Asp Asp Ile Gln Ala Arg Asp Glu Val Glu Gly
195 200 205

Phe Leu Gln Asp Thr Phe Pro Gln Gln Leu Glu Glu Ser Glu Lys Gln
210 215 220

Arg Leu Gly Gly Asp Val Gln Ser Pro Asn Cys Pro Ser Glu Asp Val
225 230 235 240

Val Ile Thr Pro Glu Ser Phe Gly Arg Asp Ser Ser Leu Thr Cys Leu
245 250 255

Ala Gly Asn Val Ser Ala Cys Asp Ala Pro Ile Leu Ser Ser Ser Arg
260 265 270

Ser Leu Asp Cys Arg Glu Ser Gly Lys Asn Gly Pro His Val Tyr Gln
275 280 285

Asp Leu Leu Leu Ser Leu Gly Thr Thr Asn Ser Thr Leu Pro Pro Pro
290 295 300

Phe Ser Leu Gln Ser Gly Ile Leu Thr Leu Asn Pro Val Ala Gln Gly
305 310 315 320

Gln Pro Ile Leu Thr Ser Leu Gly Ser Asn Gln Glu Glu Ala Tyr Val
325 330 335

Thr Met Ser Ser Phe Tyr Gln Asn Gln
340 345

<210> SEQ ID NO 102
<211> LENGTH: 443
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta_CISC

<400> SEQUENCE: 102

Met Pro Leu Gly Leu Leu Trp Leu Gly Leu Ala Leu Leu Gly Ala Leu
1 5 10 15

His Ala Gln Ala Gly Val Gln Val Glu Thr Ile Ser Pro Gly Asp Gly
20 25 30

Arg Thr Phe Pro Lys Arg Gly Gln Thr Cys Val Val His Tyr Thr Gly
35 40 45

Met Leu Glu Asp Gly Lys Lys Val Asp Ser Ser Arg Asp Arg Asn Lys
50 55 60

Pro Phe Lys Phe Met Leu Gly Lys Gln Glu Val Ile Arg Gly Trp Glu

```
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Lys Asp Thr Ile Pro Trp Leu Gly His Leu Leu Val Gly Leu Ser
    130                 135                 140

Gly Ala Phe Gly Phe Ile Ile Leu Val Tyr Leu Leu Ile Asn Cys Arg
145                 150                 155                 160

Asn Thr Gly Pro Trp Leu Lys Lys Val Leu Lys Cys Asn Thr Pro Asp
                165                 170                 175

Pro Ser Lys Phe Phe Ser Gln Leu Ser Ser Glu His Gly Gly Asp Val
            180                 185                 190

Gln Lys Trp Leu Ser Ser Pro Phe Pro Ser Ser Ser Phe Ser Pro Gly
        195                 200                 205

Gly Leu Ala Pro Glu Ile Ser Pro Leu Glu Val Leu Glu Arg Asp Lys
    210                 215                 220

Val Thr Gln Leu Leu Leu Gln Gln Asp Lys Val Pro Glu Pro Ala Ser
225                 230                 235                 240

Leu Ser Ser Asn His Ser Leu Thr Ser Cys Phe Thr Asn Gln Gly Tyr
                245                 250                 255

Phe Phe Phe His Leu Pro Asp Ala Leu Glu Ile Glu Ala Cys Gln Val
            260                 265                 270

Tyr Phe Thr Tyr Asp Pro Tyr Ser Glu Glu Asp Pro Asp Glu Gly Val
        275                 280                 285

Ala Gly Ala Pro Thr Gly Ser Ser Pro Gln Pro Leu Gln Pro Leu Ser
    290                 295                 300

Gly Glu Asp Asp Ala Tyr Cys Thr Phe Pro Ser Arg Asp Asp Leu Leu
305                 310                 315                 320

Leu Phe Ser Pro Ser Leu Leu Gly Gly Pro Ser Pro Pro Ser Thr Ala
                325                 330                 335

Pro Gly Gly Ser Gly Ala Gly Glu Glu Arg Met Pro Pro Ser Leu Gln
            340                 345                 350

Glu Arg Val Pro Arg Asp Trp Asp Pro Gln Pro Leu Gly Pro Pro Thr
        355                 360                 365

Pro Gly Val Pro Asp Leu Val Asp Phe Gln Pro Pro Pro Glu Leu Val
    370                 375                 380

Leu Arg Glu Ala Gly Glu Glu Val Pro Asp Ala Gly Pro Arg Glu Gly
385                 390                 395                 400

Val Ser Phe Pro Trp Ser Arg Pro Pro Gly Gln Gly Glu Phe Arg Ala
                405                 410                 415

Leu Asn Ala Arg Leu Pro Leu Asn Thr Asp Ala Tyr Leu Ser Leu Gln
            420                 425                 430

Glu Leu Gln Gly Gln Asp Pro Thr His Leu Val
        435                 440
```

<210> SEQ ID NO 103
<211> LENGTH: 251
<212> TYPE: PRT
<213> ORGANISM: Artificial sequence
<220> FEATURE:
<223> OTHER INFORMATION: Synthetic polypeptide
<220> FEATURE:

<221> NAME/KEY: misc_feature
<223> OTHER INFORMATION: IL2Rgamma_CISC

<400> SEQUENCE: 103

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Ser Asn Thr Ser Lys Glu Asn Pro Phe Leu Phe Ala Leu Glu Ala
    130                 135                 140

Val Val Ile Ser Val Gly Ser Met Gly Leu Ile Ile Ser Leu Leu Cys
145                 150                 155                 160

Val Tyr Phe Trp Leu Glu Arg Thr Met Pro Arg Ile Pro Thr Leu Lys
                165                 170                 175

Asn Leu Glu Asp Leu Val Thr Glu Tyr His Gly Asn Phe Ser Ala Trp
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
    210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr
                245                 250
```

<210> SEQ ID NO 104
<211> LENGTH: 358
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Ralpha_CISC

<400> SEQUENCE: 104

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
```

65 70 75 80

Glu Gly Val Ala Gln Met Ser Val Gly Gln Arg Ala Lys Leu Thr Ile
85 90 95

Ser Pro Asp Tyr Ala Tyr Gly Ala Thr Gly His Pro Gly Ile Ile Pro
100 105 110

Pro His Ala Thr Leu Val Phe Asp Val Glu Leu Leu Lys Leu Glu Gly
115 120 125

Glu Ile Asn Asn Ser Ser Gly Glu Met Asp Pro Ile Leu Leu Thr Ile
130 135 140

Ser Ile Leu Ser Phe Phe Ser Val Ala Leu Leu Val Ile Leu Ala Cys
145 150 155 160

Val Leu Trp Lys Lys Arg Ile Lys Pro Ile Val Trp Pro Ser Leu Pro
165 170 175

Asp His Lys Lys Thr Leu Glu His Leu Cys Lys Lys Pro Arg Lys Asn
180 185 190

Leu Asn Val Ser Phe Asn Pro Glu Ser Phe Leu Asp Cys Gln Ile His
195 200 205

Arg Val Asp Asp Ile Gln Ala Arg Asp Glu Val Glu Gly Phe Leu Gln
210 215 220

Asp Thr Phe Pro Gln Gln Leu Glu Glu Ser Glu Lys Gln Arg Leu Gly
225 230 235 240

Gly Asp Val Gln Ser Pro Asn Cys Pro Ser Glu Asp Val Val Ile Thr
245 250 255

Pro Glu Ser Phe Gly Arg Asp Ser Ser Leu Thr Cys Leu Ala Gly Asn
260 265 270

Val Ser Ala Cys Asp Ala Pro Ile Leu Ser Ser Ser Arg Ser Leu Asp
275 280 285

Cys Arg Glu Ser Gly Lys Asn Gly Pro His Val Tyr Gln Asp Leu Leu
290 295 300

Leu Ser Leu Gly Thr Thr Asn Ser Thr Leu Pro Pro Pro Phe Ser Leu
305 310 315 320

Gln Ser Gly Ile Leu Thr Leu Asn Pro Val Ala Gln Gly Gln Pro Ile
325 330 335

Leu Thr Ser Leu Gly Ser Asn Gln Glu Glu Ala Tyr Val Thr Met Ser
340 345 350

Ser Phe Tyr Gln Asn Gln
355

<210> SEQ ID NO 105
<211> LENGTH: 358
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL7Ralpha_CISC

<400> SEQUENCE: 105

Met Pro Leu Gly Leu Leu Trp Leu Gly Leu Ala Leu Leu Gly Ala Leu
1 5 10 15

His Ala Gln Ala Gly Val Gln Val Glu Thr Ile Ser Pro Gly Asp Gly
20 25 30

Arg Thr Phe Pro Lys Arg Gly Gln Thr Cys Val Val His Tyr Thr Gly
35 40 45

Met Leu Glu Asp Gly Lys Lys Val Asp Ser Ser Arg Asp Arg Asn Lys

```
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Glu Ile Asn Asn Ser Ser Gly Glu Met Asp Pro Ile Leu Leu Thr Ile
    130                 135                 140

Ser Ile Leu Ser Phe Phe Ser Val Ala Leu Leu Val Ile Leu Ala Cys
145                 150                 155                 160

Val Leu Trp Lys Lys Arg Ile Lys Pro Ile Val Trp Pro Ser Leu Pro
                165                 170                 175

Asp His Lys Lys Thr Leu Glu His Leu Cys Lys Lys Pro Arg Lys Asn
            180                 185                 190

Leu Asn Val Ser Phe Asn Pro Glu Ser Phe Leu Asp Cys Gln Ile His
        195                 200                 205

Arg Val Asp Asp Ile Gln Ala Arg Asp Glu Val Glu Gly Phe Leu Gln
    210                 215                 220

Asp Thr Phe Pro Gln Gln Leu Glu Glu Ser Glu Lys Gln Arg Leu Gly
225                 230                 235                 240

Gly Asp Val Gln Ser Pro Asn Cys Pro Ser Glu Asp Val Val Ile Thr
                245                 250                 255

Pro Glu Ser Phe Gly Arg Asp Ser Ser Leu Thr Cys Leu Ala Gly Asn
            260                 265                 270

Val Ser Ala Cys Asp Ala Pro Ile Leu Ser Ser Ser Arg Ser Leu Asp
        275                 280                 285

Cys Arg Glu Ser Gly Lys Asn Gly Pro His Val Tyr Gln Asp Leu Leu
    290                 295                 300

Leu Ser Leu Gly Thr Thr Asn Ser Thr Leu Pro Pro Pro Phe Ser Leu
305                 310                 315                 320

Gln Ser Gly Ile Leu Thr Leu Asn Pro Val Ala Gln Gly Gln Pro Ile
                325                 330                 335

Leu Thr Ser Leu Gly Ser Asn Gln Glu Glu Ala Tyr Val Thr Met Ser
            340                 345                 350

Ser Phe Tyr Gln Asn Gln
        355


<210> SEQ ID NO 106
<211> LENGTH: 276
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: MPL_CISC

<400> SEQUENCE: 106

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
```

-continued

```
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Glu Thr Ala Trp Ile Ser Leu Val Thr Ala Leu His Leu Val Leu Gly
    130                 135                 140

Leu Ser Ala Val Leu Gly Leu Leu Leu Leu Arg Trp Gln Phe Pro Ala
145                 150                 155                 160

His Tyr Arg Arg Leu Arg His Ala Leu Trp Pro Ser Leu Pro Asp Leu
                165                 170                 175

His Arg Val Leu Gly Gln Tyr Leu Arg Asp Thr Ala Ala Leu Ser Pro
            180                 185                 190

Pro Lys Ala Thr Val Ser Asp Thr Cys Glu Glu Val Glu Pro Ser Leu
        195                 200                 205

Leu Glu Ile Leu Pro Lys Ser Ser Glu Arg Thr Pro Leu Pro Leu Cys
    210                 215                 220

Ser Ser Gln Ala Gln Met Asp Tyr Arg Arg Leu Gln Pro Ser Cys Leu
225                 230                 235                 240

Gly Thr Met Pro Leu Ser Val Cys Pro Pro Met Ala Glu Ser Gly Ser
                245                 250                 255

Cys Cys Thr Thr His Ile Ala Asn His Ser Tyr Leu Pro Leu Ser Tyr
            260                 265                 270

Trp Gln Gln Pro
        275


<210> SEQ ID NO 107
<211> LENGTH: 10053
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: expression vector

<400> SEQUENCE: 107

agcttaatgt agtcttatgc aatactcttg tagtcttgca acatggtaac gatgagttag      60

caacatgcct tacaaggaga gaaaaagcac cgtgcatgcc gattggtgga agtaaggtgg     120

tacgatcgtg ccttattagg aaggcaacag acgggtctga catggattgg acgaaccact     180

gaattgccgc attgcagaga tattgtattt aagtgcctag ctcgatacaa taaacgggtc     240

tctctggtta gaccagatct gagcctggga gctctctggc taactaggga acccactgct     300

taagcctcaa taaagcttgc cttgagtgct tcaagtagtg tgtgcccgtc tgttgtgtga     360

ctctggtaac tagagatccc tcagaccctt ttagtcagtg tggaaaatct ctagcagtgg     420

cgcccgaaca gggacttgaa agcgaaaggg aaaccagagg agctctctcg acgcaggact     480

cggcttgctg aagcgcgcac ggcaagaggc gaggggcggc gactggtgag tacgccaaaa     540

attttgacta gcggaggcta gaaggagaga gatgggtgcg agagcgtcag tattaagcgg     600
```

```
gggagaatta gatcgcgatg ggaaaaaatt cggttaaggc caggggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc gctgatcttc agacctggag gaggagatat    960
gagggacaat tggagaagtg aattatataa atataaagta gtaaaaattg aaccattagg   1020
agtagcaccc accaaggcaa agagaagagt ggtgcagaga gaaaaaagag cagtgggaat   1080
aggagctttg ttccttgggt tcttgggagc agcaggaagc actatgggcg cagcctcaat   1140
gacgctgacg gtacaggcca gacaattatt gtctggtata gtgcagcagc agaacaattt   1200
gctgagggct attgaggcgc aacagcatct gttgcaactc acagtctggg gcatcaagca   1260
gctccaggca agaatcctgg ctgtggaaag atacctaaag gatcaacagc tcctggggat   1320
ttggggttgc tctggaaaac tcatttgcac cactgctgtg ccttggaatg ctagttggag   1380
taataaatct ctggaacaga tttggaatca cacgacctgg atggagtggg acagagaaat   1440
taacaattac acaagcttaa tacactcctt aattgaagaa tcgcaaaacc agcaagaaaa   1500
gaatgaacaa gaattattgg aattagataa atgggcaagt ttgtggaatt ggtttaacat   1560
aacaaattgg ctgtggtata taaaattatt cataatgata gtaggaggct tggtaggttt   1620
aagaatagtt tttgctgtac tttctatagt gaatagagtt aggcagggat attcaccatt   1680
atcgtttcag acccacctcc caaccccgag gggacccgac aggcccgaag gaatagaaga   1740
agaaggtgga gagagagaca gagacagatc cattcgatta gtgaacggat ctcgacggta   1800
tcggttaact tttaaaagaa aaggggggat tgggggtac agtgcagggg aaagaatagt    1860
agacataata gcaacagaca tacaaactaa agaattacaa aaacaaatta caaaaattca   1920
aaattttatc gatcacgaga ctagcctcga gaagcttgat atcgaattcc cacggggttg   1980
gacgcgtagg aacagagaaa caggagaata tgggccaaac aggatatctg tggtaagcag   2040
ttcctgcccc ggctcagggc caagaacagt tggaacagca gaatatgggc caaacaggat   2100
atctgtggta agcagttcct gccccggctc agggccaaga acagatggtc cccagatgcg   2160
gtcccgccct cagcagtttc tagagaacca tcagatgttt ccagggtgcc ccaaggacct   2220
gaaatgaccc tgtgccttat ttgaactaac caatcagttc gcttctcgct tctgttcgcg   2280
cgcttctgct ccccgagctc tatataagca gagctcgttt agtgaaccgt cagatcgcta   2340
gcaccggtgc cgccaccatg cctctgggcc tgctgtggct gggcctggcc ctgctgggcg   2400
ccctgcacgc ccaggccggc gtgcaggtgg agacaatctc ccccaggcgac ggacgcacat   2460
tccctaagcg gggccagacc tgcgtggtgc actatacagg catgctggag gatggcaaga   2520
agtttgacag ctcccgggat agaaacaagc cattcaagtt tatgctgggc aagcaggaag   2580
tgatcagagg ctgggaggag ggcgtggccc agatgtctgt gggccagagg gccaagctga   2640
ccatcagccc agactacgcc tatggagcaa caggccaccc aggaatcatc ccacctcacg   2700
ccaccctggt gttcgatgtg gagctgctga agctgggcga gggcggtagt cagaaccttg   2760
tgataccatg ggccccagaa aatctcacac ttcataaact ttccgaatca caactcgaac   2820
tcaactggaa taaccggttc ctgaatcact gtcttgaaca cctggtacaa tatcggaccg   2880
actgggatca ctcatggaca gaacaatctg tggactatag gcacaaattc tcactcccaa   2940
```

```
gcgtagacgg ccaaaaaaga tacacttttc gcgtacgatc ccgctttaat cctctctgcg   3000
gctctgctca gcactggagt gaatggtccc atcccattca ttggggatcc aacacatcaa   3060
aagagaaccc ctttctgttc gcattggagg ccgtagtcat atctgttgga tccatgggac   3120
ttattatctc cctgttgtgt gtgtacttct ggctggaacg gactatgccc aggatcccca   3180
cgctcaagaa tctggaagat ctcgtcacag aataccatgg taatttcagc gcctggagcg   3240
gagtctctaa gggtctggcc gaatccctcc aacccgatta ttctgaacgg ttgtgcctcg   3300
tatccgaaat accaccaaaa ggcggggctc tgggtgaggg cccaggggcg agtccgtgca   3360
atcaacacag cccgtattgg gcccctcctt gttatacgtt gaagcccgaa actggaagcg   3420
gagctactaa cttcagcctg ctgaagcagg ctggagacgt ggaggagaac cctggaccta   3480
tggcactgcc cgtgaccgcc ctgctgctgc ctctggccct gctgctgcac gcagcccggc   3540
ctatcctgtg gcacgagatg tggcacgagg gcctggagga ggccagcagg ctgtattttg   3600
gcgagcgcaa cgtgaagggc atgttcgagg tgctggagcc tctgcacgcc atgatggaga   3660
gaggcccaca gaccctgaag gagacatcct ttaaccaggc ctatggacgg gacctgatgg   3720
aggcacagga gtggtgcaga aagtacatga agtctggcaa tgtgaaggac ctgctgcagg   3780
cctgggatct gtactatcac gtgtttcgga gaatctccaa gggaggttca aaaccttttg   3840
agaaccttag actgatggcg cccatctctc tgcaggtagt tcacgttgag acccatagat   3900
gcaatataag ctgggaaatc tcacaagcca gccattactt tgaacggcat ttggaattcg   3960
aggcccgaac actttccccc ggtcatacgt gggaagaagc tcctctcttg acgctgaagc   4020
agaagcagga gtggatttgt ctggagactt tgactcctga tactcagtat gagttccaag   4080
ttcgggtgaa accactccaa ggcgagttca cgacgtggtc tccgtggagt caaccgttgg   4140
cgttccgcac gaagcccgct gcccttggca aagacacgat tccgtggctt gggcatctgc   4200
tcgttgggct gagtggtgcg tttggtttca tcatcttggt ctatctcttg atcaattgca   4260
gaaatacagg cccttggctg aaaaaagtgc tcaagtgtaa tacccccgac ccaagcaagt   4320
tcttctccca gctttcttca gagcatggag gcgatgtgca gaaatggctc tcttcacctt   4380
ttccctcctc aagcttctcc ccgggagggc tggcgcccga gatttcacct cttgaggtac   4440
ttgaacgaga caaggttacc caacttctcc ttcaacagga taaggtaccc gaacctgcga   4500
gccttagctc caaccactct cttacgagct gcttcaccaa tcagggatac ttctttttcc   4560
accttcccga tgcgctggaa atcgaagctt gtcaagttta ctttacctat gatccatata   4620
gcgaggaaga tcccgacgaa ggagtcgccg gtgcgcccac gggttcctca ccccaacctc   4680
tccagcctct ctcaggagaa gatgatgctt attgcacttt tcccagtaga gacgatctcc   4740
tcctcttttc tccatctctt ttggggggac cttccccccc ttctacggca cctggcgggt   4800
ctggtgctgg cgaggagcgg atgccgccgt ccctccagga gcgagtacca cgagattggg   4860
atccccagcc acttggaccc cccacccccg gcgtacctga ccttgtcgat tttcaacctc   4920
cccctgaatt ggtgctgcga gaggctgggg aggaagttcc ggacgctggg ccgagggagg   4980
gcgtgtcctt tccatggagt aggcctccag gtcaaggcga gtttagggct ctcaacgcgc   5040
ggctgccgtt gaatacagac gcttatctct cactgcagga actgcaaggt caggacccaa   5100
cacatcttgt aggatctggt gctactaatt tttctctttt gaagcaagct ggagatgttg   5160
aagagaaccc tggtccagtg agcaagggcg aggagctgtt caccggggtg gtgcccatcc   5220
tggtcgagct ggacggcgac gtaaacggcc acaagttcag cgtgtccggc gagggcgagg   5280
gcgatgccac ctacggcaag ctgaccctga agttcatctg caccaccggc aagctgcccg   5340
```

```
tgccctggcc caccctcgtg accaccctga cctacggcgt gcagtgcttc agccgctacc   5400
ccgaccacat gaagcagcac gacttcttca agtccgccat gcccgaaggc tacgtccagg   5460
agcgcaccat cttcttcaag gacgacggca actacaagac ccgcgccgag gtgaagttcg   5520
agggcgacac cctggtgaac cgcatcgagc tgaagggcat cgacttcaag gaggacggca   5580
acatcctggg gcacaagctg gagtacaact acaacagcca caacgtctat atcatggccg   5640
acaagcagaa gaacggcatc aaggtgaact tcaagatccg ccacaacatc gaggacggca   5700
gcgtgcagct cgccgaccac taccagcaga acacccccat cggcgacggc cccgtgctgc   5760
tgcccgacaa ccactacctg agcacccagt ccgccctgag caaagacccc aacgagaagc   5820
gcgatcacat ggtcctgctg gagttcgtga ccgccgccgg gatcactctc ggcatggacg   5880
agctgtacaa gtaaactagt gtcgacaatc aacctctgga ttacaaaatt tgtgaaagat   5940
tgactggtat tcttaactat gttgctcctt ttacgctatg tggatacgct gctttaatgc   6000
ctttgtatca tgctattgct tcccgtatgg ctttcatttt ctcctccttg tataaatcct   6060
ggttgctgtc tctttatgag gagttgtggc ccgttgtcag gcaacgtggc gtggtgtgca   6120
ctgtgtttgc tgacgcaacc cccactggtt ggggcattgc caccacctgt cagctccttt   6180
ccgggacttt cgctttcccc ctccctattg ccacggcgga actcatcgcc gcctgccttg   6240
cccgctgctg gacaggggct cggctgttgg gcactgacaa ttccgtggtg ttgtcgggga   6300
agctgacgtc ctttccatgg ctgctcgcct gtgttgccac ctggattctg cgcgggacgt   6360
ccttctgcta cgtcccttcg gccctcaatc cagcggacct tccttcccgc ggcctgctgc   6420
cggctctgcg gcctcttccg cgtcttcgcc ttcgccctca gacgagtcgg atctcccttt   6480
gggccgcctc cccgcctgga attcgagctc ggtaccttta agaccaatga cttacaaggc   6540
agctgtagat cttagccact ttttaaaaga aaagggggga ctggaagggc taattcactc   6600
ccaacgaaga caagatctgc tttttgcttg tactgggtct ctctggttag accagatctg   6660
agcctgggag ctctctggct aactagggaa cccactgctt aagcctcaat aaagcttgcc   6720
ttgagtgctt caagtagtgt gtgcccgtct gttgtgtgac tctggtaact agagatccct   6780
cagacccttt tagtcagtgt ggaaaatctc tagcagtagt agttcatgtc atcttattat   6840
tcagtattta taacttgcaa agaaatgaat atcagagagt gagaggaact tgtttattgc   6900
agcttataat ggttacaaat aaagcaatag catcacaaat ttcacaaata aagcattttt   6960
ttcactgcat tctagttgtg gtttgtccaa actcatcaat gtatcttatc atgtctggct   7020
ctagctatcc cgcccctaac tccgcccagt tccgcccatt ctccgcccca tggctgacta   7080
atttttttta tttatgcaga ggccgaggcc gcctcggcct ctgagctatt ccagaagtag   7140
tgaggaggct tttttggagg cctaggcttt tgcgtcgaga cgtacccaat tcgccctata   7200
gtgagtcgta ttacgcgcgc tcactggccg tcgttttaca acgtcgtgac tgggaaaacc   7260
ctggcgttac ccaacttaat cgccttgcag cacatccccc tttcgccagc tggcgtaata   7320
gcgaagaggc ccgcaccgat cgcccttccc aacagttgcg cagcctgaat ggcgaatggc   7380
gcgacgcgcc ctgtagcggc gcattaagcg cggcgggtgt ggtggttacg cgcagcgtga   7440
ccgctacact tgccagcgcc ctagcgcccg ctcctttcgc tttcttccct tcctttctcg   7500
ccacgttcgc cggctttccc cgtcaagctc taaatcgggg gctcccttta gggttccgat   7560
ttagtgcttt acggcacctc gaccccaaaa aacttgatta gggtgatggt tcacgtagtg   7620
ggccatcgcc ctgatagacg gtttttcgcc ctttgacgtt ggagtccacg ttctttaata   7680
```

-continued

```
gtggactctt gttccaaact ggaacaacac tcaaccctat ctcggtctat tcttttgatt   7740
tataagggat tttgccgatt tcggcctatt ggttaaaaaa tgagctgatt taacaaaaat   7800
ttaacgcgaa ttttaacaaa atattaacgt ttacaatttc ccaggtggca cttttcgggg   7860
aaatgtgcgc ggaaccccta tttgtttatt tttctaaata cattcaaata tgtatccgct   7920
catgagacaa taaccctgat aaatgcttca ataatattga aaaaggaaga gtatgagtat   7980
tcaacatttc cgtgtcgccc ttattccctt ttttgcggca ttttgccttc ctgtttttgc   8040
tcacccagaa acgctggtga aagtaaaaga tgctgaagat cagttgggtg cacgagtggg   8100
ttacatcgaa ctggatctca acagcggtaa gatccttgag agttttcgcc ccgaagaacg   8160
ttttccaatg atgagcactt ttaaagttct gctatgtggc gcggtattat cccgtattga   8220
cgccgggcaa gagcaactcg gtcgccgcat acactattct cagaatgact tggttgagta   8280
ctcaccagtc acagaaaagc atcttacgga tggcatgaca gtaagagaat tatgcagtgc   8340
tgccataacc atgagtgata acactgcggc caacttactt ctgacaacga tcggaggacc   8400
gaaggagcta accgcttttt tgcacaacat gggggatcat gtaactcgcc ttgatcgttg   8460
ggaaccggag ctgaatgaag ccataccaaa cgacgagcgt gacaccacga tgcctgtagc   8520
aatggcaaca acgttgcgca aactattaac tggcgaacta cttactctag cttcccggca   8580
acaattaata gactggatgg aggcggataa agttgcagga ccacttctgc gctcggccct   8640
tccggctggc tggtttattg ctgataaatc tggagccggt gagcgtgggt ctcgcggtat   8700
cattgcagca ctggggccag atggtaagcc ctcccgtatc gtagttatct acacgacggg   8760
gagtcaggca actatggatg aacgaaatag acagatcgct gagataggtg cctcactgat   8820
taagcattgg taactgtcag accaagttta ctcatatata ctttagattg atttaaaact   8880
tcatttttaa tttaaaagga tctaggtgaa gatccttttt gataatctca tgaccaaaat   8940
cccttaacgt gagttttcgt tccactgagc gtcagacccc gtagaaaaga tcaaaggatc   9000
ttcttgagat cctttttttc tgcgcgtaat ctgctgcttg caaacaaaaa aaccaccgct   9060
accagcggtg gtttgtttgc cggatcaaga gctaccaact ctttttccga aggtaactgg   9120
cttcagcaga gcgcagatac caaatactgt ccttctagtg tagccgtagt taggccacca   9180
cttcaagaac tctgtagcac cgcctacata cctcgctctg ctaatcctgt taccagtggc   9240
tgctgccagt ggcgataagt cgtgtcttac cgggttggac tcaagacgat agttaccgga   9300
taaggcgcag cggtcgggct gaacgggggg ttcgtgcaca cagcccagct tggagcgaac   9360
gacctacacc gaactgagat acctacagcg tgagctatga gaaagcgcca cgcttcccga   9420
agggagaaag gcggacaggt atccggtaag cggcagggtc ggaacaggag agcgcacgag   9480
ggagcttcca gggggaaacg cctggtatct ttatagtcct gtcgggtttc gccacctctg   9540
acttgagcgt cgatttttgt gatgctcgtc aggggggcgg agcctatgga aaaacgccag   9600
caacgcggcc tttttacggt tcctggcctt ttgctggcct tttgctcaca tgttctttcc   9660
tgcgttatcc cctgattctg tggataaccg tattaccgcc tttgagtgag ctgataccgc   9720
tcgccgcagc cgaacgaccg agcgcagcga gtcagtgagc gaggaagcgg aagagcgccc   9780
aatacgcaaa ccgcctctcc ccgcgcgttg gccgattcat taatgcagct ggcacgacag   9840
gtttcccgac tggaaagcgg gcagtgagcg caacgcaatt aatgtgagtt agctcactca   9900
ttaggcaccc caggctttac actttatgct tccggctcgt atgttgtgtg gaattgtgag   9960
cggataacaa tttcacacag gaaacagcta tgaccatgat tacgccaagc gcgcaattaa  10020
ccctcactaa agggaacaaa agctggagct gca                               10053
```

<210> SEQ ID NO 108
<211> LENGTH: 10035
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: expression vector

<400> SEQUENCE: 108
agcttaatgt agtcttatgc aatactcttg tagtcttgca acatggtaac gatgagttag 60
caacatgcct tacaaggaga gaaaaagcac cgtgcatgcc gattggtgga agtaaggtgg 120
tacgatcgtg ccttattagg aaggcaacag acgggtctga catggattgg acgaaccact 180
gaattgccgc attgcagaga tattgtattt aagtgcctag ctcgatacaa taaacgggtc 240
tctctggtta gaccagatct gagcctggga gctctctggc taactaggga acccactgct 300
taagcctcaa taaagcttgc cttgagtgct tcaagtagtg tgtgcccgtc tgttgtgtga 360
ctctggtaac tagagatccc tcagaccctt ttagtcagtg tggaaaatct ctagcagtgg 420
cgcccgaaca gggacttgaa agcgaaaggg aaaccagagg agctctctcg acgcaggact 480
cggcttgctg aagcgcgcac ggcaagaggc gaggggcggc gactggtgag tacgccaaaa 540
attttgacta gcggaggcta gaaggagaga gatgggtgcg agagcgtcag tattaagcgg 600
gggagaatta gatcgcgatg ggaaaaaatt cggttaaggc cagggggaaa gaaaaaatat 660
aaattaaaac atatagtatg ggcaagcagg gagctagaac gattcgcagt taatcctggc 720
ctgttagaaa catcagaagg ctgtagacaa atactgggac agctacaacc atcccttcag 780
acaggatcag aagaacttag atcattatat aatacagtag caaccctcta ttgtgtgcat 840
caaaggatag agataaaaga caccaaggaa gctttagaca agatagagga agagcaaaac 900
aaaagtaaga ccaccgcaca gcaagcggcc gctgatcttc agacctggag gaggagatat 960
gagggacaat tggagaagtg aattatataa atataaagta gtaaaaattg aaccattagg 1020
agtagcaccc accaaggcaa agagaagagt ggtgcagaga gaaaaaagag cagtgggaat 1080
aggagctttg ttccttgggt tcttgggagc agcaggaagc actatgggcg cagcctcaat 1140
gacgctgacg gtacaggcca gacaattatt gtctggtata gtgcagcagc agaacaattt 1200
gctgagggct attgaggcgc aacagcatct gttgcaactc acagtctggg gcatcaagca 1260
gctccaggca agaatcctgg ctgtggaaag atacctaaag gatcaacagc tcctggggat 1320
ttggggttgc tctggaaaac tcatttgcac cactgctgtg ccttggaatg ctagttggag 1380
taataaatct ctggaacaga tttggaatca cacgacctgg atggagtggg acagagaaat 1440
taacaattac acaagcttaa tacactcctt aattgaagaa tcgcaaaacc agcaagaaaa 1500
gaatgaacaa gaattattgg aattagataa atgggcaagt ttgtggaatt ggtttaacat 1560
aacaaattgg ctgtggtata taaaattatt cataatgata gtaggaggct tggtaggttt 1620
aagaatagtt tttgctgtac tttctatagt gaatagagtt aggcagggat attcaccatt 1680
atcgtttcag acccacctcc caaccccgag gggacccgac aggcccgaag gaatagaaga 1740
agaaggtgga gagagagaca gagacagatc cattcgatta gtgaacggat ctcgacggta 1800
tcggttaact tttaaaagaa aaggggggat tgggggtac agtgcagggg aaagaatagt 1860
agacataata gcaacagaca tacaaactaa agaattacaa aaacaaatta caaaaattca 1920
aaattttatc gatcacgaga ctagcctcga gaagcttgat atcgaattcc cacggggttg 1980

```
gacgcgtagg aacagagaaa caggagaata tgggccaaac aggatatctg tggtaagcag   2040
ttcctgcccc ggctcagggc caagaacagt tggaacagca gaatatgggc caaacaggat   2100
atctgtggta agcagttcct gccccggctc agggccaaga acagatggtc cccagatgcg   2160
gtcccgccct cagcagtttc tagagaacca tcagatgttt ccagggtgcc ccaaggacct   2220
gaaatgaccc tgtgccttat ttgaactaac caatcagttc gcttctcgct tctgttcgcg   2280
cgcttctgct ccccgagctc tatataagca gagctcgttt agtgaaccgt cagatcgcta   2340
gcaccggtgc cgccaccatg cctctgggcc tgctgtggct gggcctggcc ctgctgggcg   2400
ccctgcacgc ccaggccggc gtgcaggtgg agacaatctc cccaggcgac ggacgcacat   2460
tccctaagcg gggccagacc tgcgtggtgc actatacagg catgctggag gatggcaaga   2520
agtttgacag ctcccgggat agaaacaagc cattcaagtt tatgctgggc aagcaggaag   2580
tgatcagagg ctgggaggag ggcgtggccc agatgtctgt gggccagagg gccaagctga   2640
ccatcagccc agactacgcc tatggagcaa caggccaccc aggaatcatc ccacctcacg   2700
ccaccctggt gttcgatgtg gagctgctga agctgggcga gcaaaacttg gtgattcctt   2760
gggccccaga aaatctcacg cttcacaagt tgtccgaatc ccagctcgag ctcaactgga   2820
ataatagatt tcttaatcat tgtttggaac acctggttca atatagaacg gattgggacc   2880
actcatggac cgagcagtca gttgactacc gccacaaatt ttcacttccc agcgtagatg   2940
ggcagaagag gtacacattt agggtcagat ccaggtttaa tcctctgtgt ggttctgctc   3000
aacactggtc tgagtggagc catccgatcc actggggctc aaatacctct aaagaaaatc   3060
cgttcctctt tgcgctcgaa gccgttgtta tcagcgtcgg aagcatggga cttatcattt   3120
cccttctctg cgtgtacttc tggctggagc ggacgatgcc gcggattccg acgctcaaaa   3180
acctggagga ccttgtaaca gaatatcacg gtaatttctc cgcttggagt ggcgtatcaa   3240
aggggcttgc tgagtccctt caaccggatt actctgagcg cctctgcttg gtgtccgaga   3300
tacctcccaa aggaggtgca cttggggagg ggccaggcgc gtccccttgc aatcagcata   3360
gtccgtattg ggcgcccccc tgttataccc tcaaaccgga aacgggaagc ggagctacta   3420
acttcagcct gctgaagcag gctggagacg tggaggagaa ccctggacct atggcactgc   3480
ccgtgaccgc cctgctgctg cctctggccc tgctgctgca cgcagcccgg cctatcctgt   3540
ggcacgagat gtggcacgag ggcctggagg aggccagcag gctgtatttt ggcgagcgca   3600
acgtgaaggg catgttcgag gtgctggagc ctctgcacgc catgatggag agaggcccac   3660
agaccctgaa ggagacatcc tttaaccagg cctatggacg ggacctgatg gaggcacagg   3720
agtggtgcag aaagtacatg aagtctggca atgtgaagga cctgctgcag gcctgggatc   3780
tgtactatca cgtgtttcgg agaatctcca agaaaccttt tgagaacctt agactgatgg   3840
cgcccatctc tctgcaggta gttcacgttg agacccatag atgcaatata agctgggaaa   3900
tctcacaagc cagccattac tttgaacggc atttggaatt cgaggcccga acactttccc   3960
ccggtcatac gtgggaagaa gctcctctct tgacgctgaa gcagaagcag gagtggattt   4020
gtctggagac tttgactcct gatactcagt atgagttcca agttcgggtg aaaccactcc   4080
aaggcgagtt cacgacgtgg tctccgtgga gtcaaccgtt ggcgttccgc acgaagcccg   4140
ctgcccttgg caaagacacg attccgtggc ttgggcatct gctcgttggg ctgagtggtg   4200
cgtttggttt catcatcttg gtctatctct tgatcaattg cagaaataca ggcccttggc   4260
tgaaaaaagt gctcaagtgt aatacccccg acccaagcaa gttcttctcc cagctttctt   4320
```

```
cagagcatgg aggcgatgtg cagaaatggc tctcttcacc ttttccctcc tcaagcttct   4380
ccccgggagg gctggcgccc gagatttcac ctcttgaggt acttgaacga gacaaggtta   4440
cccaacttct ccttcaacag gataaggtac ccgaacctgc gagccttagc tccaaccact   4500
ctcttacgag ctgcttcacc aatcagggat acttcttttt ccaccttccc gatgcgctgg   4560
aaatcgaagc ttgtcaagtt tactttacct atgatccata tagcgaggaa gatcccgacg   4620
aaggagtcgc cggtgcgccc acgggttcct caccccaacc tctccagcct ctctcaggag   4680
aagatgatgc ttattgcact tttcccagta gagacgatct cctcctcttt tctccatctc   4740
ttttgggggg accttccccc ccttctacgg cacctggcgg gtctggtgct ggcgaggagc   4800
ggatgccgcc gtccctccag gagcgagtac cacgagattg ggatccccag ccacttggac   4860
cccccacccc cggcgtacct gaccttgtcg attttcaacc tccccctgaa ttggtgctgc   4920
gagaggctgg ggaggaagtt ccggacgctg ggccgaggga gggcgtgtcc tttccatgga   4980
gtaggcctcc aggtcaaggc gagtttaggg ctctcaacgc gcggctgccg ttgaatacag   5040
acgcttatct ctcactgcag gaactgcaag gtcaggaccc aacacatctt gtaggatctg   5100
gtgctactaa tttttctctt ttgaagcaag ctggagatgt tgaagagaac cctggtccag   5160
tgagcaaggg cgaggagctg ttcaccgggg tggtgcccat cctggtcgag ctggacggcg   5220
acgtaaacgg ccacaagttc agcgtgtccg gcgagggcga gggcgatgcc acctacggca   5280
agctgaccct gaagttcatc tgcaccaccg gcaagctgcc cgtgccctgg cccaccctcg   5340
tgaccaccct gacctacggc gtgcagtgct tcagccgcta ccccgaccac atgaagcagc   5400
acgacttctt caagtccgcc atgcccgaag gctacgtcca ggagcgcacc atcttcttca   5460
aggacgacgg caactacaag acccgcgccg aggtgaagtt cgagggcgac accctggtga   5520
accgcatcga gctgaagggc atcgacttca aggaggacgg caacatcctg gggcacaagc   5580
tggagtacaa ctacaacagc cacaacgtct atatcatggc cgacaagcag aagaacggca   5640
tcaaggtgaa cttcaagatc cgccacaaca tcgaggacgg cagcgtgcag ctcgccgacc   5700
actaccagca gaacaccccc atcggcgacg gccccgtgct gctgcccgac aaccactacc   5760
tgagcaccca gtccgccctg agcaaagacc ccaacgagaa gcgcgatcac atggtcctgc   5820
tggagttcgt gaccgccgcc gggatcactc tcggcatgga cgagctgtac aagtaaacta   5880
gtgtcgacaa tcaacctctg gattacaaaa tttgtgaaag attgactggt attcttaact   5940
atgttgctcc ttttacgcta tgtggatacg ctgctttaat gcctttgtat catgctattg   6000
cttcccgtat ggctttcatt ttctcctcct tgtataaatc ctggttgctg tctctttatg   6060
aggagttgtg gcccgttgtc aggcaacgtg gcgtggtgtg cactgtgttt gctgacgcaa   6120
cccccactgg ttggggcatt gccaccacct gtcagctcct ttccgggact ttcgctttcc   6180
ccctccctat tgccacggcg gaactcatcg ccgcctgcct tgcccgctgc tggacagggg   6240
ctcggctgtt gggcactgac aattccgtgg tgttgtcggg gaagctgacg tcctttccat   6300
ggctgctcgc ctgtgttgcc acctggattc tgcgcgggac gtccttctgc tacgtccctt   6360
cggccctcaa tccagcggac cttccttccc gcggcctgct gccggctctg cggcctcttc   6420
cgcgtcttcg ccttcgccct cagacgagtc ggatctccct ttgggccgcc tccccgcctg   6480
gaattcgagc tcggtacctt taagaccaat gacttacaag gcagctgtag atcttagcca   6540
ctttttaaaa gaaaaggggg gactggaagg gctaattcac tcccaacgaa gacaagatct   6600
gctttttgct tgtactgggt ctctctggtt agaccagatc tgagcctggg agctctctgg   6660
ctaactaggg aacccactgc ttaagcctca ataaagcttg ccttgagtgc ttcaagtagt   6720
```

```
gtgtgcccgt ctgttgtgtg actctggtaa ctagagatcc ctcagaccct tttagtcagt   6780
gtggaaaatc tctagcagta gtagttcatg tcatcttatt attcagtatt tataacttgc   6840
aaagaaatga atatcagaga gtgagaggaa cttgtttatt gcagcttata atggttacaa   6900
ataaagcaat agcatcacaa atttcacaaa taaagcattt ttttcactgc attctagttg   6960
tggtttgtcc aaactcatca atgtatctta tcatgtctgg ctctagctat cccgccccta   7020
actccgccca gttccgccca ttctccgccc catggctgac taattttttt tatttatgca   7080
gaggccgagg ccgcctcggc ctctgagcta ttccagaagt agtgaggagg cttttttgga   7140
ggcctaggct tttgcgtcga gacgtaccca attcgcccta tagtgagtcg tattacgcgc   7200
gctcactggc cgtcgtttta caacgtcgtg actgggaaaa ccctggcgtt acccaactta   7260
atcgccttgc agcacatccc cctttcgcca gctggcgtaa tagcgaagag gcccgcaccg   7320
atcgcccttc ccaacagttg cgcagcctga atggcgaatg gcgcgacgcg ccctgtagcg   7380
gcgcattaag cgcggcgggt gtggtggtta cgcgcagcgt gaccgctaca cttgccagcg   7440
ccctagcgcc cgctcctttc gctttcttcc cttcctttct cgccacgttc gccggctttc   7500
cccgtcaagc tctaaatcgg gggctccctt tagggttccg atttagtgct ttacggcacc   7560
tcgaccccaa aaaacttgat tagggtgatg gttcacgtag tgggccatcg ccctgataga   7620
cggtttttcg ccctttgacg ttggagtcca cgttctttaa tagtggactc ttgttccaaa   7680
ctggaacaac actcaaccct atctcggtct attcttttga tttataaggg attttgccga   7740
tttcggccta ttggttaaaa aatgagctga tttaacaaaa atttaacgcg aattttaaca   7800
aaatattaac gtttacaatt tcccaggtgg cacttttcgg ggaaatgtgc gcggaacccc   7860
tatttgttta tttttctaaa tacattcaaa tatgtatccg ctcatgagac aataaccctg   7920
ataaatgctt caataatatt gaaaaaggaa gagtatgagt attcaacatt tccgtgtcgc   7980
ccttattccc ttttttgcgg cattttgcct tcctgttttt gctcacccag aaacgctggt   8040
gaaagtaaaa gatgctgaag atcagttggg tgcacgagtg ggttacatcg aactggatct   8100
caacagcggt aagatccttg agagttttcg ccccgaagaa cgttttccaa tgatgagcac   8160
ttttaaagtt ctgctatgtg gcgcggtatt atcccgtatt gacgccgggc aagagcaact   8220
cggtcgccgc atacactatt ctcagaatga cttggttgag tactcaccag tcacagaaaa   8280
gcatcttacg gatggcatga cagtaagaga attatgcagt gctgccataa ccatgagtga   8340
taacactgcg gccaacttac ttctgacaac gatcggagga ccgaaggagc taaccgcttt   8400
tttgcacaac atgggggatc atgtaactcg ccttgatcgt tgggaaccgg agctgaatga   8460
agccatacca aacgacgagc gtgacaccac gatgcctgta gcaatggcaa caacgttgcg   8520
caaactatta actggcgaac tacttactct agcttcccgg caacaattaa tagactggat   8580
ggaggcggat aaagttgcag gaccacttct gcgctcggcc cttccggctg gctggtttat   8640
tgctgataaa tctggagccg gtgagcgtgg gtctcgcggt atcattgcag cactggggcc   8700
agatggtaag ccctcccgta tcgtagttat ctacacgacg gggagtcagg caactatgga   8760
tgaacgaaat agacagatcg ctgagatagg tgcctcactg attaagcatt ggtaactgtc   8820
agaccaagtt tactcatata tactttagat tgatttaaaa cttcattttt aatttaaaag   8880
gatctaggtg aagatccttt ttgataatct catgaccaaa atcccttaac gtgagttttc   8940
gttccactga gcgtcagacc ccgtagaaaa gatcaaagga tcttcttgag atcctttttt   9000
tctgcgcgta atctgctgct tgcaaacaaa aaaaccaccg ctaccagcgg tggtttgttt   9060
```

-continued

```
gccggatcaa gagctaccaa ctctttttcc gaaggtaact ggcttcagca gagcgcagat   9120

accaaatact gtccttctag tgtagccgta gttaggccac cacttcaaga actctgtagc   9180

accgcctaca tacctcgctc tgctaatcct gttaccagtg gctgctgcca gtggcgataa   9240

gtcgtgtctt accgggttgg actcaagacg atagttaccg gataaggcgc agcggtcggg   9300

ctgaacgggg ggttcgtgca cacagcccag cttggagcga acgacctaca ccgaactgag   9360

atacctacag cgtgagctat gagaaagcgc cacgcttccc gaagggagaa aggcggacag   9420

gtatccggta agcggcaggg tcggaacagg agagcgcacg agggagcttc caggggggaaa   9480

cgcctggtat ctttatagtc ctgtcgggtt tcgccacctc tgacttgagc gtcgattttt   9540

gtgatgctcg tcaggggggc ggagcctatg gaaaaacgcc agcaacgcgg cctttttacg   9600

gttcctggcc ttttgctggc cttttgctca catgttcttt cctgcgttat cccctgattc   9660

tgtggataac cgtattaccg cctttgagtg agctgatacc gctcgccgca gccgaacgac   9720

cgagcgcagc gagtcagtga gcgaggaagc ggaagagcgc ccaatacgca aaccgcctct   9780

ccccgcgcgt tggccgattc attaatgcag ctggcacgac aggtttcccg actggaaagc   9840

gggcagtgag cgcaacgcaa ttaatgtgag ttagctcact cattaggcac cccaggcttt   9900

acactttatg cttccggctc gtatgttgtg tggaattgtg agcggataac aatttcacac   9960

aggaaacagc tatgaccatg attacgccaa gcgcgcaatt aaccctcact aaagggaaca  10020

aaagctggag ctgca                                                   10035
```

```
<210> SEQ ID NO 109
<211> LENGTH: 9405
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: expression vector

<400> SEQUENCE: 109

agcttaatgt agtcttatgc aatactcttg tagtcttgca acatggtaac gatgagttag     60

caacatgcct tacaaggaga gaaaaagcac cgtgcatgcc gattggtgga agtaaggtgg    120

tacgatcgtg ccttattagg aaggcaacag acgggtctga catggattgg acgaaccact    180

gaattgccgc attgcagaga tattgtattt aagtgcctag ctcgatacaa taaacgggtc    240

tctctggtta gaccagatct gagcctggga gctctctggc taactaggga acccactgct    300

taagcctcaa taaagcttgc cttgagtgct tcaagtagtg tgtgcccgtc tgttgtgtga    360

ctctggtaac tagagatccc tcagaccctt ttagtcagtg tggaaaatct ctagcagtgg    420

cgcccgaaca gggacttgaa agcgaaaggg aaaccagagg agctctctcg acgcaggact    480

cggcttgctg aagcgcgcac ggcaagaggc gaggggcggc gactggtgag tacgccaaaa    540

attttgacta gcggaggcta gaaggagaga gatgggtgcg agagcgtcag tattaagcgg    600

gggagaatta gatcgcgatg ggaaaaaatt cggttaaggc cagggggaaa gaaaaaatat    660

aaattaaaac atatagtatg ggcaagcagg gagctagaac gattcgcagt taatcctggc    720

ctgttagaaa catcagaagg ctgtagacaa atactgggac agctacaacc atcccttcag    780

acaggatcag aagaacttag atcattatat aatacagtag caaccctcta ttgtgtgcat    840

caaaggatag agataaaaga caccaaggaa gctttagaca agatagagga agagcaaaac    900

aaaagtaaga ccaccgcaca gcaagcggcc gctgatcttc agacctggag gaggagatat    960
```

```
gagggacaat tggagaagtg aattatataa atataaagta gtaaaaattg aaccattagg   1020
agtagcaccc accaaggcaa agagaagagt ggtgcagaga gaaaaaagag cagtgggaat   1080
aggagctttg ttccttgggt tcttgggagc agcaggaagc actatgggcg cagcctcaat   1140
gacgctgacg gtacaggcca gacaattatt gtctggtata gtgcagcagc agaacaattt   1200
gctgagggct attgaggcgc aacagcatct gttgcaactc acagtctggg gcatcaagca   1260
gctccaggca agaatcctgg ctgtggaaag atacctaaag gatcaacagc tcctggggat   1320
ttggggttgc tctggaaaac tcatttgcac cactgctgtg ccttggaatg ctagttggag   1380
taataaatct ctggaacaga tttggaatca cacgacctgg atggagtggg acagagaaat   1440
taacaattac acaagcttaa tacactcctt aattgaagaa tcgcaaaacc agcaagaaaa   1500
gaatgaacaa gaattattgg aattagataa atgggcaagt ttgtggaatt ggtttaacat   1560
aacaaattgg ctgtggtata taaaattatt cataatgata gtaggaggct tggtaggttt   1620
aagaatagtt tttgctgtac tttctatagt gaatagagtt aggcagggat attcaccatt   1680
atcgtttcag acccacctcc caaccccgag gggacccgac aggcccgaag gaatagaaga   1740
agaaggtgga gagagagaca gagacagatc cattcgatta gtgaacggat ctcgacggta   1800
tcggttaact tttaaaagaa aaggggggat tggggggtac agtgcagggg aaagaatagt   1860
agacataata gcaacagaca tacaaactaa agaattacaa aaacaaatta caaaaattca   1920
aaattttatc gatcacgaga ctagcctcga gaagcttgat atcgaattcc cacggggttg   1980
gacgcgtagg aacagagaaa caggagaata tgggccaaac aggatatctg tggtaagcag   2040
ttcctgcccc ggctcagggc caagaacagt tggaacagca gaatatgggc caaacaggat   2100
atctgtggta agcagttcct gccccggctc agggccaaga acagatggtc cccagatgcg   2160
gtcccgccct cagcagtttc tagagaacca tcagatgttt ccagggtgcc ccaaggacct   2220
gaaatgaccc tgtgccttat ttgaactaac caatcagttc gcttctcgct tctgttcgcg   2280
cgcttctgct ccccgagctc tatataagca gagctcgttt agtgaaccgt cagatcgcta   2340
gcaccggtgc cgccaccatg cctctgggcc tgctgtggct gggcctggcc ctgctgggcg   2400
ccctgcacgc ccaggccggc gtgcaggtgg agacaatctc ccccaggcgac ggacgcacat   2460
tccctaagcg gggccagacc tgcgtggtgc actatacagg catgctggag gatggcaaga   2520
agtttgacag ctcccgggat agaaacaagc cattcaagtt tatgctgggc aagcaggaag   2580
tgatcagagg ctgggaggag ggcgtggccc agatgtctgt gggccagagg gccaagctga   2640
ccatcagccc agactacgcc tatggagcaa caggccaccc aggaatcatc ccacctcacg   2700
ccaccctggt gttcgatgtg gagctgctga agctgggcga gggatccaac acatcaaaag   2760
agaacccctt tctgttcgca ttggaggccg tagtcatatc tgttggatcc atgggactta   2820
ttatctccct gttgtgtgtg tacttctggc tggaacggac tatgcccagg atccccacgc   2880
tcaagaatct ggaagatctc gtcacagaat accatggtaa tttcagcgcc tggagcggag   2940
tctctaaggg tctggccgaa tccctccaac ccgattattc tgaacggttg tgcctcgtat   3000
ccgaaatacc accaaaaggc ggggctctgg gtgagggccc aggggcgagt ccgtgcaatc   3060
aacacagccc gtattgggcc cctccttgtt atacgttgaa gcccgaaact ggaagcggag   3120
ctactaactt cagcctgctg aagcaggctg gagacgtgga ggagaaccct ggacctatgg   3180
cactgcccgt gaccgccctg ctgctgcctc tggccctgct gctgcacgca gcccggccta   3240
tcctgtggca cgagatgtgg cacgagggcc tggaggaggc cagcaggctg tattttggcg   3300
agcgcaacgt gaagggcatg ttcgaggtgc tggagcctct gcacgccatg atggagagag   3360
```

```
gcccacagac cctgaaggag acatccttta accaggccta tggacgggac ctgatggagg   3420
cacaggagtg gtgcagaaag tacatgaagt ctggcaatgt gaaggacctg ctgcaggcct   3480
gggatctgta ctatcacgtg tttcggagaa tctccaaggg caaagacacg attccgtggc   3540
ttgggcatct gctcgttggg ctgagtggtg cgtttggttt catcatcttg gtctatctct   3600
tgatcaattg cagaaataca ggcccttggc tgaaaaaagt gctcaagtgt aataccccccg  3660
acccaagcaa gttcttctcc cagctttctt cagagcatgg aggcgatgtg cagaaatggc   3720
tctcttcacc ttttccctcc tcaagcttct ccccgggagg gctggcgccc gagatttcac   3780
ctcttgaggt acttgaacga gacaaggtta cccaacttct ccttcaacag gataaggtac   3840
ccgaacctgc gagccttagc tccaaccact ctcttacgag ctgcttcacc aatcagggat   3900
acttcttttt ccaccttccc gatgcgctgg aaatcgaagc ttgtcaagtt tactttacct   3960
atgatccata tagcgaggaa gatcccgacg aaggagtcgc cggtgcgccc acgggttcct   4020
caccccaacc tctccagcct ctctcaggag aagatgatgc ttattgcact tttcccagta   4080
gagacgatct cctcctcttt tctccatctc ttttgggggg accttccccc ccttctacgg   4140
cacctggcgg gtctggtgct ggcgaggagc ggatgccgcc gtccctccag gagcgagtac   4200
cacgagattg ggatccccag ccacttggac cccccacccc cggcgtacct gaccttgtcg   4260
attttcaacc tccccctgaa ttggtgctgc gagaggctgg ggaggaagtt ccggacgctg   4320
ggccgaggga gggcgtgtcc tttccatgga gtaggcctcc aggtcaaggc gagtttaggg   4380
ctctcaacgc gcggctgccg ttgaatacag acgcttatct ctcactgcag gaactgcaag   4440
gtcaggaccc aacacatctt gtaggatctg gtgctactaa tttttctctt ttgaagcaag   4500
ctggagatgt tgaagagaac cctggtccag tgagcaaggg cgaggagctg ttcaccgggg   4560
tggtgcccat cctggtcgag ctggacggcg acgtaaacgg ccacaagttc agcgtgtccg   4620
gcgagggcga gggcgatgcc acctacggca agctgaccct gaagttcatc tgcaccaccg   4680
gcaagctgcc cgtgccctgg cccaccctcg tgaccaccct gacctacggc gtgcagtgct   4740
tcagccgcta ccccgaccac atgaagcagc acgacttctt caagtccgcc atgcccgaag   4800
gctacgtcca ggagcgcacc atcttcttca aggacgacgg caactacaag acccgcgccg   4860
aggtgaagtt cgagggcgac accctggtga accgcatcga gctgaagggc atcgacttca   4920
aggaggacgg caacatcctg gggcacaagc tggagtacaa ctacaacagc cacaacgtct   4980
atatcatggc cgacaagcag aagaacggca tcaaggtgaa cttcaagatc cgccacaaca   5040
tcgaggacgg cagcgtgcag ctcgccgacc actaccagca gaacaccccc atcggcgacg   5100
gccccgtgct gctgcccgac aaccactacc tgagcaccca gtccgccctg agcaaagacc   5160
ccaacgagaa gcgcgatcac atggtcctgc tggagttcgt gaccgccgcc gggatcactc   5220
tcggcatgga cgagctgtac aagtaaacta gtgtcgacaa tcaacctctg gattacaaaa   5280
tttgtgaaag attgactggt attcttaact atgttgctcc ttttacgcta tgtggatacg   5340
ctgctttaat gcctttgtat catgctattg cttcccgtat ggctttcatt ttctcctcct   5400
tgtataaatc ctggttgctg tctctttatg aggagttgtg gcccgttgtc aggcaacgtg   5460
gcgtggtgtg cactgtgttt gctgacgcaa cccccactgg ttggggcatt gccaccacct   5520
gtcagctcct ttccgggact ttcgctttcc ccctccctat tgccacggcg gaactcatcg   5580
ccgcctgcct tgcccgctgc tggacagggg ctcggctgtt gggcactgac aattccgtgg   5640
tgttgtcggg gaagctgacg tcctttccat ggctgctcgc ctgtgttgcc acctggattc   5700
```

-continued

```
tgcgcgggac gtccttctgc tacgtccctt cggccctcaa tccagcggac cttccttccc   5760
gcggcctgct gccggctctg cggcctcttc cgcgtcttcg ccttcgccct cagacgagtc   5820
ggatctccct ttgggccgcc tccccgcctg gaattcgagc tcggtacctt taagaccaat   5880
gacttacaag gcagctgtag atcttagcca ctttttaaaa gaaaaggggg gactggaagg   5940
gctaattcac tcccaacgaa gacaagatct gctttttgct tgtactgggt ctctctggtt   6000
agaccagatc tgagcctggg agctctctgg ctaactaggg aacccactgc ttaagcctca   6060
ataaagcttg ccttgagtgc ttcaagtagt gtgtgcccgt ctgttgtgtg actctggtaa   6120
ctagagatcc ctcagaccct tttagtcagt gtggaaaatc tctagcagta gtagttcatg   6180
tcatcttatt attcagtatt tataacttgc aaagaaatga atatcagaga gtgagaggaa   6240
cttgtttatt gcagcttata atggttacaa ataaagcaat agcatcacaa atttcacaaa   6300
taaagcattt ttttcactgc attctagttg tggtttgtcc aaactcatca atgtatctta   6360
tcatgtctgg ctctagctat cccgccccta actccgccca gttccgccca ttctccgccc   6420
catggctgac taattttttt tatttatgca gaggccgagg ccgcctcggc ctctgagcta   6480
ttccagaagt agtgaggagg cttttttgga ggcctaggct tttgcgtcga gacgtaccca   6540
attcgcccta tagtgagtcg tattacgcgc gctcactggc cgtcgtttta caacgtcgtg   6600
actgggaaaa ccctggcgtt acccaactta atcgccttgc agcacatccc cctttcgcca   6660
gctggcgtaa tagcgaagag gcccgcaccg atcgcccttc ccaacagttg cgcagcctga   6720
atggcgaatg gcgcgacgcg ccctgtagcg gcgcattaag cgcggcgggt gtggtggtta   6780
cgcgcagcgt gaccgctaca cttgccagcg ccctagcgcc cgctcctttc gctttcttcc   6840
cttcctttct cgccacgttc gccggctttc cccgtcaagc tctaaatcgg gggctccctt   6900
tagggttccg atttagtgct ttacggcacc tcgaccccaa aaaacttgat tagggtgatg   6960
gttcacgtag tgggccatcg ccctgataga cggtttttcg ccctttgacg ttggagtcca   7020
cgttctttaa tagtggactc ttgttccaaa ctggaacaac actcaaccct atctcggtct   7080
attcttttga tttataaggg attttgccga tttcggccta ttggttaaaa aatgagctga   7140
tttaacaaaa atttaacgcg aattttaaca aaatattaac gtttacaatt tcccaggtgg   7200
cacttttcgg ggaaatgtgc gcggaacccc tatttgttta tttttctaaa tacattcaaa   7260
tatgtatccg ctcatgagac aataaccctg ataaatgctt caataatatt gaaaaaggaa   7320
gagtatgagt attcaacatt tccgtgtcgc ccttattccc ttttttgcgg cattttgcct   7380
tcctgttttt gctcacccag aaacgctggt gaaagtaaaa gatgctgaag atcagttggg   7440
tgcacgagtg ggttacatcg aactggatct caacagcggt aagatccttg agagttttcg   7500
ccccgaagaa cgttttccaa tgatgagcac ttttaaagtt ctgctatgtg gcgcggtatt   7560
atcccgtatt gacgccgggc aagagcaact cggtcgccgc atacactatt ctcagaatga   7620
cttggttgag tactcaccag tcacagaaaa gcatcttacg gatggcatga cagtaagaga   7680
attatgcagt gctgccataa ccatgagtga taacactgcg gccaacttac ttctgacaac   7740
gatcggagga ccgaaggagc taaccgcttt tttgcacaac atgggggatc atgtaactcg   7800
ccttgatcgt tgggaaccgg agctgaatga agccatacca aacgacgagc gtgacaccac   7860
gatgcctgta gcaatggcaa caacgttgcg caaactatta actggcgaac tacttactct   7920
agcttcccgg caacaattaa tagactggat ggaggcggat aaagttgcag gaccacttct   7980
gcgctcggcc cttccggctg gctggtttat tgctgataaa tctggagccg gtgagcgtgg   8040
gtctcgcggt atcattgcag cactggggcc agatggtaag ccctcccgta tcgtagttat   8100
```

```
ctacacgacg gggagtcagg caactatgga tgaacgaaat agacagatcg ctgagatagg   8160

tgcctcactg attaagcatt ggtaactgtc agaccaagtt tactcatata tactttagat   8220

tgatttaaaa cttcattttt aatttaaaag gatctaggtg aagatccttt ttgataatct   8280

catgaccaaa atcccttaac gtgagttttc gttccactga gcgtcagacc ccgtagaaaa   8340

gatcaaagga tcttcttgag atcctttttt tctgcgcgta atctgctgct tgcaaacaaa   8400

aaaaccaccg ctaccagcgg tggtttgttt gccggatcaa gagctaccaa ctctttttcc   8460

gaaggtaact ggcttcagca gagcgcagat accaaatact gtccttctag tgtagccgta   8520

gttaggccac cacttcaaga actctgtagc accgcctaca tacctcgctc tgctaatcct   8580

gttaccagtg gctgctgcca gtggcgataa gtcgtgtctt accgggttgg actcaagacg   8640

atagttaccg gataaggcgc agcggtcggg ctgaacgggg ggttcgtgca cacagcccag   8700

cttggagcga acgacctaca ccgaactgag atacctacag cgtgagctat gagaaagcgc   8760

cacgcttccc gaagggagaa aggcggacag gtatccggta agcggcaggg tcggaacagg   8820

agagcgcacg agggagcttc caggggggaaa cgcctggtat ctttatagtc ctgtcgggtt   8880

tcgccacctc tgacttgagc gtcgattttt gtgatgctcg tcaggggggc ggagcctatg   8940

gaaaaacgcc agcaacgcgg cctttttacg gttcctggcc ttttgctggc cttttgctca   9000

catgttcttt cctgcgttat cccctgattc tgtggataac cgtattaccg cctttgagtg   9060

agctgatacc gctcgccgca gccgaacgac cgagcgcagc gagtcagtga gcgaggaagc   9120

ggaagagcgc ccaatacgca aaccgcctct ccccgcgcgt tggccgattc attaatgcag   9180

ctggcacgac aggtttcccg actggaaagc gggcagtgag cgcaacgcaa ttaatgtgag   9240

ttagctcact cattaggcac cccaggcttt acactttatg cttccggctc gtatgttgtg   9300

tggaattgtg agcggataac aatttcacac aggaaacagc tatgaccatg attacgccaa   9360

gcgcgcaatt aaccctcact aaagggaaca aaagctggag ctgca                   9405
```

```
<210> SEQ ID NO 110
<211> LENGTH: 1293
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon optimized human FOXP3 cDNA Without stop
      codon

<400> SEQUENCE: 110
```

```
atgcctaatc ctcggcctgg aaagcctagc gctccttctc ttgctctggg accttctcct     60

ggcgcctctc catcttggag agccgctcct aaagccagcg atctgctggg agctagagga    120

cctggcggca catttcaggg cagagatctt agaggcggag cccacgctag ctcctccagc    180

cttaatccta tgcctcctag ccagctccag ctgcctacac tgcctctggt tatggtggct    240

cctagcggag ctagactggg ccctctgcct catctgcaag ctctgctgca ggacagaccc    300

cacttcatgc accagctgag caccgtggat gcccacgcaa gaacacctgt gctgcaggtt    360

caccctctgg aatccccagc catgatcagc ctgacacctc caacaacagc caccggcgtg    420

ttcagcctga aagccagacc tggactgcct cctggcatca atgtggccag cctggaatgg    480

gtgtccagag aacctgctct gctgtgcaca ttccccaatc caagcgctcc cagaaaggac    540

agcacactgt ctgccgtgcc tcagagcagc tatcccctgc ttgctaacgg cgtgtgcaag    600
```

```
tggcctggat gcgagaaggt gttcgaggaa cccgaggact tcctgaagca ctgccaggcc    660

gatcatctgc tggacgagaa aggcagagcc cagtgtctgc tccagcgcga gatggtgcag    720

tctctggaac agcagctggt cctggaaaaa gaaaagctga gcgccatgca ggcccacctg    780

gccggaaaaa tggccctgac aaaggccagc agcgtggcct cttctgataa gggcagctgc    840

tgcattgtgg ccgctggatc tcagggacct gtggttcctg cttggagcgg acctagagag    900

gcccctgatt ctctgtttgc cgtgcggaga cacctgtggg gctctcacgg caactctact    960

ttccccgagt tcctgcacaa catggactac ttcaagttcc acaacatgcg gcctccattc   1020

acctacgcca cactgatcag atgggccatt ctggaagccc ctgagaagca gagaaccctg   1080

aacgagatct accactggtt tacccggatg ttcgccttct tccggaatca ccctgccacc   1140

tggaagaacg ccatccggca caatctgagc ctgcacaagt gcttcgtgcg cgtggaatct   1200

gagaaaggcg ccgtgtggac agtggacgag ctggaattca gaaagaagag aagccagcgg   1260

cctagccggt gcagcaatcc tacacctgga cct                                1293
```

```
<210> SEQ ID NO 111
<211> LENGTH: 1296
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon optimized human FOXP3 cDNA  With stop
      codon

<400> SEQUENCE: 111

atgcctaatc ctcggcctgg aaagcctagc gctccttctc ttgctctggg accttctcct     60

ggcgcctctc catcttggag agccgctcct aaagccagcg atctgctggg agctagagga    120

cctggcggca catttcaggg cagagatctt agaggcggag cccacgctag ctcctccagc    180

cttaatccta tgcctcctag ccagctccag ctgcctacac tgcctctggt tatggtggct    240

cctagcggag ctagactggg ccctctgcct catctgcaag ctctgctgca ggacagaccc    300

cacttcatgc accagctgag caccgtggat gcccacgcaa gaacacctgt gctgcaggtt    360

caccctctgg aatccccagc catgatcagc ctgacacctc caacaacagc caccggcgtg    420

ttcagcctga aagccagacc tggactgcct cctggcatca atgtggccag cctggaatgg    480

gtgtccagag aacctgctct gctgtgcaca ttccccaatc caagcgctcc cagaaaggac    540

agcacactgt ctgccgtgcc tcagagcagc tatcccctgc ttgctaacgg cgtgtgcaag    600

tggcctggat gcgagaaggt gttcgaggaa cccgaggact tcctgaagca ctgccaggcc    660

gatcatctgc tggacgagaa aggcagagcc cagtgtctgc tccagcgcga gatggtgcag    720

tctctggaac agcagctggt cctggaaaaa gaaaagctga gcgccatgca ggcccacctg    780

gccggaaaaa tggccctgac aaaggccagc agcgtggcct cttctgataa gggcagctgc    840

tgcattgtgg ccgctggatc tcagggacct gtggttcctg cttggagcgg acctagagag    900

gcccctgatt ctctgtttgc cgtgcggaga cacctgtggg gctctcacgg caactctact    960

ttccccgagt tcctgcacaa catggactac ttcaagttcc acaacatgcg gcctccattc   1020

acctacgcca cactgatcag atgggccatt ctggaagccc ctgagaagca gagaaccctg   1080

aacgagatct accactggtt tacccggatg ttcgccttct tccggaatca ccctgccacc   1140

tggaagaacg ccatccggca caatctgagc ctgcacaagt gcttcgtgcg cgtggaatct   1200

gagaaaggcg ccgtgtggac agtggacgag ctggaattca gaaagaagag aagccagcgg   1260
```

cctagccggt gcagcaatcc tacacctgga ccttga 1296

<210> SEQ ID NO 112
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: naked FRB domain

<400> SEQUENCE: 112

Met Glu Met Trp His Glu Gly Leu Glu Glu Ala Ser Arg Leu Tyr Phe
1 5 10 15

Gly Glu Arg Asn Val Lys Gly Met Phe Glu Val Leu Glu Pro Leu His
20 25 30

Ala Met Met Glu Arg Gly Pro Gln Thr Leu Lys Glu Thr Ser Phe Asn
35 40 45

Gln Ala Tyr Gly Arg Asp Leu Met Glu Ala Gln Glu Trp Cys Arg Lys
50 55 60

Tyr Met Lys Ser Gly Asn Val Lys Asp Leu Thr Gln Ala Trp Asp Leu
65 70 75 80

Tyr Tyr His Val Phe Arg Arg Ile Ser Lys
85 90

<210> SEQ ID NO 113
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: naked FRB domain

<400> SEQUENCE: 113

Met Glu Met Trp His Glu Gly Leu Glu Glu Ala Ser Arg Leu Tyr Phe
1 5 10 15

Gly Glu Arg Asn Val Lys Gly Met Phe Glu Val Leu Glu Pro Leu His
20 25 30

Ala Met Met Glu Arg Gly Pro Gln Thr Leu Lys Glu Thr Ser Phe Asn
35 40 45

Gln Ala Tyr Gly Arg Asp Leu Met Glu Ala Gln Glu Trp Cys Arg Lys
50 55 60

Tyr Met Lys Ser Gly Asn Val Lys Asp Leu Leu Gln Ala Trp Asp Leu
65 70 75 80

Tyr Tyr His Val Phe Arg Arg Ile Ser Lys
85 90

<210> SEQ ID NO 114
<211> LENGTH: 1299
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: CISCbeta FRB_IL2Rbeta nucleotide sequence
coding sequence only

<400> SEQUENCE: 114

-continued

```
atggcactgc ccgtgaccgc cctgctgctg cctctggccc tgctgctgca cgcagcccgg     60

cctatcctgt ggcacgagat gtggcacgag ggcctggagg aggccagcag gctgtatttt    120

ggcgagcgca acgtgaaggg catgttcgag gtgctggagc ctctgcacgc catgatggag    180

agaggcccac agaccctgaa ggagacatcc tttaaccagg cctatggacg ggacctgatg    240

gaggcacagg agtggtgcag aaagtacatg aagtctggca atgtgaagga cctgctgcag    300

gcctgggatc tgtactatca cgtgtttcgg agaatctcca agccagcagc tctcggcaaa    360

gacacgattc cgtggcttgg gcatctgctc gttgggctga gcggtgcgtt tggtttcatc    420

atcttggtct atctcttgat caattgcaga aatacaggcc cttggctgaa aaaagtgctc    480

aagtgtaata cccccgaccc aagcaagttc ttctcccagc tttcttcaga gcatggaggc    540

gatgtgcaga aatggctctc ttcacctttt ccctcctcaa gcttctcccc gggagggctg    600

gcgcccgaga tttcacctct tgaggtactt gaacgagaca aggttaccca acttctcctt    660

caacaggata aggtacccga acctgcgagc cttagctcca accactctct tacgagctgc    720

ttcaccaatc agggatactt ctttttccac cttcccgatg cgctggaaat cgaagcttgt    780

caagtttact ttacctatga tccatatagc gaggaagatc ccgacgaagg agtcgccggt    840

gcgcccacgg gttcctcacc ccaacctctc cagcctctct caggagaaga tgatgcttat    900

tgcacttttc ccagtagaga cgatctcctc ctcttttctc catctctttt ggggggacct    960

tcccccccctt ctacggcacc tggcgggtct ggtgctggcg aggagcggat gccgccgtcc   1020

ctccaggagc gagtaccacg agattgggat ccccagccac ttggaccccc cacccccggc   1080

gtacctgacc ttgtcgattt tcaacctccc cctgaattgg tgctgcgaga ggctggggag   1140

gaagttccgg acgctgggcc gagggagggc gtgtcctttc catggagtag gcctccaggt   1200

caaggcgagt ttagggctct caacgcgcgg ctgccgttga atacagacgc ttatctctca   1260

ctgcaggaac tgcaaggtca ggacccaaca catcttgta                           1299
```

<210> SEQ ID NO 115
<211> LENGTH: 433
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: CISCbeta FRB_IL2Rbeta amino acid sequence

<400> SEQUENCE: 115

```
Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Pro Ala Ala Leu Gly Lys Asp Thr Ile Pro Trp Leu Gly His
```

```
        115                 120                 125

Leu Leu Val Gly Leu Ser Gly Ala Phe Gly Phe Ile Ile Leu Val Tyr
    130                 135                 140

Leu Leu Ile Asn Cys Arg Asn Thr Gly Pro Trp Leu Lys Lys Val Leu
145                 150                 155                 160

Lys Cys Asn Thr Pro Asp Pro Ser Lys Phe Phe Ser Gln Leu Ser Ser
                165                 170                 175

Glu His Gly Gly Asp Val Gln Lys Trp Leu Ser Ser Pro Phe Pro Ser
            180                 185                 190

Ser Ser Phe Ser Pro Gly Gly Leu Ala Pro Glu Ile Ser Pro Leu Glu
        195                 200                 205

Val Leu Glu Arg Asp Lys Val Thr Gln Leu Leu Leu Gln Gln Asp Lys
    210                 215                 220

Val Pro Glu Pro Ala Ser Leu Ser Ser Asn His Ser Leu Thr Ser Cys
225                 230                 235                 240

Phe Thr Asn Gln Gly Tyr Phe Phe Phe His Leu Pro Asp Ala Leu Glu
                245                 250                 255

Ile Glu Ala Cys Gln Val Tyr Phe Thr Tyr Asp Pro Tyr Ser Glu Glu
            260                 265                 270

Asp Pro Asp Glu Gly Val Ala Gly Ala Pro Thr Gly Ser Ser Pro Gln
        275                 280                 285

Pro Leu Gln Pro Leu Ser Gly Glu Asp Asp Ala Tyr Cys Thr Phe Pro
    290                 295                 300

Ser Arg Asp Asp Leu Leu Leu Phe Ser Pro Ser Leu Leu Gly Gly Pro
305                 310                 315                 320

Ser Pro Pro Ser Thr Ala Pro Gly Gly Ser Gly Ala Gly Glu Glu Arg
                325                 330                 335

Met Pro Pro Ser Leu Gln Glu Arg Val Pro Arg Asp Trp Asp Pro Gln
            340                 345                 350

Pro Leu Gly Pro Pro Thr Pro Gly Val Pro Asp Leu Val Asp Phe Gln
        355                 360                 365

Pro Pro Pro Glu Leu Val Leu Arg Glu Ala Gly Glu Glu Val Pro Asp
    370                 375                 380

Ala Gly Pro Arg Glu Gly Val Ser Phe Pro Trp Ser Arg Pro Pro Gly
385                 390                 395                 400

Gln Gly Glu Phe Arg Ala Leu Asn Ala Arg Leu Pro Leu Asn Thr Asp
                405                 410                 415

Ala Tyr Leu Ser Leu Gln Glu Leu Gln Gly Gln Asp Pro Thr His Leu
            420                 425                 430

Val
```

<210> SEQ ID NO 116
<211> LENGTH: 765
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: CISCgamma FKBP_IL2Rgamma nucleotide sequence
coding sequence only codon optimized

<400> SEQUENCE: 116

```
atgcctctgg gcctgctgtg gctgggcctg gccctgctgg gcgccctgca cgcccaggcc     60

ggcgtgcagg tggagacaat ctccccaggc gacggacgca cattccctaa gcggggccag    120
```

-continued

```
acctgcgtgg tgcactatac aggcatgctg gaggatggca agaagtttga cagctcccgg    180

gatagaaaca agccattcaa gtttatgctg ggcaagcagg aagtgatcag aggctgggag    240

gagggcgtgg cccagatgtc tgtgggccag agggccaagc tgaccatcag cccagactac    300

gcctatggag caacaggcca cccaggaatc atcccacctc acgccaccct ggtgttcgat    360

gtggagctgc tgaagctggg cgagggaggg tcacctggat ccaacacatc aaaagagaac    420

ccctttctgt tcgcattgga ggccgtagtc atatctgttg gatccatggg acttattatc    480

tccctgttgt gtgtgtactt ctggctggaa cggactatgc ccaggatccc cacgctcaag    540

aatctggaag atctcgtcac agaataccat ggtaatttca gcgcctggag cggagtctct    600

aagggtctgg ccgaatccct ccaacccgat tattctgaac ggttgtgcct cgtatccgaa    660

ataccaccaa aaggcggggc tctgggtgag ggcccagggg cgagtccgtg caatcaacac    720

agcccgtatt gggcccctcc ttgttatacg ttgaagcccg aaact                    765
```

<210> SEQ ID NO 117
<211> LENGTH: 255
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: CISCgamma FKBP_IL2Rgamma  amino acid sequence

<400> SEQUENCE: 117

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Gly Gly Ser Pro Gly Ser Asn Thr Ser Lys Glu Asn Pro Phe Leu Phe
    130                 135                 140

Ala Leu Glu Ala Val Val Ile Ser Val Gly Ser Met Gly Leu Ile Ile
145                 150                 155                 160

Ser Leu Leu Cys Val Tyr Phe Trp Leu Glu Arg Thr Met Pro Arg Ile
                165                 170                 175

Pro Thr Leu Lys Asn Leu Glu Asp Leu Val Thr Glu Tyr His Gly Asn
            180                 185                 190

Phe Ser Ala Trp Ser Gly Val Ser Lys Gly Leu Ala Glu Ser Leu Gln
        195                 200                 205

Pro Asp Tyr Ser Glu Arg Leu Cys Leu Val Ser Glu Ile Pro Pro Lys
    210                 215                 220

Gly Gly Ala Leu Gly Glu Gly Pro Gly Ala Ser Pro Cys Asn Gln His
225                 230                 235                 240
```

```
Ser Pro Tyr Trp Ala Pro Pro Cys Tyr Thr Leu Lys Pro Glu Thr
                245                 250                 255


<210> SEQ ID NO 118
<211> LENGTH: 2463
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DISC CISC_FRB nucleotide sequence  coding
      sequence only codon optimized

<400> SEQUENCE: 118

atgcctctgg gcctgctgtg gctgggcctg gccctgctgg gcgccctgca cgcccaggcc     60

ggcgtgcagg tggagacaat ctccccaggc gacggacgca cattccctaa gcggggccag    120

acctgcgtgg tgcactatac aggcatgctg gaggatggca agaagtttga cagctcccgg    180

gatagaaaca agccattcaa gtttatgctg ggcaagcagg aagtgatcag aggctgggag    240

gagggcgtgg cccagatgtc tgtgggccag agggccaagc tgaccatcag cccagactac    300

gcctatggag caacaggcca cccaggaatc atcccacctc acgccaccct ggtgttcgat    360

gtggagctgc tgaagctggg cgagggaggg tcacctggat ccaacacatc aaaagagaac    420

ccctttctgt tcgcattgga ggccgtagtc atatctgttg gatccatggg acttattatc    480

tccctgttgt gtgtgtactt ctggctggaa cggactatgc ccaggatccc cacgctcaag    540

aatctggaag atctcgtcac agaataccat ggtaatttca gcgcctggag cggagtctct    600

aagggtctgg ccgaatccct ccaacccgat tattctgaac ggttgtgcct cgtatccgaa    660

ataccaccaa aaggcggggc tctgggtgag ggcccagggg cgagtccgtg caatcaacac    720

agcccgtatt gggcccctcc ttgttatacg ttgaagcccg aaactggaag cggagctact    780

aacttcagcc tgctgaagca ggctggagac gtggaggaga accctggacc tatggcactg    840

cccgtgaccg ccctgctgct gcctctggcc ctgctgctgc acgcagcccg gcctatcctg    900

tggcacgaga tgtggcacga gggcctggag gaggccagca ggctgtattt tggcgagcgc    960

aacgtgaagg gcatgttcga ggtgctggag cctctgcacg ccatgatgga gagaggccca   1020

cagaccctga aggagacatc ctttaaccag gcctatggac gggacctgat ggaggcacag   1080

gagtggtgca gaaagtacat gaagtctggc aatgtgaagg acctgctgca ggcctgggat   1140

ctgtactatc acgtgtttcg gagaatctcc aagccagcag ctctcggcaa agacacgatt   1200

ccgtggcttg ggcatctgct cgttgggctg agcggtgcgt ttggtttcat catcttggtc   1260

tatctcttga tcaattgcag aaatacaggc ccttggctga aaaaagtgct caagtgtaat   1320

acccccgacc caagcaagtt cttctcccag ctttcttcag agcatggagg cgatgtgcag   1380

aaatggctct cttcaccttt tccctcctca agcttctccc cgggagggct ggcgcccgag   1440

atttcacctc ttgaggtact tgaacgagac aaggttaccc aacttctcct tcaacaggat   1500

aaggtacccg aacctgcgag ccttagctcc aaccactctc ttacgagctg cttcaccaat   1560

cagggatact tctttttcca ccttcccgat gcgctggaaa tcgaagcttg tcaagtttac   1620

tttacctatg atccatatag cgaggaagat cccgacgaag gagtcgccgg tgcgcccacg   1680

ggttcctcac cccaacctct ccagcctctc tcaggagaag atgatgctta ttgcactttt   1740

cccagtagag acgatctcct cctcttttct ccatctcttt tggggggacc ttcccccccct   1800

tctacggcac ctggcgggtc tggtgctggc gaggagcgga tgccgccgtc cctccaggag   1860
```

```
cgagtaccac gagattggga tccccagcca cttggacccc ccacccccgg cgtacctgac   1920

cttgtcgatt ttcaacctcc ccctgaattg gtgctgcgag aggctgggga ggaagttccg   1980

gacgctgggc cgagggaggg cgtgtccttt ccatggagta ggcctccagg tcaaggcgag   2040

tttagggctc tcaacgcgcg gctgccgttg aatacagacg cttatctctc actgcaggaa   2100

ctgcaaggtc aggacccaac acatcttgta ggatctggtg ctactaattt ttctcttttg   2160

aagcaagctg gagatgttga agagaacccc ggtccggaga tgtggcatga gggtctggaa   2220

gaagcgtctc gactgtactt tggtgagcgc aatgtgaagg gcatgtttga agtcctcgaa   2280

ccccttcatg ccatgatgga acgcggaccc cagaccttga aggagacaag ttttaaccaa   2340

gcttacggaa gagacctgat ggaagcccag gaatggtgca ggaaatacat gaaaagcggg   2400

aatgtgaagg acttgctcca agcgtgggac ctgtactatc atgtctttag gcgcattagt   2460

aag                                                                 2463
```

```
<210> SEQ ID NO 119
<211> LENGTH: 821
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: DISC CISC_FRB uDISC amino acid sequence

<400> SEQUENCE: 119

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Gly Gly Ser Pro Gly Ser Asn Thr Ser Lys Glu Asn Pro Phe Leu Phe
    130                 135                 140

Ala Leu Glu Ala Val Val Ile Ser Val Gly Ser Met Gly Leu Ile Ile
145                 150                 155                 160

Ser Leu Leu Cys Val Tyr Phe Trp Leu Glu Arg Thr Met Pro Arg Ile
                165                 170                 175

Pro Thr Leu Lys Asn Leu Glu Asp Leu Val Thr Glu Tyr His Gly Asn
            180                 185                 190

Phe Ser Ala Trp Ser Gly Val Ser Lys Gly Leu Ala Glu Ser Leu Gln
        195                 200                 205

Pro Asp Tyr Ser Glu Arg Leu Cys Leu Val Ser Glu Ile Pro Pro Lys
    210                 215                 220

Gly Gly Ala Leu Gly Glu Gly Pro Gly Ala Ser Pro Cys Asn Gln His
```

```
225                 230                 235                 240

Ser Pro Tyr Trp Ala Pro Pro Cys Tyr Thr Leu Lys Pro Glu Thr Gly
                245                 250                 255

Ser Gly Ala Thr Asn Phe Ser Leu Leu Lys Gln Ala Gly Asp Val Glu
            260                 265                 270

Glu Asn Pro Gly Pro Met Ala Leu Pro Val Thr Ala Leu Leu Leu Pro
        275                 280                 285

Leu Ala Leu Leu Leu His Ala Ala Arg Pro Ile Leu Trp His Glu Met
    290                 295                 300

Trp His Glu Gly Leu Glu Glu Ala Ser Arg Leu Tyr Phe Gly Glu Arg
305                 310                 315                 320

Asn Val Lys Gly Met Phe Glu Val Leu Glu Pro Leu His Ala Met Met
                325                 330                 335

Glu Arg Gly Pro Gln Thr Leu Lys Glu Thr Ser Phe Asn Gln Ala Tyr
            340                 345                 350

Gly Arg Asp Leu Met Glu Ala Gln Glu Trp Cys Arg Lys Tyr Met Lys
        355                 360                 365

Ser Gly Asn Val Lys Asp Leu Leu Gln Ala Trp Asp Leu Tyr Tyr His
    370                 375                 380

Val Phe Arg Arg Ile Ser Lys Pro Ala Ala Leu Gly Lys Asp Thr Ile
385                 390                 395                 400

Pro Trp Leu Gly His Leu Leu Val Gly Leu Ser Gly Ala Phe Gly Phe
                405                 410                 415

Ile Ile Leu Val Tyr Leu Leu Ile Asn Cys Arg Asn Thr Gly Pro Trp
            420                 425                 430

Leu Lys Lys Val Leu Lys Cys Asn Thr Pro Asp Pro Ser Lys Phe Phe
        435                 440                 445

Ser Gln Leu Ser Ser Glu His Gly Gly Asp Val Gln Lys Trp Leu Ser
    450                 455                 460

Ser Pro Phe Pro Ser Ser Ser Phe Ser Pro Gly Gly Leu Ala Pro Glu
465                 470                 475                 480

Ile Ser Pro Leu Glu Val Leu Glu Arg Asp Lys Val Thr Gln Leu Leu
                485                 490                 495

Leu Gln Gln Asp Lys Val Pro Glu Pro Ala Ser Leu Ser Ser Asn His
            500                 505                 510

Ser Leu Thr Ser Cys Phe Thr Asn Gln Gly Tyr Phe Phe Phe His Leu
        515                 520                 525

Pro Asp Ala Leu Glu Ile Glu Ala Cys Gln Val Tyr Phe Thr Tyr Asp
    530                 535                 540

Pro Tyr Ser Glu Glu Asp Pro Asp Glu Gly Val Ala Gly Ala Pro Thr
545                 550                 555                 560

Gly Ser Ser Pro Gln Pro Leu Gln Pro Leu Ser Gly Glu Asp Asp Ala
                565                 570                 575

Tyr Cys Thr Phe Pro Ser Arg Asp Asp Leu Leu Leu Phe Ser Pro Ser
            580                 585                 590

Leu Leu Gly Gly Pro Ser Pro Pro Ser Thr Ala Pro Gly Gly Ser Gly
        595                 600                 605

Ala Gly Glu Glu Arg Met Pro Pro Ser Leu Gln Glu Arg Val Pro Arg
    610                 615                 620

Asp Trp Asp Pro Gln Pro Leu Gly Pro Pro Thr Pro Gly Val Pro Asp
625                 630                 635                 640

Leu Val Asp Phe Gln Pro Pro Pro Glu Leu Val Leu Arg Glu Ala Gly
                645                 650                 655
```

```
Glu Glu Val Pro Asp Ala Gly Pro Arg Glu Gly Val Ser Phe Pro Trp
            660                 665                 670

Ser Arg Pro Pro Gly Gln Gly Glu Phe Arg Ala Leu Asn Ala Arg Leu
        675                 680                 685

Pro Leu Asn Thr Asp Ala Tyr Leu Ser Leu Gln Glu Leu Gln Gly Gln
    690                 695                 700

Asp Pro Thr His Leu Val Gly Ser Gly Ala Thr Asn Phe Ser Leu Leu
705                 710                 715                 720

Lys Gln Ala Gly Asp Val Glu Glu Asn Pro Gly Pro Glu Met Trp His
                725                 730                 735

Glu Gly Leu Glu Glu Ala Ser Arg Leu Tyr Phe Gly Glu Arg Asn Val
            740                 745                 750

Lys Gly Met Phe Glu Val Leu Glu Pro Leu His Ala Met Met Glu Arg
        755                 760                 765

Gly Pro Gln Thr Leu Lys Glu Thr Ser Phe Asn Gln Ala Tyr Gly Arg
    770                 775                 780

Asp Leu Met Glu Ala Gln Glu Trp Cys Arg Lys Tyr Met Lys Ser Gly
785                 790                 795                 800

Asn Val Lys Asp Leu Leu Gln Ala Trp Asp Leu Tyr Tyr His Val Phe
                805                 810                 815

Arg Arg Ile Ser Lys
            820
```

<210> SEQ ID NO 120
<211> LENGTH: 267
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: FRB express intracellularly to function as a decoy for rapamycin FRB nucleotide sequence coding sequence only decoy codon optimized WT

<400> SEQUENCE: 120

```
gagatgtggc atgagggtct ggaagaagcg tctcgactgt actttggtga gcgcaatgtg     60

aagggcatgt ttgaagtcct cgaacccctt catgccatga tggaacgcgg accccagacc    120

ttgaaggaga caagttttaa ccaagcttac ggaagagacc tgatggaagc ccaggaatgg    180

tgcaggaaat acatgaaaag cgggaatgtg aaggacttga cccaagcgtg ggacctgtac    240

tatcatgtct ttaggcgcat tagtaag                                        267
```

<210> SEQ ID NO 121
<211> LENGTH: 89
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: FRB amino acid sequence

<400> SEQUENCE: 121

```
Glu Met Trp His Glu Gly Leu Glu Glu Ala Ser Arg Leu Tyr Phe Gly
1               5                   10                  15

Glu Arg Asn Val Lys Gly Met Phe Glu Val Leu Glu Pro Leu His Ala
            20                  25                  30

Met Met Glu Arg Gly Pro Gln Thr Leu Lys Glu Thr Ser Phe Asn Gln
```

```
        35                  40                  45

Ala Tyr Gly Arg Asp Leu Met Glu Ala Gln Glu Trp Cys Arg Lys Tyr
    50                  55                  60

Met Lys Ser Gly Asn Val Lys Asp Leu Thr Gln Ala Trp Asp Leu Tyr
65                  70                  75                  80

Tyr His Val Phe Arg Arg Ile Ser Lys
                85


<210> SEQ ID NO 122
<211> LENGTH: 825
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: LNGFR coding sequence with stop codon

<400> SEQUENCE: 122

atgggggcag gtgccaccgg acgagccatg gacgggccgc gcctgctgct gttgctgctt     60

ctgggggtgt cccttggagg tgccaaggag gcatgcccca caggcctgta cacacacagc    120

ggtgagtgct gcaaagcctg caacctgggc gagggtgtgg cccagccttg tggagccaac    180

cagaccgtgt gtgagccctg cctggacagc gtgacgttct ccgacgtggt gagcgcgacc    240

gagccgtgca agccgtgcac cgagtgcgtg gggctccaga gcatgtcggc gccgtgcgtg    300

gaggccgacg acgccgtgtg ccgctgcgcc tacggctact accaggatga gacgactggg    360

cgctgcgagg cgtgccgcgt gtgcgaggcg ggctcgggcc tcgtgttctc ctgccaggac    420

aagcagaaca ccgtgtgcga ggagtgcccc gacggcacgt attccgacga ggccaaccac    480

gtggacccgt gcctgccctg caccgtgtgc gaggacaccg agcgccagct ccgcgagtgc    540

acacgctggg ccgacgccga gtgcgaggag atccctggcc gttggattac acggtccaca    600

cccccagagg gctcggacag cacagccccc agcacccagg agcctgaggc acctccagaa    660

caagacctca tagccagcac ggtggcaggt gtggtgacca cagtgatggg cagctcccag    720

cccgtggtga cccgaggcac caccgacaac ctcatccctg tctattgctc catcctggct    780

gctgtggttg tgggtcttgt ggcctacata gccttcaaga ggtga                    825


<210> SEQ ID NO 123
<211> LENGTH: 66
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: LNGFRe LNGFR epitope coding sequence  2A P2A
      self cleaving peptide

<400> SEQUENCE: 123

ggaagcggag cgactaactt cagcctgctg aagcaggccg gagatgtgga ggaaaaccct     60

ggaccg                                                                66


<210> SEQ ID NO 124
<211> LENGTH: 258
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

<223> OTHER INFORMATION: 0_25kb human FOXP3 5'HA designed for both TALEN and Cas9

<400> SEQUENCE: 124
tgctagcgtg ggcaggcaag ccaggtgctg gacctctgca cgtggggcat gtgtgggtat 60
gtacatgtac ctgtgttctt ggtgtgtgtg tgtgtgtgtg tgtgtgtgtg tgtctagagc 120
tggggtgcaa ctatggggcc cctcgggaca tgtcccagcc aatgcctgct ttgaccagag 180
gagtgtccac gtggctcagg tggtcgagta tctcataccg ccctagcaca cgtgtgactc 240
ctttccccta ttgtctac 258

<210> SEQ ID NO 125
<211> LENGTH: 296
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_3kb human FOXP3 5'HA for Cas9_T9

<400> SEQUENCE: 125
catgtgtggg tatgtacatg tacctgtgtt cttggtgtgt gtgtgtgtgt gtgtgtgtgt 60
gtgtgtctag agctggggtg caactatggg gcccctcggg acatgtccca gccaatgcct 120
gctttgacca gaggagtgtc cacgtggctc aggtggtcga gtatctcata ccgccctagc 180
acacgtgtga ctcctttccc ctattgtcta cgcagcctgc ccttggacaa ggacccgatg 240
cccaacccca ggcctggcaa gccctcggcc ccttccttgg cccttggccc atcccc 296

<210> SEQ ID NO 126
<211> LENGTH: 452
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_45kb human FOXP3 5'HA for Cas9_T9

<400> SEQUENCE: 126
agcctgtgca gggtgcaggg agggctagag gcctgaggct tgaaacagct ctcaagtgga 60
gggggaaaca accattgccc tcatagagga cacatccaca ccagggctgt gctagcgtgg 120
gcaggcaagc caggtgctgg acctctgcac gtggggcatg tgtgggtatg tacatgtacc 180
tgtgttcttg gtgtgtgtgt gtgtgtgtgt gtgtgtgtgt gtctagagct ggggtgcaac 240
tatggggccc ctcgggacat gtcccagcca atgcctgctt tgaccagagg agtgtccacg 300
tggctcaggt ggtcgagtat ctcataccgc cctagcacac gtgtgactcc tttcccctat 360
tgtctacgca gcctgccctt ggacaaggac ccgatgccca accccaggcc tggcaagccc 420
tcggcccctt ccttggccct tggcccatcc cc 452

<210> SEQ ID NO 127
<211> LENGTH: 600
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_6kb human FOXP3 5'HA for Cas9_T9

<400> SEQUENCE: 127

```
atcacttgcc aggactgtta caatagcctc ctcactagcc ccactcacag cagccagatg     60

aatcttttga gtccatgcct agtcactggg gcaaaatagg actccgagga gaaagtccga    120

gaccagctcc ggcaagatga gcaaacacag cctgtgcagg gtgcagggag ggctagaggc    180

ctgaggcttg aaacagctct caagtggagg gggaaacaac cattgccctc atagaggaca    240

catccacacc agggctgtgc tagcgtgggc aggcaagcca ggtgctggac ctctgcacgt    300

ggggcatgtg tgggtatgta catgtacctg tgttcttggt gtgtgtgtgt gtgtgtgtgt    360

gtgtgtgtgt ctagagctgg ggtgcaacta tggggcccct cgggacatgt cccagccaat    420

gcctgctttg accagaggag tgtccacgtg gctcaggtgg tcgagtatct cataccgccc    480

tagcacacgt gtgactcctt tcccctattg tctacgcagc ctgcccttgg acaaggaccc    540

gatgcccaac cccaggcctg gcaagccctc ggccccttcc ttggcccttg gcccatcccc    600


<210> SEQ ID NO 128
<211> LENGTH: 785
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_8kb human FOXP3 5'HA for Cas9_T9

<400> SEQUENCE: 128

atctcaggta atgtcagctc ggtccttcca gctgctcaag ctaaaaccca tgtcactttg     60

actctccctc ttgcccacta catccaagct gctagcactg ctcctgatcc agcttcagat    120

taagtctcag aatctaccca cttctcgcct tctccactgc caccagccca ttctgtgcca    180

gcatcatcac ttgccaggac tgttacaata gcctcctcac tagccccact cacagcagcc    240

agatgaatct tttgagtcca tgcctagtca ctggggcaaa ataggactcc gaggagaaag    300

tccgagacca gctccggcaa gatgagcaaa cacagcctgt gcagggtgca gggagggcta    360

gaggcctgag gcttgaaaca gctctcaagt ggagggggaa acaaccattg ccctcataga    420

ggacacatcc acaccagggc tgtgctagcg tgggcaggca agccaggtgc tggacctctg    480

cacgtggggc atgtgtgggt atgtacatgt acctgtgttc ttggtgtgtg tgtgtgtgtg    540

tgtgtgtgtg tgtgtctaga gctggggtgc aactatgggg cccctcggga catgtcccag    600

ccaatgcctg ctttgaccag aggagtgtcc acgtggctca ggtggtcgag tatctcatac    660

cgccctagca cacgtgtgac tcctttcccc tattgtctac gcagcctgcc cttggacaag    720

gacccgatgc ccaaccccag gcctggcaag ccctcggccc cttccttggc ccttggccca    780

tcccc                                                                785


<210> SEQ ID NO 129
<211> LENGTH: 275
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_3kb human FOXP3 5'HA for Cas9_T3

<400> SEQUENCE: 129

gacatgtccc agccaatgcc tgctttgacc agaggagtgt ccacgtggct caggtggtcg     60

agtatctcat accgccctag cacacgtgtg actcctttcc cctattgtct acgcagcctg    120
```

```
ccccttggaca aggacccgat gcccaacccc aggcctggca agccctcggc cccttccttg    180

gcccttggcc catccccagg agcctcgccc agctggaggg ctgcacccaa agcctcagac    240

ctgctggggg cccggggccc agggggaacc ttcca                                275


<210> SEQ ID NO 130
<211> LENGTH: 449
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_45kb human FOXP3 5'HA for Cas9_T3

<400> SEQUENCE: 130

catagaggac acatccacac cagggctgtg ctagcgtggg caggcaagcc aggtgctgga     60

cctctgcacg tggggcatgt gtgggtatgt acatgtacct gtgttcttgg tgtgtgtgtg    120

tgtgtgtgtg tgtgtgtgtg tctagagctg gggtgcaact atggggcccc tcgggacatg    180

tcccagccaa tgcctgcttt gaccagagga gtgtccacgt ggctcaggtg gtcgagtatc    240

tcataccgcc ctagcacacg tgtgactcct ttcccctatt gtctacgcag cctgcccttg    300

gacaaggacc cgatgcccaa ccccaggcct ggcaagccct cggccccttc cttggccctt    360

ggcccatccc caggagcctc gcccagctgg agggctgcac ccaaagcctc agacctgctg    420

ggggcccggg gcccaggggg aaccttcca                                       449


<210> SEQ ID NO 131
<211> LENGTH: 600
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_6kb human FOXP3 5'HA for Cas9_T3

<400> SEQUENCE: 131

ctagtcactg ggcaaaaata ggactccgag gagaaagtcc gagaccagct ccggcaagat     60

gagcaaacac agcctgtgca gggtgcaggg agggctagag gcctgaggct tgaaacagct    120

ctcaagtgga gggggaaaca accattgccc tcatagagga cacatccaca ccagggctgt    180

gctagcgtgg gcaggcaagc caggtgctgg acctctgcac gtggggcatg tgtgggtatg    240

tacatgtacc tgtgttcttg gtgtgtgtgt gtgtgtgtgt gtgtgtgtgt gtctagagct    300

ggggtgcaac tatggggccc ctcgggacat gtcccagcca atgcctgctt tgaccagagg    360

agtgtccacg tggctcaggt ggtcgagtat ctcataccgc cctagcacac gtgtgactcc    420

tttcccctat tgtctacgca gcctgccctt ggacaaggac ccgatgccca accccaggcc    480

tggcaagccc tcggcccctt ccttggccct tggcccatcc ccaggagcct cgcccagctg    540

gagggctgca cccaaagcct cagacctgct gggggcccgg ggcccagggg gaaccttcca    600


<210> SEQ ID NO 132
<211> LENGTH: 245
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_25kb human FOXP3 3'HA designed for both TALEN
      and Cas9
```

<400> SEQUENCE: 132
gtgaggccct gggcccagga tggggcaggc agggtggggt acctggacct acaggtgccg 60
acctttactg tggcactggg cgggaggggg gctggctggg gcacaggaag tggtttctgg 120
gtcccaggca agtctgtgac ttatgcagat gttgcagggc caagaaaatc cccacctgcc 180
aggcctcaga gattggaggc tctccccgac ctcccaatcc ctgtctcagg agaggaggag 240
gccgt 245

<210> SEQ ID NO 133
<211> LENGTH: 300
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_3kb human FOXP3 3'HA for Cas9_T9

<400> SEQUENCE: 133
gcctcgccca gctggagggc tgcacccaaa gcctcagacc tgctgggggc ccggggccca 60
gggggaacct tccagggccg agatcttcga ggcggggccc atgcctcctc ttcttccttg 120
aaccccatgc caccatcgca gctgcaggtg aggccctggg cccaggatgg ggcaggcagg 180
gtggggtacc tggacctaca ggtgccgacc tttactgtgg cactgggcgg gagggggggct 240 ggctggggca caggaagtgg tttctgggtc ccaggcaagt ctgtgactta tgcagatgtt 300

<210> SEQ ID NO 134
<211> LENGTH: 450
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_45kb human FOXP3 3'HA for Cas9_T9

<400> SEQUENCE: 134
gcctcgccca gctggagggc tgcacccaaa gcctcagacc tgctgggggc ccggggccca 60
gggggaacct tccagggccg agatcttcga ggcggggccc atgcctcctc ttcttccttg 120
aaccccatgc caccatcgca gctgcaggtg aggccctggg cccaggatgg ggcaggcagg 180
gtggggtacc tggacctaca ggtgccgacc tttactgtgg cactgggcgg gagggggggct 240 ggctggggca caggaagtgg tttctgggtc ccaggcaagt ctgtgactta tgcagatgtt 300
gcagggccaa gaaaatcccc acctgccagg cctcagagat tggaggctct ccccgacctc 360
ccaatccctg tctcaggaga ggaggaggcc gtattgtagt cccatgagca tagctatgtg 420
tccccatccc catgtgacaa gagaagagga 450

<210> SEQ ID NO 135
<211> LENGTH: 600
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_6kb human FOXP3 3'HA for Cas9_T9

<400> SEQUENCE: 135
gcctcgccca gctggagggc tgcacccaaa gcctcagacc tgctgggggc ccggggccca 60
gggggaacct tccagggccg agatcttcga ggcggggccc atgcctcctc ttcttccttg 120
aaccccatgc caccatcgca gctgcaggtg aggccctggg cccaggatgg ggcaggcagg 180
gtggggtacc tggacctaca ggtgccgacc tttactgtgg cactgggcgg gaggggggct 240
ggctggggca caggaagtgg tttctgggtc ccaggcaagt ctgtgactta tgcagatgtt 300
gcagggccaa gaaaatcccc acctgccagg cctcagagat tggaggctct ccccgacctc 360
ccaatccctg tctcaggaga ggaggaggcc gtattgtagt cccatgagca tagctatgtg 420
tccccatccc catgtgacaa gagaagagga ctggggccaa gtaggtgagg tgacagggct 480
gaggccagct ctgcaactta ttagctgttt gatctttaaa aagttactcg atctccatga 540
gcctcagttt ccatacgtgt aaaaggggga tgatcatagc atctaccatg tgggcttgca 600

<210> SEQ ID NO 136
<211> LENGTH: 794
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_8kb human FOXP3 3'HA for Cas9_T9

<400> SEQUENCE: 136
gcctcgccca gctggagggc tgcacccaaa gcctcagacc tgctgggggc ccggggccca 60
gggggaacct tccagggccg agatcttcga ggcggggccc atgcctcctc ttcttccttg 120
aaccccatgc caccatcgca gctgcaggtg aggccctggg cccaggatgg ggcaggcagg 180
gtggggtacc tggacctaca ggtgccgacc tttactgtgg cactgggcgg gaggggggct 240
ggctggggca caggaagtgg tttctgggtc ccaggcaagt ctgtgactta tgcagatgtt 300
gcagggccaa gaaaatcccc acctgccagg cctcagagat tggaggctct ccccgacctc 360
ccaatccctg tctcaggaga ggaggaggcc gtattgtagt cccatgagca tagctatgtg 420
tccccatccc catgtgacaa gagaagagga ctggggccaa gtaggtgagg tgacagggct 480
gaggccagct ctgcaactta ttagctgttt gatctttaaa aagttactcg atctccatga 540
gcctcagttt ccatacgtgt aaaaggggga tgatcatagc atctaccatg tgggcttgca 600
gtgcagagta tttgaattag acacagaaca gtgaggatca ggatggcctc tcacccacct 660
gcctttctgc ccagctgccc acactgcccc tagtcatggt ggcaccctcc ggggcacggc 720 tgggccccctt gccccactta caggcactcc tccaggacag gccacatttc atgcaccagg 780
tatggacggt gaat 794

<210> SEQ ID NO 137
<211> LENGTH: 300
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_3kb human FOXP3 3'HA for Cas9_T3

<400> SEQUENCE: 137
cgagatcttc gaggcggggc ccatgcctcc tcttcttcct tgaaccccat gccaccatcg 60
cagctgcagg tgaggccctg ggcccaggat ggggcaggca gggtggggta cctggaccta 120
caggtgccga cctttactgt ggcactgggc gggagggggg ctggctgggg cacaggaagt 180
ggtttctggg tcccaggcaa gtctgtgact tatgcagatg ttgcagggcc aagaaaatcc 240
ccacctgcca ggcctcagag attggaggct ctccccgacc tcccaatccc tgtctcagga 300

<210> SEQ ID NO 138
<211> LENGTH: 451
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_45kb human FOXP3 3'HA for Cas9_T3

<400> SEQUENCE: 138
cgagatcttc gaggcggggc ccatgcctcc tcttcttcct tgaaccccat gccaccatcg 60
cagctgcagg tgaggccctg ggcccaggat ggggcaggca gggtggggta cctggaccta 120
caggtgccga cctttactgt ggcactgggc gggagggggg ctggctgggg cacaggaagt 180
ggtttctggg tcccaggcaa gtctgtgact tatgcagatg ttgcagggcc aagaaaatcc 240
ccacctgcca ggcctcagag attggaggct ctccccgacc tcccaatccc tgtctcagga 300
gaggaggagg ccgtattgta gtcccatgag catagctatg tgtccccatc cccatgtgac 360
aagagaagag gactggggcc aagtaggtga ggtgacaggg ctgaggccag ctctgcaact 420
tattagctgt ttgatcttta aaaagttact c 451

<210> SEQ ID NO 139
<211> LENGTH: 600
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_6kb human FOXP3 3'HA for Cas9_T3

<400> SEQUENCE: 139
cgagatcttc gaggcggggc ccatgcctcc tcttcttcct tgaaccccat gccaccatcg 60
cagctgcagg tgaggccctg ggcccaggat ggggcaggca gggtggggta cctggaccta 120
caggtgccga cctttactgt ggcactgggc gggagggggg ctggctgggg cacaggaagt 180
ggtttctggg tcccaggcaa gtctgtgact tatgcagatg ttgcagggcc aagaaaatcc 240
ccacctgcca ggcctcagag attggaggct ctccccgacc tcccaatccc tgtctcagga 300
gaggaggagg ccgtattgta gtcccatgag catagctatg tgtccccatc cccatgtgac 360
aagagaagag gactggggcc aagtaggtga ggtgacaggg ctgaggccag ctctgcaact 420
tattagctgt ttgatcttta aaaagttact cgatctccat gagcctcagt ttccatacgt 480
gtaaaagggg gatgatcata gcatctacca tgtgggcttg cagtgcagag tatttgaatt 540
agacacagaa cagtgaggat caggatggcc tctcacccac ctgcctttct gcccagctgc 600

<210> SEQ ID NO 140
<211> LENGTH: 250
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_25kb AAVS1 5'HA for Cas9_P1 and Cas9_N2

<400> SEQUENCE: 140

```
tagccacctc tccatcctct tgctttcttt gcctggacac cccgttctcc tgtggattcg     60

ggtcacctct cactcctttc atttgggcag ctcccctacc ccccttacct ctctagtctg    120

tgctagctct tccagccccc tgtcatggca tcttccaggg gtccgagagc tcagctagtc    180

ttcttcctcc aacccgggcc cctatgtcca cttcaggaca gcatgtttgc tgcctccagg    240

gatcctgtgt                                                           250


<210> SEQ ID NO 141
<211> LENGTH: 600
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_6kb AAVS1 5'HA for Cas9_P1 and Cas9_N2

<400> SEQUENCE: 141

aggttccgtc ttcctccact ccctcttccc cttgctctct gctgtgttgc tgcccaagga     60

tgctctttcc ggagcacttc cttctcggcg ctgcaccacg tgatgtcctc tgagcggatc    120

ctccccgtgt ctgggtcctc tccgggcatc tctcctccct cacccaaccc catgccgtct    180

tcactcgctg ggttcccttt tccttctcct tctggggcct gtgccatctc tcgtttctta    240

ggatggcctt ctccgacgga tgtctccctt gcgtcccgcc tccccttctt gtaggcctgc    300

atcatcaccg tttttctgga caaccccaaa gtaccccgtc tccctggctt tagccacctc    360

tccatcctct tgctttcttt gcctggacac cccgttctcc tgtggattcg ggtcacctct    420

cactcctttc atttgggcag ctcccctacc ccccttacct ctctagtctg tgctagctct    480

tccagccccc tgtcatggca tcttccaggg gtccgagagc tcagctagtc ttcttcctcc    540

aacccgggcc cctatgtcca cttcaggaca gcatgtttgc tgcctccagg gatcctgtgt    600


<210> SEQ ID NO 142
<211> LENGTH: 250
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_25kb AAVS1 3'HA for Cas9_P1 and Cas9_N2

<400> SEQUENCE: 142

ctctggttct gggtactttt atctgtcccc tccaccccac agtggggcca ctagggacag     60

gattggtgac agaaaagccc catccttagg cctcctcctt cctagtctcc tgatattggg    120

tctaaccccc acctcctgtt aggcagattc cttatctggt gacacacccc catttcctgg    180

agccatctct ctccttgcca gaacctctaa ggtttgctta cgatggagcc agagaggatc    240

ctgggaggga                                                           250


<210> SEQ ID NO 143
<211> LENGTH: 600
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 0_6kb AAVS1 3'HA for Cas9_P1 and Cas9_N2

<400> SEQUENCE: 143
```

```
ctctggttct gggtactttt atctgtcccc tccaccccac agtggggcca ctagggacag     60

gattggtgac agaaaagccc catccttagg cctcctcctt cctagtctcc tgatattggg    120

tctaacccccc acctcctgtt aggcagattc cttatctggt gacacacccc catttcctgg    180

agccatctct ctccttgcca gaacctctaa ggtttgctta cgatggagcc agagaggatc    240

ctgggaggga gagcttggca gggggtggga gggaaggggg ggatgcgtga cctgcccggt    300

tctcagtggc caccctgcgc taccctctcc cagaacctga gctgctctga cgcggccgtc    360

tggtgcgttt cactgatcct ggtgctgcag cttccttaca cttcccaaga ggagaagcag    420

tttggaaaaa caaaatcaga ataagttggt cctgagttct aactttggct cttcaccttt    480

ctagtcccca atttatattg ttcctccgtg cgtcagtttt acctgtgaga taaggccagt    540

agccagcccc gtcctggcag ggctgtggtg aggagggggg tgtccgtgtg gaaaactccc    600
```

```
<210> SEQ ID NO 144
<211> LENGTH: 274
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Selection marker LNGFR RQR8 EGFRt LNGFRt
      protein sequence

<400> SEQUENCE: 144

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240
```

```
Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg


<210> SEQ ID NO 145
<211> LENGTH: 157
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: RQR8 protein sequence

<400> SEQUENCE: 145

Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val
145                 150                 155


<210> SEQ ID NO 146
<211> LENGTH: 357
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: EGFRt with GM_CSFR signal peptide

<400> SEQUENCE: 146

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80
```

-continued

```
Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355
```

<210> SEQ ID NO 147
<211> LENGTH: 347
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: MND promoter

<400> SEQUENCE: 147

```
gaacagagaa acaggagaat atgggccaaa caggatatct gtggtaagca gttcctgccc     60

cggctcaggg ccaagaacag ttggaacagc agaatatggg ccaaacagga tatctgtggt    120

aagcagttcc tgccccggct cagggccaag aacagatggt ccccagatgc ggtcccgccc    180

tcagcagttt ctagagaacc atcagatgtt tccagggtgc cccaaggacc tgaaatgacc    240

ctgtgcctta tttgaactaa ccaatcagtt cgcttctcgc ttctgttcgc gcgcttctgc    300

tccccgagct ctatataagc agagctcgtt tagtgaaccg tcagatc                  347
```

<210> SEQ ID NO 148
<211> LENGTH: 523
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: PGK promoter

<400> SEQUENCE: 148
ccacggggtt ggggttgcgc cttttccaag gcagccctgg gtttgcgcag ggacgcggct 60
gctctgggcg tggttccggg aaacgcagcg gcgccgaccc tgggtctcgc acattcttca 120
cgtccgttcg cagcgtcacc cggatcttcg ccgctaccct tgtgggcccc ccggcgacgc 180
ttcctgctcc gcccctaagt cgggaaggtt ccttgcggtt cgcggcgtgc cggacgtgac 240
aaacggaagc cgcacgtctc actagtaccc tcgcagacgg acagcgccag ggagcaatgg 300
cagcgcgccg accgcgatgg gctgtggcca atagcggctg ctcagcgggg cgcgccgaga 360
gcagcggccg ggaaggggcg gtgcgggagg cggggtgtgg ggcggtagtg tgggccctgt 420
tcctgcccgc gcggtgttcc gcattctgca agcctccgga gcgcacgtcg gcagtcggct 480
ccctcgttga ccgaatcacc gacctctctc cccaggggga tcc 523

<210> SEQ ID NO 149
<211> LENGTH: 231
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: EF1 promoter

<400> SEQUENCE: 149
aggctccggt gcccgtcagt gggcagagcg cacatcgccc acagtccccg agaagttggg 60
gggaggggtc ggcaattgaa ccggtgccta gagaaggtgg cgcggggtaa actgggaaag 120
tgatgtcgtg tactggctcc gcctttttcc cgagggtggg ggagaaccgt atataagtgc 180
agtagtcgcc gtgaacgttc tttttcgcaa cgggtttgcc gccagaacac a 231

<210> SEQ ID NO 150
<211> LENGTH: 135
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SV40 polyA

<400> SEQUENCE: 150
tgctttattt gtgaaatttg tgatgctatt gctttatttg taaccattat aagctgcaat 60
aaacaagtta acaacaacaa ttgcattcat tttatgtttc aggttcaggg ggagatgtgg 120
gaggtttttt aaagc 135

<210> SEQ ID NO 151
<211> LENGTH: 898
<212> TYPE: DNA
<213> ORGANISM: Artificial sequence
<220> FEATURE:
<223> OTHER INFORMATION: Synthetic polynucleotide
<220> FEATURE:

<221> NAME/KEY: misc_feature
<223> OTHER INFORMATION: 3'UTR of FOXP3

<400> SEQUENCE: 151
cctcaagatc aaggaaagga ggatggacga acaggggcca aactggtggg aggcagaggt 60
ggtgggggca gggatgatag gccctggatg tgcccacagg gaccaagaag tgaggtttcc 120
actgtcttgc ctgccagggc ccctgttccc ccgctggcag ccaccccctc ccccatcata 180
tcctttgccc caaggctgct cagaggggcc ccggtcctgg ccccagcccc cacctccgcc 240
ccagacacac cccccagtcg agccctgcag ccaaacagag ccttcacaac cagccacaca 300
gagcctgcct cagctgctcg cacagattac ttcagggctg gaaaagtcac acagacacac 360
aaaatgtcac aatcctgtcc ctcactcaac acaaacccca aaacacagag agcctgcctc 420
agtacactca aacaacctca aagctgcatc atcacacaat cacacacaag cacagccctg 480
acaacccaca caccccaagg cacgcaccca cagccagcct cagggcccac aggggcactg 540
tcaacacagg ggtgtgccca gaggcctaca cagaagcagc gtcagtaccc tcaggatctg 600
aggtcccaac acgtgctcgc tcacacacac ggcctgttag aattcacctg tgtatctcac 660
gcatatgcac acgcacagcc ccccagtggg tctcttgagt cccgtgcaga cacacacagc 720
cacacacact gccttgccaa aaataccccg tgtctcccct gccactcacc tcactcccat 780
tccctgagcc ctgatccatg cctcagctta gactgcagag gaactactca tttatttggg 840
atccaaggcc cccaacccac agtaccgtcc ccaataaact gcagccgagc tccccaca 898

<210> SEQ ID NO 152
<211> LENGTH: 822
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: LNGFR coding sequence without stop codon

<400> SEQUENCE: 152
atgggggcag gtgccaccgg acgagccatg gacgggccgc gcctgctgct gttgctgctt 60
ctgggggtgt cccttggagg tgccaaggag gcatgcccca caggcctgta cacacacagc 120
ggtgagtgct gcaaagcctg caacctgggc gagggtgtgg cccagccttg tggagccaac 180
cagaccgtgt gtgagccctg cctggacagc gtgacgttct ccgacgtggt gagcgcgacc 240
gagccgtgca agccgtgcac cgagtgcgtg gggctccaga gcatgtcggc gccgtgcgtg 300
gaggccgacg acgccgtgtg ccgctgcgcc tacggctact accaggatga gacgactggg 360
cgctgcgagg cgtgccgcgt gtgcgaggcg ggctcgggcc tcgtgttctc ctgccaggac 420
aagcagaaca ccgtgtgcga ggagtgcccc gacggcacgt attccgacga ggccaaccac 480
gtggacccgt gcctgccctg caccgtgtgc gaggacaccg agcgccagct ccgcgagtgc 540
acacgctggg ccgacgccga gtgcgaggag atccctggcc gttggattac acggtccaca 600
cccccagagg gctcggacag cacagccccc agcacccagg agcctgaggc acctccagaa 660
caagacctca tagccagcac ggtggcaggt gtggtgacca cagtgatggg cagctcccag 720
cccgtggtga cccgaggcac caccgacaac ctcatccctg tctattgctc catcctggct 780
gctgtggttg tgggtcttgt ggcctacata gccttcaaga gg 822

<210> SEQ ID NO 153
<211> LENGTH: 1899

<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: uDISC uCISC_FRB nucleotide sequence coding sequence only codon optimized

<400> SEQUENCE: 153

```
atgcctctgg gcctgctgtg gctgggcctg gccctgctgg gcgccctgca cgcccaggcc     60
ggcgtgcagg tggagacaat ctccccaggc gacggacgca cattccctaa gcggggccag    120
acctgcgtgg tgcactatac aggcatgctg gaggatggca agaagtttga cagctcccgg    180
gatagaaaca agccattcaa gtttatgctg ggcaagcagg aagtgatcag aggctgggag    240
gagggcgtgg cccagatgtc tgtgggccag agggccaagc tgaccatcag cccagactac    300
gcctatggag caacaggcca cccaggaatc atcccacctc acgccaccct ggtgttcgat    360
gtggagctgc tgaagctggg cgagggaggg tcacctggat ccaacacatc aaaagagaac    420
ccctttctgt tcgcattgga ggccgtagtc atatctgttg gatccatggg acttattatc    480
tccctgttgt gtgtgtactt ctggctggaa cggactatgc ccaggatccc cacgctcaag    540
aatctggaag atctcgtcac agaataccat ggtaatttca gcgcctggag cggagtctct    600
aagggtctgg ccgaatccct ccaacccgat tattctgaac ggttgtgcct cgtatccgaa    660
ataccaccaa aaggcggggc tctgggtgag ggcccagggg cgagtccgtg caatcaacac    720
agcccgtatt gggcccctcc ttgttatacg ttgaagcccg aaactggaag cggagctact    780
aacttcagcc tgctgaagca ggctggagac gtggaggaga accctggacc tatggcactg    840
cccgtgaccg ccctgctgct gcctctggcc ctgctgctgc acgcagcccg gcctatcctg    900
tggcacgaga tgtggcacga gggcctggag gaggccagca ggctgtattt tggcgagcgc    960
aacgtgaagg gcatgttcga ggtgctggag cctctgcacg ccatgatgga gagaggccca   1020
cagaccctga aggagacatc ctttaaccag gcctatggac gggacctgat ggaggcacag   1080
gagtggtgca gaaagtacat gaagtctggc aatgtgaagg acctgctgca ggcctgggat   1140
ctgtactatc acgtgtttcg gagaatctcc aagccagcag ctctcggcaa agacacgatt   1200
ccgtggcttg ggcatctgct cgttgggctg agcggtgcgt ttggtttcat catcttggtc   1260
tatctcttga tcaattgcag aaatacaggc ccttggctga aaaaagtgct caagtgtaat   1320
acccccgacc caagcaagtt cttctcccag ctttcttcag agcatggagg cgatgtgcag   1380
aaatggctct cttcaccttt tccctcctca agcttctccc cgggagggct ggcgcccgag   1440
atttcacctc ttgaggtact tgaacgagac aaggttaccc aacttctcct tcaacaggat   1500
aaggtacccg aacctgcgag ccttagcttg aatacagacg cttatctctc actgcaggaa   1560
ctgcaaggat ctggtgctac taatttttct cttttgaagc aagctggaga tgttgaagag   1620
aaccccggtc cggagatgtg gcatgagggt ctggaagaag cgtctcgact gtactttggt   1680
gagcgcaatg tgaagggcat gtttgaagtc ctcgaacccc ttcatgccat gatggaacgc   1740
ggaccccaga ccttgaagga gacaagtttt aaccaagctt acggaagaga cctgatggaa   1800
gcccaggaat ggtgcaggaa atacatgaaa agcgggaatg tgaaggactt gctccaagcg   1860
tgggacctgt actatcatgt ctttaggcgc attagtaag                          1899
```

<210> SEQ ID NO 154
<211> LENGTH: 633
<212> TYPE: PRT

<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: uDISC uCISC_FRB amino acid sequence

<400> SEQUENCE: 154

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Gly Gly Ser Pro Gly Ser Asn Thr Ser Lys Glu Asn Pro Phe Leu Phe
    130                 135                 140

Ala Leu Glu Ala Val Val Ile Ser Val Gly Ser Met Gly Leu Ile Ile
145                 150                 155                 160

Ser Leu Leu Cys Val Tyr Phe Trp Leu Glu Arg Thr Met Pro Arg Ile
                165                 170                 175

Pro Thr Leu Lys Asn Leu Glu Asp Leu Val Thr Glu Tyr His Gly Asn
            180                 185                 190

Phe Ser Ala Trp Ser Gly Val Ser Lys Gly Leu Ala Glu Ser Leu Gln
        195                 200                 205

Pro Asp Tyr Ser Glu Arg Leu Cys Leu Val Ser Glu Ile Pro Pro Lys
    210                 215                 220

Gly Gly Ala Leu Gly Glu Gly Pro Gly Ala Ser Pro Cys Asn Gln His
225                 230                 235                 240

Ser Pro Tyr Trp Ala Pro Pro Cys Tyr Thr Leu Lys Pro Glu Thr Gly
                245                 250                 255

Ser Gly Ala Thr Asn Phe Ser Leu Leu Lys Gln Ala Gly Asp Val Glu
            260                 265                 270

Glu Asn Pro Gly Pro Met Ala Leu Pro Val Thr Ala Leu Leu Leu Pro
        275                 280                 285

Leu Ala Leu Leu Leu His Ala Ala Arg Pro Ile Leu Trp His Glu Met
    290                 295                 300

Trp His Glu Gly Leu Glu Glu Ala Ser Arg Leu Tyr Phe Gly Glu Arg
305                 310                 315                 320

Asn Val Lys Gly Met Phe Glu Val Leu Glu Pro Leu His Ala Met Met
                325                 330                 335

Glu Arg Gly Pro Gln Thr Leu Lys Glu Thr Ser Phe Asn Gln Ala Tyr
            340                 345                 350

Gly Arg Asp Leu Met Glu Ala Gln Glu Trp Cys Arg Lys Tyr Met Lys
        355                 360                 365

Ser Gly Asn Val Lys Asp Leu Leu Gln Ala Trp Asp Leu Tyr Tyr His
```

```
    370                 375                 380

Val Phe Arg Arg Ile Ser Lys Pro Ala Ala Leu Gly Lys Asp Thr Ile
385                 390                 395                 400

Pro Trp Leu Gly His Leu Leu Val Gly Leu Ser Gly Ala Phe Gly Phe
                405                 410                 415

Ile Ile Leu Val Tyr Leu Leu Ile Asn Cys Arg Asn Thr Gly Pro Trp
            420                 425                 430

Leu Lys Lys Val Leu Lys Cys Asn Thr Pro Asp Pro Ser Lys Phe Phe
        435                 440                 445

Ser Gln Leu Ser Ser Glu His Gly Gly Asp Val Gln Lys Trp Leu Ser
    450                 455                 460

Ser Pro Phe Pro Ser Ser Ser Phe Ser Pro Gly Gly Leu Ala Pro Glu
465                 470                 475                 480

Ile Ser Pro Leu Glu Val Leu Glu Arg Asp Lys Val Thr Gln Leu Leu
                485                 490                 495

Leu Gln Gln Asp Lys Val Pro Glu Pro Ala Ser Leu Ser Leu Asn Thr
            500                 505                 510

Asp Ala Tyr Leu Ser Leu Gln Glu Leu Gln Gly Ser Gly Ala Thr Asn
        515                 520                 525

Phe Ser Leu Leu Lys Gln Ala Gly Asp Val Glu Glu Asn Pro Gly Pro
    530                 535                 540

Glu Met Trp His Glu Gly Leu Glu Glu Ala Ser Arg Leu Tyr Phe Gly
545                 550                 555                 560

Glu Arg Asn Val Lys Gly Met Phe Glu Val Leu Glu Pro Leu His Ala
                565                 570                 575

Met Met Glu Arg Gly Pro Gln Thr Leu Lys Glu Thr Ser Phe Asn Gln
            580                 585                 590

Ala Tyr Gly Arg Asp Leu Met Glu Ala Gln Glu Trp Cys Arg Lys Tyr
        595                 600                 605

Met Lys Ser Gly Asn Val Lys Asp Leu Leu Gln Ala Trp Asp Leu Tyr
    610                 615                 620

Tyr His Val Phe Arg Arg Ile Ser Lys
625                 630
```

<210> SEQ ID NO 155
<211> LENGTH: 19
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: NHEJ_F

<400> SEQUENCE: 155
cacgtgtgac tcctttccc 19

<210> SEQ ID NO 156
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: NHEJ_R

<400> SEQUENCE: 156
cccagtgcca cagtaaaggt 20

<210> SEQ ID NO 157
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: FAM_NHEJ probe

<400> SEQUENCE: 157
agggccgaga tcttcgaggc 20

<210> SEQ ID NO 158
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Control_F

<400> SEQUENCE: 158
cgacacttca cccctttct 20

<210> SEQ ID NO 159
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Control_R

<400> SEQUENCE: 159
ctccccaatg tgcctatgag 20

<210> SEQ ID NO 160
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: HEX_Control probe

<400> SEQUENCE: 160
gtggcggtga ctgggatggc 20

<210> SEQ ID NO 161
<211> LENGTH: 7219
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 3232_pAAV_FOXP3_0_8HA_ATG_FOXP3cDNA_WPRE3_pA_T3
specific

<400> SEQUENCE: 161
gtagaaaaga tcaaaggatc ttcttgagat cctttttttc tgcgcgtaat ctgctgcttg 60
caaacaaaaa aaccaccgct accagcggtg gtttgtttgc cggatcaaga gctaccaact 120

-continued

```
cttttttccga aggtaactgg cttcagcaga gcgcagatac caaatactgt ccttctagtg    180
tagccgtagt taggccacca cttcaagaac tctgtagcac cgcctacata cctcgctctg    240
ctaatcctgt taccagtggc tgctgccagt ggcgataagt cgtgtcttac cgggttggac    300
tcaagacgat agttaccgga taaggcgcag cggtcgggct gaacgggggg ttcgtgcaca    360
cagcccagct tggagcgaac gacctacacc gaactgagat acctacagcg tgagctatga    420
gaaagcgcca cgcttcccga agggagaaag gcggacaggt atccggtaag cggcagggtc    480
ggaacaggag agcgcacgag ggagcttcca gggggaaacg cctggtatct ttatagtcct    540
gtcgggtttc gccacctctg acttgagcgt cgatttttgt gatgctcgtc aggggggcgg    600
agcctatgga aaaacgccag caacgcggcc tttttacggt tcctggcctt ttgctggcct    660
tttgctcaca tgttctttcc tgcgttatcc cctgattctg tggataaccg tattaccgcc    720
tttgagtgag ctgataccgc tcgccgcagc cgaacgaccg agcgcagcga gtcagtgagc    780
gaggaagcgg aagagcgccc aatacgcaaa ccgcctctcc ccgcgcgttg gccgattcat    840
taatgcagct gcgcgctcgc tcgctcactg aggccgcccg ggcaaagccc gggcgtcggg    900
cgacctttgg tcgcccggcc tcagtgagcg agcgagcgcg cagagaggga gtggccaact    960
ccatcactag gggttccttg tagttaatga ttaacccgcc atgctactta tctacgtagc   1020
ggccgcattt aatgccagac tcttcatgtc tatctacacc tgcacttttg cacccaatcc   1080
aactccccgc catgtccccc atctcaggta atgtcagctc ggtccttcca gctgctcaag   1140
ctaaaaccca tgtcactttg actctccctc ttgcccacta catccaagct gctagcactg   1200
ctcctgatcc agcttcagat taagtctcag aatctaccca cttctcgcct tctccactgc   1260
caccagccca ttctgtgcca gcatcatcac ttgccaggac tgttacaata gcctcctcac   1320
tagccccact cacagcagcc agatgaatct tttgagtcca tgcctagtca ctggggcaaa   1380
ataggactcc gaggagaaag tccgagacca gctccggcaa gatgagcaaa cacagcctgt   1440
gcagggtgca gggagggcta gaggcctgag gcttgaaaca gctctcaagt ggagggggaa   1500
acaaccattg ccctcataga ggacacatcc acaccagggc tgtgctagcg tgggcaggca   1560
agccaggtgc tggacctctg cacgtggggc atgtgtgggt atgtacatgt acctgtgttc   1620
ttggtgtgtg tgtgtgtgtg tgtgtgtgtg tgtgtctaga gctggggtgc aactatgggg   1680
cccctcggga catgtcccag ccaatgcctg ctttgaccag aggagtgtcc acgtggctca   1740
ggtggtcgag tatctcatac cgccctagca cacgtgtgac tcctttcccc tattgtctac   1800
gcagcctgcc cttggacaag gacccgatgc ctaatcctcg gcctggaaag cctagcgctc   1860
cttctcttgc tctgggacct tctcctggcg cctctccatc ttggagagcc gctcctaaag   1920
ccagcgatct gctgggagct agaggacctg gcggcacatt tcagggcaga gatcttagag   1980
gcggagccca cgctagctcc tccagcctta atcctatgcc tcctagccag ctccagctgc   2040
ctacactgcc tctggttatg gtggctccta gcggagctag actgggccct ctgcctcatc   2100
tgcaagctct gctgcaggac agaccccact tcatgcacca gctgagcacc gtggatgccc   2160
acgcaagaac acctgtgctg caggttcacc ctctggaatc cccagccatg atcagcctga   2220
cacctccaac aacagccacc ggcgtgttca gcctgaaagc cagacctgga ctgcctcctg   2280
gcatcaatgt ggccagcctg gaatgggtgt ccagagaacc tgctctgctg tgcacattcc   2340
ccaatccaag cgctcccaga aaggacagca cactgtctgc cgtgcctcag agcagctatc   2400
ccctgcttgc taacggcgtg tgcaagtggc ctggatgcga gaaggtgttc gaggaacccg   2460
aggacttcct gaagcactgc caggccgatc atctgctgga cgagaaaggc agagcccagt   2520
```

gtctgctcca gcgcgagatg gtgcagtctc tggaacagca gctggtcctg gaaaaagaaa 2580
agctgagcgc catgcaggcc cacctggccg gaaaaatggc cctgacaaag gccagcagcg 2640
tggcctcttc tgataagggc agctgctgca ttgtggccgc tggatctcag ggacctgtgg 2700
ttcctgcttg gagcggacct agagaggccc ctgattctct gtttgccgtg cggagacacc 2760
tgtggggctc tcacggcaac tctactttcc ccgagttcct gcacaacatg gactacttca 2820
agttccacaa catgcggcct ccattcacct acgccacact gatcagatgg gccattctgg 2880
aagcccctga gaagcagaga accctgaacg agatctacca ctggtttacc cggatgttcg 2940
ccttcttccg gaatcaccct gccacctgga agaacgccat ccggcacaat ctgagcctgc 3000
acaagtgctt cgtgcgcgtg gaatctgaga aaggcgccgt gtggacagtg gacgagctgg 3060
aattcagaaa gaagagaagc cagcggccta gccggtgcag caatcctaca cctggacctt 3120
gaaagcttga taatcaacct ctggattaca aaatttgtga aagattgact ggtattctta 3180
actatgttgc tccttttacg ctatgtggat acgctgcttt aatgcctttg tatcatgcta 3240
ttgcttcccg tatggctttc attttctcct ccttgtataa atcctggtta gttcttgcca 3300
cggcggaact catcgccgcc tgccttgccc gctgctggac aggggctcgg ctgttgggca 3360
ctgacaattc cgtgggtcga ctgctttatt tgtgaaattt gtgatgctat tgctttattt 3420
gtaaccatta taagctgcaa taaacaagtt aacaacaaca attgcattca ttttatgttt 3480
caggttcagg gggagatgtg ggaggttttt taaagcacta gtcgagatct tcgaggcggg 3540
gcccatgcct cctcttcttc cttgaacccc atgccaccat cgcagctgca ggtgaggccc 3600
tgggcccagg atggggcagg cagggtgggg tacctggacc tacaggtgcc gacctttact 3660
gtggcactgg gcgggagggg ggctggctgg ggcacaggaa gtggtttctg ggtcccaggc 3720
aagtctgtga cttatgcaga tgttgcaggg ccaagaaaat ccccacctgc caggcctcag 3780
agattggagg ctctccccga cctcccaatc cctgtctcag gagaggagga ggccgtattg 3840
tagtcccatg agcatagcta tgtgtcccca tccccatgtg acaagagaag aggactgggg 3900
ccaagtaggt gaggtgacag ggctgaggcc agctctgcaa cttattagct gtttgatctt 3960
taaaaagtta ctcgatctcc atgagcctca gtttccatac gtgtaaaagg gggatgatca 4020
tagcatctac catgtgggct tgcagtgcag agtatttgaa ttagacacag aacagtgagg 4080
atcaggatgg cctctcaccc acctgccttt ctgcccagct gcccacactg cccctagtca 4140
tggtggcacc ctccggggca cggctgggcc ccttgcccca cttacaggca ctcctccagg 4200
acaggccaca tttcatgcac caggtatgga cggtgaatgg gcagggagga gggagcaggt 4260
gggagaactg tggggagggg ccccgagtca ggctgaaccg gatcctacgt agataagtag 4320
catggcgggt taatcattaa ctacaaggaa cccctagtga tggagttggc cactccctct 4380
ctgcgcgctc gctcgctcac tgaggccggg cgaccaaagg tcgcccgacg cccgggcttt 4440
gcccgggcgg cctcagtgag cgagcgagcg cgccagctgg cgtaatagcg aagaggcccg 4500
caccgatcgc ccttcccaac agttgcgcag cctgaatggc gaatggcgat tccgttgcaa 4560
tggctggcgg taatattgtt ctggatatta ccagcaaggc cgatagtttg agttcttcta 4620
ctcaggcaag tgatgttatt actaatcaaa gaagtattgc gacaacggtt aatttgcgtg 4680
atggacagac tcttttactc ggtggcctca ctgattataa aaacacttct caggattctg 4740
gcgtaccgtt cctgtctaaa atccctttaa tcggcctcct gtttagctcc cgctctgatt 4800
ctaacgagga aagcacgtta tacgtgctcg tcaaagcaac catagtacgc gccctgtagc 4860

```
ggcgcattaa gcgcggcggg tgtggtggtt acgcgcagcg tgaccgctac acttgccagc   4920
gccctagcgc ccgctccttt cgctttcttc ccttcctttc tcgccacgtt cgccggcttt   4980
ccccgtcaag ctctaaatcg ggggctccct ttagggttcc gatttagtgc tttacggcac   5040
ctcgacccca aaaaacttga ttagggtgat ggttcacgta gtgggccatc gccctgatag   5100
acggtttttc gccctttgac gttggagtcc acgttcttta atagtggact cttgttccaa   5160
actggaacaa cactcaaccc tatctcggtc tattcttttg atttataagg gattttgccg   5220
atttcggcct attggttaaa aaatgagctg atttaacaaa aatttaacgc gaattttaac   5280
aaaatattaa cgtttacaat ttaaatattt gcttatacaa tcttcctgtt tttggggctt   5340
ttctgattat caaccggggt acatatgatt gacatgctag ttttacgatt accgttcatc   5400
gattctcttg tttgctccag actctcaggc aatgacctga tagcctttgt agagacctct   5460
caaaaatagc taccctctcc ggcatgaatt tatcagctag aacggttgaa tatcatattg   5520
atggtgattt gactgtctcc ggcctttctc acccgtttga atctttacct acacattact   5580
caggcattgc atttaaaata tatgagggtt ctaaaaattt ttatccttgc gttgaaataa   5640
aggcttctcc cgcaaaagta ttacagggtc ataatgtttt tggtacaacc gatttagctt   5700
tatgctctga ggctttattg cttaattttg ctaattcttt gccttgcctg tatgatttat   5760
tggatgttgg aatcgcctga tgcggtattt tctccttacg catctgtgcg gtatttcaca   5820
ccgcatatgg tgcactctca gtacaatctg ctctgatgcc gcatagttaa gccagccccg   5880
acacccgcca acacccgctg acgcgccctg acgggcttgt ctgctcccgg catccgctta   5940
cagacaagct gtgaccgtct ccgggagctg catgtgtcag aggttttcac cgtcatcacc   6000
gaaacgcgcg agacgaaagg gcctcgtgat acgcctattt ttataggtta atgtcatgat   6060
aataatggtt tcttagacgt caggtggcac ttttcgggga aatgtgcgcg gaacccctat   6120
ttgtttattt ttctaaatac attcaaatat gtatccgctc atgagacaat aaccctgata   6180
aatgcttcaa taatattgaa aaaggaagag tatgagtatt caacatttcc gtgtcgccct   6240
tattcccttt tttgcggcat tttgccttcc tgtttttgct cacccagaaa cgctggtgaa   6300
agtaaaagat gctgaagatc agttgggtgc acgagtgggt tacatcgaac tggatctcaa   6360
cagcggtaag atccttgaga gttttcgccc cgaagaacgt tttccaatga tgagcacttt   6420
taaagttctg ctatgtggcg cggtattatc ccgtattgac gccgggcaag agcaactcgg   6480
tcgccgcata cactattctc agaatgactt ggttgagtac tcaccagtca cagaaaagca   6540
tcttacggat ggcatgacag taagagaatt atgcagtgct gccataacca tgagtgataa   6600
cactgcggcc aacttacttc tgacaacgat cggaggaccg aaggagctaa ccgctttttt   6660
gcacaacatg ggggatcatg taactcgcct tgatcgttgg gaaccggagc tgaatgaagc   6720
cataccaaac gacgagcgtg acaccacgat gcctgtagca atggcaacaa cgttgcgcaa   6780
actattaact ggcgaactac ttactctagc ttcccggcaa caattaatag actggatgga   6840
ggcggataaa gttgcaggac cacttctgcg ctcggccctt ccggctggct ggtttattgc   6900
tgataaatct ggagccggtg agcgtgggtc tcgcggtatc attgcagcac tggggccaga   6960
tggtaagccc tcccgtatcg tagttatcta cacgacgggg agtcaggcaa ctatggatga   7020
```

-continued

| | |
|---|---|
| acgaaataga cagatcgctg agataggtgc ctcactgatt aagcattggt aactgtcaga | 7080 |
| ccaagtttac tcatatatac tttagattga tttaaaactt catttttaat ttaaaaggat | 7140 |
| ctaggtgaag atcctttttg ataatctcat gaccaaaatc ccttaacgtg agttttcgtt | 7200 |
| ccactgagcg tcagaccccc | 7219 |